United States Patent
Broeker et al.

(10) Patent No.: US 12,060,367 B2
(45) Date of Patent: Aug. 13, 2024

(54) ANNULATED 2-AMINO-3-CYANO THIOPHENES AND DERIVATIVES FOR THE TREATMENT OF CANCER

(71) Applicants: BOEHRINGER INGELHEIM INTERNATIONAL GMBH, Ingelheim am Rhein (DE); VANDERBILT UNIVERSITY, Nashville, TN (US)

(72) Inventors: Joachim Broeker, Moedling (AT); Jason Abbott, Libertyville, IL (US); Jianwen Cui, Franklin, IL (US); Stephen W. Fesik, Nashville, TN (US); Julian Fuchs, Vienna (AT); Andreas Gollner, Vienna (AT); Lorenz Herdeis, Vienna (AT); Tim Hodges, Chicago, IL (US); Andrew Little, Sudbury, MA (US); Andreas Mantoulidis, Vienna (AT); Jason Phan, Nashville, TN (US); Juergen Ramharter, Vienna (AT); Dhruba Sarkar, Bangalore (IN); Christian Alan Paul Smethurst, Vienna (AT); Kevin Sokol, Vienna (AT); Heinz Stadtmueller, Weigelsdorf (DE); Qi Sun, Libertyville, IL (US); Matthias Treu, Vienna (AT); Alex Waterson, Murfreesboro, TN (US); Birgit Wilding, Vienna (AT); Tobias Wunberg, Hinterbruehl (AT)

(73) Assignees: BOEHRINGER INGELHEIM INTERNATIONAL GMBH, Ingelheim am Rhein (DE); VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 18/314,445

(22) Filed: May 9, 2023

(65) Prior Publication Data
US 2024/0174690 A1    May 30, 2024

Related U.S. Application Data

(63) Continuation of application No. 18/060,053, filed on Nov. 30, 2022.
(Continued)

(51) Int. Cl.
*C07D 498/10* (2006.01)
*A61P 1/00* (2006.01)
(Continued)

(52) U.S. Cl.
CPC ............ *C07D 498/10* (2013.01); *A61P 1/00* (2018.01); *A61P 1/18* (2018.01); *A61P 11/00* (2018.01);
(Continued)

(58) Field of Classification Search
CPC ....... C07D 498/10; C07D 519/00; A61P 1/00; A61P 1/18; A61P 11/00; A61P 17/00; A61P 35/00
See application file for complete search history.

(56) References Cited

U.S. PATENT DOCUMENTS

| 2018/0177767 A1 | 6/2018 | Lanman et al. |
| 2021/0380574 A1 | 12/2021 | Abbott et al. |
| 2023/0227470 A1* | 7/2023 | Broeker .................. A61P 17/00 514/210.16 |

FOREIGN PATENT DOCUMENTS

| CN | 113683616 A | 11/2021 |
| WO | 2015054572 A1 | 4/2015 |

(Continued)

OTHER PUBLICATIONS

Abbas et al., "Abbas and Ahmed: 1-18 New Approaches for the Synthesis and Ctytotoxicity New Approaches for the Synthesis and Ctytotoxicity of Thiazoles Derived from Cyclohexanone", ACTA Chim. Slov, vol. 61, 2014, pp. 835-843.
(Continued)

*Primary Examiner* — Kortney L. Klinkel
*Assistant Examiner* — Dawanna Shar-Day White
(74) *Attorney, Agent, or Firm* — Robin L. Teskin; Baker, Donelson, Bearman, Caldwell & Berkowitz PC

(57) ABSTRACT

The present invention encompasses compounds of formula (I)

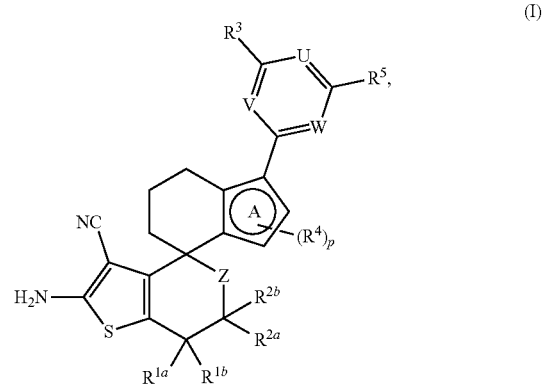

wherein $R^{1a}$, $R^{1b}$, $R^{2a}$, $R^{2b}$, Z, $R^3$ to $R^5$, A, p, U, V and W have the meanings given in the claims and specification, their use as inhibitors of KRAS, pharmaceutical compositions and preparations containing such compounds and their use as medicaments/medical uses, especially as agents for treatment and/or prevention of oncological diseases.

49 Claims, No Drawings

Related U.S. Application Data

(60) Provisional application No. 63/284,778, filed on Dec. 1, 2021, provisional application No. 63/284,754, filed on Dec. 1, 2021.

(51) Int. Cl.
    *A61P 1/18* (2006.01)
    *A61P 11/00* (2006.01)
    *A61P 17/00* (2006.01)
    *A61P 35/00* (2006.01)
    *C07D 519/00* (2006.01)

(52) U.S. Cl.
    CPC .............. *A61P 17/00* (2018.01); *A61P 35/00* (2018.01); *C07D 519/00* (2013.01)

(56) References Cited

FOREIGN PATENT DOCUMENTS

| WO | 2017201161 A1 | 11/2017 |
| WO | 2018102453 A1 | 6/2018 |
| WO | 2018140599 A1 | 8/2018 |
| WO | 2018217651 A1 | 11/2018 |
| WO | 2019099524 A1 | 5/2019 |
| WO | 2020028706 A1 | 2/2020 |
| WO | 2020102730 A1 | 5/2020 |
| WO | 2020177629 A1 | 9/2020 |
| WO | 2020236940 A1 | 11/2020 |
| WO | 2021118877 A1 | 6/2021 |
| WO | 2021120890 A1 | 6/2021 |
| WO | 2021139748 A1 | 7/2021 |
| WO | 2021150613 A1 | 7/2021 |
| WO | 2021245051 A1 | 12/2021 |
| WO | 2021245055 A1 | 12/2021 |
| WO | 2023099592 A1 | 6/2023 |
| WO | 2023099608 A1 | 6/2023 |
| WO | 2023099612 A1 | 6/2023 |
| WO | 2023099620 A1 | 6/2023 |
| WO | 2023099623 A1 | 6/2023 |

OTHER PUBLICATIONS

Abstract in English for CN113683616, dated Nov. 23, 2021.
Awad et al., "Acquired resistance to KRAS(G12C) inhibition in cancer", N Engl J Med, 2021, 384, pp. 2382-2393.
Chardin et al., "Human Sos1: a guanine nucleotide exchange factor for Ras that binds to GRB2", Science, 1993, 260 (5112), pp. 1338-1343.
Cox et al., "Drugging the undruggable RAS: Mission possible", Nat. Rev. Drug Discov., 2014, 13(11), pp. 828-851.
Eberlein et al., "Acquired Resistance to the Mutant-Selective EGFR Inhibitor AZD9291 Is Associated with Increased Dependence on RAS Signaling in Preclinical Models", Cancer Res., 2015, 75(12), pp. 2489-2500.
Herdeis et al., "Stopping the beating heart of cancer: KRAS reviewed", Curr Opin Struct Biol., 2021, 71, pp. 136-147.
Hunter et al., "Biochemical and Structural Analysis of Common Cancer-Associated KRAS Mutations", Mol. Cancer Res., 2015, 13(9), pp. 1325-1335.
International Search Report and Written Opinion for application PCT/EP2021/064612, date of mailing Jul. 2, 2021.
International Search Report and Written Opinion for application, PCT/EP2021/064616, date of mailing Jul. 23, 2021.
International Search Report and Written Opinion for application, PCT/EP2022/083906, date of mailing Feb. 21, 2023.
International Search Report and Written Opinion for application, PCT/EP2022/083936, date of mailing Mar. 9, 2023.
International Search Report and Written Opinion for application, PCT/EP2022/083953, date of mailing Mar. 20, 2023.
International Search Report and Written Opinion for application, PCT/EP2022/083954, date of mailing Mar. 13, 2023.
International Search Report and Written Opinion for application, PCT/EP2022/083930, date of mailing Feb. 22, 2023.
Leto et al., "Primary and acquired resistance to EGFR-targeted therapies in colorectal cancer: impact on future treatment strategies", J. Mol. Med. (Berl). Jul. 2014;92(7), pp. 709-722.
Markó et al., "Efficient and convergent stereocontrolled spiroannulation of ketones, Tetrahedron Letters", 2003, 44, pp. 3333-3336.
Maulide et al., "Connective Synthesis of Spirovetivanes: Total Synthesis of (±)-Agarospirol, (±)-Hinesol and (±) -?-Vetispirene", EurJOC, 2004, 19, pp. 3962-3967.
McCormick et al., "K-Ras protein as a drug target", J. Mol. Med. (Berl)., 2016, 94(3), pp. 253-258.
McCormick et al., "The potential of targeting Ras proteins in lung cancer", Expert Opin. Ther. Targets., 2015, 19(4), pp. 451-454.
Meyers et al., "Computational correction of copy number effect improves specificity of CRISPR-Cas9 essentiality screens in cancer cells", Nat Genet, 2017, 49, pp. 1779-1784.
Nimnual et al., "The Two Hats of SOS", Sci. STKE., 2002, 145, p. 36.
Ortiz-Cuaran et al., "Heterogeneous Mechanisms of Primary and Acquired Resistance to Third-Generation EGFR Inhibitors", Clin. Cancer Res., 2016, 22(19), pp. 4837-4847.
Rodriguez-Viciana et al., "RalGDS comes of age", Cancer Cell. 2005, 7(3), pp. 205-206.
Tanaka et al., "Clinical acquired resistance to KRAS(G12C) 30 inhibition through a novel KRAS switch-II pocket mutation and polyclonal alterations converging on RAS-MAPK reactivation", Cancer Discov, 2021, 11, pp. 1913-1922.
Wong et al., "Targeting wild-type KRAS-amplified gastroesophageal cancer through combined MEK and SHP2 Inhibition", Nat Med., 2018, 24(7), pp. 968-977.
Yao et al., "Tumours with class 3 BRAF mutants are sensitive to the inhibition of activated RAS", Nature, 2017, 548, pp. 234-238.
Young et al., "Ras signaling and therapies", Adv. Cancer Res., 2009, 102, pp. 1-17.

* cited by examiner

ANNULATED 2-AMINO-3-CYANO THIOPHENES AND DERIVATIVES FOR THE TREATMENT OF CANCER

FIELD OF THE INVENTION

The present invention relates to annulated 2-amino-3-cyano thiophenes and derivatives of formula (I)

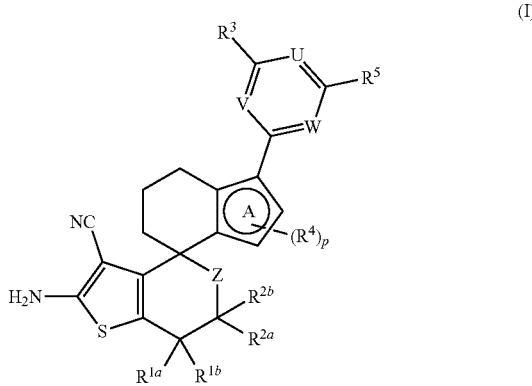

wherein $R^{1a}$, $R^{1b}$, $R^{2a}$, $R^{2b}$, Z, $R^3$ to $R^5$, A, p, U, V and W have the meanings given in the claims and specification, their use as inhibitors of KRAS, pharmaceutical compositions and preparations containing such compounds and their use as medicaments/medical uses, especially as agents for treatment and/or prevention of oncological diseases, e.g. cancer.

BACKGROUND OF THE INVENTION

V-Ki-ras2 Kirsten rat sarcoma viral oncogene homolog (KRAS) is a small GTPase of the Ras family of proteins that exists in cells in either GTP-bound or GDP-bound states (McCormick et al., J. Mol. Med. (Berl)., 2016, 94(3):253-8; Nimnual et al., Sci. STKE., 2002, 2002(145):pe36). Binding of GTPase activating proteins (GAPs) such as NF1 increases the GTPase activity of Ras family proteins. The binding of guanine nucleotide exchange factors (GEFs) such as SOS1 (Son of Sevenless 1) promotes release of GDP from Ras family proteins, enabling GTP binding (Chardin et al., Science, 1993, 260(5112):1338-43). When in the GTP-bound state, Ras family proteins are active and engage effector proteins including C-RAF and phosphoinositide 3-kinase (PI3K) to promote the RAF/mitogen or extracellular signal-regulated kinases (MEK/ERK) pathway, PI3K/AKT/mammalian target of rapamycin (mTOR) pathway and RalGDS (Ral guanine nucleotide dissociation stimulator) pathway (McCormick et al., J. Mol. Med. (Berl)., 2016, 94(3):253-8; Rodriguez-Viciana et al., Cancer Cell. 2005, 7(3):205-6). These pathways affect diverse cellular processes such as proliferation, survival, metabolism, motility, angiogenesis, immunity and growth (Young et al., Adv. Cancer Res., 2009, 102:1-17; Rodriguez-Viciana et al., Cancer Cell. 2005, 7(3):205-6).

Cancer-associated mutations in Ras family proteins suppress their intrinsic and GAP-induced GTPase activity leading to an increased population of GTP-bound/active mutant Ras family proteins (McCormick et al., Expert Opin. Ther. Targets, 2015, 19(4):451-4; Hunter et al., Mol. Cancer Res., 2015, 13(9):1325-35). This in turn leads to persistent activation of effector pathways (e.g. RAF/MEK/ERK, PI3K/AKT/mTOR, RalGDS pathways) downstream of mutant Ras family proteins. KRAS mutations (e.g. amino acids G12, G13, Q61, A146) are found in a variety of human cancers including lung cancer, colorectal cancer and pancreatic cancer (Cox et al., Nat. Rev. Drug Discov., 2014, 13(11):828-51). Alterations (e.g. mutation, overexpression, gene amplification) in Ras family proteins/Ras genes have also been described as a resistance mechanism against cancer drugs such as the EGFR antibodies cetuximab and panitumumab (Leto et al., J. Mol. Med. (Berl). 2014 July; 92(7):709-22) and the EGFR tyrosine kinase inhibitor osimertinib/AZD9291 (Ortiz-Cuaran et al., Clin. Cancer Res., 2016, 22(19):4837-47; Eberlein et al., Cancer Res., 2015, 7 5(12):2489-500).

In a subset of tumor indications such as gastric cancer, gastroesophageal junction cancer and esophageal cancer prominent amplification of the wildtype (WT) KRAS proto-oncogene acts as a driver alteration and renders tumor models bearing this genotype addicted to KRAS in vitro and in vivo (Wong et al. Nat Med., 2018, 24(7):968-977). In contrast, non-amplified KRAS WT cell lines are KRAS independent, unless they carry secondary alterations in genes indirectly causing activation of KRAS (Meyers et al., Nat Genet., 2017, 49:1779-1784). Based on these data, a therapeutic window is expected for a KRAS targeting agent with a KRAS WT targeting activity.

Genetic alterations affecting e.g. codon 12 of KRAS substitute the glycine residue naturally occurring at this position for different amino acids such as aspartic acid (the G12D mutation or KRAS G12D), cysteine (the G12C mutation or KRAS G12C), valine (the G12V mutation or KRAS G12V) among others. Similarly, mutations within codons 13, 61 and 146 of KRAS are commonly found in the KRAS gene. Altogether KRAS mutations are detectable in 35% of lung, 45% of colorectal, and up to 90% of pancreatic cancers (Herdeis et al., Curr Opin Struct Biol., 2021, 71:136-147).

In summary, binders/inhibitors of wildtype or mutated KRAS (e.g., G12D, G12V and G12C) are expected to deliver anti-cancer efficacy.

Thus, there is the need to develop new compounds efficacious in the treatment of cancers mediated by KRAS, especially KRAS mutated in position 12 or 13 and/or in wild-type amplified KRAS mediated cancer, which also possess desirable pharmacological properties, including but not limited to: metabolic stability, plasma protein binding, solubility and permeability.

DETAILED DESCRIPTION OF THE INVENTION

It has now been found that, surprisingly, compounds of formula (I)

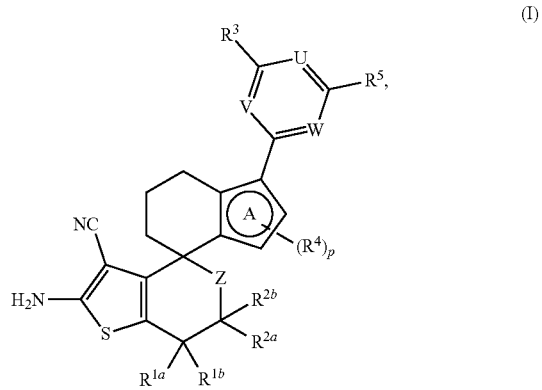

wherein $R^{1a}, R^{1b}, R^{2a}, R^{2b}, Z, R^3$ to $R^5$, A, p, U, V and W have the meanings given hereinafter act as inhibitors of KRAS and are involved in controlling cell proliferation. Thus, the compounds according to the invention may be used for example for the treatment of diseases characterized by excessive or abnormal cell proliferation.

Surprisingly, the compounds described herein have been found to possess anti-tumour activity, being useful in inhibiting the uncontrolled cellular proliferation which arises from malignant diseases. It is believed that this anti-tumor activity is, inter alia, derived from inhibition of KRAS mutated in position 12 or 13, preferably G12D, G12V or G13D mutant KRAS, or inhibition of WT KRAS, especially KRAS WT amplified. Advantageously, the compounds can be selective for certain KRAS mutants, preferably KRAS G12D, or can be effective against a panel of KRAS mutants including KRAS wildtype amplified.

In addition, the compounds of the invention advantageously possess desirable pharmacological properties, including but not limited to: metabolic stability, plasma protein binding, solubility and permeability.

Thus, in a first aspect, the present invention relates to a compound of formula (I)

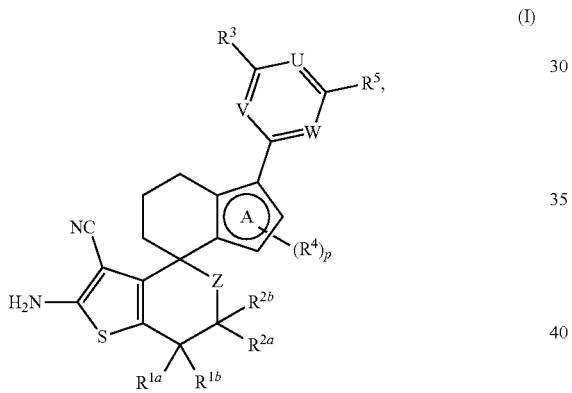

(I)

wherein $R^{1a}$ and $R^{1b}$ are both independently selected from the group consisting of hydrogen, $C_{1-4}$alkyl, $C_{1-4}$haloalkyl, $C_{1-4}$alkoxy, $C_{1-4}$haloalkoxy, halogen, —NH$_2$, —NH($C_{1-4}$alkyl), —N($C_{1-4}$alkyl)$_2$, $C_{3-5}$cycloalkyl and 3-5 membered heterocyclyl;

$R^{2a}$ and $R^{2b}$ are both independently selected from the group consisting of hydrogen, $C_{1-4}$alkyl, $C_{1-4}$haloalkyl, $C_{1-4}$alkoxy, $C_{1-4}$haloalkoxy, halogen, —NH$_2$, —NH($C_{1-4}$alkyl), —N($C_{1-4}$alkyl)$_2$, $C_{3-5}$cycloalkyl and 3-5 membered heterocyclyl;

and/or, optionally, one of $R^{1a}$ or $R^{1b}$ and one of $R^{2a}$ or $R^{2b}$ together with the carbon atoms they are attached form a cyclopropane ring;

Z is —(CR$^{6a}$R$^{6b}$)$_n$—;

each $R^{6a}$ and $R^{6b}$ is independently selected from the group consisting of hydrogen, $C_{1-4}$alkyl, $C_{1-4}$haloalkyl, $C_{1-4}$alkoxy, $C_{1-4}$haloalkoxy, halogen, —NH$_2$, —NH($C_{1-4}$alkyl), —N($C_{1-4}$alkyl)$_2$, $C_{3-5}$cycloalkyl and 3-5 membered heterocyclyl;

or $R^{6a}$ and $R^{6b}$ together with the carbon atom they are attached to form a cyclopropane ring;

n is selected from the group consisting of 0, 1 and 2;

$R^3$ is selected from the group consisting of halogen, $C_{1-6}$alkyl, $C_{1-6}$haloalkyl, —N$_3$, $C_{3-10}$cycloalkyl, 3-11 membered heterocyclyl, $C_{6-10}$aryl and 5-10 membered heteroaryl, wherein the $C_{1-6}$alkyl, $C_{1-6}$haloalkyl, $C_{3-10}$cycloalkyl, 3-11 membered heterocyclyl, $C_{6-10}$aryl and 5-10 membered heteroaryl are all optionally and independently substituted with one or more, identical or different $R^7$ and/or $R^8$;

each $R^7$ is independently selected from the group consisting of halogen, —CN, —OR$^8$, —NR$^8$R$^8$, —C(=O)R$^8$, —C(=O)OR$^8$, —C(=O)NR$^8$R$^8$, —NHC(=O)OR$^8$ and the bivalent substituent =O;

each $R^8$ is independently selected from the group consisting of hydrogen, $C_{1-6}$alkyl, $C_{3-10}$cycloalkyl, 3-11 membered heterocyclyl, $C_{6-10}$aryl and 5-10 membered heteroaryl, wherein the $C_{1-6}$alkyl, $C_{3-10}$cycloalkyl, 3-11 membered heterocyclyl, $C_{6-10}$aryl and 5-10 membered heteroaryl are all optionally substituted with one or more, identical or different $R^9$ and/or $R^{10}$;

each $R^9$ is independently selected from the group consisting of —OR$^{10}$, —NR$^{10}$R$^{10}$ and —C(O)NR$^{10}$R$^{10}$;

each $R^{10}$ is independently selected from the group consisting of hydrogen, $C_{1-6}$alkyl, $C_{3-10}$cycloalkyl, 3-11 membered heterocyclyl and 5-10 membered heteroaryl, wherein the $C_{1-6}$alkyl is optionally substituted with a substituent selected from the group consisting of $C_{1-6}$alkoxy, $C_{3-10}$cycloalkyl and 3-11 membered heterocyclyl optionally substituted with $C_{1-6}$alkyl;

W is nitrogen (—N=) or —CH=;

V is nitrogen (—N=) or —CH=;

U is nitrogen (—N=) or —C(R$^{11}$)=;

$R^{11}$ is selected from hydrogen, halogen and $C_{1-4}$alkoxy;

ring A is a ring selected from the group consisting of pyrrole, furan, thiophene, imidazole, pyrazole, oxazole, isoxazole, thiazole, isothiazole and triazole;

each $R^4$, if present, is independently selected from the group consisting of $C_{1-6}$alkyl, $C_{1-6}$haloalkyl, $C_{1-6}$alkoxy, $C_{1-6}$haloalkoxy, cyano-$C_{1-6}$alkyl, halogen, —OH, —NH$_2$, —NH($C_{1-4}$alkyl), —N($C_{1-4}$alkyl)$_2$, —CN, $C_{3-5}$cycloalkyl and 3-5 membered heterocyclyl;

p is selected from the group consisting of 0, 1, 2 and 3;

$R^5$ is a 3-11 membered heterocyclyl optionally substituted with one or more identical or different $C_{1-6}$alkyl, $C_{1-6}$alkoxy or a 5-6 membered heterocyclyl, wherein the $C_{1-6}$alkyl is optionally substituted with cyclopropyl;

or $R^5$ is —O—$C_{1-6}$alkyl substituted with a 3-11 membered heterocyclyl, wherein the 3-11 membered heterocyclyl is optionally substituted with one or more, identical or different $R^{12}$, each $R^{12}$ is selected from the group consisting of $C_{1-6}$alkyl, $C_{1-6}$alkoxy, halogen and 3-11 membered heterocyclyl;

or a salt thereof.

In another aspect, the invention relates to the compound of the formula (I), or a salt thereof, wherein $R^{1a}$ and $R^{1b}$ are both independently selected from the group consisting of hydrogen and $C_{1-4}$alkyl.

In another aspect, the invention relates to the compound of the formula (I), or a salt thereof, wherein $R^{2a}$ and $R^{2b}$ are both independently selected from the group consisting of hydrogen and halogen.

In another aspect, the invention relates to the compound of the formula (I), or a salt thereof, wherein $R^{1a}$ and $R^{1b}$ are both independently selected from the group consisting of hydrogen and methyl.

In another aspect, the invention relates to the compound of the formula (I), or a salt thereof, wherein $R^{2a}$ and $R^{2b}$ are both independently selected from the group consisting of hydrogen and fluorine.

In another aspect, the invention relates to the compound of the formula (I), or a salt thereof, wherein $R^{1a}$, $R^{1b}$, $R^{2a}$ and $R^{2b}$ are hydrogen.

In another aspect, the invention relates to the compound of the formula (I), or a salt thereof, wherein n is 0.

In another aspect, the invention relates to the compound of the formula (I), or a salt thereof, wherein n is 1; and
- each $R^{6a}$ and $R^{6b}$ is independently selected from the group consisting of hydrogen, $C_{1-4}$alkyl, $C_{1-4}$haloalkyl, $C_{1-4}$alkoxy, $C_{1-4}$haloalkoxy, halogen, —$NH_2$, —NH($C_{1-4}$alkyl), —N($C_{1-4}$alkyl)$_2$, $C_{3-5}$cycloalkyl and 3-5 membered heterocyclyl.

In another aspect, the invention relates to the compound of the formula (I), or a salt thereof, wherein Z is —$CH_2$—.

In another aspect, the invention relates to the compound of the formula (I), or a salt thereof, wherein n is 2;
- each $R^{6a}$ and $R^{6b}$ is independently selected from the group consisting of hydrogen, $C_{1-4}$alkyl, $C_{1-4}$haloalkyl, $C_{1-4}$alkoxy, $C_{1-4}$haloalkoxy, halogen, —$NH_2$, —NH($C_{1-4}$alkyl), —N($C_{1-4}$alkyl)$_2$, $C_{3-5}$cycloalkyl and 3-5 membered heterocyclyl.

In another aspect, the invention relates to the compound of the formula (I), or a salt thereof, wherein p is 0.

In another aspect, the present invention relates to a compound of the formula (I*) or a salt thereof

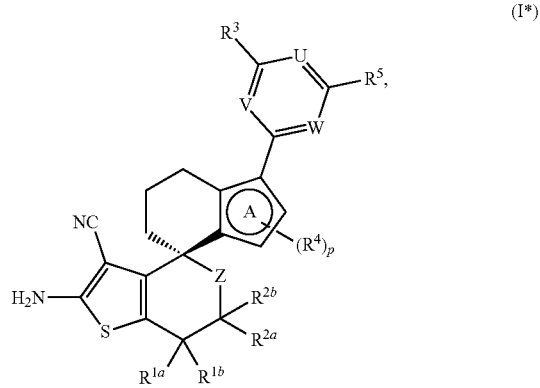

(I*)

wherein
$R^{1a}$, $R^{1b}$, $R^{2a}$, $R^{2b}$, $R^3$, $R^4$, $R^5$, Z, U, V, W, ring A and p are as defined herein above or below.

In another aspect the present invention relates to a compound of the formula (Ia) or a salt thereof

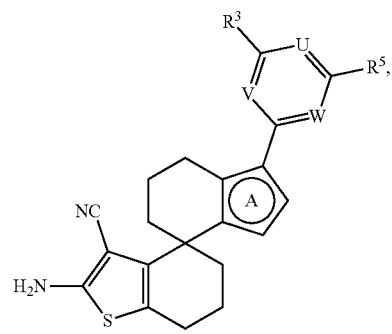

(Ia)

wherein
A, V, U, W, $R^3$ and $R^5$ are defined herein.

In another aspect, the invention relates to a compound of formula (Ib) or a salt thereof

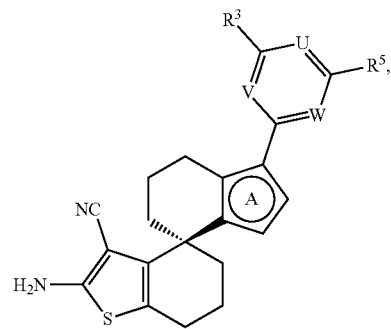

(Ib)

wherein
A, V, U, W, $R^3$ and $R^5$ are defined herein.

In another aspect, the invention relates to the compound of the invention, or a salt thereof, wherein ring A is a ring selected from the group consisting of imidazole, pyrazole, oxazole, isoxazole, thiazole, isothiazole and triazole.

In another aspect, the invention relates to the compound of the invention, or a salt thereof, wherein ring A is a ring selected from the group consisting of pyrrole, furan, thiophene, imidazole, pyrazole, isoxazole, isothiazole and triazole.

In another aspect, the invention relates to the compound of the invention, or a salt thereof, wherein ring A is selected from the group consisting of

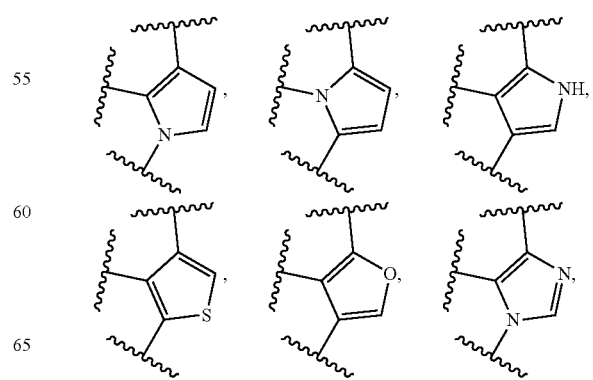

-continued

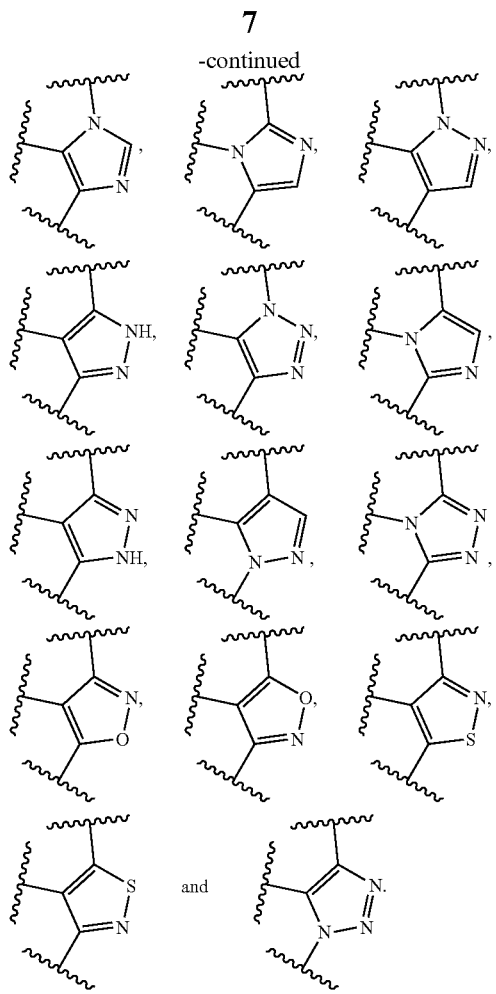

In another aspect, the invention relates to the compound of the invention, or a salt thereof, wherein ring A is isoxazole or isothiazole.

In another aspect, the invention relates to the compound of the invention, or a salt thereof, wherein ring A is selected from

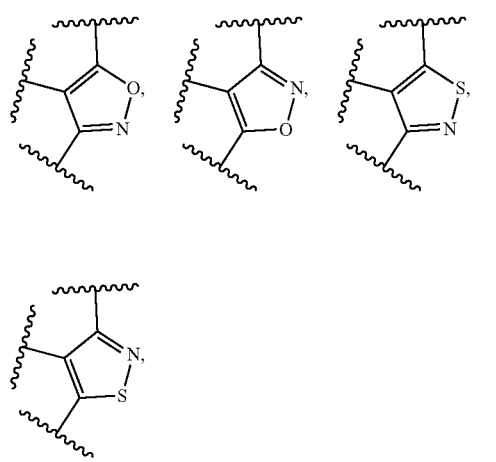

In another aspect, the invention relates to the compound of the invention, or a salt thereof, wherein ring A is In another aspect the invention relates to a compound of formula (Ic), or a salt thereof

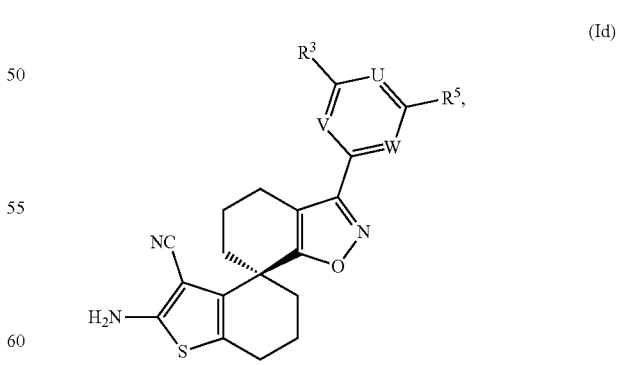

wherein
V, U, W, $R^3$ and $R^5$ are as defined herein.

In another aspect the invention relates to a compound of formula (Id), or a salt thereof (Id)

wherein
V, U, W, $R^3$ and $R^5$ are as defined herein.

In another aspect the invention relates to a compound of formula (Ie), or a salt thereof

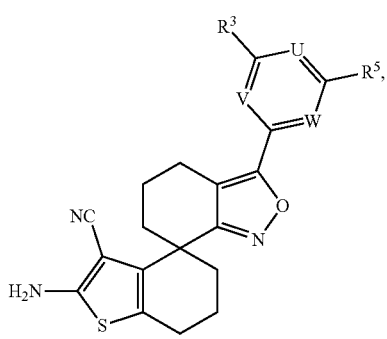

(Ie)

wherein
V, U, W, R$^3$ and R$^5$ are as defined herein.

In another aspect, the invention relates to a compound of formula (If), or a salt thereof

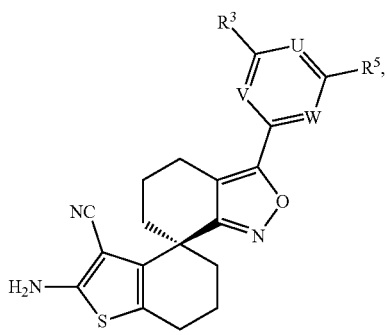

(If)

wherein
V, U, W, R$^3$ and R$^5$ are as defined herein.

In another aspect, the invention relates to the compound of the formula (I), (I*), (Ia), (Ib), (Ic), (Id), (Ie) or (If), or a salt thereof, wherein at least one of W, V and U is nitrogen.

In another aspect, the invention relates to the compound of the formula (I), (I*), (Ia), (Ib), (Ic), (Id), (Ie) or (If), or a salt thereof, wherein
W is nitrogen (—N═);
V is nitrogen (—N═);
U is ═C(R$^{11}$)—;
R$^{11}$ is selected from hydrogen, halogen and C$_{1-4}$alkoxy.

In another aspect, the invention relates to the compound of the formula (I), (I*), (Ia), (Ib), (Ic), (Id), (Ie) or (If), or a salt thereof, wherein
W is —CH═;
V is nitrogen (—N═);
U is ═C(R$^{11}$)—;
R$^{11}$ is selected from hydrogen, halogen and C$_{1-4}$alkoxy.

In another aspect, the invention relates to the compound of the formula (I), (I*), (Ia), (Ib), (Ic), (Id), (Ie) or (If), or a salt thereof, wherein
V is —CH═;
W is nitrogen (—N═);
U is ═C(R$^{11}$)—;
R$^{11}$ is selected from hydrogen, halogen and C$_{1-4}$alkoxy.

In another aspect, the invention relates to the compound of the formula (I), (I*), (Ia), (Ib), (Ic), (Id), (Ie) or (If), or a salt thereof, wherein
R$^{11}$ is selected from hydrogen, fluorine, chlorine and —O—CH$_3$.

In another aspect, the invention relates to the compound of the formula (I), (I*), (Ia), (Ib), (Ic), (Id), (Ie) or (If), or a salt thereof, wherein
V is nitrogen (—N═);
W is —CH═;
U is nitrogen (—N═).

In another aspect, the invention relates to the compound of the formula (I), (I*), (Ia), (Ib), (Ic), (Id), (Ie) or (If), or a salt thereof, wherein
W is nitrogen (—N═);
V is —CH═;
U is nitrogen (—N═).

In another aspect, the invention relates to the compound of the formula (I), (I*), (Ia), (Ib), (Ic), (Id), (Ie) or (If), or a salt thereof, wherein
W is —CH═;
V is —CH═;
U is nitrogen (—N═).

In another aspect, the invention relates to the compound of the formula (I), (I*), (Ia), (Ib), (Ic), (Id), (Ie) or (If), or a salt thereof, wherein
W is nitrogen (—N═);
V is nitrogen (—N═);
U is nitrogen (—N═).

In another aspect, the invention relates to the compound of the formula (I), (I*), (Ia), (Ib), (Ic), (Id), (Ie) or (If), or a salt thereof, wherein
W is nitrogen (—N═);
V is nitrogen (—N═);
U is ═C(R$^{11}$)—;
R$^{11}$ is selected from hydrogen, halogen and C$_{1-4}$alkoxy;
or wherein
V is nitrogen (—N═);
W is —CH═;
U is nitrogen (—N═).

In another aspect, the invention relates to the compound of the formula (I), (I*), (Ia), (Ib), (Ic), (Id), (Ie) or (If), or a salt thereof, wherein
R$^5$ is a 6-11 membered heterocyclyl optionally substituted with one or more identical or different C$_{1-6}$alkyl, C$_{1-6}$alkoxy or a 5-6 membered heterocyclyl, wherein the C$_{1-6}$alkyl is optionally substituted with cyclopropyl.

In another aspect, the invention relates to the compound of the formula (I), (I*), (Ia), (Ib), (Ic), (Id), (Ie) or (If), or a salt thereof, wherein
R$^5$ is a 7 membered heterocyclyl, optionally substituted with one or more identical or different C$_{1-4}$alkyl.

In another aspect, the invention relates to the compound of the formula (I), (I*), (Ia), (Ib), (Ic), (Id), (Ie) or (If), or a salt thereof, wherein
R$^5$ is —O—C$_{1-6}$alkyl substituted with a 5-8 membered heterocyclyl, wherein the 5-8 membered heterocyclyl is optionally substituted with one or more, identical or different R$^{12}$,
each R$^{12}$ is selected from the group consisting of C$_{1-6}$alkyl, C$_{1-6}$alkoxy, halogen and 5 membered heterocyclyl.

In another aspect, the invention relates to the compound of the formula (I), (I*), (Ia), (Ib), (Ic), (Id), (Ie) or (If) or a salt thereof, wherein
R$^5$ is selected from the group consisting of

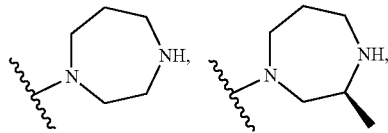

-continued
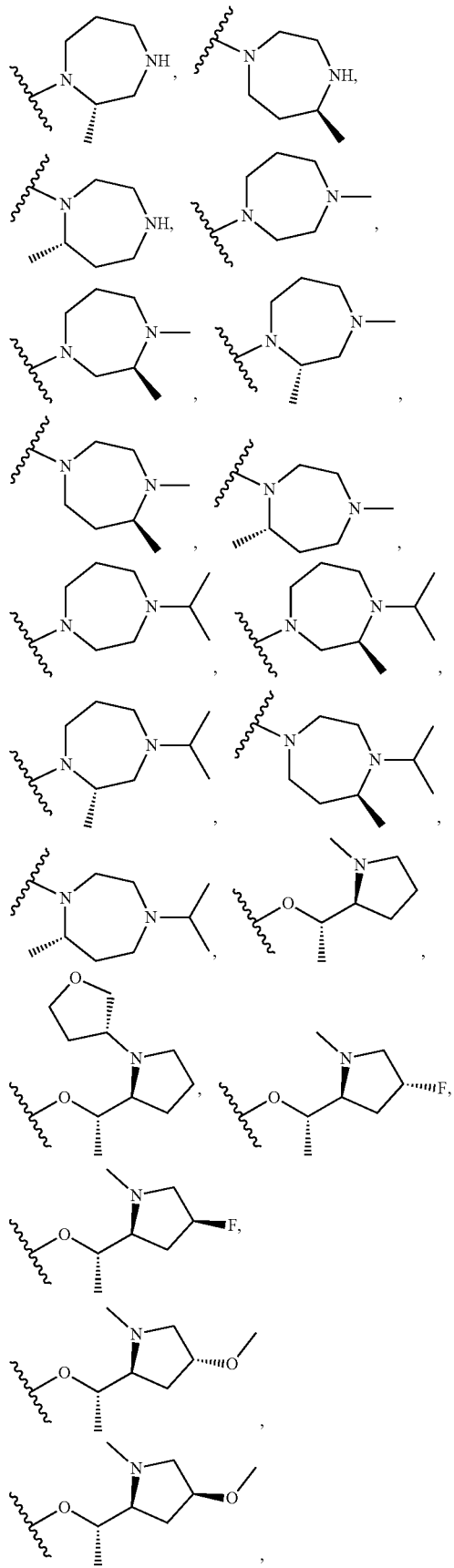
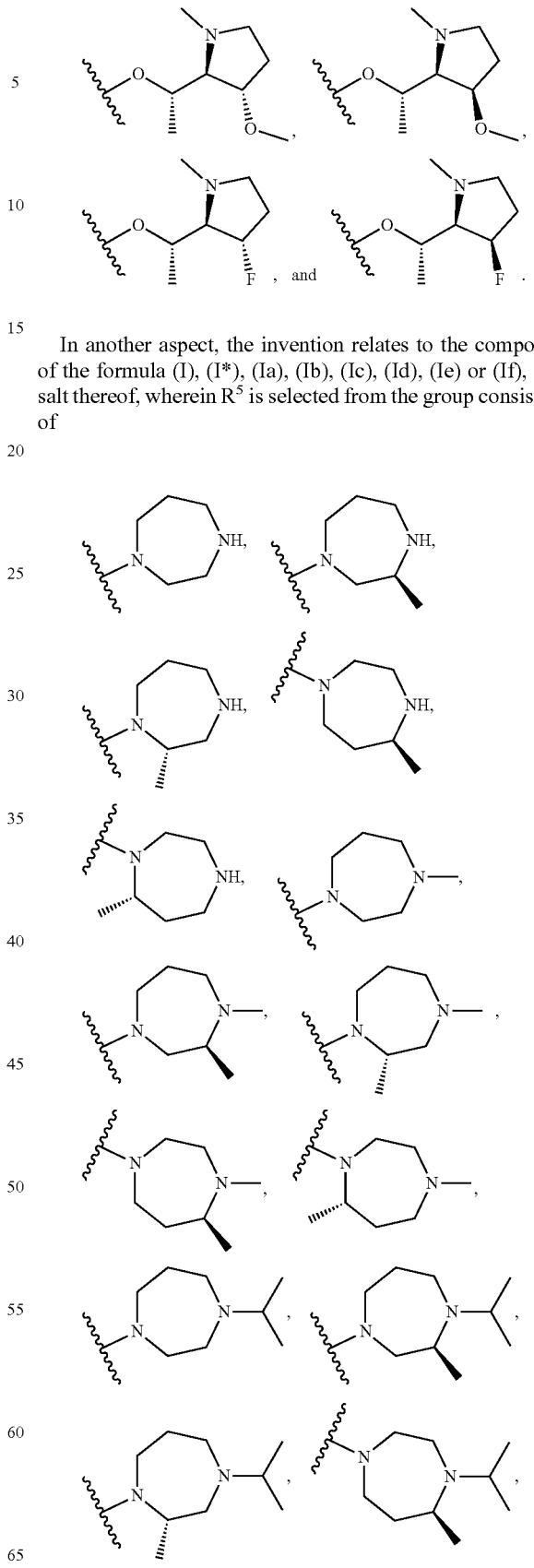
In another aspect, the invention relates to the compound of the formula (I), (I*), (Ia), (Ib), (Ic), (Id), (Ie) or (If), or a salt thereof, wherein $R^5$ is selected from the group consisting of

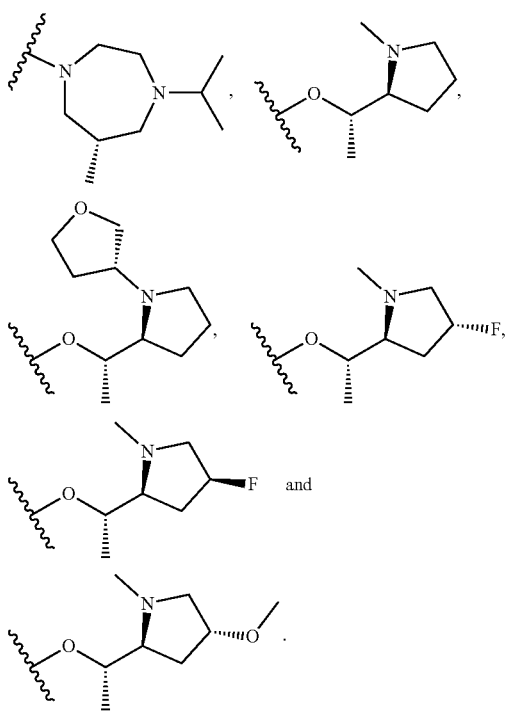

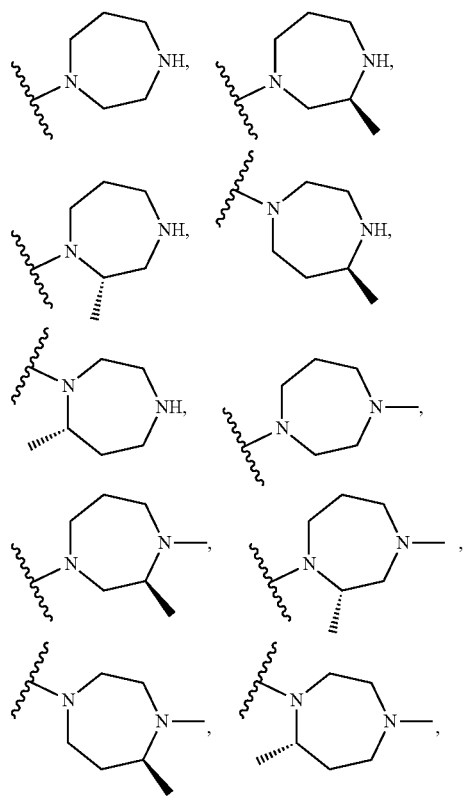

In another aspect, the invention relates to the compound of the formula (I), (I*), (Ia), (Ib), (Ic), (Id), (Ie) or (If), or a salt thereof, wherein R⁵ is selected from the group consisting of

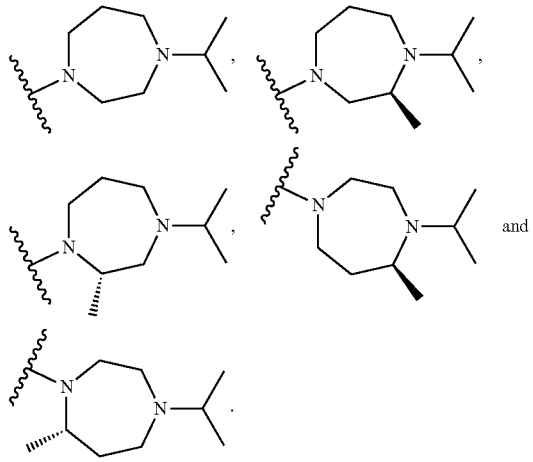

In another aspect, the invention relates to the compound of the formula (I), (I*), (Ia), (Ib), (Ic), (Id), (Ie) or (If), or a salt thereof, wherein R⁵ is selected from the group consisting of

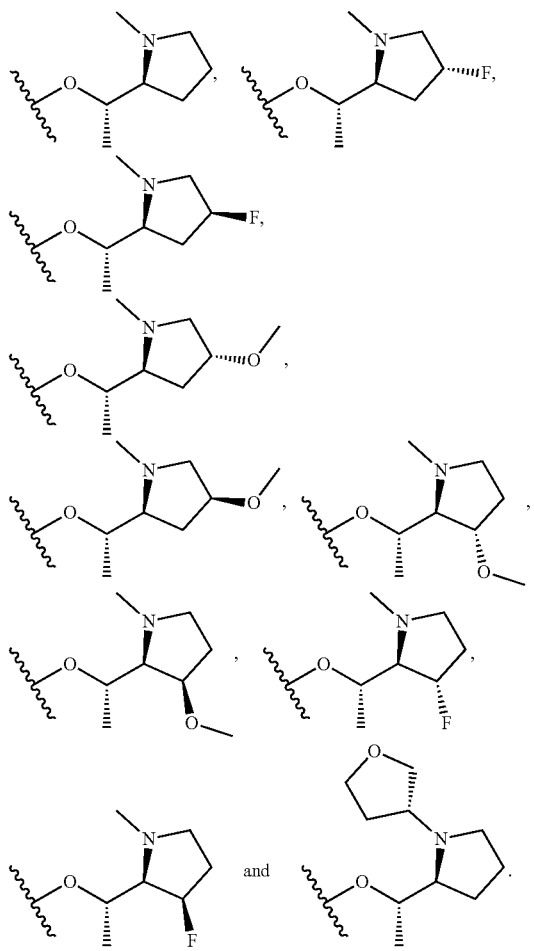

In another aspect, the invention relates to the compound of the formula (I), (I*), (Ia), (Ib), (Ic), (Id), (Ie) or (If), or a salt thereof, wherein R⁵ is selected from the group consisting of

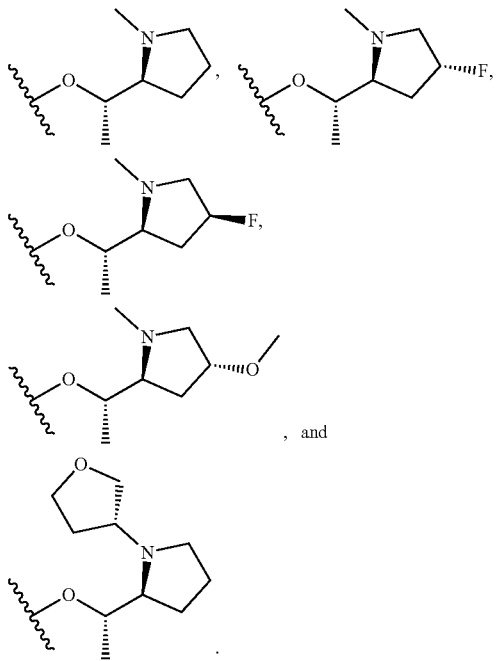

In another aspect, the invention relates to the compound of the formula (I), (I*), (Ia), (Ib), (Ic), (Id), (Ie) or (If), or a salt thereof, wherein R⁵ is selected from the group consisting of

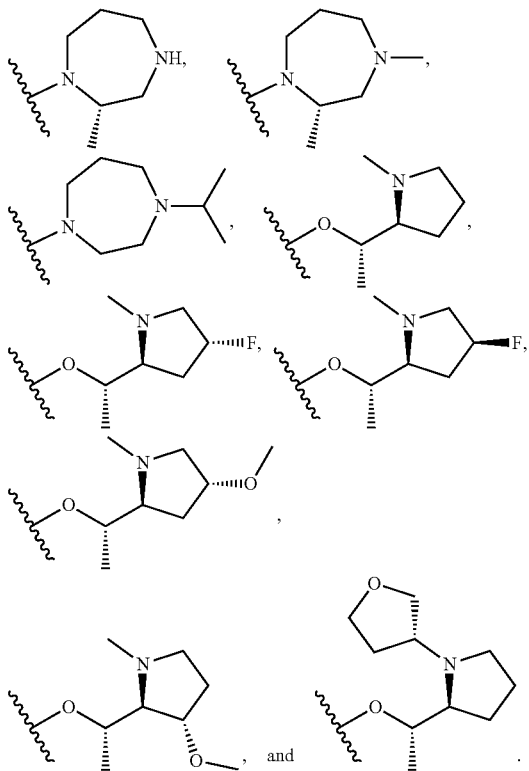

In another aspect, the invention relates to the compound of the formula (I), (I*), (Ia), (Ib), (Ic), (Id), (Ie) or (If), or a salt thereof, wherein
  R³ is selected from the group consisting of halogen, $C_{1-6}$alkyl, $C_{1-6}$haloalkyl, —N₃, $C_{3-10}$cycloalkyl, 3-11 membered heterocyclyl, $C_{6-10}$aryl and 5-10 membered heteroaryl, wherein the $C_{1-6}$alkyl, $C_{1-6}$haloalkyl, $C_{3-10}$cycloalkyl, 3-11 membered heterocyclyl, $C_{6-10}$aryl and 5-10 membered heteroaryl are all optionally and independently substituted with one or more, identical or different R⁷ and/or R⁸;
  each R⁷ is independently selected from the group consisting of halogen, —CN, —OH, $C_{1-6}$alkoxy, —NR⁸R⁸, —C(=O)R⁸, —C(=O)OR⁸, —C(=O)NR⁸R⁸, —NHC(=O)OR⁸ and the bivalent substituent =O;
  each R⁸ is independently selected from the group consisting of hydrogen, $C_{1-6}$alkyl, $C_{3-10}$cycloalkyl, 3-11 membered heterocyclyl, phenyl and 5-10 membered heteroaryl, wherein the $C_{1-6}$alkyl, 3-11 membered heterocyclyl and 5-10 membered heteroaryl are all optionally substituted with one or more, identical or different R⁹ and/or R¹⁰;
  each R⁹ is independently selected from the group consisting of —OR¹⁰;
  each R¹⁰ is independently selected from the group consisting of hydrogen, $C_{1-6}$alkyl, 3-11 membered heterocyclyl and 5-10 membered heteroaryl.

In another aspect, the invention relates to the compound of the formula (I), (I*), (Ia), (Ib), (Ic), (Id), (Ie) or (If), or a salt thereof, wherein
  R³ is selected from the group consisting of halogen, $C_{1-6}$alkyl, $C_{1-6}$haloalkyl, —N₃, $C_{3-10}$cycloalkyl, 3-11 membered heterocyclyl, $C_{6-10}$aryl and 5-10 membered heteroaryl, wherein the $C_{1-6}$alkyl, $C_{1-6}$haloalkyl, $C_{3-10}$cycloalkyl, 3-11 membered heterocyclyl, $C_{6-10}$aryl and 5-10 membered heteroaryl are all optionally and independently substituted with one or more, identical or different R⁷ and/or R⁸;
  each R⁷ is independently selected from the group consisting of —OR⁸, —NR⁸R⁸, halogen, —CN, —C(=O)R⁸, —C(=O)OR⁸, —C(=O)NR⁸R⁸, —NHC(=O)OR⁸ and the bivalent substituent =O;
  each R⁸ is independently selected from the group consisting of hydrogen, $C_{1-6}$alkyl, $C_{3-10}$cycloalkyl, 3-11 membered heterocyclyl, $C_{6-10}$aryl and 5-10 membered heteroaryl, wherein the $C_{1-6}$alkyl, 3-11 membered heterocyclyl, $C_{6-10}$aryl and 5-10 membered heteroaryl are all optionally substituted with one or more, identical or different R⁹ and/or R¹⁰;
  each R⁹ is independently selected from the group consisting of —OR¹⁰;
  each R¹⁰ is independently selected from the group consisting of hydrogen, $C_{1-6}$alkyl, 3-11 membered heterocyclyl and 5-10 membered heteroaryl.

In another aspect, the invention relates to the compound of the formula (I), (I*), (Ia), (Ib), (Ic), (Id), (Ie) or (If), or a salt thereof, wherein R³ is selected from the group consisting of halogen, $C_{1-6}$alkyl, $C_{1-6}$haloalkyl and —N₃.

In another aspect, the invention relates to the compound of the formula (I), (I*), (Ia), (Ib), (Ic), (Id), (Ie) or (If), or a salt thereof, wherein R³ is selected from the group consisting of chlorine, methyl, —CF₃ and —N₃.

In another aspect, the invention relates to the compound of the formula (I), (I*), (Ia), (Ib), (Ic), (Id), (Ie) or (If), or a salt thereof, wherein R³ is selected from the group consisting of 3-11 membered heterocyclyl, C₆₋₁₀aryl and 5-10 membered heteroaryl, wherein the 3-11 membered heterocyclyl, C₆₋₁₀aryl and 5-10 membered heteroaryl are all optionally and independently substituted with one or more, identical or different R⁷ and/or R⁸;

each R⁷ is independently selected from the group consisting of halogen, —CN, —OH, C₁₋₆alkoxy, —NR⁸R⁸, —C(═O)R⁸, —C(═O)OR⁸, —C(═O)NR⁸R⁸, —NHC(═O)OR⁸ and the bivalent substituent ═O;

each R⁸ is independently selected from the group consisting of hydrogen, C₁₋₆alkyl, C₃₋₁₀cycloalkyl, 3-11 membered heterocyclyl, C₆₋₁₀aryl and 5-10 membered heteroaryl, wherein the C₁₋₆alkyl, C₃₋₁₀cycloalkyl, 3-11 membered heterocyclyl, C₆₋₁₀aryl and 5-10 membered heteroaryl are all optionally substituted with one or more, identical or different R⁹ and/or R¹⁰;

each R⁹ is independently selected from the group consisting of —OR¹⁰, —NR¹⁰R¹⁰ and —C(O)NR¹⁰R¹⁰;

each R¹⁰ is independently selected from the group consisting of hydrogen, C₁₋₆alkyl, C₃₋₁₀cycloalkyl, 3-11 membered heterocyclyl and 5-10 membered heteroaryl, wherein the C₁₋₆alkyl is optionally substituted with a substituent selected from the group consisting of C₁₋₆alkoxy, C₃₋₁₀cycloalkyl and 3-11 membered heterocyclyl optionally substituted with C₁₋₆alkyl.

In another aspect, the invention relates to the compound of the formula (I), (I*), (Ia), (Ib), (Ic), (Id), (Ie) or (If), or a salt thereof, wherein R³ is selected from the group consisting of 3-11 membered heterocyclyl, C₆₋₁₀aryl and 5-10 membered heteroaryl, wherein the 3-11 membered heterocyclyl, C₆₋₁₀aryl and 5-10 membered heteroaryl are all optionally and independently substituted with one or more, identical or different R⁷ and/or R⁸;

each R⁷ is independently selected from the group consisting of halogen, —CN, —OH, C₁₋₆alkoxy, —NR⁸R⁸, —C(═O)R⁸, —C(═O)OR⁸, —C(═O)NR⁸R⁸, —NHC(═O)OR⁸ and the bivalent substituent ═O;

each R⁸ is independently selected from the group consisting of hydrogen, C₁₋₆alkyl, C₃₋₁₀cycloalkyl, 3-11 membered heterocyclyl, C₆₋₁₀aryl and 5-10 membered heteroaryl, wherein the C₁₋₆alkyl, 3-11 membered heterocyclyl, C₆₋₁₀aryl and 5-10 membered heteroaryl are all optionally substituted with one or more, identical or different R⁹ and/or R¹⁰;

each R⁹ is independently selected from the group consisting of OR¹⁰;

each R¹⁰ is independently selected from the group consisting of hydrogen, C₁₋₆alkyl, 3-11 membered heterocyclyl and 5-10 membered heteroaryl.

In another aspect, the invention relates to the compound of the formula (I), (I*), (Ia), (Ib), (Ic), (Id), (Ie) or (If), or a salt thereof, wherein R³ is selected from the group consisting of 3-11 membered heterocyclyl and 5-10 membered heteroaryl, wherein the 3-11 membered heterocyclyl and 5-10 membered heteroaryl are all optionally and independently substituted with one or more, identical or different R⁷ and/or R⁸;

each R⁷ is independently selected from the group consisting of halogen, —CN, —OR⁸, —NR⁸R⁸, —C(═O)R⁸, —C(═O)OR⁸, —C(═O)NR⁸R⁸, —NHC(═O)OR⁸ and the bivalent substituent ═O;

each R⁸ is independently selected from the group consisting of hydrogen, C₁₋₆alkyl, C₃₋₁₀cycloalkyl, 3-11 membered heterocyclyl, C₆₋₁₀aryl and 5-10 membered heteroaryl, wherein the C₁₋₆alkyl, C₃₋₁₀cycloalkyl, 3-11 membered heterocyclyl, C₆₋₁₀aryl and 5-10 membered heteroaryl are all optionally substituted with one or more, identical or different R⁹ and/or R¹⁰;

each R⁹ is —OH or C₁₋₆alkoxy;

each R¹⁰ is independently selected from the group consisting of C₁₋₆alkyl, 3-11 membered heterocyclyl and 5-10 membered heteroaryl.

In another aspect, the invention relates to the compound of the formula (I), (I*), (Ia), (Ib), (Ic), (Id), (Ie) or (If), or a salt thereof, wherein R³ is selected from the group consisting of 3-11 membered heterocyclyl and 5-10 membered heteroaryl, wherein the 3-11 membered heterocyclyl and 5-10 membered heteroaryl are all optionally and independently substituted with one or more, identical or different R⁷ and/or R⁸;

each R⁷ is independently selected from the group consisting of halogen, —CN, —OH, C₁₋₆alkoxy, —NR⁸R⁸, —C(═O)R⁸, —C(═O)OR⁸, —C(═O) NR⁸R⁸, —NHC(═O)OR⁸ and the bivalent substituent ═O;

each R⁸ is independently selected from the group consisting of hydrogen, C₁₋₆alkyl, C₃₋₁₀cycloalkyl, 3-11 membered heterocyclyl, C₆₋₁₀aryl and 5-10 membered heteroaryl, wherein the C₁₋₆alkyl, 3-11 membered heterocyclyl, C₆₋₁₀aryl and 5-10 membered heteroaryl are all optionally substituted with one or more, identical or different R⁹ and/or R¹⁰;

each R⁹ is —OH or C₁₋₆alkoxy;

each R¹⁰ is independently selected from the group consisting of C₁₋₆alkyl, 3-11 membered heterocyclyl and 5-10 membered heteroaryl.

In another aspect, the invention relates to the compound of the formula (I), (I*), (Ia), (Ib), (Ic), (Id), (Ie) or (If) or a salt thereof, wherein R³ is selected from the group consisting of

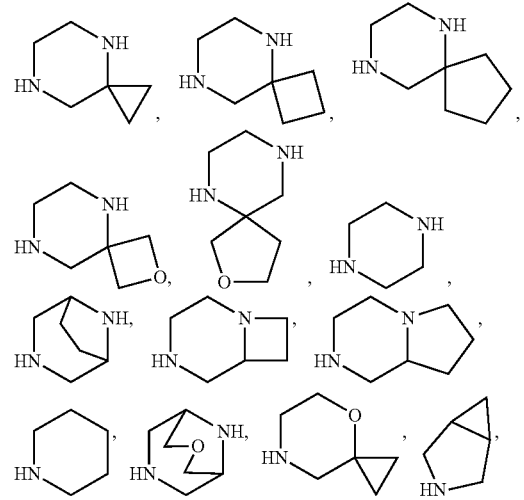

-continued

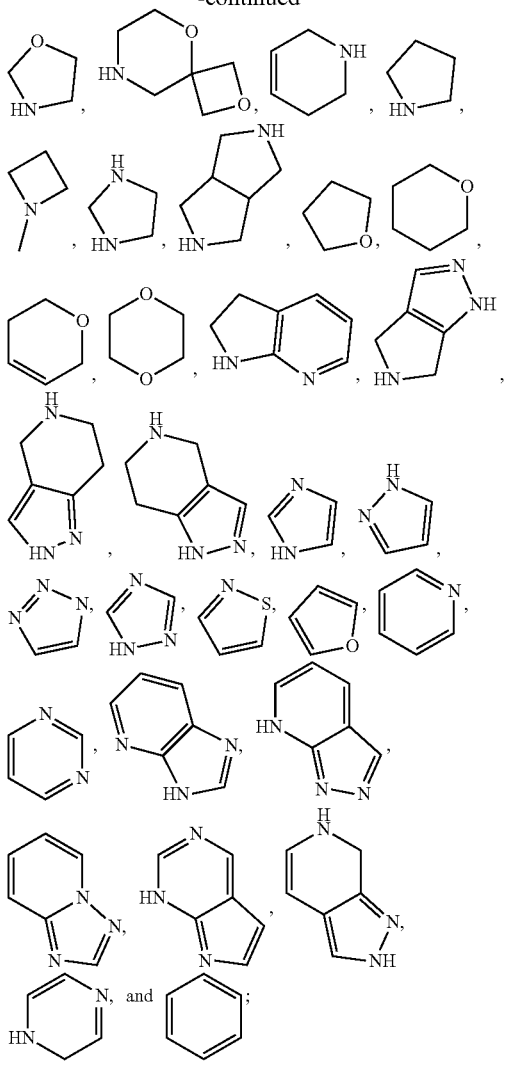

each of which groups is bound to formula (I), (I*), (Ia), (Ib), (Ic), (Id), (Ie) or (If) at any ring position by removal of a hydrogen atom and is optionally and independently substituted with one or more, identical or different $R^7$ and/or $R^8$, wherein each $R^7$ is independently selected from the group consisting of halogen, —CN, —$OR^8$, —$NR^8R^8$, —C(=O)$R^8$, —C(=O)$OR^8$, —C(=O)$NR^8R^8$, —NHC(=O)$OR^8$ and the bivalent substituent =O;

each $R^8$ is independently selected from the group consisting of hydrogen, $C_{1-6}$alkyl, $C_{3-10}$cycloalkyl, 3-11 membered heterocyclyl, $C_{6-10}$aryl and 5-10 membered heteroaryl, wherein the $C_{1-6}$alkyl, $C_{3-10}$cycloalkyl, 3-11 membered heterocyclyl, $C_{6-10}$aryl and 5-10 membered heteroaryl are all optionally substituted with one or more, identical or different $R^9$ and/or $R^{10}$;

each $R^9$ is —OH or $C_{1-6}$alkoxy;

each $R^{10}$ is independently selected from the group consisting of $C_{1-6}$alkyl, 3-11 membered heterocyclyl and 5-10 membered heteroaryl.

In another aspect, the invention relates to the compound of the formula (I), (I*) (Ia), (Ib), (Ic), (Id), (Ie) or (If) or a salt thereof, wherein $R^3$ is selected from the group consisting of

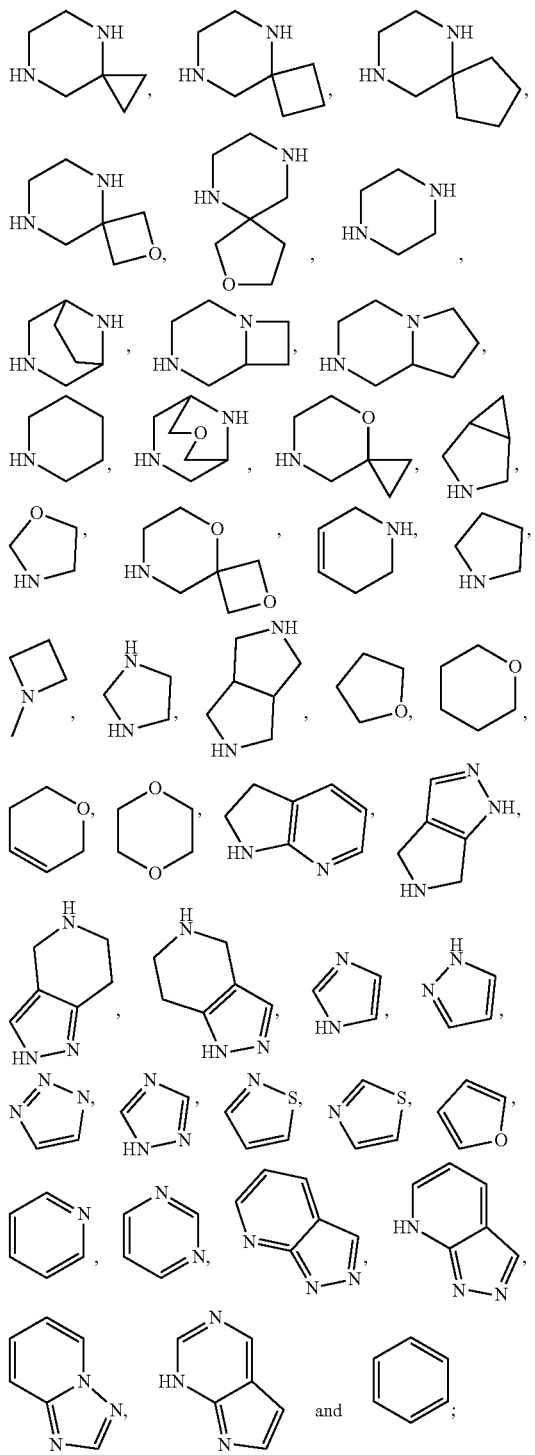

each of which group is optionally and independently substituted with one or more, identical or different $R^7$ and/or $R^8$, wherein each $R^7$ is independently selected from the group consisting of halogen, —CN, —$OR^8$, —$NR^8R^8$, —C(=O)$R^8$, —C(=O)$OR^8$, —C(=O)$NR^8R^8$, —NHC(=O)$OR^8$ and the bivalent substituent =O;

each $R^8$ is independently selected from the group consisting of hydrogen, $C_{1-6}$alkyl, $C_{3-10}$cycloalkyl, 3-11 membered heterocyclyl, $C_{6-10}$aryl and 5-10 membered heteroaryl, wherein the $C_{1-6}$alkyl, 3-11 membered heterocyclyl, $C_{6-10}$aryl and 5-10 membered heteroaryl are all optionally substituted with one or more, identical or different $R^9$ and/or $R^{10}$;

each $R^9$ is —OH or $C_{1-6}$alkoxy;

each $R^{10}$ is independently selected from the group consisting of $C_{1-6}$alkyl, 3-11 membered heterocyclyl and 5-10 membered heteroaryl.

In another aspect, the invention relates to the compound of the formula (I), (I*), (Ia), (Ib), (Ic), (Id), (Ie) or (If), or a salt thereof, wherein $R^3$ is selected from the group consisting of

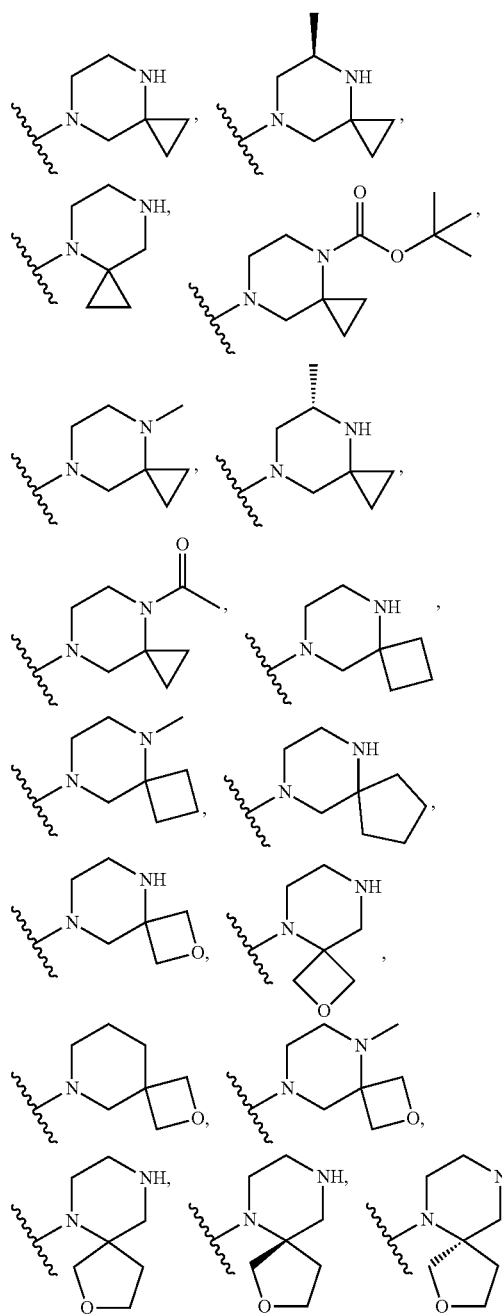

-continued

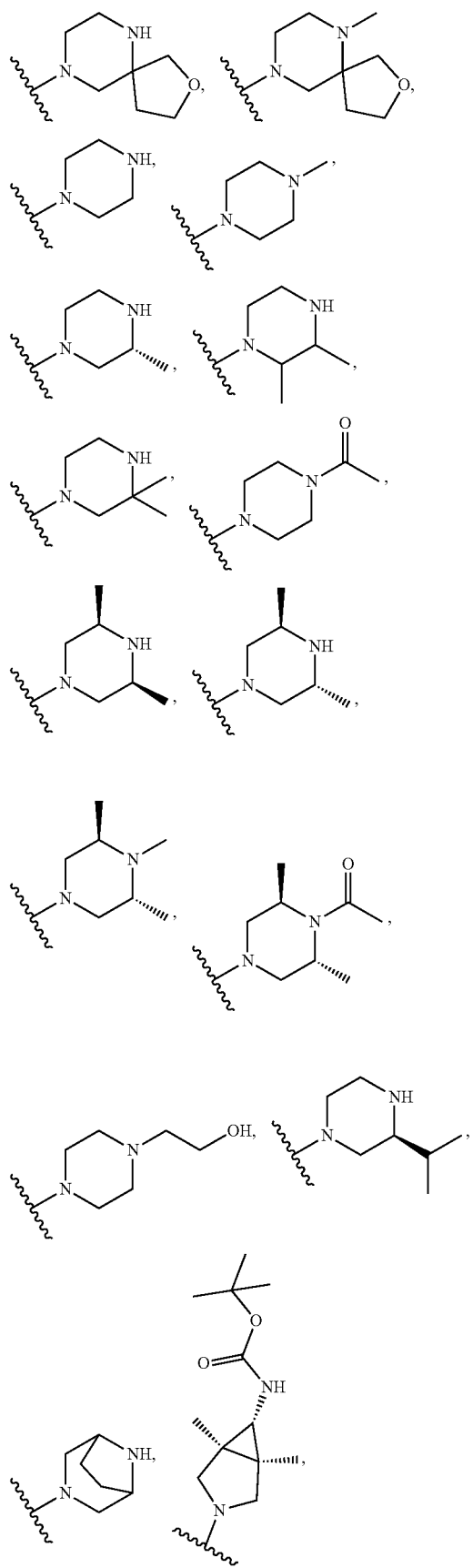

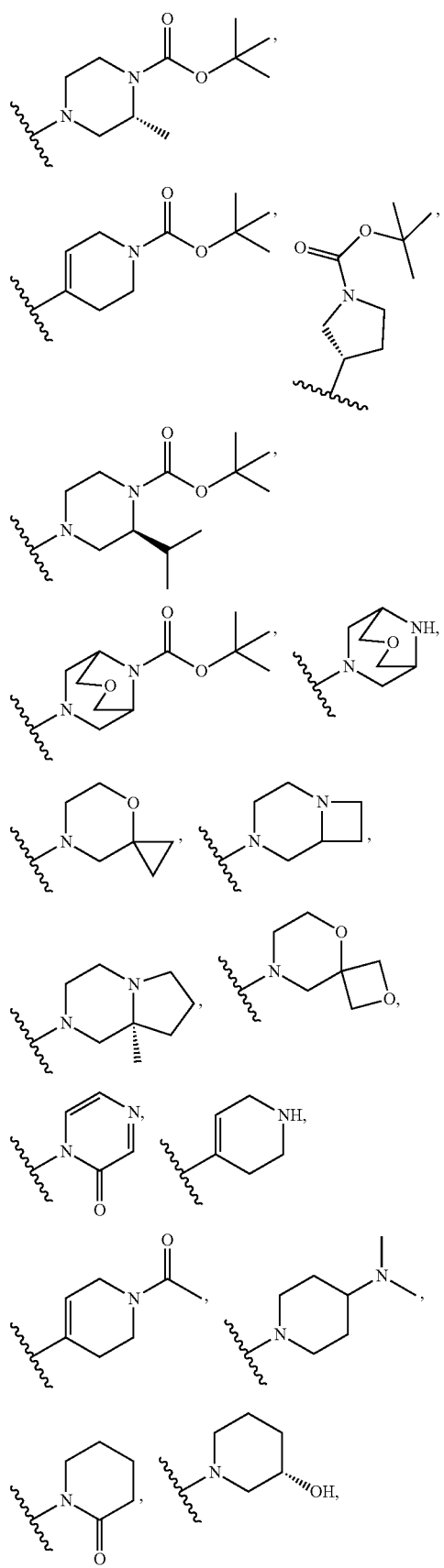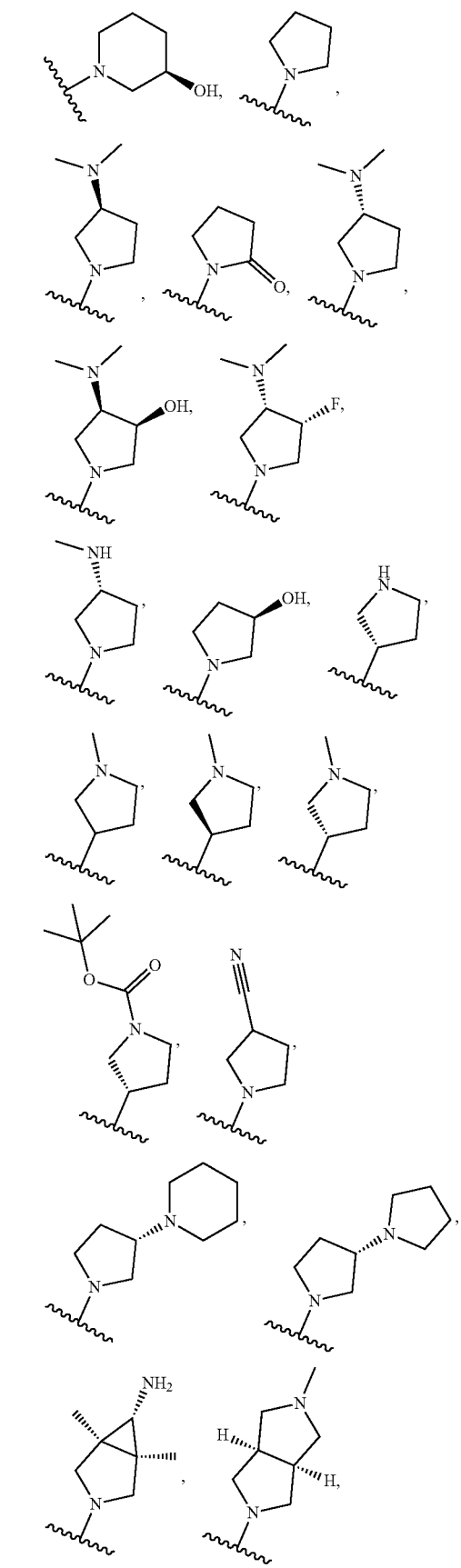

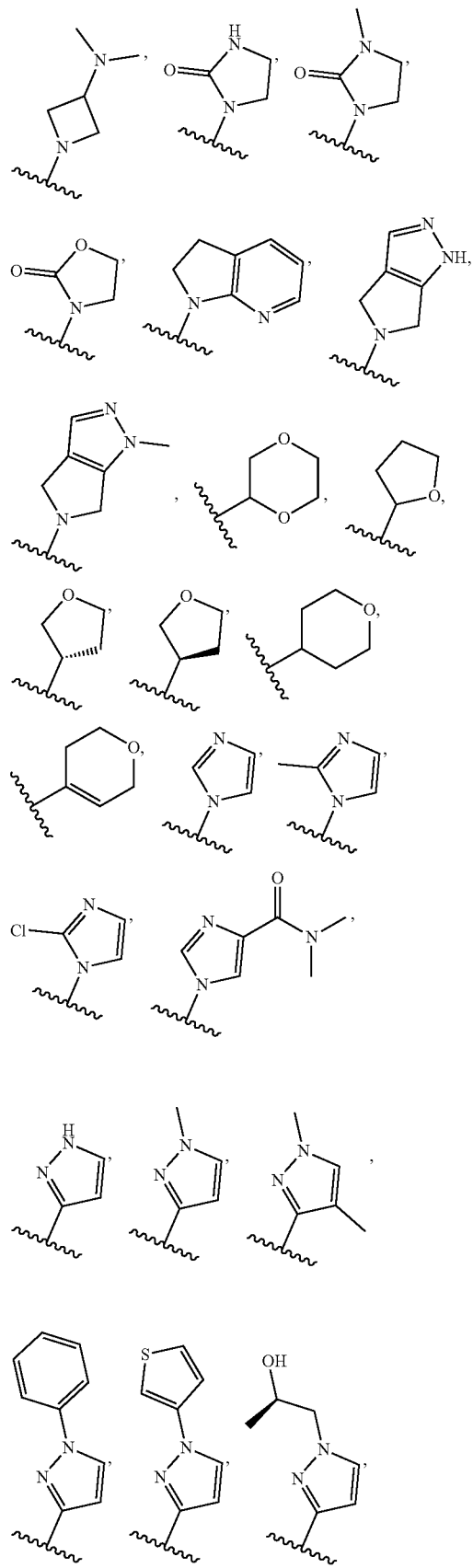
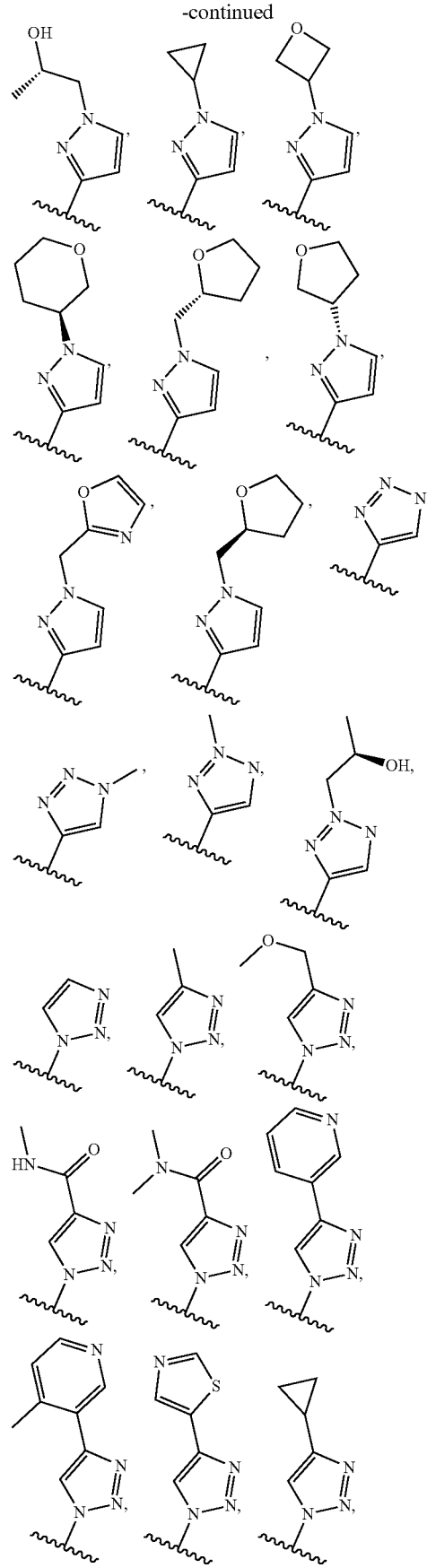

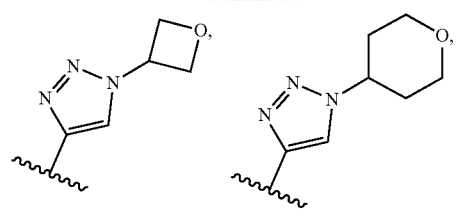
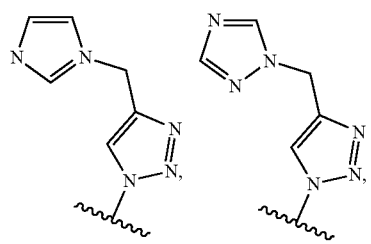
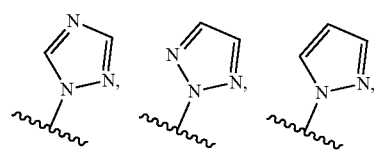
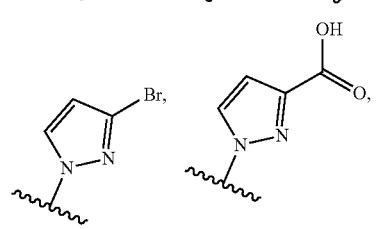
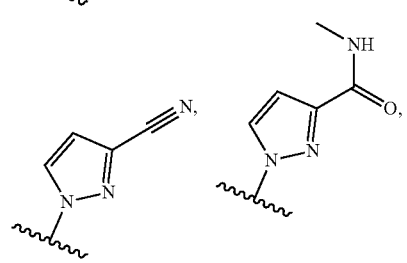
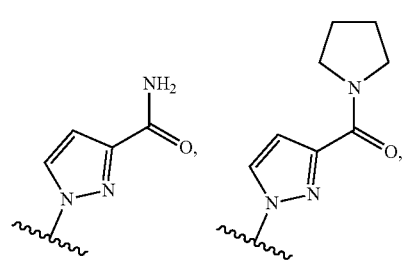
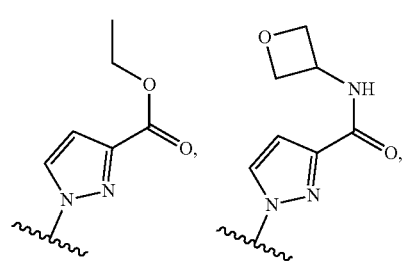
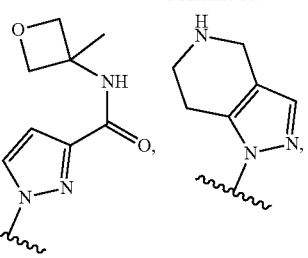
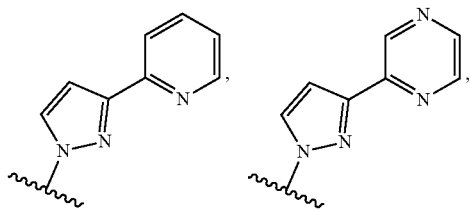
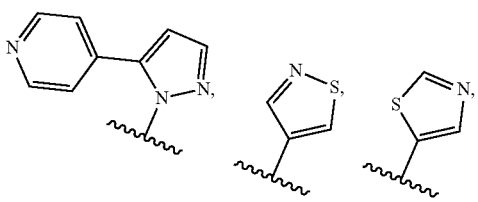
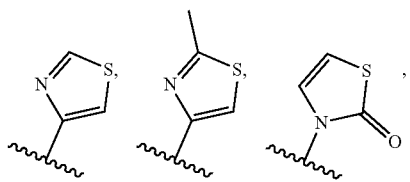
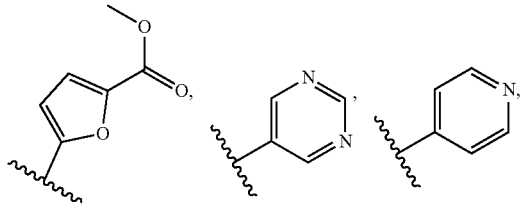
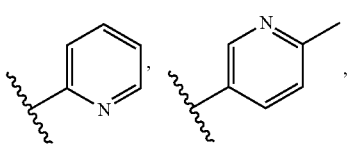
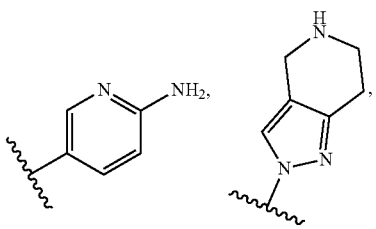
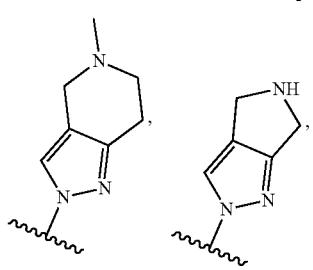

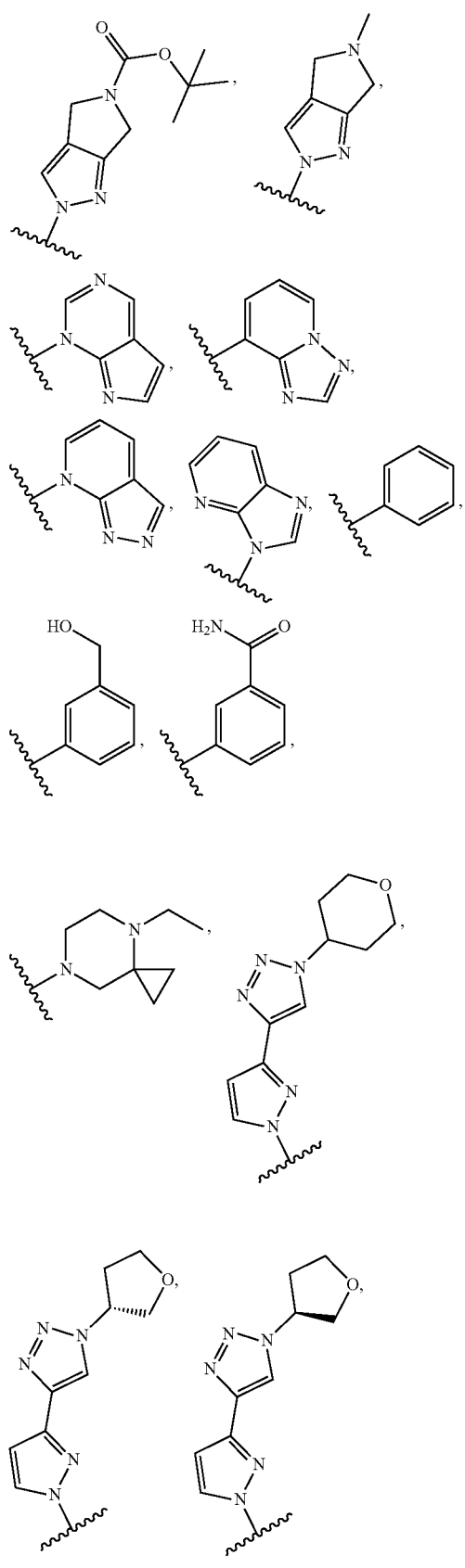
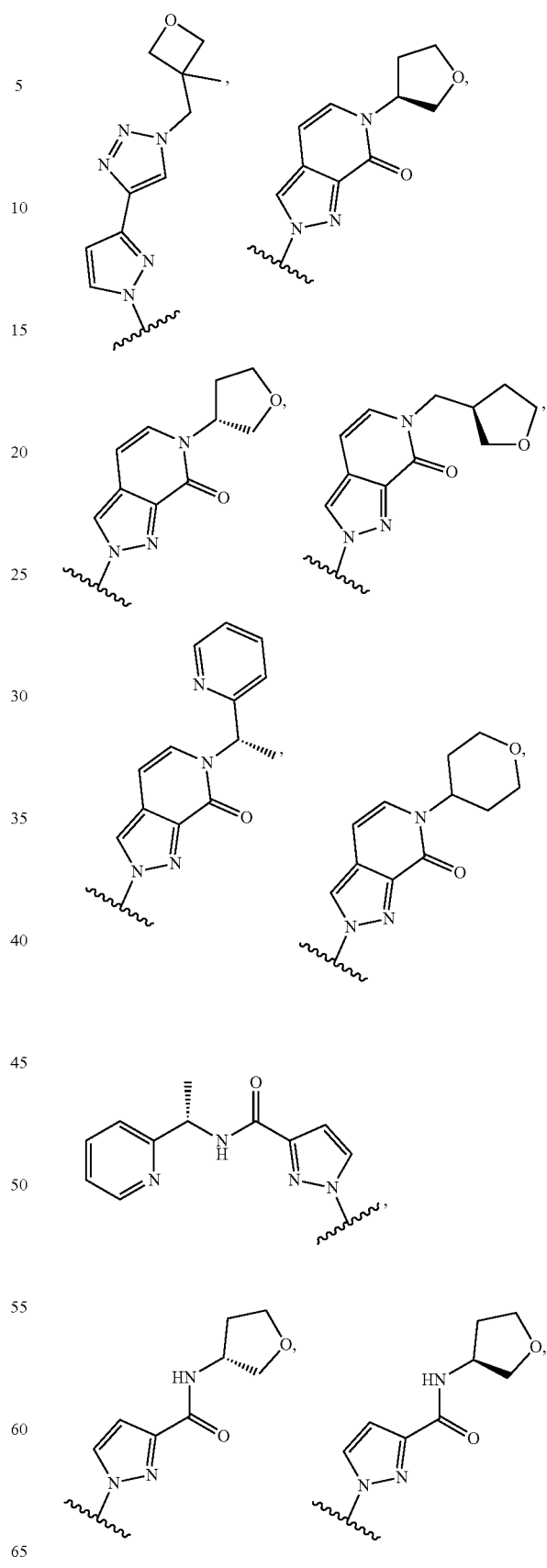

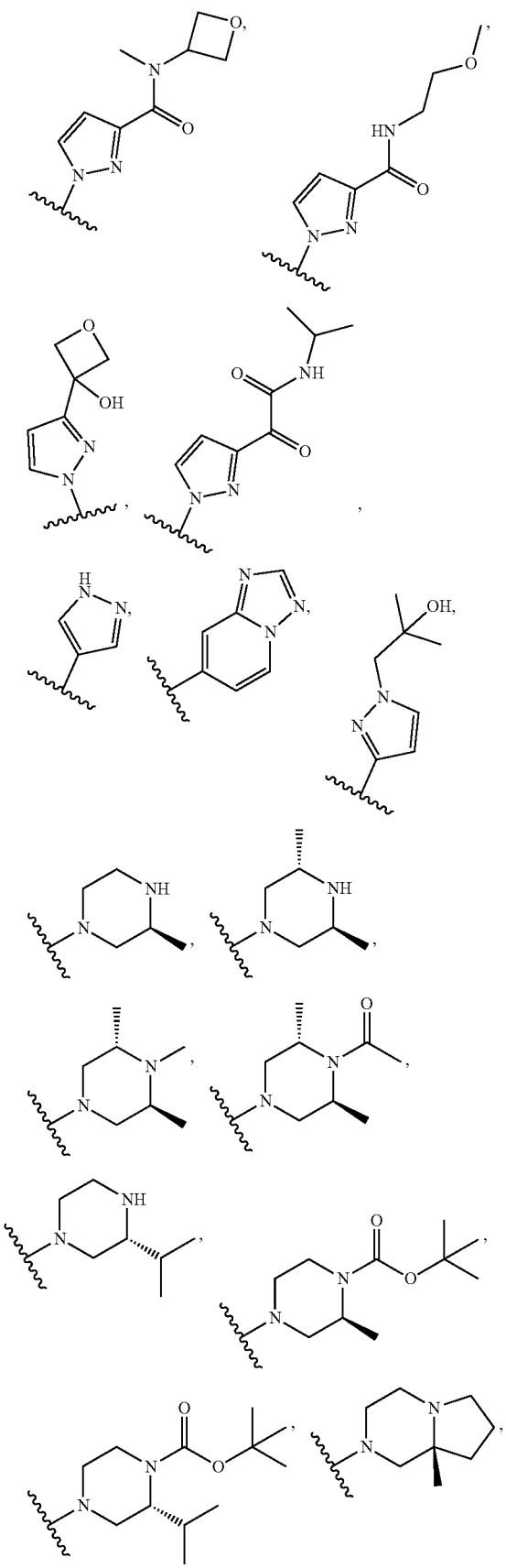
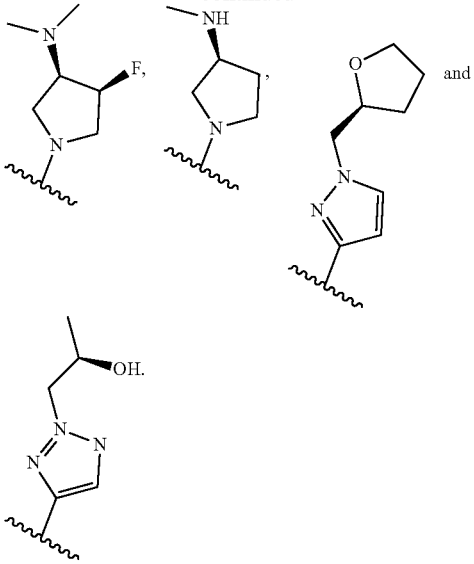

In another aspect, the invention relates to the compound of the formula (I), (I*), (Ia), (Ib), (Ic), (Id), (Ie) or (If), or a salt thereof, wherein
  $R^3$ is 3-11 membered heterocyclyl optionally substituted with one or more, identical or different $R^7$ and/or $R^8$;
  each $R^7$ is independently selected from the group consisting of —OH, $C_{1-6}$alkoxy, —C(=O)R and the bivalent substituent =O,
  each $R^8$ is independently selected from the group consisting of hydrogen, $C_{1-6}$alkyl, $C_{3-10}$cycloalkyl, 3-11 membered heterocyclyl, and 5-10 membered heteroaryl.

In another aspect, the invention relates to the compound of the formula (Ic), (Id), (Ie) or (If), or a salt thereof, wherein
  $R^3$ is 3-11 membered heterocyclyl optionally substituted with one or more, identical or different $R^7$ and/or $R^8$;
  each $R^7$ is independently selected from the group consisting of —OH, $C_{1-6}$alkoxy, —C(=O)$R^8$ and the bivalent substituent =O;
  each $R^8$ is independently selected from the group consisting of hydrogen, $C_{1-6}$alkyl, $C_{3-10}$cycloalkyl, 3-11 membered heterocyclyl and 5-10 membered heteroaryl.

In another aspect, the invention relates to the compound of the formula (Ic), (Id), (Ie) or (If), or a salt thereof, wherein
  $R^3$ is a nitrogen containing 5 membered heterocyclyl optionally and independently substituted with one or more, identical or different $R^7$ and/or $R^8$;
  each $R^7$ is independently selected from the group consisting of —OH, $C_{1-6}$alkoxy, —$NR^8R^8$, halogen, —CN, —C(=O)$R^8$, —C(=O)O$R^8$, —C(=O)$NR^8R^8$, —NHC(=O)O$R^8$ and the bivalent substituent =O;
  each $R^8$ is independently selected from the group consisting of hydrogen, $C_{1-6}$alkyl and 3-11 membered heterocyclyl.

In another aspect, the invention relates to the compound of the formula (Ic), (Id), (Ie) or (If), or a salt thereof, wherein
  $R^3$ is an oxygen containing 3-11 membered heterocyclyl;

In another aspect, the invention relates to the compound of the formula (Ic), (Id), (Ie) or (If), or a salt thereof, wherein
  $R^3$ is selected from the group consisting of 5-10 membered heteroaryl optionally substituted with one or more, identical or different $R^7$ and/or $R^8$;

each R⁷ is independently selected from the group consisting of halogen, —OH, C₁₋₆alkoxy, —CN, —C(=O)R⁸, —C(=O)OR⁸, —C(=O)NR⁸R⁸ and the bivalent substituent =O;
each R⁸ is independently selected from the group consisting of hydrogen, C₁₋₆alkyl, C₃₋₁₀cycloalkyl, 3-11 membered heterocyclyl and 5-10 membered heteroaryl, wherein the C₁₋₆alkyl, C₃₋₁₀cycloalkyl, 3-11 membered heterocyclyl and 5-10 membered heteroaryl are all optionally substituted with one or more, identical or different R¹⁰;
each R¹⁰ is independently selected from the group consisting of C₁₋₆alkyl, 3-11 membered heterocyclyl and 5-10 membered heteroaryl.

In another aspect, the invention relates to the compound of the formula (Ic), (Id), (Ie) or (If), or a salt thereof, wherein R³ is selected from the group consisting of 5-10 membered heteroaryl optionally substituted with one or more, identical or different R⁷ and/or R⁸;
each R⁷ is independently selected from the group consisting of halogen, —OH, C₁₋₆alkoxy, —CN, —C(=O)R⁸, —C(=O)OR⁸, —C(=O)NR⁸R⁸, and the bivalent substituent =O;
each R⁸ is independently selected from the group consisting of hydrogen, C₁₋₆alkyl, C₃₋₁₀cycloalkyl, 3-11 membered heterocyclyl and 5-10 membered heteroaryl, wherein the C₁₋₆alkyl, 3-11 membered heterocyclyl and 5-10 membered heteroaryl are all optionally substituted with one or more, identical or different R¹⁰;
each R¹⁰ is independently selected from the group consisting of hydrogen, C₁₋₆alkyl, 3-11 membered heterocyclyl and 5-10 membered heteroaryl.

In another aspect, the invention relates to the compound of the formula (Ic), (Id), (Ie) or (If), or a salt thereof, wherein R³ is 5-10 membered heteroaryl optionally substituted with —C(=O)NR⁸R⁸;
each R⁸ is independently selected from the group consisting of hydrogen, C₁₋₆alkyl, C₃₋₁₀cycloalkyl and 3-11 membered heterocyclyl, wherein the C₁₋₆alkyl is optionally substituted with a 3-11 membered heterocyclyl.

In another aspect, the invention relates to the compound of the formula (Ic), (Id), (Ie) or (If), or a salt thereof, wherein R³ is

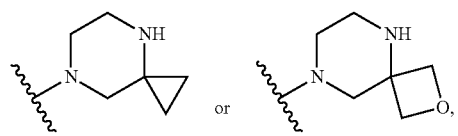 [SMILES: *N1CCNC2(CC2)C1 ; *N1CCNC2(COC2)C1]

both optionally and independently substituted with C₁₋₆alkyl;
W is nitrogen (—N=);
V is nitrogen (—N=);
U is —C(R¹¹)=; wherein R¹¹ is hydrogen or fluorine; and
R⁵ is

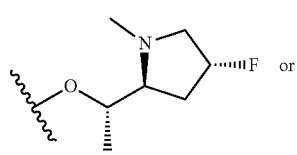

-continued

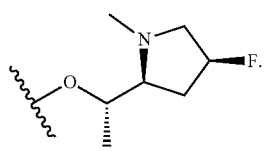

In another aspect, the invention relates to the compound of the formula (Ic), (Id), (Ie) or (If), or a salt thereof, wherein R³ is selected from the group consisting of

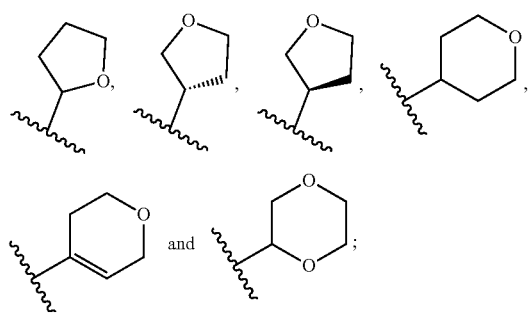

W is nitrogen (—N=);
V is nitrogen (—N=);
U is —CH=;
R⁵ is

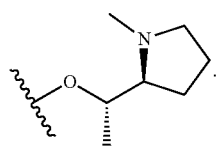 [SMILES: *O[C@@H](C)[C@@H]1CCCN1C]

In another aspect, the invention relates to the compound of the formula (Ic), (Id), (Ie) or (If), or a salt thereof, wherein R³ is selected from the group consisting of

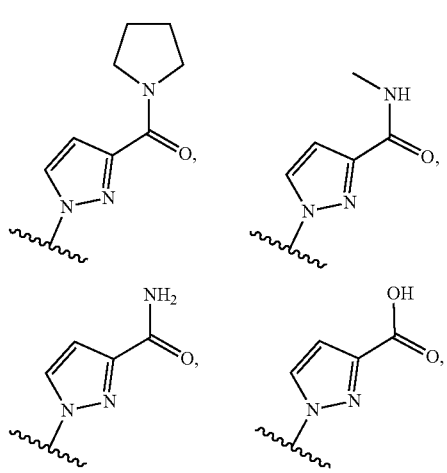

-continued

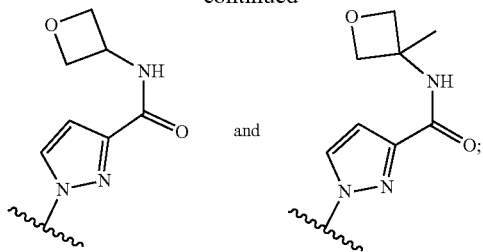

W is —N═;
V is —N═;
U is —CH═;
R⁵ is

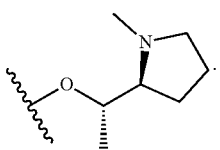 [SMILES: *O[C@@H](C)[C@@H]1CCCN1C]

In another aspect, the invention relates to the compound of the formula (Ic), (Id), (Ie) or (If), or a salt thereof, wherein R³ is a 3-11 membered heterocyclyl selected from the group consisting of

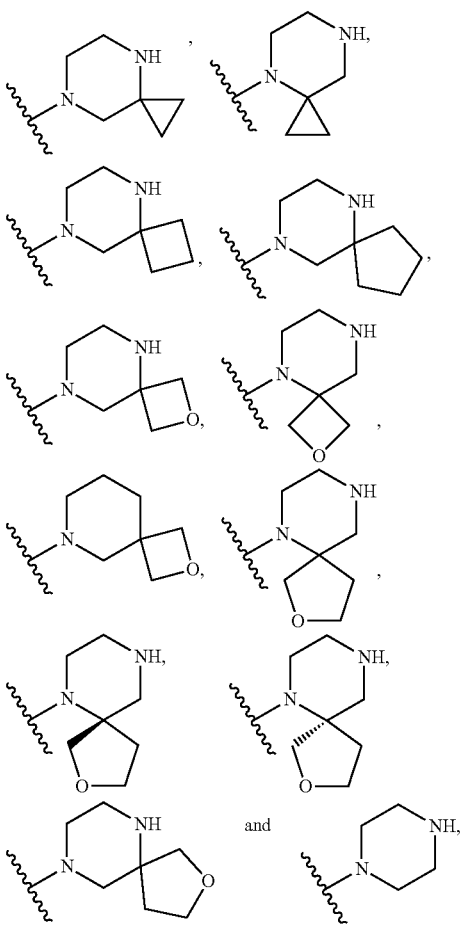

each of which 3-11 membered heterocyclyl is optionally and independently substituted with one or more, identical or different R⁷ and/or R⁸;
each R⁷ is independently selected from the group consisting of —OH, C$_{1-6}$alkoxy, —C(═O)R⁸ and the bivalent substituent ═O;
each R⁸ is independently selected from the group consisting of hydrogen, C$_{1-6}$alkyl, C$_{3-10}$cycloalkyl, 3-11 membered heterocyclyl and 5-10 membered heteroaryl.

In another aspect, the invention relates to the compound of the formula (Ic), (Id), (Ie) or (If), or a salt thereof, wherein R³ is a 3-11 membered heterocyclyl or a 8-9 membered heteroaryl selected from the group consisting of

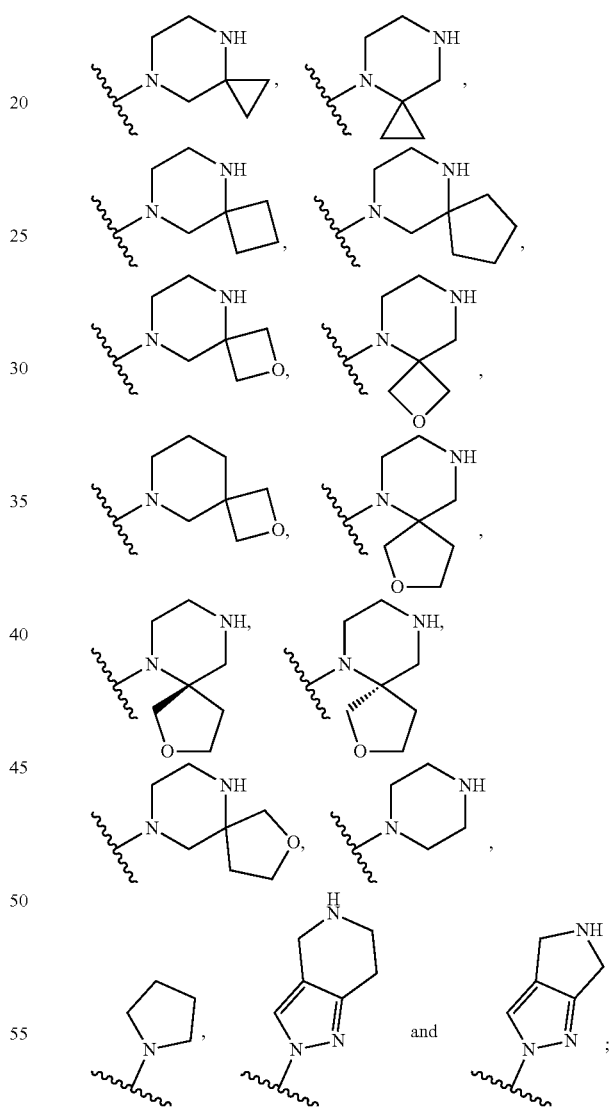

each of which 3-11 membered heterocyclyl or 8-9 membered heteroaryl is optionally and independently substituted with one or more, identical or different R⁷ and/or R⁸;
each R⁷ is independently selected from the group consisting of —OR⁸, —NR⁸R⁸, halogen, —CN, —C(═O)R⁸, —C(═O)OR⁸, —C(═O)NR⁸R⁸, —NHC(═O)OR⁸ and the bivalent substituent ═O;

each R⁸ is independently selected from the group consisting of hydrogen, $C_{1-6}$alkyl, $C_{3-10}$cycloalkyl, 3-11 membered heterocyclyl, $C_{6-10}$aryl and 5-10 membered heteroaryl, wherein the $C_{1-6}$alkyl, 3-11 membered heterocyclyl, $C_{6-10}$aryl and 5-10 membered heteroaryl are all optionally substituted with one or more, identical or different R⁹ and/or R¹⁰;

each R⁹ is —OH or $C_{1-6}$alkoxy;

each R¹⁰ is independently selected from the group consisting of $C_{1-6}$alkyl, 3-11 membered heterocyclyl and 5-10 membered heteroaryl.

In another aspect, the invention relates to the compound of the formula (Ic), (Id), (Ie) or (If), or a salt thereof, wherein R³ is a 5-10 membered heteroaryl selected from the group consisting of

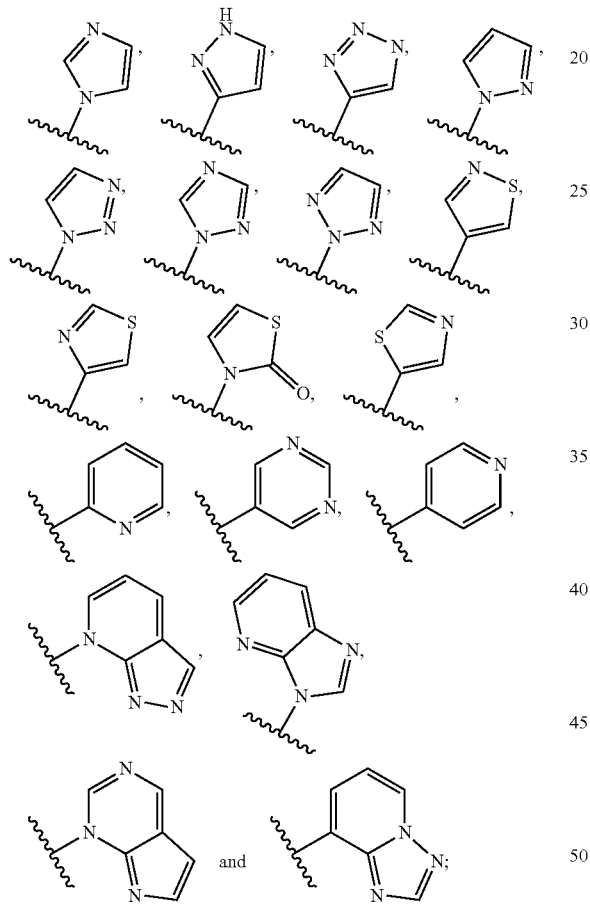

each of which 5-10 membered heteroaryl is optionally and independently substituted with one or more, identical or different R⁷ and/or R⁸;

each R⁷ is independently selected from the group consisting of halogen, —CN, —C(=O)R⁸, —C(=O)OR⁸, —C(=O)NR⁸R⁸, and the bivalent substituent =O;

each R⁸ is independently selected from the group consisting of hydrogen, $C_{1-6}$alkyl, $C_{3-10}$cycloalkyl, 3-11 membered heterocyclyl and 5-10 membered heteroaryl, wherein the $C_{1-6}$alkyl, 3-11 membered heterocyclyl and 5-10 membered heteroaryl are all optionally substituted with one or more, identical or different R⁹;

each R⁹ is independently selected from the group consisting of $C_{1-6}$alkyl and 3-11 membered heterocyclyl and 5-10 membered heteroaryl.

In another aspect, the invention relates to the compound of the formula (Ic), (Id), (Ie) or (If), or a salt thereof, wherein R³ is selected from the group consisting of

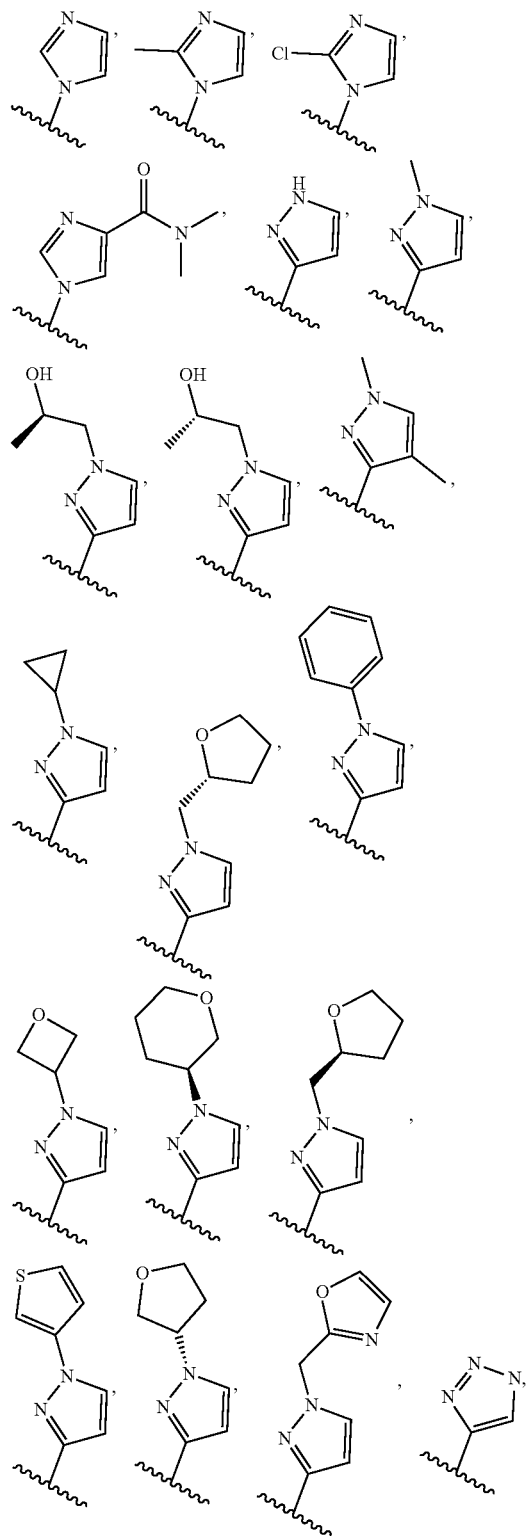

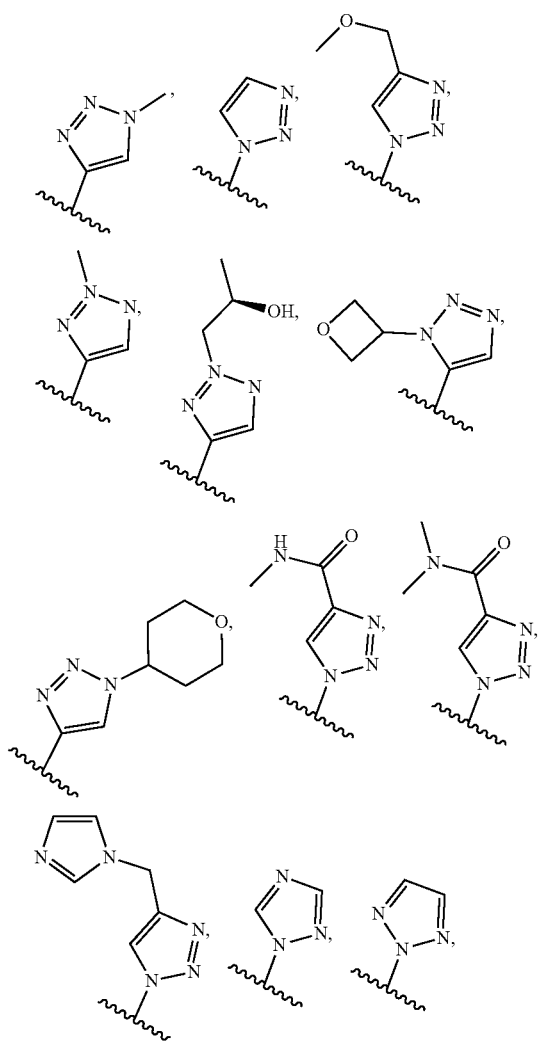
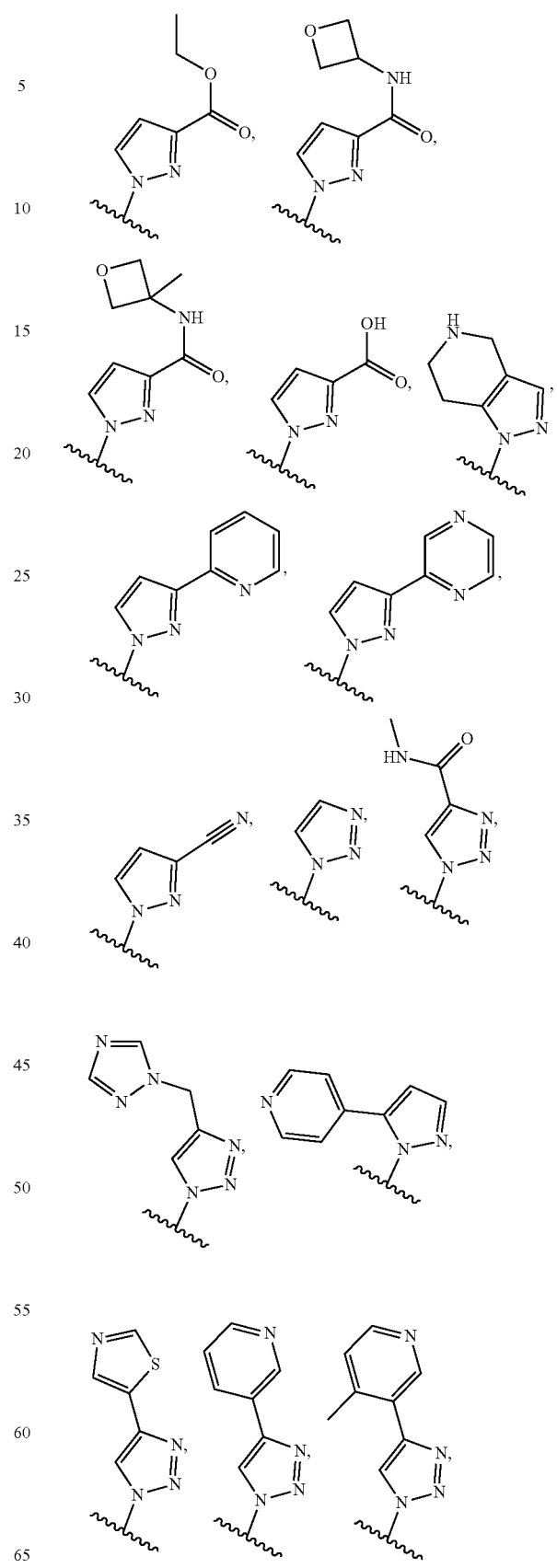

-continued

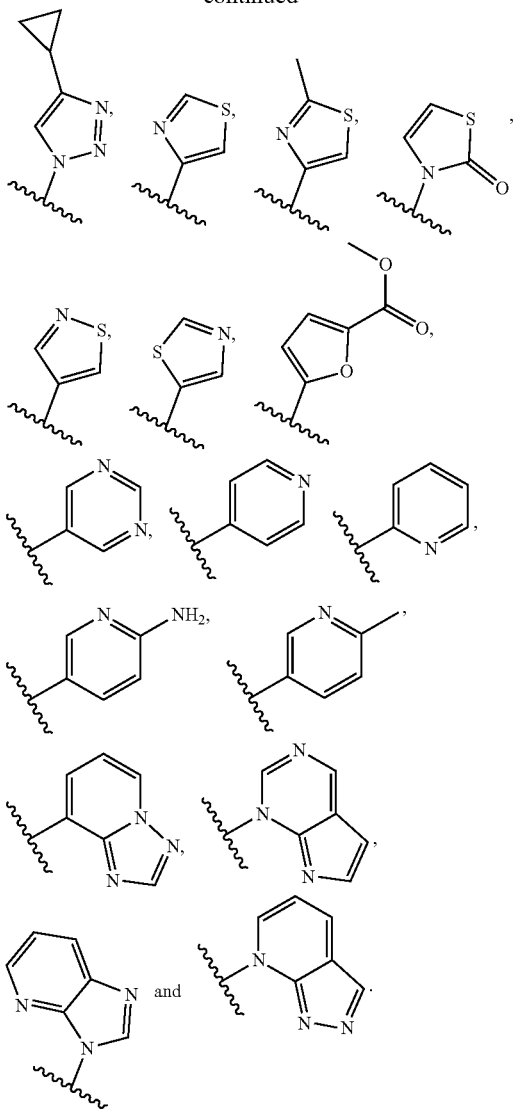

Preferred embodiments of the invention are example compounds I-1 to I-61, II-1 to II-214 and any subset thereof.

In particular, preferred embodiments of the invention are example compounds I-1 to I-45, II-1 to II-178 and any subset thereof.

It is to be understood that any two or more aspects and/or preferred embodiments of formula (I) —or subformulas thereof—may be combined in any way leading to a chemically stable structure to obtain further aspects and/or preferred embodiments of formula (I) —or subformulas thereof.

The present invention further relates to hydrates, solvates, polymorphs, metabolites, derivatives, stereoisomers and prodrugs of a compound of formula (I), (I*), (Ia), (Ib), (Ic), (Id), (Ie) or (If) (including all embodiments thereof).

The present invention further relates to a hydrate of a compound of formula (I), (I*), (Ia), (Ib), (Ic), (Id), (Ie) or (If) (including all embodiments thereof).

The present invention further relates to a solvate of a compound of formula (I), (I*), (Ia), (Ib), (Ic), (Id), (Ie) or (If) (including all embodiments thereof).

Compounds of formula (I), (I*), (Ia), (Ib), (Ic), (Id), (Ie) or (If) (including all embodiments thereof) which e.g. bear ester groups are potential prodrugs the ester being cleaved under physiological conditions and are also part of the invention.

The present invention further relates to a pharmaceutically acceptable salt of a compound of formula (I), (I*), (Ia), (Ib), (Ic), (Id), (Ie) or (If) (including all embodiments thereof).

The present invention further relates to a pharmaceutically acceptable salt of a compound of formula (I), (I*), (Ia), (Ib), (Ic), (Id), (Ie) or (If) (including all embodiments thereof) with inorganic or organic acids or bases.

Pharmaceutical Compositions

A further object of the invention is a pharmaceutical composition comprising a compound of formula (I), (I*), (Ia), (Ib), (Ic), (Id), (Ie) or (If) —or a pharmaceutically acceptable salt thereof—and one or more pharmaceutically acceptable excipient(s).

In one aspect, said pharmaceutical composition optionally comprises one or more other pharmacologically active substance(s). Said one or more other pharmacologically active substance(s) may be the pharmacologically active substances or combination partners as herein defined.

Suitable pharmaceutical compositions for administering the compounds of formula (I), (I*), (Ia), (Ib), (Ic), (Id), (Ie) or (If) according to the invention will be apparent to those with ordinary skill in the art and include for example tablets, pills, capsules, suppositories, lozenges, troches, solutions, suspensions—particularly solutions, suspensions or other mixtures for injection (s.c., i.v., i.m.) and infusion (injectables) —elixirs, syrups, sachets, emulsions, inhalatives or dispersible powders. The content of the compounds of formula (I), (I*), (Ia), (Ib), (Ic), (Id), (Ie) or (If) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the compounds of formula (I), (I*), (Ia), (Ib), (Ic), (Id), (Ie) or (If) with known pharmaceutically acceptable excipients, for example inert diluents, carriers, disintegrants, adjuvants, surfactants, binders and/or lubricants. The tablets may also comprise several layers.

Coated tablets may be prepared accordingly by coating cores produced analogously to the tablets with excipients normally used for tablet coatings, for example collidone or shellac, gum arabic, talc, titanium dioxide or sugar. To achieve delayed release or prevent incompatibilities the core may also consist of a number of layers. Similarly, the tablet coating may consist of a number of layers to achieve delayed release, possibly using the excipients mentioned above for the tablets.

Syrups or elixirs containing one or more compounds of formula (I), (I*), (Ia), (Ib), (Ic), (Id), (Ie) or (If) or combinations with one or more other pharmaceutically active substance(s) may additionally contain excipients like a sweetener such as saccharine, cyclamate, glycerol or sugar and a flavour enhancer, e.g. a flavouring such as vanillin or orange extract. They may also contain excipients like suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of excipients like isotonic agents, preservatives such as p-hydroxybenzoates, or stabilisers such as alkali metal salts of ethylenediamine tetra acetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more compounds of formula (I), (I*), (Ia), (Ib), (Ic), (Id), (Ie) or (If) or combinations with one or more other pharmaceutically active substance(s) may for example be prepared by mixing the compounds/active substance(s) with inert excipients such as lactose or sorbitol and packing them into gelatine capsules.

Suitable suppositories may be made for example by mixing with excipients provided for this purpose such as neutral fats or polyethylene glycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulfate).

The pharmaceutical compositions are administered by the usual methods, preferably by oral or transdermal route, most preferably by oral route. For oral administration the tablets may of course contain, apart from the above-mentioned excipients, additional excipients such as sodium citrate, calcium carbonate and dicalcium phosphate together with various excipients such as starch, preferably potato starch, gelatine and the like. Moreover, lubricants such as magnesium stearate, sodium lauryl sulfate and talc may be used at the same time for the tabletting process. In the case of aqueous suspensions, the active substances may be combined with various flavour enhancers or colourings in addition to the excipients mentioned above.

For parenteral use, solutions of the active substances with suitable liquid excipients may be used.

The dosage range of the compounds of formula (I), (I*), (Ia), (Ib), (Ic), (Id), (Ie) or (If) applicable per day is usually from 1 mg to 2000 mg, preferably from 250 to 1250 mg.

However, it may sometimes be necessary to depart from the amounts specified, depending on the body weight, age, the route of administration, severity of the disease, the individual response to the drug, the nature of its formulation and the time or interval over which the drug is administered (continuous or intermittent treatment with one or multiple doses per day). Thus, in some cases it may be sufficient to use less than the minimum dose given above, whereas in other cases the upper limit may have to be exceeded. When administering large amounts, it may be advisable to divide them up into a number of smaller doses spread over the day.

Thus, in a further aspect the invention relates to a pharmaceutical composition comprising at least one (preferably one) compound of formula (I), (I*), (Ia), (Ib), (Ic), (Id), (Ie) or (If) —or a pharmaceutically acceptable salt thereof—and one or more pharmaceutically acceptable excipient(s).

The compounds of formula (I), (I*), (Ia), (Ib), (Ic), (Id), (Ie) or (If) —or the pharmaceutically acceptable salts thereof—and the pharmaceutical compositions comprising such compound and salts may also be co-administered with other pharmacologically active substances, e.g. with other anti-neoplastic compounds (e.g. chemotherapy), i.e. used in combination (see combination treatment further below).

The elements of such combinations may be administered (whether dependently or independently) by methods customary to the skilled person and as they are used in monotherapy, e.g. by oral, enterical, parenteral (e.g., intramuscular, intraperitoneal, intravenous, transdermal or subcutaneous injection, or implant), nasal, vaginal, rectal, or topical routes of administration and may be formulated, alone or together, in suitable dosage unit formulations containing conventional non-toxic pharmaceutically acceptable excipients appropriate for each route of administration.

The combinations may be administered at therapeutically effective single or divided daily doses. The active components of the combinations may be administered in such doses which are therapeutically effective in monotherapy, or in such doses which are lower than the doses used in monotherapy, but when combined result in a desired (joint) therapeutically effective amount.

However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmacological or therapeutic effect.

Thus, in a further aspect the invention also relates to a pharmaceutical composition comprising a compound of formula (I), (I*), (Ia), (Ib), (Ic), (Id), (Ie) or (If) —or a pharmaceutically acceptable salt thereof—and one or more (preferably one or two, most preferably one) other pharmacologically active substance(s).

In a further aspect the invention also relates to a pharmaceutical preparation comprising a compound of formula (I), (I*), (Ia), (Ib), (Ic), (Id), (Ie) or (If) —or a pharmaceutically acceptable salt thereof—and one or more (preferably one or two, most preferably one) other pharmacologically active substance(s).

Pharmaceutical compositions to be co-administered or used in combination can also be provided in the form of a kit.

Thus, in a further aspect the invention also relates to a kit comprising
- a first pharmaceutical composition or dosage form comprising a compound of formula (I), (I*), (Ia), (Ib), (Ic), (Id), (Ie) or (If) and, optionally, one or more pharmaceutically acceptable excipient(s), and
- a second pharmaceutical composition or dosage form comprising another pharmacologically active substance and, optionally, one or more pharmaceutically acceptable excipient(s).

In one aspect such kit comprises a third pharmaceutical composition or dosage form comprising still another pharmacologically active substance and, optionally, one or more pharmaceutically acceptable excipient(s).

Medical Uses—Methods of Treatment

Indications—Patient Populations

The present invention is directed to compounds inhibiting KRAS, preferably KRAS mutated at residue 12, such as KRAS G12C, KRAS G12D, KRAS G12V, KRAS G12A and KRAS G12R inhibitors, preferably inhibitors of KRAS G12C and/or KRAS G12D, or inhibitors selective for KRAS G12D, as well as compounds inhibiting KRAS wildtype, preferably amplified, KRAS mutated at residue 13, such as KRAS G13D, or KRAS mutated at residue 61, such as KRAS Q61H. In particular, compounds of formula (I), (I*), (Ia), (Ib), (Ic), (Id), (Ie) or (If) (including all embodiments thereof) are potentially useful in the treatment and/or prevention of diseases and/or conditions mediated by KRAS, preferably by KRAS mutated at residue 12, e.g. KRAS G12C, KRAS G12D, KRAS G12V, more preferably G12D, or by an amplification of KRAS wildtype, or by KRAS mutated at residue 13, e.g. KRAS G13D, or by KRAS mutated at residue 61, such as KRAS Q61H.

Thus, in a further aspect the invention relates to a compound of formula (I), (I*), (Ia), (Ib), (Ic), (Id), (Ie) or (If) —or a pharmaceutically acceptable salt thereof—for use as a medicament.

In a further aspect the invention relates to a compound of formula (I), (I*), (Ia), (Ib), (Ic), (Id), (Ie) or (If) —or a pharmaceutically acceptable salt thereof—for use in a method of treatment of the human or animal body.

In a further aspect the invention relates to a compound of formula (I), (I*), (Ia), (Ib), (Ic), (Id), (Ie) or (If) —or a pharmaceutically acceptable salt thereof—for use in the treatment and/or prevention of a disease and/or condition mediated by KRAS, preferably by KRAS mutated at residue 12, e.g. KRAS G12C, KRAS G12D, KRAS G12V, more preferably G12D, or by an amplification of KRAS wildtype, or by KRAS mutated at residue 13, e.g. KRAS G13D.

In a further aspect the invention relates to the use of a compound of formula (I), (I*), (Ia), (Ib), (Ic), (Id), (Ie) or (If) —or a pharmaceutically acceptable salt thereof—in the manufacture of a medicament for the treatment and/or prevention of a disease and/or condition mediated by KRAS, preferably by KRAS mutated at residue 12, e.g. KRAS G12C, KRAS G12D, KRAS G12V, more preferably G12D, or by an amplification of KRAS wildtype, or by KRAS mutated at residue 13, e.g. KRAS G13D.

In a further aspect the invention relates to a method for the treatment and/or prevention of a disease and/or condition mediated by KRAS, preferably by KRAS mutated at residue 12, e.g. KRAS G12C, KRAS G12D, KRAS G12V, more preferably G12D, or by an amplification of KRAS wildtype, or by KRAS mutated at residue 13, e.g. KRAS G13D comprising administering a therapeutically effective amount of a compound of formula (I), (I*), (Ia), (Ib), (Ic), (Id), (Ie) or (If) —or a pharmaceutically acceptable salt thereof—to a human being.

In a further aspect the invention relates to a compound of formula (I), (I*), (Ia), (Ib), (Ic), (Id), (Ie) or (If) —or a pharmaceutically acceptable salt thereof—for use in the treatment and/or prevention of cancer.

In a further aspect the invention relates to a compound of formula (I), (I*), (Ia), (Ib), (Ic), (Id), (Ie) or (If) —or a pharmaceutically acceptable salt thereof—for use in a method of treatment and/or prevention of cancer in the human or animal body.

In a further aspect the invention relates to the use of a compound of formula (I), (I*), (Ia), (Ib), (Ic), (Id), (Ie) or (If) —or a pharmaceutically acceptable salt thereof—in the manufacture of a medicament for the treatment and/or prevention of cancer.

In a further aspect the invention relates to a method for the treatment and/or prevention of cancer comprising administering a therapeutically effective amount of a compound of formula (I), (I*), (Ia), (Ib), (Ic), (Id), (Ie) or (If) —or a pharmaceutically acceptable salt thereof—to a human being.

Preferably, the cancer as defined herein (above or below) comprises a KRAS mutation. In particular, KRAS mutations include e.g. mutations of the KRAS gene and of the KRAS protein, such as overexpressed KRAS, amplified KRAS or KRAS, KRAS mutated at residue 12, KRAS mutated at residue 13, KRAS mutated at residue 61, KRAS mutated at residue 146, in particular KRAS G12A, KRAS G12C, KRAS G12D, KRAS G12V, KRAS G12S, KRAS G13C, KRAS G13D, KRAS G13V, KRAS Q61H, KRAS Q61E, KRAS Q61P, KRAS A146P, KRAS A146T, KRAS A146V. KRAS may present one or more of these mutations/alterations.

Preferably, the cancer as defined herein (above or below) comprises a BRAF mutation in addition or in alternative to the KRAS mutation. Said BRAF mutation is in particular a class III BRAF mutation, e.g. as defined in Z. Yao, Nature, 2017, 548, 234-238.

Preferably, the cancer as defined herein (above or below) comprises a mutation in a receptor tyrosine kinase (RTK), including EGFR, MET and ERBB2 mutations, in addition or in alternative to the KRAS mutation.

In a further aspect the invention relates to a compound of formula (I), (I*), (Ia), (Ib), (Ic), (Id), (Ie) or (If) —or a pharmaceutically acceptable salt thereof—for use in the treatment and/or prevention of cancer, wherein the cancer comprises a KRAS mutation, said KRAS mutation being preferably selected from the group consisting of: KRAS G12C, KRAS G12D, KRAS G12V, KRAS G13D; or an amplification of KRAS wildtype, amplification of the KRAS gene or overexpression of KRAS.

In a further aspect the invention relates to the use of a compound of formula (I), (I*), (Ia), (Ib), (Ic), (Id), (Ie) or (If) —or a pharmaceutically acceptable salt thereof—in the manufacture of a medicament for the treatment and/or prevention of cancer, wherein the cancer comprises a KRAS mutation, said KRAS mutation being preferably selected from the group consisting of: KRAS G12C, KRAS G12D, KRAS G12V, KRAS G13D; or an amplification of KRAS wildtype, amplification of the KRAS gene or overexpression of KRAS.

In a further aspect the invention relates to a method for the treatment and/or prevention of cancer comprising administering a therapeutically effective amount of a compound of formula (I), (I*), (Ia), (Ib), (Ic), (Id), (Ie) or (If) —or a pharmaceutically acceptable salt thereof—to a human being, wherein the cancer comprises a KRAS mutation, said KRAS mutation being preferably selected from the group consisting of: KRAS G12C, KRAS G12D, KRAS G12V, KRAS G13D; or an amplification of KRAS wildtype, amplification of the KRAS gene or overexpression of KRAS.

In a further aspect the invention relates to a compound of formula (I), (I*), (Ia), (Ib), (Ic), (Id), (Ie) or (If) —or a pharmaceutically acceptable salt thereof—for use in the treatment and/or prevention of cancer, wherein the cancer comprises a KRAS G12D mutation.

In a further aspect the invention relates to a compound of formula (I), (I*), (Ia), (Ib), (Ic), (Id), (Ie) or (If) —or a pharmaceutically acceptable salt thereof—for use in the treatment and/or prevention of cancer, wherein the cancer comprises a KRAS G12V mutation.

In a further aspect the invention relates to a compound of formula (I), (I*), (Ia), (Ib), (Ic), (Id), (Ie) or (If) —or a pharmaceutically acceptable salt thereof—for use in the treatment and/or prevention of cancer, wherein the cancer comprises a KRAS G13D mutation.

In a further aspect the invention relates to a compound of formula (I), (I*), (Ia), (Ib), (Ic), (Id), (Ie) or (If) —or a pharmaceutically acceptable salt thereof—for use in the treatment and/or prevention of cancer, wherein the cancer comprises wildtype amplified KRAS.

Another aspect is based on identifying a link between the KRAS status of a patient and potential susceptibility to treatment with a compound of formula (I), (I*), (Ia), (Ib), (Ic), (Id), (Ie) or (If). A KRAS inhibitor, such as a compound of formula (I), (I*), (Ia), (Ib), (Ic), (Id), (Ie) or (If), may then advantageously be used to treat patients with a disease dependent on KRAS who may be resistant to other therapies. This therefore provides opportunities, methods and tools for selecting patients for treatment with a compound of formula (I), (I*), (Ia), (Ib), (Ic), (Id), (Ie) or (If), particularly cancer patients. The selection is based on whether the tumor cells to be treated possess wild-type, preferably amplified, or KRAS mutated at residue 12, preferably G12C, G12D or G12V gene, or KRAS mutated at residue 13, preferably G13D gene. The KRAS gene status could therefore be used as a biomarker to indicate that selecting treatment with a compound of formula (I), (I*), (Ia), (Ib), (Ic), (Id), (Ie) or (If) may be advantageous.

According to one aspect, there is provided a method for selecting a patient for treatment with a compound of formula (I), (I*), (Ia), (Ib), (Ic), (Id), (Ie) or (If), the method comprising
- providing a tumor cell-containing sample from a patient;
- determining whether the KRAS gene in the patient's tumor cell-containing sample encodes for wild-type (glycine at position 12) or mutant (cysteine, aspartic acid, valine, alanine or arginine at position 12, aspartic acid at position 13, amplification and/or overexpression) KRAS protein; and
- selecting a patient for treatment with a compound of formula (I), (I*), (Ia), (Ib), (Ic), (Id), (Ie) or (If) based thereon.

The method may include or exclude the actual patient sample isolation step.

According to another aspect, there is provided a compound of formula (I), (I*), (Ia), (Ib), (Ic), (Id), (Ie) or (If) —or a pharmaceutically acceptable salt thereof—for use in treating a cancer with tumor cells harbouring a KRAS mutation or an amplification of KRAS wildtype.

According to another aspect, there is provided a compound of formula (I), (I*), (Ia), (Ib), (Ic), (Id), (Ie) or (If) —or a pharmaceutically acceptable salt thereof—for use in treating a cancer with tumor cells harbouring a G12C mutant, G12D mutant, G12V mutant, G12A mutant, G13D mutant or G12R mutant KRAS gene or an amplification of KRAS wildtype.

According to another aspect, there is provided a compound of formula (I), (I*), (Ia), (Ib), (Ic), (Id), (Ie) or (If) —or a pharmaceutically acceptable salt thereof—for use in treating a cancer with tumor cells harbouring a G12C mutant, G12D mutant, G12V mutant or G13D mutant KRAS gene or an amplification of KRAS wildtype.

According to another aspect, there is provided a compound of formula (I), (I*), (Ia), (Ib), (Ic), (Id), (Ie) or (If) —or a pharmaceutically acceptable salt thereof—for use in treating a cancer with tumor cells harbouring a G12D mutant KRAS gene.

According to another aspect, there is provided a compound of formula (I), (I*), (Ia), (Ib), (Ic), (Id), (Ie) or (If) —or a pharmaceutically acceptable salt thereof—for use in treating a cancer with tumor cells harbouring a G12V mutant KRAS gene.

According to another aspect, there is provided a compound of formula (I), (I*), (Ia), (Ib), (Ic), (Id), (Ie) or (If) —or a pharmaceutically acceptable salt thereof—for use in treating a cancer with tumor cells harbouring a G13D mutant KRAS gene.

According to another aspect, there is provided a compound of formula (I), (I*), (Ia), (Ib), (Ic), (Id), (Ie) or (If) —or a pharmaceutically acceptable salt thereof—for use in treating a cancer with tumor cells harbouring wildtype amplified KRAS or overexpressed KRAS.

According to another aspect, there is provided a method of treating a cancer with tumor cells harbouring a G12C mutant, G12D mutant, G12V mutant, G12A mutant, G13D mutant or G12R mutant KRAS gene or an amplification of KRAS wildtype gene comprising administering an effective amount of a compound of formula (I), (I*), (Ia), (Ib), (Ic), (Id), (Ie) or (If) —or a pharmaceutically acceptable salt thereof—to a human being.

According to another aspect, there is provided a method of treating a cancer with tumor cells harbouring a G12C mutant, G12D mutant, G12V mutant, G12A mutant or G12R mutant KRAS gene or an amplification of KRAS wildtype gene comprising administering an effective amount of a compound of formula (I), (I*), (Ia), (Ib), (Ic), (Id), (Ie) or (If) —or a pharmaceutically acceptable salt thereof.

Determining whether a tumor or cancer comprises a G12C KRAS mutation can be undertaken by assessing the nucleotide sequence encoding the KRAS protein, by assessing the amino acid sequence of the KRAS, protein, or by assessing the characteristics of a putative KRAS mutant protein. The sequence of wild-type human KRAS is known in the art. Methods for detecting a mutation in a KRAS nucleotide sequence are known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, samples are evaluated for G12C KRAS mutations by real-time PCR. In real-time PCR, fluorescent probes specific for the KRAS G12C mutation are used. When a mutation is present, the probe binds and fluorescence is detected. In some embodiments, the KRAS G12C mutation is identified using a direct sequencing method of specific regions (e.g. exon 2 and/or exon 3) in the KRAS gene. This technique will identify all possible mutations in the region sequenced. Methods for detecting a mutation in a KRAS protein are known by those of skill in the art. These methods include, but are not limited to, detection of a KRAS mutant using a binding agent (e.g. an antibody) specific for the mutant protein, protein electrophoresis, Western blotting and direct peptide sequencing.

Methods for determining whether a tumor or cancer comprises a G12C KRAS mutation can use a variety of samples. In some embodiments, the sample is taken from a subject having a tumor or cancer. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is processed to a cell lysate. In some embodiments, the sample is processed to DNA or RNA. In some embodiments the sample is a liquid biopsy and the test is done on a sample of blood to look for cancer cells from a tumor that are circulating in the blood or for pieces of DNA from tumor cells that are in the blood.

Analogously it can be determined whether a tumor or cancer comprises a KRAS G12D, KRAS G12V, KRAS G12A, KRAS G13D and KRAS G12R mutation or is a KRAS wildtype, preferably amplified.

Preferably, the disease/condition/cancer/tumors/cancer cells to be treated/prevented with a compound of formula (I), (I*), (Ia), (Ib), (Ic), (Id), (Ie) or (If) —or a pharmaceutically acceptable salt thereof—according to the methods and uses as herein (above and below) defined and disclosed is selected from the group consisting of pancreatic cancer, lung cancer, colorectal cancer, cholangiocarcinoma, appendiceal cancer, multiple myeloma, melanoma, uterine cancer, endometrial cancer, thyroid cancer, acute myeloid leukaemia, bladder cancer, urothelial cancer, gastric cancer, cervical cancer, head and neck squamous cell carcinoma, diffuse large B cell lymphoma, oesophageal cancer, gastroesophageal cancer, chronic lymphocytic leukaemia, hepatocellular cancer, breast cancer, ovarian cancer, prostate cancer, glioblastoma, renal cancer and sarcomas.

Preferably, the disease/condition/cancer/tumors/cancer cells to be treated/prevented with a compound of formula (I), (I*), (Ia), (Ib), (Ic), (Id), (Ie) or (If) —or a pharmaceutically acceptable salt thereof—according to the methods and uses as herein (above and below) defined and disclosed is selected from the group consisting of: pancreatic cancer, lung cancer, ovarian cancer, colorectal cancer (CRC), gastric cancer, gastroesophageal junction cancer (GEJC) and esophageal cancer.

In another aspect, the disease/condition/cancer/tumors/ cancer cells to be treated/prevented with a compound of formula (I), (I*), (Ia), (Ib), (Ic), (Id), (Ie) or (If) —or a pharmaceutically acceptable salt thereof—according to the methods and uses as herein (above and below) defined and disclosed is selected from the group consisting of pancreatic cancer (preferably pancreatic ductal adenocarcinoma (PDAC)), lung cancer (preferably non-small cell lung cancer (NSCLC)), gastric cancer, cholangiocarcinoma and colorectal cancer (preferably colorectal adenocarcinoma). Preferably, said pancreatic cancer, lung cancer, cholangiocarcinoma, colorectal cancer (CRC), pancreatic ductal adenocarcinoma (PDAC), non-small cell lung cancer (NSCLC) or colorectal adenocarcinoma comprises a KRAS mutation, in particular a KRAS G12D or KRAS G12V mutation. Preferably (in alternative or in combination with the previous preferred embodiment), said non-small cell lung cancer (NSCLC) comprises a mutation (in particular a loss-of-function mutation) in the NF1 gene.

In another aspect, the disease/condition/cancer/tumors/ cancer cells to be treated/prevented with a compound of formula (I), (I*), (Ia), (Ib), (Ic), (Id), (Ie) or (If) —or a pharmaceutically acceptable salt thereof—according to the methods and uses as herein (above and below) defined and disclosed is gastric cancer, ovarian cancer or esophageal cancer, said gastric cancer or esophageal cancer being preferably selected from the group consisting of: gastric adenocarcinoma (GAC), esophageal adenocarcinoma (EAC) and gastroesophageal junction cancer (GEJC). Preferably, said gastric cancer, ovarian cancer, esophageal cancer, gastric adenocarcinoma (GAC), esophageal adenocarcinoma (EAC) or gastroesophageal junction cancer (GEJC) comprises a KRAS mutation or wildtype amplified KRAS.

Particularly preferred, the cancer to be treated/prevented with a compound of formula (I), (I*), (Ia), (Ib), (Ic), (Id), (Ie) or (If) —or a pharmaceutically acceptable salt thereof—according to the methods and uses as herein (above and below) defined and disclosed is selected from the group consisting of:

lung adenocarcinoma (preferably non-small cell lung cancer (NSCLC)) harbouring a KRAS mutation at position 12 (preferably a G12C, G12D, G12V, G12A, G12R mutation), at position 13 (preferably G13D) or an amplification of KRAS wildtype;

colorectal adenocarcinoma harbouring a KRAS mutation at position 12 (preferably a G12C, G12D, G12V, G12A, G12R mutation), at position 13 (preferably G13D) or an amplification of KRAS wildtype;

pancreatic adenocarcinoma (preferably pancreatic ductal adenocarcinoma (PDAC)) harbouring a RAS mutation at position 12 (preferably a KRAS and preferably a G12C, G12D, G12V, G12A, G12R mutation), at position 13 (preferably G13D) or an amplification of KRAS wildtype.

Preferably, "cancer" as used herein (above or below) includes drug-resistant cancer and cancer that has failed one, two or more lines of mono- or combination therapy with one or more anti-cancer agents. In particular, "cancer" (and any embodiment thereof) refers to any cancer (especially the cancer species defined hereinabove and hereinbelow) that is resistant to treatment with a KRAS G12C inhibitor.

Different resistance mechanisms have already been reported. For example, the following articles describe resistance in patients following treatment with a KRAS G12C inhibitor: (i) Awad M M, Liu S, Rybkin, II, Arbour K C, Dilly J, Zhu V W, et al. Acquired resistance to KRAS(G12C) inhibition in cancer. N Engl J Med 2021; 384:2382-93 and (ii) Tanaka N, Lin J J, Li C, Ryan M B, Zhang J, Kiedrowski L A, et al. Clinical acquired resistance to KRAS(G12C) inhibition through a novel KRAS switch-II pocket mutation and polyclonal alterations converging on RAS-MAPK reactivation. Cancer Discov 2021; 11:1913-22.

In another aspect the disease/condition/cancer/tumors/ cancer cells to be treated/prevented with a compound of formula (I), (I*), (Ia), (Ib), (Ic), (Id), (Ie) or (If) —or a pharmaceutically acceptable salt thereof—according to the methods and uses as herein (above and below) defined and disclosed is a RASopathy, preferably selected from the group consisting of Neurofibromatosis type 1 (NF1), Noonan Syndrome (NS), Noonan Syndrome with Multiple Lentigines (NSML) (also referred to as LEOPARD syndrome), Capillary Malformation-Arteriovenous Malformation Syndrome (CM-AVM), Costello Syndrome (CS), Cardio-Facio-Cutaneous Syndrome (CFC), Legius Syndrome (also known as NF1-like Syndrome) and Hereditary gingival fibromatosis.

Additionally, the following cancers, tumors and other proliferative diseases may be treated with compounds of formula (I), (I*), (Ia), (Ib), (Ic), (Id), (Ie) or (If) —or a pharmaceutically acceptable salt thereof—without being restricted thereto. Preferably, the methods of treatment, methods, uses, compounds for use and pharmaceutical compositions for use as disclosed herein (above and below) are applied in treatments of diseases/conditions/cancers/tumors which (i.e. the respective cells) harbour a KRAS mutation at position 12 (preferably a G12C, G12D, G12V, G12A, G12R mutation) or an amplification of KRAS wildtype alternatively they have been identified to harbour a KRAS mutation at position 12 (preferably a G12C, G12D, G12V, G12A, G12R mutation) as herein described and/or referred or an amplification of KRAS wildtype:

cancers/tumors/carcinomas of the head and neck: e.g. tumors/carcinomas/cancers of the nasal cavity, paranasal sinuses, nasopharynx, oral cavity (including lip, gum, alveolar ridge, retromolar trigone, floor of mouth, tongue, hard palate, buccal mucosa), oropharynx (including base of tongue, tonsil, tonsillar pilar, soft palate, tonsillar fossa, pharyngeal wall), middle ear, larynx (including supraglottis, glottis, subglottis, vocal cords), hypopharynx, salivary glands (including minor salivary glands);

cancers/tumors/carcinomas of the lung: e.g. non-small cell lung cancer (NSCLC) (squamous cell carcinoma, spindle cell carcinoma, adenocarcinoma, large cell carcinoma, clear cell carcinoma, bronchioalveolar), small cell lung cancer (SCLC) (oat cell cancer, intermediate cell cancer, combined oat cell cancer);

neoplasms of the mediastinum: e.g. neurogenic tumors (including neurofibroma, neurilemoma, malignant schwannoma, neurosarcoma, ganglioneuroblastoma, ganglioneuroma, neuroblastoma, pheochromocytoma, paraganglioma), germ cell tumors (including seminoma, teratoma, non-seminoma), thymic tumors (including thymoma, thymolipoma, thymic carcinoma, thymic carcinoid), mesenchymal tumors (including fibroma, fibrosarcoma, lipoma, liposarcoma, myxoma, mesothelioma, leiomyoma, leiomyosarcoma, rhabdomyosarcoma, xanthogranuloma, mesenchymoma, hemangioma, hemangioendothelioma, hemangiopericytoma, lymphangioma, lymphangiopericytoma, lymphangiomyoma);

cancers/tumors/carcinomas of the gastrointestinal (GI) tract: e.g. tumors/carcinomas/cancers of the esophagus, stomach (gastric cancer), gastroesophageal junction cancer pancreas, liver and biliary tree (including hepatocellular carcinoma (HCC), e.g. childhood HCC, fibrolamellar HCC, combined HCC, spindle cell HCC, clear cell HCC, giant cell HCC, carcinosarcoma HCC, sclerosing HCC; hepatoblastoma; cholangiocarcinoma; cholangiocellular carcinoma; hepatic cystadenocarcinoma; angiosarcoma, hemangioendothelioma, leiomyosarcoma, malignant schwannoma, fibrosarcoma, Klatskin tumor), gall bladder, extrahepatic bile ducts, small intestine (including duodenum, jejunum, ileum), large intestine (including cecum, colon, rectum, anus; colorectal cancer, gastrointestinal stroma tumor (GIST)), genitourinary system (including kidney, e.g. renal pelvis, renal cell carcinoma (RCC), nephroblastoma (Wilms' tumor), hypernephroma, Grawitz tumor; ureter; urinary bladder, e.g. urachal cancer, urothelial cancer; urethra, e.g. distal, bulbomembranous, prostatic; prostate (androgen dependent, androgen independent, castration resistant, hormone independent, hormone refractory), penis) gastric cancer;

cancers/tumors/carcinomas of the testis: e.g. seminomas, non-seminomas, gynecologic cancers/tumors/carcinomas: e.g. tumors/carcinomas/cancers of the ovary, fallopian tube, peritoneum, cervix, vulva, vagina, uterine body (including endometrium, fundus);

cancers/tumors/carcinomas of the breast: e.g. mammary carcinoma (infiltrating ductal, colloid, lobular invasive, tubular, adenocystic, papillary, medullary, mucinous), hormone receptor positive breast cancer (estrogen receptor positive breast cancer, progesterone receptor positive breast cancer), Her2 positive breast cancer, triple negative breast cancer, Paget's disease of the breast;

cancers/tumors/carcinomas of the endocrine system: e.g. tumors/carcinomas/cancers of the endocrine glands, thyroid gland (thyroid carcinomas/tumors; papillary, follicular, anaplastic, medullary), parathyroid gland (parathyroid carcinoma/tumor), adrenal cortex (adrenal cortical carcinoma/tumors), pituitary gland (including prolactinoma, craniopharyngioma), thymus, adrenal glands, pineal gland, carotid body, islet cell tumors, paraganglion, pancreatic endocrine tumors (PET; non-functional PET, PPoma, gastrinoma, insulinoma, VIPoma, glucagonoma, somatostatinoma, GRFoma, ACTHoma), carcinoid tumors;

sarcomas of the soft tissues: e.g. fibrosarcoma, fibrous histiocytoma, liposarcoma, leiomyosarcoma, rhabdomyosarcoma, angiosarcoma, lymphangiosarcoma, Kaposi's sarcoma, glomus tumor, hemangiopericytoma, synovial sarcoma, giant cell tumor of tendon sheath, solitary fibrous tumor of pleura and peritoneum, diffuse mesothelioma, malignant peripheral nerve sheath tumor (MPNST), granular cell tumor, clear cell sarcoma, melanocytic schwannoma, plexosarcoma, neuroblastoma, ganglioneuroblastoma, neuroepithelioma, extraskeletal Ewing's sarcoma, paraganglioma, extraskeletal chondrosarcoma, extraskeletal osteosarcoma, mesenchymoma, alveolar soft part sarcoma, epithelioid sarcoma, extrarenal rhabdoid tumor, desmoplastic small cell tumor;

sarcomas of the bone: e.g. myeloma, reticulum cell sarcoma, chondrosarcoma (including central, peripheral, clear cell, mesenchymal chondrosarcoma), osteosarcoma (including parosteal, periosteal, high-grade surface, small cell, radiation-induced osteosarcoma, Paget's sarcoma), Ewing's tumor, malignant giant cell tumor, adamantinoma, (fibrous) histiocytoma, fibrosarcoma, chordoma, small round cell sarcoma, hemangioendothelioma, hemangiopericytoma, osteochondroma, osteoid osteoma, osteoblastoma, eosinophilic granuloma, chondroblastoma;

mesothelioma: e.g. pleural mesothelioma, peritoneal mesothelioma;

cancers of the skin: e.g. basal cell carcinoma, squamous cell carcinoma, Merkel's cell carcinoma, melanoma (including cutaneous, superficial spreading, lentigo maligna, acral lentiginous, nodular, intraocular melanoma), actinic keratosis, eyelid cancer;

neoplasms of the central nervous system and brain: e.g. astrocytoma (cerebral, cerebellar, diffuse, fibrillary, anaplastic, pilocytic, protoplasmic, gemistocytary), glioblastoma, gliomas, oligodendrogliomas, oligoastrocytomas, ependymomas, ependymoblastomas, choroid plexus tumors, medulloblastomas, meningiomas, schwannomas, hemangioblastomas, hemangiomas, hemangiopericytomas, neuromas, ganglioneuromas, neuroblastomas, retinoblastomas, neurinomas (e.g. acoustic), spinal axis tumors;

lymphomas and leukemias: e.g. B-cell non-Hodgkin lymphomas (NHL) (including small lymphocytic lymphoma (SLL), lymphoplasmacytoid lymphoma (LPL), mantle cell lymphoma (MCL), follicular lymphoma (FL), diffuse large cell lymphoma (DLCL), Burkitt's lymphoma (BL)), T-cell non-Hodgkin lymphomas (including anaplastic large cell lymphoma (ALCL), adult T-cell leukemia/lymphoma (ATLL), cutaneous T-cell lymphoma (CTCL), peripheral T-cell lymphoma (PTCL)), lymphoblastic T-cell lymphoma (T-LBL), adult T-cell lymphoma, lymphoblastic B-cell lymphoma (B-LBL), immunocytoma, chronic B-cell lymphocytic leukemia (B-CLL), chronic T-cell lymphocytic leukemia (T-CLL) B-cell small lymphocytic lymphoma (B-SLL), cutaneous T-cell lymphoma (CTLC), primary central nervous system lymphoma (PCNSL), immunoblastoma, Hodgkin's disease (HD) (including nodular lymphocyte predominance HD (NL-PHD), nodular sclerosis HD (NSHD), mixed-cellularity HD (MCHD), lymphocyte-rich classic HD, lymphocyte-depleted HD (LDHD)), large granular lymphocyte leukemia (LGL), chronic myelogenous leukemia (CML), acute myelogenous/myeloid leukemia (AML), acute lymphatic/lymphoblastic leukemia (ALL), acute promyelocytic leukemia (APL), chronic lymphocytic/lymphatic leukemia (CLL), prolymphocytic leukemia (PLL), hairy cell leukemia, chronic myelogenous/myeloid leukemia (CML), myeloma, plasmacytoma, multiple myeloma (MM), plasmacytoma, myelodysplastic syndromes (MDS), chronic myelomonocytic leukemia (CMML);

cancers of unknown primary site (CUP);

All cancers/tumors/carcinomas mentioned above which are characterized by their specific location/origin in the body are meant to include both the primary tumors and the metastatic tumors derived therefrom.

All cancers/tumors/carcinomas mentioned above may be further differentiated by their histopathological classification:

Epithelial cancers, e.g. squamous cell carcinoma (SCC) (carcinoma in situ, superficially invasive, verrucous carcinoma, pseudosarcoma, anaplastic, transitional cell, lymphoepithelial), adenocarcinoma (AC) (well-differentiated, mucinous, papillary, pleomorphic giant cell, ductal, small cell, signet-ring cell, spindle cell, clear cell, oat cell, colloid, adenosquamous, mucoepidermoid, adenoid cystic), mucinous cystadenocarcinoma, acinar cell carcinoma, large cell carcinoma, small cell carcinoma, neuroendocrine tumors (small cell carcinoma, paraganglioma, carcinoid); oncocytic carcinoma;

Nonepithilial cancers, e.g. sarcomas (fibrosarcoma, chondrosarcoma, rhabdomyosarcoma, leiomyosarcoma, hemangiosarcoma, giant cell sarcoma, lymphosarcoma, fibrous histiocytoma, liposarcoma, angiosarcoma, lymphangiosarcoma, neurofibrosarcoma), lymphoma, melanoma, germ cell tumors, hematological neoplasms, mixed and undifferentiated carcinomas;

The compounds of the invention may be used in therapeutic regimens in the context of first line, second line, or any further line treatments.

The compounds of the invention may be used for the prevention, short-term or long-term treatment of the above-mentioned diseases/conditions/cancers/tumors, optionally also in combination with radiotherapy and/or surgery.

The methods of treatment, methods, uses and compounds for use as disclosed herein (above and below) can be performed with any compound of formula (I), (I*), (Ia), (Ib), (Ic), (Id), (Ie) or (If) —or a pharmaceutically acceptable salt thereof—as disclosed or defined herein and with any pharmaceutical composition or kit comprising a compound of formula (I), (I*), (Ia), (Ib), (Ic), (Id), (Ie) or (If) —or a pharmaceutically acceptable salt thereof (each including all individual embodiments or generic subsets of compounds of formula (I), (I*), (Ia), (Ib), (Ic), (Id), (Ie) or (If)).

Combination Treatment

The compounds of formula (I), (I*), (Ia), (Ib), (Ic), (Id), (Ie) or (If) —or the pharmaceutically acceptable salts thereof—and the pharmaceutical compositions comprising such compounds or salts may also be co-administered with other pharmacologically active substances, e.g. with other anti-neoplastic compounds (e.g. chemotherapy), or used in combination with other treatments, such as radiation or surgical intervention, either as an adjuvant prior to surgery or post-operatively. Preferably, the pharmacologically active substance(s) for co-administration is/are (an) anti-neoplastic compound(s).

Thus, in a further aspect the invention relates to a compound of formula (I), (I*), (Ia), (Ib), (Ic), (Id), (Ie) or (If) —or a pharmaceutically acceptable salt thereof—for use as hereinbefore defined wherein said compound is administered before, after or together with one or more other pharmacologically active substance(s).

In a further aspect the invention relates to a compound of formula (I), (I*), (Ia), (Ib), (Ic), (Id), (Ie) or (If) —or a pharmaceutically acceptable salt thereof—for use as hereinbefore defined, wherein said compound is administered in combination with one or more other pharmacologically active substance(s).

In a further aspect the invention relates to the use of a compound of formula (I), (I*), (Ia), (Ib), (Ic), (Id), (Ie) or (If) —or a pharmaceutically acceptable salt thereof—as hereinbefore defined wherein said compound is to be administered before, after or together with one or more other pharmacologically active substance(s).

In a further aspect the invention relates to a method (e.g. a method for the treatment and/or prevention) as hereinbefore defined wherein the compound of formula (I), (I*), (Ia), (Ib), (Ic), (Id), (Ie) or (If) —or a pharmaceutically acceptable salt thereof—is administered before, after or together with a therapeutically effective amount of one or more other pharmacologically active substance(s).

In a further aspect the invention relates to a method (e.g. a method for the treatment and/or prevention) as hereinbefore defined wherein the compound of formula (I), (I*), (Ia), (Ib), (Ic), (Id), (Ie) or (If) —or a pharmaceutically acceptable salt thereof—is administered in combination with a therapeutically effective amount of one or more other pharmacologically active substance(s).

In a further aspect the invention relates to a method for the treatment and/or prevention of cancer comprising administering to a patient in need thereof a therapeutically effective amount of a compound of formula (I), (I*), (Ia), (Ib), (Ic), (Id), (Ie) or (If) —or a pharmaceutically acceptable salt thereof—and a therapeutically effective amount of one or more other pharmacologically active substance(s), wherein the compound of formula (I), (I*), (Ia), (Ib), (Ic), (Id), (Ie) or (If) —or a pharmaceutically acceptable salt thereof—is administered simultaneously, concurrently, sequentially, successively, alternately or separately with the one or more other pharmacologically active substance(s).

In a further aspect the invention relates to a method for the treatment and/or prevention of cancer comprising administering to a patient in need thereof a therapeutically effective amount of an inhibitor of a KRAS mutated at residue 12 or 13, such as KRAS G12C, KRAS G12D, KRAS G12V, KRAS G12A, KRAS G13D and/or KRAS G12R inhibitors, preferably KRAS G12C, KRAS G12D or selective KRAS G12D inhibitors—or a pharmaceutically acceptable salt thereof—and a therapeutically effective amount of one or more other pharmacologically active substance(s), wherein the inhibitor—or a pharmaceutically acceptable salt thereof—is administered in combination with the one or more other pharmacologically active substance(s).

In a further aspect the invention relates to a method for the treatment and/or prevention of cancer comprising administering to a patient in need thereof a therapeutically effective amount of an inhibitor of KRAS wildtype amplified or overexpressed—or a pharmaceutically acceptable salt thereof—and a therapeutically effective amount of one or more other pharmacologically active substance(s), wherein the inhibitor—or a pharmaceutically acceptable salt thereof—is administered in combination with the one or more other pharmacologically active substance(s).

In a further aspect the invention relates to a compound of formula (I), (I*), (Ia), (Ib), (Ic), (Id), (Ie) or (If) —or a pharmaceutically acceptable salt thereof—for use in the treatment and/or prevention of cancer, wherein the compound of formula (I), (I*), (Ia), (Ib), (Ic), (Id), (Ie) or (If) —or a pharmaceutically acceptable salt thereof—is administered simultaneously, concurrently, sequentially, successively, alternately or separately with the one or more other pharmacologically active substance(s).

In a further aspect the invention relates to an inhibitor of a KRAS mutated at residue 12 or 13, such as KRAS G12C, KRAS G12D, KRAS G12V, KRAS G12A, KRAS G13D and/or KRAS G12R inhibitors, preferably KRAS G12C, KRAS G12D or selective KRAS G12D inhibitors—or a pharmaceutically acceptable salt thereof—for use in the treatment and/or prevention of cancer, wherein the inhibitor—or a pharmaceutically acceptable salt thereof—is administered in combination with the one or more other pharmacologically active substance(s).

In a further aspect the invention relates to an inhibitor of KRAS wildtype amplified or overexpressed—or a pharmaceutically acceptable salt thereof—for use in the treatment and/or prevention of cancer, wherein the inhibitor—or a pharmaceutically acceptable salt thereof—is administered in combination with the one or more other pharmacologically active substance(s).

In a further aspect the invention relates to a kit comprising
a first pharmaceutical composition or dosage form comprising a compound of formula (I), (I*), (Ia), (Ib), (Ic), (Id), (Ie) or (If) —or a pharmaceutically acceptable salt thereof—and, optionally, one or more pharmaceutically acceptable excipient(s), and
a second pharmaceutical composition or dosage form comprising another pharmacologically active substance, and, optionally, one or more pharmaceutically acceptable excipient(s),
for use in the treatment and/or prevention of cancer, wherein the first pharmaceutical composition is to be administered simultaneously, concurrently, sequentially, successively, alternately or separately with the second and/or additional pharmaceutical composition or dosage form.

In one aspect such kit for said use comprises a third pharmaceutical composition or dosage form comprising a third pharmaceutical composition or dosage form comprising still another pharmacologically active substance, and, optionally, one or more pharmaceutically acceptable excipient(s)

In a further embodiment of the invention the components (i.e. the combination partners) of the combinations, kits, uses, methods and compounds for use according to the invention (including all embodiments) are administered simultaneously.

In a further embodiment of the invention the components (i.e. the combination partners) of the combinations, kits, uses, methods and compounds for use according to the invention (including all embodiments) are administered concurrently.

In a further embodiment of the invention the components (i.e. the combination partners) of the combinations, kits, uses, methods and compounds for use according to the invention (including all embodiments) are administered sequentially.

In a further embodiment of the invention the components (i.e. the combination partners) of the combinations, kits, uses, methods and compounds for use according to the invention (including all embodiments) are administered successively.

In a further embodiment of the invention the components (i.e. the combination partners) of the combinations, kits, uses, methods and compounds for use according to the invention (including all embodiments) are administered alternately.

In a further embodiment of the invention the components (i.e. the combination partners) of the combinations, kits, uses, methods and compounds for use according to the invention (including all embodiments) are administered separately.

The pharmacologically active substance(s) to be used together/in combination with the compound of formula (I), (I*), (Ia), (Ib), (Ic), (Id), (Ie) or (If) —or a pharmaceutically acceptable salt thereof—(including all individual embodiments or generic subsets of compounds) or in the medical uses, uses, methods of treatment and/or prevention, pharmaceutical compositions as herein (above and below) defined can be selected from any one or more of the following (preferably there is one or two additional pharmacologically active substance used in all these embodiments):

1. an inhibitor of EGFR and/or ErbB2 (HER2) and/or ErbB3 (HER3) and/or ErbB4 (HER4) or of any mutants thereof
    a. irreversible inhibitors: e.g. afatinib, dacomitinib, canertinib, neratinib, avitinib, poziotinib, AV 412, PF-6274484, HKI 357, olmutinib, osimertinib, almonertinib, nazartinib, lazertinib, pelitinib;
    b. reversible inhibitors: e.g. erlotinib, gefitinib, icotinib, sapitinib, lapatinib, varlitinib, vandetanib, TAK-285, AEE788, BMS599626/AC-480, GW 583340;
    c. anti-EGFR antibodies: e.g. necitumumab, panitumumab, cetuximab, amivantamab;
    d. anti-HER2 antibodies: e.g. pertuzumab, trastuzumab, trastuzumab emtansine;
    e. inhibitors of mutant EGFR;
    f. an inhibitor of HER2 with exon 20 mutations;
    g. preferred irreversible inhibitor is afatinib;
    h. preferred anti-EGFR antibody is cetuximab.
2. an inhibitor of MEK and/or of mutants thereof
    a. e.g. trametinib, cobimetinib, binimetinib, selumetinib, refametinib;
    b. preferred is trametinib
    c. a MEK inhibitor as disclosed in WO 2013/136249;
    d. a MEK inhibitor as disclosed in WO 2013/136254
3. an inhibitor of SOS1 and/or of any mutants thereof (i.e. a compound that modulates/inhibits the GEF functionality of SOS1, e.g. by binding to SOS1 and preventing protein-protein interaction between SOS1 and a (mutant) Ras protein, e.g. KRAS)
    a. e.g. BAY-293;
    b. a SOS1 inhibitor as disclosed in WO 2018/115380;
    c. a SOS1 inhibitor as disclosed in WO 2019/122129;
    d. a SOS1 inhibitor as disclosed in WO 2020/180768, WO 2020/180770, WO 2018/172250 and WO 2019/201848.
4. an inhibitor of YAP1, WWTR1, TEAD1, TEAD2, TEAD3 and/or TEAD4
    a. reversible inhibitors of TEAD transcription factors (e.g. disclosed in WO 2018/204532);
    b. irreversible inhibitors of TEAD transcription factors (e.g. disclosed in WO 2020/243423);

c. protein-protein interaction inhibitors of the YAP/TAZ:TEAD interaction (e.g. disclosed in WO 2021/186324);
d. inhibitors of TEAD palmitoylation.
5. an oncolytic virus
6. a RAS vaccine
   a. e.g. TG02 (Targovax).
7. a cell cycle inhibitor
   a. e.g. inhibitors of CDK4/6 and/or of any mutants thereof
      i. e.g. palbociclib, ribociclib, abemaciclib, trilaciclib, PF-06873600;
      ii. preferred are palbociclib and abemaciclib;
      iii. most preferred is abemaciclib.
   b. e.g. vinca alkaloids
      i. e.g. vinorelbine.
   c. e.g. inhibitors of Aurora kinase and/or of any mutants thereof
      i. e.g. alisertib, barasertib.
8. an inhibitor of PTK2 (=FAK) and/or of any mutants thereof
   a. e.g. TAE226, BI 853520.
9. an inhibitor of SHP2 and/or of any mutants thereof
   a. e.g. SHP099, TNO155, RMC-4550, RMC-4630, IACS-13909.
10. an inhibitor of PI3 kinase (=PI3K) and/or of any mutants thereof
    a. e.g. inhibitors of PI3Kα and/or of any mutants thereof
       i. e.g. alpelisib, serabelisib, GDC-0077, HH-CYH33, AMG 511, buparlisib, dactolisib, pictilisib, taselisib.
11. an inhibitor of FGFR1 and/or FGFR2 and/or FGFR3 and/or of any mutants thereof
    a. e.g. ponatinib, infigratinib, nintedanib.
12. an inhibitor of AXL and/or of any mutants thereof
13. a taxane
    a. e.g. paclitaxel, nab-paclitaxel, docetaxel;
    b. preferred is paclitaxel.
14. a platinum-containing compound
    a. e.g. cisplatin, carboplatin, oxaliplatin
    b. preferred is oxaliplatin.
15. an anti-metabolite
    a. e.g. 5-fluorouracil, capecitabine, floxuridine, cytarabine, gemcitabine, pemetrexed, combination of trifluridine and tipiracil (=TAS102);
    b. preferred is 5-fluorouracil.
16. an immunotherapeutic agent
    a. e.g. an immune checkpoint inhibitor
       i. e.g. an anti-CTLA4 mAb, anti-PD1 mAb, anti-PD-L1 mAb, anti-PD-L2 mAb, anti-LAG3 mAb, anti-TIM3 mAb;
       ii. preferred is an anti-PD1 mAb;
       iii. e.g. ipilimumab, nivolumab, pembrolizumab, tislelizumab atezolizumab, avelumab, durvalumab, pidilizumab, PDR-001 (=spartalizumab), AMG-404, ezabenlimab;
       iv. preferred are nivolumab, pembrolizumab, ezabenlimab and PDR-001 (=spartalizumab);
       v. most preferred is ezabenlimab, pembrolizumab and nivolumab.
17. a topoisomerase inhibitor
    a. e.g. irinotecan, liposomal irinotecan (nal-IRI), topotecan, etoposide;
    b. most preferred is irinotecan and liposomal irinotecan (nal-IRI).
18. an inhibitor of A-Raf and/or B-Raf and/or C-Raf and/or of any mutants thereof
    a. e.g. encorafenib, dabrafenib, vemurafenib, PLX-8394, RAF-709 (=example 131 in WO 2014/151616), LXH254, sorafenib, LY-3009120 (=example 1 in WO 2013/134243), lifirafenib, TAK-632, agerafenib, CCT196969, RO5126766, RAF265.
19. an inhibitor of mTOR
    a. e.g. rapamycin, temsirolimus, everolimus, ridaforolimus, zotarolimus, sapanisertib, Torin 1, dactolisib, GDC-0349, VS-5584, vistusertib, AZD8055.
20. an epigenetic regulator
    a. e.g. a BET inhibitor
       i. e.g. JQ-1, GSK 525762, OTX-015, CPI-0610, TEN-010, OTX-015, PLX51107, ABBV-075, ABBV-744, BMS986158, TGI-1601, CC-90010, AZD5153, I-BET151, BI 894999;
21. an inhibitor of IGF1/2 and/or of IGF1-R and/or of any mutants thereof
    a. e.g. xentuzumab (antibody 60833 in WO 2010/066868), MEDI-573 (=dusigitumab), linsitinib.
22. an inhibitor of a Src family kinase and/or of any mutants thereof
    a. e.g. an inhibitor of a kinase of the SrcA subfamily and/or of any mutants thereof, i.e. an inhibitor of Src, Yes, Fyn, Fgr and/or of any mutants thereof;
    b. e.g. an inhibitor of a kinase of the SrcB subfamily and/or of any mutants thereof, i.e. an inhibitor of Lck, Hck, Blk, Lyn and/or of any mutants thereof;
    c. e.g. an inhibitor of a kinase of the Frk subfamily and/or of any mutants thereof, i.e. an inhibitor of Frk and/or of any mutants thereof;
    d. e.g. dasatinib, ponatinib, bosutinib, vandetanib, KX-01, saracatinib, KX2-391, SU 6656, WH-4-023.
23. an apoptosis regulator
    a. e.g. an MDM2 inhibitor, e.g. an inhibitor of the interaction between p53 (preferably functional p53, most preferably wt p53) and MDM2 and/or of any mutants thereof;
       i. e.g. HDM-201, NVP-CGM097, RG-7112, MK-8242, RG-7388, SAR405838, AMG-232, DS-3032, RG-7775, APG-115;
       ii. preferred are HDM-201, RG-7388 and AMG-232;
       iii. an MDM2 inhibitor as disclosed in WO 2015/155332;
       iv. an MDM2 inhibitor as disclosed in WO 2016/001376;
       v. an MDM2 inhibitor as disclosed in WO 2016/026937;
       vi. an MDM2 inhibitor as disclosed in WO 2017/060431;
    b. e.g. a PARP inhibitor;
    c. e.g. an MCL-1 inhibitor;
       i. e.g. AZD-5991, AMG-176, AMG-397, S64315, S63845, A-1210477;
24. an inhibitor of c-MET and/or of any mutants thereof
    a. e.g. savolitinib, cabozantinib, foretinib;
    b. MET antibodies, e.g. emibetuzumab, amivantamab;
25. an inhibitor of ERK and/or of any mutants thereof
    a. e.g. ulixertinib, LTT462;
26. an inhibitor of farnesyl transferase and/or of any mutants thereof
    a. e.g. tipifarnib;

In a further embodiment of the (combined) use and method (e.g. method for the treatment and/or prevention) as hereinbefore described one other pharmacologically active substance is to be administered before, after or together with the compound of formula (I), (I*), (Ia), (Ib), (Ic), (Id), (Ie) or (If) —or a pharmaceutically acceptable salt thereof— wherein said one other pharmacologically active substance is
- a SOS1 inhibitor; or
- a MEK inhibitor; or
- trametinib, or
- an anti-PD-1 antibody; or
- ezabenlimab; or
- cetuximab; or
- afatinib; or
- standard of care (SoC) in a given indication; or
- a PI3 kinase inhibitor; or
- an inhibitor of TEAD palmitoylation; or
- a YAP/TAZ:TEAD inhibitor.

In a further embodiment of the (combined) use and method (e.g. method for the treatment and/or prevention) as hereinbefore described one other pharmacologically active substance is to be administered in combination with the compound of formula (I), (I*), (Ia), (Ib), (Ic), (Id), (Ie) or (If) —or a pharmaceutically acceptable salt thereof—wherein said one other pharmacologically active substance is
- a SOS1 inhibitor; or
- a MEK inhibitor; or
- trametinib; or
- an anti-PD-1 antibody; or
- ezabenlimab; or
- cetuximab; or
- afatinib; or
- standard of care (SoC) in a given indication; or
- a PI3 kinase inhibitor; or
- an inhibitor of TEAD palmitoylation; or
- a YAP/TAZ:TEAD inhibitor.

In a further aspect of the (combined) use and method (e.g. method for the treatment and/or prevention) as hereinbefore described two other pharmacologically active substances are to be administered before, after or together with the compound of formula (I), (I*), (Ia), (Ib), (Ic), (Id), (Ie) or (If) —or a pharmaceutically acceptable salt thereof—wherein said two other pharmacologically active substances are
- a MEK inhibitor and a SOS1 inhibitor; or
- trametinib and a SOS1 inhibitor; or
- an anti-PD-1 antibody (preferably ezabenlimab) and an anti-LAG-3 antibody; or
- an anti-PD-1 antibody (preferably ezabenlimab) and a SOS1 inhibitor; or
- a MEK inhibitor and an inhibitor selected from the group consisting of an EGFR inhibitor and/or ErbB2 (HER2) inhibitor and/or inhibitor of any mutants thereof; or
- a SOS1 inhibitor and an inhibitor selected from the group consisting of an EGFR inhibitor and/or ErbB2 (HER2) inhibitor and/or inhibitor of any mutants thereof; or
- a MEK inhibitor and afatinib; or
- a MEK inhibitor and cetuximab; or
- trametinib and afatinib; or
- trametinib and cetuximab; or
- a SOS1 inhibitor and afatinib; or
- a SOS1 inhibitor and cetuximab; or
- a SOS1 inhibitor and an inhibitor of TEAD palmitoylation; or
- a SOS1 inhibitor and a YAP/TAZ:TEAD inhibitor.

In a further aspect of the (combined) use and method (e.g. method for the treatment and/or prevention) as hereinbefore described two other pharmacologically active substances are to be administered in combination with the compound of formula (I), (I*), (Ia), (Ib), (Ic), (Id), (Ie) or (If) —or a pharmaceutically acceptable salt thereof—wherein said two other pharmacologically active substances are
- a MEK inhibitor and a SOS1 inhibitor; or
- trametinib and a SOS1 inhibitor; or
- an anti-PD-1 antibody (preferably ezabenlimab) and an anti-LAG-3 antibody; or
- an anti-PD-1 antibody (preferably ezabenlimab) and a SOS1 inhibitor; or
- a MEK inhibitor and an inhibitor selected from the group consisting of an EGFR inhibitor and/or ErbB2 (HER2) inhibitor and/or inhibitor of any mutants thereof; or
- a SOS1 inhibitor and an inhibitor selected from the group consisting of an EGFR inhibitor and/or ErbB2 (HER2) inhibitor and/or inhibitor of any mutants thereof; or
- a MEK inhibitor and afatinib; or
- a MEK inhibitor and cetuximab; or
- trametinib and afatinib; or
- trametinib and cetuximab; or
- a SOS1 inhibitor and afatinib; or
- a SOS1 inhibitor and cetuximab; or
- a SOS1 inhibitor and an inhibitor of TEAD palmitoylation; or
- a SOS1 inhibitor and a YAP/TAZ:TEAD inhibitor.

Additional pharmacologically active substance(s) which can also be used together/in combination with the compound of formula (I), (I*), (Ia), (Ib), (Ic), (Id), (Ie) or (If) —or a pharmaceutically acceptable salt thereof—(including all individual embodiments or generic subsets of compounds of formula (I), (I*), (Ia), (Ib), (Ic), (Id), (Ie) or (If)) or in the medical uses, uses, methods of treatment and/or prevention, pharmaceutical compositions, kits as herein (above and below) defined include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors and/or of their corresponding receptors (growth factors such as for example platelet derived growth factor (PDGF), fibroblast growth factor (FGF), vascular endothelial growth factor (VEGF), epidermal growth factor (EGF), insulin-like growth factors (IGF), human epidermal growth factor (HER, e.g. HER2, HER3, HER4) and hepatocyte growth factor (HGF) and/or their corresponding receptors), inhibitors are for example (anti-) growth factor antibodies, (anti-)growth factor receptor antibodies and tyrosine kinase inhibitors, such as for example cetuximab, gefitinib, afatinib, nintedanib, imatinib, lapatinib, bosutinib, bevacizumab and trastuzumab); antimetabolites (e.g. antifolates such as methotrexate, raltitrexed, pyrimidine analogues such as 5-fluorouracil (5-FU), ribonucleoside and deoxyribonucleoside analogues, capecitabine and gemcitabine, purine and adenosine analogues such as mercaptopurine, thioguanine, cladribine and pentostatin, cytarabine (ara C), fludarabine); antitumor antibiotics (e.g. anthracyclines such as doxorubicin, doxil (pegylated liposomal doxorubicin hydrochloride, myocet (non-pegylated liposomal doxorubicin), daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and Iomustin, thiotepa); antimitotic agents (e.g. Vinca alkaloids such as for example vinblastine, vindesin, vinorelbin and vincristine; and taxanes such as paclitaxel, docetaxel); angiogenesis inhibitors (e.g. tasquinimod), tubuline inhibitors; DNA synthesis inhibitors, PARP inhibitors, topoisomerase inhibitors (e.g. epipodophyllotoxins such as for example etoposide and etopophos, teniposide, amsacrin, topotecan, irinotecan, mitoxantrone), serine/threonine kinase inhibitors (e.g. PDK 1 inhibitors, Raf inhibitors, A-Raf inhibitors, B-Raf inhibitors, C-Raf inhibitors, mTOR inhibitors, mTORC1/2 inhibitors, PI3K inhibitors, PI3Kα inhibitors, dual mTOR/PI3K inhibitors, STK 33 inhibitors, AKT inhibitors, PLK 1 inhibitors, inhibitors of CDKs, Aurora kinase inhibitors), tyrosine kinase inhibitors (e.g. PTK2/FAK inhibitors), protein protein interaction inhibitors (e.g. IAP inhibitors/SMAC mimetics, Mci-1, MDM2/MDMX), MEK inhibitors, ERK inhibitors, FLT3 inhibitors, BRD4 inhibitors, IGF-1R inhibitors, TRAILR2 agonists, Bcl-xL inhibitors, Bcl-2 inhibitors (e.g. venetoclax), Bcl-2/Bcl-xL inhibitors, ErbB receptor inhibitors, BCR-ABL inhibitors, ABL inhibitors, Src inhibitors, rapamycin analogs (e.g. everolimus, temsirolimus, ridaforolimus, sirolimus), androgen synthesis inhibitors, androgen receptor inhibitors, DNMT inhibitors, HDAC inhibitors, ANG1/2 inhibitors, CYP17 inhibitors, radiopharmaceuticals, proteasome inhibitors (e.g. carfilzomib), immunotherapeutic agents such as immune checkpoint inhibitors (e.g. CTLA4, PD1, PD-L1, PD-L2, LAG3, and TIM3 binding molecules/immunoglobulins, such as e.g. ipilimumab, nivolumab, pembrolizumab), ADCC (antibody-dependent cell-mediated cytotoxicity) enhancers (e.g. anti-CD33 antibodies, anti-CD37 antibodies, anti-CD20 antibodies), t-cell engagers (e.g. bi-specific T-cell engagers (BiTEs®) like e.g. CD3×BCMA, CD3×CD33, CD3×CD19), PSMA×CD3), tumor vaccines, immunomodulator, e.g. STING agonist, and various chemotherapeutic agents such as amifostine, anagrelide, clodronate, filgrastim, interferon, interferon alpha, leucovorin, procarbazine, levamisole, mesna, mitotane, pamidronate and porfimer.

It is to be understood that the combinations, compositions, kits, methods, uses, pharmaceutical compositions or compounds for use according to this invention may envisage the simultaneous, concurrent, sequential, successive, alternate or separate administration of the active ingredients or components. It will be appreciated that the compound of formula (I), (I*), (Ia), (Ib), (Ic), (Id), (Ie) or (If) —or a pharmaceutically acceptable salt thereof—and the one or more other pharmacologically active substance(s) can be administered formulated either dependently or independently, such as e.g. the compound of formula (I), (I*), (Ia), (Ib), (Ic), (Id), (Ie) or (If) —or a pharmaceutically acceptable salt thereof—and the one or more other pharmacologically active substance(s) may be administered either as part of the same pharmaceutical composition/dosage form or, preferably, in separate pharmaceutical compositions/dosage forms.

In this context, "combination" or "combined" within the meaning of this invention includes, without being limited, a product that results from the mixing or combining of more than one active ingredient and includes both fixed and non-fixed (e.g. free) combinations (including kits) and uses, such as e.g. the simultaneous, concurrent, sequential, successive, alternate or separate use of the components or ingredients. The term "fixed combination" means that the active ingredients are administered to a patient simultaneously in the form of a single entity or dosage. The term "non-fixed combination" means that the active ingredients are administered to a patient as separate entities either simultaneously, concurrently or sequentially with no specific time limits, wherein such administration provides therapeutically effective levels of the compounds in the body of the patient.

The administration of the compound of formula (I), (I*), (Ia), (Ib), (Ic), (Id), (Ie) or (If) —or a pharmaceutically acceptable salt thereof—and the one or more other pharmacologically active substance(s) may take place by co-administering the active components or ingredients, such as e.g. by administering them simultaneously or concurrently in one single or in two or more separate formulations or dosage forms. Alternatively, the administration of the compound of formula (I), (I*), (Ia), (Ib), (Ic), (Id), (Ie) or (If) —or a pharmaceutically acceptable salt thereof—and the one or more other pharmacologically active substance(s) may take place by administering the active components or ingredients sequentially or in alternation, such as e.g. in two or more separate formulations or dosage forms.

For example, simultaneous administration includes administration at substantially the same time. This form of administration may also be referred to as "concomitant" administration. Concurrent administration includes administering the active agents within the same general time period, for example on the same day(s) but not necessarily at the same time. Alternate administration includes administration of one agent during a time period, for example over the course of a few days or a week, followed by administration of the other agent(s) during a subsequent period of time, for example over the course of a few days or a week, and then repeating the pattern for one or more cycles. Sequential or successive administration includes administration of one agent during a first time period (for example over the course of a few days or a week) using one or more doses, followed by administration of the other agent(s) during a second and/or additional time period (for example over the course of a few days or a week) using one or more doses. An overlapping schedule may also be employed, which includes administration of the active agents on different days over the treatment period, not necessarily according to a regular sequence. Variations on these general guidelines may also be employed, e.g. according to the agents used and the condition of the subject.

Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to:

The use of the prefix $C_{x-y}$, wherein x and y each represent a positive integer (x<y), indicates that the chain or ring structure or combination of chain and ring structure as a whole, specified and mentioned in direct association, may consist of a maximum of y and a minimum of x carbon atoms.

The indication of the number of members in groups that contain one or more heteroatom(s) (e.g. heteroaryl, heteroarylalkyl, heterocyclyl, heterocycylalkyl) relates to the total number of atoms of all the ring members or the total of all the ring and carbon chain members.

The indication of the number of carbon atoms in groups that consist of a combination of carbon chain and carbon ring structure (e.g. cycloalkylalkyl, arylalkyl) relates to the total number of carbon atoms of all the carbon ring and carbon chain members. Obviously, a ring structure has at least three members.

In general, for groups comprising two or more subgroups (e.g. heteroarylalkyl, heterocycylalkyl, cycloalkylalkyl, arylalkyl) the last named subgroup is the radical attachment point, for example, the substituent aryl-$C_{1-6}$alkyl means an aryl group which is bound to a $C_{1-6}$alkyl group, the latter of which is bound to the core or to the group to which the substituent is attached.

In groups like HO, $H_2N$, (O)S, (O)$_2$S, NC (cyano), HOOC, $F_3C$ or the like, the skilled artisan can see the radical attachment point(s) to the molecule from the free valences of the group itself.

The expression "compound of the invention" and grammatical variants thereof comprises compounds of formula (I), (I*), (Ia), (Ib), (Ic), (Id), (Ie) and (If), including all salts, aspects and preferred embodiments thereof as herein defined. Any reference to a compound of the invention or to a compound of formula (I), (I*), (Ia), (Ib), (Ic), (Id), (Ie) and (If) is intended to include a reference to the respective (sub)aspects and embodiments.

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

The term "$C_{1-5}$alkyl" includes for example $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

Further examples of alkyl are methyl (Me; —$CH_3$), ethyl (Et; —$CH_2CH_3$), 1-propyl (n-propyl; n-Pr; —$CH_2CH_2CH_3$), 2-propyl (i-Pr; iso-propyl; —$CH(CH_3)_2$), 1-butyl (n-butyl; n-Bu; —$CH_2CH_2CH_2CH_3$), 2-methyl-1-propyl (iso-butyl; i-Bu; —$CH_2CH(CH_3)_2$), 2-butyl (sec-butyl; sec-Bu; —$CH(CH_3)CH_2CH_3$), 2-methyl-2-propyl (tert-butyl; t-Bu; —$C(CH_3)_3$), 1-pentyl (n-pentyl; —$CH_2CH_2CH_2CH_2CH_3$), 2-pentyl (—$CH(CH_3)CH_2CH_2CH_3$), 3-pentyl (—$CH(CH_2CH_3)_2$), 3-methyl-1-butyl (iso-pentyl; —$CH_2CH_2CH(CH_3)_2$), 2-methyl-2-butyl (—$C(CH_3)_2CH_2CH_3$), 3-methyl-2-butyl (—$CH(CH_3)CH(CH_3)_2$), 2,2-dimethyl-1-propyl (neo-pentyl; —$CH_2C(CH_3)_3$), 2-methyl-1-butyl (—$CH_2CH(CH_3)CH_2CH_3$), 1-hexyl (n-hexyl; —$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 2,3-dimethyl-1-butyl (—$CH_2CH(CH_3)CH(CH_3)CH_3$), 2,2-dimethyl-1-butyl (—$CH_2C(CH_3)_2CH_2CH_3$), 3,3-dimethyl-1-butyl (—$CH_2CH_2C(CH_3)_3$), 2-methyl-1-pentyl (—$CH_2CH(CH_3)CH_2CH_2CH_3$), 3-methyl-1-pentyl (—$CH_2CH_2CH(CH_3)CH_2CH_3$), 1-heptyl (n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl (n-octyl), 1-nonyl (n-nonyl); 1-decyl (n-decyl) etc.

By the terms propyl, butyl, pentyl, hexyl, heptyl, octyl, nonyl, decyl etc. without any further definition are meant saturated hydrocarbon groups with the corresponding number of carbon atoms, wherein all isomeric forms are included.

The above definition for alkyl also applies if alkyl is a part of another (combined) group such as for example $C_{x-y}$alkylamino or $C_{x-y}$alkyloxy.

The term alkylene can also be derived from alkyl. Alkylene is bivalent, unlike alkyl, and requires two binding partners. Formally, the second valency is produced by removing a hydrogen atom in an alkyl. Corresponding groups are for example —$CH_3$ and —$CH_2$—, —$CH_2CH_3$ and —$CH_2CH_2$— or >$CHCH_3$ etc.

The term "$C_{1-4}$alkylene" includes for example —$(CH_2)$—, —$(CH_2$—$CH_2)$—, —$(CH(CH_3))$—, —$(CH_2$—$CH_2$—$CH_2)$—, —$(C(CH_3)_2)$—, —$(CH(CH_2CH_3))$—, —$(CH(CH_3)$—$CH_2)$—, —$(CH_2$—$CH(CH_3))$—, —$(CH_2$—$CH_2$—$CH_2)$—, —$(CH_2$—$CH_2$—$CH(CH_3))$—, —$(CH(CH_3)$—$CH_2$—$CH_2)$—, —$(CH_2$—$CH(CH_3)$—$CH_2)$—, —$(CH_2$—$C(CH_3)_2)$—, —$(C(CH_3)_2$—$CH_2)$—, —$(CH(CH_3)$—$CH(CH_3))$—, —$(CH_2$—$CH(CH_2CH_3))$—, —$(CH(CH_2CH_3)$—$CH_2)$—, —$(CH(CH_2CH_2CH_3))$—, —$(CH(CH(CH_3))_2)$— and —$C(CH_3)(CH_2CH_3)$—.

Other examples of alkylene are methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, hexylene etc.

By the generic terms propylene, butylene, pentylene, hexylene etc. without any further definition are meant all the conceivable isomeric forms with the corresponding number of carbon atoms, i.e. propylene includes 1-methylethylene and butylene includes 1-methylpropylene, 2-methylpropylene, 1,1-dimethylethylene and 1,2-dimethylethylene.

The above definition for alkylene also applies if alkylene is part of another (combined) group such as for example in HO-$C_{x-y}$alkyleneamino or $H_2N$-$C_{x-y}$alkyleneoxy.

Unlike alkyl, alkenyl consists of at least two carbon atoms, wherein at least two adjacent carbon atoms are joined together by a C—C double bond and a carbon atom can only be part of one C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Examples of alkenyl are vinyl (ethenyl), prop-1-enyl, allyl (prop-2-enyl), isopropenyl, but-1-enyl, but-2-enyl, but-3-enyl, 2-methyl-prop-2-enyl, 2-methyl-prop-1-enyl, 1-methyl-prop-2-enyl, 1-methyl-prop-1-enyl, 1-methylidenepropyl, pent-1-enyl, pent-2-enyl, pent-3-enyl, pent-4-enyl, 3-methyl-but-3-enyl, 3-methyl-but-2-enyl, 3-methyl-but-1-enyl, hex-1-enyl, hex-2-enyl, hex-3-enyl, hex-4-enyl, hex-5-enyl, 2,3-dimethyl-but-3-enyl, 2,3-dimethyl-but-2-enyl, 2-methylidene-3-methylbutyl, 2,3-dimethyl-but-1-enyl, hexa-1,3-dienyl, hexa-1,4-dienyl, penta-1,4-dienyl, penta-1,3-dienyl, buta-1,3-dienyl, 2,3-dimethylbuta-1,3-diene etc.

By the generic terms propenyl, butenyl, pentenyl, hexenyl, butadienyl, pentadienyl, hexadienyl, heptadienyl, octadienyl, nonadienyl, decadienyl etc. without any further definition are meant all the conceivable isomeric forms with the corresponding number of carbon atoms, i.e. propenyl includes prop-1-enyl and prop-2-enyl, butenyl includes but-1-enyl, but-2-enyl, but-3-enyl, 1-methyl-prop-1-enyl, 1-methyl-prop-2-enyl etc.

Alkenyl may optionally be present in the cis or trans or E or Z orientation with regard to the double bond(s).

The above definition for alkenyl also applies when alkenyl is part of another (combined) group such as for example in $C_{x-y}$alkenylamino or $C_{x-y}$alkenyloxy.

Unlike alkylene, alkenylene consists of at least two carbon atoms, wherein at least two adjacent carbon atoms are joined together by a C—C double bond and a carbon atom can only be part of one C—C double bond. If in an alkylene as hereinbefore defined having at least two carbon atoms, two hydrogen atoms at adjacent carbon atoms are formally removed and the free valencies are saturated to form a second bond, the corresponding alkenylene is formed.

Examples of alkenylene are ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene etc.

By the generic terms propenylene, butenylene, pentenylene, hexenylene etc. without any further definition are meant all the conceivable isomeric forms with the corresponding number of carbon atoms, i.e. propenylene includes 1-methylethenylene and butenylene includes 1-methylpropenylene, 2-methylpropenylene, 1,1-dimethylethenylene and 1,2-dimethylethenylene.

Alkenylene may optionally be present in the cis or trans or E or Z orientation with regard to the double bond(s).

The above definition for alkenylene also applies when alkenylene is a part of another (combined) group as for example in HO-$C_{x-y}$alkenyleneamino or $H_2N$-$C_{x-y}$alkenyleneoxy.

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Examples of alkynyl are ethynyl, prop-1-ynyl, prop-2-ynyl, but-1-ynyl, but-2-ynyl, but-3-ynyl, 1-methyl-prop-2-ynyl, pent-1-ynyl, pent-2-ynyl, pent-3-ynyl, pent-4-ynyl, 3-methyl-but-1-ynyl, hex-1-ynyl, hex-2-ynyl, hex-3-ynyl, hex-4-ynyl, hex-5-ynyl etc.

By the generic terms propynyl, butynyl, pentynyl, hexynyl, heptynyl, octynyl, nonynyl, decynyl etc. without any further definition are meant all the conceivable isomeric forms with the corresponding number of carbon atoms, i.e. propynyl includes prop-1-ynyl and prop-2-ynyl, butynyl includes but-1-ynyl, but-2-ynyl, but-3-ynyl, 1-methyl-prop-1-ynyl, 1-methyl-prop-2-ynyl, etc.

If a hydrocarbon chain carries both at least one double bond and also at least one triple bond, by definition it belongs to the alkynyl subgroup.

The above definition for alkynyl also applies if alkynyl is part of another (combined) group, as for example in $C_{x-y}$alkynylamino or $C_{x-y}$alkynyloxy.

Unlike alkylene, alkynylene consists of at least two carbon atoms, wherein at least two adjacent carbon atoms are joined together by a C—C triple bond. If in an alkylene as hereinbefore defined having at least two carbon atoms, two hydrogen atoms in each case at adjacent carbon atoms are formally removed and the free valencies are saturated to form two further bonds, the corresponding alkynylene is formed.

Examples of alkynylene are ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene etc.

By the generic terms propynylene, butynylene, pentynylene, hexynylene etc. without any further definition are meant all the conceivable isomeric forms with the corresponding number of carbon atoms, i.e. propynylene includes 1-methylethynylene and butynylene includes 1-methylpropynylene, 2-methylpropynylene, 1,1-dimethylethynylene and 1,2-dimethylethynylene.

The above definition for alkynylene also applies if alkynylene is part of another (combined) group, as for example in HO-$C_{x-y}$alkynyleneamino or $H_2N$-$C_{x-y}$alkynyleneoxy.

By heteroatoms are meant oxygen, nitrogen and sulphur atoms.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —C≡C—$CF_3$, —$CHFCH_2CH_3$, —$CHFCH_2CF_3$ etc.

From the previously defined haloalkyl (haloalkenyl, haloalkynyl) are also derived the terms haloalkylene (haloalkenylene, haloalkynylene). Haloalkylene (haloalkenylene, haloalkynylene), unlike haloalkyl (haloalkenyl, haloalkynyl), is bivalent and requires two binding partners. Formally, the second valency is formed by removing a hydrogen atom from a haloalkyl (haloalkenyl, haloalkynyl).

Corresponding groups are for example —$CH_2F$ and —CHF—, —$CHCH_2F$ and —CHFCHF— or >$CFCH_2F$ etc.

The above definitions also apply if the corresponding halogen-containing groups are part of another (combined) group.

Halogen denotes fluorine, chlorine, bromine and/or iodine atoms.

Cycloalkyl is made up of the subgroups monocyclic cycloalkyl, bicyclic cycloalkyl and spiro-cycloalkyl. The ring systems are saturated and formed by linked carbon atoms. In bicyclic cycloalkyl two rings are joined together so that they have at least two carbon atoms in common. In spiro-cycloalkyl one carbon atom (spiroatom) belongs to two rings together.

If a cycloalkyl is to be substituted, the substitutions may take place independently of one another, in the form of mono- or polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl (octahydroindenyl), bicyclo[4.4.0]decyl (decahydronaphthyl), bicyclo[2.2.1]heptyl (norbornyl), bicyclo[4.1.0]heptyl (norcaranyl), bicyclo[3.1.1]heptyl (pinanyl), spiro[2.5]octyl, spiro[3.3]heptyl etc.

The above definition for cycloalkyl also applies if cycloalkyl is part of another (combined) group as for example in $C_{x-y}$cycloalkylamino, $C_{x-y}$cycloalkyloxy or $C_{x-y}$cycloalkylalkyl.

If the free valency of a cycloalkyl is saturated, then an alicycle is obtained.

The term cycloalkylene can thus be derived from the previously defined cycloalkyl.

Cycloalkylene, unlike cycloalkyl, is bivalent and requires two binding partners. Formally, the second valency is obtained by removing a hydrogen atom from a cycloalkyl. Corresponding groups are for example:

cyclohexyl and

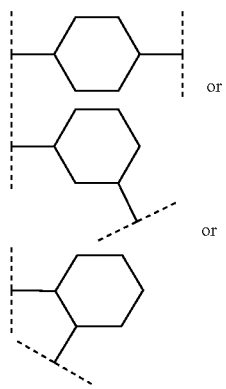

(cyclohexylene).

The above definition for cycloalkylene also applies if cycloalkylene is part of another (combined) group as for example in HO-$C_{x-y}$cycloalkyleneamino or $H_2N$-$C_{x-y}$cycloalkyleneoxy.

Cycloalkenyl is made up of the subgroups monocyclic cycloalkenyl, bicyclic cycloalkenyl and spiro-cycloalkenyl. However, the systems are unsaturated, i.e. there is at least one C—C double bond but no aromatic system. If in a cycloalkyl as hereinbefore defined two hydrogen atoms at adjacent cyclic carbon atoms are formally removed and the free valencies are saturated to form a second bond, the corresponding cycloalkenyl is obtained.

If a cycloalkenyl is to be substituted, the substitutions may take place independently of one another, in the form of mono- or polysubstitutions in each case, on all the hydrogen-carrying carbon atoms. Cycloalkenyl itself may be linked as a substituent to the molecule via every suitable position of the ring system.

Examples of cycloalkenyl are cycloprop-1-enyl, cycloprop-2-enyl, cyclobut-1-enyl, cyclobut-2-enyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclobuta-1,3-dienyl, cyclopenta-1,4-dienyl, cyclopenta-1,3-dienyl, cyclopenta-2,4-dienyl, cyclohexa-1,3-dienyl, cyclohexa-1,5-dienyl, cyclohexa-2,4-dienyl, cyclohexa-1,4-dienyl, cyclohexa-2,5-dienyl, bicyclo[2.2.1]hepta-2,5-dienyl (norborna-2,5-dienyl), bicyclo[2.2.1]hept-2-enyl (norbornenyl), spiro[4,5]dec-2-enyl etc.

The above definition for cycloalkenyl also applies when cycloalkenyl is part of another (combined) group as for example in $C_{x-y}$cycloalkenylamino, $C_{x-y}$cycloalkenyloxy or $C_{x-y}$cycloalkenylalkyl.

If the free valency of a cycloalkenyl is saturated, then an unsaturated alicycle is obtained.

The term cycloalkenylene can thus be derived from the previously defined cycloalkenyl.

Cycloalkenylene, unlike cycloalkenyl, is bivalent and requires two binding partners. Formally, the second valency is obtained by removing a hydrogen atom from a cycloalkenyl. Corresponding groups are for example:

cyclopentenyl and

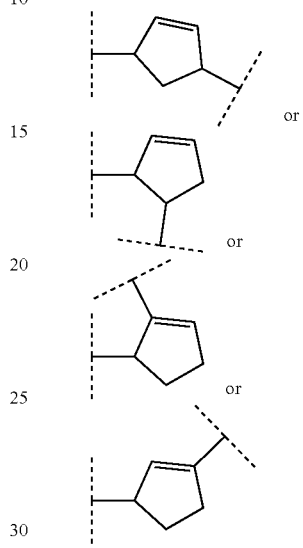

(cyclopentenylene) etc.

The above definition for cycloalkenylene also applies if cycloalkenylene is part of another (combined) group as for example in HO-$C_{x-y}$cycloalkenyleneamino or $H_2N$-$C_{x-y}$cycloalkenyleneoxy.

Aryl denotes mono-, bi- or tricyclic carbocycles with at least one aromatic carbocycle. Preferably, it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be partially saturated.

If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl, naphthyl, indanyl (2,3-dihydroindenyl), indenyl, anthracenyl, phenanthrenyl, tetrahydronaphthyl (1,2,3,4-tetrahydronaphthyl, tetralinyl), dihydronaphthyl (1,2-dihydronaphthyl), fluorenyl etc. Most preferred is phenyl.

The above definition of aryl also applies if aryl is part of another (combined) group as for example in arylamino, aryloxy or arylalkyl.

If the free valency of an aryl is saturated, then an aromatic group is obtained.

The term arylene can also be derived from the previously defined aryl. Arylene, unlike aryl, is bivalent and requires two binding partners. Formally, the second valency is formed by removing a hydrogen atom from an aryl. Corresponding groups are for example:

phenyl and

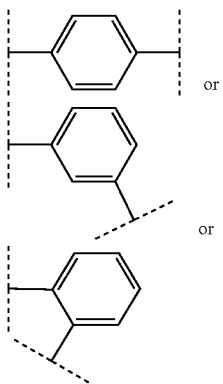

(o, m, p-phenylene),
naphthyl and

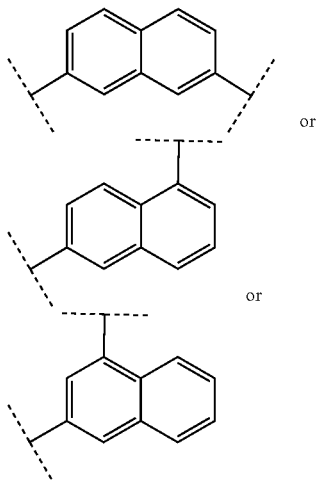

etc.

The above definition for arylene also applies if arylene is part of another (combined) group as for example in HO-aryleneamino or H₂N-aryleneoxy.

Heterocyclyl denotes ring systems, which are derived from the previously defined cycloalkyl, cycloalkenyl and aryl by replacing one or more of the groups —CH₂— independently of one another in the hydrocarbon rings by the groups —O—, —S— or —NH— or by replacing one or more of the groups =CH— by the group =N—, wherein a total of not more than five heteroatoms may be present, at least one carbon atom must be present between two oxygen atoms and between two sulphur atoms or between an oxygen and a sulphur atom and the ring as a whole must have chemical stability. Heteroatoms may optionally be present in all the possible oxidation stages (sulphur→sulfoxide —SO—, sulphone —SO₂—; nitrogen→N-oxide). In a heterocyclyl there is no heteroaromatic ring, i.e. no heteroatom is part of an aromatic system.

A direct result of the derivation from cycloalkyl, cycloalkenyl and aryl is that heterocyclyl is made up of the sub-groups monocyclic heterocyclyl, bicyclic heterocyclyl, tricyclic heterocyclyl and spiro-heterocyclyl, which may be present in saturated or unsaturated form.

By unsaturated is meant that there is at least one double bond in the ring system in question, but no heteroaromatic system is formed. In bicyclic heterocyclyl two rings are linked together so that they have at least two (hetero)atoms in common. In spiro-heterocyclyl one carbon atom (spiroatom) belongs to two rings together.

If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system. Substituents on heterocyclyl do not count for the number of members of a heterocyclyl.

Examples of heterocyclyl are tetrahydrofuryl, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, 1,3-dioxolanyl, tetrahydropyranyl, tetrahydrothiopyranyl, [1,4]-oxazepanyl, tetrahydrothienyl, homothiomorpholinyl-S,S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-S-oxide, tetrahydrothienyl-S,S-dioxide, homothiomorpholinyl-S-oxide, 2,3-dihydroazet, 2H-pyrrolyl, 4H-pyranyl, 1,4-dihydro-pyridinyl, 8-aza-bicyclo[3.2.1]octyl, 8-aza-bicyclo[5.1.0]octyl, 2-oxa-5-azabicyclo[2.2.1]heptyl, 8-oxa-3-aza-bicyclo[3.2.1]octyl, 3,8-diaza-bicyclo[3.2.1]octyl, 2,5-diaza-bicyclo[2.2.1]heptyl, 1-aza-bicyclo[2.2.2]octyl, 3,8-diaza-bicyclo[3.2.1]octyl, 3,9-diaza-bicyclo[4.2.1]nonyl, 2,6-diaza-bicyclo[3.2.2]nonyl, 1,4-dioxa-spiro[4.5]decyl, 1-oxa-3,8-diaza-spiro[4.5]decyl, 2,6-diaza-spiro[3.3]heptyl, 2,7-diaza-spiro[4.4]nonyl, 2,6-diaza-spiro[3.4]octyl, 3,9-diaza-spiro[5.5]undecyl, 2.8-diaza-spiro[4,5]decyl etc.

Further examples are the structures illustrated below, which may be attached via each hydrogen-carrying atom (exchanged for hydrogen):

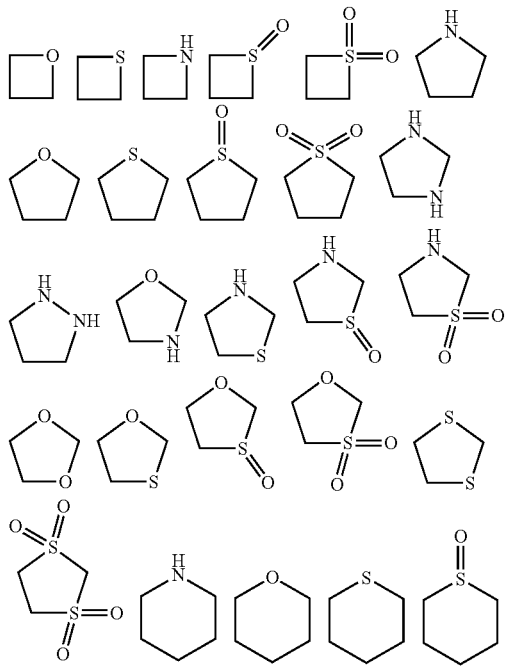

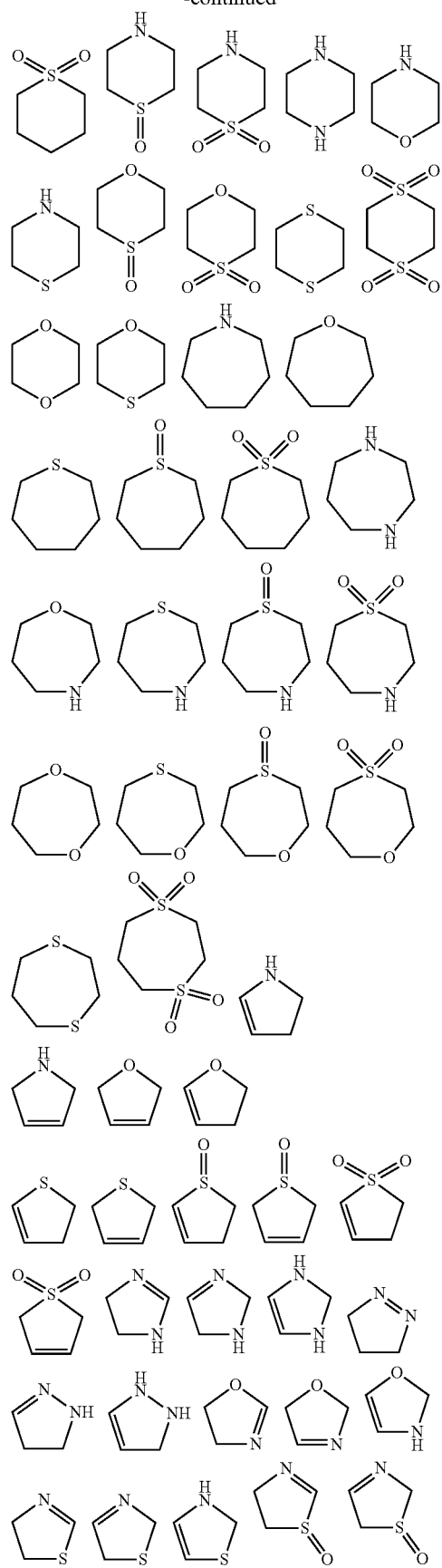
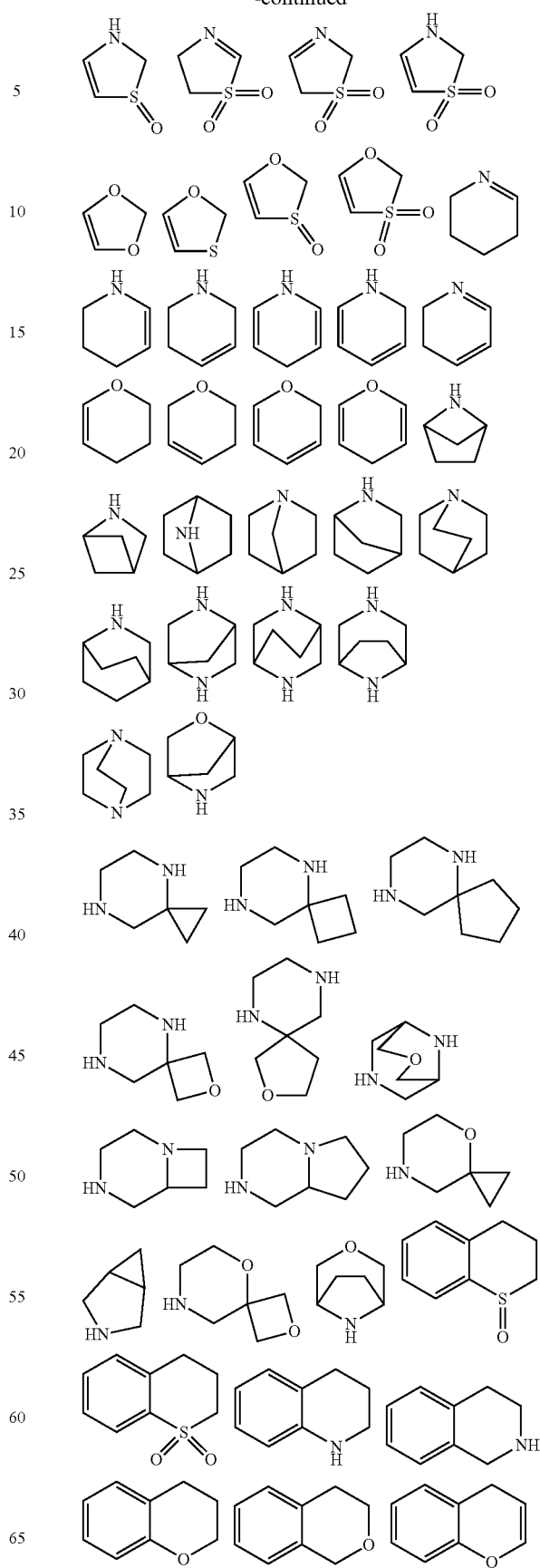

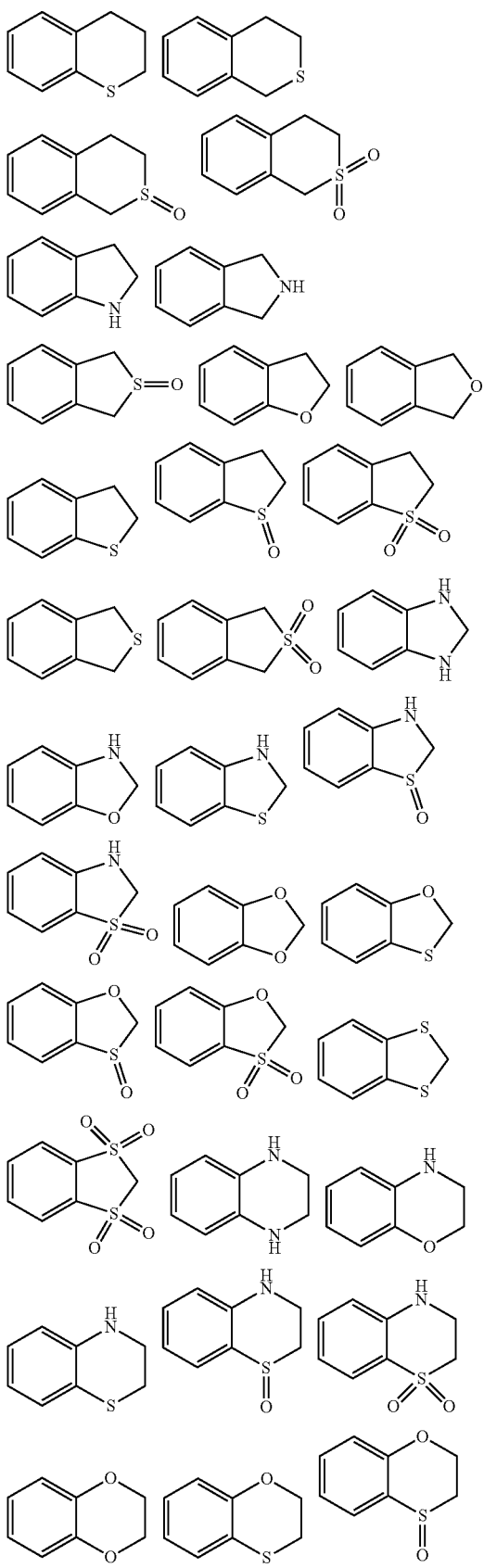

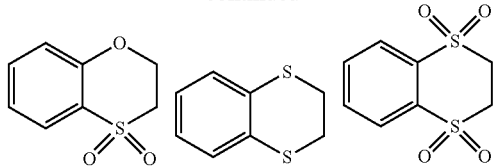

Preferred monocyclic heterocyclyl is 4 to 7 membered and has one or two heteroatoms independently selected from oxygen, nitrogen and sulfur.

Preferred monocyclic heterocyclyls are: piperazinyl, piperidinyl, morpholinyl, pyrrolidinyl, and azetidinyl.

Preferred bicyclic heterocyclyl is 6 to 10 membered and has one or two heteroatoms independently selected from oxygen, nitrogen and sulfur.

Preferred tricyclic heterocyclyl is 9 membered and has one or two heteroatoms independently selected from oxygen, nitrogen and sulfur.

Preferred spiro-heterocyclyl is 7 to 11 membered and has one or two heteroatoms independently selected from oxygen, nitrogen and sulfur.

The above definition of heterocyclyl also applies if heterocyclyl is part of another (combined) group as for example in heterocyclylamino, heterocyclyloxy or heterocyclylalkyl.

If the free valency of a heterocyclyl is saturated, then a heterocycle is obtained.

The term heterocyclylene is also derived from the previously defined heterocyclyl.

Heterocyclylene, unlike heterocyclyl, is bivalent and requires two binding partners. Formally, the second valency is obtained by removing a hydrogen atom from a heterocyclyl. Corresponding groups are for example:

piperidinyl and

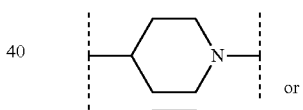

or

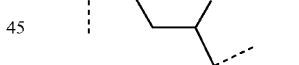

or

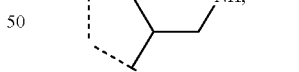

2,3-dihydro-1H-pyrrolyl and

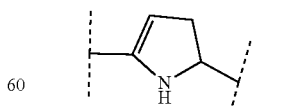

or

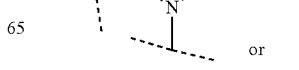

or

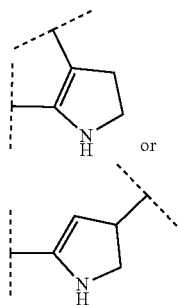

etc.

The above definition of heterocyclylene also applies if heterocyclylene is part of another (combined) group as for example in HO-heterocyclyleneamino or H₂N-heterocyclyleneoxy.

Heteroaryl denotes monocyclic heteroaromatic rings or polycyclic rings with at least one heteroaromatic ring, which compared with the corresponding aryl or cycloalkyl (cycloalkenyl) contain, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system.

If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen. Substituents on heteroaryl do not count for the number of members of a heteroaryl.

Examples of heteroaryl are furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, triazinyl, pyridyl-N-oxide, pyrrolyl-N-oxide, pyrimidinyl-N-oxide, pyridazinyl-N-oxide, pyrazinyl-N-oxide, imidazolyl-N-oxide, isoxazolyl-N-oxide, oxazolyl-N-oxide, thiazolyl-N-oxide, oxadiazolyl-N-oxide, thiadiazolyl-N-oxide, triazolyl-N-oxide, tetrazolyl-N-oxide, indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridyl, imidazopyridyl, naphthyridinyl, benzoxazolyl, pyridopyridyl, pyrimidopyridyl, purinyl, pteridinyl, benzothiazolyl, imidazopyridyl, imidazothiazolyl, quinolinyl-N-oxide, indolyl-N-oxide, isoquinolyl-N-oxide, quinazolinyl-N-oxide, quinoxalinyl-N-oxide, phthalazinyl-N-oxide, indolizinyl-N-oxide, indazolyl-N-oxide, benzothiazolyl-N-oxide, benzimidazolyl-N-oxide etc.

Further examples are the structures illustrated below, which may be attached via each hydrogen-carrying atom (exchanged for hydrogen):

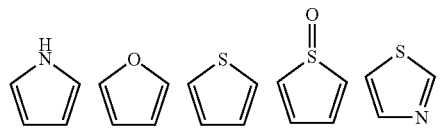

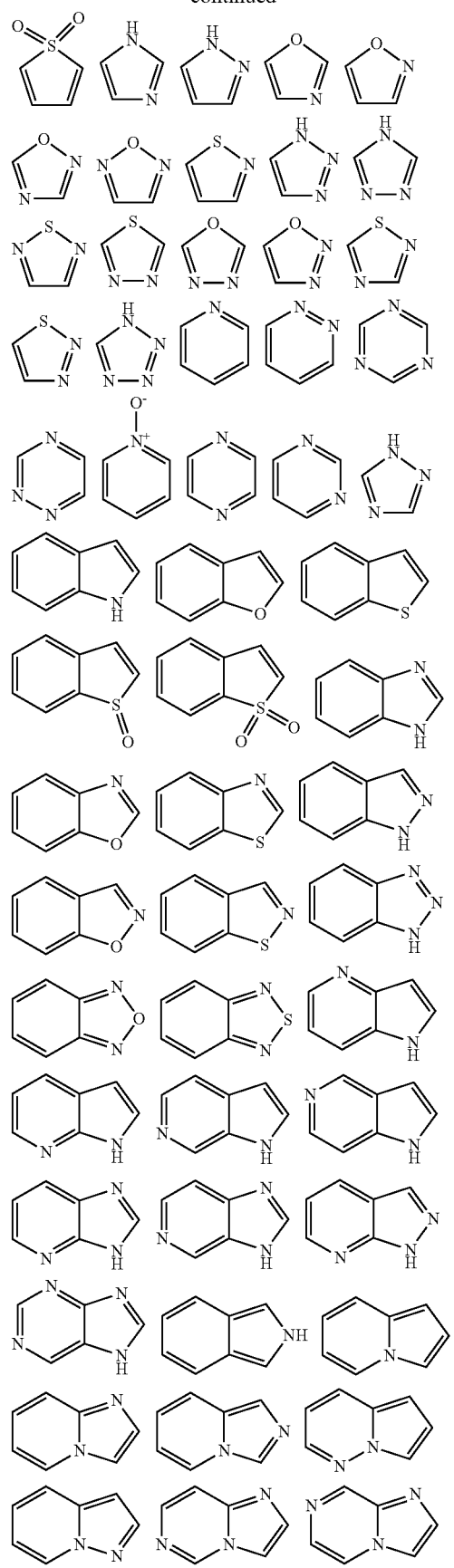

-continued

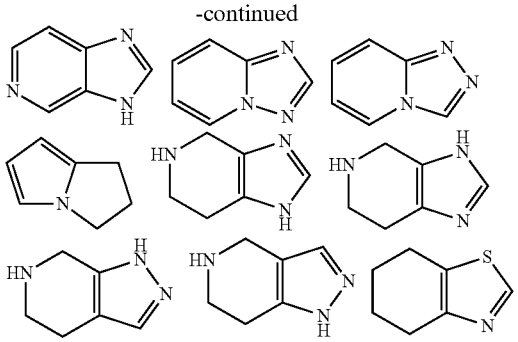

Preferably, heteroaryls are 5-6 membered monocyclic or 9-10 membered bicyclic, each with 1 to 4 heteroatoms independently selected from oxygen, nitrogen and sulfur.

The above definition of heteroaryl also applies if heteroaryl is part of another (combined) group as for example in heteroarylamino, heteroaryloxy or heteroarylalkyl.

If the free valency of a heteroaryl is saturated, a heteroaromatic group is obtained.

The term heteroarylene is also derived from the previously defined heteroaryl.

Heteroarylene, unlike heteroaryl, is bivalent and requires two binding partners. Formally, the second valency is obtained by removing a hydrogen atom from a heteroaryl. Corresponding groups are for example:

pyrrolyl and

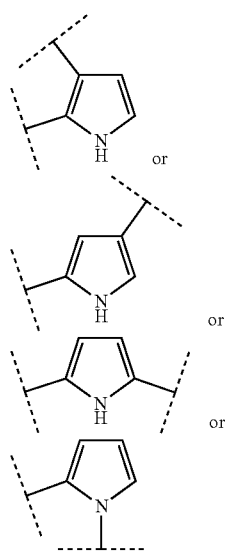

etc.

The above definition of heteroarylene also applies if heteroarylene is part of another (combined) group as for example in HO-heteroaryleneamino or H$_2$N-heteroarylene-oxy.

By substituted is meant that a hydrogen atom which is bound directly to the atom under consideration, is replaced by another atom or another group of atoms (substituent). Depending on the starting conditions (number of hydrogen atoms) mono- or polysubstitution may take place on one atom. Substitution with a particular substituent is only possible if the permitted valencies of the substituent and of the atom that is to be substituted correspond to one another and the substitution leads to a stable compound (i.e. to a compound which is not converted spontaneously, e.g. by rearrangement, cyclisation or elimination).

Bivalent substituents such as =S, =NR, =NOR, =NNRR, =NN(R)C(O)NRR, =N$_2$ or the like, may only be substituents on carbon atoms, whereas the bivalent substituents =O and =NR may also be a substituent on sulphur. Generally, substitution may be carried out by a bivalent substituent only at ring systems and requires replacement of two geminal hydrogen atoms, i.e. hydrogen atoms that are bound to the same carbon atom that is saturated prior to the substitution. Substitution by a bivalent substituent is therefore only possible at the group —CH$_2$— or sulphur atoms (=O group or =NR group only, one or two =O groups possible or, e.g., one =O group and one =NR group, each group replacing a free electron pair) of a ring system.

Isotopes: It is to be understood that all disclosures of an atom or compound of the invention include all suitable isotopic variations. In particular, a reference to hydrogen also includes deuterium.

Stereochemistry/solvates/hydrates: Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates and hydrates of the free compound or solvates and hydrates of a salt of the compound.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents.

Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases, or by resolution of a racemic mixture using an appropriate resolving agent, e.g. by means of diastereomeric salt formation of the racemic compound with optically active acids or bases, subsequent resolution of the salts and release of the desired compound from the salt, or by derivatization of the corresponding racemic compounds with optically active chiral auxiliary reagents, subsequent diastereomer separation and removal of the chiral auxiliary group, or by kinetic resolution of a racemate (e.g. by enzymatic resolution); by enantioselective crystallization from a conglomerate of enantiomorphous crystals under suitable conditions, or by (fractional) crystallization from a suitable solvent in the presence of an optically active chiral auxiliary.

Salts: The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio.

As used herein "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminomethane.

The pharmaceutically acceptable salts of the present invention can be synthesized from the parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts), also comprise a part of the invention.

In a representation such as for example

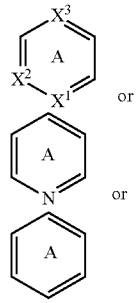

or the letter A has the function of a ring designation in order to make it easier, for example, to indicate the attachment of the ring in question to other rings.

For bivalent groups in which it is crucial to determine which adjacent groups they bind and with which valency, the corresponding binding partners are indicated in brackets where necessary for clarification purposes, as in the following representations:

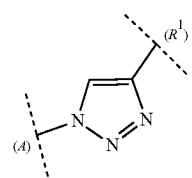

or (R²) —C(=O)NH— or (R²) —NHC(=O)—.

If such a clarification is missing then the bivalent group can bind in both directions, i.e., e.g., —C(=O)NH— also includes —NHC(=O)— (and vice versa).

Groups or substituents are frequently selected from among a number of alternative groups/substituents with a corresponding group designation (e.g. $R^a$, $R^b$ etc). If such a group is used repeatedly to define a compound according to the invention in different parts of the molecule, it is pointed out that the various uses are to be regarded as totally independent of one another.

By a therapeutically effective amount for the purposes of this invention is meant a quantity of substance that is capable of obviating symptoms of illness or of preventing or alleviating these symptoms, or which prolong the survival of a treated patient.

List of abbreviations "Advised not to line off as Table per Training. Text: Capture as Parts list."

Ac acetyl
ACN acetonitrile
aq. aquatic, aqueous
ATP adenosine triphosphate
Bn benzyl
Boc tert-butyloxycarbonyl
Bu butyl
c concentration
CDI 1,1'-carbonyldiimidazole
d day(s)
TLC thin layer chromatography
DCM dichloromethane
DIPEA N-ethyl-N,N-diisopropylamine (Hunig's base)
DMAP 4-N,N-dimethylaminopyridine
DME 1,2-dimethoxyethane
DMF N,N-dimethylformamide
DMSO Dimethyl sulfoxide
dppf 1.1'-bis(diphenylphosphino)ferrocene
equiv. equivalent(s)
ESI electron spray ionization
Et ethyl
Et₂O diethyl ether
EtOAc ethyl acetate
EtOH ethanol
h hour(s)
HATU O-(7-azabenzotriazol-1-yl)-N,N,N',N'-tetramethyl-uronium hexafluorophosphate
HPLC high performance liquid chromatography
i iso
conc. concentrated
LC liquid chromatography
LiHMDS lithium bis(trimethylsilyl)amide
m-CPBA meta-chloroperoxybenzoic acid
Me methyl
MeOH methanol
min minute(s)
MS mass spectrometry
NP normal phase
n.a. not available
PBS phosphate-buffered saline Ph phenyl
Pr propyl
Py pyridine
rac racemic
red. reduction
Rf ($R_f$) retention factor
RP reversed phase
rt ambient temperature
s second(s)
SFC supercritical fluid chromatography
$S_N$ nucleophilic substitution
tBu tert-butyl
TEA triethyl amine
temp. temperature
tert tertiary
Tf triflate
TFA trifluoroacetic acid
THF tetrahydrofuran
TLC thin layer chromatography
$t_{Ret.}$ retention time (HPLC)
Ts tosylate
UPLC ultra performance liquid chromatography
UV ultraviolet
Wt weight

Examples

Features and advantages of the present invention will become apparent from the following detailed examples which illustrate the principles of the invention by way of example without restricting its scope:

Preparation of the Compounds According to the Invention

General

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

If a compound is to be represented both by a structural formula and by its nomenclature, in the event of a conflict the structural formula is decisive.

Microwave reactions are carried out in an initiator/reactor made by Biotage or in an Explorer made by CEM or in Synthos 3000 or Monowave 3000 made by Anton Paar in sealed containers (preferably 2, 5 or 20 mL), preferably with stirring.

Chromatography

The thin layer chromatography is carried out on ready-made silica gel 60 TLC plates on glass (with fluorescence indicator F-254) made by Merck.

The preparative high pressure chromatography (RP HPLC) of the example compounds according to the invention is carried out on Agilent or Gilson systems with columns made by Waters (names: SunFire™ Prep C18, OBD™ 10 µm, 50×150 mm or SunFire™ Prep O18 OBD™ 5 µm, 30×50 mm or XBridge™ Prep C18, OBD™ 10 µm, 50×150 mm or XBridge™ Prep C18, OBD™ 5 µm, 30×150 mm or XBridge™ Prep C18, OBD™ 5 µm, 30×50 mm) and YMC (names: Actus-Triart Prep C18, 5 µm, 30×50 mm).

Different gradients of $H_2O$/ACN are used to elute the compounds, while for Agilent systems 5% acidic modifier (20 mL HCOOH to 1 L $H_2O$/ACN (1/1)) is added to the water (acidic conditions). For Gilson systems the water is added 0.1% HCOOH.

For the chromatography under basic conditions for Agilent systems $H_2O$/ACN gradients are used as well, while the water is made alkaline by addition of 5% basic modifier (50 g $NH_4HCO_3$+50 mL $NH_3$ (25% in $H_2O$) to 1 L with $H_2O$). For Gilson systems the water is made alkaline as follows: 5 mL $NH_4HCO_3$ solution (158 g in 1 L $H_2O$) and 2 mL $NH_3$ (28% in $H_2O$) are replenished to 1 L with $H_2O$.

The supercritical fluid chromatography (SFC) of the intermediates and example compounds according to the invention is carried out on a JASCO SFC-system with the following colums: Chiralcel OJ (250×20 mm, 5 µm), Chiralpak AD (250×20 mm, 5 µm), Chiralpak AS (250×20 mm, 5 µm), Chiralpak IC (250×20 mm, 5 µm), Chiralpak IA (250×20 mm, 5 µm), Chiralcel OJ (250×20 mm, 5 µm), Chiralcel OD (250×20 mm, 5 µm), Phenomenex Lux C2 (250×20 mm, 5 µm).

The analytical HPLC (reaction control) of intermediate and final compounds is carried out using columns made by Waters (names: XBridge™ C18, 2.5 µm, 2.1×20 mm or XBridge™ C18, 2.5 µm, 2.1×30 mm or Aquity UPLC BEH C18, 1.7 µm, 2.1×50 mm) and YMC (names: Triart C18, 3.0 µm, 2.0×30 mm) and Phenomenex (names: Luna C18, 5.0 µm, 2.0×30 mm). The analytical equipment is also equipped with a mass detector in each case.

HPLC-Mass Spectroscopy/UV-Spectrometry

The retention times/MS-ESI⁺ for characterizing the example compounds according to the invention are produced using an HPLC-MS apparatus (high performance liquid chromatography with mass detector). Compounds that elute at the injection peak are given the retention time $t_{Ret.}$=0.00.

Method A

| HPLC | Agilent 1100 system |
|---|---|
| MS | 1200 Series LC/MSD(API-ES +/− 3000 V, Quadrupol, G6140) |
| MSD signal settings | Scan pos/neg 120-900 m/z |
| Detection signal | 315 nm (bandwidth 170 nm, reference off) |
| Spectrum range | 230-400 nm |
| Peak width | <0.01 min |
| Column | Waters, Xbridge C18, 2.5 µm, 2.1 × 20 mm column |
| Column temperature | 60° C. |
| Solvent | A: 20 mM aq. $NH_4HCO_3$/$NH_3$ pH 9<br>B: ACN HPLC grade |
| Flow | 1.00 mL/min |
| Gradient | 0.00-1.50 min    10% to 95% B<br>1.50-2.00 min    95% B<br>2.00-2.10 min    95% to 10% B |

Method B

| HPLC | Agilent 1260 system |
|---|---|
| MS | 1200 Series LC/MSD (MM-ES + APCI +/− 3000 V, Quadrupol, G6130) |
| Detection | UV: 254 nm (bandwidth 8, reference off)<br>UV: 230 nm (bandwidth 8, reference off)<br>UV spectrum range: 190-400 nm; step: 4 nm<br>MS: positive and negative mode |
| Mass range | 100-800 m/z |
| Column | Waters; Part. No. 186003389; XBridge BEH C18, 2.5 µm, 30 × 2.1 mm |
| Column temperature | 45° C. |

-continued

| | |
|---|---|
| Solvent | A: 5 mM NH$_4$HCO$_3$/19 mM NH3 in H2O; |
| | B: ACN (HPLC grade) |
| Flow | 1.40 mL/min |
| Gradient | 0.00-1.00 min: 5% B to 100% B |
| | 1.00-1.37 min: 100% B |
| | 1.37-1.40 min: 100% B to 5% B |

Method C

| | |
|---|---|
| HPLC | Agilent 1260 Series |
| MS | Agilent LC/MSD Quadrupole |
| Detection | MS: positive and negative mode |
| Mass range | 100-750 m/z |
| Column | Waters X-Bridge BEH C18, 2.5 μm, 2.1 × 30 mm XP |
| Column temperature | 45° C. |
| Solvent | A: 20 mM NH$_4$HCO$_3$/30 mM NH$_3$ in H$_2$O; |
| | B: ACN (HPLC grade) |
| Flow | 1.40 mL/min |
| Gradient | 0.00-1.00 min: 15% B to 95% B |
| | 1.00-1.30 min: 95% B |

Method D

| | |
|---|---|
| HPLC | Agilent 1100/1200 system |
| MS | 1200 Series LC/MSD (MM-ES + APCI +/− 3000 V, Quadrupol, G6130B) |
| MSD signal settings | Scan pos 150-750 |
| Detection signal | UV 254 nm, 230 nm, 214 nm (bandwidth 8, reference off) |
| Spectrum | range: 190-400 nm; slit: 4 nm |
| Peak width | >0.0031 min (0.063 s response time, 80 Hz) |
| Column | Waters, Part. No. 186003389, XBridge BEH C18, 2.5 μm, 2.1 × 30 mm) column |
| Column temperature | 45° C. |
| Solvent | A: 5 mM NH$_4$HCO$_3$/18 mM NH3 in H2O (pH = 9.2) |
| | B: ACN (HPLC grade) |
| Flow | 1.4 mL/min |
| Gradient | 0.0-1.0 min 15% to 95% B |
| | 1.0-1.1 min 95% B |
| | Stop time: 1.3 min |

Method E

| | |
|---|---|
| HPLC | Agilent 1100/1200 system |
| MS | 1200 Series LC/MSD (MM-ES + APCI +/− 3000 Quadrupol, G6130B) |
| MSD signal settings | Scan pos/neg 150-750 |
| Detection signal | UV 254 nm, 230 nm, 214 nm (bandwidth 8, reference off) |
| Spectrum | range: 190-400 nm; slit: 4 nm |
| Peak width | >0.0031 min (0.063 s response time, 80 Hz) |
| Column | Waters, Part. No. 186003389, XBridge BEH C18, 2.5 μm, 2.1 × 30 mm) column |
| Column temperature | 45° C. |
| Solvent | A: 5 mM NH$_4$HCO$_3$/18 mM NH3 in H2O (pH = 9.2) |
| | B: ACN (HPLC grade) |
| Flow | 1.4 mL/min |
| Gradient | 0.0-1.0 min 15% to 95% B |
| | 1.0-1.1 min 95% B |
| | Stop time: 1.3 min |

Method F

| | |
|---|---|
| HPLC | Agilent 1100/1200 system |
| MS | 1200 Series LC/MSD (API-ES +/− 3000/3500 V, Quadrupol, G6140A) |
| MSD signal settings | Scan pos/neg 150-750 |
| Detection signal | UV 254 nm, 230 nm, 214 nm (bandwidth 10, reference off) |
| Spectrum | range: 190-400 nm; slit: 4 nm |
| Peak width | >0.0031 min (0.063 s response time, 80 Hz) |
| Column | YMC; Part. No. TA12S03-0302WT; Triart C18, 3 μm, 12 nm; 30 × 2.0 mm column |
| Column temperature | 45° C. |
| Solvent | A: H2O + 0.11% formic acid |
| | B: ACN + 0.1% formic acid (HPLC grade) |
| Flow | 1.4 mL/min |
| Gradient | 0.0-1.0 min 15% to 95% B |
| | 1.0-1.1 min 95% B |
| Stop time: | 1.23 min |

Method G

| | |
|---|---|
| UPLC-MS | Waters Acquity-UPLC-SQ Detector-2 |
| MSD signal settings | Scan pos & Neg 100-1500, Source Voltage: Capillary Vol(kV)-3.50, Cone(V): 50 Source Temp: Desolvation Temp(° C.): 350 Source Gas Flow: Desolvation(L/Hr): 750, Cone(L/Hr): 50 |
| Detection signal | Diode Array |
| Spectrum | Range: 200-400 nm; Resolution: 1.2 nm |
| Sampling rate | 10 point/sec |
| Column | AQUITY UPLC BEH C18 1.7 μm, 2.1 × 50 mm |
| Column temperature | 35° C. |
| Solvent | A: 0.07% formic acid in ACN |
| | B: 0.07% formic acid in water |
| Flow | 0.6 mL/min |
| Gradient | 0.0-0.30 min 97% B |
| | 0.30-2.20 min 97% to 2% B |
| | 2.20-3.30 min 2% B |
| | 3.30-4.50 min 2% to 97% B |
| | 4.50-4.51 min 97% B |

Method H

| | |
|---|---|
| UPLC-MS | Waters Acquity-Binary Solvent Manager-UPLC-SQ Detector-2 |
| MSD signal settings | Scan pos & Neg 100-1500, Source Voltage: Capillary Vol(kV)-3.50, Cone(V): 50 Source Temp: Desolvation Temp(° C.): 350 Source Gas Flow: Desolvation(L/Hr): 750, Cone(L/Hr): 50 |
| Detection signal | Diode Array |
| Spectrum | Range: 200-400 nm; Resolution: 1.2 nm |
| Sampling rate | 10 point/sec |
| Column | AQUITY UPLC BEH C18 1.7 μm, 2.1 × 50 mm |
| Column temperature | 35° C. |
| Solvent | A: 0.07% formic acid in ACN |
| | B: 0.07% formic acid in water |
| Flow | 0.6 mL/min |
| Gradient | 0.0-0.40 min 97% B |
| | 0.40-2.50 min 97% to 2% B |
| | 2.50-3.40 min 2% B |
| | 3.40-3.50 min 2% to 97% B |
| | 3.50-4.0 min 97% B |

Method I

| | |
|---|---|
| LC-MS | Waters Arc-HPLC-SQ Detector-2 |
| MSD signal settings | ESI Scan pos & neg |
| | Capillary Voltage 3.50 Kv cone voltage 30 V Desolvation gas |
| | 750 L/hr Desolvation Temp 350° C. |
| Column | X-Bridge C18, 4.6 × 75 mm, 3.5 μ |
| Column temperature | 35° C. |
| Solvent | A: 10 mM ammonium acetate in water |
| | B: ACN |
| Flow | 1.0 mL/min |
| Gradient | 0.0-0.75 min    5% B |
| | 0.75-1.50 min    5% to 40% B |
| | 1.50-5.0 min    40% to 98% B |
| | 5.0-7.0 min    98% B |

Method J

| | |
|---|---|
| LC-MS | Waters Acquity-UPLC-SQ Detector-2 |
| MSD signal settings | ESI Scan pos & neg |
| | Capillary Voltage 3.50 Kv cone voltage |
| | 50 V Desolvation gas |
| | 750 L/hr Desolvation Temp 350° C. |
| Column | Waters Acquity-UPLC-SQ Detector-2 |
| Column temperature | 35° C. |
| Solvent | A: 0.05% TFA in ACN |
| | B: 0.05% TFA in water |
| Flow | 0.6 mL/min |
| Gradient | 0.0-0.3 min    97% B |
| | 0.3-2.2 min    97% to 2% B |
| | 2.2-3.3 min    2% B |

Method K

| | |
|---|---|
| LC-MS | Waters Arc-HPLC-SQ Detector-2 |
| MSD signal settings | ESI Scan pos & neg |
| | Capillary Voltage 3.50 Kv cone voltage |
| | 30 V Desolvation gas |
| | 750 L/hr Desolvation Temp 350° C. |
| Column | X-Bridge C18, 4.6 × 50 mm, 3.5 μ |
| Column temperature | 35° C. |
| Solvent | A: 10 mM ammonium acetate in water |
| | B: ACN |
| Flow | 2.0 mL/min |
| Gradient | 0.0-0.2 min    10% B |
| | 0.2-2.50 min    10% to 75% B |
| | 2.50-3.0 min    75% to 100% B |
| | 3.0-4.8 min    100% B |

Method L

| | |
|---|---|
| HPLC | Agilent 1260 Series |
| MS | Agilent LC/MSD Quadrupole |
| Detection | MS: positive and negative mode |
| Mass range | 550-1200 m/z |
| Column | Waters X-Bridge BEH C18, 2.5 μm, 2.1 × 30 mm XP |
| Column temperature | 45° C. |
| Solvent | A: 20 mM $NH_4HCO_3$/30 mM $NH_3$ in $H_2O$; |
| | B: ACN (HPLC grade) |
| Flow | 1.40 mL/min |
| Gradient | 0.00-1.50 min: 50% B to 95% B |
| | 1.50-2.00 min: 95% B |

Method M

| | |
|---|---|
| HPLC | Agilent 1260 Series |
| MS | Agilent LC/MSD Quadrupole |
| Detection | MS: positive and negative mode |
| Mass range | 550-1200 m/z |
| Column | Waters X-Bridge BEH C18, 2.5 μm, 2.1 × 30 mm XP |
| Column temperature | 45° C. |
| Solvent | A: 20 mM $NH_4HCO_3$/30 mM $NH_3$ in $H_2O$; |
| | B: ACN (HPLC grade) |
| Flow | 1.40 mL/min |
| Gradient | 0.00-1.00 min: 50% B to 95% B |
| | 1.00-1.30 min: 95% B |

Method N

| | |
|---|---|
| HPLC | Agilent 1260 Series |
| MS | Agilent LC/MSD Quadrupole |
| Detection | MS: positive and negative mode |
| Mass range | 100-750 m/z |
| Column | YMC-Triart C18, 3 μm, 12 nm, 2.0 × 30 mm |
| Column temperature: | 45° C. |
| Solvent | A: H2O + 0.1% formic acid; |
| | B: ACN (HPLC grade) + 0.1% formic acid |
| Flow: | 1.40 mL/min |
| Gradient: | 0.00-1.00 min: 15% B to 95% B |
| | 1.00-1.30 min: 95% B |

Method O

| | |
|---|---|
| HPLC | Waters-Alliance 2996 |
| Detection signal | PDA Detector |
| Spectrum | Range: 200-400 nm; Resolution: 1.2 nm |
| Sampling rate | 1 point/sec |
| ELSD Parameters | Gas Pressure: 50 PSI, Drift tube Temp: 50° C., Gain: 500 |
| Column | Atlantis T3 (4.6 × 250 mm) 5.0 μm |
| Column temperature | Ambient |
| Solvent | A: 10 mM Ammonium Acetate |
| | B: ACN |
| Flow | 0.7 mL/min |
| Gradient | 0.0-1.20 min    2% B |
| | 1.2-10.0 min    2% to 98% B |
| | 10.0-12.0 min    98% B |
| | 12.0-14.0 min    97% to 2% B |
| | 14.0-16.0 min    2% B |

Method P

| | |
|---|---|
| UPLC-MS | Waters Acquity-UPLC-SQ Detector-2 |
| MSD signal settings | Scan Positive & Negative 100-1500, |
| | Source Voltage: Capillary Voltage(kV)-3.50, Cone(V): 50 |
| | Source Temp: Desolvation Temp(° C.): 350 |
| | Source Gas Flow: Desolvation(L/Hr): 650 |
| Detection signal | Diode Array |
| Spectrum | Range: 200-400 nm; Resolution: 1.2 nm |
| Sampling rate | 10 point/sec |
| ELSD Parameters: | GAS: 2.0 SLM, Nebulizer Temp: 40° C., Evaporative Temp: 45° C. |
| Column | AQUITY UPLC BEH C18 1.7 μm, 2.1 × 50 mm |
| Column temperature | 50° C. |
| Solvent | A: 0.05% formic acid in water |
| | B: 0.05% formic acid in ACN |

-continued

| | |
|---|---|
| Flow | 0.6 mL/min |
| Gradient | 0.0-2.20 min 3% to 98% B |
| | 2.20-3.20 min 98% B |
| | 3.20-3.50 min 98% to 3% B |
| | 3.50-4.20 min 2% B |

Method Q

| | |
|---|---|
| HPLC-MS | Waters Arc-HPLC with 2998PDA Detector and SQ Detector-2 |
| MSD signal settings | Scan Pos & Neg 100-1500, Source Votage: Capillary Vol(kV)- 3.50, Cone(V): 30 Source Temp: Desolvation Temp(° C.): 350 Source Gas Flow: Desolvation(L/Hr): 750 |
| Detection signal | PDA Detector |
| Spectrum | Range: 200-400 nm; Resolution: 1.2 nm |
| Sampling rate | 10 point/sec |
| Column | X-Bridge C18, 4.6 × 50 mm, 3.5 μm |
| Column temperature | 35° C. |
| Solvent | A: 10 mM ammonium acetate in water B: ACN |
| Flow | 1.0 mL/min |
| Gradient | 0.0-0.75 min 5% B |
| | 0.75-1.50 min 5% to 40% B |
| | 1.50-5.0 min 40% to 98% B |
| | 5.0-7.0 min 98% B |
| | 7.0-9.0 min 98% to 5% B |
| | 9.0-10.01 min 5% B |

Method R

| GCMS | |
|---|---|
| HPLC | Agilent 1200 system |
| Column | Chiralpak IE, 5.0 μm, 2.1 × 150 mm column |
| Column temperature | 40° C. |
| Solvent | EtOH/Heptane 1:1 + 0.1% diethylamine (isocratic) |
| Flow | 0.60 mL/min |

Method U

| | |
|---|---|
| GC | Agilent Technologies-7890B GC System with 7693 Auto Sampler and 5977A MSD |
| Injection Temperature | 230° C. |
| Column Flow | 2.0 ml/min |
| Solvent delay | 1.5 min |
| Split Ratio | 10:01 |
| Column Oven Temperature Program | 100° C./1 min, 20° C./min/310°/5 min |
| Total run time | 16 min |
| Interface Temperature | 150° C. |
| Ion Source Temperature | 230° C. |
| Gas | He |

-continued

| | |
|---|---|
| Column & Column dimension | ZB-5MS (30 m × 0.32 mm; 1 μm) |
| MSD Scan Range | 50-900 |

Method V

| | |
|---|---|
| GC | Agilent Technologies-7890B GC System with 7693 Auto Sampler and 5977A MSD |
| Injection Temperature | 230° C. |
| Column Flow | 2.0 mL/min |
| Solvent delay | 1.5 min |
| Split Ratio | 10:01 |
| Column Oven Temperature Program | 40° C./2 min, 15° C./min/200° C./1 min, 25° C./min/310° C./0 min, |
| Total run time | 18 min |
| Interface Temperature | 150° C. |
| Ion Source Temperature | 230° C. |
| Gas | He |
| Column & Column dimension | ZB-5MS (30 m × 0.32 mm; 1 μm) |
| MSD Scan Range | 50-900 |

Method W

| | |
|---|---|
| GC | Agilent Technologies-7890B GC System with 7693 Auto Sampler and 5977A MSD |
| Injection Temperature | 230° C. |
| Column Flow | 2.0 mL/min |
| Solvent delay | 1.5 min |
| Split Ratio | 10:01 |
| Column Oven Temperature Program | 60° C./3 min, 20° C./min/310° C./2 min |
| Total run time | 18 min |
| Interface Temperature | 150° C. |
| Ion Source Temperature | 230° C. |
| Gas | He |
| Column & Column dimension | ZB-5MS (30 m × 0.32 mm; 1 μm) |

Method SFC-1

| | |
|---|---|
| Make | Waters UPC$^2$-MS |
| Soft | Empower3 |
| MS | QDa |
| Column | CHIRALCEL OX-3(4.6*150 MM) 3 μm |
| A-Solvent | CO2 |
| B-solvent | ACN |
| Total Flow | 3 g/min |
| % of Co-Solvent | 15 |
| ABPR | 1500 psi |
| Colum temp | 30° C. |
| PDA range | 200 nm to 400 nm |
| Resolution | 1.2 nm |
| MS Parameters | — |
| QDa MS scan range | 100 Da to 1000 Da |
| Cone voltage | |
| Positive scan | 20 V |
| Negative Scan | 15 V |

Method SFC-2

| | |
|---|---|
| Make | Waters UPC²-MS |
| Soft | Empower3 |
| MS | QDa |
| Column | (R,R) WHELK-01(4.6 × 150 mm)3.5 μm |
| A-Solvent | CO2 |
| B-solvent | 0.5% isopropylamine in isopropanol |
| Total Flow | 3 g/min |
| % of Co-Solvent | 40 |
| ABPR | 1500 psi |
| Colum temp | 30° C. |
| PDA range | 200 nm to 400 nm |
| Resolution | 1.2 nm |
| MS Parameters | — |
| QDa MS scan range | 100 Da to 1000 Da |
| | Cone voltage |
| Positive scan | 20 V |
| Negative Scan | 15 V |

The compounds according to the invention and intermediates are prepared by the methods of synthesis described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or their synthesis is described in the prior art or they may be prepared analogously to known prior art compounds or methods described herein, i.e. it is within the skills of an organic chemist to synthesize these compounds. Substances described in the literature can be prepared according to the published methods of synthesis. If a chemical structure in the following is depicted without exact configuration of a stereo center, e.g. of an asymmetrically substituted carbon atom, then both configurations shall be deemed to be included and disclosed in such a representation. The representation of a stereo center in racemic form shall always deem to include and disclose both enantiomers (if no other defined stereo center exists) or all other potential diastereomers and enantiomers (if additional, defined or undefined, stereo centers exist).

Synthesis of Spiroketone Intermediates A

Experimental Procedure for the Synthesis of A-2a

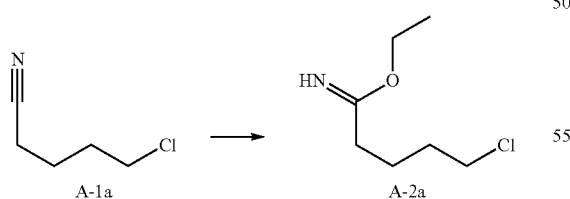

To a suspension of 5-chloropentanenitrile (22.9 g, 195 mmol, 1.00 equiv.) in EtOH (136 mL) is added acetyl chloride (111 mL, 1.56 mol, 8.00 equiv.) dropwise at 0° C. The reaction mixture is allowed to warm to rt and stirred for 12 h. The mixture is concentrated under reduced pressure and washed with Et$_2$O and the crude product A-2a is used as the HCl salt directly in the next step without further purification (HPLC method: A; $t_{ret}$=1.03 min; [M+H]$^+$=164).

Experimental Procedure for the Synthesis of A-3a

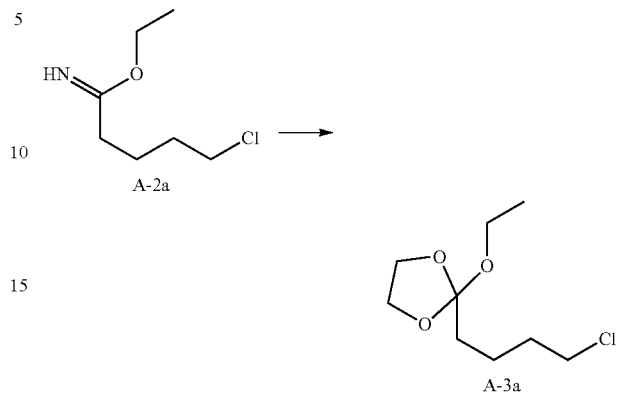

Crude A-2a (HCl salt) (28.0 g, 140 mmol, 1.00 equiv.) and ethylene glycol (7.38 g, 119 mmol, 0.90 equiv.) are dissolved in DCM (300 mL) and stirred at rt for 6 d. The resulting suspension is concentrated under reduced pressure, diluted with Et$_2$O (200 mL) and filtered. The filtrate is concentrated under reduced pressure, taken up in DCM (200 mL) and treated with a KOH solution (2 M in water, 150 mL). The mixture is stirred at rt overnight keeping the phases intact. The phases are separated, the water phase is extracted with DCM (2×) and the combined organic phases are dried over magnesium sulfate, filtered and concentrated under reduced pressure. The crude orthoester A-3a is used for the next step without further purification (HPLC method: A; $t_{ret}$=1.37 min; [M+H]$^+$=163).

Experimental Procedure for the Synthesis of A-4a

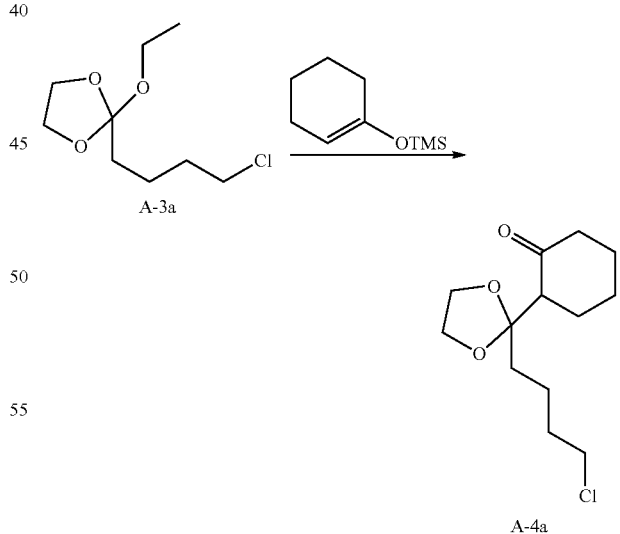

Crude A-3a (22.3 g, 107 mmol, 1.00 equiv.), 1-cyclohexenyloxytrimethylsilane (16.4 mL, 82.3 mmol, 0.80 equiv.) and zinc chloride (10.2 g, 74.8 mmol, 0.70 equiv.) are dissolved in DCM (120 mL) and stirred at rt for 5 h. The reaction mixture is treated by addition of saturated sodium bicarbonate solution. The organic phase is separated, dried over magnesium sulfate, filtered and concentrated under reduced pressure. The crude product is purified by NP-chromatography to give the desired compound A-4a (HPLC method: A; $t_{ret}$=1.25 min; [M+H]$^+$=283).

Experimental Procedure for the Synthesis of A-5a

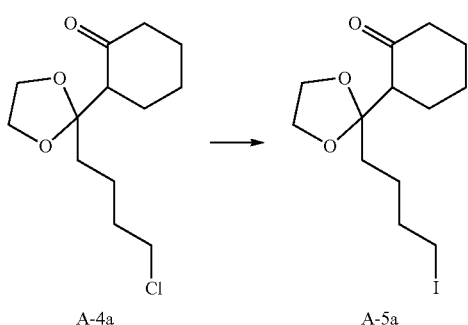 [SMILES: O=C1CCCCC1C1(CCCCCl)OCCO1 ; O=C1CCCCC1C1(CCCCI)OCCO1]

A-4a (14.9 g, 57.1 mmol, 1.00 equiv.) and sodium iodide (25.9 g, 171 mmol, 3.00 equiv.) are dissolved in acetone (120 mL) and stirred under reflux for 16 h. The reaction mixture is concentrated under reduced pressure, diluted with DCM and washed with a saturated sodium thiosulfate solution. The organic phase is separated, dried over magnesium sulfate, filtered and concentrated under reduced pressure. The crude product A-5a is used for the next step without further purification.

Experimental Procedure for the Synthesis of A-6b

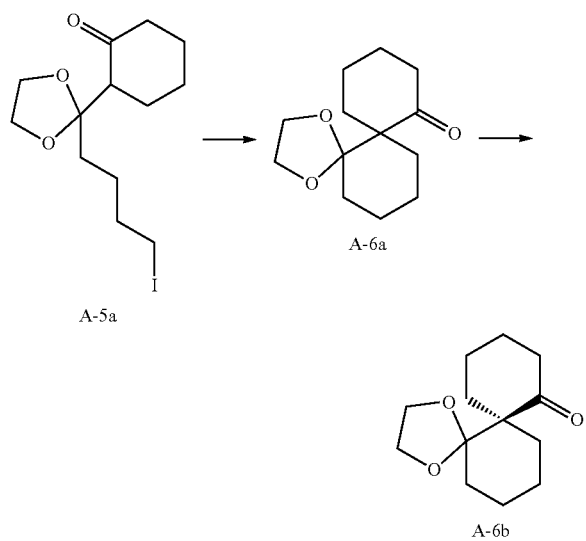

A-5a (30.0 g, 85.0 mmol, 1.00 equiv.) is dissolved in THF. The mixture is treated with potassium tert.-butoxide (28.7 g, 256 mmol, 3.0 equiv.) at 0° C. and stirred at rt overnight. The reaction mixture is quenched by addition of water (2 mL), diluted by addition of Et$_2$O and saturated sodium hydrogencarbonate solution. The organic phase is separated, dried over magnesium sulfate, filtered and concentrated under reduced pressure. The crude product is purified by NP-chromatography to give (racemic) compound A-6a (HPLC method: A; $t_{ret}$=1.17 min; [M+H]$^+$=225).

Reaction sequence A-1a→A-6a is based on Marko et al., THL 2003, 44, 3333-3336 and Maulide et al., Eur. J. Org. Chem. 2004, 19:3962-3967.

Enantiomer A-6b can then be obtained after chiral separation via SFC (using a Lux Cellulose-4 column (250×30 mm, 5 µm), 30° C. column temperature, 90% CO$_2$, 10% ACN as cosolvent) with enantiomer A-6b (HPLC method: A; $t_{ret}$=1.17 min; [M+H]$^+$=225/SFC method: SFC-1; $t_{ret}$=2.99 min) eluting as the 2$^{nd}$ peak after the other enantiomer.

Alternative Procedure for the Synthesis of A-6b

Step 1

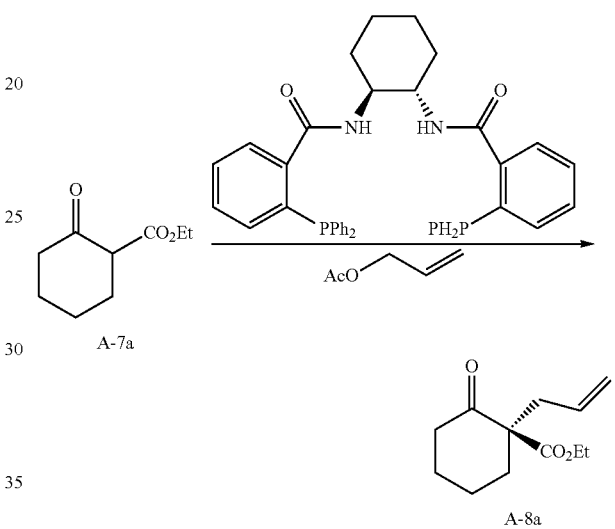

A dry and clean reactor is charged with toluene (234 L) under nitrogen (note: 2.5V toluene in total for this reaction). Water (1.56 kg, 85.5 mol, keep H$_2$O:Pd=160:1) is added followed by rinsing the charging line with 1,1,3,3-tetramethylguanidine (175.5 kg, 1527.6 mol, 2.0 equiv.) under nitrogen and then toluene (13 L). A-7a (130.0 kg, 763.8 mol) is added under nitrogen followed by rinsing with toluene (13 L). Allyl acetate (98.8 kg, 992.9 mol, 1.3 equiv.) is added under nitrogen and rinsed with toluene (13 L). Under agitation, the mixture is cooled to 10° C. in 0.5 h. The batch is degassed by sparging the solution with nitrogen for ~30 min. (S,S)-DACH-Ph Trost ligand (0.429 kg, 0.619 mol, 0.081 mol %) in degassed toluene (13 L) (note: keep Pd:ligand=1:1.15) is added followed by rinsing with degassed toluene (13 L). Allylpalladium(II) chloride dimer (97.5 g, 267 mol, 0.035 mol %) in degassed toluene (13 L) is added followed by rinsing with degassed toluene (13 L). The batch is kept at 10-15° C. at least 8 h. After the reaction is complete by HPLC, a solution of N-acetyl-L-cysteine (3.9 kg, 22.9 mol, 0.03 equiv.) in water (260 L) below 25° C. is added. The resulting solution is warmed to 20-25° C. and kept at 20-25° C. at least for 1 h. After phase cut to discard the bottom aqueous layer, 10 wt % NH$_4$Cl aqueous solution (260 L) is added. After the mixture is agitated for 10 min, the bottom aqueous layer is drained. The organic phase is further washed with water (130 L). The organic layer is filtered through a very short pad of Celite and the reactor and Celite bed is rinsed with toluene (65 L). The filtrate is charged into a clean reactor and then toluene is distilled off under vacuum at 40-50° C. The crude product is directly used for the next step or the product is drained into a container with the help of minimum amount of toluene (65 L) and stored at 20-23° C. 150 kg of A-8a is usually obtained as a light yellow oil in 96% yield with ≥90:10 enantomeric ratio.

¹H NMR (500 MHz, CDCl₃): δ 5.75 (ddt, J=14.8, 9.4, 7.5 Hz, 1H), 5.06-5.00 (m, 2H), 4.19 (q, J=7.1 Hz, 2H), 2.61 (dd, J=13.9, 7.1 Hz, 1H), 2.51-2.43 (m, 3H), 2.33 (dd, J=13.9, 7.9 Hz, 1H), 2.03-1.98 (m, 1H), 1.78-1.60 (m, 3H), 1.50-1.42 (m, 1H), 1.25 (t, J=7.1 Hz, 3H). 13C NMR (125 MHz, CDCl₃): b 207.7, 171.6, 133.5, 118.4, 61.3, 61.0, 41.3, 39.4, 35.9, 27.7, 22.6, 14.3. ESI-MS: m/z 211 [M+H]⁺.

Step 2

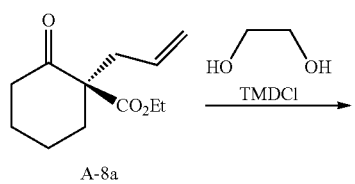

A-8a

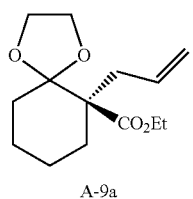

A-9a

To the reactor containing A-8a (150 kg, 713.4 mol) from step 1 (less than 1V toluene if used) is added ethylene glycol (600 L) to give a yellow biphasic mixture. After the mixture is cooled to 10-15° C., TMSCl (193.5 kg, 1783.5 mol, 2.5 equiv.) is added over not less than 15 min, at a rate to maintain the internal temperature between 20-30° C. (orange biphasic mixture obtained). Sufficient agitation is needed to achieve mixing. After the batch is kept at 20-25° C. for 2 h, agitation is stopped and kept for at least 15 min at 20-25° C. The batch is cooled to 0-5° C. NaOH (96 kg, 1854.8 mol, 2.6 equiv.) in water (600 L) is added at a rate to maintain the internal temperature below 20° C. (light yellow cloudy biphasic mixture obtained). Toluene (300 L) is added and then the batch is agitated for 10 min. After phase cut to drain the bottom aqueous layer (note: some precipitate may form at interphase), the organic layer is washed with water (300 L) two times. The organic phase is filtered through a short pad of Celite to remove insoluble solids/interphase. The organic solution is charged into a clean and dry reactor and then the solvent is distilled off at 40-50° C. to a minimum stirrable volume. The crude product A-9a (189 kg, 95.2 wt %, 100% yield) is drained to a container with the help of minimum amount of toluene.

¹H NMR (500 MHz, CDCl₃): δ 5.65 (ddt, J=14.7, 8.1, 6.6 Hz, 1H), 5.07-4.98 (m, 2H), 4.20-4.10 (m, 2H), 3.97-3.88 (m, 4H), 2.81 (dd, J=13.9, 6.6 Hz, 1H), 2.35 (dd, J=13.9, 8.1 Hz, 1H), 2.04-1.98 (m, 1H), 1.75-1.35 (m, 7H), 1.26 (t, J=7.1 Hz, 3H). 13C NMR (125 MHz, CDCl₃): δ 173.7, 134.3, 117.6, 110.9, 65.0, 64.7, 60.5, 54.6, 36.2, 32.3, 30.3, 23.3, 20.9, 14.4. ESI-MS: m/z 255 [M+H]⁺.

Step 3

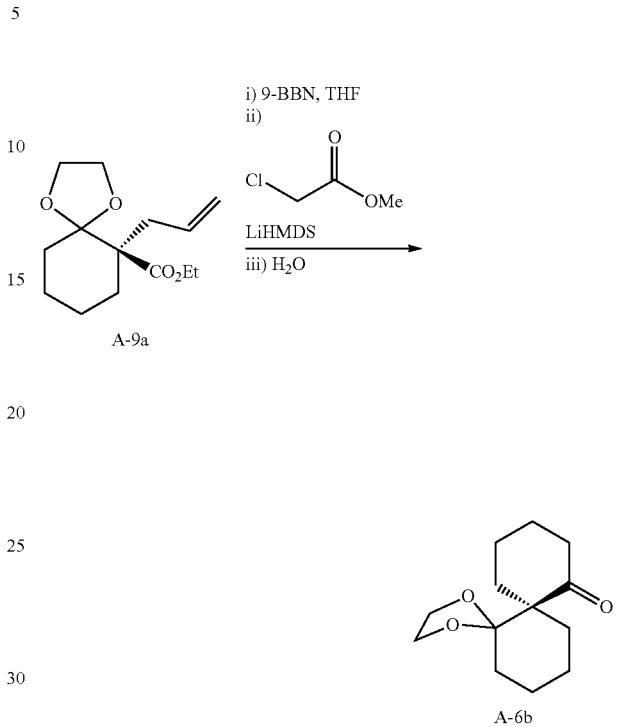

To a dry and clean reactor is added 9-BBN (688.5 kg, 401 mol, 1.2 equiv.) under nitrogen. The solution is cooled to 0-5° C. to obtain a slurry. A-9a (85.0 kg, 334.2 mol) from step 2 is added at 0-5° C. and rinsed with THF (40 L). The mixture is warmed to 20-23° C. in 1 h and kept at 20-23° C. for not less than 1 h. After that the mixture is cooled to −45 to −40° C., methyl chloroacetate (69.6 kg, 1.3 equiv) is added in one portion followed by dropwise addition of LiHMDS (909.5 kg, 1102.9 mol) while keeping temperature below −35° C. The batch is then warmed to 20-23° C. in 1 h and then kept at 20-23° C. at least for 18 h. ~12-13 V solvent is removed by distillation under vacuum with heating (35° C.). EtOH (255 kg) is added followed by a solution of NaOH (13.4 kg) in H₂O (212.5 L). The mixture is heated at reflux (at 66-70° C.) for at least 14 h.

After that ~5-6 V solvent is removed by distillation at reflux, the batch is cooled to 20-25° C. and then filtered through a short pad of Celite to remove insoluble material and rinsed with heptane (160 L). ~5-6 V solvent (or most of the residual THF and ethanol) is distilled under vacuum at 40-50° C. The batch is cooled to 20-25° C. After that, water (255 L) is added, the crude product is extracted twice with heptane (2364.8 kg). The combined heptane layers are washed once with water (85 L). After solvent removal by distillation under vacuum at 40-50° C., the crude product (52.7 kg, 87.5 wt %) is obtained as a yellow oil in 52.6% assay yield. The crude product A-6b is used for next step directly.

¹H NMR (500 MHz, CDCl₃): δ 4.01-3.82 (m, 4H), 2.50-2.44 (m, 1H), 2.38 2.34 (m, 1H), 2.28-2.22 (m, 1H), 2.11-2.05 (m, 1H), 2.01-1.95 (m, 1H), 1.92-1.86 (m, 1H), 1.81-1.58 (m, 6H), 1.54-1.43 (m, 3H), 1.27-1.18 (m, 1H). ESI-MS: m/z 225 [M+H]⁺.

Synthesis of Alcohol-, Pyrazole-, and Tosylate-Intermediates B

Experimental Procedure for the Synthesis of B-2a

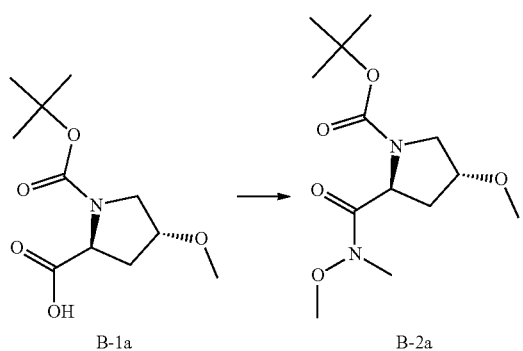 [SMILES: CO[C@@H]1C[C@@H](C(=O)O)N(C(=O)OC(C)(C)C)C1 ; CO[C@@H]1C[C@@H](C(=O)N(C)OC)N(C(=O)OC(C)(C)C)C1]

B-1a (4.92 g, 19.1 mmol, 1.00 equiv.), N,N'-carbonyl-diimidazole (5.14 g, 28.6 mmol, 1.50 equiv.) and molecular sieves (3 A, 500 mg) are dissolved in DCM (29.5 mL) and stirred for 40 min at rt. After complete activation, N,O-Dimethylhydroxylamine hydrochloride (2.79 g, 28.6 mmol, 1.50 equiv.) is added and the reaction is stirred again for 2 h at rt. After complete conversion, water (100 mL) and DCM (150 mL) are added and the phases are separated, the water phase is extracted with DCM (2×). The combined organic phase is washed with brine and concentrated under reduced pressure. The residue is purified by NP chromatography to give the product B-2a.

The following intermediates B-2 (Table 1) are available in an analogous manner. The crude product is purified by chromatography if necessary.

TABLE 1

| # | structure | $t_{ret}$ [min] | $[M + H]^+$ | HPLC method |
|---|---|---|---|---|
| B-2a | 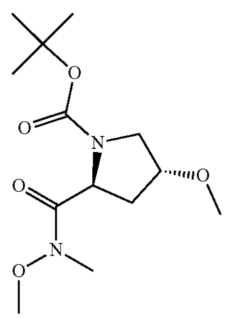 [SMILES: CO[C@@H]1C[C@@H](C(=O)N(C)OC)N(C(=O)OC(C)(C)C)C1] | 0.43 | 189 ($[M + H - Boc]^+$) | C |
| B-2b | 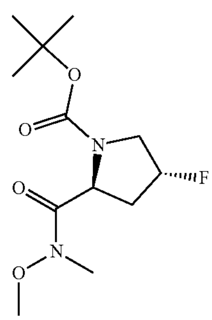 [SMILES: CON(C)C(=O)[C@@H]1C[C@@H](F)CN1C(=O)OC(C)(C)C] | 0.47 | 177 ($[M + H - Boc]^+$) | C |
| B-2c | 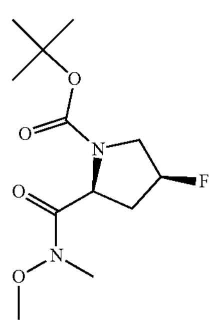 [SMILES: CON(C)C(=O)[C@@H]1C[C@H](F)CN1C(=O)OC(C)(C)C] | 1.47 | 177 ($[M + H - Boc]^+$) | H |

TABLE 1-continued

| # | structure | t_ret [min] | [M + H]+ | HPLC method |
|---|---|---|---|---|
| B-2d | 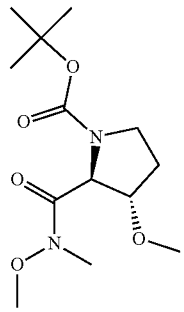 [SMILES: CO[C@H]1CCN(C(=O)OC(C)(C)C)[C@@H]1C(=O)N(C)OC] | 0.44 | 189 ([M + H − Boc]+) | C |

Experimental Procedure for the Synthesis of B-3a

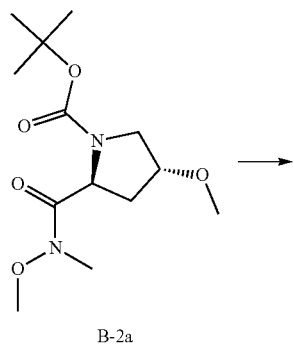

B-2a

→

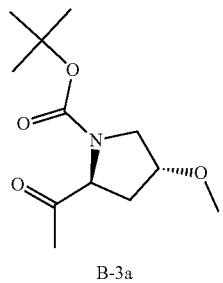

B-3a

B-2a (4.88 g, 16.9 mmol, 1.00 equiv.) is dissolved in THF (15 mL) under an argon atmosphere and cooled to −10° C. Bromo(methyl)magnesium (3.4 M in MeTHF, 6.46 mL, 22.0 mmol, 1.3 equiv.) is added and stirred for 1 h at −10° C. After complete conversion, the reaction mixture is cooled to −20° C. and quenched by addition of brine. The resulting mixture is extracted with DCM (3×). The combined organic phase is concentrated under reduced pressure to obtain B-3a.

The following intermediates B-3 (Table 2) are available in an analogous manner. The crude product is purified by chromatography if necessary.

TABLE 2

| # | structure | t_ret [min] | [M + H]+ | HPLC method |
|---|---|---|---|---|
| B-3a | 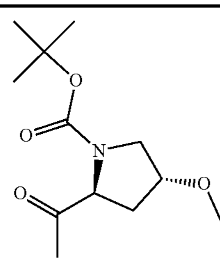 | 0.97 | 144 ([M + H − Boc]+) | A |
| B-3b | 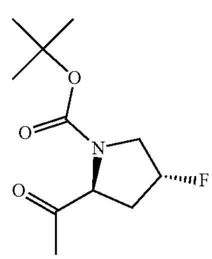 [SMILES: CC(=O)[C@@H]1C[C@@H](F)CN1C(=O)OC(C)(C)C] | 0.50 | 132 ([M + H − Boc]+) | C |

TABLE 2-continued

| # | structure | $t_{ret}$ [min] | $[M + H]^+$ | HPLC method |
|---|---|---|---|---|
| B-3c | 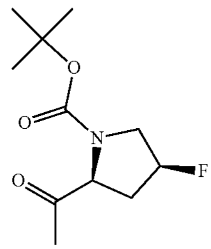 [SMILES: CC(=O)[C@@H]1C[C@H](F)CN1C(=O)OC(C)(C)C] | 1.56 | 132 ($[M + H - Boc]^+$) | H |
| B-3d | 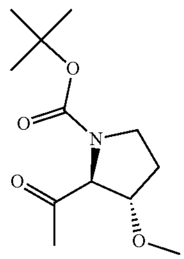 [SMILES: CO[C@H]1CCN(C(=O)OC(C)(C)C)[C@@H]1C(C)=O] | 0.48 | 144 ($[M + H - Boc]^+$) | C |

Experimental Procedure for the Synthesis of B-4a

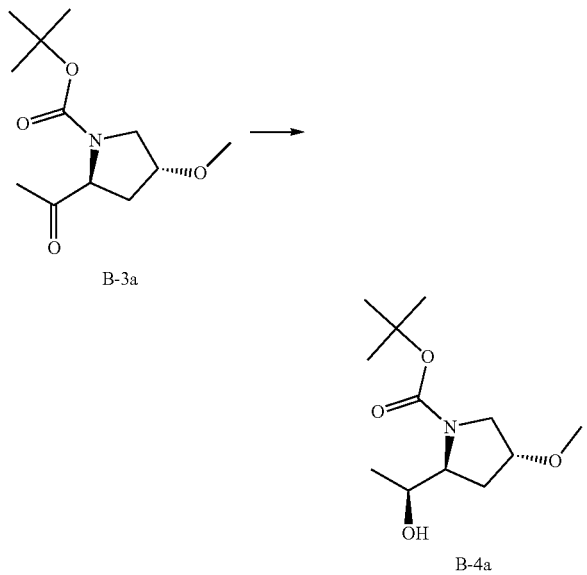

(R)-Methyl oxazaborolidine (0.99 g, 3.3 mmol, 0.20 equiv.) is dissolved in THF (2 mL) under an argon atmosphere and cooled to −5° C. Borane-dimethyl sulfide complex (1.0 M, 22 mL 22.0 mmol, 1.3 equiv.) is added. The mixture is stirred for 30 min at rt. The mixture is cooled to −5° C. and B-3a (4.1 g, 17 mmol, 1 equiv.) is added slowly, dropwise. The reaction is stirred at rt for 1 h. After complete conversion of starting material, the reaction is cooled to −10° C. and quenched by addition of MeOH. The mixture is concentrated under reduced pressure. The residue is dissolved in water (150 mL) and formic acid (0.5 mL) and extracted with DCM (3×). The combined organic phase is concentrated under reduced pressure and purified by NP chromatography to give the product B-4a.

The following intermediates B-4 (Table 3) are available in an analogous manner. The crude product is purified by chromatography if necessary.

TABLE 3

| # | structure | $t_{ret}$ [min] | $[M + H]^+$ | HPLC method |
|---|---|---|---|---|
| B-4a | 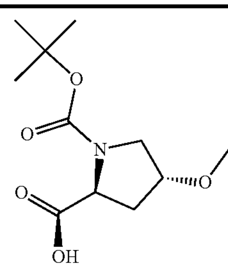 | 0.44 | 190 ($[M + H - tBu]^+$) | C |

TABLE 3-continued

| # | structure | $t_{ret}$ [min] | [M + H]⁺ | HPLC method |
|---|---|---|---|---|
| B-4b | 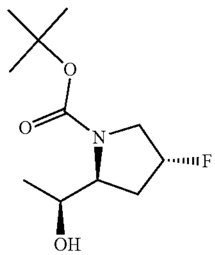 [SMILES: C[C@H](O)[C@@H]1C[C@@H](F)CN1C(=O)OC(C)(C)C] | 0.46 | 178 ([M + H − tBu]⁺) | C |
| B-4c | 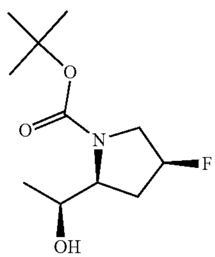 [SMILES: C[C@H](O)[C@@H]1C[C@H](F)CN1C(=O)OC(C)(C)C] | 1.96 | 178 ([M + H − tBu]⁺) | H |
| B-4d | 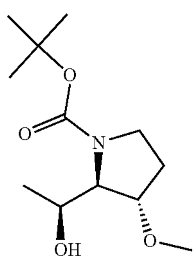 [SMILES: CO[C@H]1CCN(C(=O)OC(C)(C)C)[C@@H]1[C@H](C)O] | 0.44 | 190 ([M + H − tBu]⁺) | C |

Experimental Procedure for the Synthesis of B-5a

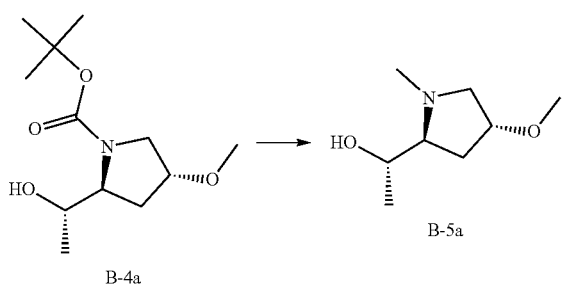 [SMILES: CO[C@@H]1C[C@@H]([C@H](C)O)N(C(=O)OC(C)(C)C)C1 ; CO[C@@H]1C[C@@H]([C@H](C)O)N(C)C1]

B-4a (306 mg, 12.5 mmol, 1.00 equiv.) is dissolved in THF, (30.6 mL) under an argon atmosphere. Lithium aluminium hydride (1 M in THF, 24.9 mL, 25.0 mmol, 2.00 equiv.) is added slowly. The reaction is stirred at 60° C. for 1 h. After complete conversion, the reaction is cooled to rt, Rochelle salt solution and KOH is added and stirred for 1 h. The existing suspension is extracted with DCM (3×), the combined organic phase is concentrated under reduced pressure to yield B-5a.

The following intermediates B-5 (Table 4) are available in an analogous manner. Deuterated intermediates B-5 are obtained analogously but lithium aluminium hydride is exchanged by lithium aluminium deuteride. The crude product is purified by chromatography if necessary.

TABLE 4

| # | structure | $t_{ret}$ [min] | [M + H]⁺ | HPLC method |
|---|---|---|---|---|
| B-5a | 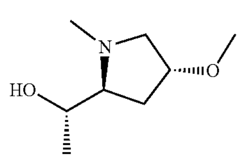 | 0.92 | 160 | A |

TABLE 4-continued

| # | structure | $t_{ret}$ [min] | $[M + H]^+$ | HPLC method |
|---|---|---|---|---|
| B-5b | 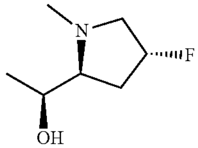 | 0.92 | 148 | A |
| B-5c | 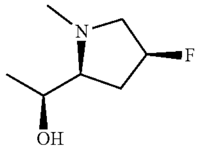 | 0.24 | 148 | H |
| B-5d | 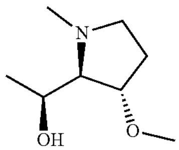 | 0.07 | 160 | C |
| B-5e | 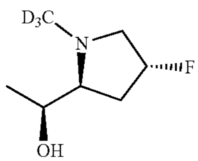 | 5.34 | 149 | V |

Experimental Procedure for the Synthesis of B-7a

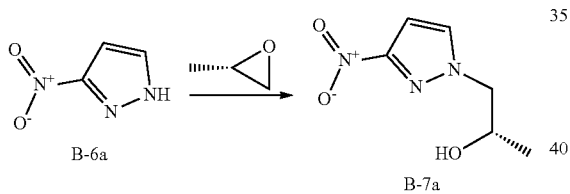

B-6a (502 mg, 4.22 mmol, 1.00 equiv.) is dissolved in ACN (6 mL), caesium carbonate (2.04 g, 6.24 mmol, 1.49 equiv.) and (2S)-2-methyloxirane (420 μL, 5.93 mmol, 1.41 equiv.) is added. The reaction is stirred for 18 h at 80° C. under a nitrogen atmosphere. After complete conversion, the reaction mixture is filtered, washed with ACN and the filtrate is concentrated under reduced pressure. The mixture is purified by RP chromatography yielding B-7a.

The intermediates B-7 (Table 5) are available in an analogous manner using the corresponding epoxide or alkyl halide. The crude product is purified by chromatography if necessary.

TABLE 5

| # | structure | $t_{ret}$ [min] | $[M + H]^+$ | HPLC method |
|---|---|---|---|---|
| B-7a | | 0.14 | 172 | C |
| B-7b | 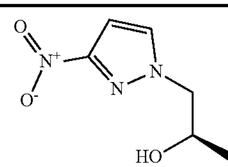 | 0.15 | 172 | C |
| B-7c | 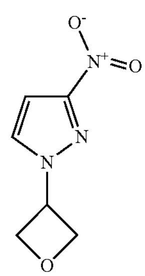 [SMILES: O=[N+]([O-])c1ccn(C2COC2)n1] | 0.31 | 170 | C |

Experimental Procedure for the Synthesis of B-8a

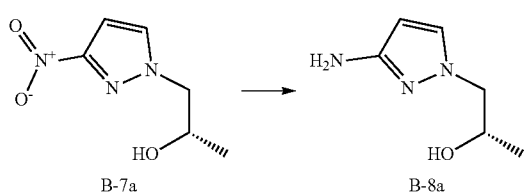

B-7a (545 mg, 3.18 mmol, 1.00 equiv.) is dissolved in EtOH (40 mL) and palladium (10% on carbon, 40.0 mg, 0.04 mmol, 0.01 equiv.) is added. The reaction is stirred under a hydrogen atmosphere (3 bar) for 4 h at rt. After complete conversion, the reaction mixture is filtered, washed with EtOH and concentrated under reduced pressure to give B-8a, which is used for the next step without purification.

The intermediates B-8 (Table 6) are available in an analogous manner. The crude product is purified by chromatography if necessary.

TABLE 6

| # | structure | $t_{ret}$ [min] | [M + H]$^+$ | HPLC method |
|---|---|---|---|---|
| B-8a | 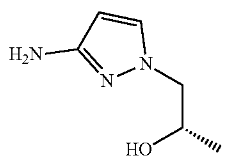 | 0.08 | 142 | C |
| B-8b | 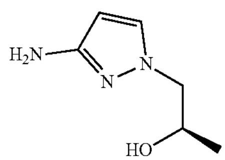 | 0.08 | 142 | C |
| B-8c | 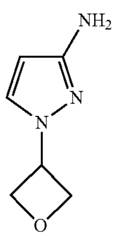 | 0.14 | 140 | A |

Experimental Procedure for the Synthesis of B-9a

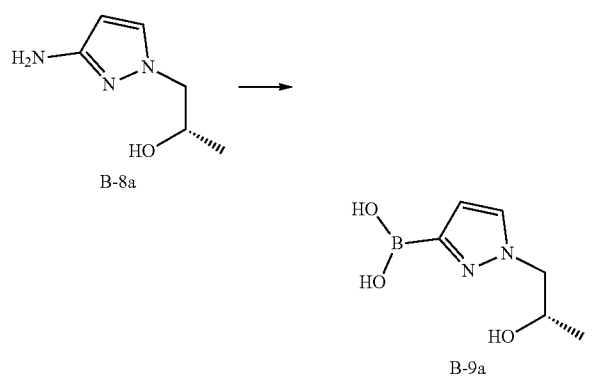

B-8a (222 mg, 1.57 mmol, 1.00 equiv.) and bis(pinacolato)diboron (450 mg, 1.73 mmol, 1.10 equiv.) are dissolved in ACN (5 mL). Tert-butyl nitrite (504 µL, 4.25 mmol, 2.70 equiv.) is added and the reaction is stirred for 2 h at 80° C. under nitrogen atmosphere. After complete conversion, the reaction mixture is concentrated under reduced pressure yielding B-9a, which is used for the next step without purification.

The intermediates B-9 (Table 7) are available in an analogous manner. The crude product is purified by chromatography if necessary.

TABLE 7

| # | structure | $t_{ret}$ [min] | [M + H]$^+$ | HPLC method |
|---|---|---|---|---|
| B-9a | 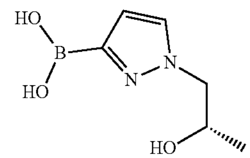 | 0.08 | 170 | C |
| B-9b | 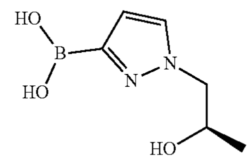 | 0.07 | 170 | C |
| B-9c | 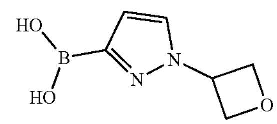 [SMILES: OB(O)c1ccn(C2COC2)n1] | 0.07 | 168 | C |

Experimental Procedure for the Synthesis of B-11a

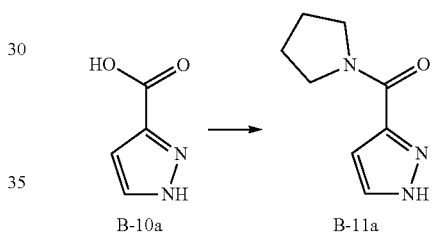

1H-Pyrazole-3-carboxylic acid (500 mg, 4.46 mmol, 1.00 equiv.) is dissolved in ACN (4.5 mL). Pyrrolidine (745 µL, 8.92 mmol, 2.00 equiv.), DIPEA (1.50 mL, 8.92 mmol, 2.00 equiv.) and 1-propanephosphonic anhydride (2.00 mL, 6.69 mmol, 1.50 equiv.) are added and the reaction mixture is stirred at rt for 1 h until complete conversion. The reaction mixture is diluted with saturated NaHCO$_3$ and extracted with DCM and the organic phase is dried, filtered and solvent is removed under vacuum. The crude product is purified via NP chromatography to obtain B-11a (HPLC method: C, $t_{ret}$=0.14 min; [M+H]$^+$=166).

Experimental Procedure for the Synthesis of B-13a

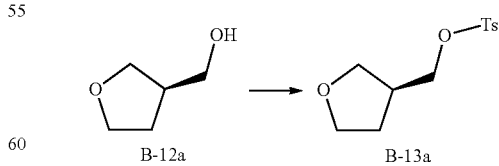

To a solution of B-12a (5.00 g, 4.90 mmol, 1.00 equiv.) and pyridine (7.75 g, 9.79 mmol, 2.00 equiv.) in DCM (50 ml) is added p-toluenesulfonyl chloride (14.0 g, 73.4 mol, 1.5 equiv.) at 0° C. The reaction mixture is allowed to warm to rt. After 16 h, the reaction mixture is diluted with water and extracted with DCM (2×). The combined organic layers are washed with HCl (1 M) and dried over with Na$_2$SO$_4$, then concentrated under vacuum to afford the product B-13a.

The intermediates B-13 (Table 8) are available in an analogous manner. The crude product is purified by chromatography if necessary.

TABLE 8

| # | structure | $t_{ret}$ [min] | [M + H]$^+$ | HPLC method |
|---|---|---|---|---|
| B-13a | 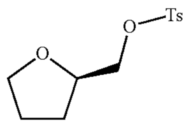 [SMILES: Cc1ccc(S(=O)(=O)OC[C@H]2CCCO2)cc1] | 2.37 | 257 | G |
| B-13b | 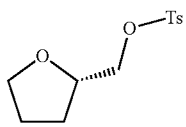 [SMILES: Cc1ccc(S(=O)(=O)OC[C@@H]2CCCO2)cc1] | 0.63 | 257 | C |
| B-13c | 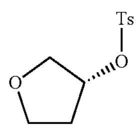 [SMILES: Cc1ccc(S(=O)(=O)O[C@@H]2CCOC2)cc1] | 1.08 | 260 | A |
| B-13d | 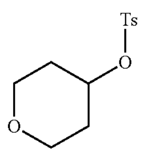 [SMILES: Cc1ccc(S(=O)(=O)OC2CCOCC2)cc1] | 1.14 | 274 | A |
| B-13e | 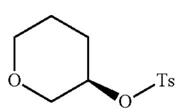 [SMILES: Cc1ccc(S(=O)(=O)O[C@@H]2CCCOC2)cc1] | 1.18 | 274 | A |
| B-13f | 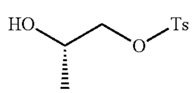 | 0.96 | 231 | A |
| B-13g | 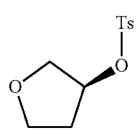 [SMILES: Cc1ccc(S(=O)(=O)O[C@H]2CCOC2)cc1] | 1.09 | 260 | A |
| B-13h | 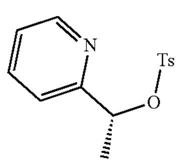 [SMILES: Cc1ccc(S(=O)(=O)O[C@H](C)c2ccccn2)cc1] | 0.60 | 278 | C |

Experimental Procedure for the Synthesis of B-15a

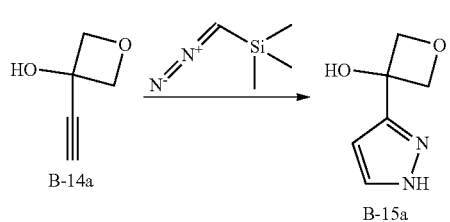

3-Ethynyloxetan-3-ol (120 mg, 1.16 mmol, 1.00 equiv.) and (trimethylsilyl)diazomethane (2M solution in hexanes, 2.00 mL, 4.00 mmol, 3.46 equiv.) are combined and stirred in a closed vial for 3 h at 50° C. until complete conversion. The reaction mixture is cooled to rt diluted with MeOH, and solvent is removed under vacuum to obtain crude B-15a (HPLC method: C, $t_{ret}$=0.08 min; [M+H]$^+$=141). The crude product is used for the next step without purification.

Synthesis of Pyrimidine Derivatives C

Experimental Procedure for the Synthesis of Intermediates C-2a

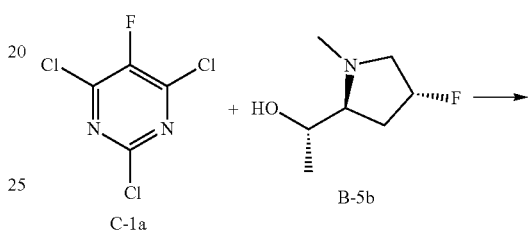

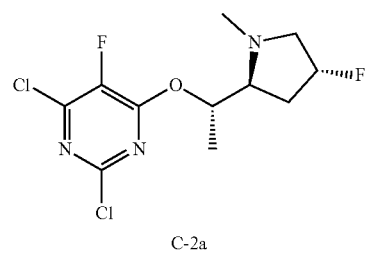

To a solution of 2,4,6-trichloro-5-fluoropyrimidine (1.00 g, 4.87 mmol, 1.00 equiv.) and B-5b (739 mg, 487 mmol, 1.00 equiv.) in THF (10 mL) at −78° C., sodium bis(trimethylsilyl)amide (1 M, 5.00 mL, 5.00 mmol, 1.03 equiv.) is added dropwise and the mixture is stirred for 10 min. After complete conversion, the reaction mixture is quenched with water, extracted with DCM, and the organic phase is dried, filtered, and concentrated. The crude product is purified via NP chromatography yielding C-2a (HPLC method: B, $t_{ret}$=1.00 min; [M+H]$^+$=312).

Experimental Procedure for the Synthesis of Intermediates C-3a

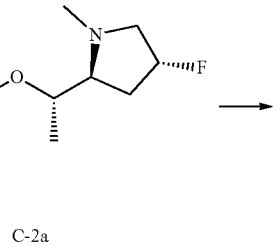

Experimental Procedure for the Synthesis of C-5a

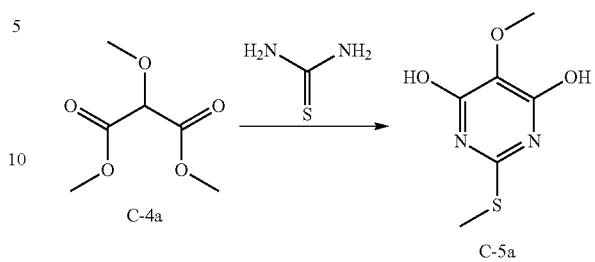

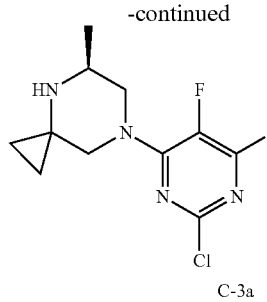
C-3a

To a solution of C-2a (445 mg, 1.43 mmol, 1.00 equiv.) in DMSO (1 mL) is added DIPEA (996 µL, 5.70 mmol, 4.00 equiv.) and (S)-5-methyl,4-7-diazaspiro[2.5]octane dihydrochloride (300 mg, 1.43 mmol, 1.00 equiv.). After 72 h at rt, complete conversion is observed. The crude product is purified via RP chromatography yielding C-3a.

The following intermediates C-3 (Table 9) are available in an analogous manner using the corresponding amine. The crude product is purified by chromatography if necessary.

To a stirred solution of 2-methoxy-malonic acid dimethyl ester (36.0 g, 222 mmol, 1.00 equiv.) and thiourea (25.4 g, 333 mmol, 1.50 equiv.) in MeOH (360 mL), sodium methoxide (27.8 g, 555 mmol, 2.5 equiv.) is added at rt and the mixture is stirred at 80° C. for 24 h. After complete conversion, iodomethane (41.0 g, 289 mmol, 1.30 equiv.) is added slowly at rt and the mixture is stirred at rt for 16 h. After complete conversion, the reaction mixture is concentrated, water is added, and the reaction mixture is stirred for 30 min. The product is collected by filtration, washed with water, and dried under vacuum. The crude product C-5a is used for the next step without purification. (HPLC method: H, $t_{ret}$=0.89 min; [M+H]$^+$=189).

TABLE 9

| # | structure | $t_{ret}$ [min] | [M + H]$^+$ | HPLC method |
|---|---|---|---|---|
| C-3a | 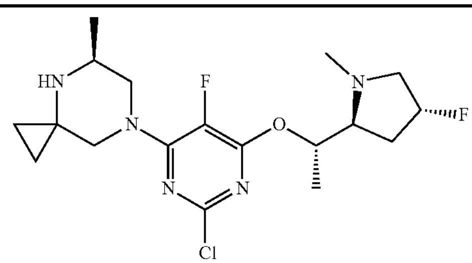 | 0.99 | 402 | B |
| C-3b | 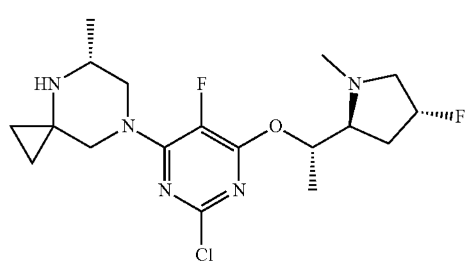 [SMILES: C[C@@H]1CN(c2nc(Cl)nc(O[C@@H](C)[C@@H]3C[C@@H](F)CN3C)c2F)CC2(CC2)N1] | 0.99 | 402 | B |
| C-3c | 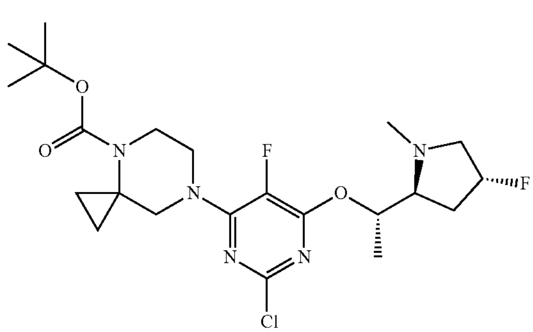 [SMILES: C[C@H](Oc1nc(Cl)nc(N2CCN(C(=O)OC(C)(C)C)C3(CC3)C2)c1F)[C@@H]1C[C@@H](F)CN1C] | 1.20 | 488 | B |

Experimental Procedure for the Synthesis of Intermediate C-6a

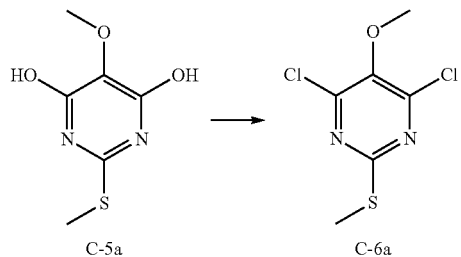

C-5a  →  C-6a

To a stirred mixture of C-5a (3.1 g, 16 mmol, 1.0 equiv.) and N,N-diethylaniline (0.4 mL) at 0° C., POCl₃ (13 g, 81 mmol, 5.0 equiv.) is added slowly and the resulting mixture is stirred for 16 h at 90° C. After complete conversion the mixture is cooled to rt, excess POCl₃ is evaporated, water is added, and the product is isolated by extraction with EtOAc. The crude product is purified via NP chromatography to obtain C-6a (HPLC method: H, $t_{ret}$=2.12 min; [M+H]⁺=225).

Experimental Procedure for the Synthesis of Intermediate C-7a

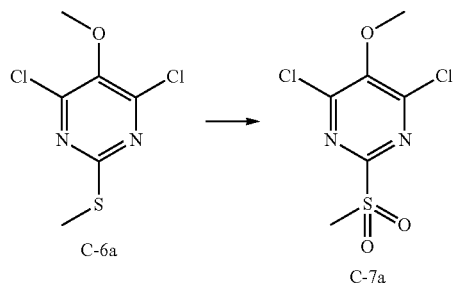

C-6a  →  C-7a

To a stirred solution of C-6a (24.0 g, 107 mmol, 1.00 equiv.) in DCM (240 mL) at 0° C., m-CPBA (55.0 g, 321 mmol, 3.0 equiv.) is added and the mixture is allowed to reach rt and stirred for additional 16 h. After complete conversion, the mixture is diluted with DCM washed with saturated NaHCO₃, and the organic layer is dried, filtered, and concentrated to yield C-7a which is used for the next step without purification. (HPLC method: H, $t_{ret}$=1.68 min; [M+H]⁺=257).

Experimental Procedure for the Synthesis of C-9a

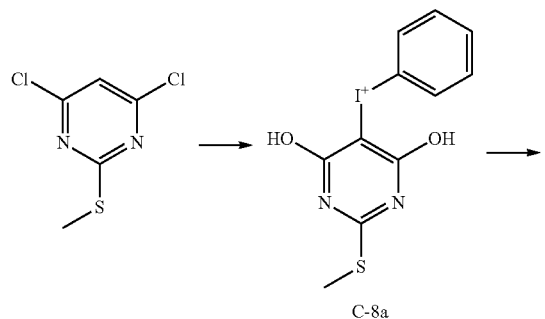

C-8a

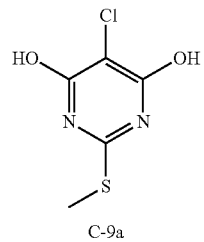

C-9a

6-Hydroxy-2-methylsulfanyl-3H-pyrimidin-4-one (120 g, 0.759 mol, 1.00 equiv.) and sodium carbonate (80.4 g, 0.759 mol, 1.00 equiv.) are dissolved in water (1898 mL). (Diacetoxyiodo)benzene (244.3 g, 0.759 mol, 1.00 equiv.) and sodium carbonate (80.4 g, 0.759 mol, 1.00 equiv.) are dissolved in water (1898 mL). The two solutions are combined and stirred at 40° C. for 2 h. The precipitate is filtered, washed with water, and dried to obtain C-8a which is used for the next step without purification.

HCl (2.8M, 140 mL, 0.389 mol, 0.70 equiv.) is added to a suspension of crude C-8a (200 g, 0.555 mol, 1.00 equiv.) in ethanol (1000 mL). The reaction mixture is heated to reflux for 20 min., concentrated under reduced pressure, and the residue obtained is washed with petroleum ether to obtain C-9a (HPLC method: H, $t_{ret}$=0.98 min; [M+H]⁺=193) which is used for the next step without purification.

Experimental Procedure for the Synthesis of Intermediate C-10a

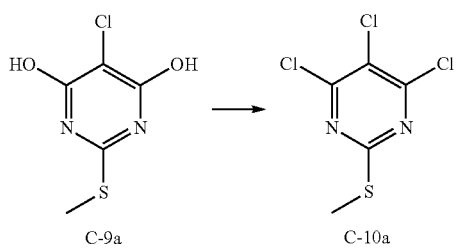

C-9a  →  C-10a

Crude C-9a (98.0 g, 0.509 mol, 1.00 equiv.) is added to a solution of freshly distilled POCl₃ (356 mL, 3.816 mol, 7.50 equiv.). The resulting mixture is heated to reflux for 16 h. After complete conversion the mixture is allowed to come to rt. The mixture is slowly added to ice-cold water, extracted with EtOAc, and the organic layers are dried, filtered and concentrated under reduced pressure. The crude product is purified by NP chromatography to obtain C-10a (HPLC method: G, $t_{ret}$=2.49 min; [M+H]⁺=229).

Experimental Procedure for the Synthesis of Intermediate C-11a

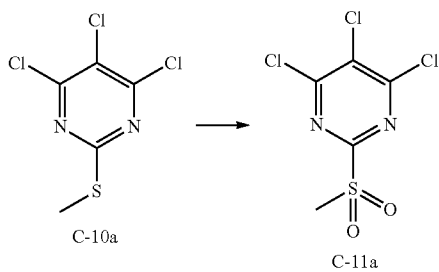

To a stirred solution of C-10a (60.0 g, 261 mmol, 1.00 equiv.) in DCM (1200 mL) at 0° C., m-CPBA (157.4 g, 915 mmol, 3.50 equiv.) is added and the mixture is allowed to reach rt and stirred for additional 16 h. After complete conversion, the mixture is diluted with DCM washed with aq. saturated NaHCO₃, and the organic layer is dried, filtered, and concentrated to yield C-11a which is used for the next step without purification. (HPLC method: V, $t_{ret}$=10.91 min; $[M+H]^+$=260).

Synthesis of Nitrile-Intermediates D

Experimental Procedure for the Synthesis of D-2a

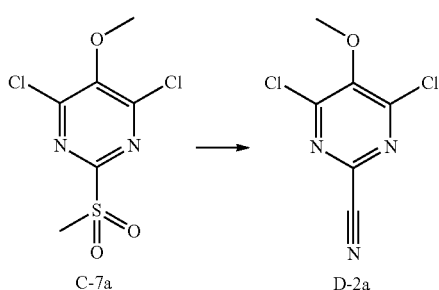

To a stirred solution of C-7a (24.0 g, 93.4 mmol, 1.0 equiv.) in ACN (216 mL) and water (24 mL) under nitrogen at 0° C., NaCN (5.49 g, 112 mmol, 1.2 equiv.) is added and the mixture is allowed to reach rt and stirred for additional 1 h. After complete conversion, water and EtOAc is added, the organic layer is separated, washed with water, dried, filtered, and concentrated and the crude product is purified via NP chromatography yielding D-2a.

The following intermediates D-2 (Table 10) are available in an analogous manner. The crude product is purified by chromatography if necessary.

TABLE 10

| # | structure | $t_{ret}$ [min] | $[M + H]^+$ | HPLC method |
|---|---|---|---|---|
| D-2a | (structure) | 1.85 | 204 | H |
| D-2b | (structure) | 6.78 | 207 | V |

Experimental Procedure for the Synthesis of D-6a

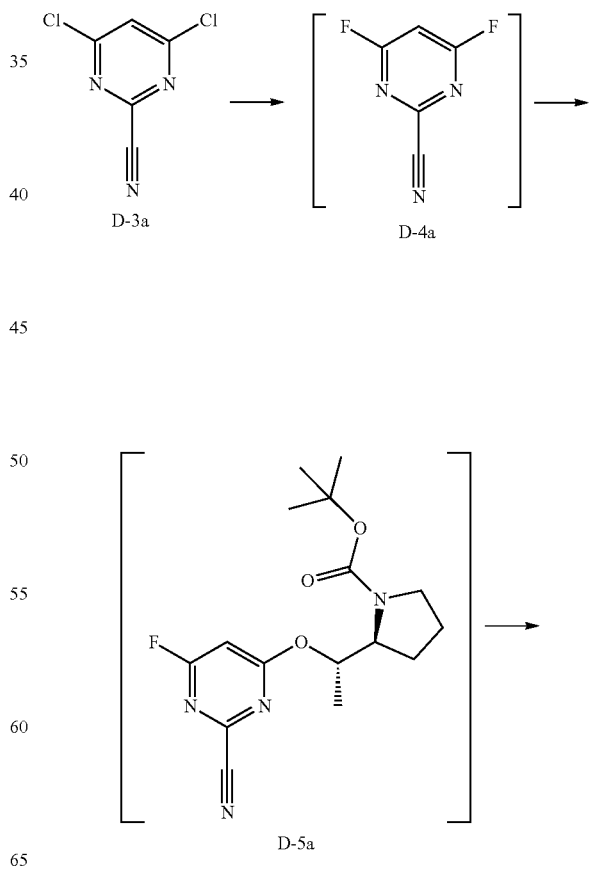

-continued

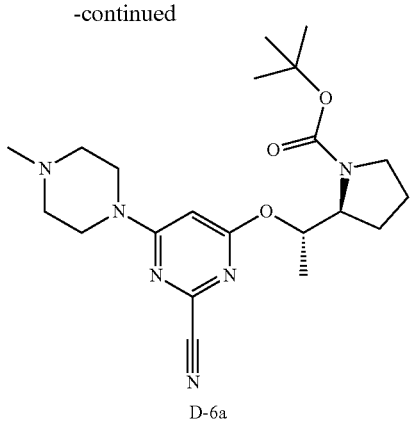

D-6a

To a solution of 4,6-dichloropyrimidine-2-carbonitrile D-3a (2000 mg, 10.356 mmol, 90% purity, 1.0 equiv.) in anhydrous DMSO (5 mL) is added cesium fluoride (6.286 g, 41.382 mmol, 4 equiv.) and the resulting mixture is stirred at 60° C. for 1 h until full conversion of the starting material to 4,6-difluoropyrimidine-2-carbonitrile D-4a is observed. The resulting suspension is filtered and the remaining solid is washed with anhydrous ACN (2 mL). Then tert-butyl-(2S)-2-[(1S)-1-hydroxyethyl]pyrrolidine-1-carboxylate (2449 mg, 11.376 mmol, 1.1 equiv.) and DIPEA (3.517 mL, 20.684 mmol, 2 equiv.) is added to the filtrate (8 mL), which is stirred at 60° C. for 1 h and after full conversion of the starting materials is observed N-methylpiperazine (1.262 mL, 11.376 mmol, 1.1 equiv.) is also added to the mixture. The mixture is then stirred at 60° C. for 30 min. After full conversion to D-5a is observed the reaction is filtered and the crude product is purified via RP chromatography yielding D-6a.

The following intermediates D-6 (Table 11) are available in an analogous manner. The crude product is purified by chromatography if necessary.

TABLE 11

| # | structure | $t_{ret}$ [min] | $[M + H]^+$ | HPLC method |
|---|---|---|---|---|
| D-6a | 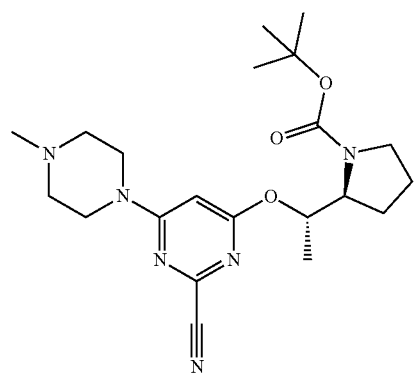 [SMILES: C[C@H](Oc1cc(N2CCN(C)CC2)nc(C#N)n1)[C@@H]1CCCN1C(=O)OC(C)(C)C] | 1.46 | 417 | A |
| D-6b | 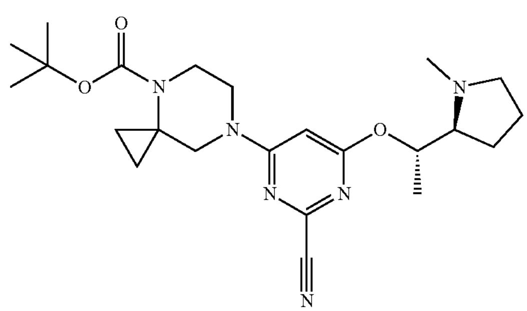 [SMILES: C[C@H](Oc1cc(N2CCN(C(=O)OC(C)(C)C)C3(CC3)C2)nc(C#N)n1)[C@@H]1CCCN1C] | 1.63 | 443 | A |
| D-6c | 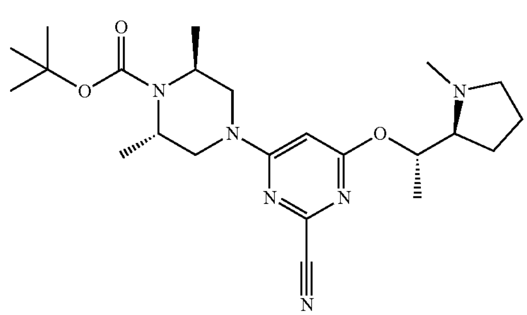 [SMILES: C[C@H](Oc1cc(N2C[C@H](C)N(C(=O)OC(C)(C)C)[C@@H](C)C2)nc(C#N)n1)[C@@H]1CCCN1C] | 0.91 | 445.2 | B |

TABLE 11-continued

| # | structure | $t_{ret}$ [min] | $[M + H]^+$ | HPLC method |
|---|---|---|---|---|
| D-6d | 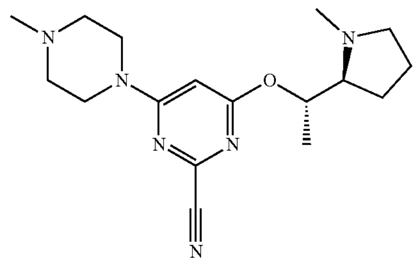 [SMILES: C[C@H](Oc1cc(N2CCN(C)CC2)nc(C#N)n1)[C@@H]1CCCN1C] | 1.15 | 331 | A |
| D-6e | 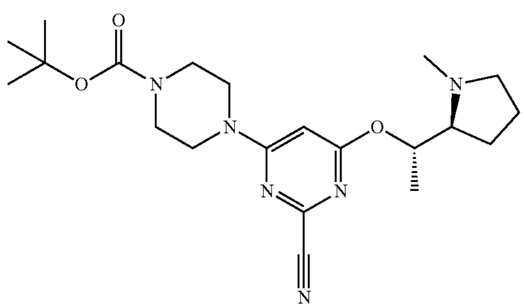 [SMILES: C[C@H](Oc1cc(N2CCN(C(=O)OC(C)(C)C)CC2)nc(C#N)n1)[C@@H]1CCCN1C] | 0.83 | 417 | C |

Experimental Procedure for the Synthesis of D-8a

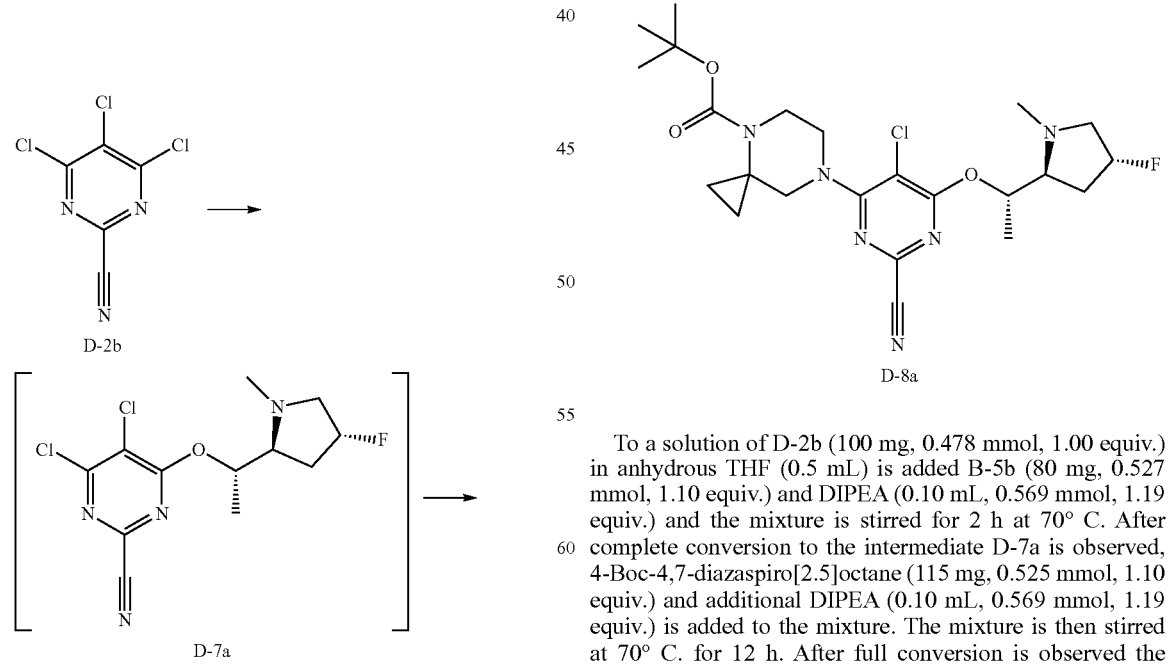

To a solution of D-2b (100 mg, 0.478 mmol, 1.00 equiv.) in anhydrous THF (0.5 mL) is added B-5b (80 mg, 0.527 mmol, 1.10 equiv.) and DIPEA (0.10 mL, 0.569 mmol, 1.19 equiv.) and the mixture is stirred for 2 h at 70° C. After complete conversion to the intermediate D-7a is observed, 4-Boc-4,7-diazaspiro[2.5]octane (115 mg, 0.525 mmol, 1.10 equiv.) and additional DIPEA (0.10 mL, 0.569 mmol, 1.19 equiv.) is added to the mixture. The mixture is then stirred at 70° C. for 12 h. After full conversion is observed the reaction mixture is concentrated and purified by RP chromatography to give the desired product D-8a (HPLC method: A, $t_{ret}$=1.74 min; $[M+H]^+$=495).

Experimental Procedure for the Synthesis of D-10a

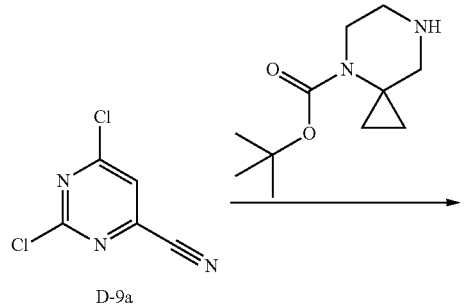

D-9a

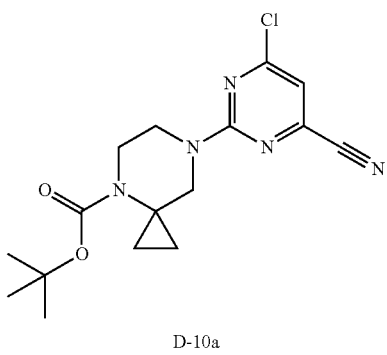

D-10a 2,6-Dichloropyrimidine-4-carbonitrile D-9a (3.0 g, 0.02 mol, 1.00 equiv.) is dissolved in DCM (21.4 mL), DIPEA (5.69 mL, 33.5 mmol, 2.00 equiv.) is added and cooled down at 0° C., 4-Boc-4,7-diazaspiro[2.5]octane (3.55 g, 0.02 mol, 1.00 equiv.) is added dropwise. The reaction is stirred at rt until complete conversion of starting material is observed. Mixture is concentrated under reduced pressure and purified by NP chromatography to give D-10a (HPLC method: A, $t_{ret}$=1.47 min; [M+H]$^+$=350).

Experimental Procedure for the Synthesis of D-11a

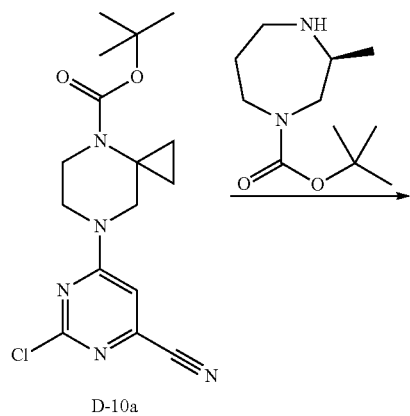

D-10a

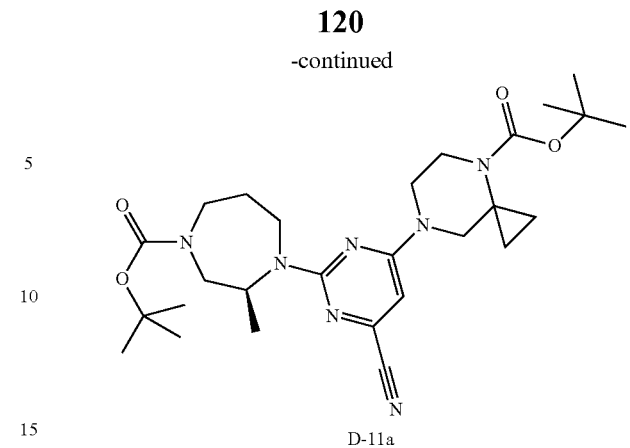

D-11a

D-10a (4.7 g, 0.01 mol, 1.00 equiv.) is dissolved in DMSO (10 mL), (S)-tert-butyl-3-methyl-1,4-diazepane-1-carboxylate (6.30 g, 0.03 mol, 2.10 equiv.) and DIPEA (4.69 mL, 0.03 mol, 2.00 equiv.) are added. The reaction is stirred overnight at 80° C. After complete conversion of starting material is observed the reaction is concentrated under reduced pressure and purified by RP chromatography to give D-11a (HPLC method: A, $t_{ret}$=1.72 min; [M+H]$^+$=528).

Experimental Procedure for the Synthesis of D-13a

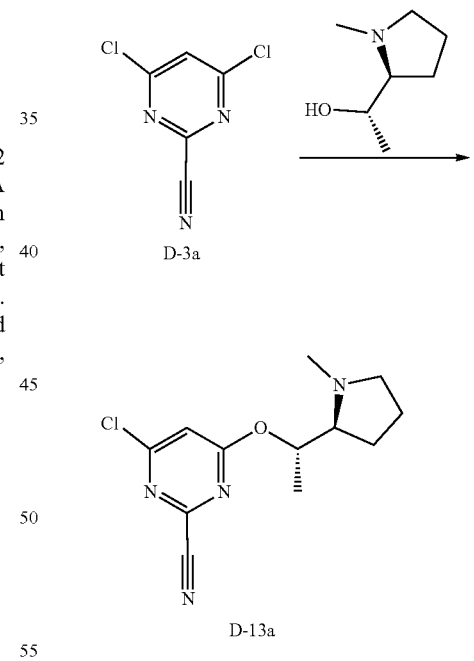

D-3a

D-13a 4,6-Dichloropyrimidine-2-carbonitrile D-3a (1.00 g, 5.74 mmol, 1.00 equiv.) and (1S)-1-[(2S)-1-methylpyrrolin-2-yl]ethanol (656 mg, 0.01 mol, 1.10 equiv.) are dissolved in DMSO (1 mL) and ACN (1 mL). DIPEA (1.62 mL, 0.01 mol, 2.00 equiv.) is added and the reaction is stirred for 2 h at 60° C. After full conversion of starting material is observed the reaction mixture is concentrated under reduced pressure and extracted with DCM/NaHCO$_3$. The combined organic phase is concentrated under reduced pressure and purified by RP chromatography, yielding D-13a (HPLC method: A, $t_{ret}$=1.31 min; [M+H]$^+$=267).

Synthesis of Esters and Acids E

Experimental Procedure for the Synthesis of Intermediates E-1a

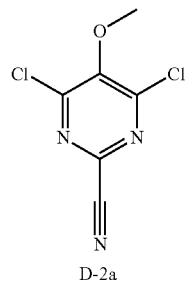

D-2a

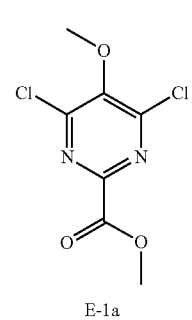

E-1a

D-2a (7.00 g, 34.3 mmol, 1.0 equiv.) is added to a stirred solution of HCl (4 M in MeOH, 105 mL, 420 mmol, 12.4 equiv.) at 0° C. The mixture is allowed to reach rt and stirred for additional 16 h. After complete conversion, the reaction mixture is concentrated and the crude product is purified via NP chromatography to give the desired product E-1a (HPLC method: H, $t_{ret}$=1.48 min; [M+H]$^+$=237).

Experimental Procedure for the Synthesis of Intermediates E-2a

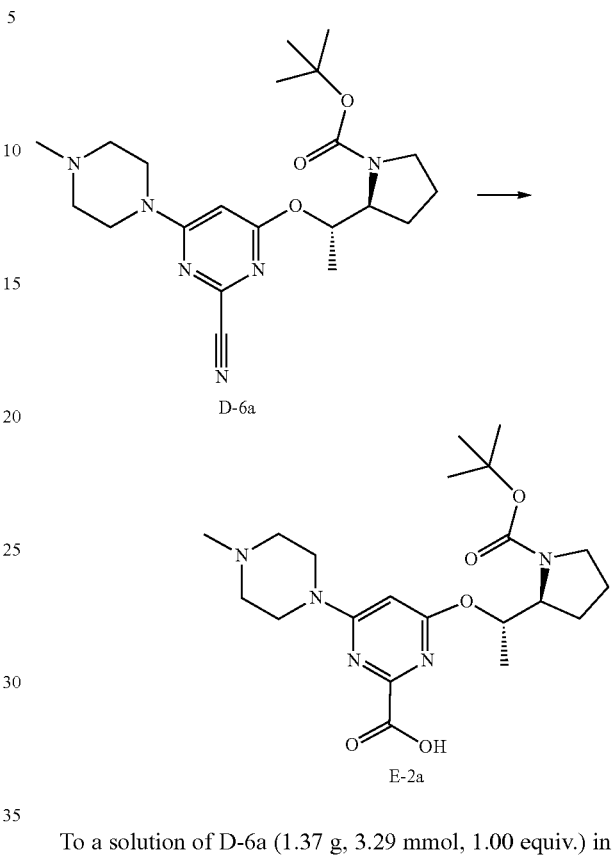

To a solution of D-6a (1.37 g, 3.29 mmol, 1.00 equiv.) in MeOH (5 mL) is added a solution of sodium hydroxide (4 M in water, 4.93 mL, 19.7 mmol, 6.00 equiv.) and the resulting mixture is stirred at 65° C. for 2 h. After complete conversion, the solvent is removed under reduced pressure, and the mixture is neutralized and purified by RP chromatography to give the desired product E-2a.

The following intermediates E-2 (Table 12) are available in an analogous manner. The crude product is purified by chromatography if necessary.

TABLE 12

| # | structure | $t_{ret}$ [min] | [M + H]$^+$ | HPLC method |
|---|-----------|-----------------|-------------|-------------|
| E-2a | 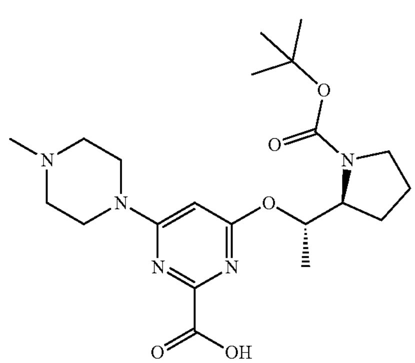 [SMILES: C[C@H](Oc1cc(N2CCN(C)CC2)nc(C(=O)O)n1)[C@@H]1CCCN1C(=O)OC(C)(C)C] | 0.41 | 436 | C |

TABLE 12-continued

| # | structure | t_ret [min] | [M + H]+ | HPLC method |
|---|---|---|---|---|
| E-2b | 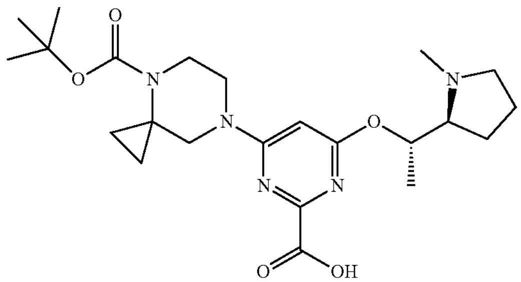 [SMILES: C[C@H](Oc1cc(N2CCN(C(=O)OC(C)(C)C)C3(CC3)C2)nc(C(=O)O)n1)[C@@H]1CCCN1C] | 0.99 | 462 | A |
| E-2c | 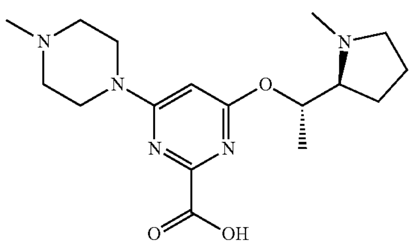 [SMILES: C[C@H](Oc1cc(N2CCN(C)CC2)nc(C(=O)O)n1)[C@@H]1CCCN1C] | 0.16 | 350 | C |
| E-2d | 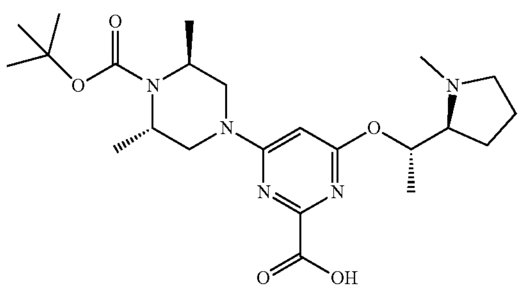 [SMILES: C[C@H](Oc1cc(N2C[C@H](C)N(C(=O)OC(C)(C)C)[C@@H](C)C2)nc(C(=O)O)n1)[C@@H]1CCCN1C] | 1.02 | 464 | A |
| E-2e | 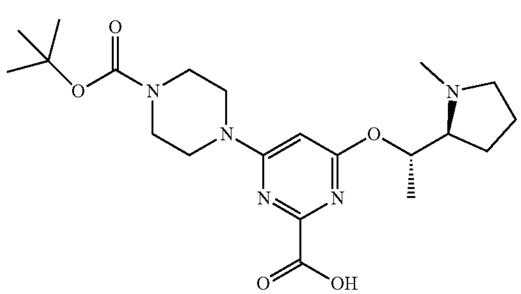 [SMILES: C[C@H](Oc1cc(N2CCN(C(=O)OC(C)(C)C)CC2)nc(C(=O)O)n1)[C@@H]1CCCN1C] | 0.43 | 436 | C |

Experimental Procedure for the Synthesis of Intermediates E-3a

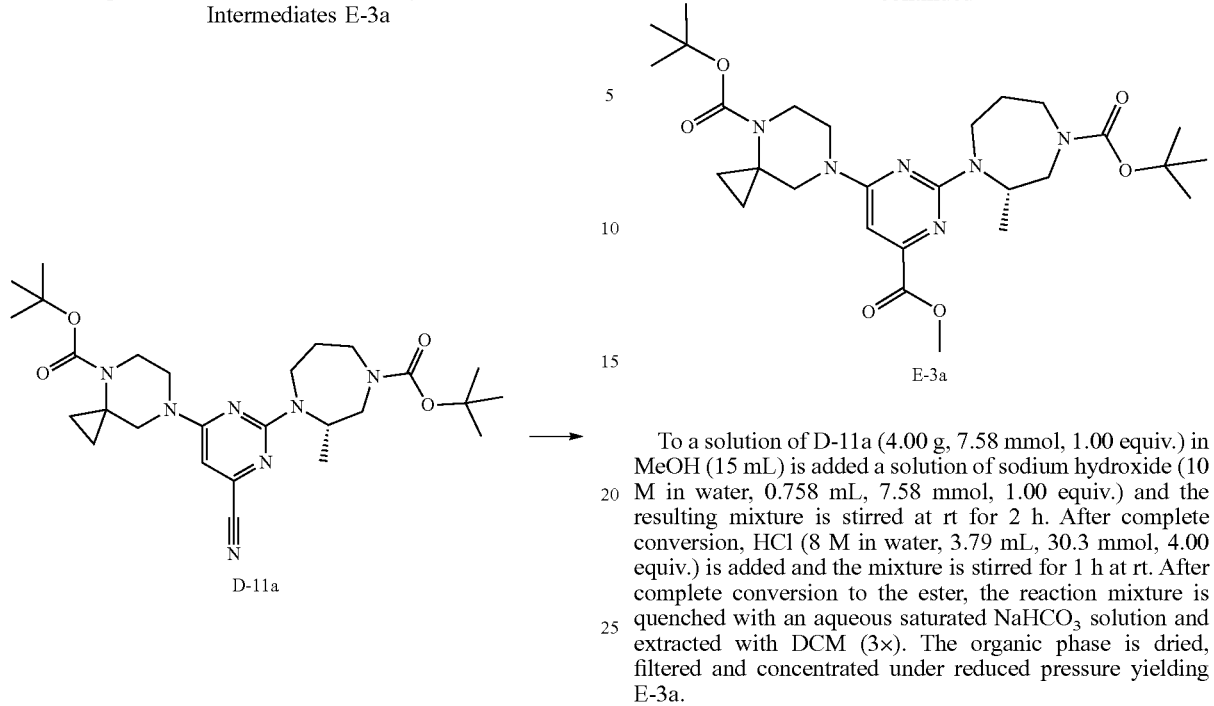

To a solution of D-11a (4.00 g, 7.58 mmol, 1.00 equiv.) in MeOH (15 mL) is added a solution of sodium hydroxide (10 M in water, 0.758 mL, 7.58 mmol, 1.00 equiv.) and the resulting mixture is stirred at rt for 2 h. After complete conversion, HCl (8 M in water, 3.79 mL, 30.3 mmol, 4.00 equiv.) is added and the mixture is stirred for 1 h at rt. After complete conversion to the ester, the reaction mixture is quenched with an aqueous saturated NaHCO$_3$ solution and extracted with DCM (3×). The organic phase is dried, filtered and concentrated under reduced pressure yielding E-3a.

The following intermediates E-3 (Table 13) are available in an analogous manner. The crude product is purified by chromatography if necessary.

TABLE 13

| # | structure | t$_{ret}$ [min] | [M + H]$^+$ | HPLC method |
|---|-----------|-----------------|-------------|-------------|
| E-3a | 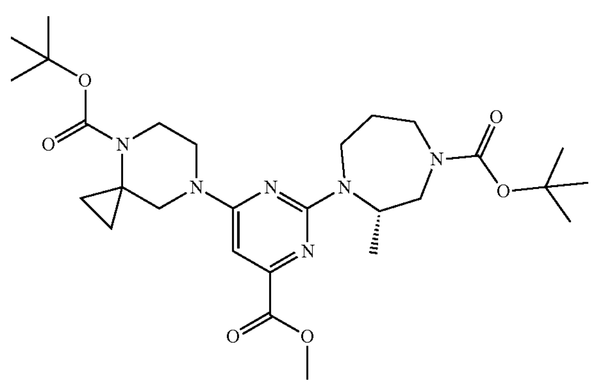 [SMILES: COC(=O)c1cc(N2CCN(C(=O)OC(C)(C)C)C3(CC3)C2)nc(N2CCCN(C(=O)OC(C)(C)C)C[C@@H]2C)n1] | 0.96 | 561 | C |
| E-3b | 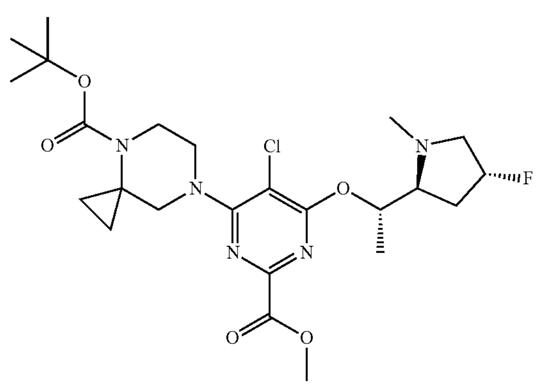 [SMILES: COC(=O)c1nc(O[C@@H](C)[C@@H]2C[C@@H](F)CN2C)c(Cl)c(N2CCN(C(=O)OC(C)(C)C)C3(CC3)C2)n1] | 1.65 | 528 | C |

Experimental Procedure for the Synthesis of E-4a

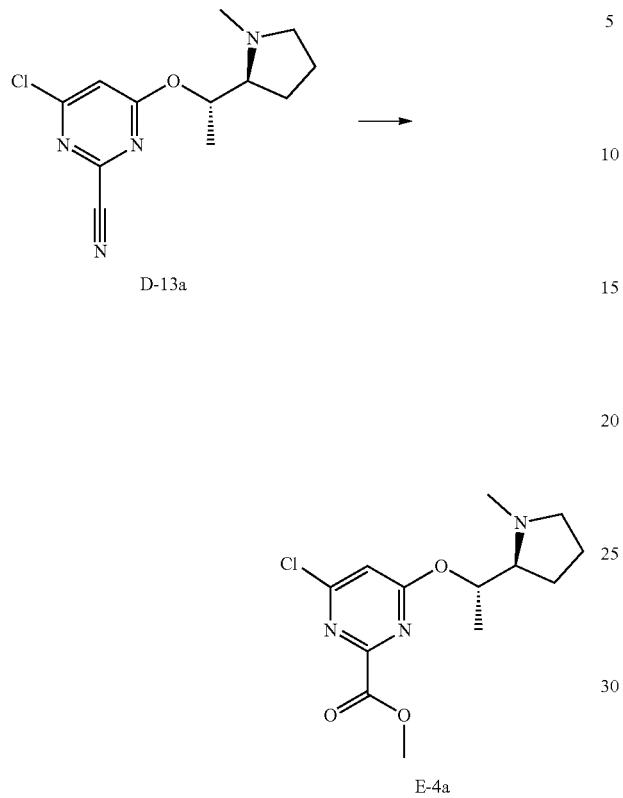

D-13a (400 mg, 1.49 mmol, 1.00 equiv.) is dissolved in MeOH (2 mL) and cooled to 0° C. Thionyl chloride (0.13 mL, 0.2 mmol, 1.20 equiv.) is added dropwise and stirred at rt until complete conversion of starting material is observed. The reaction mixture is cooled to 0° C. and quenched with NaHCO$_3$, then extracted with EtOAc. The combined organic phase is concentrated under reduced pressure and purified by NP chromatography yielding E-4a (HPLC method: K, $t_{ret}$=1.69 min; [M+H]$^+$=300).

Experimental Procedure for the Synthesis of E-5a

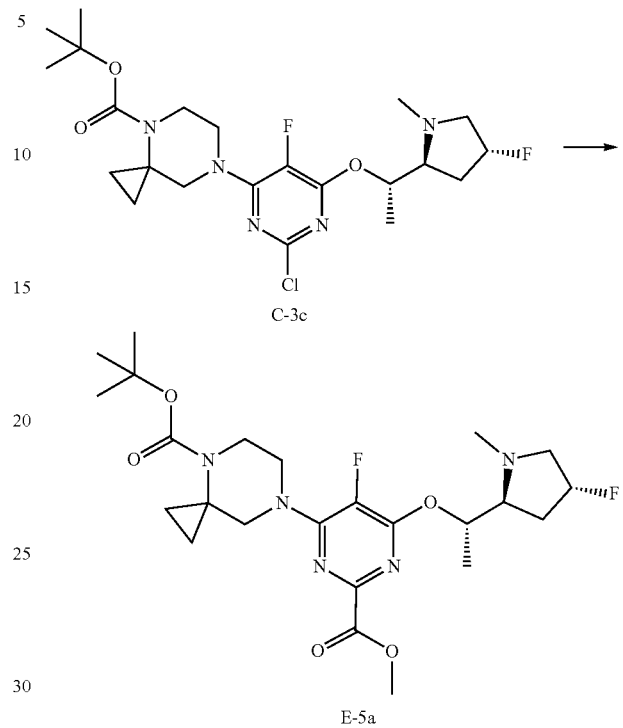

To a solution of C-3c (980 mg, 2.01 mmol, 1.00 equiv.) in MeOH (15 mL) is added TEA (0.835 mL, 6.03 mmol, 3.0 equiv.) and Pd(dppf)Cl$_2$ CH$_2$Cl$_2$ (166 mg, 0.201 mmol, 0.10 equiv.). The mixture is stirred for 22 h at 90° C. under CO pressure (150 psi) in a pressure reactor. After complete conversion, the reaction mixture is diluted with aqueous saturated NaHCO$_3$ solution and extracted with DCM. The organic phase is dried, filtered and concentrated and the crude product is purified via RP chromatography yielding E-5a.

The following intermediates E-5 (Table 14) are available in an analogous manner. The crude product is purified by chromatography if necessary.

TABLE 14

| # | structure | $t_{ret}$ [min] | [M + H]$^+$ | HPLC method |
|---|---|---|---|---|
| E-5a | 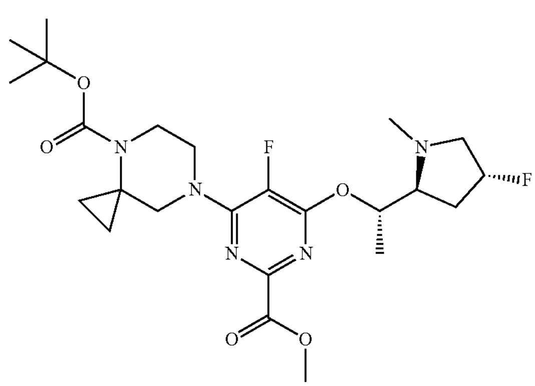 [SMILES: COC(=O)c1nc(O[C@@H](C)[C@@H]2C[C@@H](F)CN2C)c(F)c(N2CCN(C(=O)OC(C)(C)C)C3(CC3)C2)n1] | 1.11 | 512 | B |

TABLE 14-continued

| # | structure | $t_{ret}$ [min] | $[M + H]^+$ | HPLC method |
|---|---|---|---|---|
| E-5b | 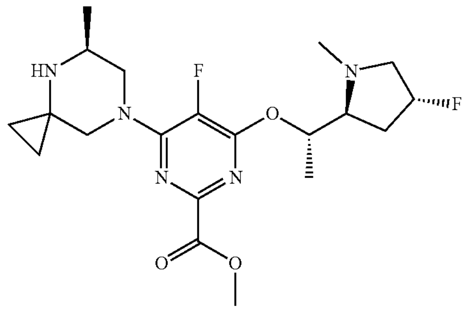 [SMILES: COC(=O)c1nc(O[C@@H](C)[C@@H]2C[C@@H](F)CN2C)c(F)c(N2C[C@H](C)NC3(CC3)C2)n1] | 0.86 | 426 | B |
| E-5c | 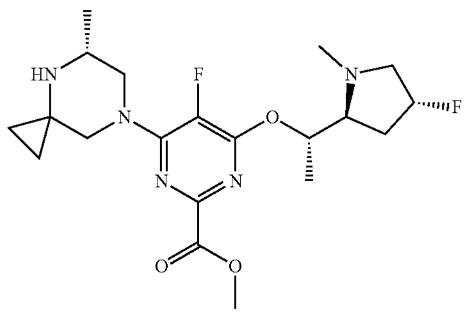 [SMILES: COC(=O)c1nc(O[C@@H](C)[C@@H]2C[C@@H](F)CN2C)c(F)c(N2C[C@@H](C)NC3(CC3)C2)n1] | 0.86 | 426 | B |

Experimental Procedure for the Synthesis of Intermediates E-7a

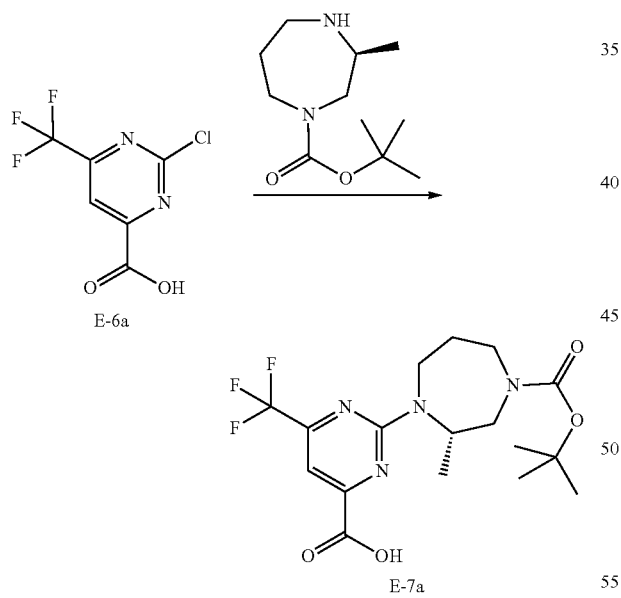

2-Chloro-6-(trifluoromethyl)pyrimidine-4-carbocylic acid E-6a (1.00 g, 4.19 mmol, 1.00 equiv.) is dissolved in DMSO (2 mL), (S)-Tert-butyl-3-methyl-1,4-diazepane-1-carboxylate (1.97 g, 8.81 mmol, 2.1 equiv.) and DIPEA (1.83 mL, 0.01 mmol, 2.50 equiv.) is added. The reaction is stirred overnight at 80° C. After complete conversion of starting material is observed the mixture is purified by RP chromatography.

The following intermediates E-7 (Table 15) are available in an analogous manner. The crude product is purified by chromatography if necessary.

TABLE 15

| # | structure | $t_{ret}$ [min] | $[M + H]^+$ | HPLC method |
|---|---|---|---|---|
| E-7a | 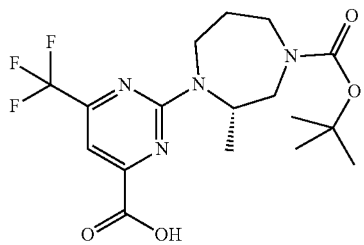 [SMILES: C[C@H]1CN(C(=O)OC(C)(C)C)CCCN1c1nc(C(=O)O)cc(C(F)(F)F)n1] | 0.53 | 349 | C |
| E-7b | 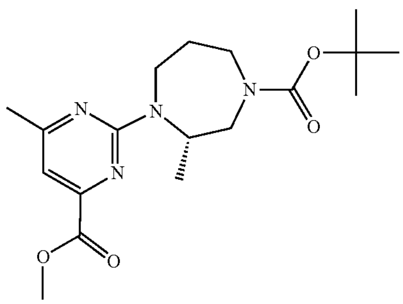 [SMILES: COC(=O)c1cc(C)nc(N2CCCN(C(=O)OC(C)(C)C)C[C@@H]2C)n1] | 0.84 | 365 | C |

Experimental Procedure for the Synthesis of Intermediates E-9a

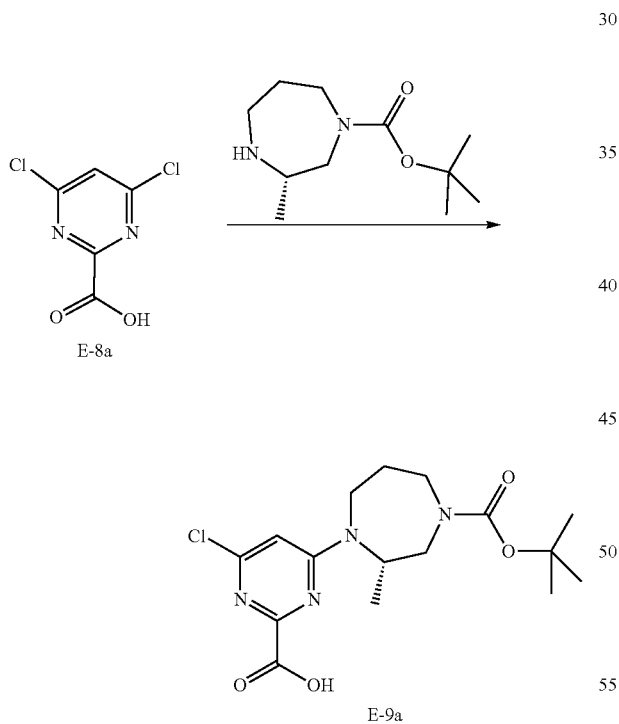

E-8a

E-9a 4,6-Dichloropyrimidine-2-carboxylic acid E-8a (900 mg, 4.66 mmol, 1.00 equiv.) is dissolved in DMSO (2 mL) and DIPEA (1.5 mL, 8.8 mmol, 2.0 equiv.) and (S)-tert-butyl 3-methyl-1,4-diazepane-1-carboxylate (1.04 g, 4.896 mmol, 95% purity, 1.05 equiv.) is added dropwise. The reaction mixture is then stirred at 40° C. for 18 h. The mixture is diluted with ACN and purified by RP chromatography to give the desired product E-9a (HPLC method: A, $t_{ret}$=0.82 min; $[M+H]^+$=371).

Experimental Procedure for the Synthesis of Intermediates E-11a

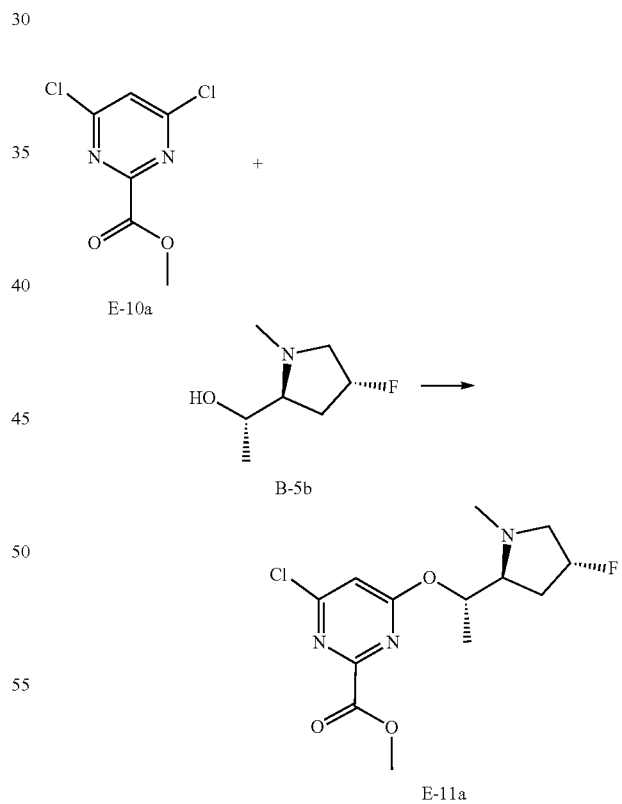

E-10a

B-5b

E-11a

E-10a (3.00 g, 14.5 mmol, 1.00 equiv.) is dissolved in DCM (30 mL) and DIPEA (5.34 mL, 29 mmol, 2.0 equiv.) and B-5b (3.20 g, 21.8 mmol, 1.5 equiv.) is added. The reaction mixture is then stirred at rt for 18 h. After complete conversion, the mixture is concentrated, water is added, and the mixture is extracted with EtOAc and the organic phases are washed with brine, dried, filtered and concentrated. The crude product is purified by NP chromatography yielding E-11a.

The following intermediates E-11 (Table 16) are available in an analogous manner. The crude product E-11 is purified by chromatography if necessary.

TABLE 16

| # | structure | $t_{ret}$ [min] | $[M + H]^+$ | HPLC method |
|---|---|---|---|---|
| E-11a | 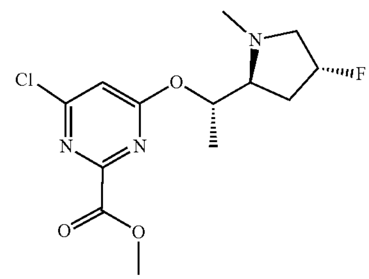 [SMILES: COC(=O)c1nc(Cl)cc(O[C@@H](C)[C@@H]2C[C@@H](F)CN2C)n1] | 1.13 | 318 | A |
| E-11b | 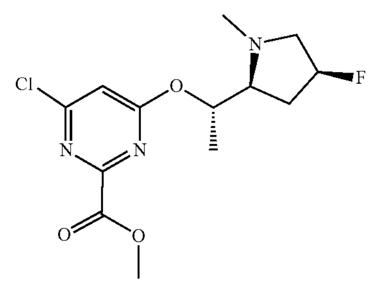 [SMILES: COC(=O)c1nc(Cl)cc(O[C@@H](C)[C@@H]2C[C@H](F)CN2C)n1] | 1.02 | 318 | H |
| E-11c | 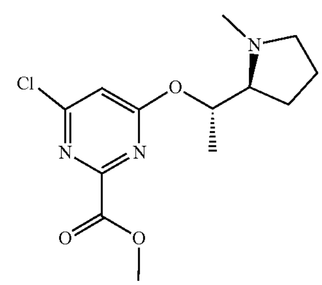 [SMILES: COC(=O)c1nc(Cl)cc(O[C@@H](C)[C@@H]2CCCN2C)n1] | 0.67 | 207 | A |
| E-11d | 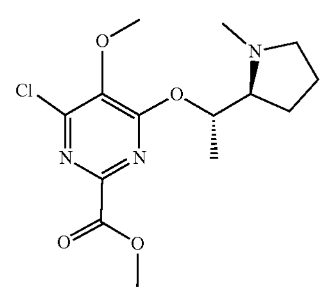 [SMILES: COC(=O)c1nc(Cl)c(OC)c(O[C@@H](C)[C@@H]2CCCN2C)n1] | 1.09 | 330 | H |

Experimental Procedure for the Synthesis of E-11e

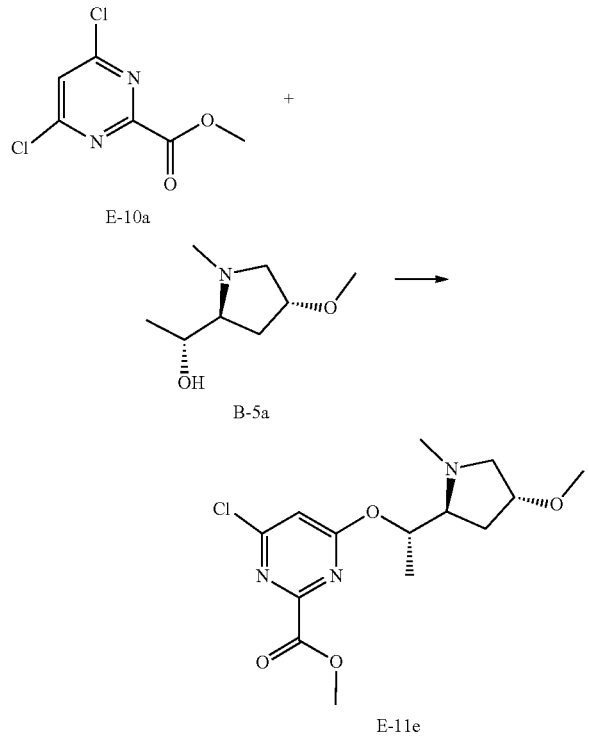

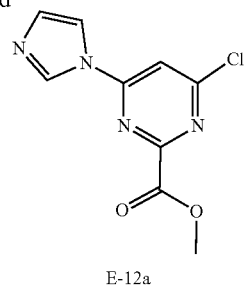

E-12a

Methyl 4,6-dichloropyrimidine-2-carboxylate (450 mg, 21.4 mmol, 1 equiv.) is dissolved in THF (18 mL). In a second flask imidazole (1.42 mg, 20.7 mmol, 0.97 equiv.) is dissolved in THF (18 mL) and cooled to 0° C., LiHMDS (20.1 mL, 20.1 mmol, 0.94 equiv.) is added dropwise. At −30° C. the LiHMDS/Imidazol solution is added dropwise to the solution of E-10a. The reaction is stirred 30 min at rt. After complete conversion is observed the reaction is concentrated under reduced pressure and purified by NP chromatography to give E-12a (HPLC method: C, $t_{ret}$=0.23 min; [M+H]$^+$=239).

Experimental Procedure for the Synthesis of E-13a

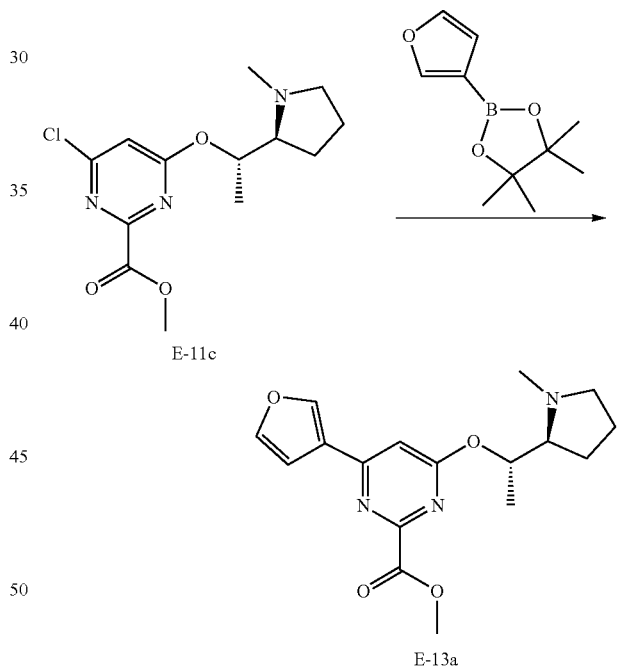

B-5a (100 mg, 0.48 mmol, 1.00 equiv.) is dissolved in THF (500 µL), LiHMDS (591 µL, 0.59 mmol, 1.10 equiv.) is added and stirred for 5 min. Meanwhile methyl 4,6-dichloropyrimidine-2-carboxylate (170 mg, 0.81 mmol, 1.5 equiv.) is dissolved in THF (500 µL). The solution of B-5a is added dropwise over 5 min to the methyl 4,6-dichloropyrimidine-2-carboxylate solution. The reaction is stirred for 25 min. After complete conversion of starting material is observed, the reaction is filtered and purified by RP chromatography to give E-11e (HPLC method: A, $t_{ret}$=1.08 min; [M+H]$^+$=330).

Experimental Procedure for the Synthesis of Intermediates E-12a

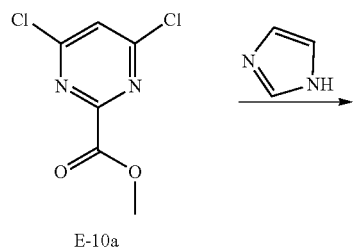

To the stirred mixture of E-11c (50.0 mg, 0.166 mmol, 1.00 equiv.), 2-Furan-3-yl-4,4,5,5-tetramethyl-[1,3,2]dioxaborolane (0.04 g, 0.206 mmol, 1.2 equiv.) and cesium carbonate (81.5 mg, 0.25 mmol, 1.50 equiv.) in dioxane (4.5 mL) in a sealed tube; argon gas is purged for 10 min then Pd(dppf)Cl$_2$ (36.6 mg, 0.05 mmol, 0.30 equiv.) is added at rt and the reaction is heated to 90° C. for 18 h. After complete conversion of starting material is observed, the mixture is filtered through Celite and washed with DCM. The Filtrate is concentrated under reduced pressure and purified by NP chromatography to give desire product E-13a.

The intermediates E-13 (Table 17) are available in an analogous manner. The crude product is purified by chromatography if necessary.

TABLE 17

| # | structure | $t_{ret}$ [min] | $[M + H]^+$ | HPLC method |
|---|---|---|---|---|
| E-13a | 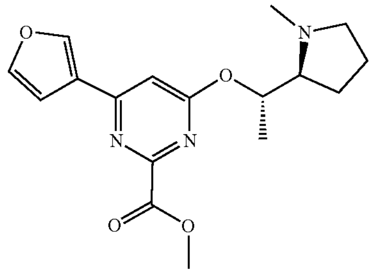 [SMILES: COC(=O)c1nc(O[C@@H](C)[C@@H]2CCCN2C)cc(-c2ccoc2)n1] | 1.56 | 332 | G |
| E-13b | 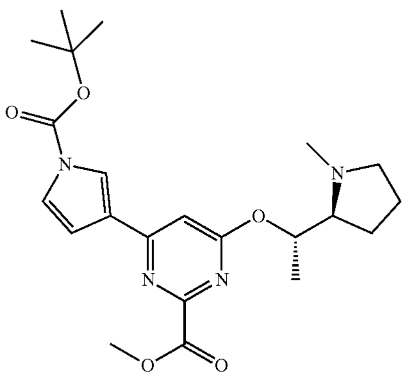 [SMILES: COC(=O)c1nc(O[C@@H](C)[C@@H]2CCCN2C)cc(-c2ccn(C(=O)OC(C)(C)C)c2)n1] | 1.57 | 431 | H |

Experimental Procedure for the Synthesis of E-14a and E-14b

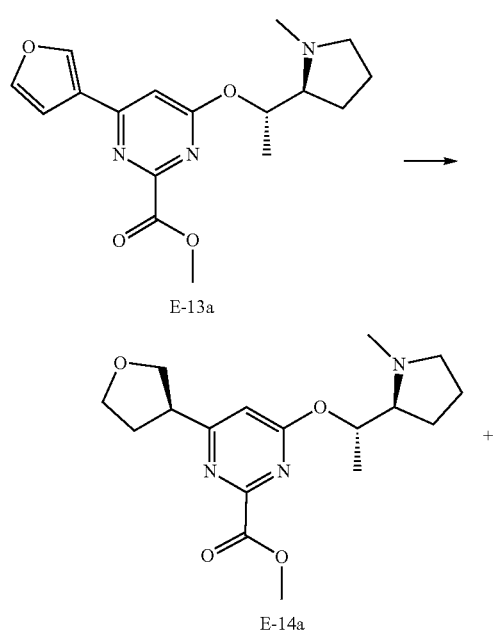

E-13a

E-14a

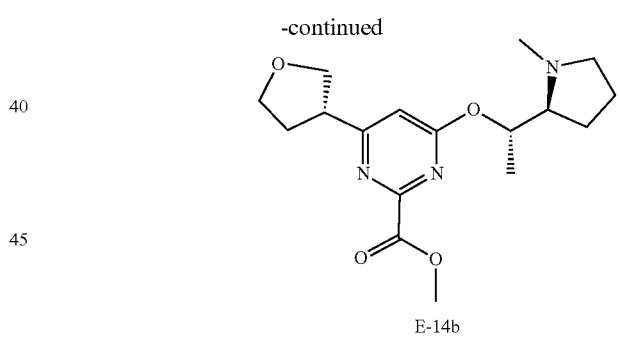

E-14b

E-13a (6.10 g, 0.02 mol, 1.00 equiv.) is dissolved in MeOH, palladium (10% on carbon, 5.88 mg, 0.06 mmol, 3.00 equiv.) is added and the reaction is stirred under a hydrogen atmosphere for 48 h at rt. After complete conversion of starting material is observed, the mixture is filtered and washed with 10% MeOH in DCM. The filtrate is concentrated under reduced pressure to give crude product.

The intermediates E-14 (Table 18) are available in an analogous manner. The crude product is purified by chromatography if necessary.

The diastereomeric mixture E-14a/b is purified by chiral HPLC (column/dimensions: Lux Amylose-2 (250×30) mm, 5 μm; solvent: n-hexane/ethanol (75:25); column temp: ambient) to give both diastereomers E-14a and E-14b (E-14a eluting as peak 1 before E-14b as peak 2).

TABLE 18

| # | structure | $t_{ret}$ [min] | $[M + H]^+$ | HPLC method |
|---|---|---|---|---|
| E-14a | 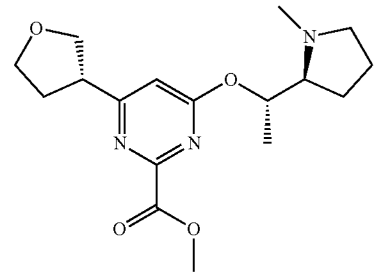 [SMILES: COC(=O)c1nc(O[C@@H](C)[C@@H]2CCCN2C)cc([C@@H]2CCOC2)n1] | 1.44 | 336 | G |
| E-14b | 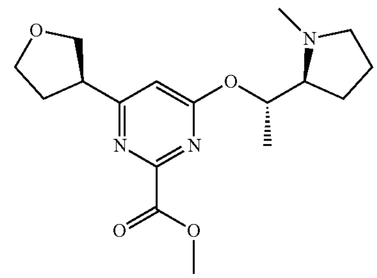 [SMILES: COC(=O)c1nc(O[C@@H](C)[C@@H]2CCCN2C)cc([C@H]2CCOC2)n1] | 1.48 | 336 | G |
| E-14c | 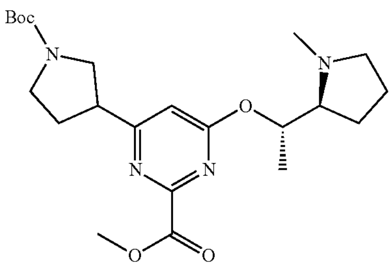 [SMILES: COC(=O)c1nc(O[C@@H](C)[C@@H]2CCCN2C)cc(C2CCN(C(=O)OC(C)(C)C)C2)n1] | 1.39 | 435 | H |

Experimental Procedure for the Synthesis of Intermediates E-15a

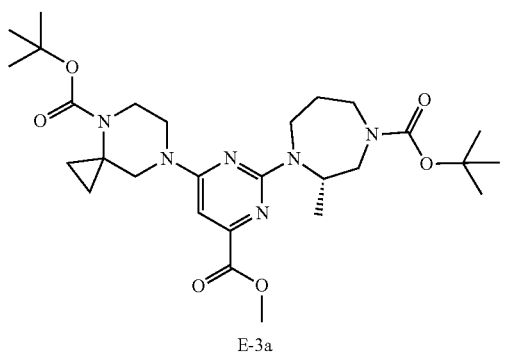
E-3a

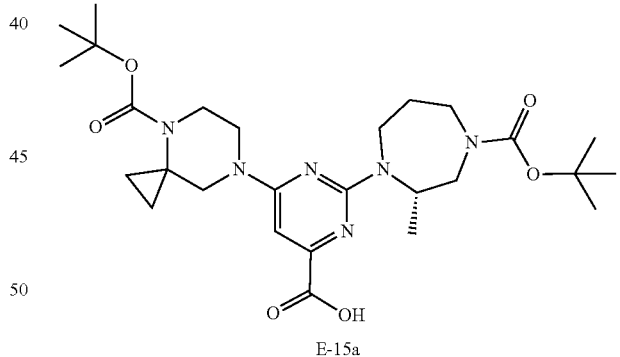
E-15a

To a solution of E-3a (4.20 g, 7.49 mmol, 1.00 equiv.) in ACN (5 mL) is added a solution of sodium hydroxide (1 M in water, 10.5 mL, 10.5 mmol, 1.40 equiv.) and the resulting reaction mixture is stirred at rt for 1.5 h. After complete conversion, the solvent is removed under reduced pressure and the remaining aqueous solution is carefully neutralized with an aqueous solution of HCl (8 M). The mixture is diluted with ACN and purified by acidic RP chromatography to give the desired product E-15a.

The following intermediates E-15 (Table 19) are available in an analogous manner. The crude product is purified by chromatography if necessary.

TABLE 19

| # | structure | $t_{ret}$ [min] | $[M + H]^+$ | HPLC method |
|---|---|---|---|---|
| E-15a | 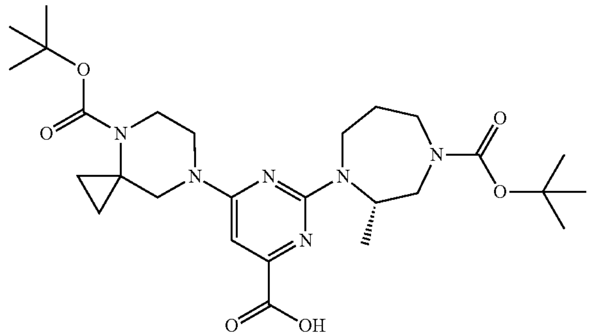 [SMILES: C[C@H]1CN(C(=O)OC(C)(C)C)CCCN1c1nc(C(=O)O)cc(N2CCN(C(=O)OC(C)(C)C)C3(CC3)C2)n1] | 1.22 | 547 | A |
| E-15b | 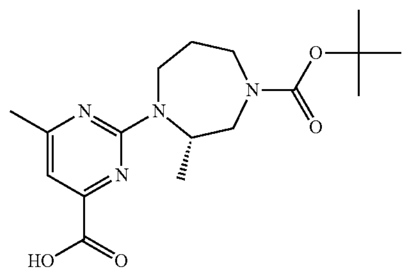 [SMILES: Cc1cc(C(=O)O)nc(N2CCCN(C(=O)OC(C)(C)C)C[C@@H]2C)n1] | 0.91 | 351 | A |
| E-15c | 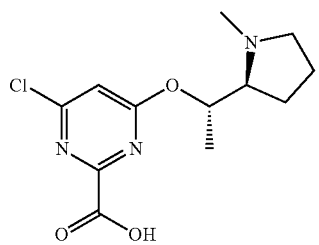 [SMILES: C[C@H](Oc1cc(Cl)nc(C(=O)O)n1)[C@@H]1CCCN1C] | 0.08 | 386 | C |

Experimental Procedure for the Synthesis of E-16a

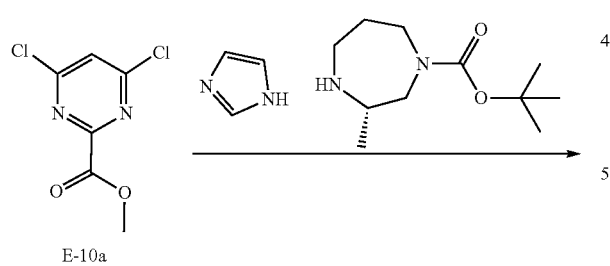

E-10a

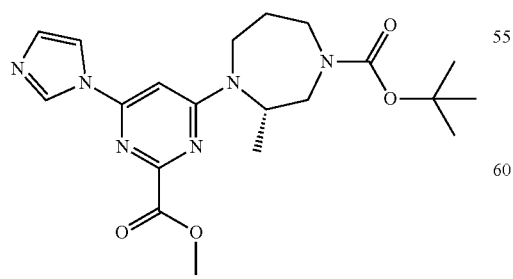

E-16a

To a solution of methyl 4,6-dichloropyrimidine-2-carboxylate E-10a (2.50, 11.8 mmol, 1.00 equiv.) in DMSO (2.00 mL) is added DIPEA (4.02 mL, 23.6 mmol, 2.00 equiv.) and a solution of imidazole (885 mg, 13.0 mmol, 1.10 equiv.) in ACN (2.00 mL). After 2 h at 45° C. full conversion is observed and (S)-tert-butyl 3-methyl-1,4-diazepane-1-carboxylate (2.90 g, 13.0 mmol, 1.10 equiv.) is added. The resulting reaction mixture is stirred over night at 45° C. The reaction mixture is diluted with brine and extracted with DCM. The combined organic phase is concentrated under reduced pressure and purified by RP chromatography to give the desired product E-16a (HPLC method: A, $t_{ret}$=1.16 min; $[M+H]^+$=417).

Synthesis of Diketones F

When multiple HPLC retention times are reported it means that different tautomers are present.

Experimental Procedure for the Synthesis of F-1a

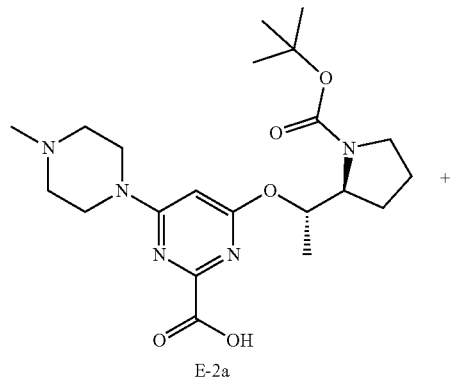

E-2a

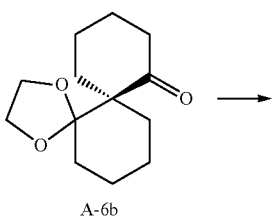

A-6b

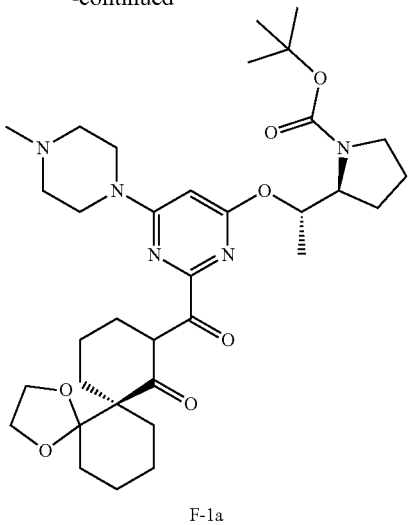

F-1a

E-2a (832 mg, 1.91 mmol, 1.0 equiv.) and 1-(1H-imidazole-1-carbonyl)-1H-imidazole (620 mg, 3.82 mmol, 2.0 equiv.) under Argon atmosphere are dissolved in THF (5 mL) and stirred 1 h at rt. After completely activation of acid a solution of A-6b (473 mg, 2.01 mmol, 1.1 equiv.) and LiHMDS (1.0 M in THF, 4 mL, 4.01 mmol, 2.1 equiv.) is added to the reaction mixture and washed with THF (5 mL). The resulting mixture is stirred overnight at 60° C. After full conversion, the reaction is diluted with an aqueous saturated NaHCO$_3$ solution and extracted three times with DCM. The organic phases are combined, dried, filtered and concentrated under reduced pressure to give the crude product. The crude product is dissolved in ACN and water, filtered and purified by basic RP chromatography to give the desired product F-1a.

The intermediates F-1 (Table 20) are available in an analogous manner. The crude product F-1 is purified by chromatography if necessary.

TABLE 20

| # | structure | t$_{ret}$ [min] | [M + H]$^+$ | HPLC method |
|---|---|---|---|---|
| F-1a | 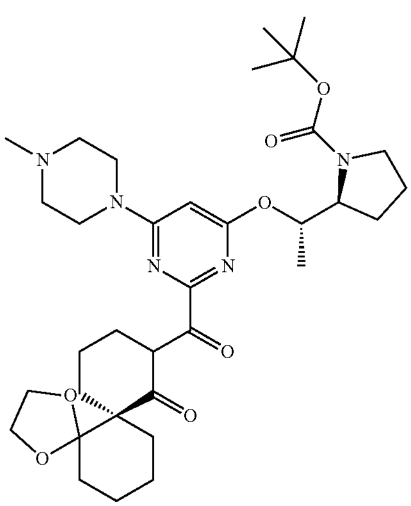 | 0.89 0.92 1.02 | 642 | C |

TABLE 20-continued

| # | structure | $t_{ret}$ [min] | [M + H]$^+$ | HPLC method |
|---|---|---|---|---|
| F-1b | 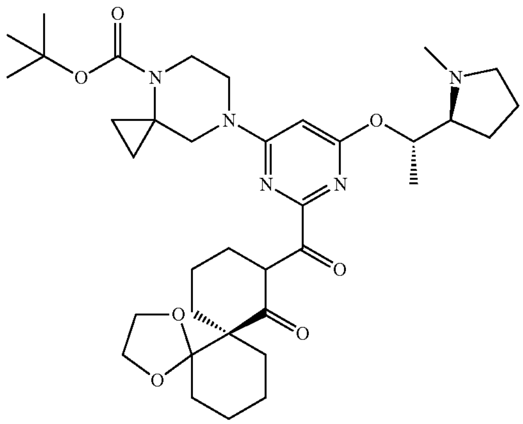 | 0.96<br>1.02<br>1.15 | 668 | C |
| F-1c | 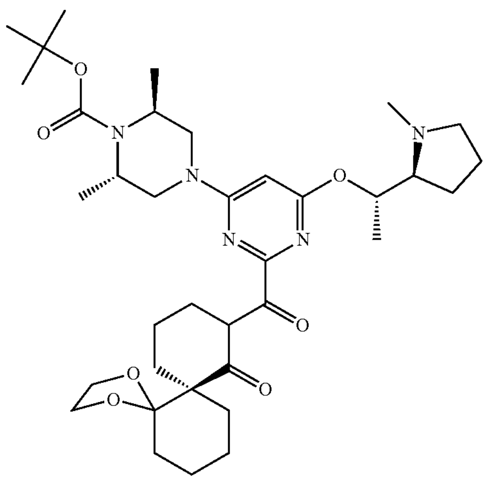 | 1.74<br>1.80<br>1.94 | 670 | A |
| F-1d | 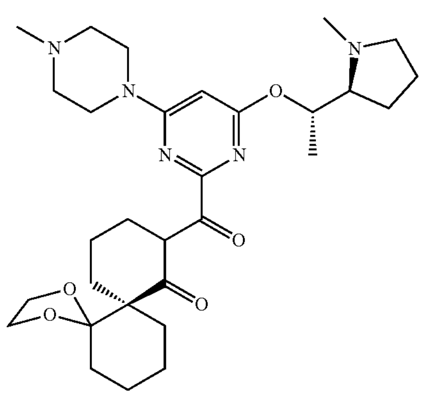 | 0.72<br>0.79<br>0.88 | 556 | C |

TABLE 20-continued

| # | structure | t_ret [min] | [M + H]+ | HPLC method |
|---|---|---|---|---|
| F-1e | 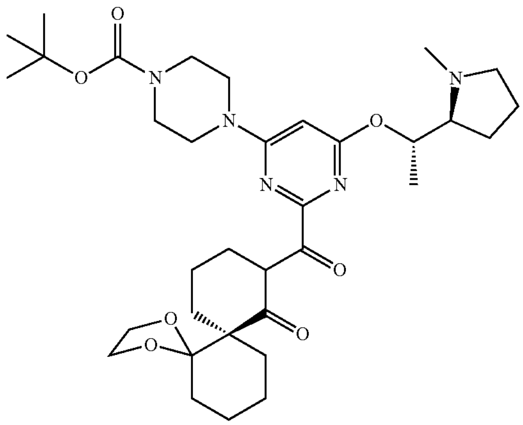 | 0.92<br>0.99<br>1.05<br>1.08 | 642 | C |
| F-1f | 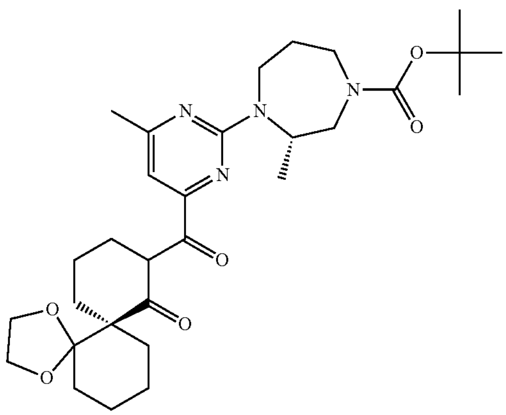 | 0.82<br>0.90<br>1.15 | 557 | L |
| F-1g | 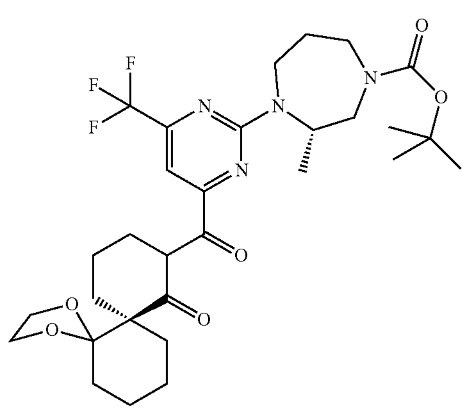 | 1.03<br>1.09 | 611 | C |

TABLE 20-continued

| # | structure | $t_{ret}$ [min] | $[M + H]^+$ | HPLC method |
|---|---|---|---|---|
| F-1h | 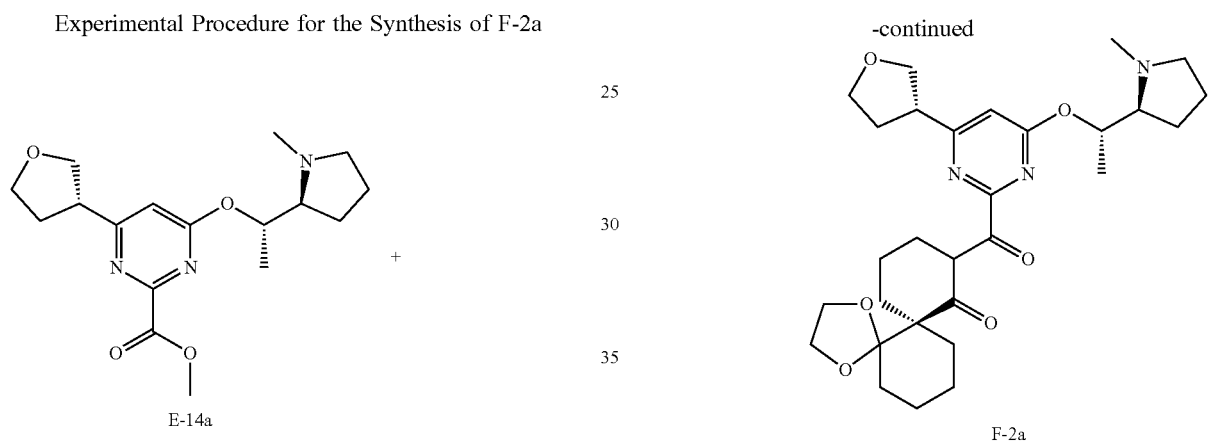 | 1.15<br>1.23<br>1.37 | 753 | L |

Experimental Procedure for the Synthesis of F-2a

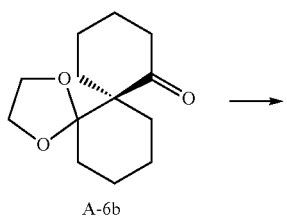

E-14a (203 mg, 0.58 mmol, 1.00 equiv.) is dissolved in THF (10 mL), activated molecular sieves 3 Å is added and stirred at 50° C. for 20 min under an argon atmosphere. Then magnesium bromide ethyl etherate (225 mg, 0.87 mmol, 1.5 equiv.) is added and further stirred at 50° C. for 30 min.

Meanwhile a second solution is prepared using A-6b (152 mg, 0.67 mmol, 1.17 equiv.), which is also predried using activated molecular sieves 3 Å at 50° C. for 20 min in THF (5 ml). Then LiHMDS (1 M in THF, 1.6 mL, 1.6 mmol, 2.77 equiv.) is added and stirred for 15 min. After that the second solution is added to the first solution and stirred for 1 h at 50° C. until complete conversion to the product is observed.

The mixture is quenched carefully with NaHCO$_3$, concentrated under reduced pressure and extracted with DCM/water. The combined organic phase is concentrated under reduced pressure and purified by RP chromatography to give F-2a.

The following intermediates F-2 (Table 21) are available in an analogous manner. The crude product is purified by chromatography if necessary.

TABLE 21

| # | structure | $t_{ret}$ [min] | $[M + H]^+$ | HPLC method |
|---|---|---|---|---|
| F-2a | 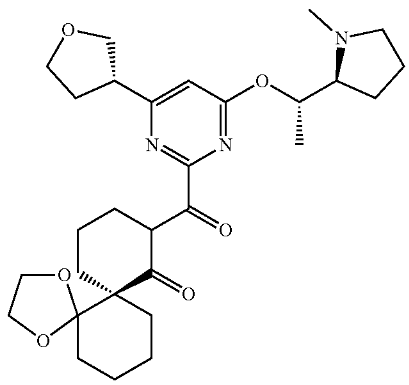 | 0.71<br>0.77<br>0.83<br>0.89 | 528 | C |
| F-2b | 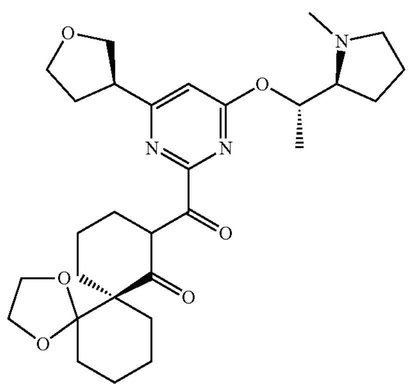 | 0.76<br>0.83<br>0.86 | 528 | C |
| F-2c | 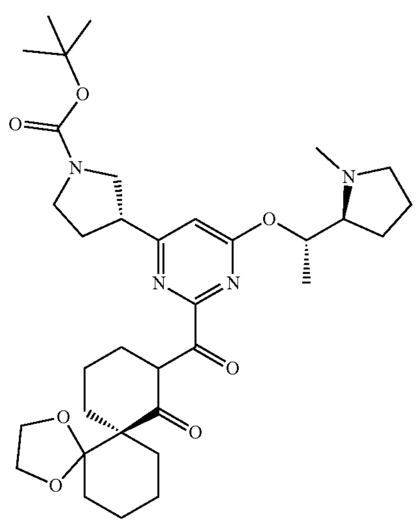 | 2.13<br>2.21 | 627 | G |

TABLE 21-continued

| # | structure | $t_{ret}$ [min] | [M + H]⁺ | HPLC method |
|---|---|---|---|---|
| F-2d | 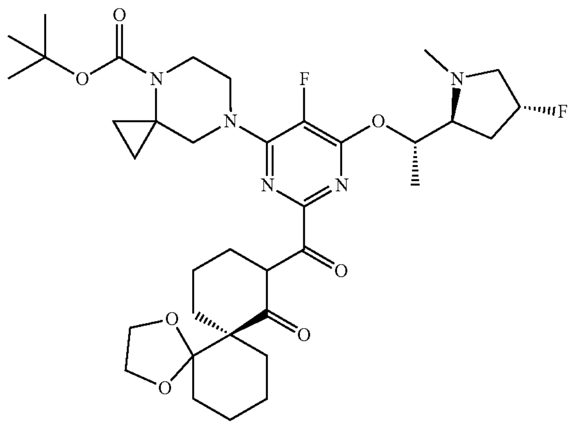 | 1.12<br>1.27<br>1.33 | 704 | B |
| F-2e | 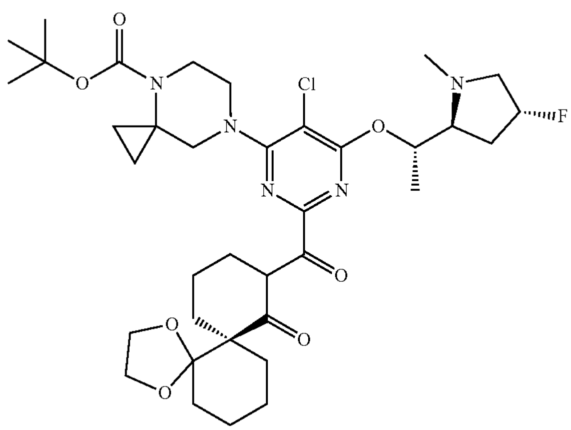 | 1.27<br>1.31<br>1.36 | 721 | B |
| F-2f | 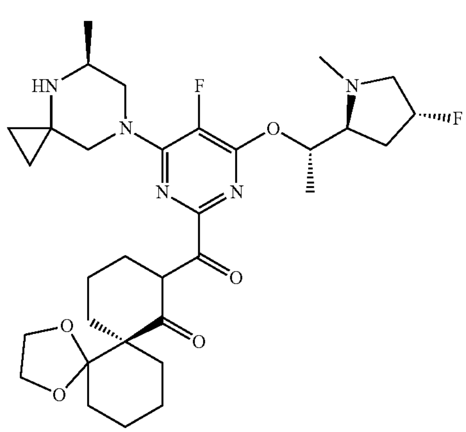 | 1.04<br>1.09<br>1.18 | 618 | B |

TABLE 21-continued

| # | structure | $t_{ret}$ [min] | $[M + H]^+$ | HPLC method |
|---|---|---|---|---|
| F-2g | 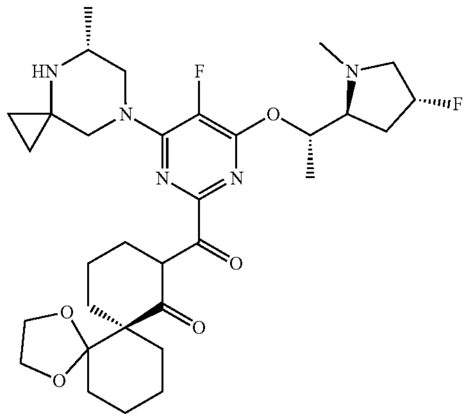 | 0.74<br>0.81<br>0.89 | 609 | C |
| F-2h | 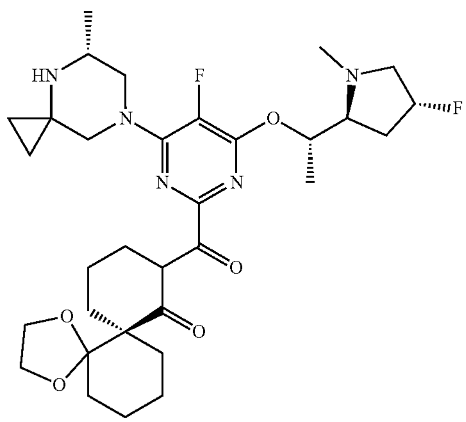 | 1.03<br>1.08<br>1.17 | 618 | VAB |

Experimental Procedure for the Synthesis of F-4a

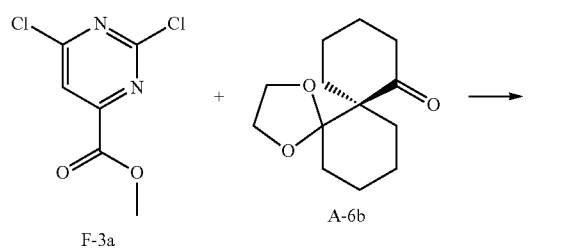

A-6b (1.4 g, 5.31 mmol, 1.1 equiv.) and magnesium bromide diethyl etherate (2.5 g, 9.66 mmol, 2.0 equiv.) are dissolved in DCM (10.0 mL). F-3a (1.0 g, 4.83 mmol, 1.0 equiv.), dissolved in DCM (10 mL), is added dropwise. DIPEA (2.1 mL, 12.08 mmol, 2.5 equiv.) is added and the reaction mixture is stirred 7 h at rt. The reaction is quenched with 1 M HCl, diluted with DCM and water. The organic phase is separated, evaporated and the resulting residue is purified by RP chromatography to afford F-4a (HPLC method: C, $t_{ret}$=0.633 min; $[M+H]^+$=399).

Experimental Procedure for the Synthesis of F-5a

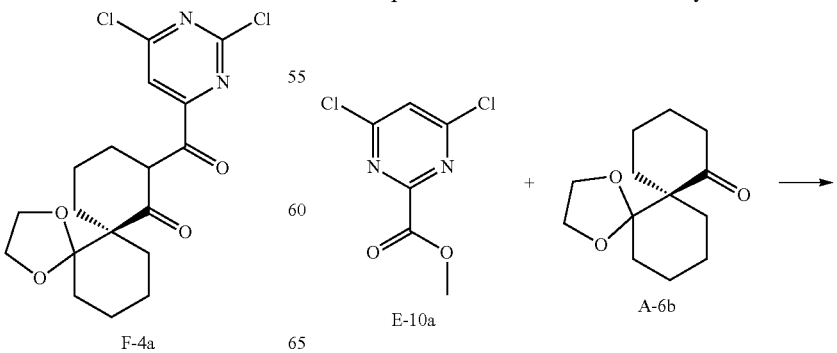

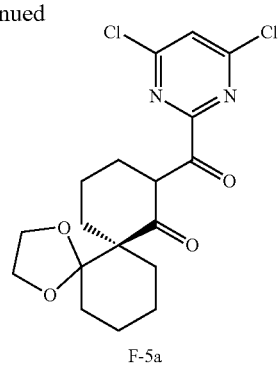

F-5a 4,6-Dichloropyrimidine-2-carboxylic acid methyl ester (2.00 g, 9.67 mmol, 1.00 equiv.) is dissolved in dry ACN (5 mL) under nitrogen atmosphere. Magnesium bromide diethyl etherate (2.99 g, 11.6 mmol, 1.20 equiv.), a solution of A-6b (2.38 g, 10.6 mmol, 1.10 equiv.) in ACN (5 mL), and DIPEA (2.67 mL, 14.5 mmol, 1.50 equiv.) is added, and the reaction mixture is stirred at 50° C. for 20 h. After complete conversion, the reaction mixture is carefully quenched with HCl (1 M), diluted with water, extracted with DCM, and the organic phases are dried, filtered, and concentrated to obtain crude F-5a. The crude compound is purified by normal phase chromatography (HPLC-Method: H, $t_{ret}$=2.50 min; [M+H]=399/401).

Experimental Procedure for the Synthesis of F-6a

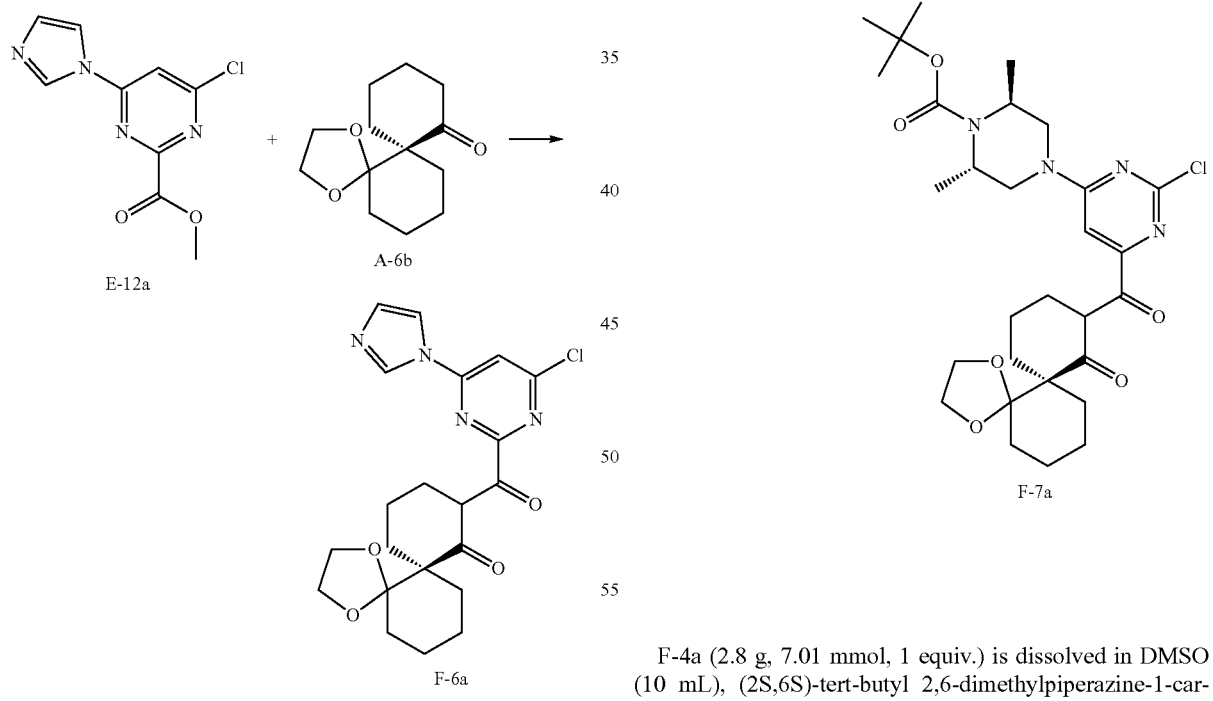

A-6b (3.71 g, 0.02 mol, 1.05 equiv.) is dissolved in THF (10 mL) and LiHMDS (1 M in THF, 31.3 mL, 31.3 mmol, 2 equiv.) is added at rt and stirred for 10 min. E-12a (3.73 g, 0.02 mol, 1 equiv.) and magnesium bromide diethyl etherate (1.63 g, 6.25 mmol 0.4 equiv.) is dissolved in THF (40 mL) and stirred under an argon atmosphere at 50° C. The solution from A-6b is added at 50° C.

The reaction mixture is stirred at 50° C. for 1 h. After complete conversion, the reaction mixture is concentrated under reduced pressure. Water is added and acidified with formic acid, filtered over Celite and extracted with DCM. The combined organic phase is concentrated under reduced pressure and purified by RP chromatography to give F-6a (HPLC method: C, $t_{ret}$=0.45, 0.62, 0.71 min; [M+H]$^+$=431).

Experimental Procedure for the Synthesis of F-7a

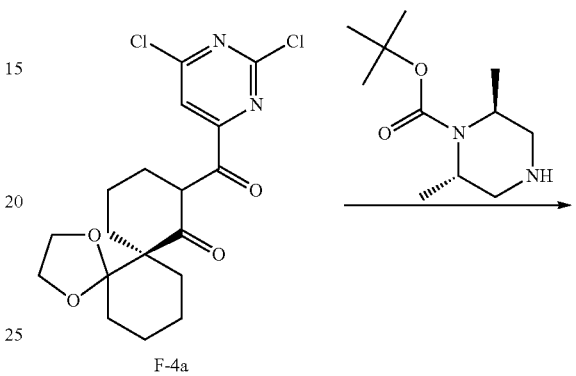

F-4a (2.8 g, 7.01 mmol, 1 equiv.) is dissolved in DMSO (10 mL), (2S,6S)-tert-butyl 2,6-dimethylpiperazine-1-carboxylate (1.7 g, 7.71 mmol, 1.1 equiv.) and DIPEA (3.6 mL, 21.0 mmol, 3.0 equiv.) are added and the solution is stirred at 60° C. for 1 h. After cooling to rt, the reaction mixture is diluted with DCM and water. The organic phase is separated, evaporated and the resulting residue is purified by NP chromatography to afford F-7a.

The following intermediates F-7 (Table 22) are available in an analogous manner using different starting materials.

TABLE 22

| # | structure | $t_{ret}$ [min] | $[M + H]^+$ | HPLC method |
|---|---|---|---|---|
| F-7a | 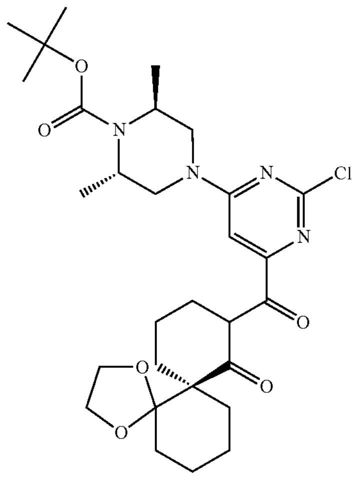 | 1.76<br>1.81 | 577 | A |
| F-7b | 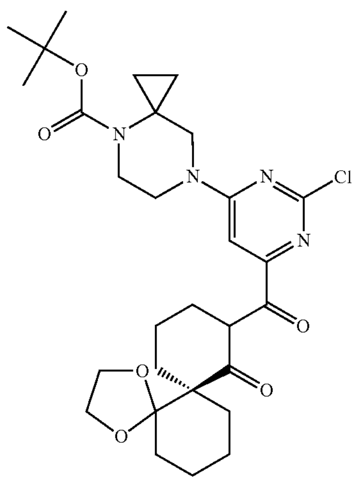 | 1.04<br>1.08 | 575 | C |

Experimental Procedure for the Synthesis of F-8a

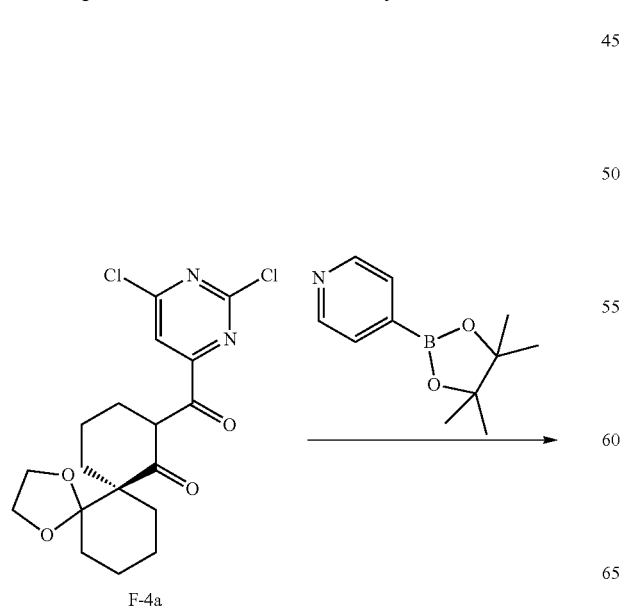

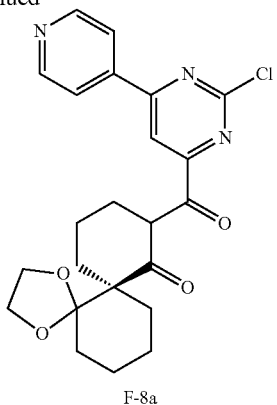

F-4a (1.27 g, 2.77 mmol, 1.0 equiv.) is dissolved in dioxane (10 mL) and an aqueous cesium carbonate solution (2 M, 3.46 mL, 6.93 mmol, 2.5 equiv.) is added and stirred at 80° C. for 15 min. Then pyridine-4-boronic acid (357 mg, 2.91 mmol, 1.1 equiv.) and Pd(dppf)Cl$_2$ CH$_2$Cl$_2$ (238 mg, 0.28 mmol, 0.1 equiv.) are added to the reaction mixture and stirred for 30 min at 90° C. until complete conversion of the starting material is observed. The reaction mixture is filtered and diluted with water and extracted three times with DCM. The organic phase is evaporated, and the residue is dissolved in DMF and purified by RP chromatography to give the desired product F-8a (HPLC-Method: C, $t_{ret}$=0.80/86 min; [M+H]=440).

Experimental Procedure for the Synthesis of F-9a

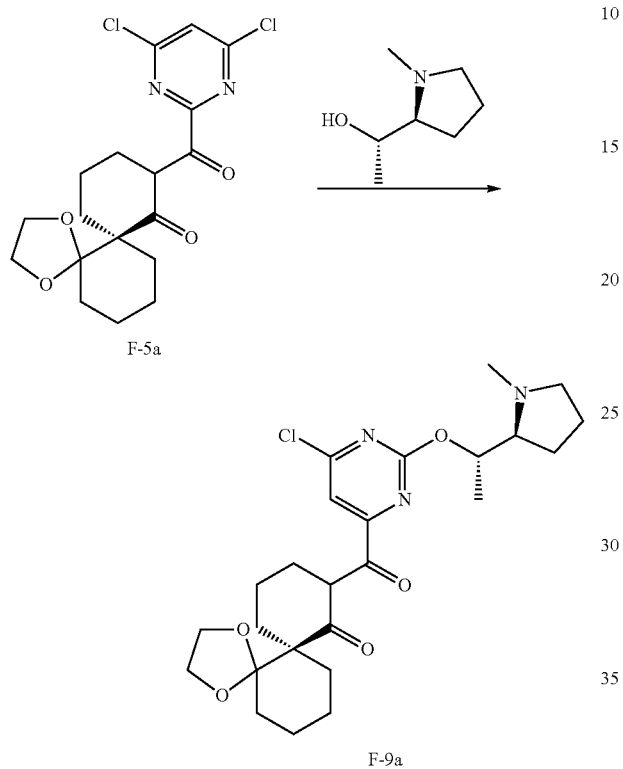

F-5a (10.0 g, 19.4 mmol, 1.00 equiv.) is dissolved in DMSO (10 mL), (1S)-1-[(2S)-1-methylpyrrolidin-2-yl]ethanol (2.76 g, 21.4 mmol, 1.10 equiv.) and DIPEA (6.78 mL, 38.8 mmol, 2.0 equiv.) are added and the solution is stirred at rt overnight. The reaction mixture is diluted with DCM and water. The organic phase is separated, evaporated and the resulting residue is purified by RP chromatography to afford F-9a. (HPLC-method: A, $t_{ret}$=1.58/1.66 min; [M+H]=492).

Experimental Procedure for the Synthesis of F-10a

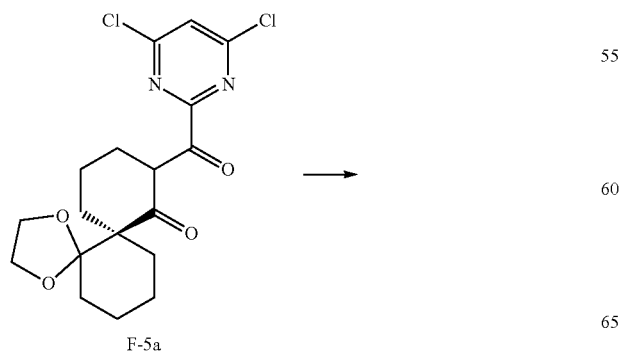

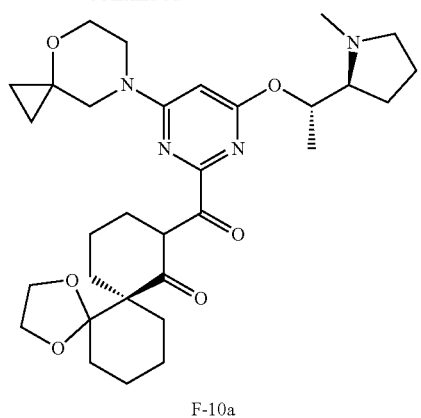

F-10a (1S)-1-[(2S)-1-methylpyrrolidin-2-yl]ethanol (245 mg, 1.71 mmol, 1.10 equiv.) is dissolved in DMSO (2 mL), DIPEA (542 µL, 3.11 mmol, 2.00 equiv.) is added. F-5a (1.00 g, 2.50 mmol, 1.00 equiv.) dissolved in DMSO (2 mL) is added dropwise. The reaction mixture is stirred overnight.

4-Oxo-7-azaspiro[2.5]octane (281 mg, 2.48 mmol, 1.60 equiv.) and DIPEA (271 µL, 1.55 mmol, 1.00 equiv.) is added and the reaction is stirred for 2 d at 50° C. After complete conversion of starting material is observed, the mixture is concentrated under reduced pressure and purified by RP chromatography to give F-10a (HPLC-Method: C, $t_{ret}$=0.82/0.89 min; [M+H]=569).

Experimental Procedure for the Synthesis of F-11a

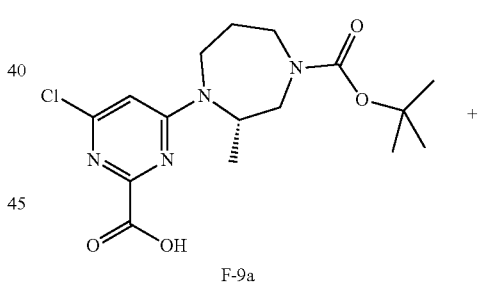

F-9a

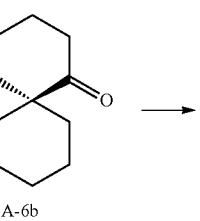

A-6b

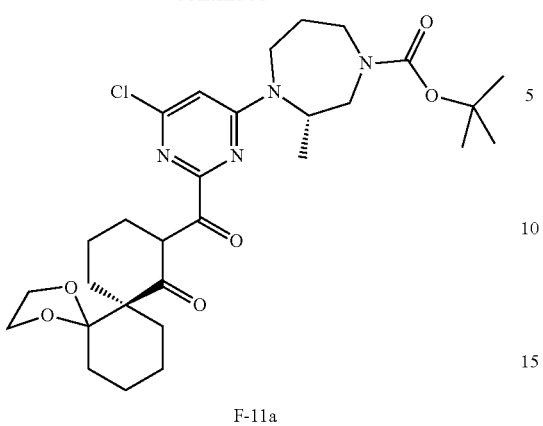

F-11a

E-9a (1.05 g, 2.83 mmol, 1.00 equiv.) and 1-(1H-imidazole-1-carbonyl)-1H-imidazole (918 mg, 5.66 mmol, 2.00 equiv.) under argon atmosphere are dissolved in THF (5 mL) and stirred 1 h at rt. After complete activation of the acid, a solution of A-6b (1.34 mg, 5.98 mmol, 2.00 equiv.) and LiHMDS (1.0 M in THF, 5.95 mL, 5.95 mmol, 2.10 equiv.) is added to the reaction mixture and washed with THF (5 mL). The resulting mixture is stirred overnight at 60° C. After full conversion, the reaction mixture is diluted with an aqueous saturated NaHCO₃ solution and extracted three times with DCM. The organic phases are combined, dried, filtered and concentrated under reduced pressure. The crude product is dissolved in ACN and water, filtered and purified by basic RP chromatography to give the desired product F-11a (HPLC-Method: C, $t_{ret}$=0.888/0.936/0.978 min; [M+H]=557).

Experimental Procedure for the Synthesis of F-12a

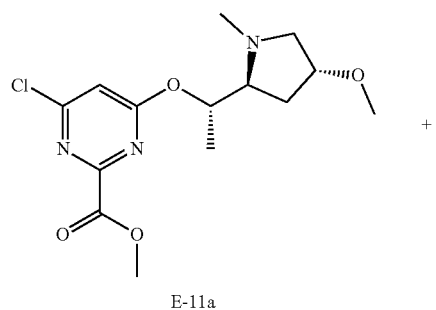

E-11a

+

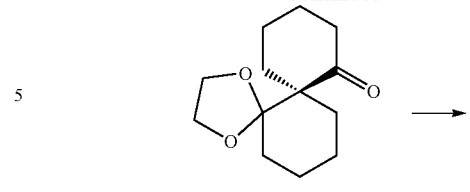

A-6b

→

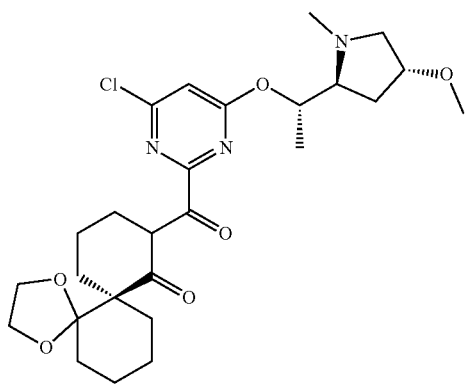

F-12a

E-11e (1.80 g, 0.01 mol, 1 equiv.) is dissolved in THF (18 mL), activated molecular sieves 3 Å are added (200 mg pro 1 ml solvent) and stirred at 50° C. for 20 min under an argon atmosphere. Then magnesium bromide ethyl etherate (2.11 g, 0.01 mol, 1.5 equiv.) is added and further stirred at 50° C. for 30 min. Meanwhile a second solution is prepared using the A-6b (1.47 g, 0.01 mol, 1.5 equiv.), which is also predried using activated molecular sieves 3 Å at 50° C. for 20 min in THF (8 ml). Then LiHMDS (1 M in THF, 13.7 mL, 0.01 mol, 2.5 equiv.) is added and stirred for 15 min. After that the second solution is added to the first solution and stirred for 1 h at 50° C. After complete conversion, the reaction mixture is carefully quenched with water, THF is removed under reduced pressure. The residue pH is adjusted to 7-8 by using 1N HCl and extracted with 5% MeOH in DCM (2×), the combined organic layer is washed with brine solution dried over Na₂SO₄ filtered and concentrated to obtain crude F-12a. The crude compound is purified by NP chromatography.

The following intermediates F-12 (Table 23) are available in an analogous manner. The crude product is purified by chromatography if necessary.

TABLE 23

| # | structure | t_ret [min] | [M + H]+ | HPLC method |
|---|---|---|---|---|
| F-12a | 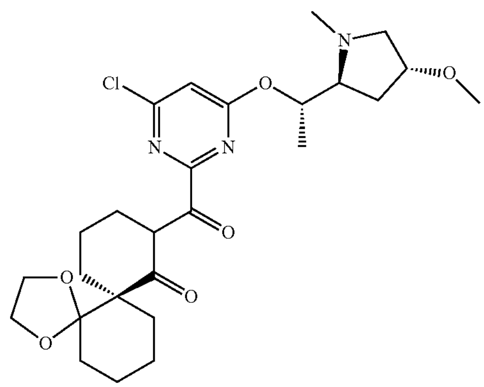 | 5.69<br>6.00<br>6.13 | 522 | I |
| F-12b | 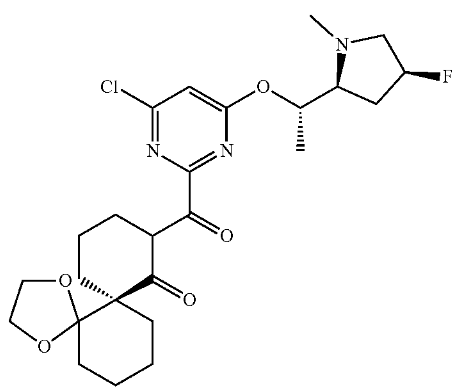 | 1.61<br>1.78 | 510 | H |
| F-12c | 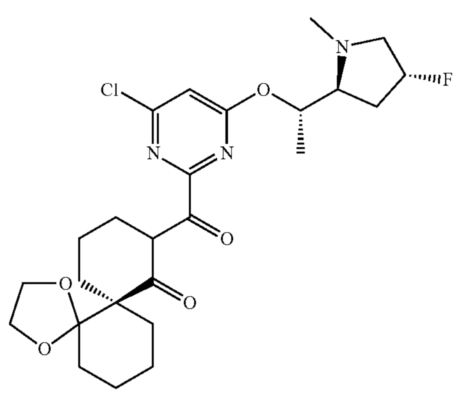 | 1.62<br>1.75 | 510 | H |
| F-12d | 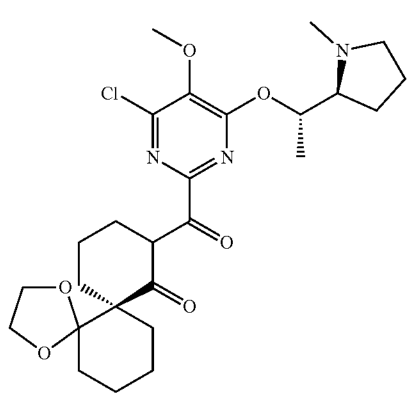 | 1.54<br>1.68 | 522 | H |

Synthesis of Isoxazole-Intermediates G
Experimental Procedure for the Synthesis of G-4a
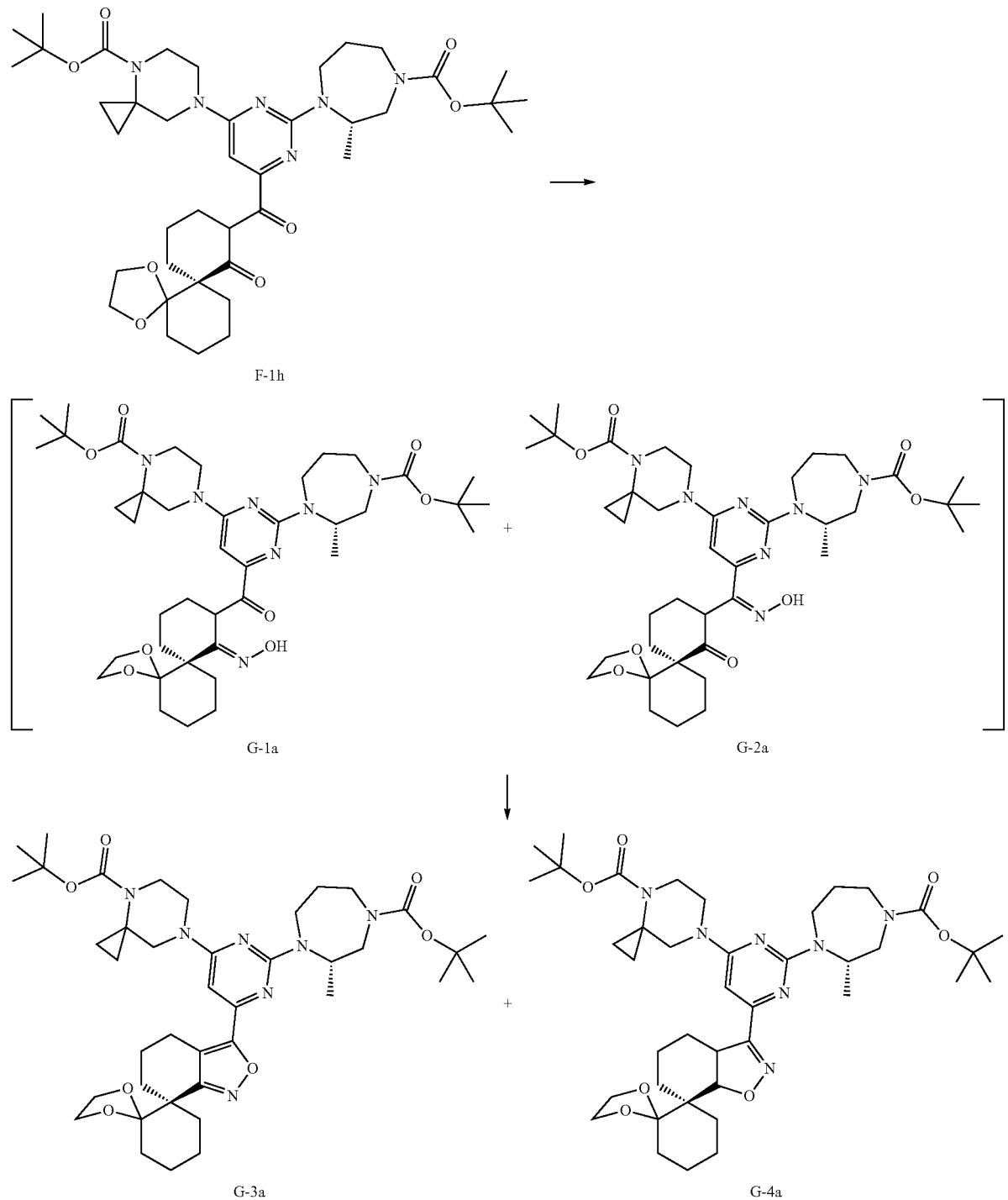

F-1 h (944 mg, 1.25 mmol, 1.00 equiv.) is dissolved in dioxane (5 mL) and hydroxylamine solution (50% in water, 0.15 mL, 2.51 mmol, 2.00 equiv.) is added. The reaction is stirred overnight under N₂ atmosphere at 80° C. After complete conversion, the reaction mixture is concentrated under reduced pressure and purified by RP chromatography to give the mixture of G-1a and G-2a.

The mixture of G-1a and G-2a (522 mg, 0.679 mmol, 1.00 equiv.) is dissolved in DCM (5 mL) and DIPEA (260 µL, 1.5 mmol, 2.20 equiv.) and methanesulfonyl chloride (54.2 µL, 0.71 mmol, 1.04 equiv.) is added. The resulting solution is stirred at rt until complete conversion is observed. The reaction is evaporated and extracted with DCM/water. The organic solvent is evaporated, the resulting residue is purified by RP chromatography to afford G-3a and G-4a.

The following intermediates G-3 and G-4 (Table 24) are available in an analogous manner. The crude product is purified by chromatography if necessary.

TABLE 24

| # | structure | $t_{ret}$ [min] | [M + H]⁺ | HPLC method |
|---|---|---|---|---|
| G-3a | 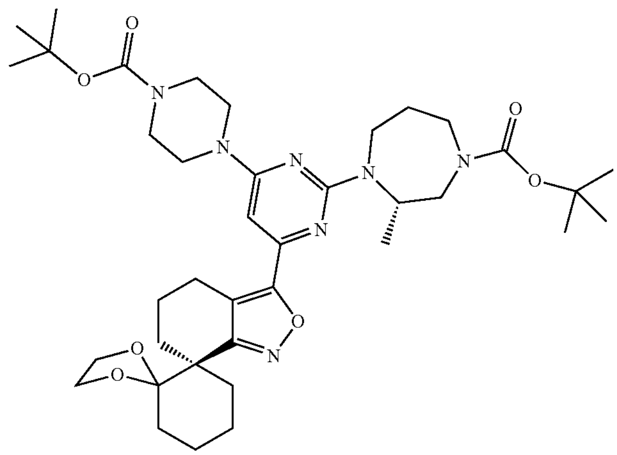 [SMILES: C[C@H]1CN(C(=O)OC(C)(C)C)CCCN1c1nc(-c2onc3c2CCC[C@@]32CCCCC23OCCO3)cc(N2CCN(C(=O)OC(C)(C)C)CC2)n1] | 1.42 | 750 | M |
| G-4a | 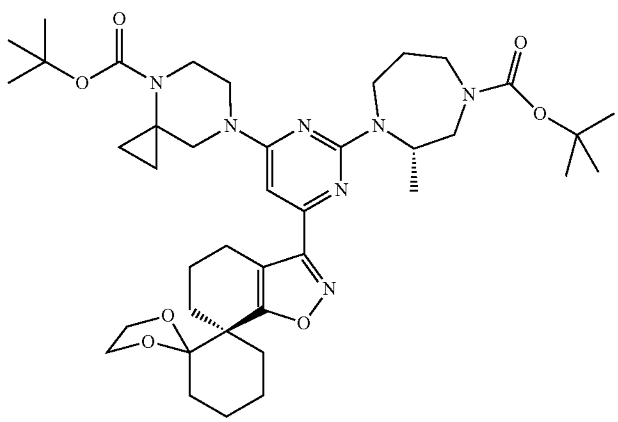 [SMILES: C[C@H]1CN(C(=O)OC(C)(C)C)CCCN1c1nc(-c2noc3c2CCC[C@@]32CCCCC23OCCO3)cc(N2CCN(C(=O)OC(C)(C)C)C3(CC3)C2)n1] | 1.36 | 750 | M |
| G-3b | 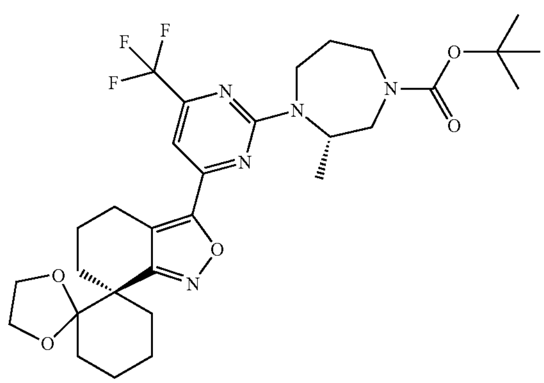 [SMILES: C[C@H]1CN(C(=O)OC(C)(C)C)CCCN1c1nc(-c2onc3c2CCC[C@@]32CCCCC23OCCO3)cc(C(F)(F)F)n1] | 1.00 | 608 | C |

TABLE 24-continued
| # | structure | $t_{ret}$ [min] | $[M + H]^+$ | HPLC method |
|---|---|---|---|---|
| G-3c | 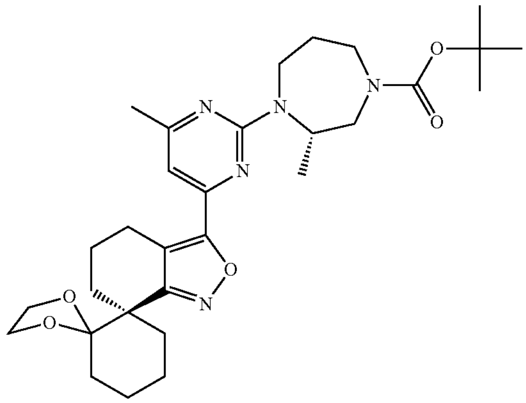 [SMILES: Cc1cc(-c2onc3c2CCC[C@@]32CCCCC23OCCO3)nc(N2CCCN(C(=O)OC(C)(C)C)C[C@@H]2C)n1] | 1.10 | 554 | C |
Experimental Procedure for the Synthesis of G-7a and G-8a
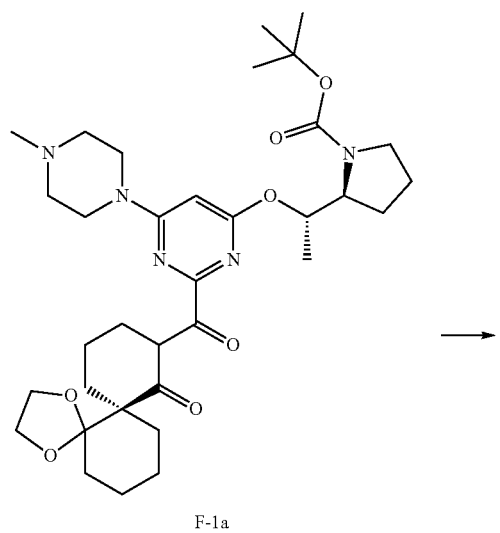
F-1a -continued

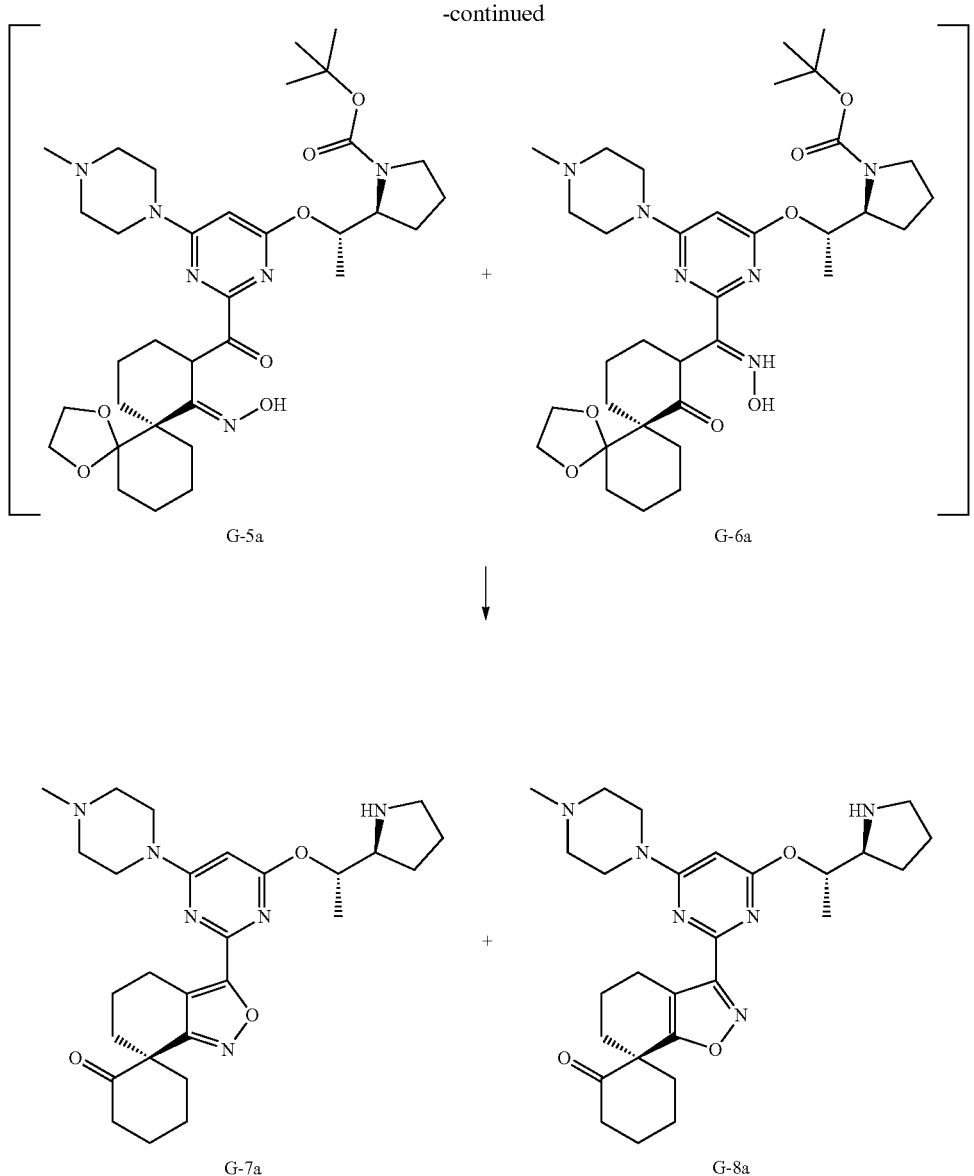

F-1a (541 mg, 0.843 mmol, 1.0 equiv.) is dissolved in dioxane (5 mL) and hydroxylamine is added (50% in water, 103 μL, 1.69 mmol, 2.0 equiv.). The reaction mixture is stirred overnight at 80° C. After full conversion of starting material, the reaction is diluted with aq. satd. NaHCO$_3$ solution and extracted with DCM (3×). The organic phase is combined, dried, filtered and concentrated under reduced pressure to give the crude product.

The mixture of crude G-5a and G-6a (116 mg, 0.18 mmol, 1 equiv.) is dissolved in dioxane (1.5 mL) and HCl (4 M in dioxane, 177 μL, 0.71 mmol, 4.00 equiv.) is added. The reaction is stirred for 4 h at 60° C. After complete conversion the mixture is concentrated under reduced pressure to give the crude product. The crude product is purified by RP chromatography to give G-7a and G-8a.

The following intermediates G-7 and G-8 (Table 25) are available in an analogous manner. The crude product is purified by chromatography if necessary.

TABLE 25

| # | structure | $t_{ret}$ [min] | $[M + H]^+$ | HPLC method |
|---|---|---|---|---|
| G-8a | 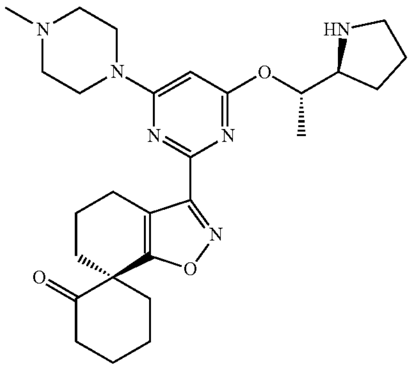 [SMILES: C[C@H](Oc1cc(N2CCN(C)CC2)nc(-c2noc3c2CCC[C@@]32CCCCC2=O)n1)[C@@H]1CCCN1] | 0.63 | 495 | C |
| G-7b | 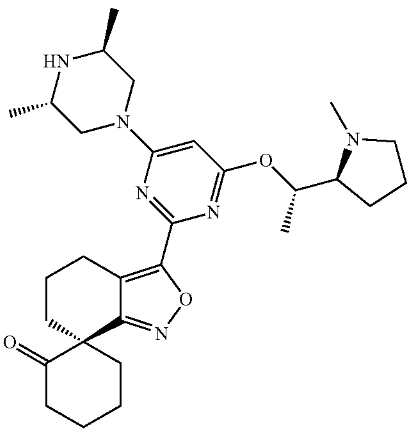 [SMILES: C[C@H](Oc1cc(N2C[C@H](C)N[C@@H](C)C2)nc(-c2onc3c2CCC[C@@]32CCCCC2=O)n1)[C@@H]1CCCN1C] | 0.75 | 523 | C |
| G-8b | 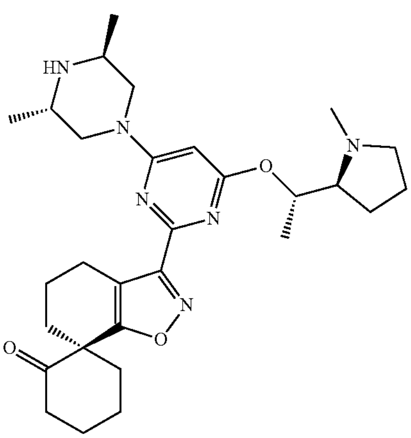 [SMILES: C[C@H](Oc1cc(N2C[C@H](C)N[C@@H](C)C2)nc(-c2noc3c2CCC[C@@]32CCCCC2=O)n1)[C@@H]1CCCN1C] | 1.35 | 523 | A |
| G-7c | 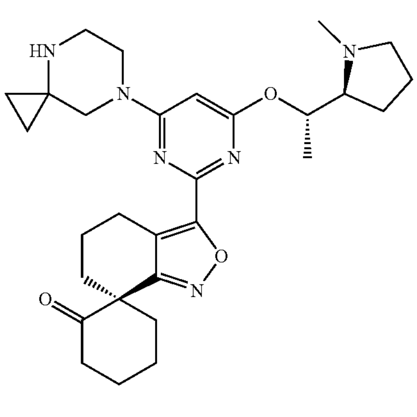 [SMILES: C[C@H](Oc1cc(N2CCNC3(CC3)C2)nc(-c2onc3c2CCC[C@@]32CCCCC2=O)n1)[C@@H]1CCCN1C] | 1.42 | 521 | A |

TABLE 25-continued

| # | structure | t_ret [min] | [M + H]+ | HPLC method |
|---|---|---|---|---|
| G-8c | 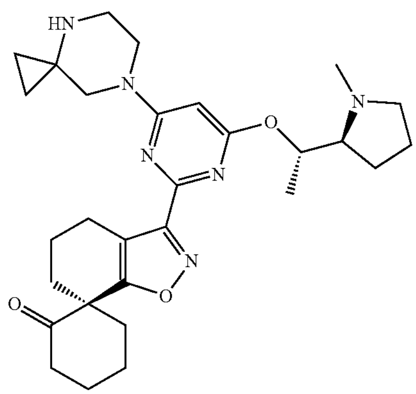 [SMILES: C[C@H](Oc1cc(N2CCNC3(CC3)C2)nc(-c2noc3c2CCC[C@@]32CCCCC2=O)n1)[C@@H]1CCCN1C] | 1.36 | 521 | A |
| G-8d | 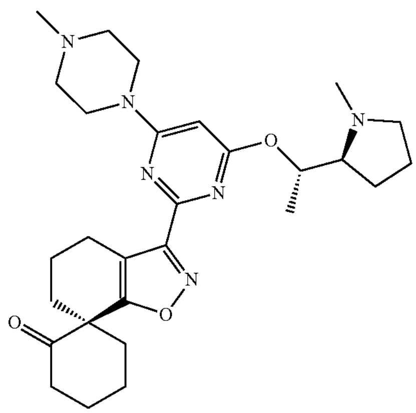 [SMILES: C[C@H](Oc1cc(N2CCN(C)CC2)nc(-c2noc3c2CCC[C@@]32CCCCC2=O)n1)[C@@H]1CCCN1C] | 1.50 | 509 | A |
| G-8e | 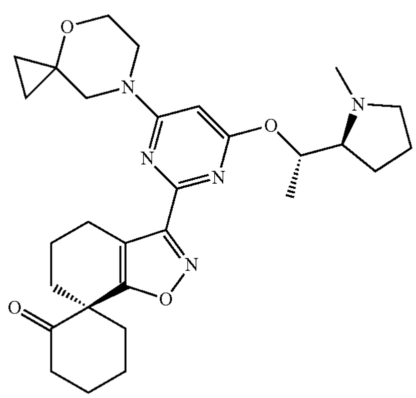 [SMILES: C[C@H](Oc1cc(N2CCOC3(CC3)C2)nc(-c2noc3c2CCC[C@@]32CCCCC2=O)n1)[C@@H]1CCCN1C] | 0.81 | 522 | C |
| G-8f | 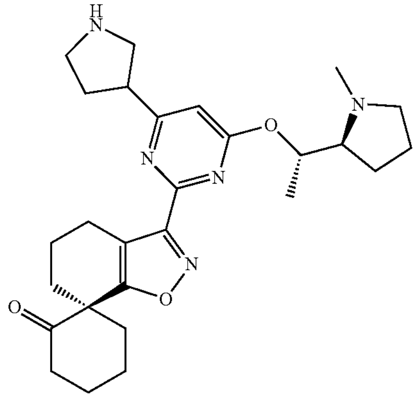 [SMILES: C[C@H](Oc1cc(C2CCNC2)nc(-c2noc3c2CCC[C@@]32CCCCC2=O)n1)[C@@H]1CCCN1C] | 1.57 | 480 | G |

Experimental Procedure for the Synthesis of G-9a and G-10a

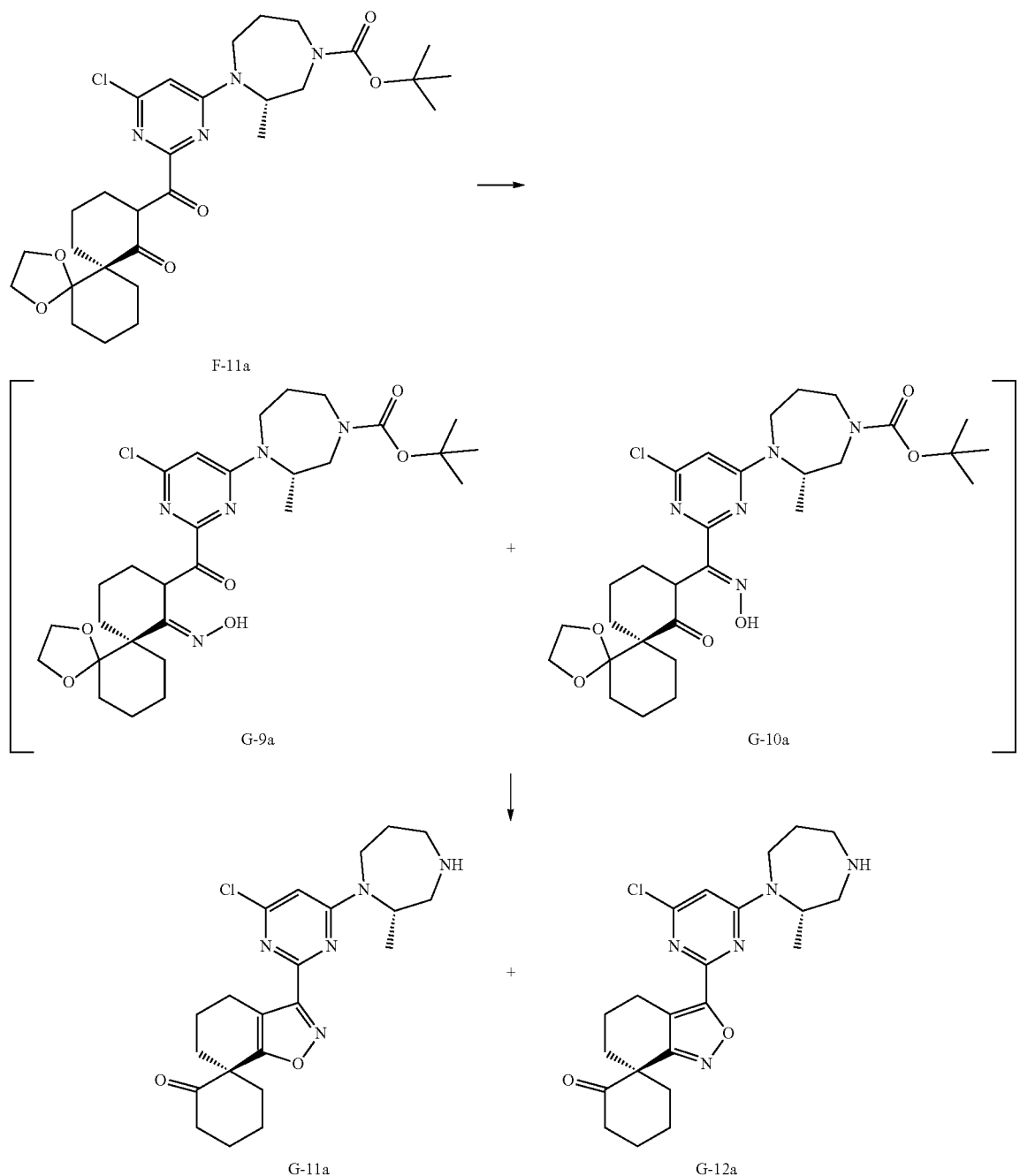

F-11a (1.10 g, 1.91 mmol, 1.0 equiv.) is dissolved in 1,4-dioxane (3 mL) and hydroxylamine is added (50% in water, 140 µL, 2.29 mmol, 1.2 equiv.). The reaction mixture is stirred overnight at rt. After full conversion, the reaction mixture is diluted with aq. satd. NaHCO₃ solution and extracted three times with DCM. The organic phase is combined, dried, filtered and concentrated under reduced pressure to give the crude product.

The crude mixture of G-9a and G-10a (1.0 g, 1.68 mmol, 1.0 equiv.) is dissolved in 1,4-dioxane (6 mL) and HCl (4 M in water, 2.11 mL, 8.44 mmol, 5.0 equiv.) is added. The reaction mixture is stirred 3 h at rt. After full conversion, the reaction is diluted with aq. satd. NaHCO₃ solution and extracted three times with CM. The organic phase is combined, dried, filtered and concentrated under reduced pressure to give the crude product. The crude product is dissolved in ACN and water, filtered and purified by basic RP chromatography to give the desired products G-11a and G-12a.

The following intermediates G-11 and G-12 (Table 26) are available in an analogous manner. The crude product is purified by chromatography if necessary.

TABLE 26

| # | structure | $t_{ret}$ [min] | [M + H]⁺ | HPLC method |
|---|---|---|---|---|
| G-11a | 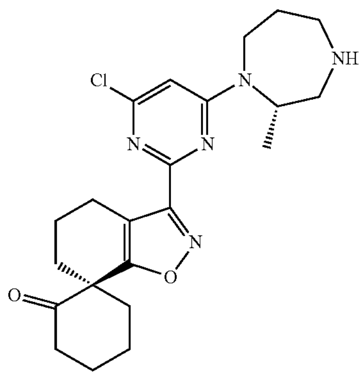 [SMILES: C[C@H]1CNCCCN1c1cc(Cl)nc(-c2noc3c2CCC[C@@]32CCCCC2=O)n1] | 0.67 | 430 | C |
| G-11b | 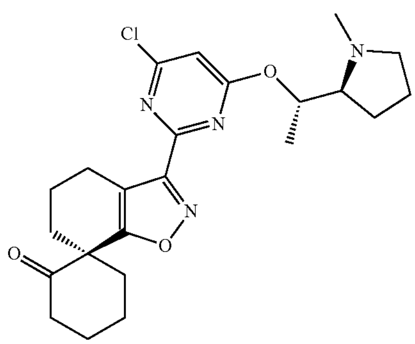 [SMILES: C[C@H](Oc1cc(Cl)nc(-c2noc3c2CCC[C@@]32CCCCC2=O)n1)[C@@H]1CCCN1C] | 1.57 | 445 | A |
| G-12b | 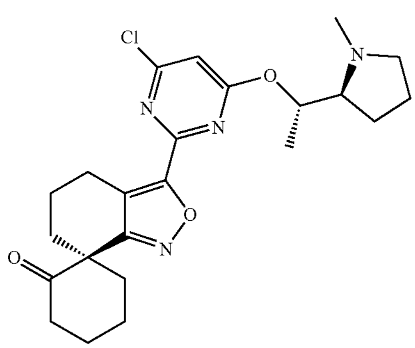 [SMILES: C[C@H](Oc1cc(Cl)nc(-c2onc3c2CCC[C@@]32CCCCC2=O)n1)[C@@H]1CCCN1C] | 1.62 | 445 | A |
| G-11c | 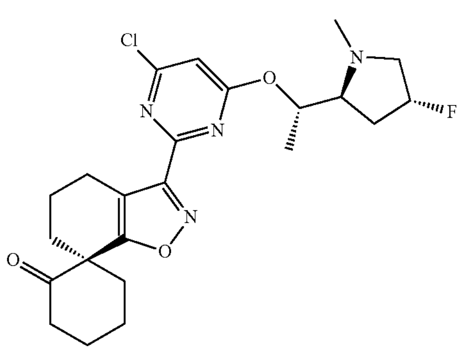 [SMILES: C[C@H](Oc1cc(Cl)nc(-c2noc3c2CCC[C@@]32CCCCC2=O)n1)[C@@H]1C[C@@H](F)CN1C] | 1.52 | 463 | A |

TABLE 26-continued

| # | structure | $t_{ret}$ [min] | [M + H]$^+$ | HPLC method |
|---|---|---|---|---|
| G-12c | 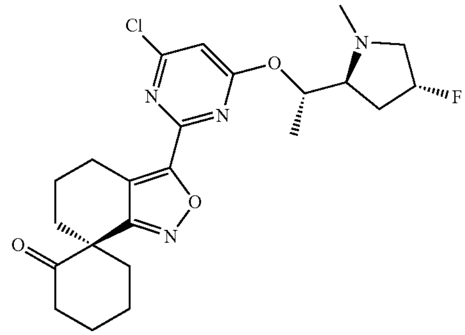 [SMILES: C[C@H](Oc1cc(Cl)nc(-c2onc3c2CCC[C@@]32CCCCC2=O)n1)[C@@H]1C[C@@H](F)CN1C] | 1.55 | 463 | A |
| G-11d | 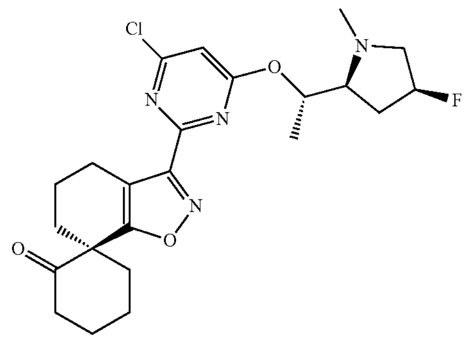 [SMILES: C[C@H](Oc1cc(Cl)nc(-c2noc3c2CCC[C@@]32CCCCC2=O)n1)[C@@H]1C[C@H](F)CN1C] | 1.65 | 463 | H |
| G-11e | 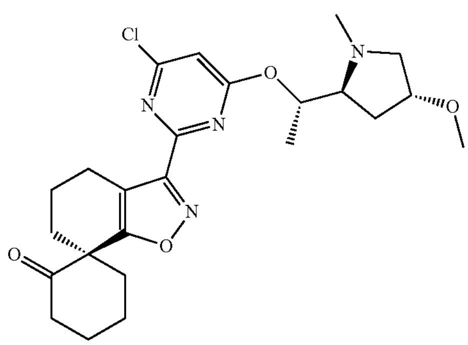 [SMILES: CO[C@@H]1C[C@@H]([C@H](C)Oc2cc(Cl)nc(-c3noc4c3CCC[C@@]43CCCCC3=O)n2)N(C)C1] | 3.01 | 475 | K |

Experimental Procedure for the Synthesis of A-10a

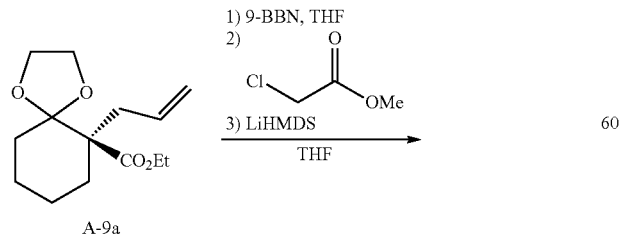

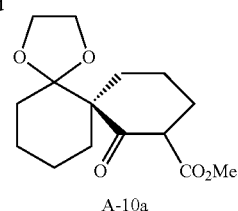

A dry and clean reactor is charged with 9-BBN (387 mL, 193.5 mmol, 1.2 equiv., 0.5 M in THF) under nitrogen. The solution is cooled to 0-5° C. to obtain a slurry. A-9a (41.0 g, 161.2 mmol) is added at 0-5° C. and rinsed with THF (20.5 mL). The mixture is warmed to 20-23° C. in 1 h and kept at 20-23° C. for not less than 1 h. After the mixture is cooled to −45 to −40° C., methyl chloroacetate is added in one portion followed by dropwise addition of LiHMDS (355 mL, 532.0 mmol, 3.3 equiv.) while keeping temperature below −35° C. The batch is then warmed to 20-23° C. in 1 h and then kept at 20-23° C. at least for 18 h. The batch is cooled to 5-10° C., AcOH (30.4 mL, 3.3 equiv.) is added below 20° C. followed by water (41 mL) below 20° C. AcOH (30.4 mL, 3.3 equiv) is added below 20° C. to reach pH ~6-7. ~15-16 V of THF is removed under vacuum below 35° C. MTBE (246 mL) and water (205 mL) are added. After phase cut to discard the bottom aqueous layer, the mixture is cooled to 0-5° C., a solution of sodium percarbonate (37.2 g, 322.4 mmol, 2.0 equiv.) in water (320 mL) is added below 20° C. After 1 h at 20-23° C., 20 wt % sodium sulfite solution (31 mL) is added. After 15 min at 20-23° C., the bottom aqueous layer is separated and discarded. The organic layer is washed with 5 wt % ammonium chloride solution (123 mL) and water (328 mL). The organic layer is treated with 5% activated carbon for 30 min prior to filtration. After ~4-5 V of solvent is removed under vacuum below 35° C. the crude product A-10a (80% yield, HPLC method: C, $t_{ret}$=0.84 min; [M+H]$^+$=283) is obtained as orange-brown oil.

Experimental Procedure for the Synthesis of G-70a

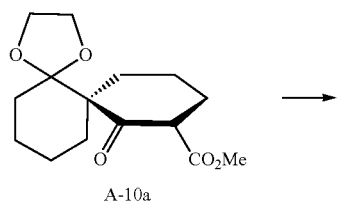

A-10a

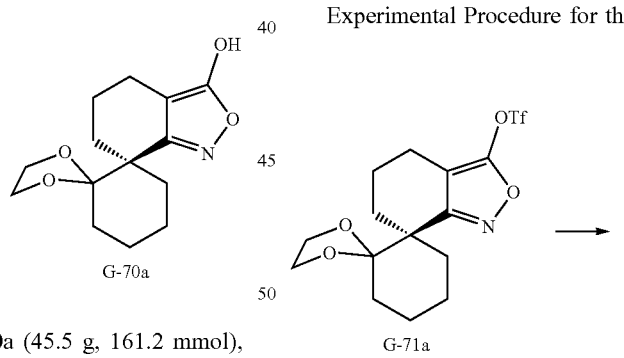

A reactor is charged with A-10a (45.5 g, 161.2 mmol), ethanol (91.0 mL), NaOAc (39.7 g, 483.6 mmol, 3.0 equiv.), water (45.5 mL) and NH$_2$OH·HCl (33.6 g, 483.6 mmol, 3.0 equiv.). The mixture is heated at 73-78° C. for not less than 16 h. After the batch is cooled to 20-23° C., water (227.6 mL) is added over 0.5 h. Then MTBE (136.5 mL) is added over 0.5 h followed by heptane (113.8 mL) over 1 h. After 0.5 h at 20-23° C., the solid is collected by filtration. The solid is washed successively with MTBE (45 mL) and water (91.0 mL). The solid is dried under vacuum to give the product G-70a as an off-white solid (18.27 g, 93.2 wt %) in 40% yield.
$^1$H NMR (500 MHz, DMSO-d6): δ 11.48 (br s, 1H), 4.04 (q, J=6.0 Hz, 1H), 3.89-3.80 (m, 2H), 3.60 (q, J=6.8 Hz, 1H), 2.10-1.95 (m, 2H), 1.92-1.76 (m, 4H), 1.69-1.39 (m, 8H). ESI-MS: m/z 266 [M+H]$^+$.

Experimental Procedure for the Synthesis of G-71a

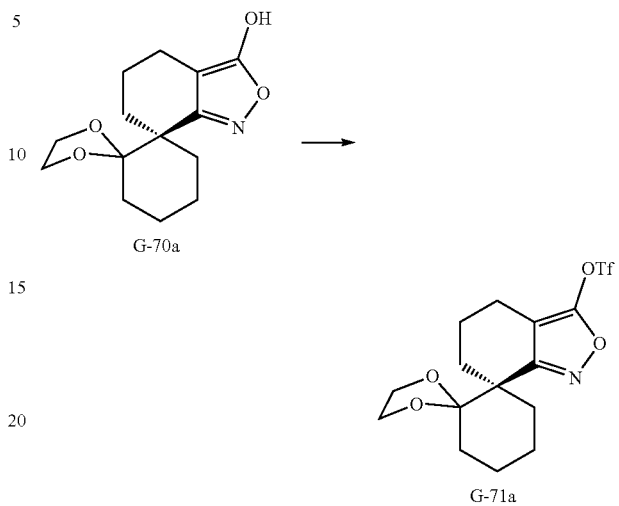

A clean reactor is charged with G-70a (100.0 g, 376.9 mmol, 1.0 equiv.), and K$_3$PO$_4$ (240.0 g, 1130.8 mmol, 3.0 equiv.) in water (499.0 g, 500.0 mL) and toluene (432.5 g, 500.0 mL). The bi-phase mixture is agitated to sufficient mixing. After the mixture is cooled to 0~5° C., Tf$_2$O (186.0 g, 110.9 mL, 659.6 mmol, 1.750 equiv.) is added with a syringe pump over 2 h below 5° C. After phase cut, the organic layer is filtered through a Celite bed with Na$_2$SO$_4$. After rinsing with toluene (50 mL), the crude product G-71a (149.8 g, 100% yield) is used for the next step directly.
$^1$H NMR (500 MHz, CDCl$_3$): δ 3.95-3.91 (m, 3H), 3.77-3.74 (m, 1H), 2.51-2.44 (m, 2H), 2.16-1.80 (m, 4H), 1.77-1.48 (m, 8H). ESI-MS: m/z 398 [M+H]$^+$.

Experimental Procedure for the Synthesis of G-72a

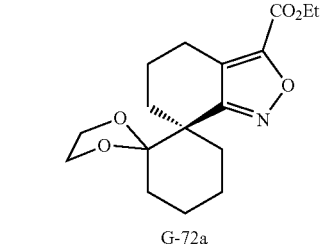

A dry and clean autoclave reactor is charged with G-71a (750 g, 1.89 mol, 1 equiv.), Pd(OAc)$_2$ (8.48 g, 37.7 mmol, 0.02 equiv.), rac-BINAP (23.5 g, 37.7 mmol, 0.02 equiv), 2-MeTHF (3 L), EtOH (870 g, 18.9 mol, 10 equiv.) and DIPEA (293 g, 2.26 mol, 1.2 equiv.). The reactor is purged with nitrogen (100 psi) two times and then purged with CO (100 psi) two times. The reactor is pressurized to 200 psi CO and heated at 55-60° C. for not less than 12 h. The mixture is transferred to a reactor and the autoclave reactor is rinsed with 2-MeTHF (0.75 L) into the reactor. The mixture is washed with water (3.75 L). After filtration through a short Celite pad, the solvent is removed by vacuum distill to give the crude product G-72a (531.9 g, 87.7% yield) which is used for the next step without purification.

$^1$H NMR (400 MHz, CDCl$_3$): δ 4.38 (q, J=7.1 Hz, 2H), 3.95-3.85 (m, 3H), 3.76-3.73 (m, 1H), 2.85 (dt, J=17.5, 5.5 Hz, 1H), 2.64 (ddd, J=17.5, 9.6, 6.0 Hz, 1H), 2.22-2.14 (m, 1H), 2.04-1.88 (m, 3H), 1.78-1.45 (m, 8H), 1.37 (t, J=7.1 Hz, 3H). ESI-MS: m/z 322 [M+H]$^+$.

Experimental Procedure for the Synthesis of G-73a

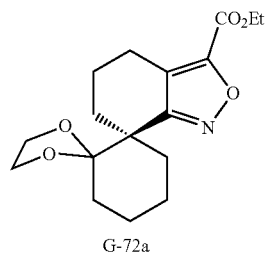

G-72a

A dry and clean reactor is charged with G-72a (482.0 g, 1.5 mol, 1 equiv.) and EtOH (3 V) and vacuum distilled ~3 V to remove residual 2-MeTHF from the previous carbonylation step. EtOH (1.45 L) and NH$_4$OH (1.93 L) are added. The mixture is kept at 20-25° C. for not less than 15 h. Water (1.69 L) is added over 30 min. After 30 min at 20-25° C., the solid is collected and washed with 1:2 EtOH/water (0.96 L) and water (0.48 L). The solid is slurried in 1:1 MTBE/hexane (0.96 L) for 1 h. The solid is collected by filtration and dried under vacuum at 40-45° C. overnight to give the product G-73a (332.4 g, 75.8% yield, water content ≤0.5% based on Karl Fischer titration) as a tan solid.

$^1$H NMR (500 MHz, DMSO-d6): δ 8.05 (s, 1H), 7.78 (s, 1H), 3.94-3.72 (m, 4H), 2.78 (dt, J=17.1, 5.0 Hz, 1H), 2.54-2.48 (m, 1H), 2.20-2.14 (m, 1H), 1.93-1.78 (m, 3H), 1.70-1.42 (m, 8H). ESI-MS: m/z 293 [M+H]$^+$.

Experimental Procedure for the Synthesis of G-74a

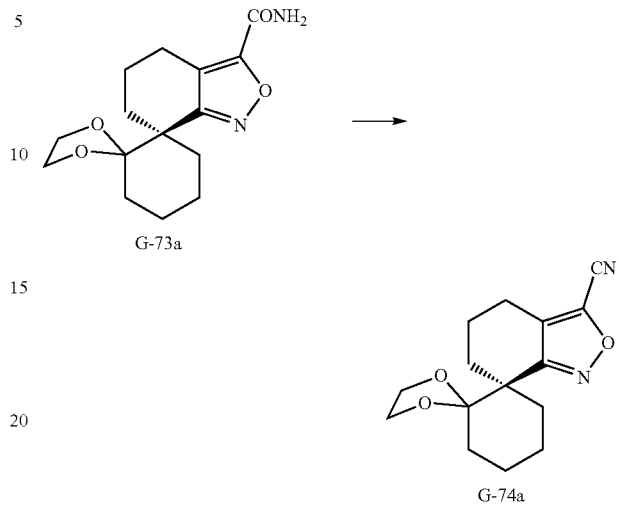

A dry and clean reactor is charged with G-73a (383 g, 86.7 wt %, 1.137 mol, 1 equiv.), MeCN (1.15 L) and pyridine (216 g, 0.19 L, 2.4 equiv.). After the mixture is cooled to 0-5° C., trifluoroacetic anhydride (287 g, 1.36 mol, 1.2 equiv.) is added below 5° C. After 5 min at 0-5° C., water (1.54 L) is added below 15° C. The product is extracted with MTBE (1.92 L) and washed with 5% sodium bicarbonate solution (1.15 L). The organic layer is filtered through silica gel pad (380 g) and rinsed with MTBE (0.58 L). After resolvent removal by distillation under vacuum, the product G-74a (421.8 g, 97.8% yield) is obtained as an orange-brown oil.

$^1$H NMR (500 MHz, CDCl$_3$): δ 3.98-3.85 (m, 3H), 3.80-3.75 (m, 1H), 2.72 (dt, J=17.0, 5.2 Hz, 1H), 2.60 (ddd, J=17.0, 9.5, 5.8 Hz, 1H), 2.20-2.12 (m, 1H), 2.07-1.94 (m, 3H), 1.82-1.48 (m, 8H). ESI-MS: m/z 275 [M+H]$^+$.

Experimental Procedure for the Synthesis of G-76a

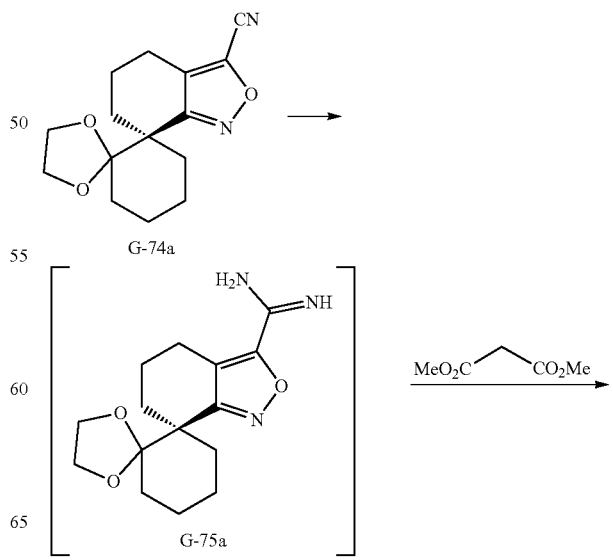

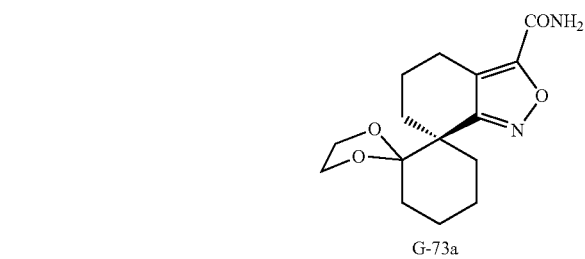

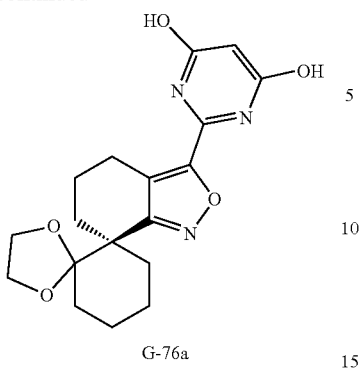

G-76a

A dry flask is charged with crude G-74a (265 g, 72.3 wt %, 698.4 mmol) in MeOH (1590 mL) and cat. NaOMe (8.0 mL, 25% in MeOH, 34.9 mmol). The mixture is stirred at rt for 1 h to achieve >99% conversion. After solid NH₄Cl (52.0 g, 977.8 mmol, 1.4 equiv.) is added, the resulting mixture is stirred at rt to achieve >95% conversion (if not, more NH₄Cl is added). After dimethyl malonate (168 g, 1047.7 mmol, 1.5 equiv.) is added at rt, NaOMe (377 g, 25% in MeOH, 2.5 equiv.) is added. The resulting mixture is heated to reflux for 4 h to achieve >95% conversion. After the mixture is cooled to 23° C., water (795 mL) is added followed by addition of 6N HCl (349 mL) slowly below 20° C. to reach pH ~3. To the slurry is added MTBE (530 mL). After 1 h at rt, the solid is collected by filtration, washed with 3V water (796 mL) and MTBE (530 mL) to give the product G-76a (178 g) as an off-white solid with 71% crude yield. The crude product is used for next step directly.

¹H NMR (500 MHz, CDCl₃): δ 5.82 (s, 1H), 3.96-3.74 (m, 4H), 2.74-2.70 (m, 1H), 2.62-2.59 (m, 1H), 2.22-2.10 (m, 1H), 2.12-1.90 (m, 3H), 1.80-1.48 (m, 8H). ESI-MS: m/z 360 [M+H]⁺.

Experimental Procedure for the Synthesis of G-77a

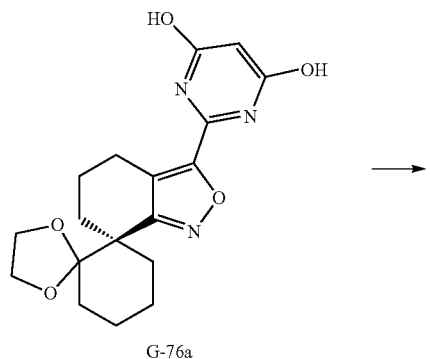

G-76a

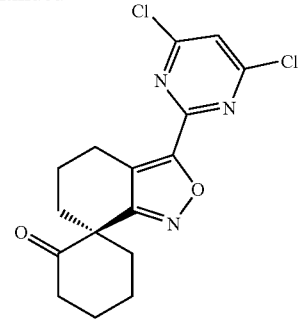

G-77a

A dry flask is charged with G-76a (80.0 g, 253.7 mmol), DMAP (4.0 g), tetramethyl ammonium chloride (4.0 g), and POCl₃ (400 mL). The mixture is heated at 80° C. for 1.5 h to achieve >99% conv. POCl₃ is removed under vacuum to get a thick light-yellow slurry. MTBE (160 mL) is added. Then the mixture is cooled to 5° C. Water (800 mL) is slowly added. The resulting white slurry is stirred at 23° C. for 1 h. The solid is collected by filtration and then washed successively with water (480 mL) and MTBE (160 mL). After drying under vacuum at 60° C. overnight, 84.3 g of the product G-77a are isolated as a white solid in >99 purity % and ~93% yield.

¹H NMR (600 MHz, DMSO-d6): δ 8.05 (s, 1H), 2.96-2.91 (m, 1H), 2.76-2.69 (m, 2H), 2.53-2.48 (m, 2H), 2.37-2.34 (m, 1H), 1.97-1.96 (m, 2H), 1.88-1.82 (m, 4H), 1.70-1.61 (m, 1H), 1.52-1.41 (m, 1H). 13C NMR (125 MHz, DMSO-d6): b 209.8, 164.3, 161.4, 157.3, 155.7, 120.8, 120.2, 50.3, 38.1, 37.5, 31.0, 26.6, 20.7, 19.9, 18.0. ESI-MS: m/z 353 [M+H]⁺.

Experimental Procedure for the Synthesis of G-78a

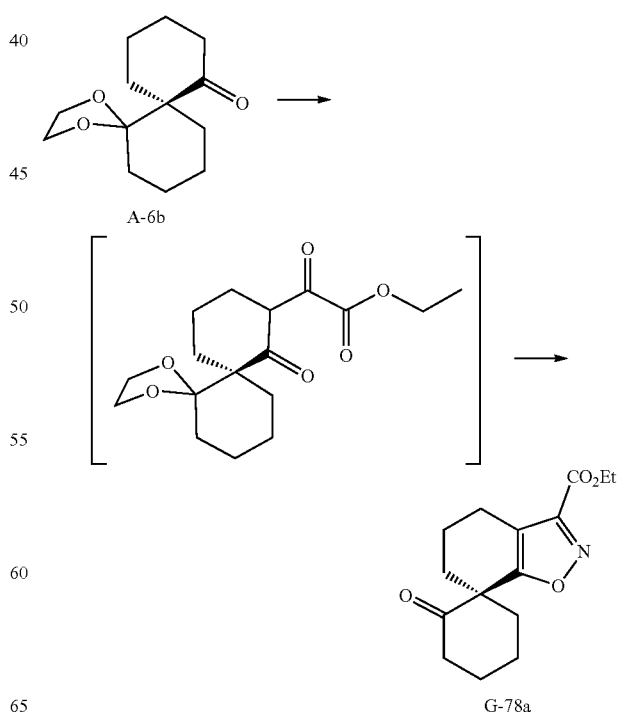

A dry and clean reactor is charged with LiHMDS (1 M in THF) (406.4 kg, 456.1 mol, 1.1 equiv). The solution is cooled to 0-5° C., crude A-6b (93.0 kg, 414.6 mol) is added below 5° C. and rinsed with THF (46.5 kg) to aid transfer. After 30 min at 0-5° C., diethyl oxalate (72.5 kg, 497.5 mol, 1.2 equiv) is added below 5° C. After the mixture is warmed to 20-25° C. in 1 h, the mixture is kept at 20-25° C. for not less than 3 h. After the batch is cooled to 10-15° C., cooled HCl solution [prepare by adding acetyl chloride (73.6 kg, 932.9 mol, 2.25 equiv) to EtOH (293.9 kg) at 0-5° C.] is added to the batch below 25° C. to reach final pH ~6-7 of the yellow slurry. Solid NH$_2$OH·HCl (28.8 kg, 414.4 mol, 1.05 equiv.) is added in one portion and the resulting mixture is heated to reflux 66-70° C. for 6-10 h. After that 5V of solvent is removed by distillation at reflux 66-70° C. EtOH (73.5 kg) is used to remove residual THF. Water (372.0 kg) and EtOH (293.9 kg) are added. After 3-6 h at 70-75° C., the mixture is cooled to 30-35° C. 0.5-1% G-78a crystals are seeded. After 2-4 h at 30-35° C., heptane (63.2 kg) is added in not less than 1 h. After 60 min at 20-25° C., water (279.0 kg) is added over 4-6 h. After 1 h at 20-25° C., the solid is collected and washed with 1:2 EtOH/water (51.2 kg EtOH and 130.2 kg water) and then heptane (63.2 kg) two times. The solid is dried under vacuum under nitrogen stream to give the product G-78a (93.0 kg) with 65% yield.

$^1$H NMR (500 MHz, CDCl$_3$): δ 4.42 (q, J=7.1 Hz, 2H), 2.73 (dt, J=16.8, 5.1 Hz, 1H), 2.64 (dt, J=14.3, 6.0 Hz, 1H), 2.60-2.51 (m, 2H), 2.43-2.30 (m, 2H), 2.09-1.96 (m, 3H), 1.91-1.81 (m, 3H), 1.76-1.67 (m, 1H), 1.65-1.58 (m, 1H), 1.40 (t, J=7.1 Hz, 3H). ESI-MS: m/z 278 [M+H]$^+$.

Experimental Procedure for the Synthesis of G-79a

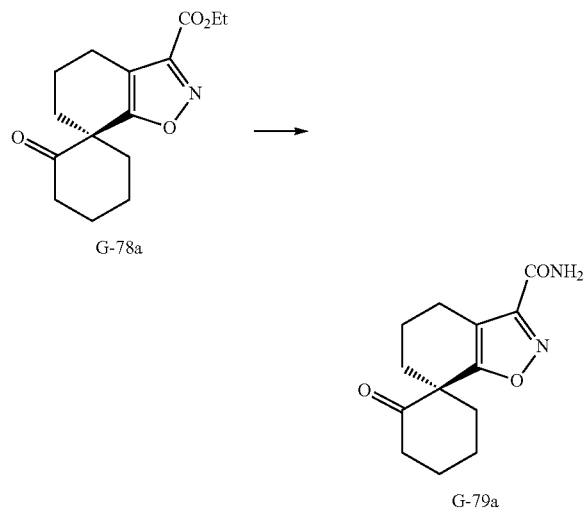

A dry and clean reactor is charged with G-78a (72.0 kg, 259.6 mol), EtOH (56.9 kg) and NH$_4$OH (aq) (280.8 kg). The mixture was kept at 20-25° C. for not less than 16 h. After water (144.0 kg) is added over 30 min, the slurry is kept at 20-25° C. for 30 min. The solid is collected by filtration, washed with 1:3 EtOH/water (28.5 kg EtOH and 108 kg water) and then heptane (97.9 kg). After drying, under vacuum over 1 h at 23° C., the solid was dried under vacuum at 50-55° C. overnight to give the product G-79a (61.4 kg, 87.2% yield, enantiomeric ratio 95:5 (254 nm), water content ≤0.5% based on Karl Fischer titration).

A dry and clean reactor is charged with crude G-79a (60.0 kg, 1.0 equiv.), 1,4-dioxane (240.0 kg) and activated carbon (3.0 kg, 5 wt %). The mixture is stirred at 55-65° C. for 2-4 h. After filtration at high temperature (55~65° C.), the filter cake is washed with 1,4-dioxane (33.0 kg). The filtrate is transferred into a clean reactor. The temperature is adjusted to 45-55° C. and stirred at 45-55° C. for 1-2 h. Water (240.0 kg) is added over 2 h. The temperature is adjusted to 45-55° C. and stirred at 45-55° C. for 1-2 h. The mixture is cooled down to 35-45° C. and stirred at 35~45° C. for 2-4 h. Water (87.0 kg) is added over 4 h. The mixture is cooled down to 15-25° C. and stirred at 15-25° C. for 12-14 h. The solid is collected by a centrifuge, washed with water (120.0 kg) and dried under vacuum at 50-55° C. overnight to give the product G-79a (44.8 kg, 71% yield) as a light yellow to off-white solid. The undesired isomer should be less than 0.5%.

$^1$H NMR (500 MHz, DMSO-d6): δ 7.99 (s, 1H), 7.71 (s, 1H), 2.80-2.69 (m, 1H), 2.60-2.53 (m, 1H), 2.50-2.42 (m, 1H), 2.40-2.28 (m, 2H), 2.26-2.18 (m, 1H), 2.05-1.70 (m, 7H), 1.48-1.39 (m, 1H). ESI-MS: m/z 249 [M+H]$^+$.

Experimental Procedure for the Synthesis of G-80a

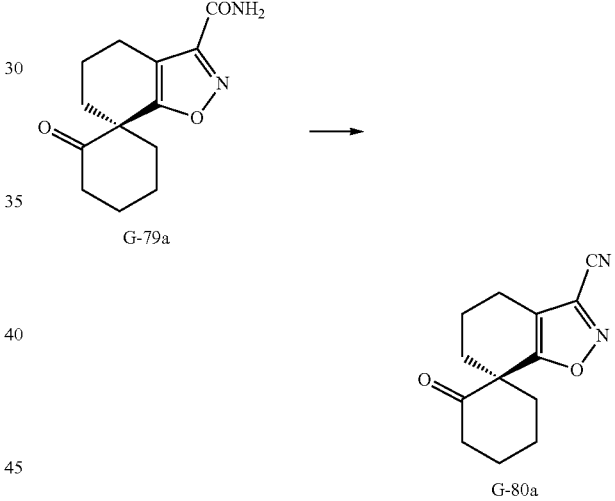

A dry and clean reactor is charged with G-79a (40.0 kg, 161.1 mol), MeCN (96.0 kg) and pyridine (30.8 kg, 386.6 mol, 2.4 equiv.). After the mixture is cooled to 0-5° C., TFAA (40.8 kg, 193.3 mol, 1.2 equiv.) is added slowly below 5° C. After 5 min at 0-5° C., water (120.0 kg) is added over 30 min at 0-5° C. and seeded with 0.5% G-80a crystals. After 15 min at 0-5° C., water (120.0 kg) is added over 30 min. After 30 min at 0-5° C. for 30 min, the solid is collected by filtration, washed with 1:3 MeCN/water (15.6 acetonitrile and 60.0 kg water) and then water (80.0 kg). The solid is dried under vacuum to give the crude product (33.0 kg, 93.6% yield) as a tan solid.

A dry and clean reactor is charged with crude G-80a (32.5 kg, 1.0 equiv.) and MTBE (48.1 kg), the slurry is agitated at 20-25° C. for 30 min. Heptane (132.6 kg) is added over 1 h. After 30 min at 20-25° C., the solid is collected, dried under vacuum to give the product G-80a (26.6 kg, 82.0% yield) as a white solid with >99:1 enantiomeric ratio (254 nm) and >98% purity (220 nm).

¹H NMR (500 MHz, DMSO-d6): b 2.83-2.73 (m, 1H), 2.60-2.40 (m, 3H), 2.34-2.20 (m, 2H), 2.06-1.75 (m, 7H), 1.53-1.43 (m, 1H). ESI-MS: m/z 231 [M+H]⁺.

Experimental Procedure for the Synthesis of G-82a

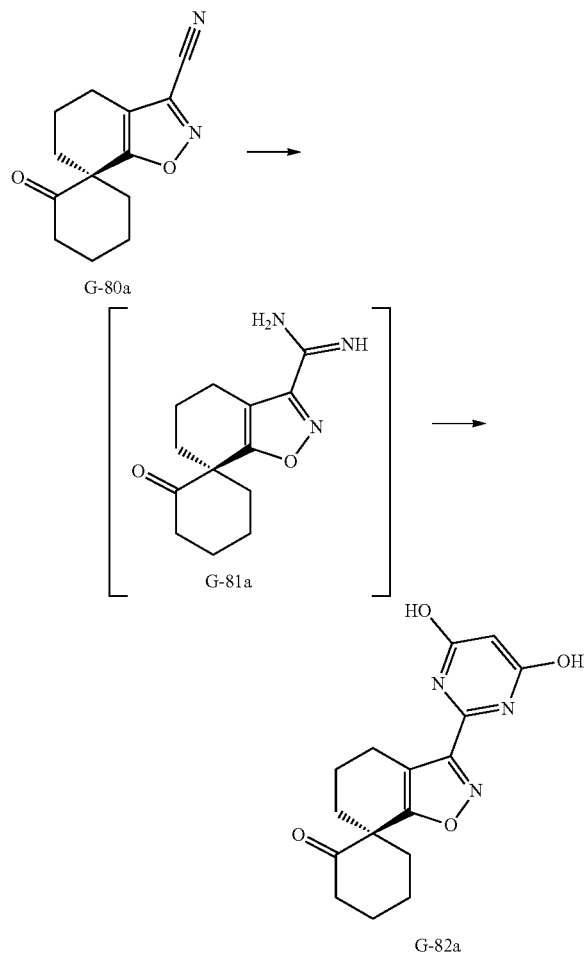

To a stirred solution of G-80a (25.0 g, 108.6 mmol, 1.0 equiv.) in MeOH (150 mL), is added NaOMe (30% in MeOH, 4.89 g, 27.1 mmol, 0.25 equiv.) and the resulting mixture is stirred for 2 h at rt. Then NH₄Cl (6.39 g, 119.4 mmol, 1.1 equiv.) is added and the mixture is stirred for 16 h at rt. After complete conversion to the desired amidine, the mixture is filtered through a Celite bed and concentrated. The residue is dissolved in DMF (125 mL), 1,8-diazabicyclo[5.4.0]undec-7-ene (32.3 g, 212.3 mmol, 2.1 equiv.) and diethyl malonate (13.4 g, 101.1 mmol, 1.0 equiv.) are added at 0° C. and the resulting mixture is stirred for 16 h at 90° C. After complete conversion, ice cold water is added, the mixture is acidified with 1 N HCl and the precipitate is collected by filtration. The precipitate is dried under reduced pressure yielding crude G-82a (HPLC-Method: H, t_{ret}=1.51 min; [M+H]=316) which is used for the next step without purification.

Experimental Procedure for the Synthesis of G-83a

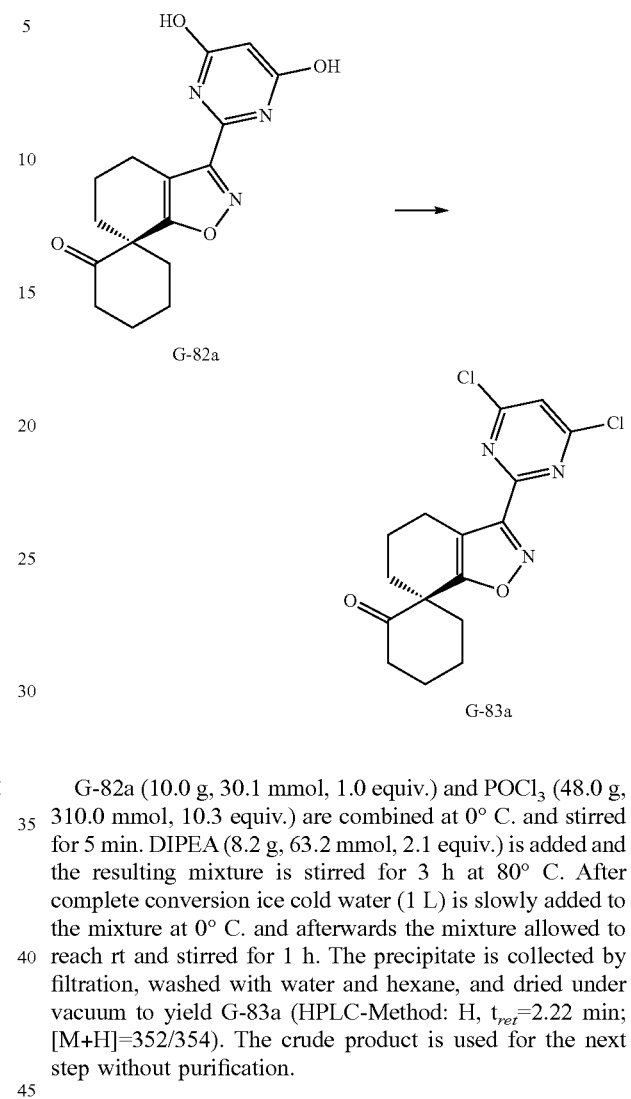

G-82a (10.0 g, 30.1 mmol, 1.0 equiv.) and POCl₃ (48.0 g, 310.0 mmol, 10.3 equiv.) are combined at 0° C. and stirred for 5 min. DIPEA (8.2 g, 63.2 mmol, 2.1 equiv.) is added and the resulting mixture is stirred for 3 h at 80° C. After complete conversion ice cold water (1 L) is slowly added to the mixture at 0° C. and afterwards the mixture allowed to reach rt and stirred for 1 h. The precipitate is collected by filtration, washed with water and hexane, and dried under vacuum to yield G-83a (HPLC-Method: H, t_{ret}=2.22 min; [M+H]=352/354). The crude product is used for the next step without purification.

Experimental Procedure for the Synthesis of G-84a

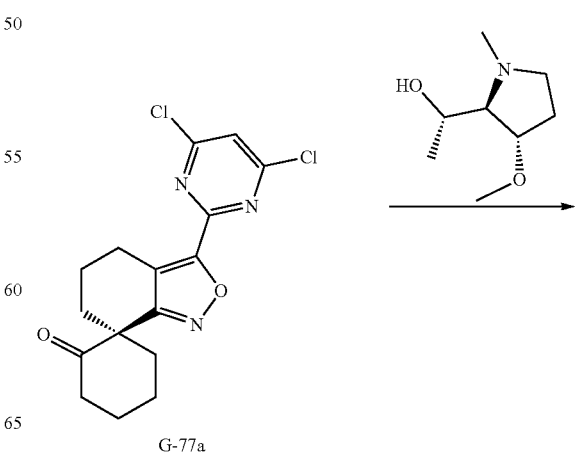

-continued

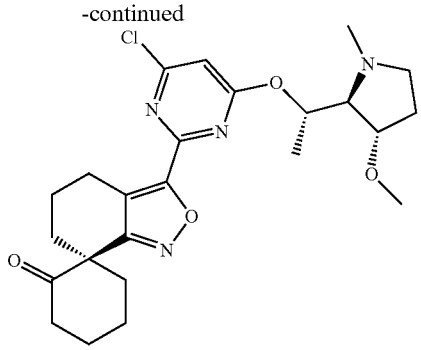

G-84a

B-5d (694 mg, 4.09 mmol, 1.2 equiv.) is dissolved in dry THF (13 mL) and cooled to 0° C. LiHMDS (1.0 M in THF, 5.11 mL, 5.11 mmol, 1.5 equiv.) is added dropwise at 0° C. and the mixture is stirred for additional 15 min. G-77a (1.20 g, 3.41 mmol, 1.0 equiv.) is dissolved in dry THF (13 mL) and added dropwise at 0° C. The mixture is stirred for 1.5 h at 65° C. After complete conversion, the mixture is diluted with aq. satd. NaHCO$_3$ solution and extracted three times with DCM. The organic phases are combined, filtered and concentrated under reduced pressure to obtain G-84a. The crude product is used for the next step without purification.

The following intermediates G-84 (Table 27) are available in an analogous manner. The crude product is purified by chromatography if necessary.

TABLE 27

| # | structure | t$_{ret}$ [min] | [M + H]$^+$ | HPLC method |
|---|---|---|---|---|
| G-84a | 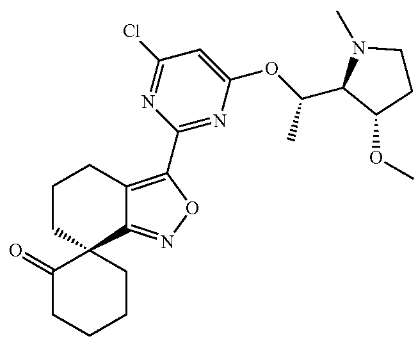 [SMILES: CO[C@H]1CCN(C)[C@@H]1[C@H](C)Oc1cc(Cl)nc(-c2onc3c2CCC[C@@]32CCCCC2=O)n1] | 0.89 | 475 | C |
| G-84b | 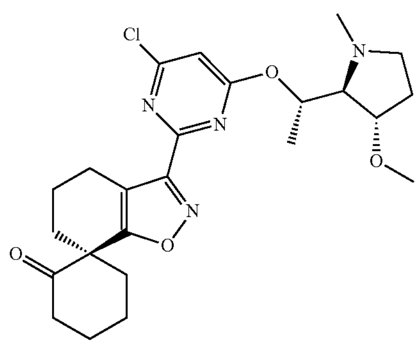 [SMILES: CO[C@H]1CCN(C)[C@@H]1[C@H](C)Oc1cc(Cl)nc(-c2noc3c2CCC[C@@]32CCCCC2=O)n1] | 1.52 | 475 | A |
| G-84c | 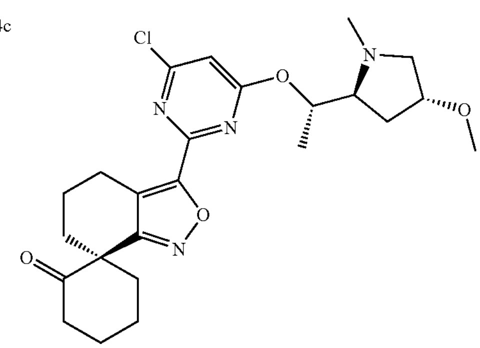 | 1.52 | 475 | A |

TABLE 27-continued

| # | structure | $t_{ret}$ [min] | [M + H]$^+$ | HPLC method |
|---|---|---|---|---|
| G-84d | 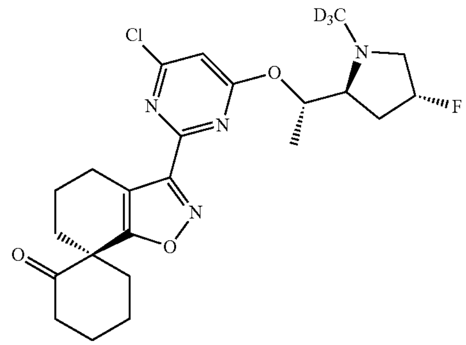 [SMILES: [2H]C([2H])([2H])N1C[C@H](F)C[C@H]1[C@H](C)Oc1cc(Cl)nc(-c2noc3c2CCC[C@@]32CCCCC2=O)n1] | 2.10 | 466 | G |

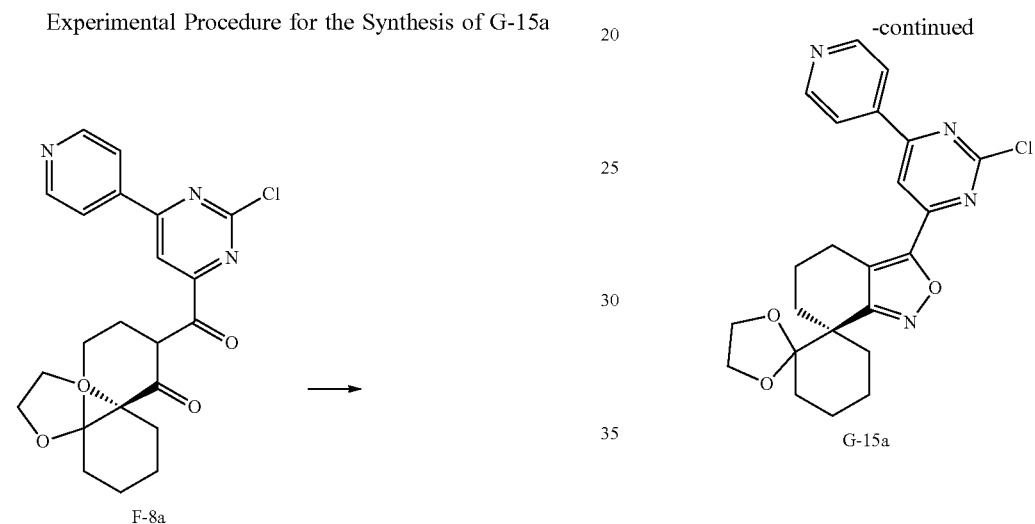

Experimental Procedure for the Synthesis of G-15a

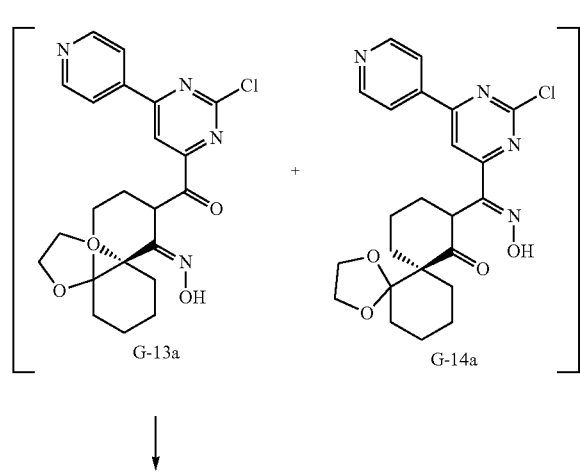

F-8a (356 mg, 0.804 mmol, 1.0 equiv.) is dissolved in dioxane (2 mL) and hydroxylamine solution (50% in water, 98.6 μL, 1.61 mmol, 2.0 equiv.) is added. The resulting solution is stirred at 40° C. until complete conversion is observed. The solvents are evaporated, the resulting residue is purified by RP chromatography to afford G-13a (G-14a is observed as a side product and separated by chromatography). G-13a (136.0 mg, 0.29 mmol 1.0 equiv.) is dissolved in DCM (2 mL) and DIPEA (114.38 μL, 0.65 mmol, 2.2 equiv.) and methanesulfonyl chloride (34.2 μL, 0.45 mmol, 1.5 equiv.) is added. The resulting solution is stirred at rt until complete conversion is observed. The reaction mixture is concentrated under reduced pressure and extracted with DCM (3×) and water. The organic solvent is evaporated, the resulting residue is purified by RP chromatography to afford G-15a.

The following intermediates G-15 (Table 28) are available in an analogous manner. The crude product is purified by chromatography if necessary.

TABLE 28

| # | structure | $t_{ret}$ [min] | $[M + H]^+$ | HPLC method |
|---|---|---|---|---|
| G-15a | 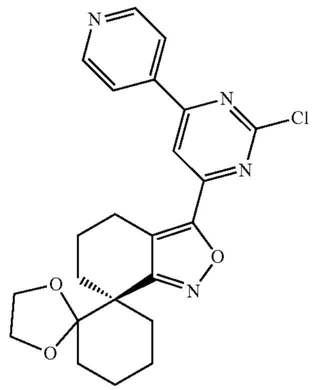 [SMILES: Clc1nc(-c2ccncc2)cc(-c2onc3c2CCC[C@@]32CCCCC23OCCO3)n1] | 1.64 | 439 | A |
| G-15b | 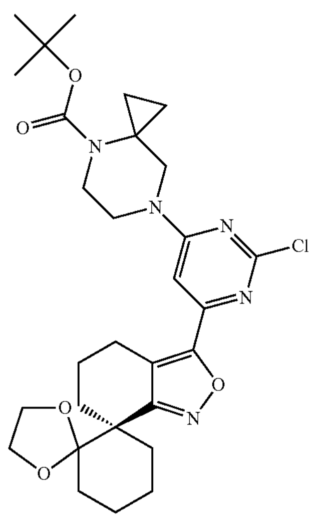 [SMILES: CC(C)(C)OC(=O)N1CCN(c2cc(-c3onc4c3CCC[C@@]43CCCCC34OCCO4)nc(Cl)n2)CC12CC2] | 1.89 | 572 | A |
| G-15c | 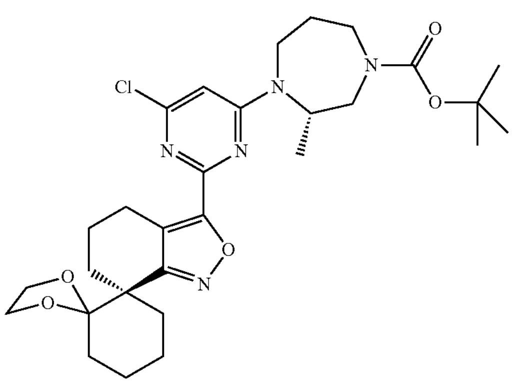 [SMILES: C[C@H]1CN(C(=O)OC(C)(C)C)CCCN1c1cc(Cl)nc(-c2onc3c2CCC[C@@]32CCCCC23OCCO3)n1] | 0.99 | 574 | C |

Experimental Procedure for the Synthesis of G-18a
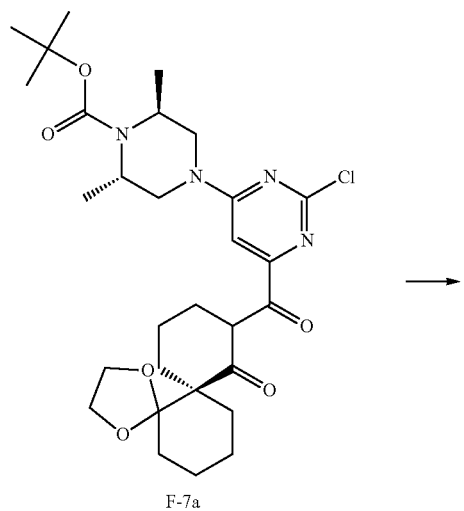
F-7a
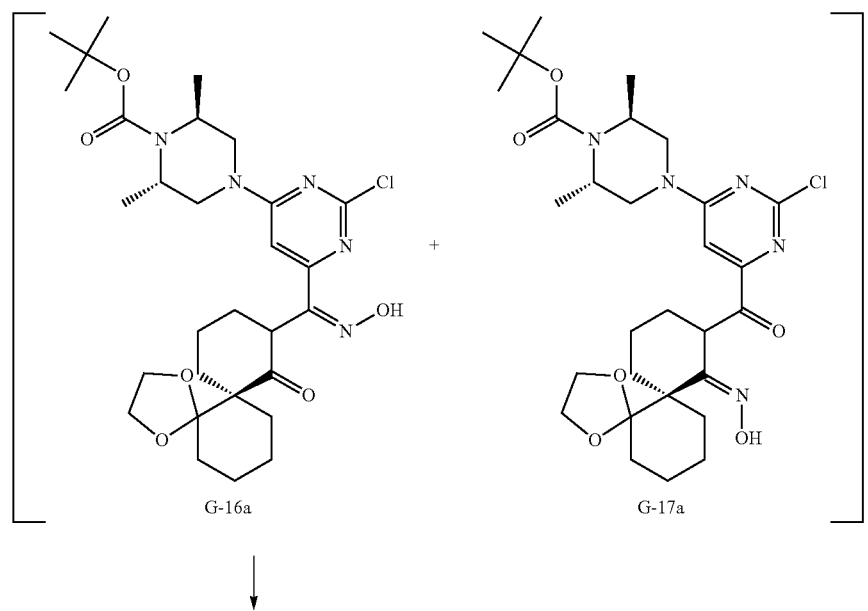
G-16a + G-17a -continued

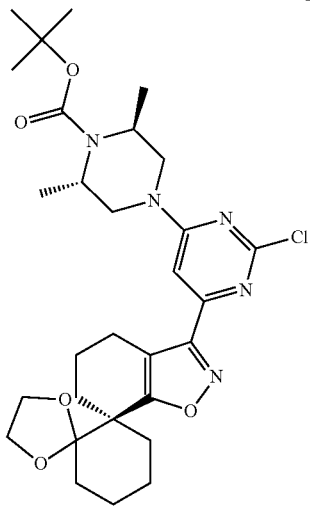

G-18a

F-7a (740 mg, 1.28 mmol, 1.00 equiv.) is dissolved in pyridine (5.0 mL), hydroxylamine hydrochloride (135 mg, 1.92 mmol, 1.5 equiv.) is added and the solution is stirred at 80° C. for 2 h. After cooling to rt, the reaction mixture is acidified with 2 M HCl and extracted with DCM (2×). The combined organic phases are washed with 1 M HCl, the solvents are evaporated, and the resulting residue is purified by NP chromatography to afford G-16a. G-17a is observed as a side product and is not isolated.

G-16a (425 mg, 0.65 mmol, 1.00 equiv.) is dissolved acetic acid (1.0 mL) and stirred at 50° C. overnight. The reaction mixture is quenched with saturated $Na_2CO_3$. The suspension is extracted with DCM, the organic phase is separated, evaporated and the resulting residue is purified by NP chromatography to afford G-18a.

The following intermediates G-18 (Table 29) are available in an analogous manner. The crude product is purified by chromatography if necessary.

TABLE 29

| # | structure | $t_{ret}$ [min] | $[M + H]^+$ | HPLC method |
|---|---|---|---|---|
| G-18a | 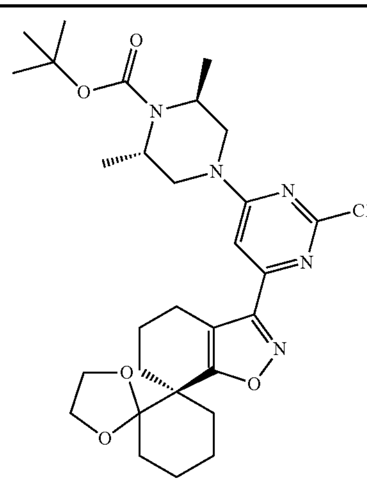 | 1.89 | 574 | A |

TABLE 29-continued
| # | structure | $t_{ret}$ [min] | $[M + H]^+$ | HPLC method |
|---|---|---|---|---|
| G-18b | 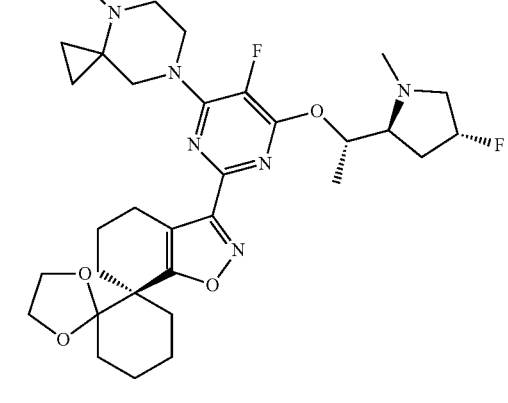 | 1.32 | 701 | B |
| G-18c | 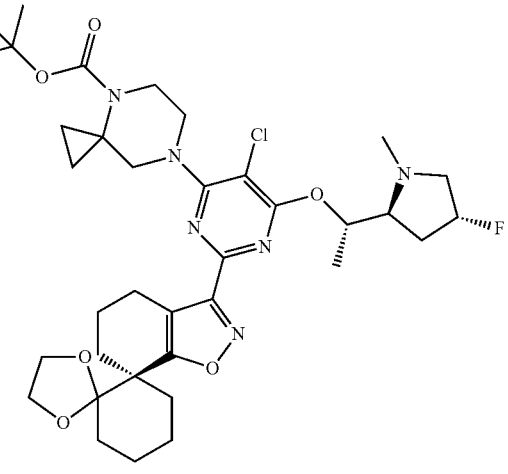 | 1.34 | 717 | B |
| G-18d | 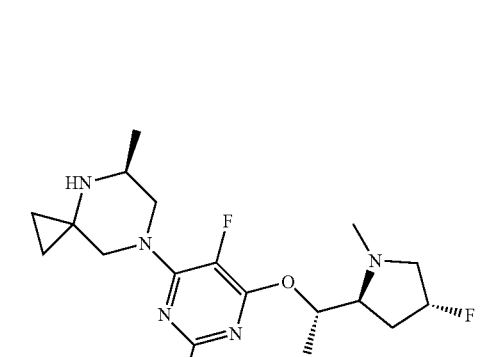 | 1.15 | 615 | B |

TABLE 29-continued

| # | structure | $t_{ret}$ [min] | [M + H]⁺ | HPLC method |
|---|---|---|---|---|
| G-18e | 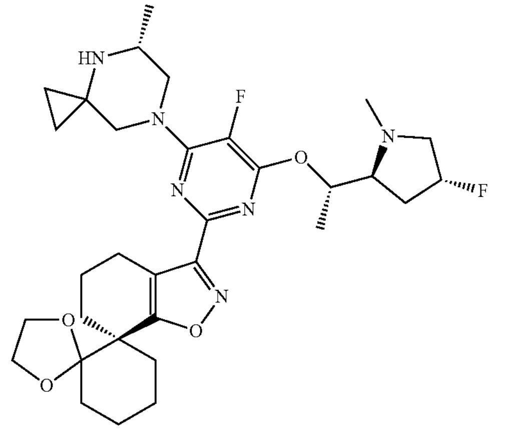 [SMILES: C[C@@H]1CN(c2nc(-c3noc4c3CCC[C@@]43CCCCC34OCCO4)nc(O[C@@H](C)[C@@H]3C[C@@H](F)CN3C)c2F)CC2(CC2)N1] | 1.13 | 615 | B |

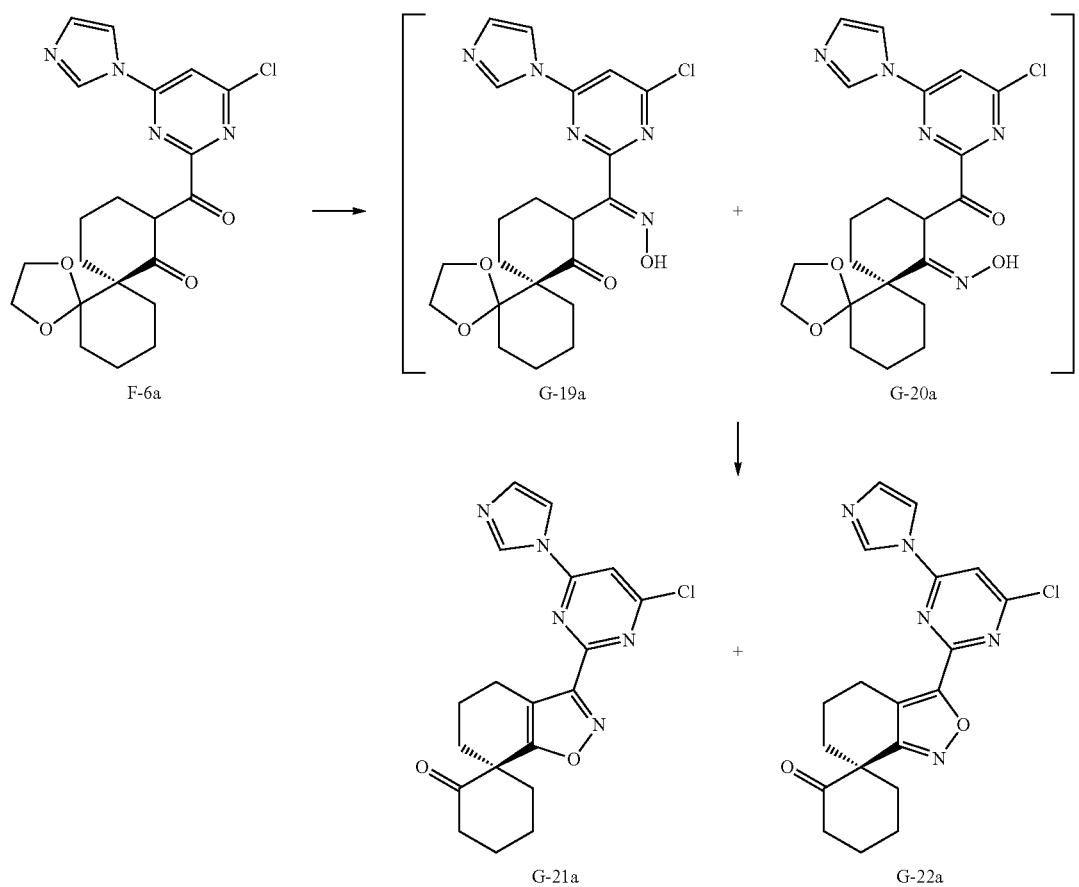

Experimental Procedure for the Synthesis of G-21a

F-6a (1.98 g, 4.60 mmol, 1 equiv.) is dissolved in dioxane (40 mL) and MeOH (10 mL), formic acid (250 μL, 6.63 mmol, 1.44 mmol) and hydroxylamine solution (50% in water, 310 μL, 5.05 mmol, 1.44 equiv.) is added and stirred overnight. After complete conversion, the reaction is concentrated under reduced pressure and purified by NP chromatography to give product G-19a and G-20a.

G-19a (350 mg, 0.78 mmol, 1.00 equiv.) is dissolved in HCl (4 M in dioxane, 2.5 mL) and stirred for 5 min at rt. HCl (4 M, 2.5 mL) is then added and the reaction is stirred for 30 min at rt. After complete conversion, the reaction mixture is basified with NaHCO₃ and extracted with DCM. The combined organic phase is concentrated under reduced pressure to give the product G-21a.

The following intermediates G-21 and G-22 (Table 30) are available in an analogous manner. The crude product is purified by chromatography if necessary.

TABLE 30

| # | structure | $t_{ret}$ [min] | $[M + H]^+$ | HPLC method |
|---|---|---|---|---|
| G-21a | 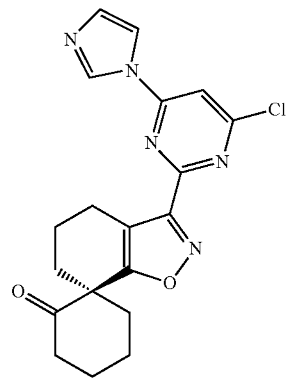 [SMILES: O=C1CCCC[C@@]12CCCc1c(-c3nc(Cl)cc(-n4ccnc4)n3)noc12] | 0.63 | 384 | C |
| G-21b | 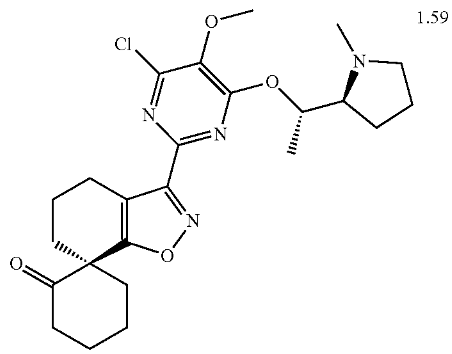 | 1.59 | 537 | H |
| G-21c | 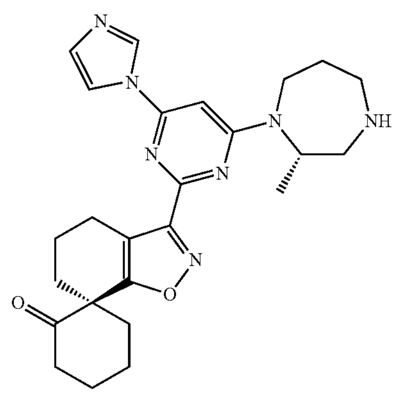 [SMILES: C[C@H]1CNCCCN1c1cc(-n2ccnc2)nc(-c2noc3c2CCC[C@@]32CCCCC2=O)n1] | 1.19 | 462 | A |
| G-22d | 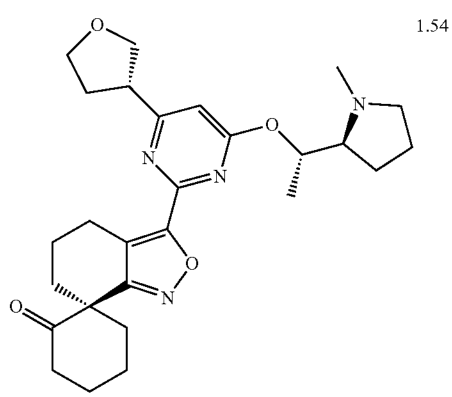 | 1.54 | 481 | A |

TABLE 30-continued
| # | structure | $t_{ret}$ [min] | $[M + H]^+$ | HPLC method |
|---|---|---|---|---|
| G-21d | 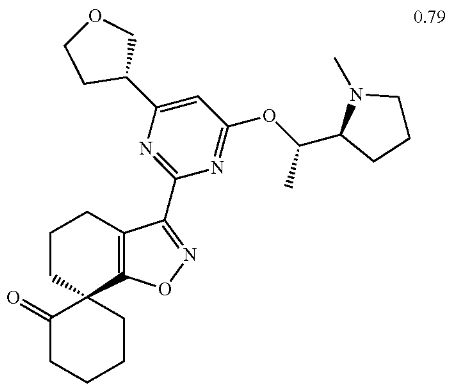 | 0.79 | 481 | C |
| G-21e | 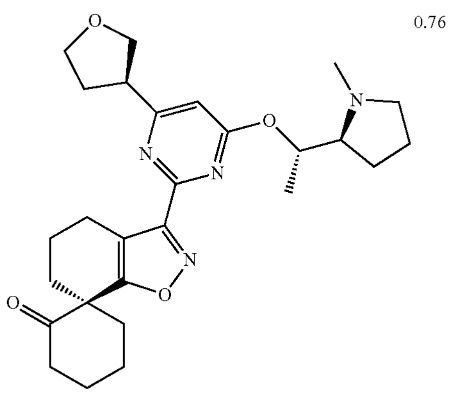 | 0.76 | 481 | C |
Experimental Procedure for the Synthesis of G-25a
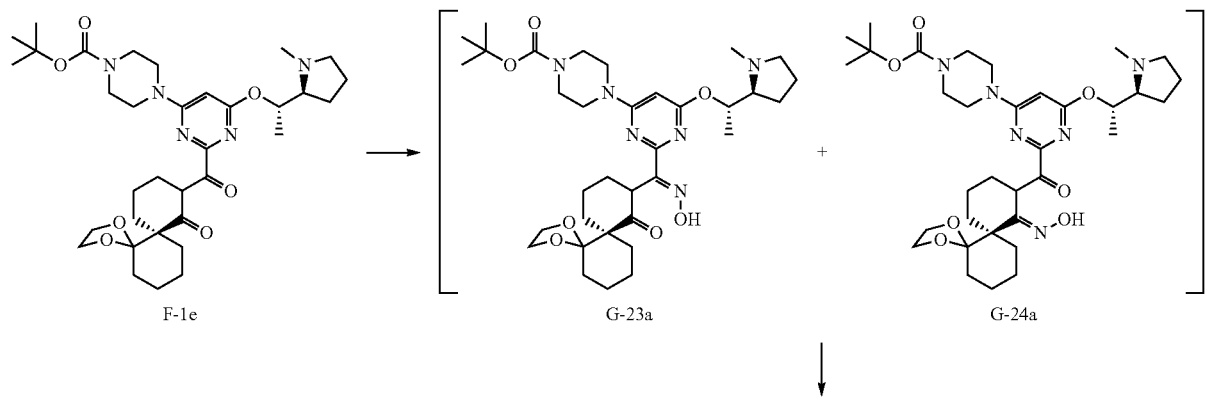

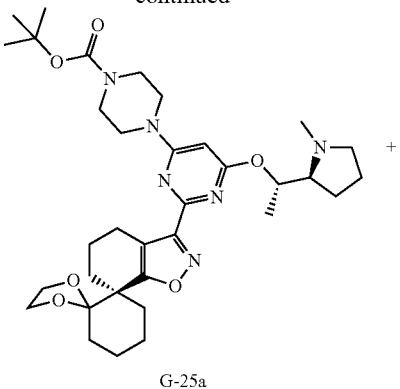

G-25a

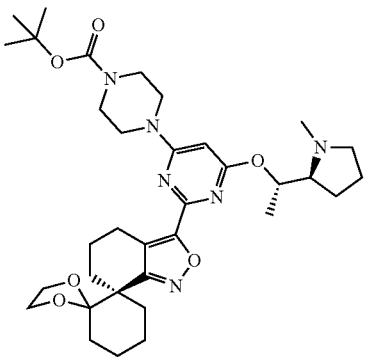

G-26a

F-1e (350 mg, 0.54 mmol, 1.00 equiv.) is dissolved in pyridine (3 mL), hydroxylamine hydrochloride (56.9 mg, 0.81 mmol, 1.5 equiv.) is added. The reaction is stirred for 3 d at 90° C. After complete conversion of starting material is observed, the reaction is concentrated under reduced pressure and extracted with NaHCO$_3$/DCM. The combined organic phase is concentrated under reduced pressure and purified by RP chromatography to give G-25a. G-26a is observed as a minor side product and is not isolated (HPLC-Method: C, t$_{ret}$=1.01 min; [M+H]=639).

Experimental Procedure for the Synthesis of G-27a

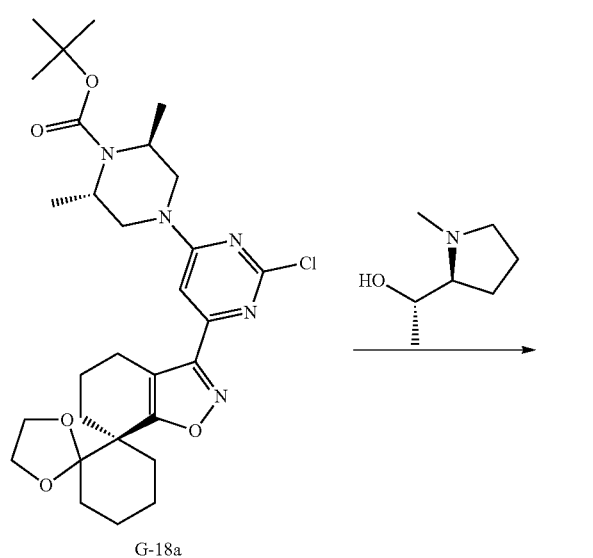

G-18a

-continued

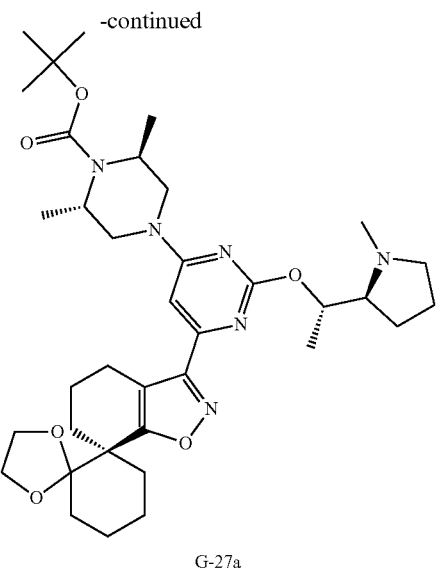

G-27a (1S)-1-[(2S)-1-methylpyrrolidin-2-yl]ethan-1-ol (1.78 g, 10.5 mmol, 3.0 equiv.) and potassium tert-butoxide (1.17 g, 10.5 mmol, 3.0 equiv.) are dissolved in 1-4 dioxane (500 mL) and stirred at 50° C. for 30 min. G-18a (2.0 g, 3.48 mmol, 1 equiv.) is added and the solution is stirred at 85° C. for 3 h. The solvent is evaporated and the resulting residue is purified by NP chromatography to afford G-27a (HPLC-Method: A, t$_{ret}$=1.92 min; [M+H]=667).

215

Experimental Procedure for the Synthesis of G-28a

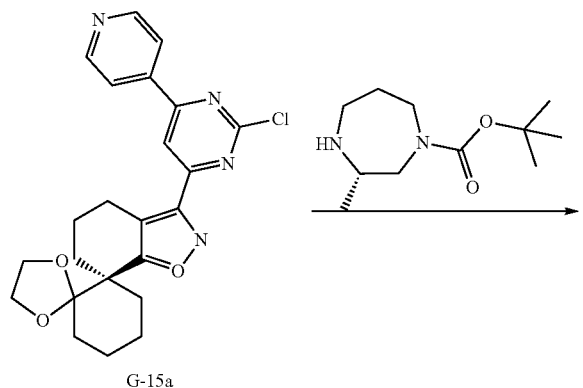

G-15a

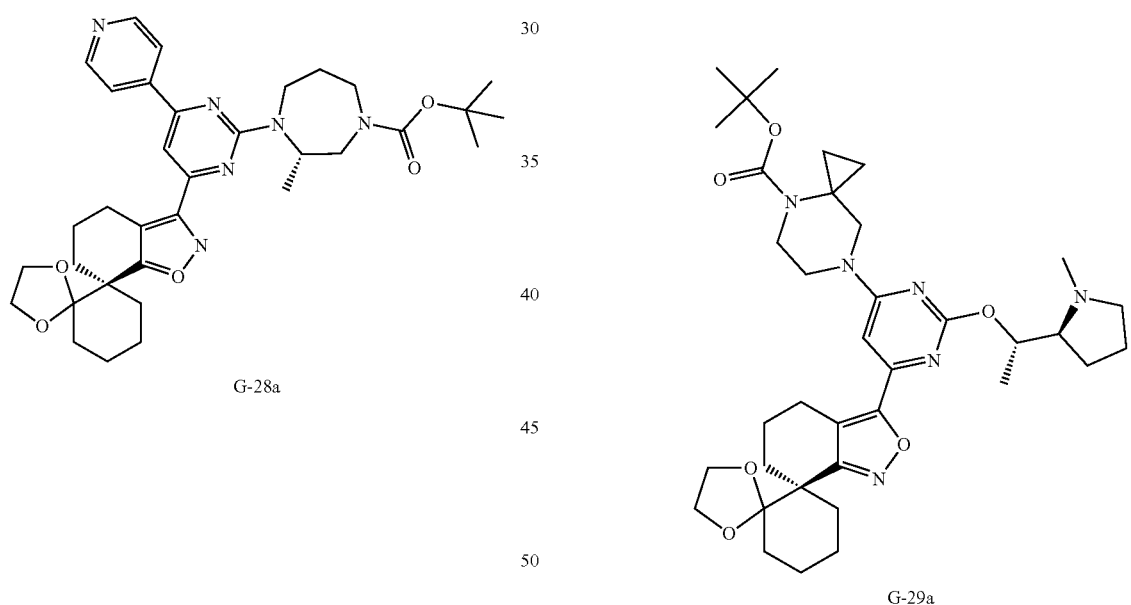

G-28a

G-15a (114 mg, 0.260 mmol, 1.0 equiv.) is dissolved in DMSO (1 mL) and DIPEA (90.4 µL, 0.519 mmol, 2.0 equiv.) is added. Then (S)-tert-butyl 3-methyl-1,4-diazepane-1-carboxylate (121 mg, 0.545 mmol, 2.1 equiv.) is added to the reaction mixture and stirred at 70° C. for 17 h until complete conversion of the starting materials is observed. The reaction mixture is diluted with water and extracted three times with DCM. The organic solvent is evaporated and the resulting residue is purified by RP chromatography to afford G-28a (HPLC-Method: C, $t_{ret}$=1.06 min; [M+H]=617).

216

Experimental Procedure for the Synthesis of G-29a

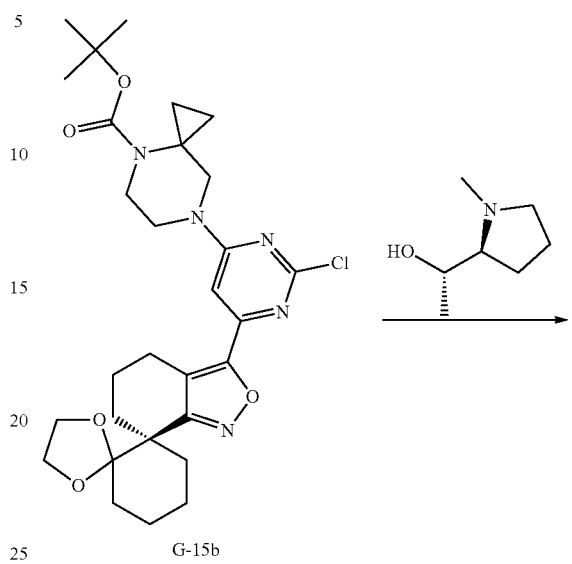

G-15b

G-29a (1S)-1-[(2S)-1-methylpyrrolidin-2-yl]ethan-1-ol (122 µL mg, 0.865 mmol, 3.0 equiv.) and potassium tert.-butoxide (97.0 mg, 0.865 mmol, 3.0 equiv.) are dissolved in THF (2 mL) and stirred at 50° C. for 30 min. G-15b (165 mg, 0.28 mmol, 1 equiv.) is added and the solution is stirred at 85° C. for 3 h. The solvent is evaporated and the resulting residue is purified by RP chromatography to afford G-29a (HPLC-Method: C, $t_{ret}$=1.12 min; [M+H]=665).

Experimental Procedure for the Synthesis of G-30a

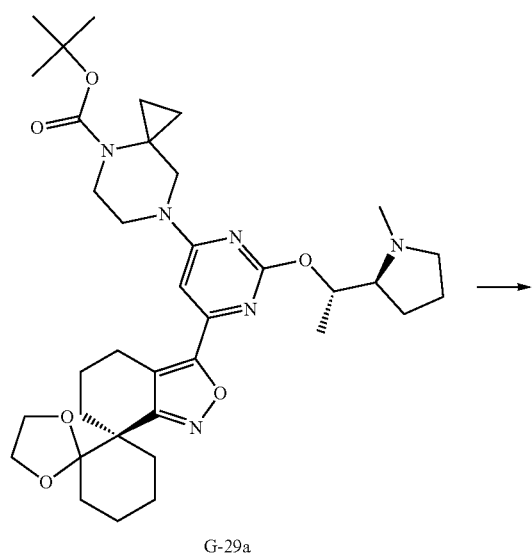

G-29a

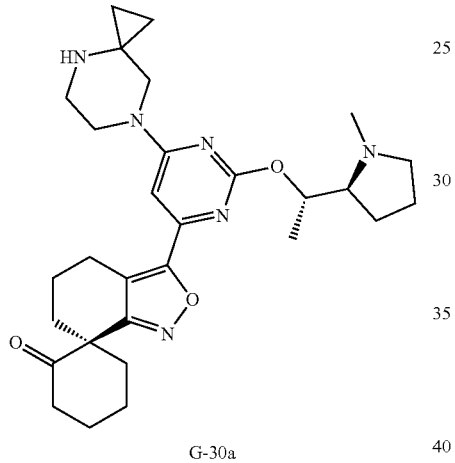

G-30a

G-29a (183 mg, 275 μmol, 1.0 equiv.) and HCl (8 M, 172 μL, 1.38 mmol, 5.0 equiv.) are dissolved in MeOH (2.0 mL) and stirred at 60° C. until total conversion. The reaction mixture is concentrated under reduced pressure and extracted with EtOAc/NaHCO₃. The combined organic phase is concentrated under reduced pressure to give G-30a (HPLC-Method: A, t$_{ret}$=1.41 min; [M+H]=521).

Experimental Procedure for the Synthesis of G-31a

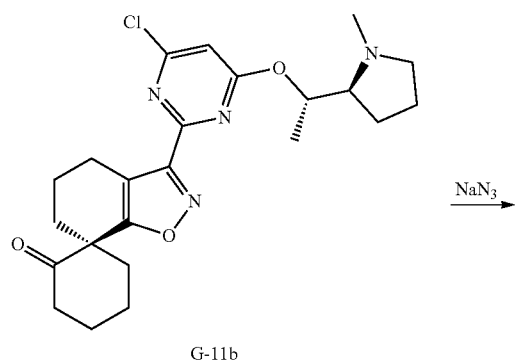

G-11b

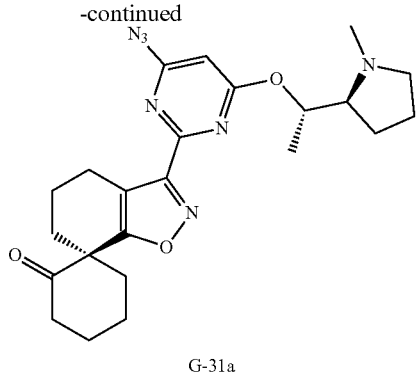

G-31a

G-11b (3.00 g, 6.45 mmol, 1.0 equiv.) is dissolved in DMF (7 mL), sodium azide (504 mg, 7.74 mmol, 1.2 equiv.) is added and the reaction is stirred for 18 h at 50° C. After compete conversion of starting material the reaction is cooled down to rt and is extracted with DCM/Water. The combined organic phase is concentrated under reduced pressure to give G-31a (HPLC-Method: C, t$_{ret}$=0.88 min; [M+H]=452).

Experimental Procedure for the Synthesis of G-32a

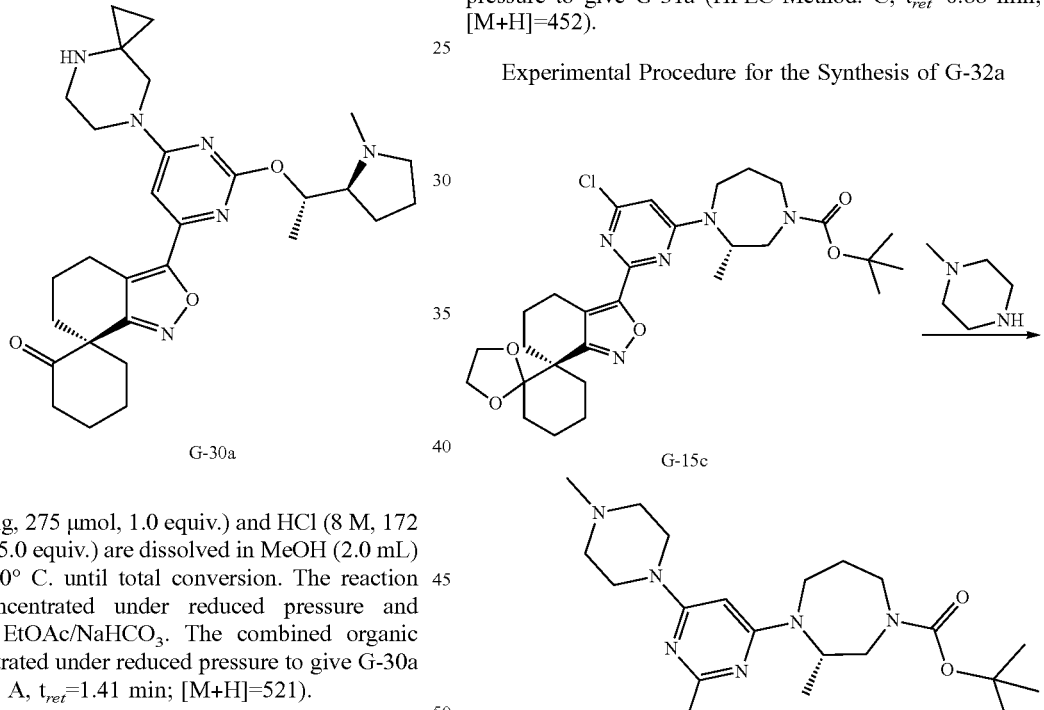

G-15c (80.0 mg, 0.139 mmol, 1.0 equiv.) is dissolved in DMSO (1 mL) and DIPEA (47.4 μL, 0.279 mmol, 2.0 equiv.) and N-methylpiperazine (20.9 mg, 0.209 mmol, 1.5 equiv.) is added. The reaction mixture is stirred at 90° C. until complete conversion is observed. The mixture is diluted with aq. satd. NaHCO₃ solution and extracted three times with DCM. The organic phases are combined, filtered and concentrated under reduced pressure. The resulting residue is dissolved in ACN and purified by basic RP chromatography (gradient elution: 40% to 98% ACN in water) to give the desired product 32a (HPLC method: C, $t_{ret}$=0.953 min; [M+H]$^+$=638).

Experimental Procedure for the Synthesis of G-33a

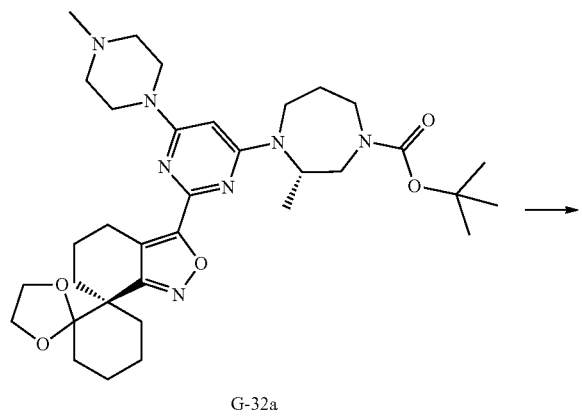

G-32a

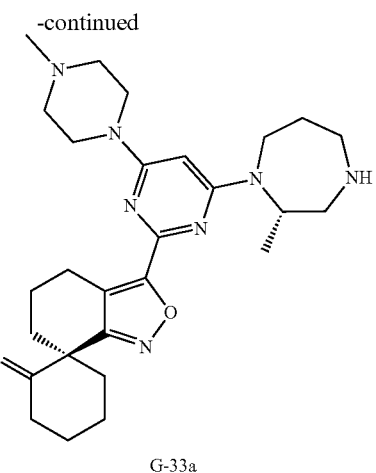

G-33a

G-32a (139 mg, 0.225 mmol, 1.0 equiv.) is dissolved in dioxane (1 mL) and HCl solution (2 M in water, 0.79 mL, 1.58 mmol, 7.0 equiv.) is added. The resulting solution is stirred at 60° C. for 2 h until complete conversion of the starting materials is observed. The reaction mixture is diluted with aq. saturated NaHCO$_3$ solution and extracted three times with DCM. The organic solvent is evaporated, and the resulting residue is purified by RP chromatography to afford G-33a.

The following intermediates G-33 (Table 31) are available in an analogous manner. The crude product is purified by chromatography if necessary.

TABLE 31

| # | structure | $t_{ret}$ [min] | [M + H]$^+$ | HPLC method |
|---|---|---|---|---|
| G-33a | 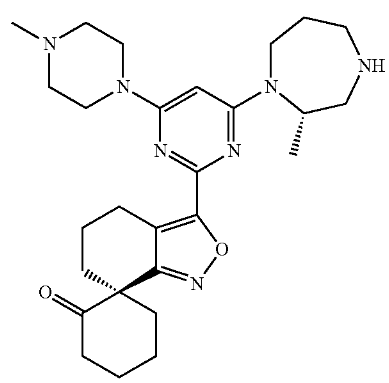 [SMILES: C[C@H]1CNCCCN1c1cc(N2CCN(C)CC2)nc(-c2onc3c2CCC[C@@]32CCCCC2=O)n1] | 1.46 | 494 | A |
| G-33b | 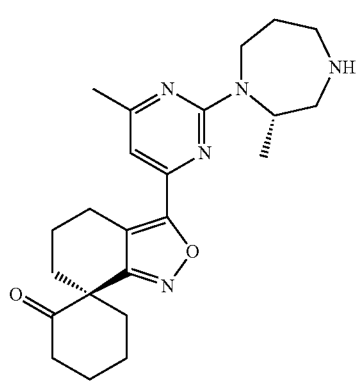 [SMILES: Cc1cc(-c2onc3c2CCC[C@@]32CCCCC2=O)nc(N2CCCNC[C@@H]2C)n1] | 1.42 | 410 | A |

TABLE 31-continued

| # | structure | $t_{ret}$ [min] | $[M + H]^+$ | HPLC method |
|---|---|---|---|---|
| G-33c | 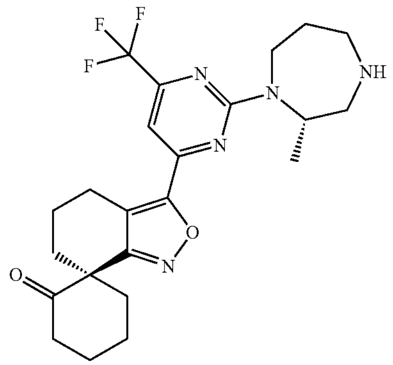 [SMILES: C[C@H]1CNCCCN1c1nc(-c2onc3c2CCC[C@@]32CCCCC2=O)cc(C(F)(F)F)n1] | 0.88 | 464 | C |
| G-33d | 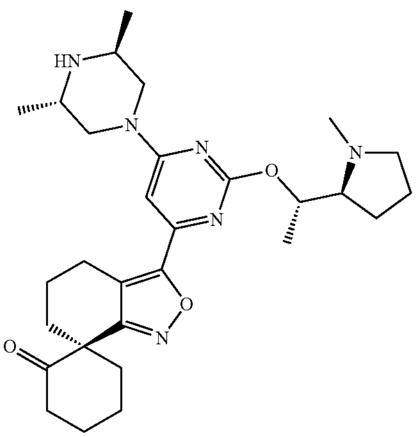 [SMILES: C[C@H](Oc1nc(-c2onc3c2CCC[C@@]32CCCCC2=O)cc(N2C[C@H](C)N[C@@H](C)C2)n1)[C@@H]1CCCN1C] | 1.60 | 523 | A |

Experimental Procedure for the Synthesis of G-34a

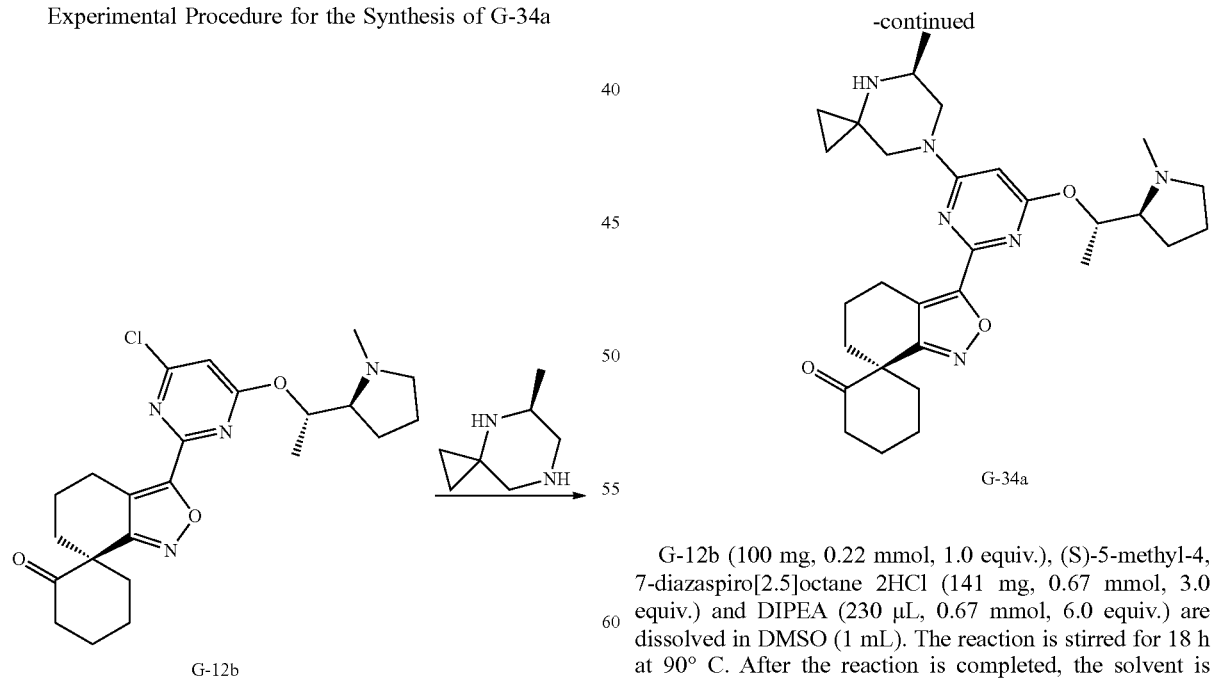

G-12b (100 mg, 0.22 mmol, 1.0 equiv.), (S)-5-methyl-4,7-diazaspiro[2.5]octane 2HCl (141 mg, 0.67 mmol, 3.0 equiv.) and DIPEA (230 µL, 0.67 mmol, 6.0 equiv.) are dissolved in DMSO (1 mL). The reaction is stirred for 18 h at 90° C. After the reaction is completed, the solvent is removed under reduced pressure and the residue purified by basic RP chromatography to give the desired product G-34a.

The following intermediates G-34 (Table 32) are available in an analogous manner. The crude product is purified by chromatography if necessary.

The diastereomeric mixture G-34c can be separated via chiral HPLC (Chiralpack IE, 250×20 mm, 5µ; solvent: ethanol/heptane 60:40+0.1% diethyl amine) to obtain G-34c1 (eluting 1$^{st}$ as peak1) and G-34c2 (eluting afterwards as peak2).

TABLE 32

| # | structure | t$_{ret}$ [min] | [M + H]$^+$ | HPLC method |
|---|---|---|---|---|
| G-34a | 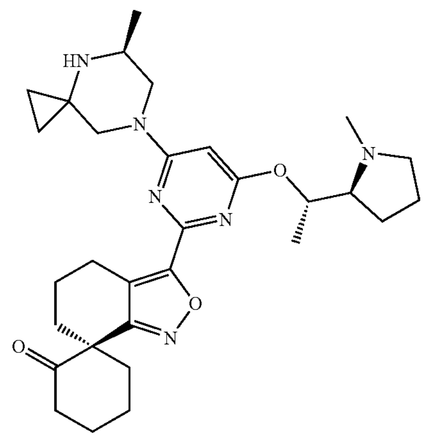 [SMILES: C[C@H](Oc1cc(N2C[C@H](C)NC3(CC3)C2)nc(-c2onc3c2CCC[C@@]32CCCCC2=O)n1)[C@@H]1CCCN1C] | 1.51 | 535 | A |
| G-34b | 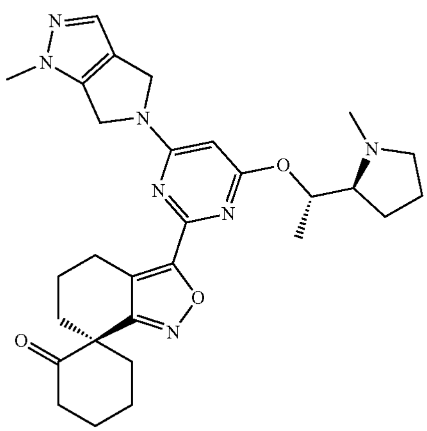 [SMILES: C[C@H](Oc1cc(N2Cc3cnn(C)c3C2)nc(-c2onc3c2CCC[C@@]32CCCCC2=O)n1)[C@@H]1CCCN1C] | 0.81 | 532 | C |
| G-34c | 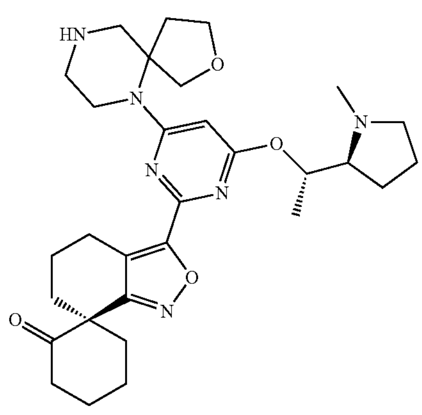 [SMILES: C[C@H](Oc1cc(N2CCNCC23CCOC3)nc(-c2onc3c2CCC[C@@]32CCCCC2=O)n1)[C@@H]1CCCN1C] | 1.33 | 551 | A |

TABLE 32-continued
| # | structure | t_ret [min] | [M + H]+ | HPLC method |
|---|---|---|---|---|
| G-34c1 | 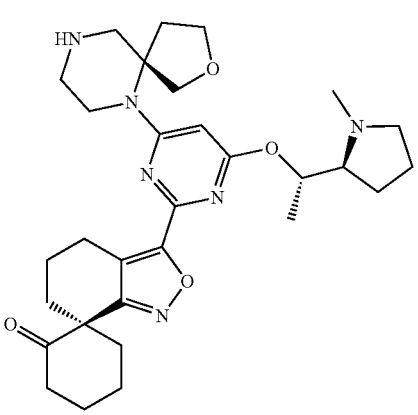 [SMILES: C[C@H](Oc1cc(N2CCNC[C@]23CCOC3)nc(-c2onc3c2CCC[C@@]32CCCCC2=O)n1)[C@@H]1CCCN1C] | 2.12 | | R |
| G-34c2 | 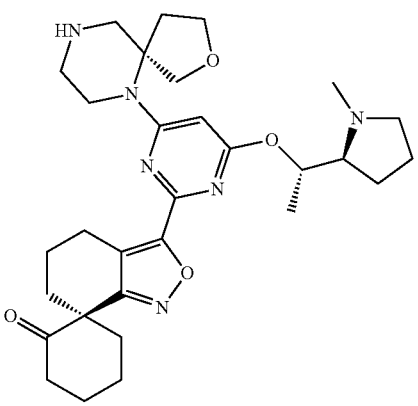 [SMILES: C[C@H](Oc1cc(N2CCNC[C@@]23CCOC3)nc(-c2onc3c2CCC[C@@]32CCCCC2=O)n1)[C@@H]1CCCN1C] | 2.82 | | R |
| G-34d | 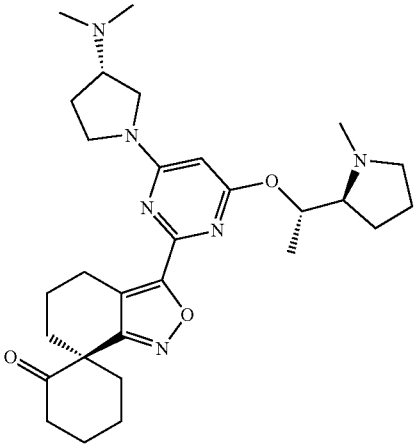 [SMILES: C[C@H](Oc1cc(N2CC[C@H](N(C)C)C2)nc(-c2onc3c2CCC[C@@]32CCCCC2=O)n1)[C@@H]1CCCN1C] | 1.53 | 523 | A |

TABLE 32-continued

| # | structure | $t_{ret}$ [min] | $[M + H]^+$ | HPLC method |
|---|---|---|---|---|
| G-34e | 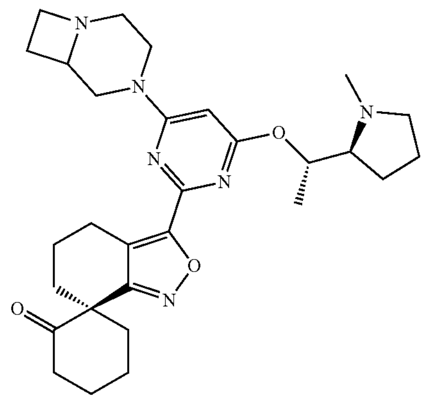 [SMILES: C[C@H](Oc1cc(N2CCN3CCC3C2)nc(-c2onc3c2CCC[C@@]32CCCCC2=O)n1)[C@@H]1CCCN1C] | 0.71 | 521 | C |
| G-34f | 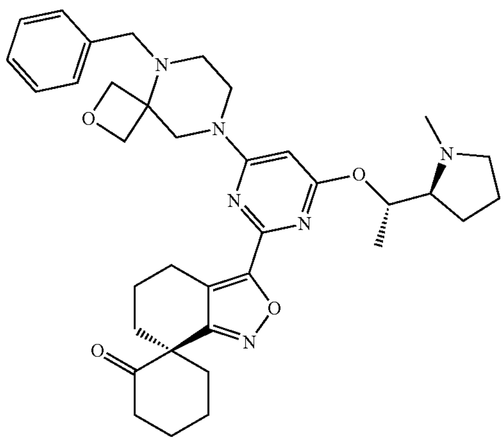 [SMILES: C[C@H](Oc1cc(N2CCN(Cc3ccccc3)C3(COC3)C2)nc(-c2onc3c2CCC[C@@]32CCCCC2=O)n1)[C@@H]1CCCN1C] | 0.99 | 627 | C |
| G-34g | 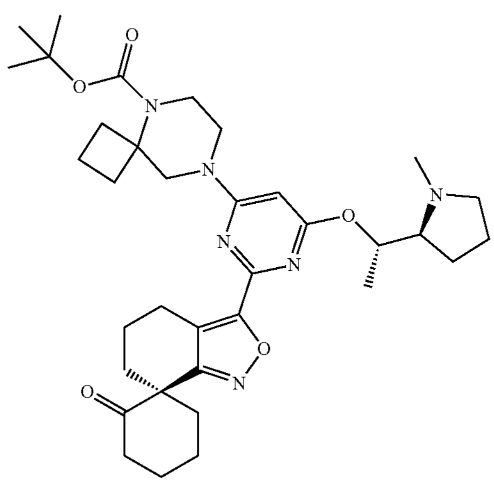 [SMILES: C[C@H](Oc1cc(N2CCN(C(=O)OC(C)(C)C)C3(CCC3)C2)nc(-c2onc3c2CCC[C@@]32CCCCC2=O)n1)[C@@H]1CCCN1C] | 1.08 | 635 | C |

TABLE 32-continued

| # | structure | t_ret [min] | [M + H]+ | HPLC method |
|---|---|---|---|---|
| G-34h | 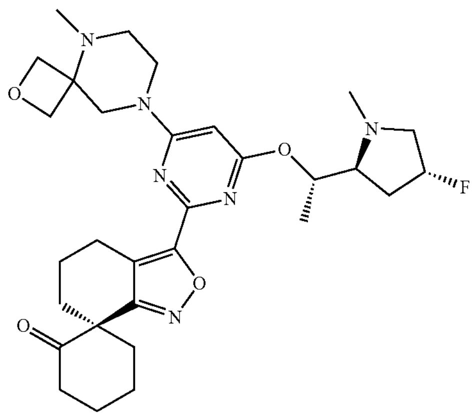 [SMILES: C[C@H](Oc1cc(N2CCN(C)C3(COC3)C2)nc(-c2onc3c2CCC[C@@]32CCCCC2=O)n1)[C@@H]1C[C@@H](F)CN1C] | 1.01 | 569 | B |
| G-34i | 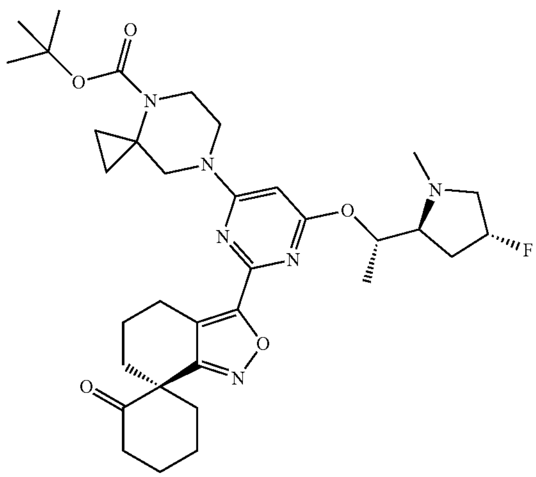 [SMILES: C[C@H](Oc1cc(N2CCN(C(=O)OC(C)(C)C)C3(CC3)C2)nc(-c2onc3c2CCC[C@@]32CCCCC2=O)n1)[C@@H]1C[C@@H](F)CN1C] | 1.24 | 639 | B |
| G-34j | 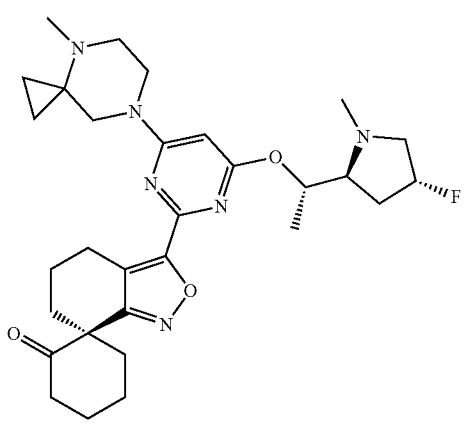 [SMILES: C[C@H](Oc1cc(N2CCN(C)C3(CC3)C2)nc(-c2onc3c2CCC[C@@]32CCCCC2=O)n1)[C@@H]1C[C@@H](F)CN1C] | 1.10 | 553 | B |

TABLE 32-continued

| # | structure | t_ret [min] | [M + H]+ | HPLC method |
|---|---|---|---|---|
| G-34k | 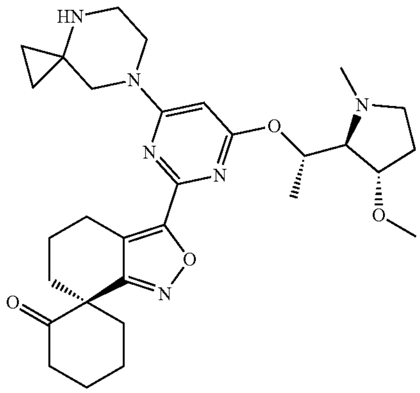 [SMILES: CO[C@H]1CCN(C)[C@@H]1[C@H](C)Oc1cc(N2CCNC3(CC3)C2)nc(-c2onc3c2CCC[C@@]32CCCCC2=O)n1] | 1.02 | 551 | B |
| G-34l | 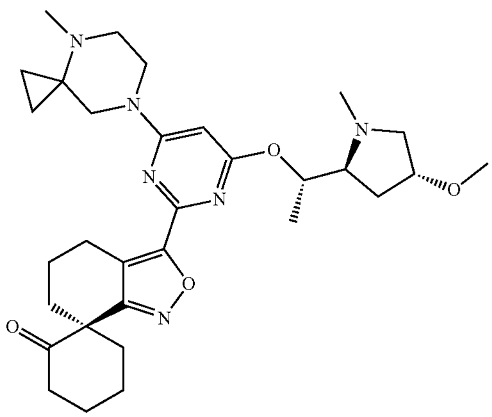 [SMILES: CO[C@@H]1C[C@@H]([C@H](C)Oc2cc(N3CCN(C)C4(CC4)C3)nc(-c3onc4c3CCC[C@@]43CCCCC3=O)n2)N(C)C1] | 1.06 | 565 | B |
| G-34m | 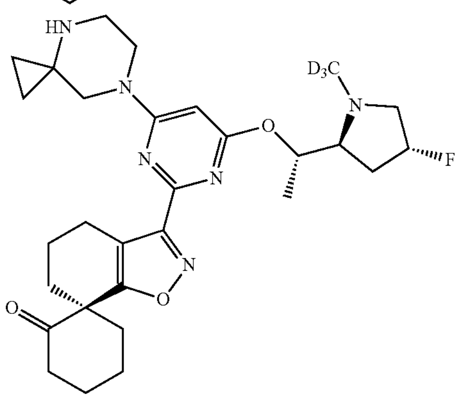 | 0.99 | 542 | B |
| G-34n | 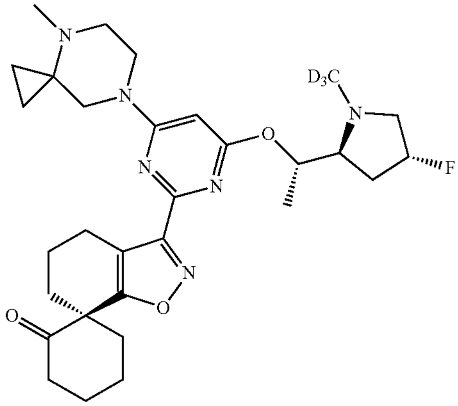 [SMILES: [2H]C([2H])([2H])N1C[C@H](F)C[C@H]1[C@H](C)Oc1cc(N2CCN(C)C3(CC3)C2)nc(-c2noc3c2CCC[C@@]32CCCCC2=O)n1] | 1.05 | 556 | B |

Experimental Procedure for the Synthesis of G-35a

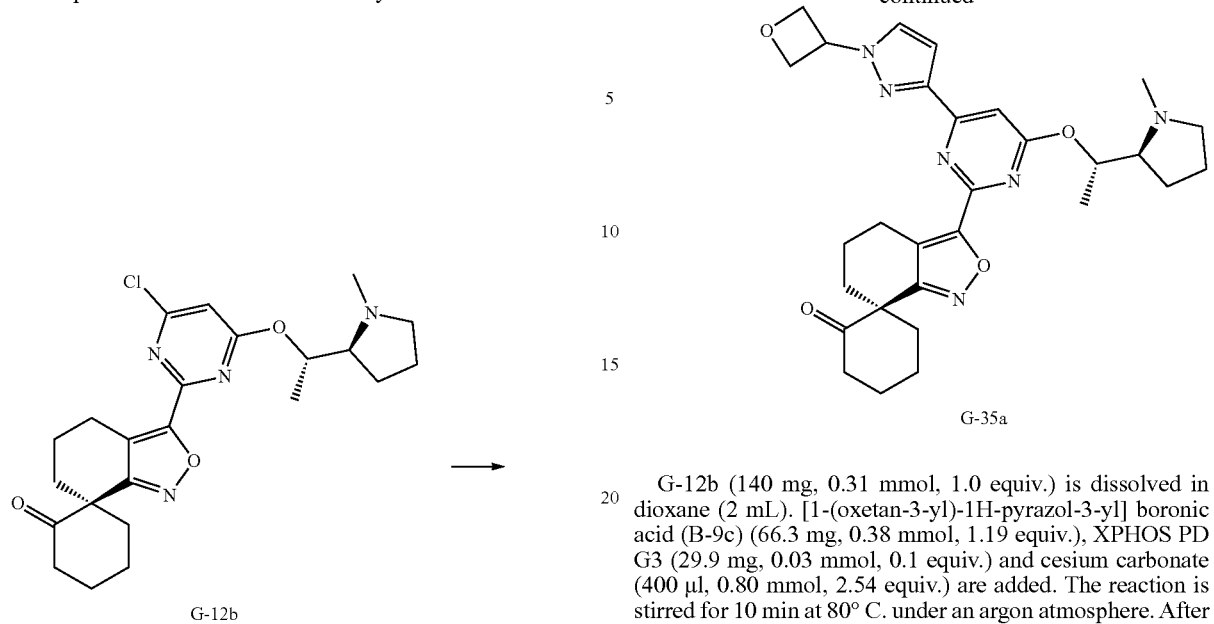

G-12b (140 mg, 0.31 mmol, 1.0 equiv.) is dissolved in dioxane (2 mL). [1-(oxetan-3-yl)-1H-pyrazol-3-yl] boronic acid (B-9c) (66.3 mg, 0.38 mmol, 1.19 equiv.), XPHOS PD G3 (29.9 mg, 0.03 mmol, 0.1 equiv.) and cesium carbonate (400 μl, 0.80 mmol, 2.54 equiv.) are added. The reaction is stirred for 10 min at 80° C. under an argon atmosphere. After complete conversion is observed the reaction is extracted with DCM/water. The combined organic phase is concentrated under reduced pressure, dissolved in ACN/water and purified by RP chromatography to give the desired product G-35a.

The following intermediates G-35 (Table 33) are available in an analogous manner. The crude product is purified by chromatography if necessary.

TABLE 33

| # | structure | $t_{ret}$ [min] | $[M + H]^+$ | HPLC method |
|---|---|---|---|---|
| G-35a | 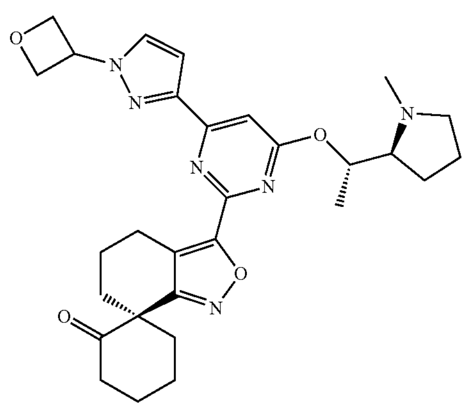 [SMILES: C[C@H](Oc1cc(-c2ccn(C3COC3)n2)nc(-c2onc3c2CCC[C@@]32CCCCC2=O)n1)[C@@H]1CCCN1C] | 0.81 | 533 | C |

TABLE 33-continued

| # | structure | t_ret [min] | [M + H]+ | HPLC method |
|---|---|---|---|---|
| G-35b | 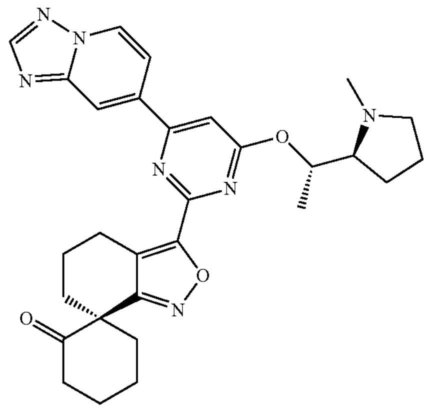 [SMILES: C[C@H](Oc1cc(-c2ccn3ncnc3c2)nc(-c2onc3c2CCC[C@@]32CCCCC2=O)n1)[C@@H]1CCCN1C] | 1.45 | 528 | A |
| G-35c | 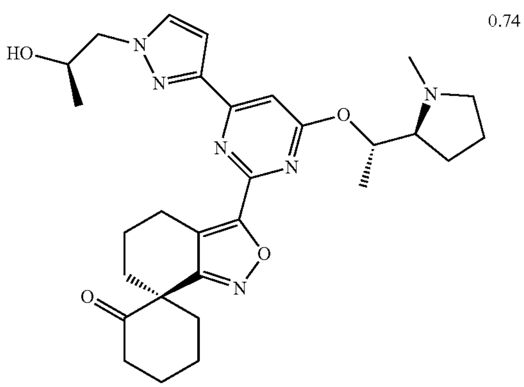 | 0.74 | 535 | C |
| G-35d | 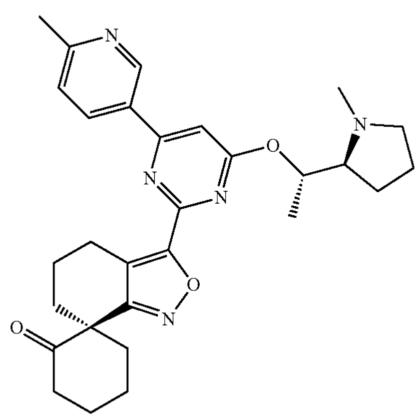 [SMILES: Cc1ccc(-c2cc(O[C@@H](C)[C@@H]3CCCN3C)nc(-c3onc4c3CCC[C@@]43CCCCC3=O)n2)cn1] | 1.55 | 502 | A |
| G-35e | 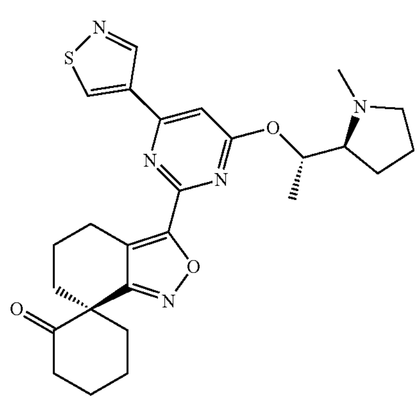 [SMILES: C[C@H](Oc1cc(-c2cnsc2)nc(-c2onc3c2CCC[C@@]32CCCCC2=O)n1)[C@@H]1CCCN1C] | 0.86 | 494 | C |

TABLE 33-continued

| # | structure | $t_{ret}$ [min] | $[M + H]^+$ | HPLC method |
|---|---|---|---|---|
| G-35f | 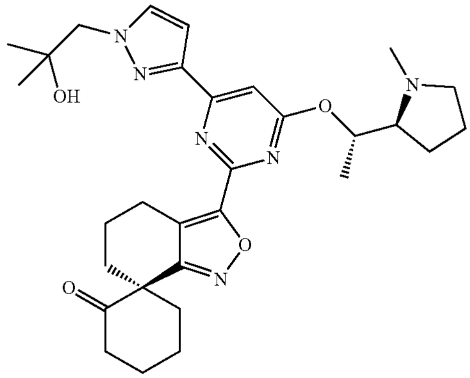 [SMILES: C[C@H](Oc1cc(-c2ccn(CC(C)(C)O)n2)nc(-c2onc3c2CCC[C@@]32CCCCC2=O)n1)[C@@H]1CCCN1C] | 0.81 | 549 | C |
| G-35g | 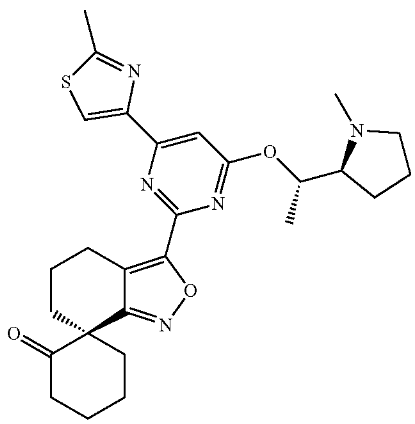 [SMILES: Cc1nc(-c2cc(O[C@@H](C)[C@@H]3CCCN3C)nc(-c3onc4c3CCC[C@@]43CCCCC3=O)n2)cs1] | 1.70 | 508 | A |
| G-35h | 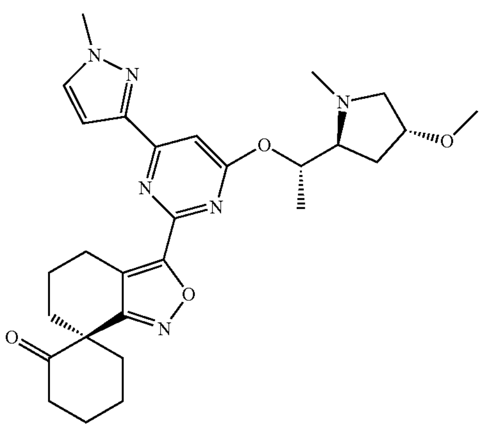 [SMILES: CO[C@@H]1C[C@@H]([C@H](C)Oc2cc(-c3ccn(C)n3)nc(-c3onc4c3CCC[C@@]43CCCCC3=O)n2)N(C)C1] | 0.78 | 521 | C |
| G-35i | 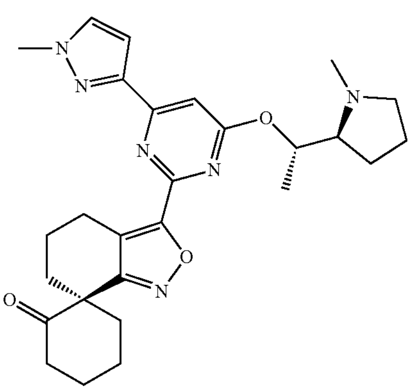 [SMILES: C[C@H](Oc1cc(-c2ccn(C)n2)nc(-c2onc3c2CCC[C@@]32CCCCC2=O)n1)[C@@H]1CCCN1C] | 1.51 | 491 | A |

TABLE 33-continued

| # | structure | t_ret [min] | [M + H]+ | HPLC method |
|---|---|---|---|---|
| G-35j | 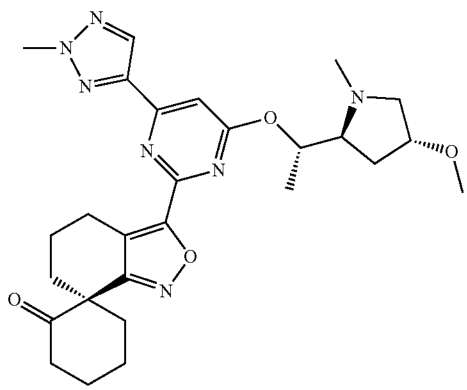 [SMILES: CO[C@@H]1C[C@@H]([C@H](C)Oc2cc(-c3cnn(C)n3)nc(-c3onc4c3CCC[C@@]43CCCCC3=O)n2)N(C)C1] | 0.81 | 522 | C |
| G-35k | 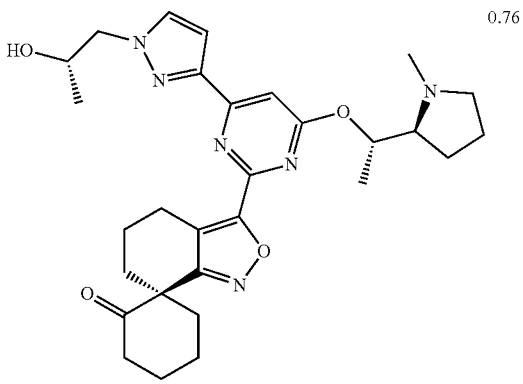 | 0.76 | 535 | C |
| G-35l | 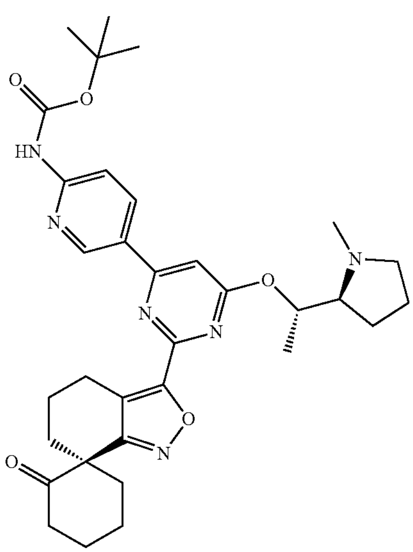 [SMILES: C[C@H](Oc1cc(-c2ccc(NC(=O)OC(C)(C)C)nc2)nc(-c2onc3c2CCC[C@@]32CCCCC2=O)n1)[C@@H]1CCCN1C] | 1.02 | 603 | C |

Experimental Procedure for the Synthesis of G-35n

Experimental Procedure for the Synthesis of G-36a

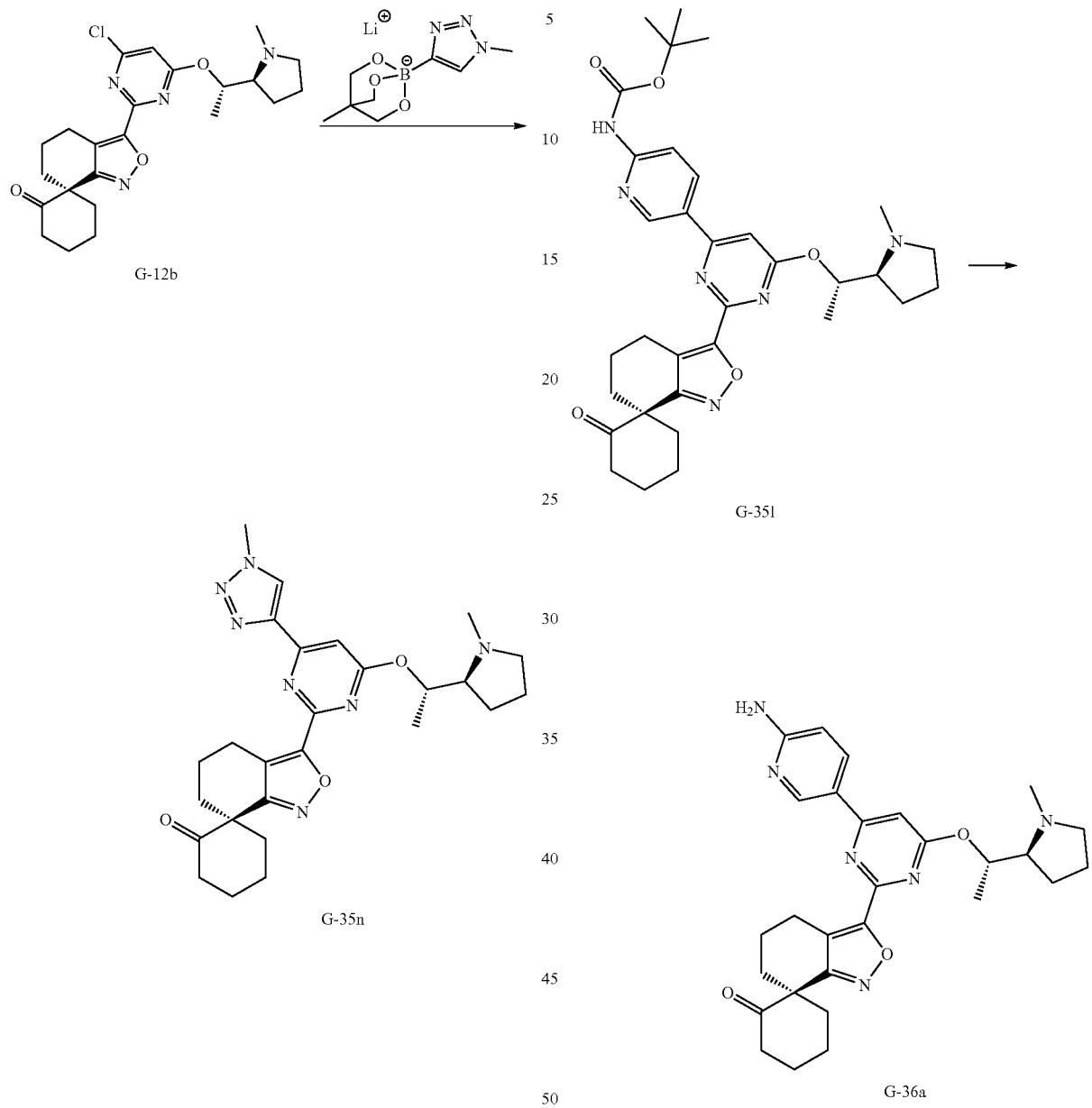

G-12b (118 mg, 0.27 mmol, 1.0 equiv.), 1-methyl-1H-1,2,3-triazole-4-boronic acid, ate complex with 1,1,1-tris(hydroxymethyl)ethane lithium salt (69.0 mg, 0.32 mmol, 1.20 equiv.). Pd(dppf)Cl$_2$ DCM (45.6 mg, 0.05 mol, 0.20 equiv.) are dissolved in dioxan (1.5 ml) and cesium carbonate (190 mg, 0.58 mol. 2.2 equiv.) dissolved in water (165 μL) and added to the reaction. The reaction is stirred for 18 h at 90° C. After full conversion the reaction mixture is filtered and extracted with DCM (3×). The combined organic phase is concentrated under reduced pressure and purifies by RP chromatography to afford G-35n (HPLC-Method: A, t$_{ret}$=1.41 min; [M+H]=492).

G-351 (61.0 mg, 0.1 mmol, 1.0 equiv.) is dissolved in Dioxan (1 mL) and HCl (4 M, 101 μL, 0.4 mmol, 4.0 equiv.) is added. Reaction stirred for 3 h at 50° C. After complete consumption of starting material, the reaction is quenched by the addition of NaHCO$_3$ and extracted with DCM (3×). The combined organic phases are filtered and concentrated under reduced pressure. The residue is dissolved in ACN and purified by RP chromatography to give the desired product G-36a (HPLC-Method: C, t$_{ret}$=0.72 min; [M+H]=503).

Experimental Procedure for the Synthesis of G-37a

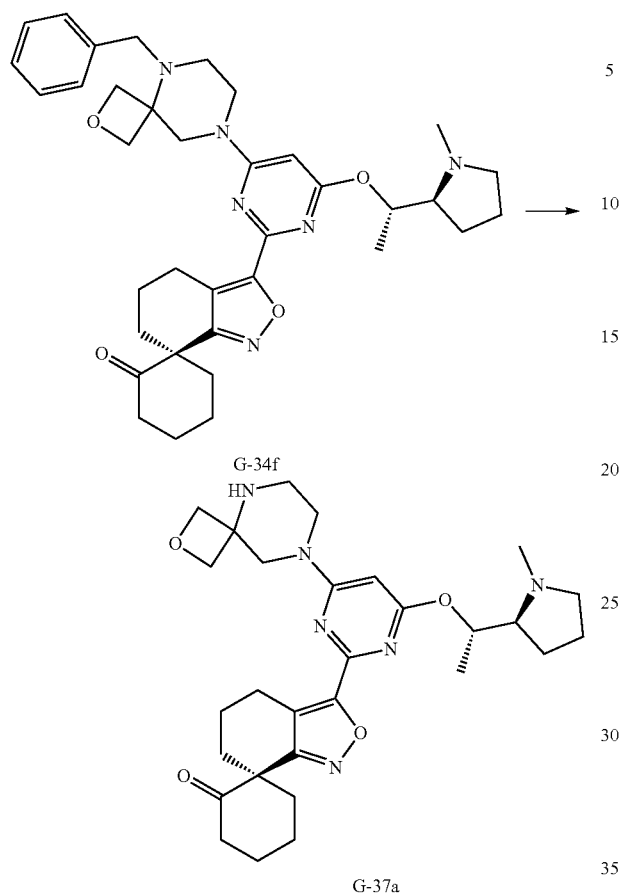

G-34f

G-37a

G-34f (157 mg, 0.25 mmol, 1.0 equiv.) is dissolved in MeOH (2 mL) palladium (10% on carbon, 26.7 mg, 0.1 equiv.) is added. The reaction is stirred for 17 h at rt under 5 bar hydrogen atmosphere. After complete conversion, the reaction mixture is filtered and concentrated under reduced pressure. The residue is dissolved in DMF and purified by RP chromatography to give product G-37a (HPLC-Method: C, $t_{ret}$=0.67 min; [M+H]=537).

Experimental Procedure for the Synthesis of G-38a

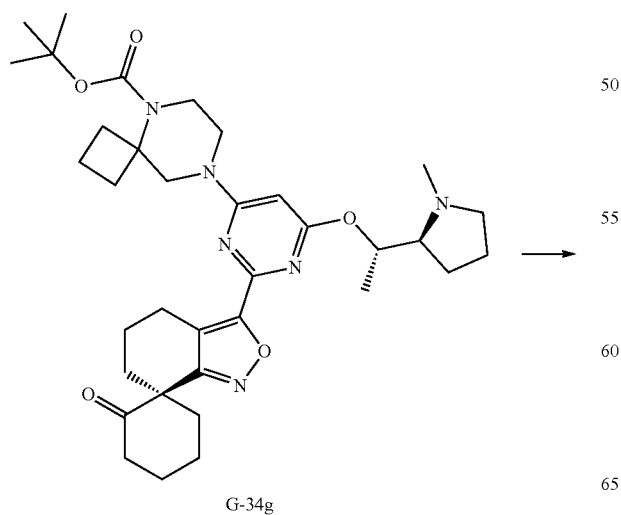

G-34g

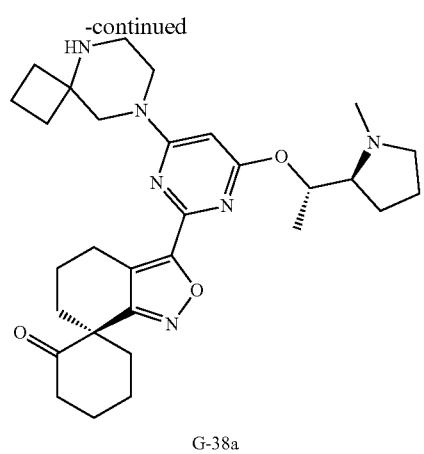

G-38a

G-34g (185 mg, 0.29 mmol, 1.0 equiv.) is dissolved in DCM (3 mL) and TFA (110 μL, 1.48 mmol, 5.07 equiv.) is added. The reaction is stirred for 20 h at 40° C. After complete conversion of starting material, the reaction is concentrated under reduced pressure, basified, dissolved in DMSO, and purified by RP chromatography to give the product G-38a (HPLC-Method C, $t_{ret}$=0.80 min; [M+H]=535).

Experimental Procedure for the Synthesis of G-39a

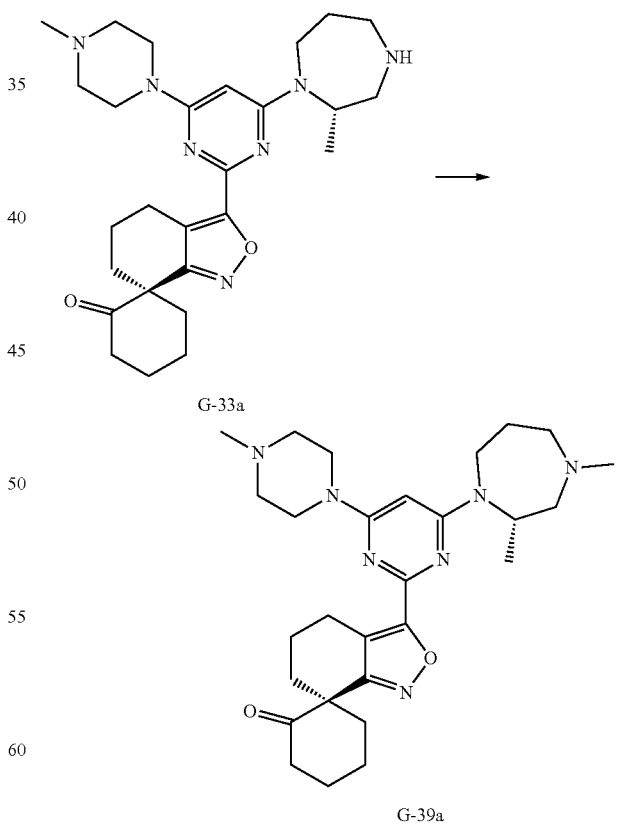

G-33a

G-39a

G-33a (52.0 mg, 0.105 mmol, 1.0 equiv.) is dissolved in DCM (2 mL) under Argon and cooled down to 0° C. Formaldehyde (9.47 μL, 0.126 mmol, 1.2 equiv.) is added followed by the addition of sodium triacetoxyborohydride (94.0 mg, 0.443 mmol, 4 equiv.). The solution is stirred for 30 min at 0° C. After complete consumption of starting material, the reaction is quenched by the addition of water. The aqueous phase is extracted with DCM (3×). The combined organic phases are filtered and concentrated under reduced pressure. The residue is purified by RP chromatography to give the desired product G-39a (HPLC method: C, $t_{ret}$=0.72 min; [M+H]$^{+}$=508).

Experimental Procedure for the Synthesis of G-40a

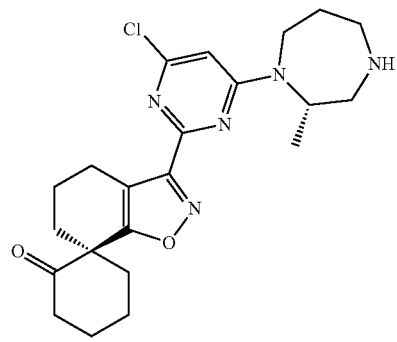

G-11a

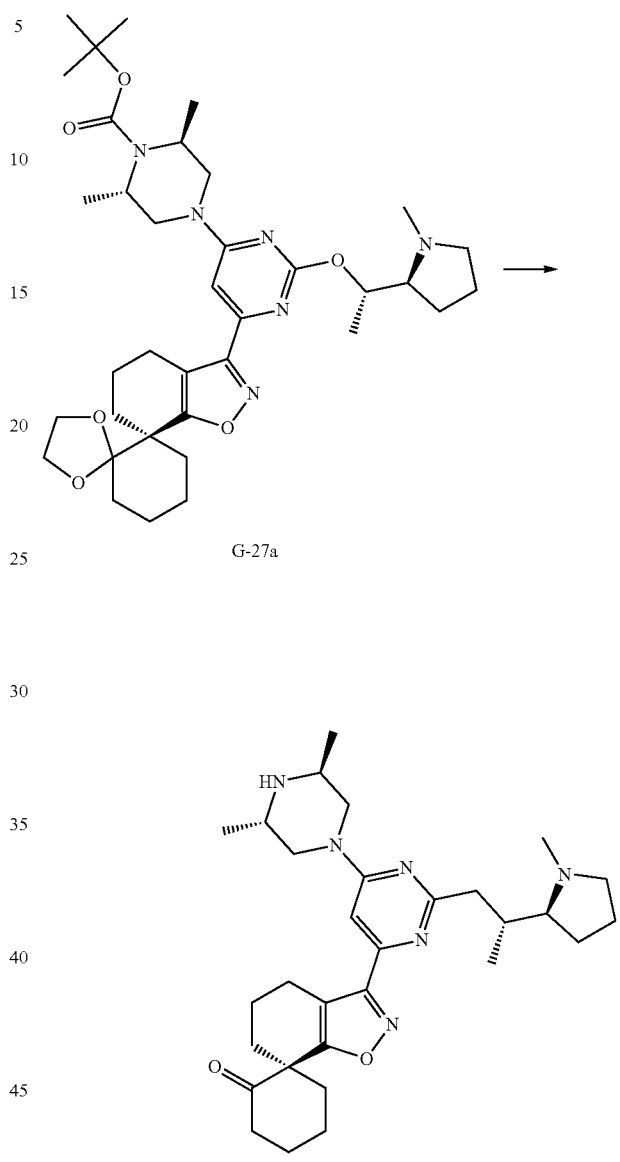

G-40a

G-11a (500 mg, 1.07 mmol, 1.00 equiv.) is dissolved in MeOH (10 mL) and formaldehyde (403 μL, 5.36 mmol, 5 equiv.) and acetic acid (27 μL, 0.54 mmol, 0.50 equiv.) is added followed by the addition of sodium cyanoborohydride (142 mg, 2.14 mmol, 2.00 equiv.). The solution is stirred for 1 h at rt. After complete consumption of starting material, the reaction is quenched by the addition of water and sat NaHCO$_3$. The aqueous phase is extracted with DCM (3×). The combined organic phases are filtered and concentrated under reduced pressure. The residue is dissolved in ACN and purified by RP chromatography to give the desired product G-40a (HPLC method: A, $t_{ret}$=1.39 min; [M+H]$^{+}$=444).

Experimental Procedure for the Synthesis of G-41a

G-27a

G-41a

G-27a (1.00 g, 1.50 mmol, 1.00 equiv.) is dissolved in DCM (3.0 mL), TFA (500 μL, 6.48 mmol, 4.32 equiv.) is added and the solution is stirred at 50° C. for 1 h. The solvents are evaporated, the resulting residue is dissolved in DCM and aq. saturated Na$_2$CO$_3$. The organic phase is separated, and the remaining aqueous phase extracted with DCM (2×). The combined organic phases are dried with magnesium sulfate, solvents are evaporated and the resulting residue is purified by RP chromatography to afford G-41a (HPLC method: A, $t_{ret}$=1.34 min; [M+H]$^{+}$=523).

Experimental Procedure for the Synthesis of G-42a

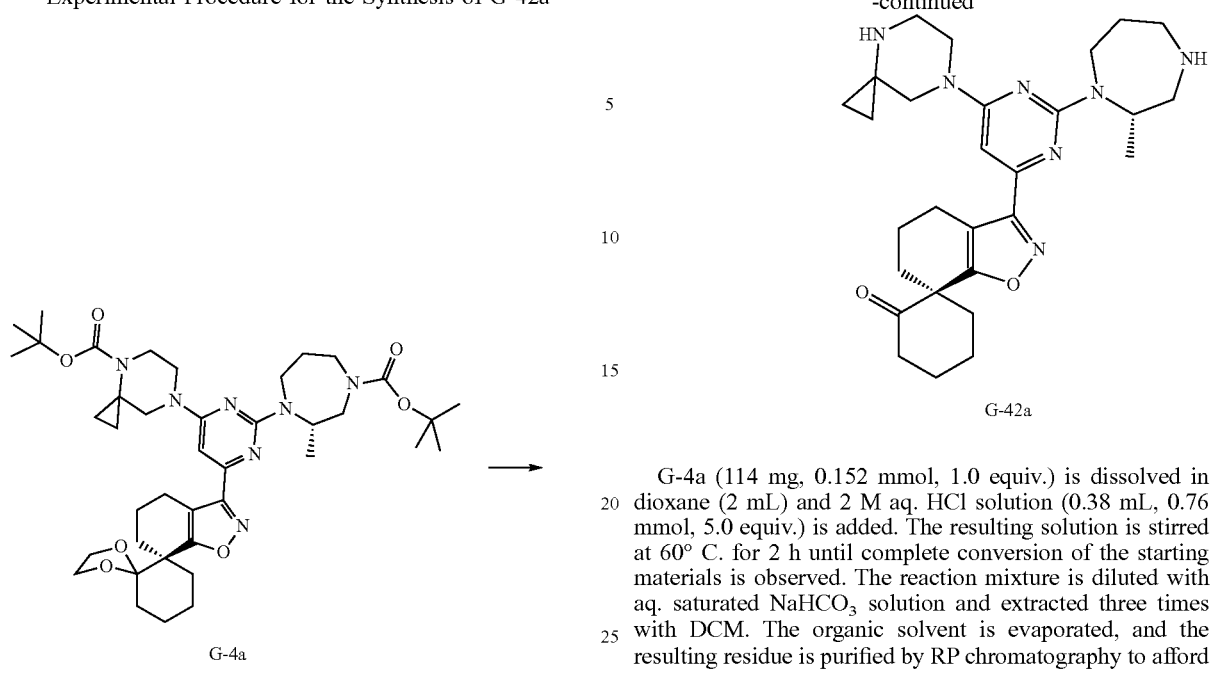

G-4a (114 mg, 0.152 mmol, 1.0 equiv.) is dissolved in dioxane (2 mL) and 2 M aq. HCl solution (0.38 mL, 0.76 mmol, 5.0 equiv.) is added. The resulting solution is stirred at 60° C. for 2 h until complete conversion of the starting materials is observed. The reaction mixture is diluted with aq. saturated NaHCO$_3$ solution and extracted three times with DCM. The organic solvent is evaporated, and the resulting residue is purified by RP chromatography to afford G-42a.

The following intermediates G-42 (Table 34) are available in an analogous manner. The crude product is purified by chromatography if necessary.

TABLE 34

| # | structure | t$_{ret}$ [min] | [M + H]$^+$ | HPLC method |
|---|---|---|---|---|
| G-42a | 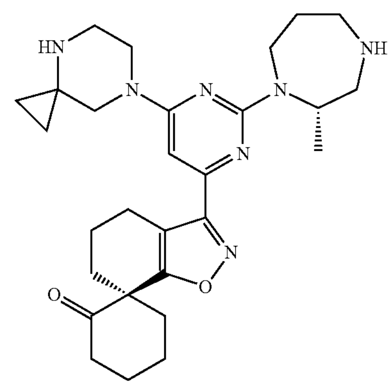 [SMILES: C[C@H]1CNCCCN1c1nc(-c2noc3c2CCC[C@@]32CCCCC2=O)cc(N2CCNC3(CC3)C2)n1] | 1.29 | 506 | A |
| G-42b | 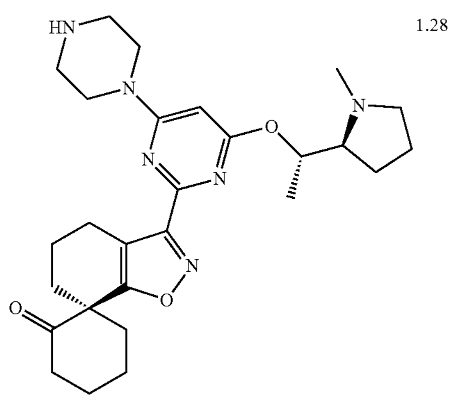 | 1.28 | 495 | A |

TABLE 34-continued

| # | structure | $t_{ret}$ [min] | [M + H]$^+$ | HPLC method |
|---|---|---|---|---|
| G-42c | 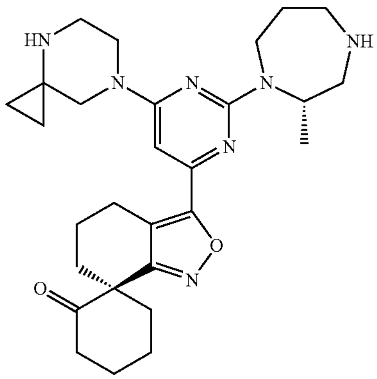 [SMILES: C[C@H]1CNCCCN1c1nc(-c2onc3c2CCC[C@@]32CCCCC2=O)cc(N2CCNC3(CC3)C2)n1] | 1.39 | 506 | A |

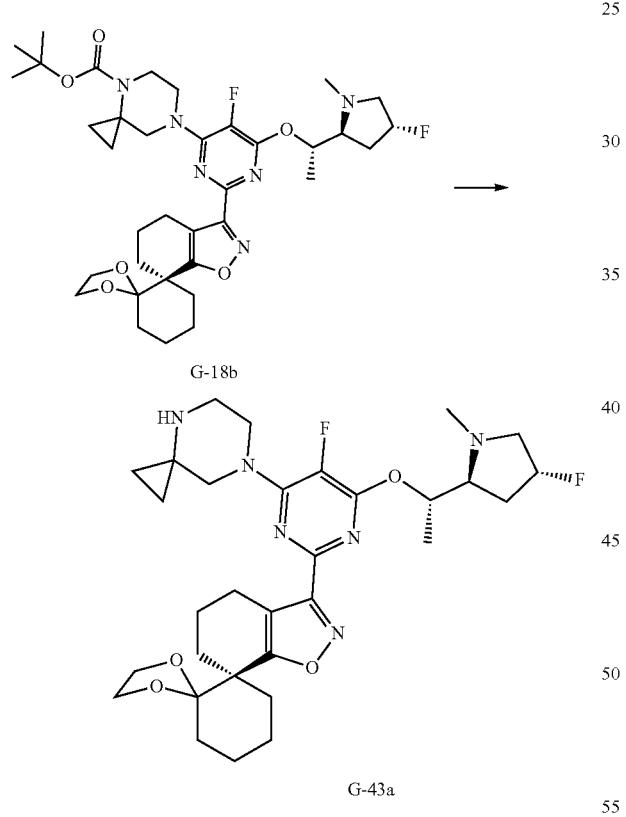

Experimental Procedure for the Synthesis of G-43a

G-18b

G-43a

G-18b (1.15 g, 1.64 mmol, 1.0 equiv.) is treated with HCl (4N in 1,4-dioxane, 15 mL, 60.0 mmol, 36.6 equiv.) and the mixture is stirred for 1 h at 80° C. After complete conversion, the reaction mixture is diluted with aq. saturated NaHCO$_3$ solution and extracted three times with DCM. The organic phase is dried, filtered and evaporated. The resulting residue is purified by RP chromatography to afford G-43a.

The following intermediates G-43 (Table 35) are available in an analogous manner. The crude product is purified by chromatography if necessary.

TABLE 35

| # | structure | t_ret [min] | [M + H]+ | HPLC method |
|---|---|---|---|---|
| G-43a | 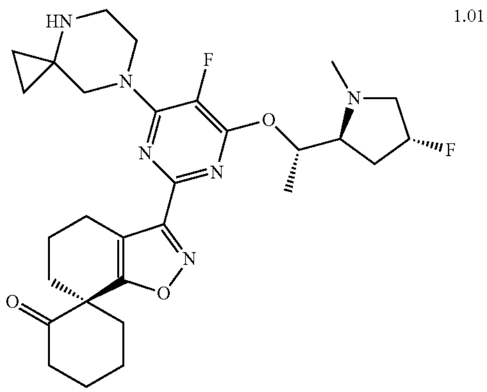 | 1.01 | 557 | B |
| G-43b | 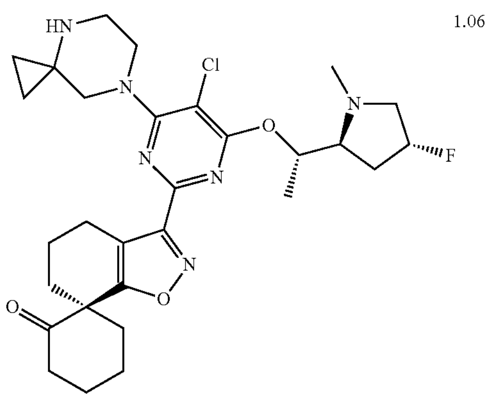 | 1.06 | 573 | B |
| G-43c | 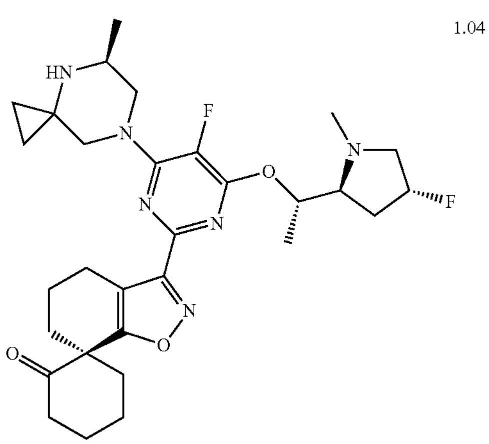 | 1.04 | 571 | B |

TABLE 35-continued

| # | structure | $t_{ret}$ [min] | $[M + H]^+$ | HPLC method |
|---|---|---|---|---|
| G-43d | 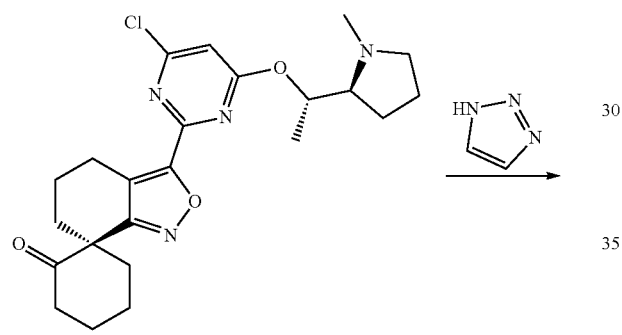 | 1.04 | 571 | B |

Experimental Procedure for the Synthesis of G-44a

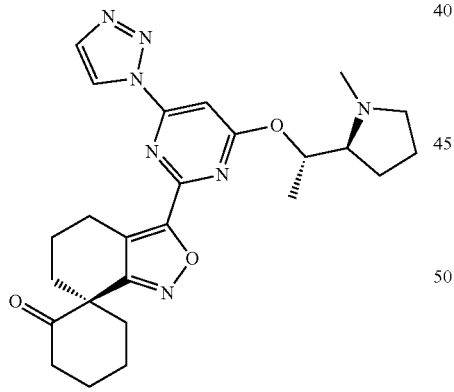

G-12b (120 mg, 0.269 mmol, 1.0 equiv.), 1H-1,2,3-triazole (37.3 mg, 0.539 mmol, 2.0 equiv.) and cesium carbonate (220 mg, 0.67 mmol, 2.5 equiv.) are dissolved in DMSO (1 mL) and stirred for 1 h at 80° C. After complete conversion, DCM is added, and the reaction is washed with water. The organic phase is concentrated under reduced pressure and purified by RP chromatography to give the desired product G-44a.

The following intermediates G-44 (Table 36) are available in an analogous manner. The crude product is purified by chromatography if necessary.

TABLE 36
| # | structure | $t_{ret}$ [min] | [M + H]$^+$ | HPLC method |
|---|---|---|---|---|
| G-44a | 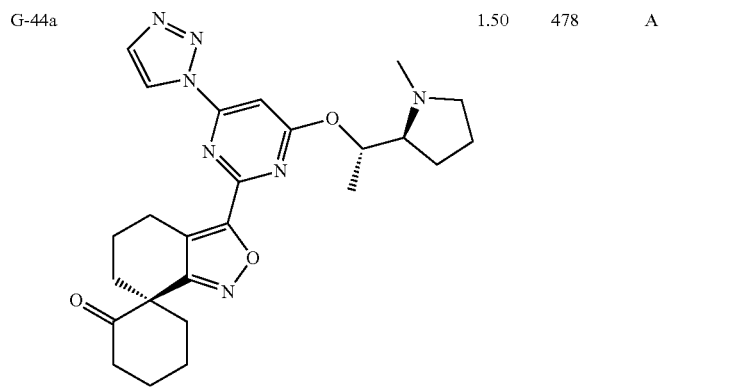 | 1.50 | 478 | A |
| G-44b | 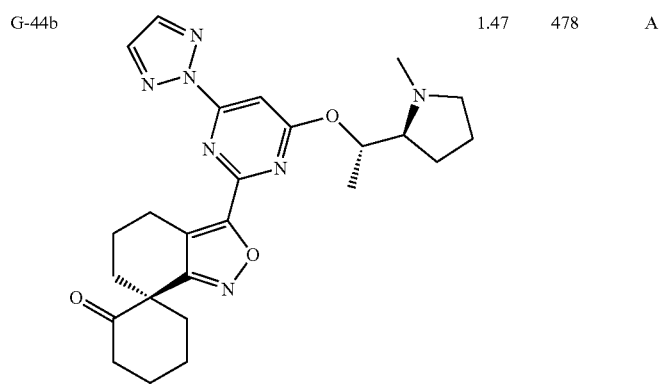 | 1.47 | 478 | A |
| G-44c | 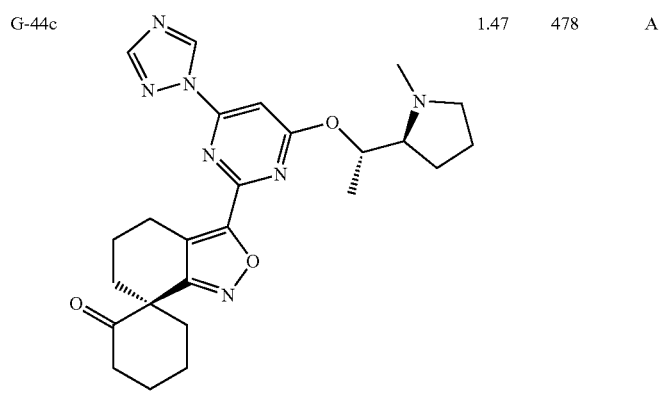 | 1.47 | 478 | A |

TABLE 36-continued

| # | structure | $t_{ret}$ [min] | [M + H]⁺ | HPLC method |
|---|---|---|---|---|
| G-44d | 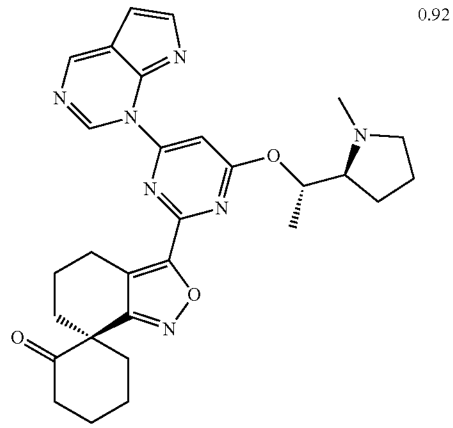 | 0.92 | 528 | C |
| G-44e | 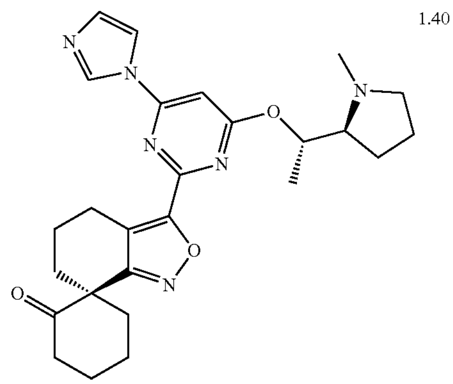 | 1.40 | 477 | A |

Experimental Procedure for the Synthesis of G-45a

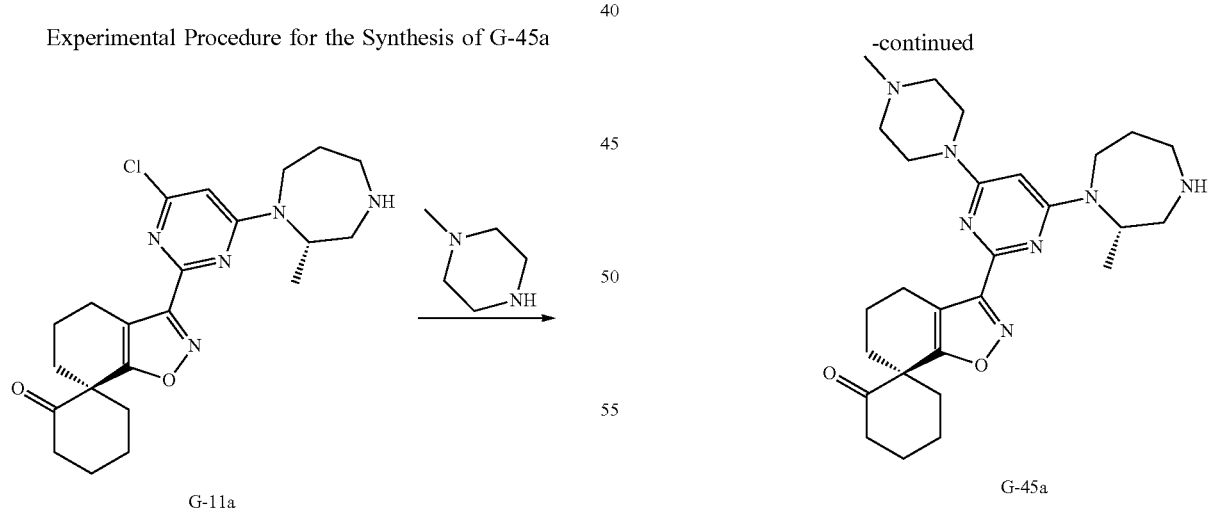

G-11a (217 mg, 0.505 mmol, 1.0 equiv.) is dissolved in DMSO (2 mL) and DIPEA (172 µL, 1.01 mmol, 2.0 equiv.) and N-methylpiperazine (75.8 mg, 0.757 mmol, 1.5 equiv.) is added. The reaction mixture is stirred at 90° C. until complete conversion is observed. The mixture is diluted with aq. satd. NaHCO₃ solution and extracted three times with DCM. The organic phase are combined, filtered and concentrated under reduced pressure. The resulting residue is dissolved in ACN and purified by basic RP chromatography to give the desired product G-45a.

The following intermediates G-45 (Table 37) are available in an analogous manner. The crude product is purified by chromatography if necessary.

The diastereomeric mixture G-451 is separated via chiral HPLC (Colum: Chiralpack IE, 250×20 mm, 5µ; solvent: ethanol/heptane 1:1+0.1% diethyl amine) to obtain G-4511 (eluting $1^{st}$ as peak 1) and G-4512 (eluting afterwards as peak 2).

TABLE 37

| # | structure | $t_{ret}$ [min] | $[M + H]^+$ | HPLC method |
|---|---|---|---|---|
| G-45a | 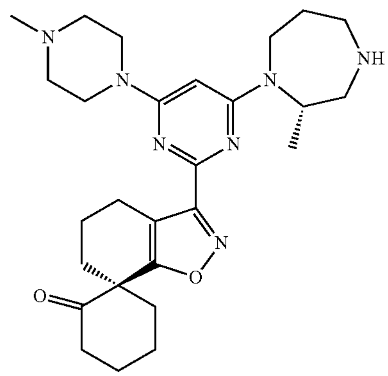 [SMILES: C[C@H]1CNCCCN1c1cc(N2CCN(C)CC2)nc(-c2noc3c2CCC[C@@]32CCCCC2=O)n1] | 1.38 | 494 | A |
| G-45b | 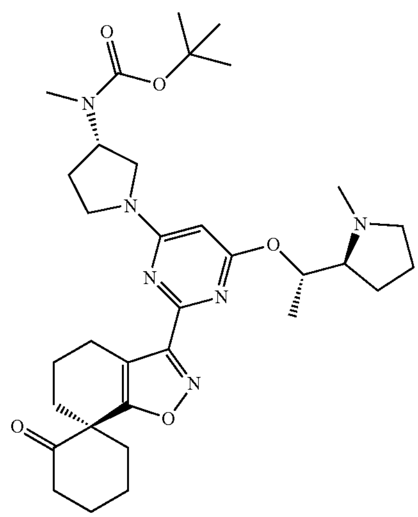 [SMILES: C[C@H](Oc1cc(N2CC[C@H](N(C)C(=O)OC(C)(C)C)C2)nc(-c2noc3c2CCC[C@@]32CCCCC2=O)n1)[C@@H]1CCCN1C] | 0.76 | 609 | A |
| G-45c | 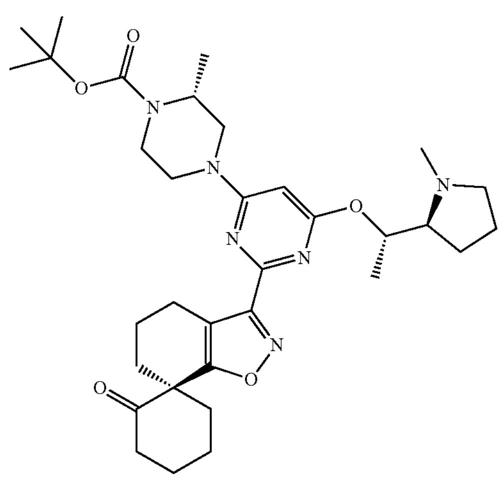 [SMILES: C[C@H](Oc1cc(N2CCN(C(=O)OC(C)(C)C)[C@H](C)C2)nc(-c2noc3c2CCC[C@@]32CCCCC2=O)n1)[C@@H]1CCCN1C] | 0.93 | 609 | E |

TABLE 37-continued

| # | structure | t_ret [min] | [M + H]+ | HPLC method |
|---|---|---|---|---|
| G-45d | 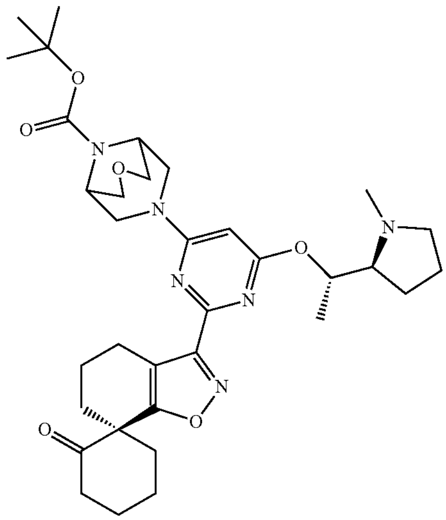 [SMILES: C[C@H](Oc1cc(N2CC3COCC(C2)N3C(=O)OC(C)(C)C)nc(-c2noc3c2CCC[C@@]32CCCCC2=O)n1)[C@@H]1CCCN1C] | 0.88 | 637 | E |
| G-45e | 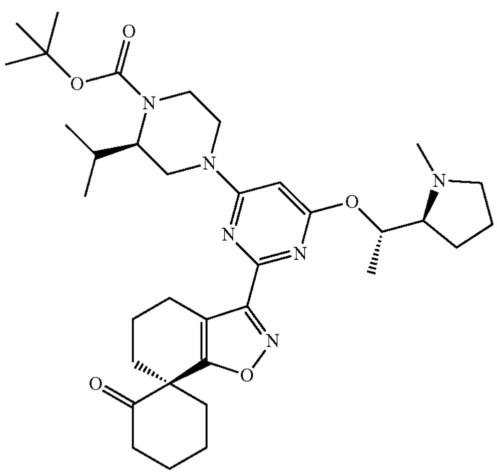 [SMILES: CC(C)[C@@H]1CN(c2cc(O[C@@H](C)[C@@H]3CCCN3C)nc(-c3noc4c3CCC[C@@]43CCCCC3=O)n2)CCN1C(=O)OC(C)(C)C] | 1.04 | 637 | E |
| G-45f | 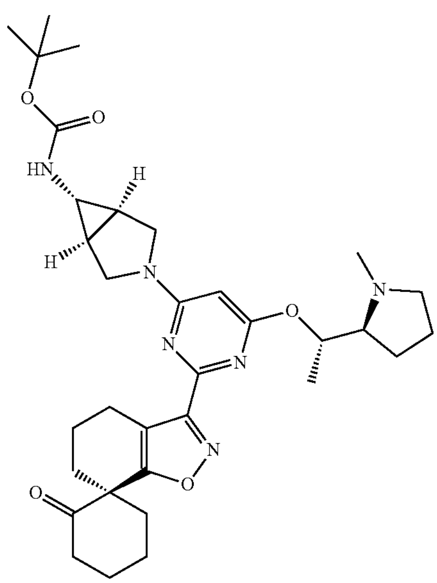 [SMILES: C[C@H](Oc1cc(N2C[C@@H]3[C@H](C2)[C@H]3NC(=O)OC(C)(C)C)nc(-c2noc3c2CCC[C@@]32CCCCC2=O)n1)[C@@H]1CCCN1C] | 0.88 | 607 | E |

TABLE 37-continued

| # | structure | $t_{ret}$ [min] | $[M + H]^+$ | HPLC method |
|---|---|---|---|---|
| G-45h | 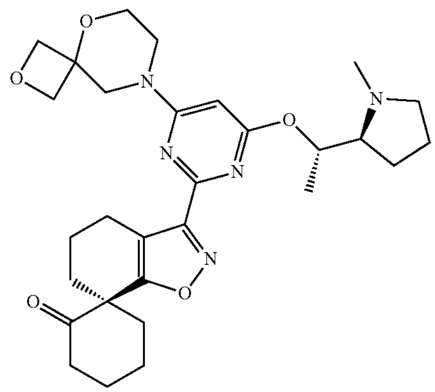 [SMILES: C[C@H](Oc1cc(N2CCOC3(COC3)C2)nc(-c2noc3c2CCC[C@@]32CCCCC2=O)n1)[C@@H]1CCCN1C] | 1.38 | 538 | A |
| G-45i | 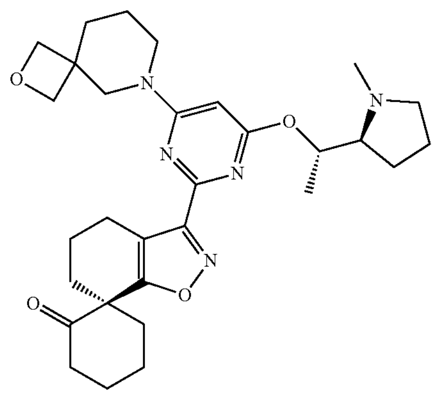 [SMILES: C[C@H](Oc1cc(N2CCCC3(COC3)C2)nc(-c2noc3c2CCC[C@@]32CCCCC2=O)n1)[C@@H]1CCCN1C] | 1.46 | 536 | A |
| G-45j | 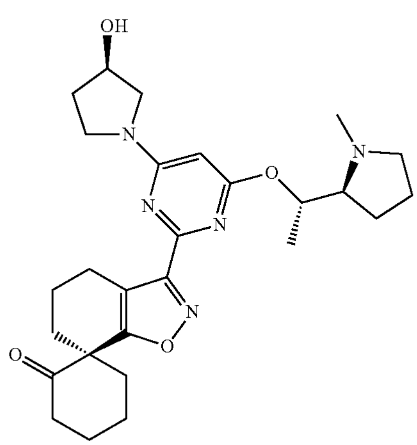 [SMILES: C[C@H](Oc1cc(N2CC[C@@H](O)C2)nc(-c2noc3c2CCC[C@@]32CCCCC2=O)n1)[C@@H]1CCCN1C] | 0.64 | 496 | C |

TABLE 37-continued
| # | structure | $t_{ret}$ [min] | $[M + H]^+$ | HPLC method |
|---|---|---|---|---|
| G-45k | 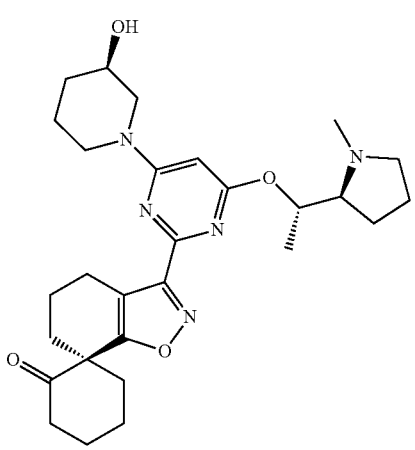 [SMILES: C[C@H](Oc1cc(N2CCC[C@@H](O)C2)nc(-c2noc3c2CCC[C@@]32CCCCC2=O)n1)[C@@H]1CCCN1C] | 0.73 | 510 | C |
| G-45l | 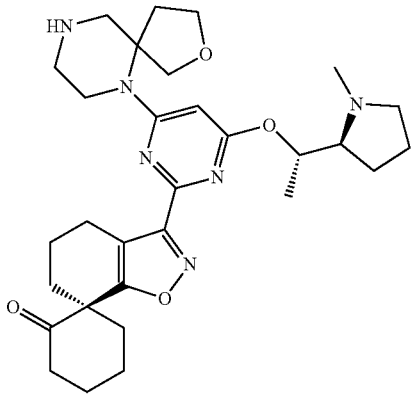 [SMILES: C[C@H](Oc1cc(N2CCNCC23CCOC3)nc(-c2noc3c2CCC[C@@]32CCCCC2=O)n1)[C@@H]1CCCN1C] | 1.28 | 551 | A |
| G-45l1 | 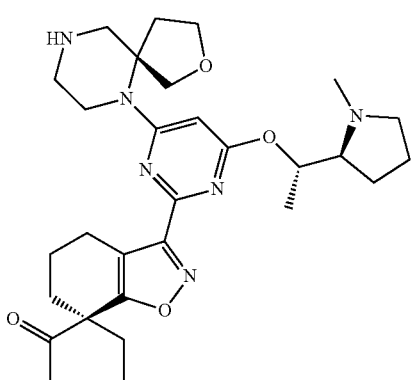 | 2.84 | | R |

TABLE 37-continued

| # | structure | t_ret [min] | [M + H]+ | HPLC method |
|---|-----------|-------------|----------|-------------|
| G-45l2 | 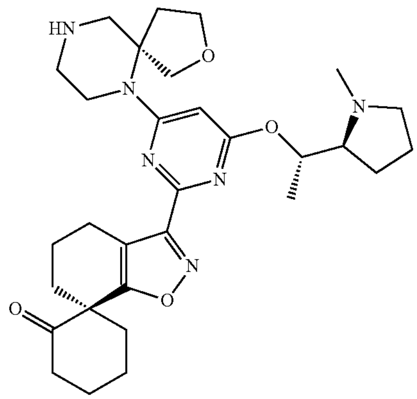 [SMILES: C[C@H](Oc1cc(N2CCNC[C@@]23CCOC3)nc(-c2noc3c2CCC[C@@]32CCCCC2=O)n1)[C@@H]1CCCN1C] | 3.25 | | R |
| G-45m | 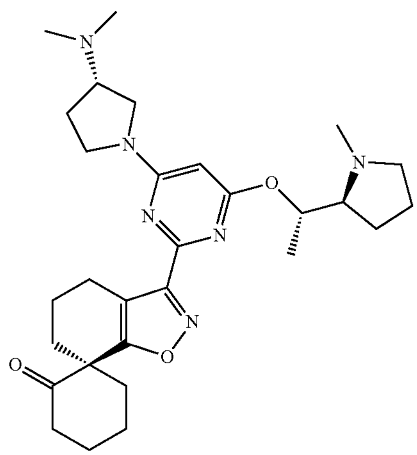 [SMILES: C[C@H](Oc1cc(N2CC[C@H](N(C)C)C2)nc(-c2noc3c2CCC[C@@]32CCCCC2=O)n1)[C@@H]1CCCN1C] | 0.75 | 523 | C |
| G-45n | 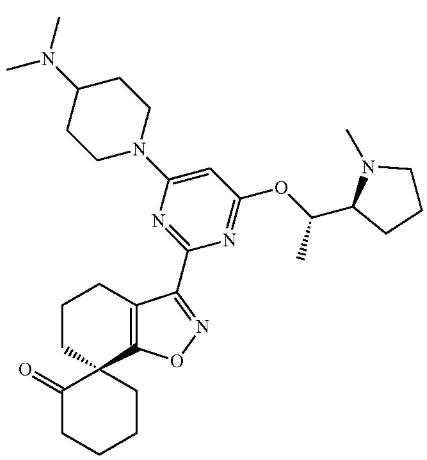 [SMILES: C[C@H](Oc1cc(N2CCC(N(C)C)CC2)nc(-c2noc3c2CCC[C@@]32CCCCC2=O)n1)[C@@H]1CCCN1C] | 0.74 | 537.4 | C |

TABLE 37-continued

| # | structure | t_ret [min] | [M + H]+ | HPLC method |
|---|---|---|---|---|
| G-45o | 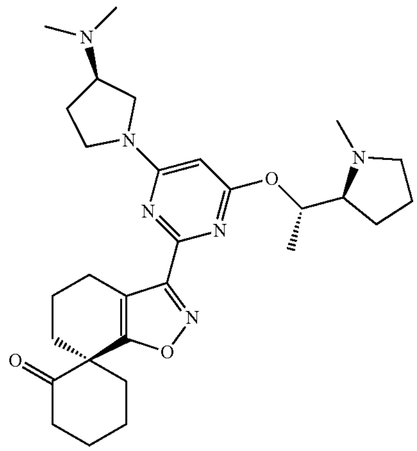 [SMILES: C[C@H](Oc1cc(N2CC[C@@H](N(C)C)C2)nc(-c2noc3c2CCC[C@@]32CCCCC2=O)n1)[C@@H]1CCCN1C] | 0.79 | 523 | C |
| G-45p | 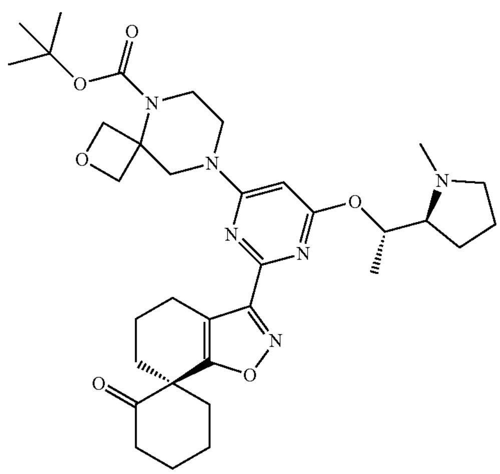 [SMILES: C[C@H](Oc1cc(N2CCN(C(=O)OC(C)(C)C)C3(COC3)C2)nc(-c2noc3c2CCC[C@@]32CCCCC2=O)n1)[C@@H]1CCCN1C] | 0.91 | 637 | C |
| G-45q | 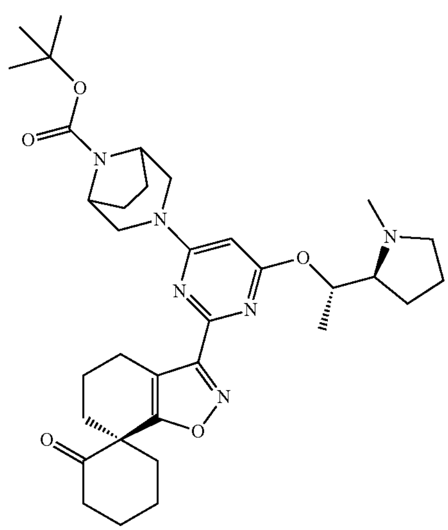 [SMILES: C[C@H](Oc1cc(N2CC3CCC(C2)N3C(=O)OC(C)(C)C)nc(-c2noc3c2CCC[C@@]32CCCCC2=O)n1)[C@@H]1CCCN1C] | 1.77 | 621 | A |

TABLE 37-continued

| # | structure | $t_{ret}$ [min] | $[M + H]^+$ | HPLC method |
|---|---|---|---|---|
| G-45r | 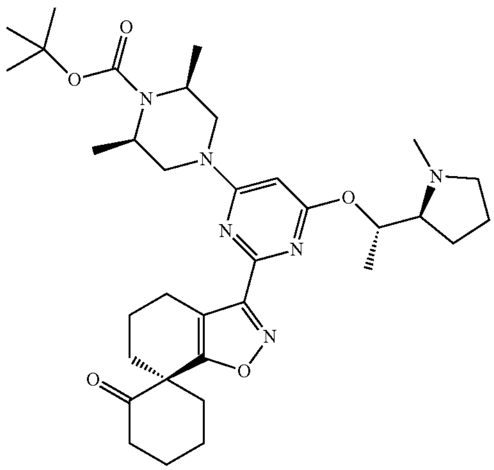 [SMILES: C[C@H](Oc1cc(N2C[C@@H](C)N(C(=O)OC(C)(C)C)[C@@H](C)C2)nc(-c2noc3c2CCC[C@@]32CCCCC2=O)n1)[C@@H]1CCCN1C] | 1.77 | 623 | A |
| G-45s | 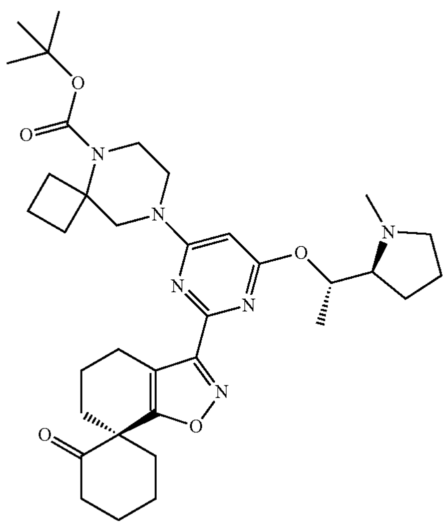 [SMILES: C[C@H](Oc1cc(N2CCN(C(=O)OC(C)(C)C)C3(CCC3)C2)nc(-c2noc3c2CCC[C@@]32CCCCC2=O)n1)[C@@H]1CCCN1C] | 1.06 | 635 | C |
| G-45t | 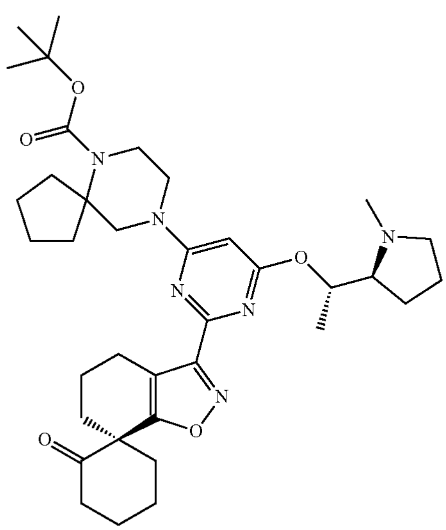 [SMILES: C[C@H](Oc1cc(N2CCN(C(=O)OC(C)(C)C)C3(CCCC3)C2)nc(-c2noc3c2CCC[C@@]32CCCCC2=O)n1)[C@@H]1CCCN1C] | 2.02 | 649 | A |

TABLE 37-continued

| # | structure | $t_{ret}$ [min] | $[M + H]^+$ | HPLC method |
|---|---|---|---|---|
| G-45u | 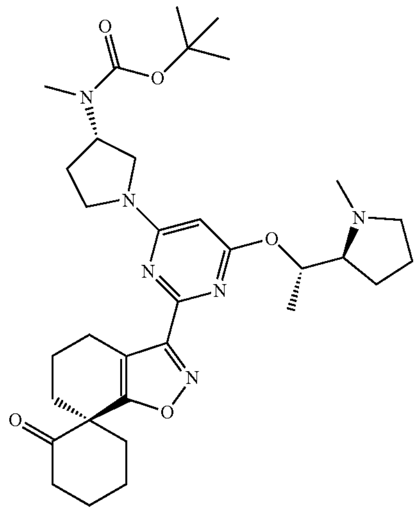 [SMILES: C[C@H](Oc1cc(N2CC[C@H](N(C)C(=O)OC(C)(C)C)C2)nc(-c2noc3c2CCC[C@@]32CCCCC2=O)n1)[C@@H]1CCCN1C] | 1.76 | 609 | A |
| G-45v | 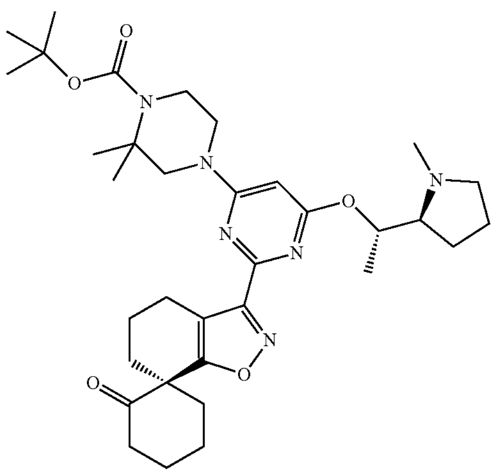 [SMILES: C[C@H](Oc1cc(N2CCN(C(=O)OC(C)(C)C)C(C)(C)C2)nc(-c2noc3c2CCC[C@@]32CCCCC2=O)n1)[C@@H]1CCCN1C] | 1.05 | 623 | E |
| G-45w | 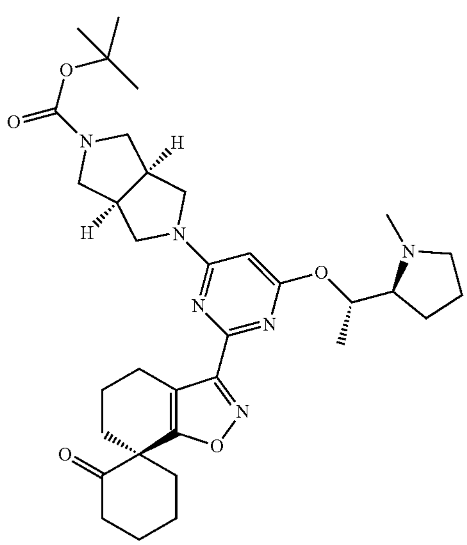 [SMILES: C[C@H](Oc1cc(N2C[C@H]3CN(C(=O)OC(C)(C)C)C[C@H]3C2)nc(-c2noc3c2CCC[C@@]32CCCCC2=O)n1)[C@@H]1CCCN1C] | 1.15 | 621 | B |

TABLE 37-continued

| # | structure | $t_{ret}$ [min] | $[M + H]^+$ | HPLC method |
|---|---|---|---|---|
| G-45x | 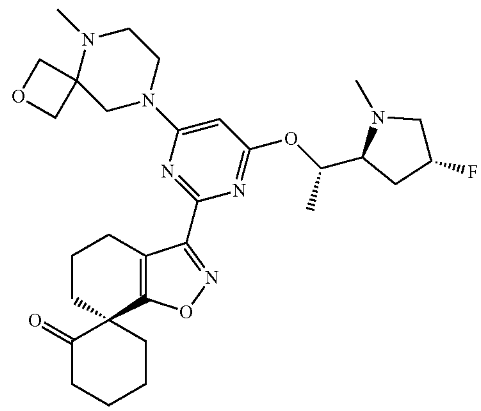 [SMILES: C[C@H](Oc1cc(N2CCN(C)C3(COC3)C2)nc(-c2noc3c2CCC[C@@]32CCCCC2=O)n1)[C@@H]1C[C@@H](F)CN1C] | 0.97 | 569 | B |
| G-45y | 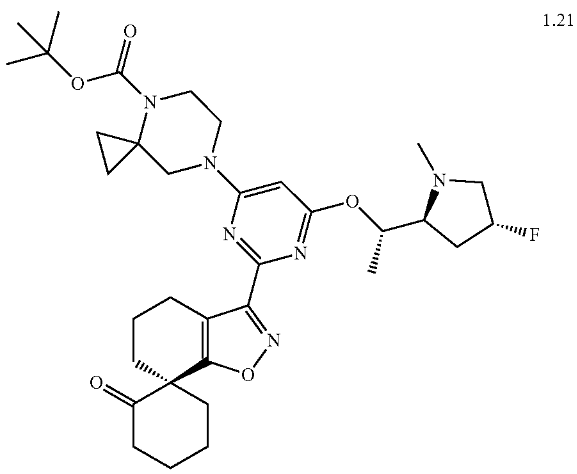 | 1.21 | 639 | B |
| G-45z | 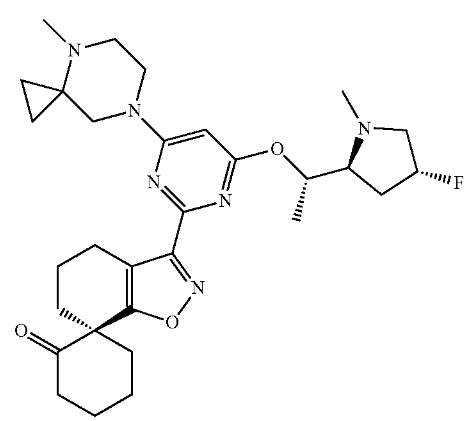 [SMILES: C[C@H](Oc1cc(N2CCN(C)C3(CC3)C2)nc(-c2noc3c2CCC[C@@]32CCCCC2=O)n1)[C@@H]1C[C@@H](F)CN1C] | 1.04 | 553 | B |

TABLE 37-continued

| # | structure | t_ret [min] | [M + H]+ | HPLC method |
|---|---|---|---|---|
| G-45aa | 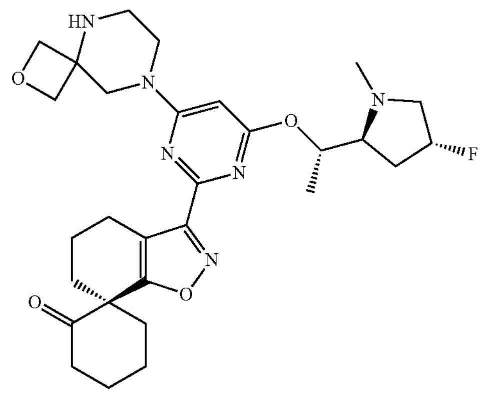 [SMILES: C[C@H](Oc1cc(N2CCNC3(COC3)C2)nc(-c2noc3c2CCC[C@@]32CCCCC2=O)n1)[C@@H]1C[C@@H](F)CN1C] | 0.91 | 555 | B |
| G-45ab | 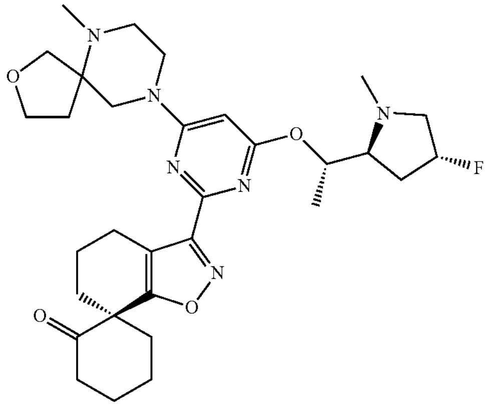 [SMILES: C[C@H](Oc1cc(N2CCN(C)C3(CCOC3)C2)nc(-c2noc3c2CCC[C@@]32CCCCC2=O)n1)[C@@H]1C[C@@H](F)CN1C] | 0.98 | 583 | B |
| G-45ac | 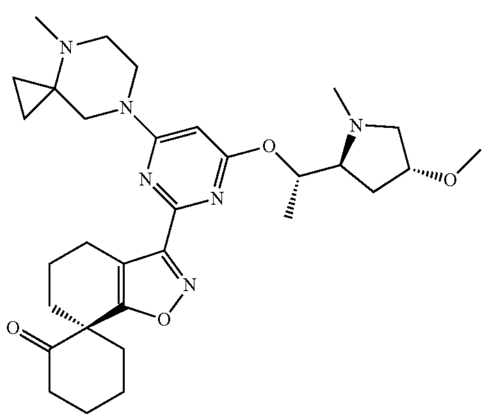 [SMILES: CO[C@@H]1C[C@@H]([C@H](C)Oc2cc(N3CCN(C)C4(CC4)C3)nc(-c3noc4c3CCC[C@@]43CCCCC3=O)n2)N(C)C1] | 1.02 | 565 | B |
| G-45ad | 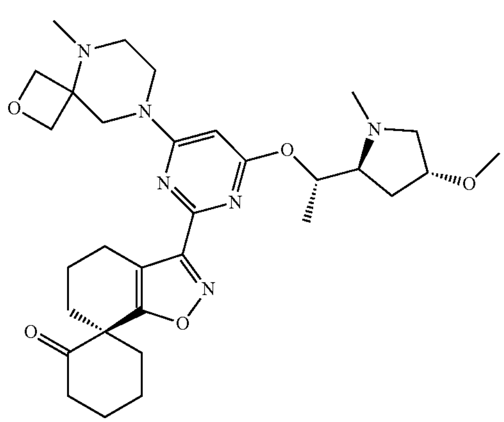 [SMILES: CO[C@@H]1C[C@@H]([C@H](C)Oc2cc(N3CCN(C)C4(COC4)C3)nc(-c3noc4c3CCC[C@@]43CCCCC3=O)n2)N(C)C1] | 0.91 | 581 | B |

TABLE 37-continued

| # | structure | $t_{ret}$ [min] | $[M + H]^+$ | HPLC method |
|---|---|---|---|---|
| G-45ae | 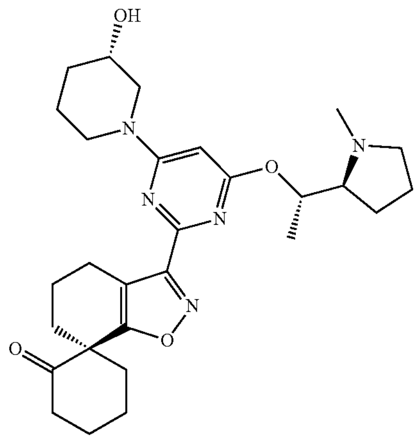 [SMILES: C[C@H](Oc1cc(N2CCC[C@H](O)C2)nc(-c2noc3c2CCC[C@@]32CCCCC2=O)n1)[C@@H]1CCCN1C] | 0.72 | 510 | C |
| G-45af | 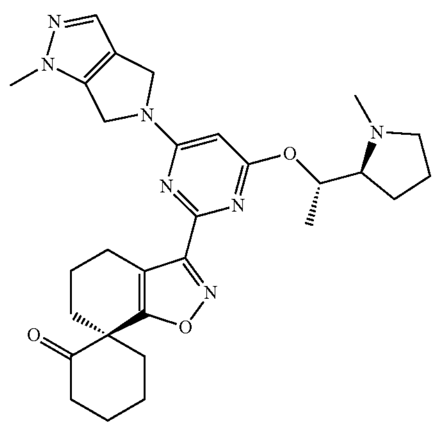 [SMILES: C[C@H](Oc1cc(N2Cc3cnn(C)c3C2)nc(-c2noc3c2CCC[C@@]32CCCCC2=O)n1)[C@@H]1CCCN1C] | 0.75 | 532 | C |
| G-45ag | 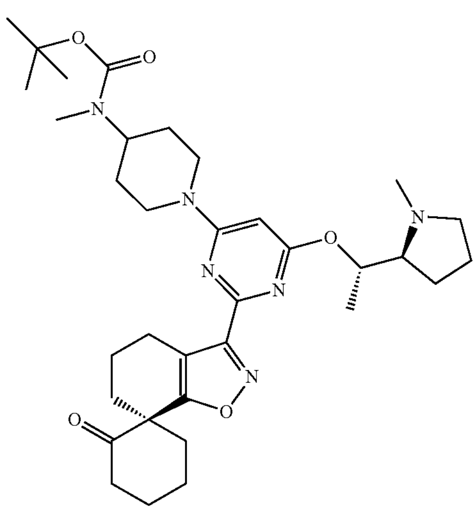 [SMILES: C[C@H](Oc1cc(N2CCC(N(C)C(=O)OC(C)(C)C)CC2)nc(-c2noc3c2CCC[C@@]32CCCCC2=O)n1)[C@@H]1CCCN1C] | 0.98 | 623 | C |

Experimental Procedure for the Synthesis of G-46a

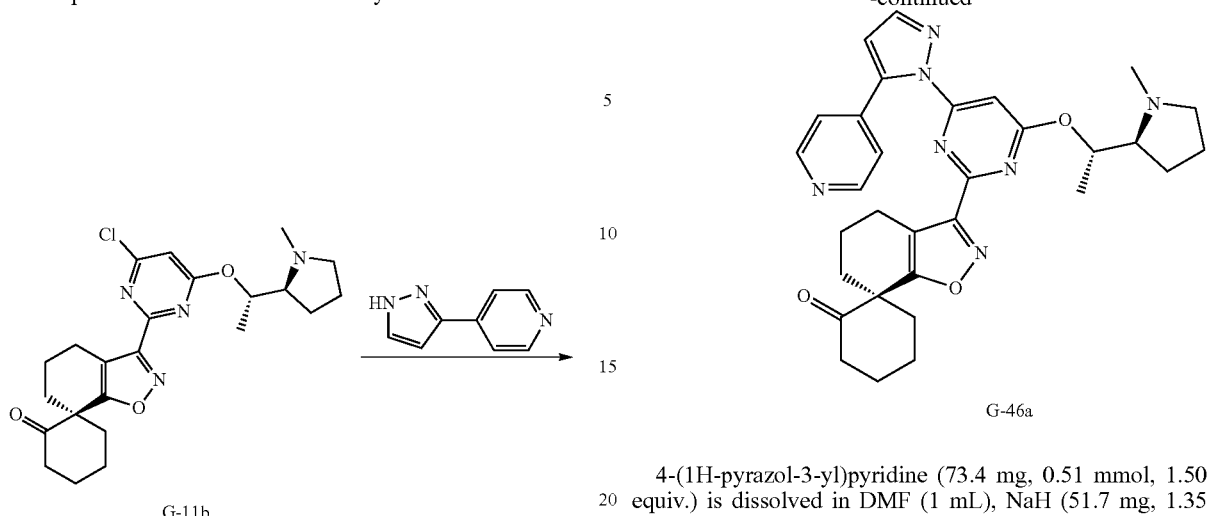

4-(1H-pyrazol-3-yl)pyridine (73.4 mg, 0.51 mmol, 1.50 equiv.) is dissolved in DMF (1 mL), NaH (51.7 mg, 1.35 mmol 4.0 equiv.) is added and stirred for 20 min at rt. G-11b (150 mg, 0.34 mmol, 1.0 equiv.) is added and the reaction is stirred for 1 h at 40° C. After complete conversion, the reaction is extracted with EtOAc/water. The organic phase is concentrated under reduced pressure and purified by RP chromatography to give the desired product G-46a.

The following intermediates G-46 (Table 38) are available in an analogous manner. The crude product is purified by chromatography if necessary.

TABLE 38

| # | Structure | $t_{ret}$ [min] | $[M + H]^+$ | HPLC method |
|---|---|---|---|---|
| G-46a | 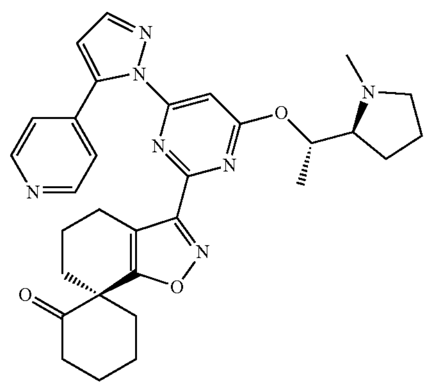 [SMILES: C[C@H](Oc1cc(-n2nccc2-c2ccncc2)nc(-c2noc3c2CCC[C@@]32CCCCC2=O)n1)[C@@H]1CCCN1C] | 1.60 | 554 | A |
| G-46b | 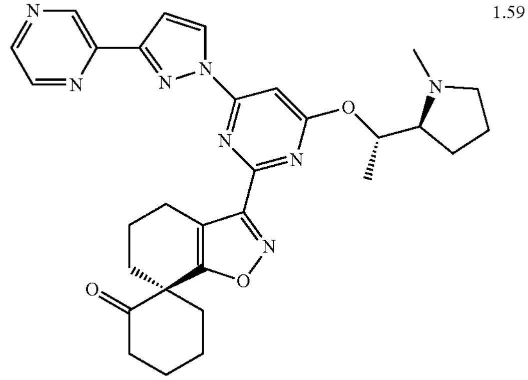 | 1.59 | 555 | A |

TABLE 38-continued

| # | Structure | $t_{ret}$ [min] | [M + H]$^+$ | HPLC method |
|---|---|---|---|---|
| G-46c | 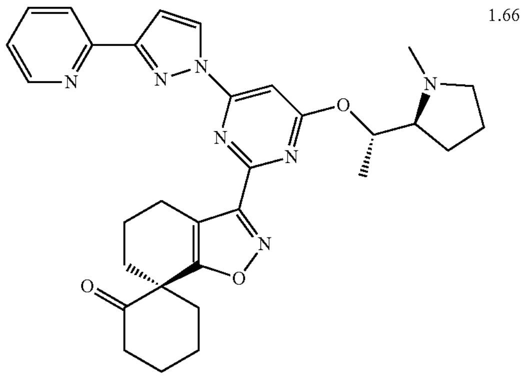 | 1.66 | 554 | A |
| G-46d | 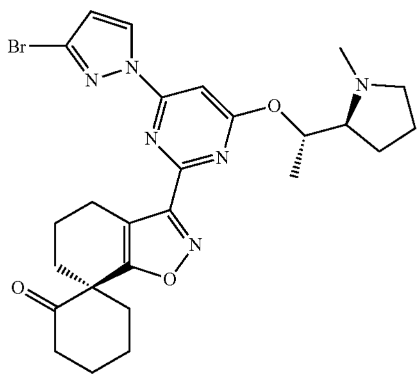 [SMILES: C[C@H](Oc1cc(-n2ccc(Br)n2)nc(-c2noc3c2CCC[C@@]32CCCCC2=O)n1)[C@@H]1CCCN1C] | 1.74 | 555 | A |
| G-46e | 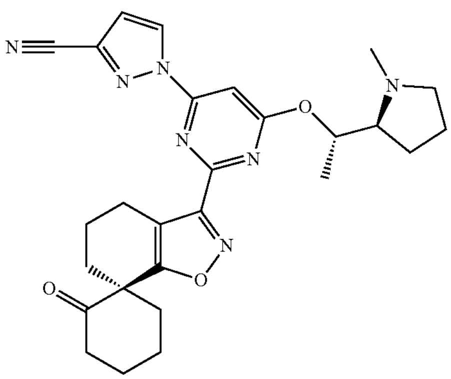 [SMILES: C[C@H](Oc1cc(-n2ccc(C#N)n2)nc(-c2noc3c2CCC[C@@]32CCCCC2=O)n1)[C@@H]1CCCN1C] | 1.62 | 502 | A |
| G-46f | 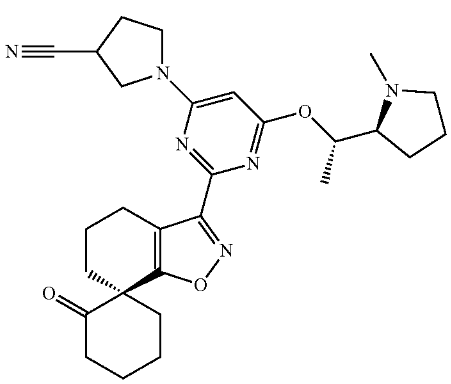 [SMILES: C[C@H](Oc1cc(N2CCC(C#N)C2)nc(-c2noc3c2CCC[C@@]32CCCCC2=O)n1)[C@@H]1CCCN1C] | 1.42 | 505 | A |

TABLE 38-continued

| # | Structure | t_ret [min] | [M + H]+ | HPLC method |
|---|-----------|-------------|----------|-------------|
| G-46g | 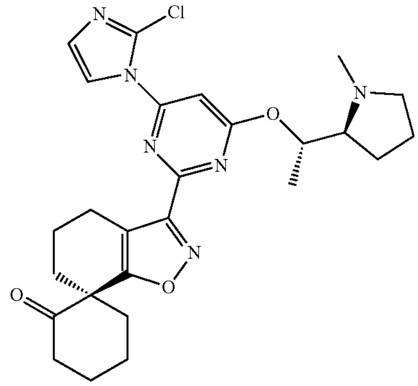 [SMILES: C[C@H](Oc1cc(-n2ccnc2Cl)nc(-c2noc3c2CCC[C@@]32CCCCC2=O)n1)[C@@H]1CCCN1C] | 1.47 | 511 | A |
| G-46h | 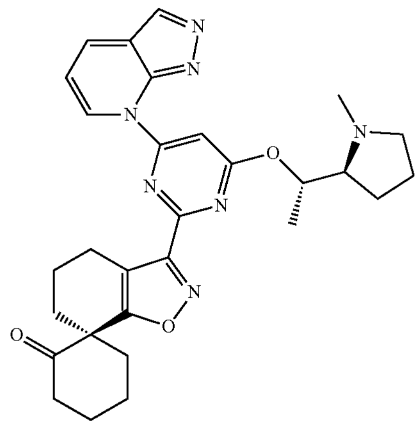 [SMILES: C[C@H](Oc1cc(-n2cccc3cnnc2-3)nc(-c2noc3c2CCC[C@@]32CCCCC2=O)n1)[C@@H]1CCCN1C] | 1.59 | 608 | A |
| G-46i | 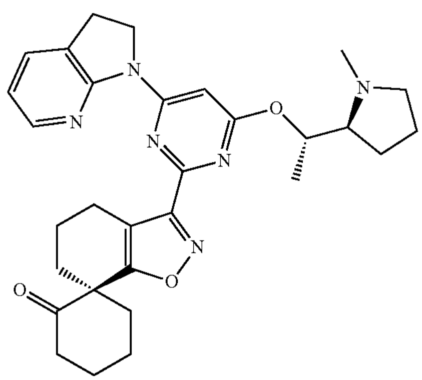 [SMILES: C[C@H](Oc1cc(N2CCc3cccnc32)nc(-c2noc3c2CCC[C@@]32CCCCC2=O)n1)[C@@H]1CCCN1C] | 1.74 | 529 | A |
| G-46j | 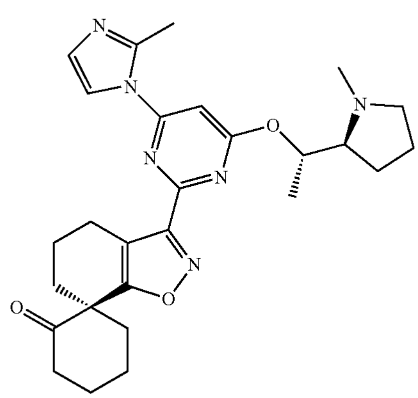 [SMILES: Cc1nccn1-c1cc(O[C@@H](C)[C@@H]2CCCN2C)nc(-c2noc3c2CCC[C@@]32CCCCC2=O)n1] | 0.72 | 491 | C |

Experimental Procedure for the Synthesis of G-47a

Experimental Procedure for the Synthesis of G-48a

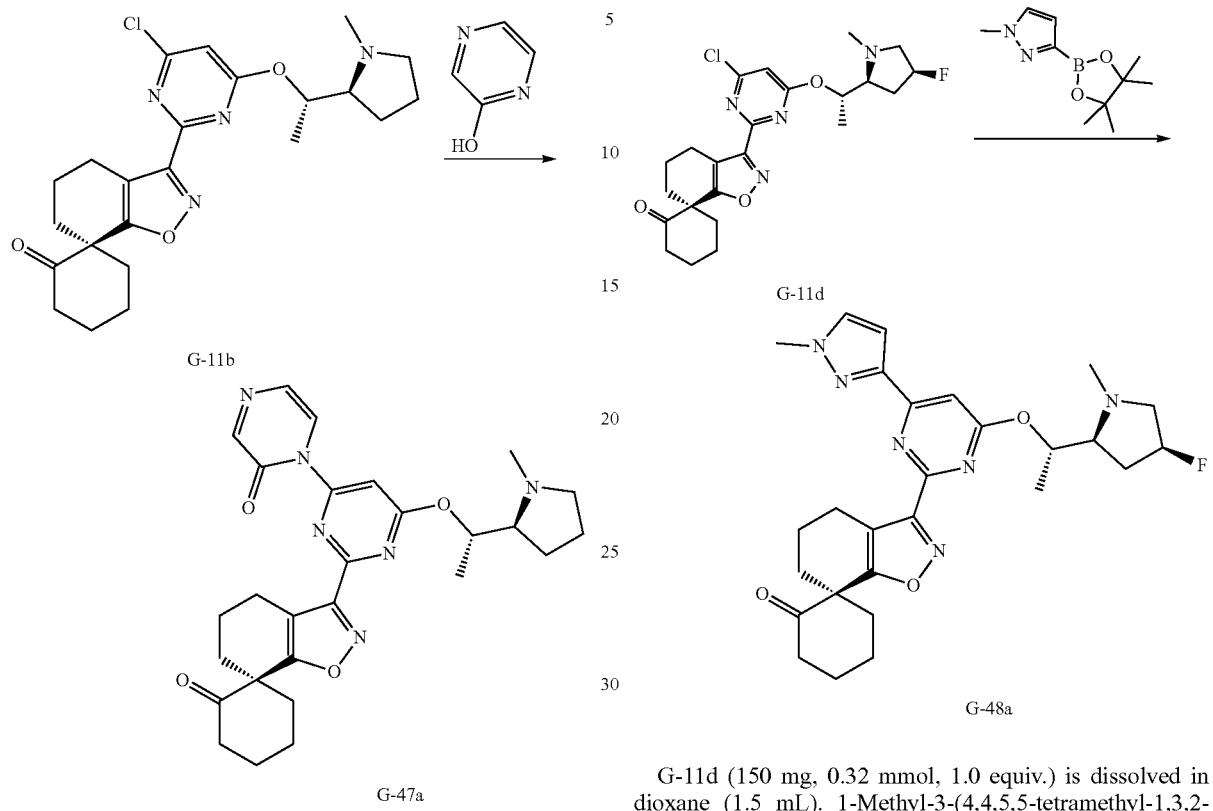

G-11b (150 mg, 271.7 µmol, 1.0 equiv.), 2-Hydroxypyrazine (31.3 mg, 326.1 µmol, 1.2 equiv.) and t-BuONa (2 M in THF, 190.20 µL, 0.38 mmol, 1.4equiv.) is dissolved in THF (2 mL) and stirred at 65° C. for 18 h. After complete conversion, the reaction is extracted with DCM/water. The combined organic phase is concentrated under reduced pressure and purified by RP chromatography to give the desired product G-47a (HPLC-Method: A, $t_{ret}$=1.39 min; [M+H]=505).

G-11d (150 mg, 0.32 mmol, 1.0 equiv.) is dissolved in dioxane (1.5 mL). 1-Methyl-3-(4,4,5,5-tetramethyl-1,3,2-dioxaborolan-2-yl)-1 h-pyrazole (82.7 mg, 0.39 mmol, 1.2 equiv.), XPHOS PD G3 (26.0 mg, 0.03 mmol, 0.09 equiv.) and cesium carbonate (0.4 ml, 0.80 mmol, 2.46 equiv.) are added. The reaction is stirred for 2 h at 80° C. After complete conversion is observed the reaction is extracted with DCM/water. The combined organic phase is concentrated under reduced pressure, dissolved in ACN/water and purified by RP chromatography to give the desired product G-48a.

The following intermediates G-48 (Table 39) are available in an analogous manner. The crude product is purified by chromatography if necessary.

TABLE 39

| # | structure | $t_{ret}$ [min] | [M + H]⁺ | HPLC method |
|---|-----------|-----------------|----------|-------------|
| G-48a | 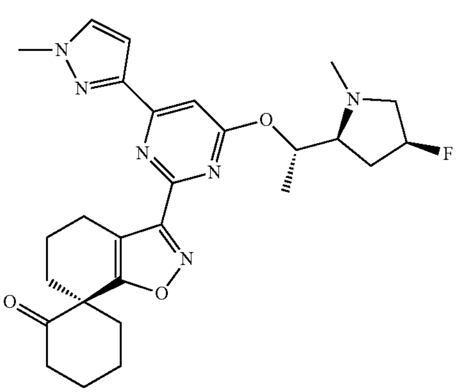 [SMILES: C[C@H](Oc1cc(-c2ccn(C)n2)nc(-c2noc3c2CCC[C@@]32CCCCC2=O)n1)[C@@H]1C[C@H](F)CN1C] | 0.75 | 509 | C |

TABLE 39-continued

| # | structure | $t_{ret}$ [min] | $[M + H]^+$ | HPLC method |
|---|---|---|---|---|
| G-48b | 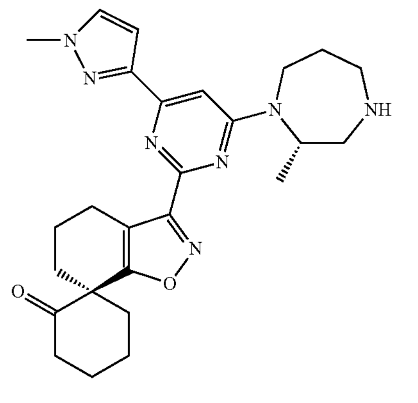 [SMILES: C[C@H]1CNCCCN1c1cc(-c2ccn(C)n2)nc(-c2noc3c2CCC[C@@]32CCCCC2=O)n1] | 1.21 | 476 | A |
| G-48c | 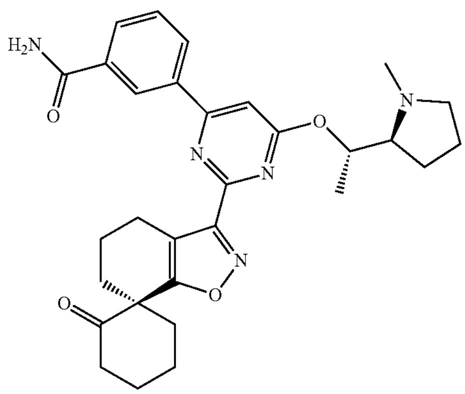 [SMILES: C[C@H](Oc1cc(-c2cccc(C(N)=O)c2)nc(-c2noc3c2CCC[C@@]32CCCCC2=O)n1)[C@@H]1CCCN1C] | 1.37 | 530 | A |
| G-48d | 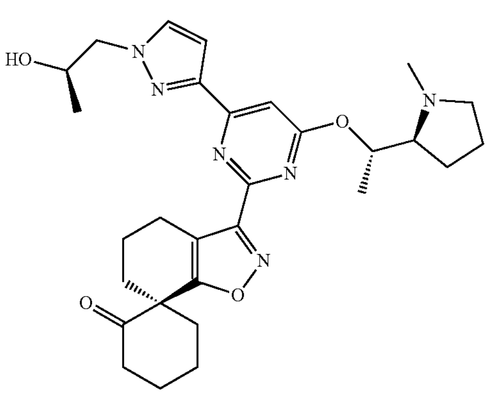 [SMILES: C[C@H](Oc1cc(-c2ccn(C[C@@H](C)O)n2)nc(-c2noc3c2CCC[C@@]32CCCCC2=O)n1)[C@@H]1CCCN1C] | 0.73 | 535 | C |

TABLE 39-continued

| # | structure | $t_{ret}$ [min] | [M + H]⁺ | HPLC method |
|---|---|---|---|---|
| G-48e | 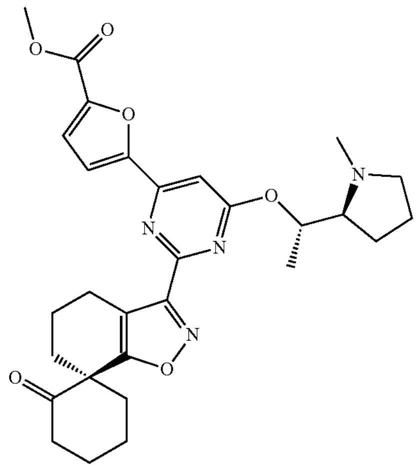 [SMILES: COC(=O)c1ccc(-c2cc(O[C@@H](C)[C@@H]3CCCN3C)nc(-c3noc4c3CCC[C@@]43CCCCC3=O)n2)o1] | 1.60 | 535 | A |
| G-48f | 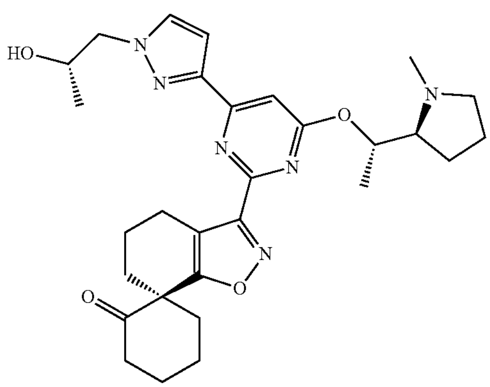 [SMILES: C[C@H](O)Cn1ccc(-c2cc(O[C@@H](C)[C@@H]3CCCN3C)nc(-c3noc4c3CCC[C@@]43CCCCC3=O)n2)n1] | 0.70 | 535 | C |
| G-48g | 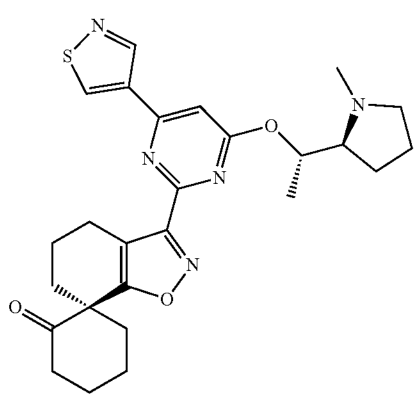 [SMILES: C[C@H](Oc1cc(-c2cnsc2)nc(-c2noc3c2CCC[C@@]32CCCCC2=O)n1)[C@@H]1CCCN1C] | 1.54 | 494 | A |

TABLE 39-continued

| # | structure | t_ret [min] | [M + H]+ | HPLC method |
|---|---|---|---|---|
| G-48h | 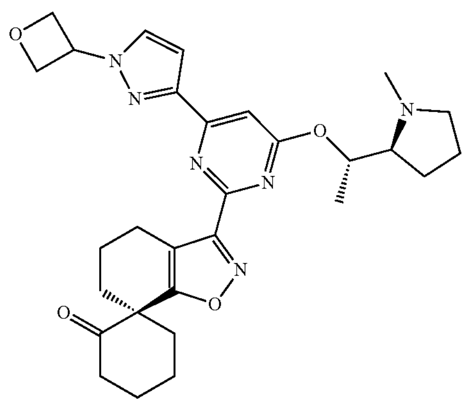 [SMILES: C[C@H](Oc1cc(-c2ccn(C3COC3)n2)nc(-c2noc3c2CCC[C@@]32CCCCC2=O)n1)[C@@H]1CCCN1C] | 0.77 | 533 | C |
| G-48i | 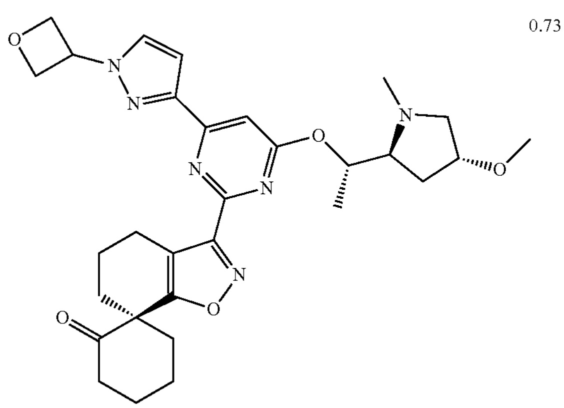 | 0.73 | 563 | C |
| G-48j | 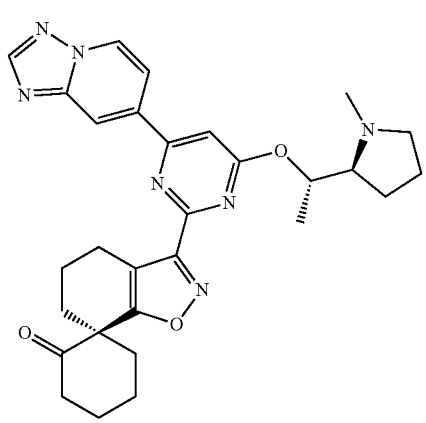 [SMILES: C[C@H](Oc1cc(-c2ccn3ncnc3c2)nc(-c2noc3c2CCC[C@@]32CCCCC2=O)n1)[C@@H]1CCCN1C] | 0.74 | 528 | C |

TABLE 39-continued

| # | structure | t_ret [min] | [M + H]+ | HPLC method |
|---|---|---|---|---|
| G-48k | 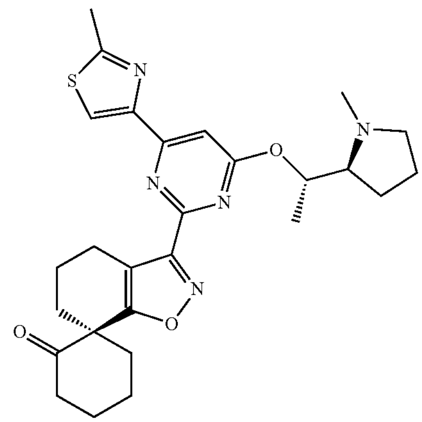 [SMILES: Cc1nc(-c2cc(O[C@@H](C)[C@@H]3CCCN3C)nc(-c3noc4c3CCC[C@@]43CCCCC3=O)n2)cs1] | 1.61 | 508 | A |
| G-48l | 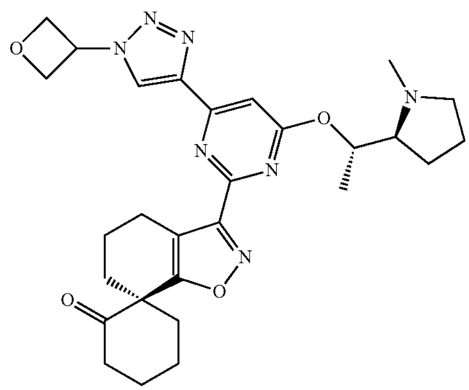 [SMILES: C[C@H](Oc1cc(-c2cn(C3COC3)nn2)nc(-c2noc3c2CCC[C@@]32CCCCC2=O)n1)[C@@H]1CCCN1C] | 0.79 | 534 | C |
| G-48m | 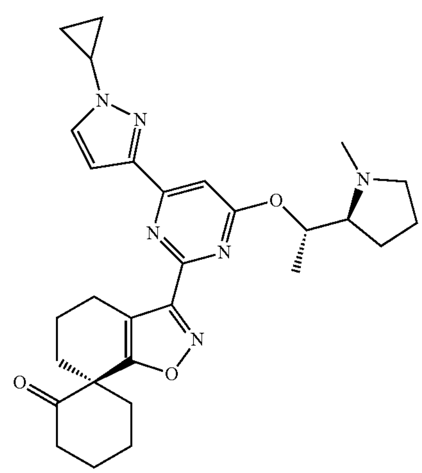 [SMILES: C[C@H](Oc1cc(-c2ccn(C3CC3)n2)nc(-c2noc3c2CCC[C@@]32CCCCC2=O)n1)[C@@H]1CCCN1C] | 1.58 | 517 | A |

TABLE 39-continued

| # | structure | $t_{ret}$ [min] | [M + H]$^+$ | HPLC method |
|---|---|---|---|---|
| G-48n | 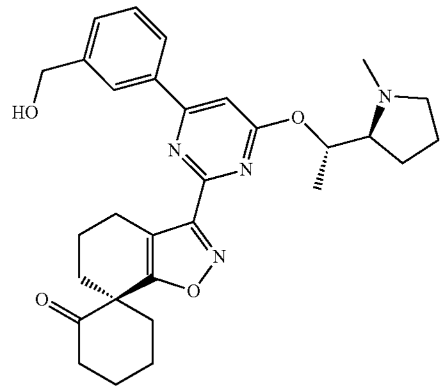 [SMILES: C[C@H](Oc1cc(-c2cccc(CO)c2)nc(-c2noc3c2CCC[C@@]32CCCCC2=O)n1)[C@@H]1CCCN1C] | 1.47 | 517 | A |
| G-48o | 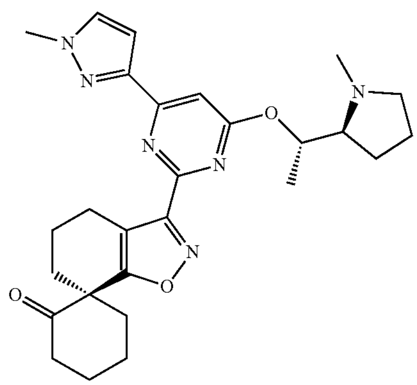 [SMILES: C[C@H](Oc1cc(-c2ccn(C)n2)nc(-c2noc3c2CCC[C@@]32CCCCC2=O)n1)[C@@H]1CCCN1C] | 1.44 | 491 | A |
| G-48p | 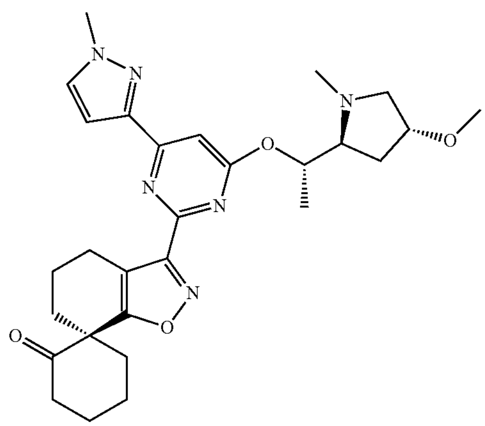 [SMILES: CO[C@@H]1C[C@@H]([C@H](C)Oc2cc(-c3ccn(C)n3)nc(-c3noc4c3CCC[C@@]43CCCCC3=O)n2)N(C)C1] | 0.74 | 521 | C |
| G-48q | 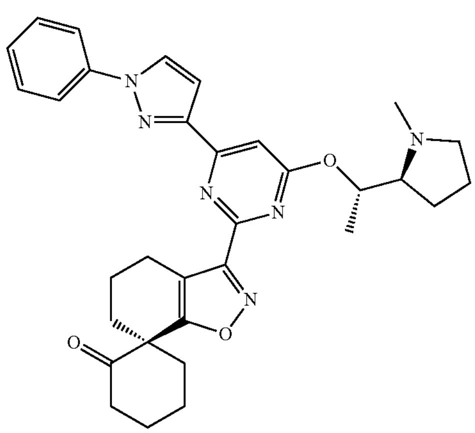 [SMILES: C[C@H](Oc1cc(-c2ccn(-c3ccccc3)n2)nc(-c2noc3c2CCC[C@@]32CCCCC2=O)n1)[C@@H]1CCCN1C] | 1.78 | 553 | A |

TABLE 39-continued

| # | structure | $t_{ret}$ [min] | [M + H]⁺ | HPLC method |
|---|---|---|---|---|
| G-48r | 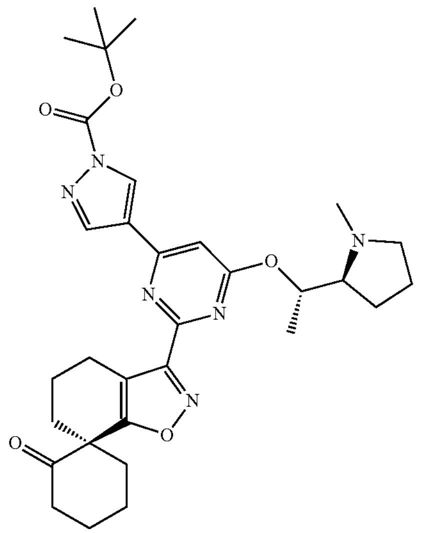 [SMILES: C[C@H](Oc1cc(-c2cnn(C(=O)OC(C)(C)C)c2)nc(-c2noc3c2CCC[C@@]32CCCCC2=O)n1)[C@@H]1CCCN1C] | 1.63 | 577 | A |
| G-48s | 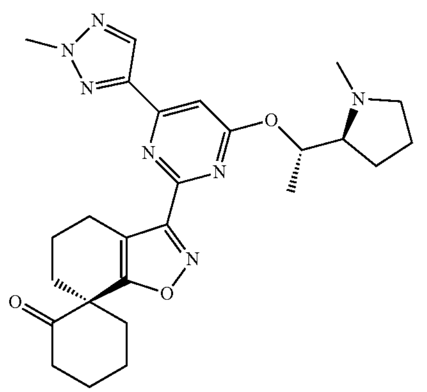 [SMILES: C[C@H](Oc1cc(-c2cnn(C)n2)nc(-c2noc3c2CCC[C@@]32CCCCC2=O)n1)[C@@H]1CCCN1C] | 1.50 | 492 | A |
| G-48t | 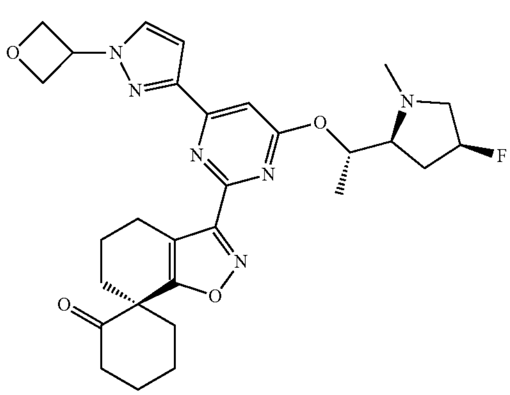 [SMILES: C[C@H](Oc1cc(-c2ccn(C3COC3)n2)nc(-c2noc3c2CCC[C@@]32CCCCC2=O)n1)[C@@H]1C[C@H](F)CN1C] | 0.74 | 551 | C |

TABLE 39-continued

| # | structure | t_ret [min] | [M + H]+ | HPLC method |
|---|---|---|---|---|
| G-48u | 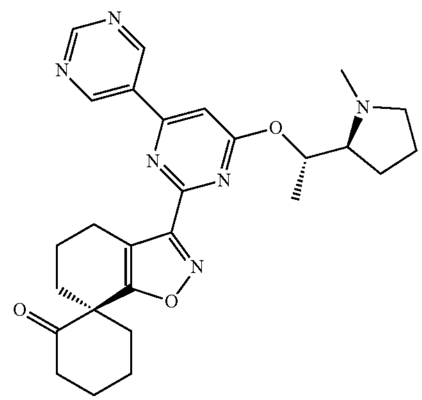 [SMILES: C[C@H](Oc1cc(-c2cncnc2)nc(-c2noc3c2CCC[C@@]32CCCCC2=O)n1)[C@@H]1CCCN1C] | 1.36 | 489 | A |
| G-48v | 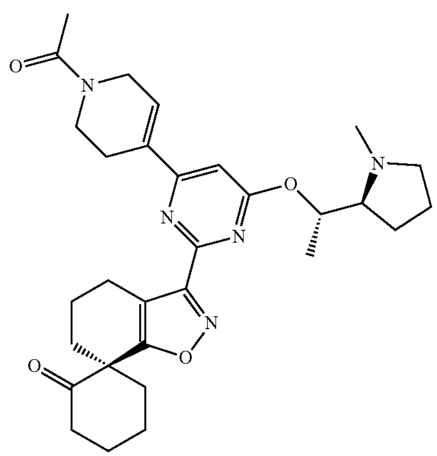 [SMILES: CC(=O)N1CC=C(c2cc(O[C@@H](C)[C@@H]3CCCN3C)nc(-c3noc4c3CCC[C@@]43CCCCC3=O)n2)CC1] | 1.36 | 534 | A |
| G-48w | 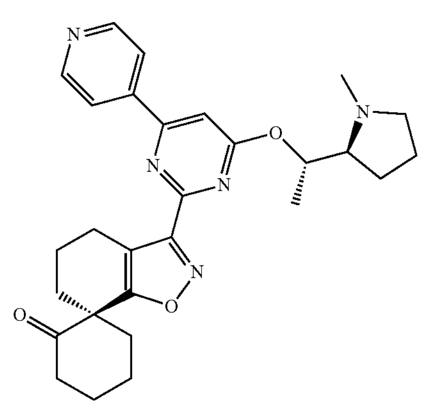 [SMILES: C[C@H](Oc1cc(-c2ccncc2)nc(-c2noc3c2CCC[C@@]32CCCCC2=O)n1)[C@@H]1CCCN1C] | 1.43 | 488 | A |

TABLE 39-continued

| # | structure | t_ret [min] | [M + H]+ | HPLC method |
|---|---|---|---|---|
| G-48x | 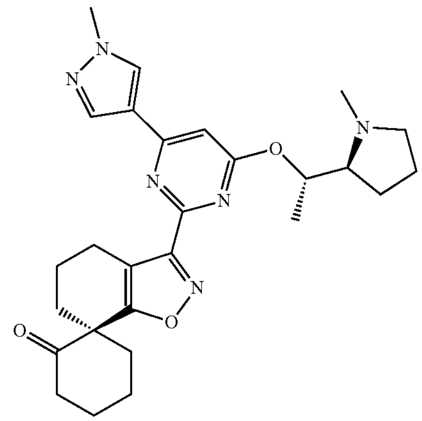 [SMILES: C[C@H](Oc1cc(-c2cnn(C)c2)nc(-c2noc3c2CCC[C@@]32CCCCC2=O)n1)[C@@H]1CCCN1C] | 1.39 | 491 | A |
| G-48y | 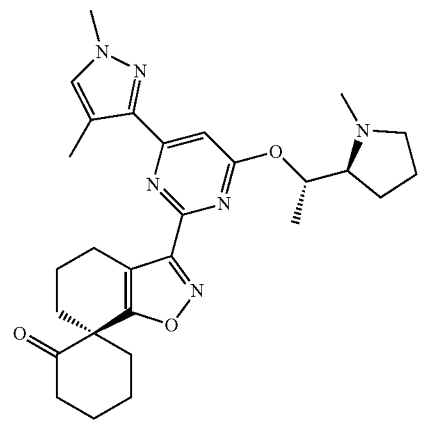 [SMILES: Cc1cn(C)nc1-c1cc(O[C@@H](C)[C@@H]2CCCN2C)nc(-c2noc3c2CCC[C@@]32CCCCC2=O)n1] | 1.58 | 505 | A |
| G-48z | 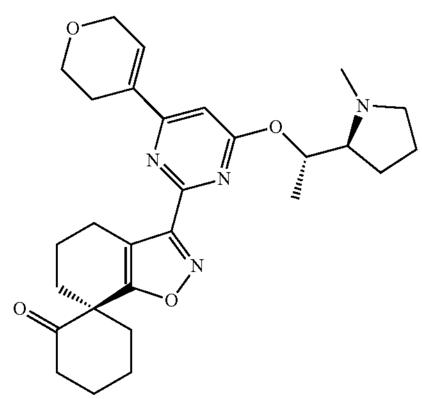 [SMILES: C[C@H](Oc1cc(C2=CCOCC2)nc(-c2noc3c2CCC[C@@]32CCCCC2=O)n1)[C@@H]1CCCN1C] | 1.51 | 493 | A |
| G-48aa | 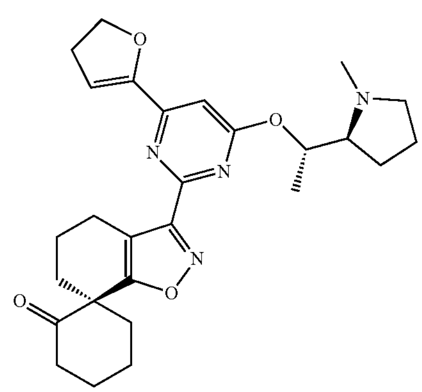 [SMILES: C[C@H](Oc1cc(C2=CCCO2)nc(-c2noc3c2CCC[C@@]32CCCCC2=O)n1)[C@@H]1CCCN1C] | 0.91 | 479 | C |

TABLE 39-continued

| # | structure | $t_{ret}$ [min] | [M + H]⁺ | HPLC method |
|---|---|---|---|---|
| G-48ab | 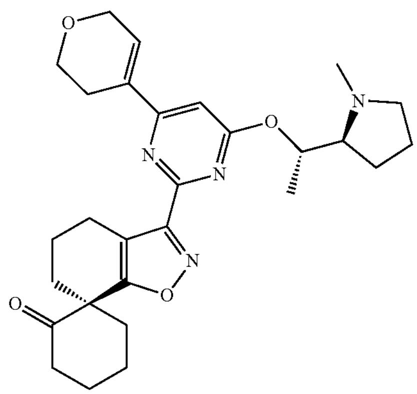 [SMILES: C[C@H](Oc1cc(C2=CCOCC2)nc(-c2noc3c2CCC[C@@]32CCCCC2=O)n1)[C@@H]1CCCN1C] | 1.51 | 493 | A |
| G-48ac | 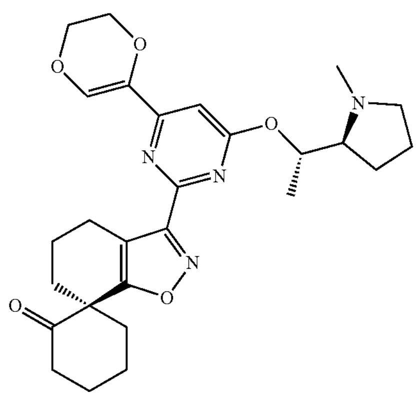 [SMILES: C[C@H](Oc1cc(C2=COCCO2)nc(-c2noc3c2CCC[C@@]32CCCCC2=O)n1)[C@@H]1CCCN1C] | 0.85 | 495 | C |
| G-48ad | 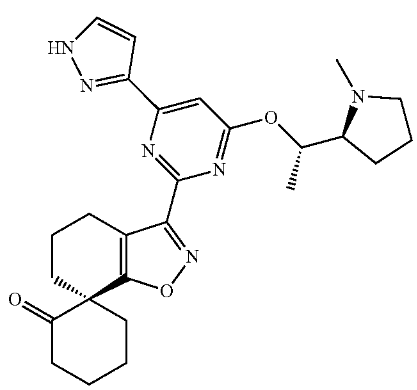 [SMILES: C[C@H](Oc1cc(-c2cc[nH]n2)nc(-c2noc3c2CCC[C@@]32CCCCC2=O)n1)[C@@H]1CCCN1C] | 1.37 | 477 | A |
| G-48ae | 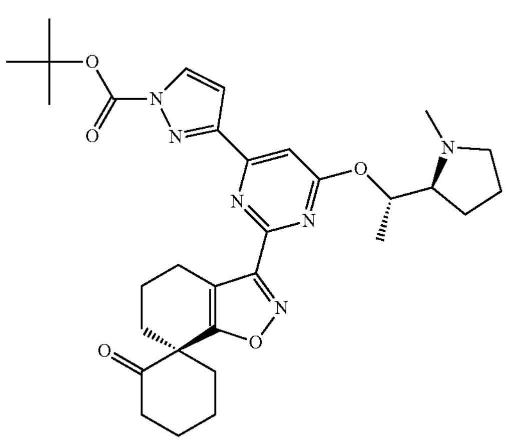 [SMILES: C[C@H](Oc1cc(-c2ccn(C(=O)OC(C)(C)C)n2)nc(-c2noc3c2CCC[C@@]32CCCCC2=O)n1)[C@@H]1CCCN1C] | 1.70 | 577 | A |

TABLE 39-continued
| # | structure | t_ret [min] | [M + H]+ | HPLC method |
|---|---|---|---|---|
| G-48af | 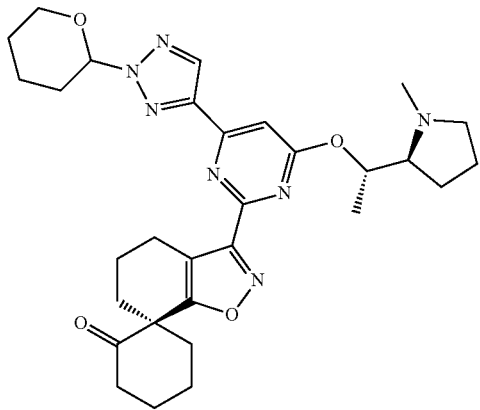 [SMILES: C[C@H](Oc1cc(-c2cnn(C3CCCCO3)n2)nc(-c2noc3c2CCC[C@@]32CCCCC2=O)n1)[C@@H]1CCCN1C] | 0.94 | 562 | C |
| G-48ag | 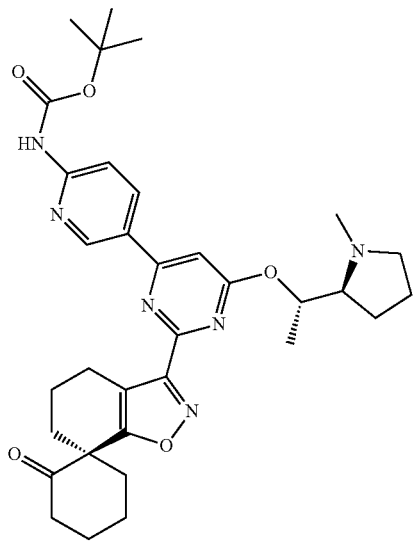 [SMILES: C[C@H](Oc1cc(-c2ccc(NC(=O)OC(C)(C)C)nc2)nc(-c2noc3c2CCC[C@@]32CCCCC2=O)n1)[C@@H]1CCCN1C] | 0.94 | 603 | C |
| G-48ah | 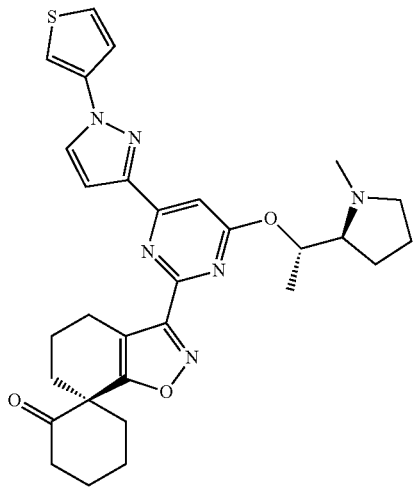 [SMILES: C[C@H](Oc1cc(-c2ccn(-c3ccsc3)n2)nc(-c2noc3c2CCC[C@@]32CCCCC2=O)n1)[C@@H]1CCCN1C] | 1.71 | 559 | A |

TABLE 39-continued

| # | structure | $t_{ret}$ [min] | $[M + H]^+$ | HPLC method |
|---|-----------|-----------------|-------------|-------------|
| G-48ai | 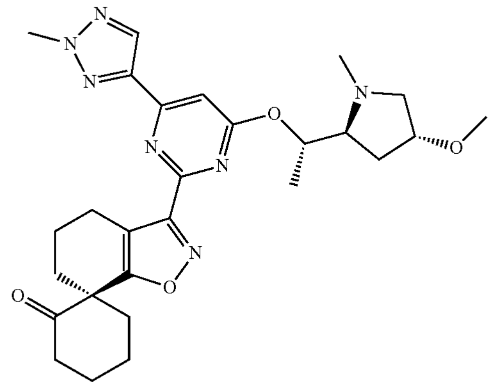 [SMILES: CO[C@@H]1C[C@@H]([C@H](C)Oc2cc(-c3cnn(C)n3)nc(-c3noc4c3CCC[C@@]43CCCCC3=O)n2)N(C)C1] | 1.44 | 522 | A |

Experimental Procedure for the Synthesis of G-49a

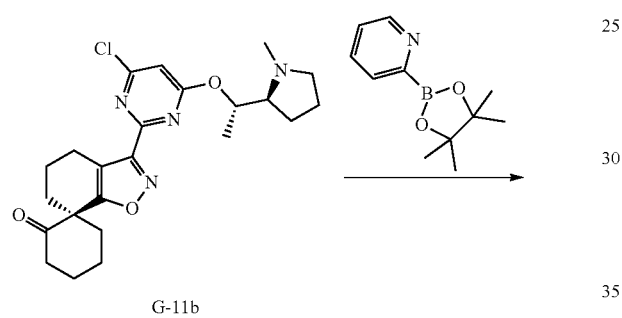

G-11b

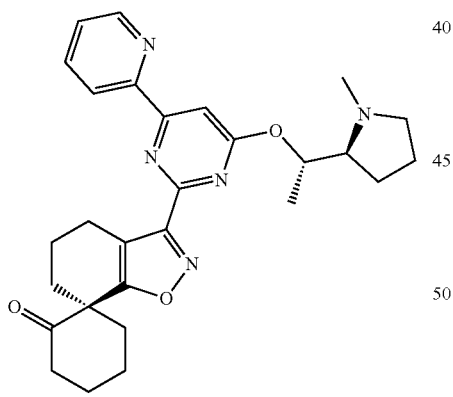

G-49a

G-11b (50 mg, 0.10 mmol, 1.0 equiv.), 2-(4,4,5,5-tetramethyl-1,3,4 dioxaborolan-2-yl)pyridine (41.39 mg, 0.19 mmol, 2.0 equiv.), Pd(dppf)Cl$_2$ (7 mg, 0.01 mmol, 0.1 equiv.), copper(I)chloride (9.68 mg, 0.10 mmol, 1.0 equiv.), and cesium carbonate (128 mg, 0.38 mmol, 4.0 equiv.) are dissolved in DMF (1 mL) and stirred under an argon atmosphere 18 h at 90° C. The reaction is extracted with DCM/water, the organic phase is concentrated under reduced pressure and purified by RP chromatography to give the desired product G-49a (HPLC-method: A, $t_{ret}$=1.56 min; [M+H]=488).

Experimental Procedure for the Synthesis of G-50a

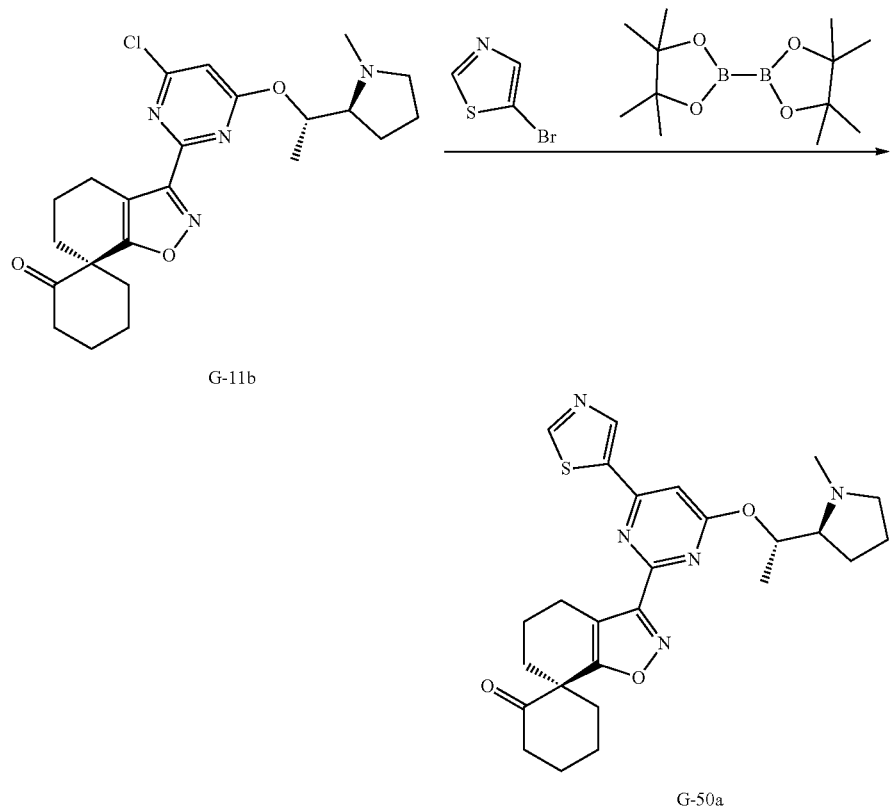

G-11b (148 mg 0.30 mmol, 1 equiv.), 5-bromothiazole (50 mg, 0.30 mmol, 1.0 equiv.), bis(pinacolato)diboron (163 mg, 0.63 mmol, 2.10 equiv.), APhos PD G3 methanesulfonate (10.4 mg, 0.02 mmol, 0.06 equiv.), potassium acetate (60.3 mg, 0.61 mmol, 2.06 equiv.) and tripotassium phosphate (4 M in water, 161 μL, 0.64 mmol, 2.15 equiv.) are dissolved in dioxane (1 mL) and stirred under nitrogen for 18 h at 90° C. After complete conversion, the reaction mixture is extracted with EtOAc/water. the organic phase is concentrated under reduced pressure and purified by RP chromatography to give the desired product G-50a (HPLC-method: C, $t_{ret}$=0.79 min; [M+H]=494).

Experimental Procedure for the Synthesis of G-51a

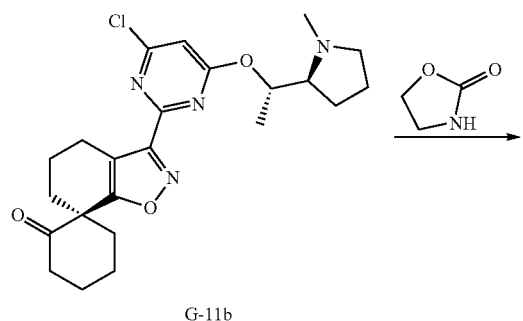

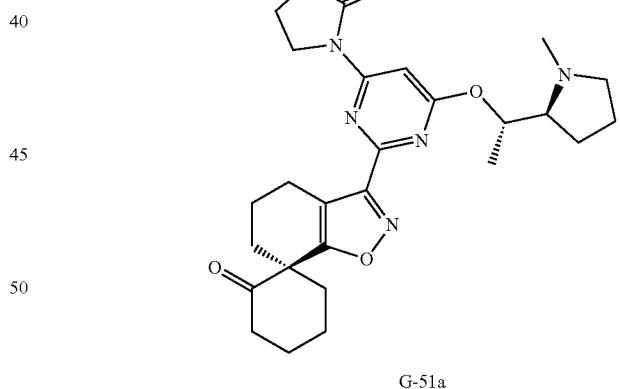

G-11b (150 mg, 0.34 mmol, 1.0 equiv.) is dissolved in dioxane (18 mL), 2-oxazolidone (59.9 mg, 0.67 mmol, 2.0 equiv.), Pd(dppf)Cl$_2$ (24.7 mg, 0.03 mmol, 0.1 equiv.) and NaOtBu (2.0M in THF, 185 μL, 0.37 mmol, 1.1 equiv.) are added. The reaction is stirred 3 d at 60° C. after complete conversion is observed the reaction is filtered and concentrated under reduced pressure. The residue is extracted with DCM/water. The combined organic phase is concentrated under reduced pressure and purified by RP chromatography to afford G-51a (HPLC-method: C, $t_{ret}$=0.78 min; [M+H]=496).

Experimental Procedure for the Synthesis of G-52a

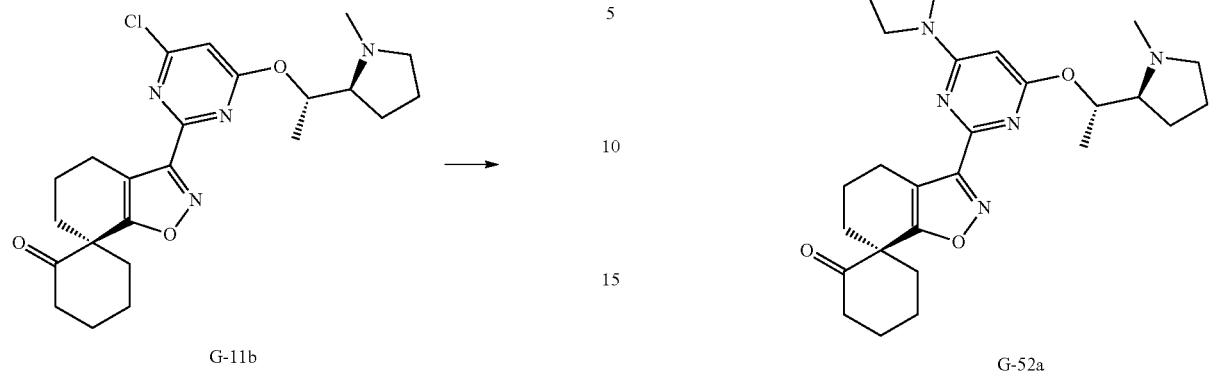

G-11b (120 mg, 0.27 mmol, 1.0 equiv.), 1-methylimidazolin-2-one (81.0 mg, 0.81 mmol, 3.0 equiv.), Xantphos PD G3 (16.15 mg, 0.02 mmol, 0.06 equiv.) cesium carbonate (131 mg, 0.40 mmol, 1.5 equiv.) are dissolved in dioxane (960 µL) and stirred under an argon atmosphere for 16 h at 110° C. After complete conversion, the reaction mixture is filtered and purified by RP chromatography to give the desired product G-52a.

The following intermediates G-52 (Table 40) are available in an analogous manner. The crude product is purified by chromatography if necessary.

TABLE 40

| # | structure | $t_{ret}$ [min] | $[M + H]^+$ | HPLC method |
|---|---|---|---|---|
| G-52a | 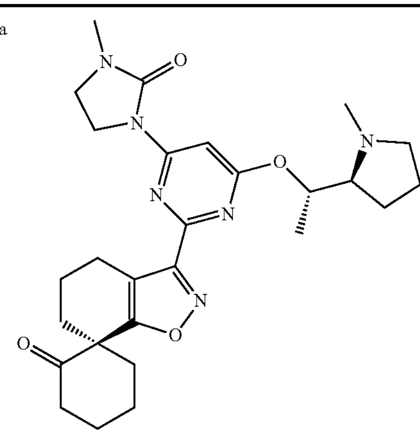 | 0.75 | 509 | C |
| G-52b | 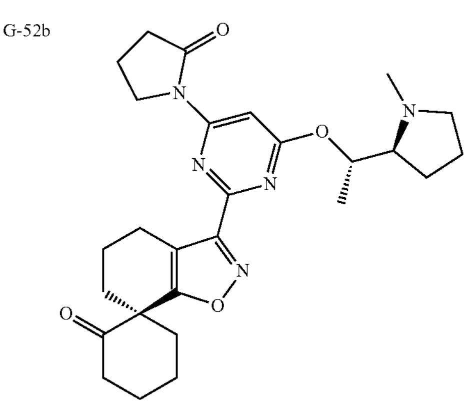 | 0.78 | 494 | C |

TABLE 40-continued

| # | structure | $t_{ret}$ [min] | [M + H]$^+$ | HPLC method |
|---|---|---|---|---|
| G-52c | 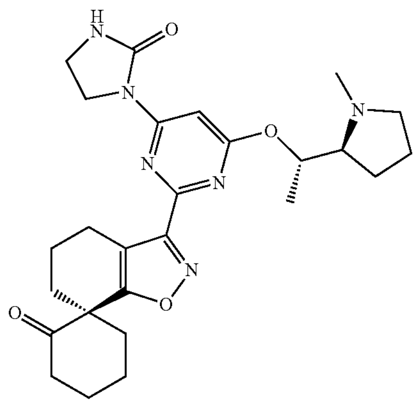 [SMILES: C[C@H](Oc1cc(N2CCNC2=O)nc(-c2noc3c2CCC[C@@]32CCCCC2=O)n1)[C@@H]1CCCN1C] | 0.67 | 495 | C |
| G-52d | 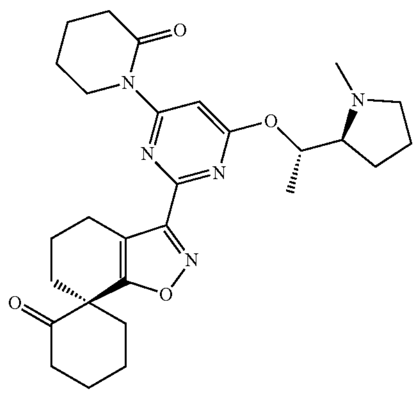 [SMILES: C[C@H](Oc1cc(N2CCCCC2=O)nc(-c2noc3c2CCC[C@@]32CCCCC2=O)n1)[C@@H]1CCCN1C] | 0.79 | 508 | C |

Experimental Procedure for the Synthesis of G-53a

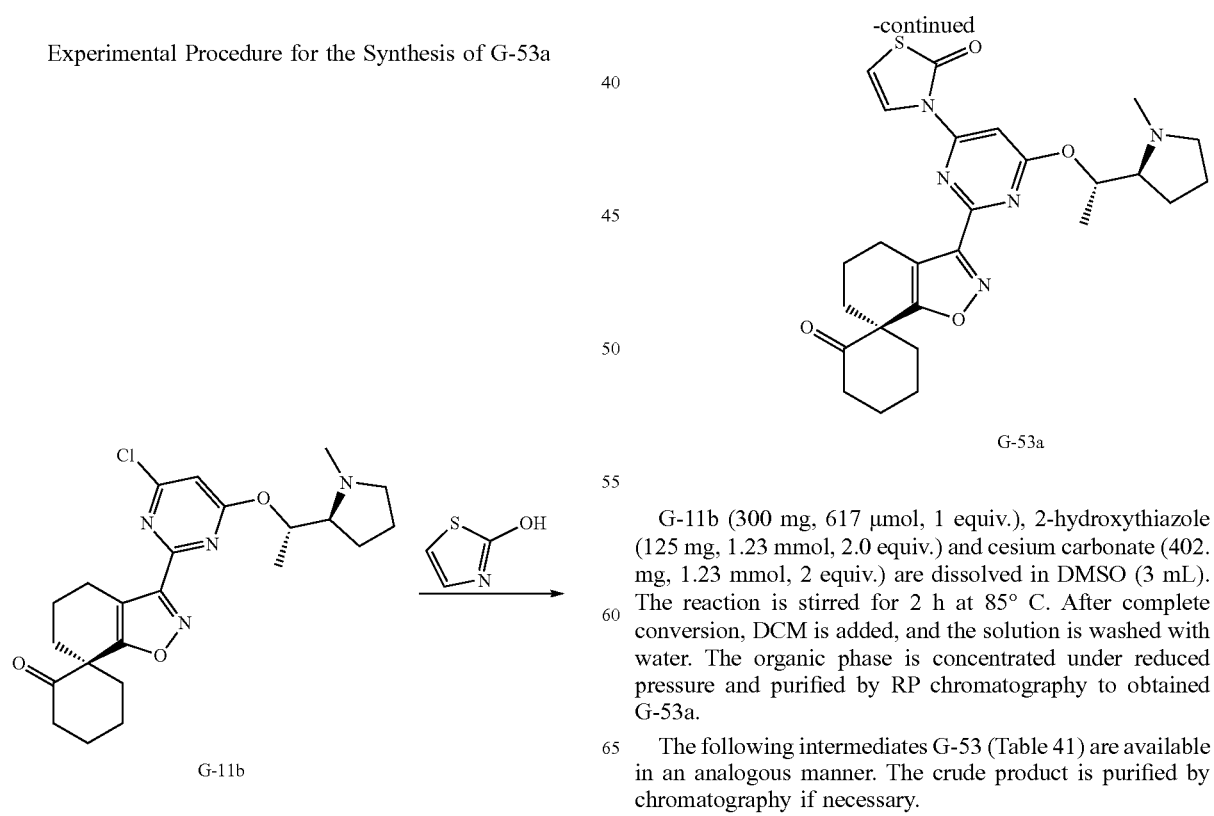

G-11b (300 mg, 617 µmol, 1 equiv.), 2-hydroxythiazole (125 mg, 1.23 mmol, 2.0 equiv.) and cesium carbonate (402. mg, 1.23 mmol, 2 equiv.) are dissolved in DMSO (3 mL). The reaction is stirred for 2 h at 85° C. After complete conversion, DCM is added, and the solution is washed with water. The organic phase is concentrated under reduced pressure and purified by RP chromatography to obtained G-53a.

The following intermediates G-53 (Table 41) are available in an analogous manner. The crude product is purified by chromatography if necessary.

TABLE 41

| # | structure | $t_{ret}$ [min] | [M + H]+ | HPLC method |
|---|---|---|---|---|
| G-53a | 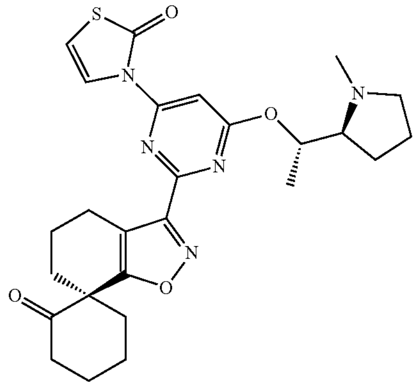 [SMILES: C[C@H](Oc1cc(-n2ccsc2=O)nc(-c2noc3c2CCC[C@@]32CCCCC2=O)n1)[C@@H]1CCCN1C] | 1.58 | 510 | A |
| G-53b | 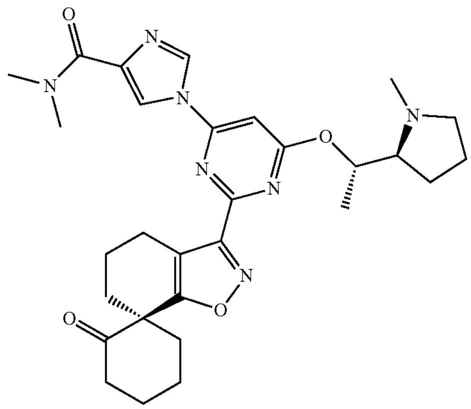 [SMILES: C[C@H](Oc1cc(-n2cnc(C(=O)N(C)C)c2)nc(-c2noc3c2CCC[C@@]32CCCCC2=O)n1)[C@@H]1CCCN1C] | 0.71 | 547 | C |
| G-53c | 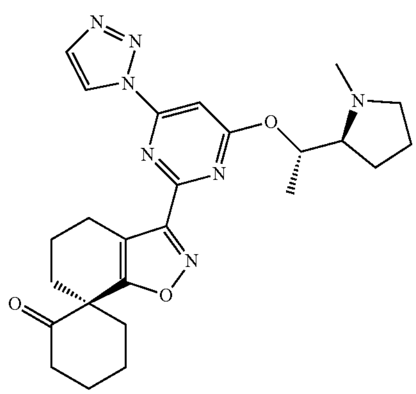 [SMILES: C[C@H](Oc1cc(-n2ccnn2)nc(-c2noc3c2CCC[C@@]32CCCCC2=O)n1)[C@@H]1CCCN1C] | 1.43 | 478 | A |
| G-53d | 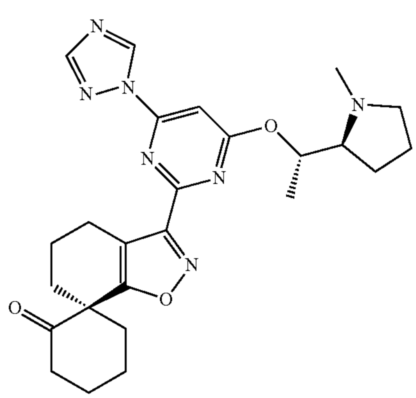 [SMILES: C[C@H](Oc1cc(-n2cncn2)nc(-c2noc3c2CCC[C@@]32CCCCC2=O)n1)[C@@H]1CCCN1C] | 1.41 | 478 | A |

TABLE 41-continued

| # | structure | t_ret [min] | [M + H]+ | HPLC method |
|---|---|---|---|---|
| G-53e | 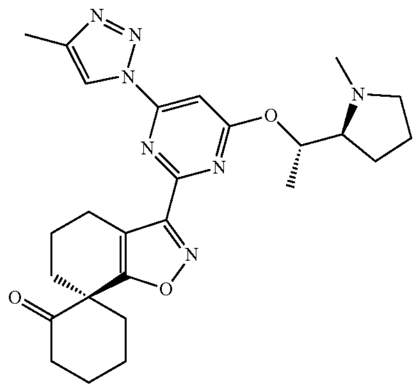 [SMILES: Cc1cn(-c2cc(O[C@@H](C)[C@@H]3CCCN3C)nc(-c3noc4c3CCC[C@@]43CCCCC3=O)n2)nn1] | 0.83 | 493 | C |
| G-53f | 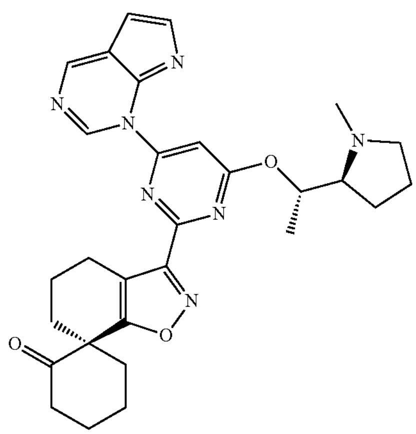 [SMILES: C[C@H](Oc1cc(-n2cncc3ccnc2-3)nc(-c2noc3c2CCC[C@@]32CCCCC2=O)n1)[C@@H]1CCCN1C] | 1.59 | 528 | A |
| G-53g | 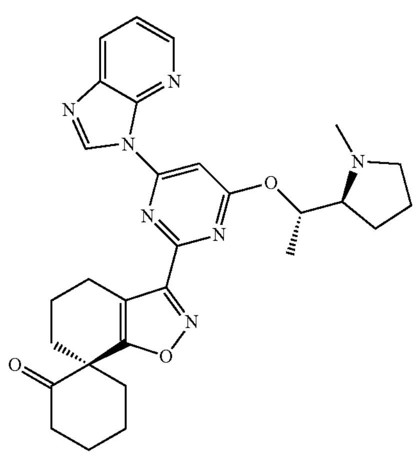 [SMILES: C[C@H](Oc1cc(-n2cnc3cccnc32)nc(-c2noc3c2CCC[C@@]32CCCCC2=O)n1)[C@@H]1CCCN1C] | 1.58 | 528 | A |

TABLE 41-continued
| # | structure | t_ret [min] | [M + H]+ | HPLC method |
|---|---|---|---|---|
| G-53h | 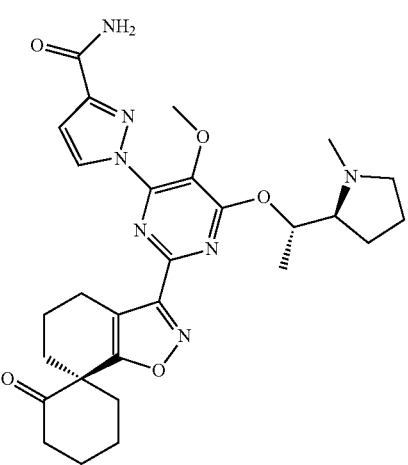 [SMILES: COc1c(O[C@@H](C)[C@@H]2CCCN2C)nc(-c2noc3c2CCC[C@@]32CCCCC2=O)nc1-n1ccc(C(N)=O)n1] | 1.34 | 550 | A |
| G-53i | 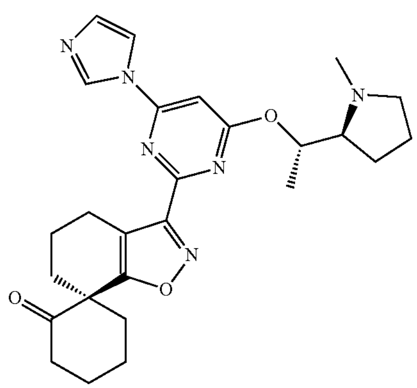 [SMILES: C[C@H](Oc1cc(-n2ccnc2)nc(-c2noc3c2CCC[C@@]32CCCCC2=O)n1)[C@@H]1CCCN1C] | 1.35 | 477 | A |
| G-53j | 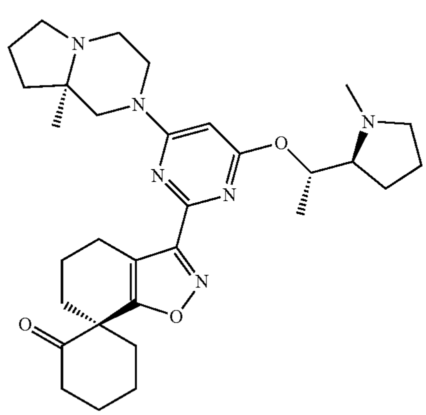 [SMILES: C[C@H](Oc1cc(N2CCN3CCC[C@]3(C)C2)nc(-c2noc3c2CCC[C@@]32CCCCC2=O)n1)[C@@H]1CCCN1C] | 1.79 | 549 | A |

TABLE 41-continued

| # | structure | $t_{ret}$ [min] | $[M + H]^+$ | HPLC method |
|---|---|---|---|---|
| G-53k | 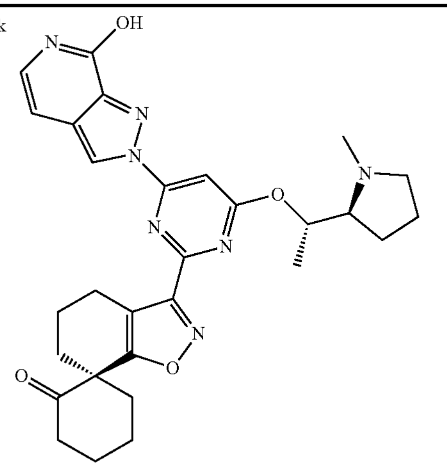 | 1.33 | 544 | A |

Experimental Procedure for the Synthesis of G-54a

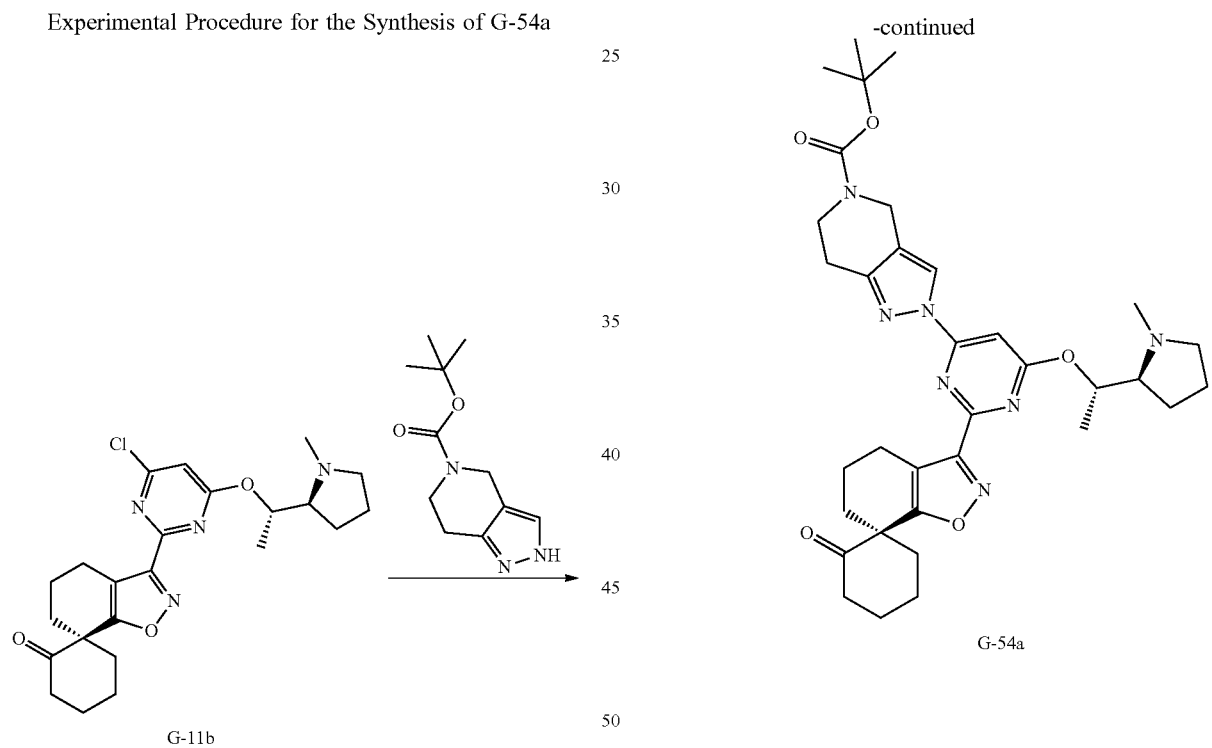

G-11b (200 mg, 449 μmol, 1.0 equiv.), tert-butyl-6,7-dihydro-1H-pyrazolo[4-3-c]pyridine-5(4H)-carboxylate (148 mg, 629 μmol, 1.4 equiv.), cesium carbonate (293 mg, 0.899 mmol, 2.0 equiv.), CuI (17.1 mg, 90 μmol, 0.20 equiv.), and 4,7-dimethoxy-1,10-phenanthroline are dissolved in DMF (1 mL). The mixture is purged with argon and stirred for 24 h at 80° C. After complete conversion, the reaction mixture is treated with some drops of aqueous ammonia and the product is isolated by RP chromatography to obtain G-54a.

The following intermediates G-54 (Table 42) are available in an analogous manner. The crude product is purified by chromatography if necessary.

TABLE 42
| # | structure | $t_{ret}$ [min] | $[M + H]^+$ | HPLC method |
|---|---|---|---|---|
| G-54a | 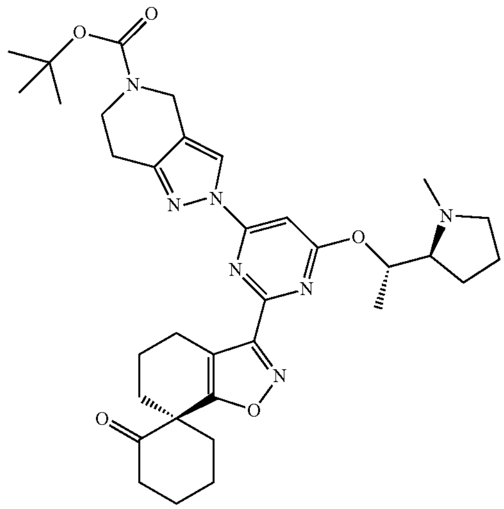 [SMILES: C[C@H](Oc1cc(-n2cc3c(n2)CCN(C(=O)OC(C)(C)C)C3)nc(-c2noc3c2CCC[C@@]32CCCCC2=O)n1)[C@@H]1CCCN1C] | 1.01 | 632 | D |
| G-54b | 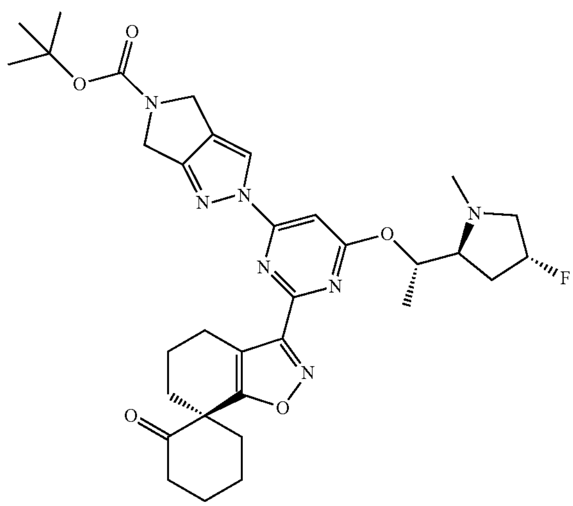 [SMILES: C[C@H](Oc1cc(-n2cc3c(n2)CN(C(=O)OC(C)(C)C)C3)nc(-c2noc3c2CCC[C@@]32CCCCC2=O)n1)[C@@H]1C[C@@H](F)CN1C] | 0.98 | 636 | D |
Experimental Procedure for the Synthesis of G-55a
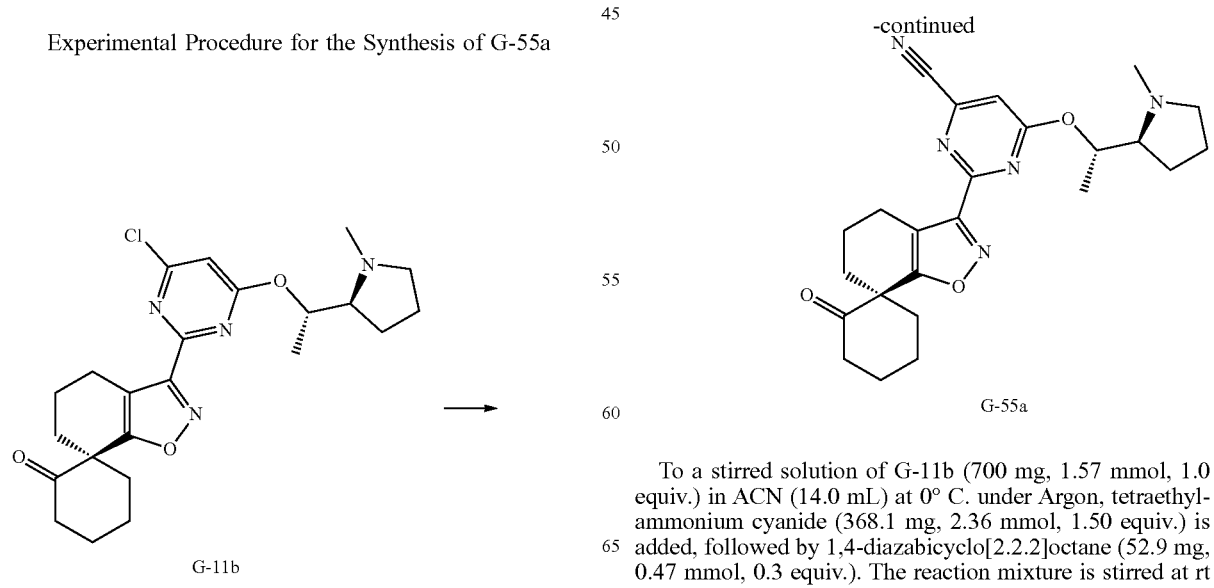
To a stirred solution of G-11b (700 mg, 1.57 mmol, 1.0 equiv.) in ACN (14.0 mL) at 0° C. under Argon, tetraethylammonium cyanide (368.1 mg, 2.36 mmol, 1.50 equiv.) is added, followed by 1,4-diazabicyclo[2.2.2]octane (52.9 mg, 0.47 mmol, 0.3 equiv.). The reaction mixture is stirred at rt overnight until TLC shows complete conversion. The solvent is removed under reduced pressure. The crude product is purified by NP chromatography to obtain G-55a (HPLC method: A; $t_{ret}$=1.48 min; [M+H]$^+$=436).

Experimental Procedure for the Synthesis of G-56a

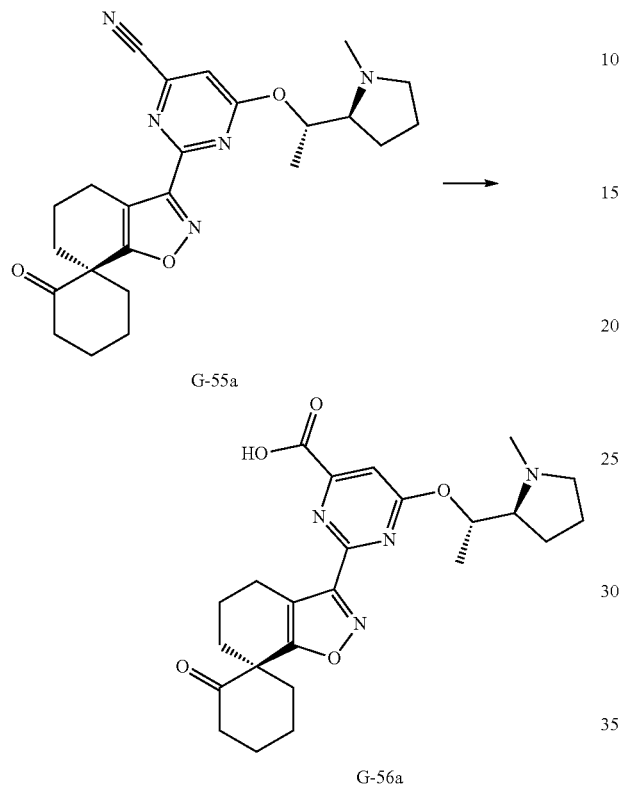

G-55a

G-56a

To a stirred solution of G-55a (300 mg, 0.69 mmol, 1.0 equiv.), in THF (2.0 mL) and water (2.0 mL), NaOH (83 mg, 2.1 mmol, 3.0 equiv.) is added at rt, then reaction mixture is stirred for 90 min at 50° C. until TLC shows complete conversion. The solvent is removed under reduced pressure. The crude product is purified by NP chromatography to obtain G-56a (HPLC method: A; $t_{ret}$=0.97 min; [M+H]$^+$=455).

Experimental Procedure for the Synthesis of G-57a

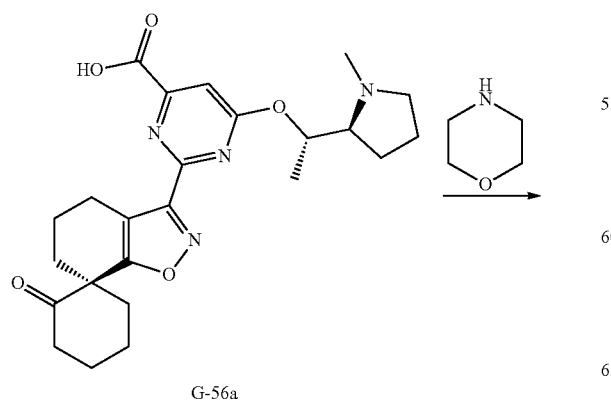

G-56a

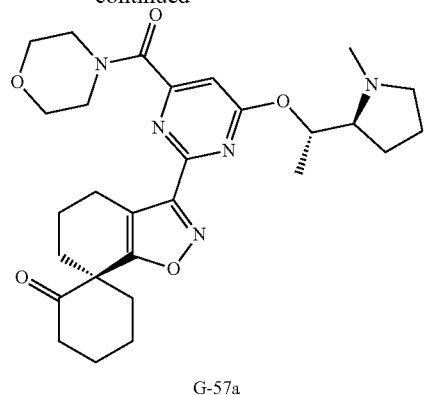

G-57a

To a stirred mixture of G-56a (100 mg, 0.22 mmol, 1.0 equiv.), and HATU (126 mg, 0.33 mmol, 1.50 equiv.) in dioxane (2.0 mL), DIPEA (112 µL, 0.66 mmol, 3.0 equiv.) is added at rt, then the reaction mixture is stirred for 30 min at rt. Morpholine (21.1 µL, 0.242 mmol, 1.10 equiv.) is added and the mixture is stirred at rt overnight until complete conversion. The crude product is purified by RP chromatography to give product G-57a (HPLC method: D; $t_{ret}$=0.67 min; [M+H]$^+$=524).

Experimental Procedure for the Synthesis of G-58a

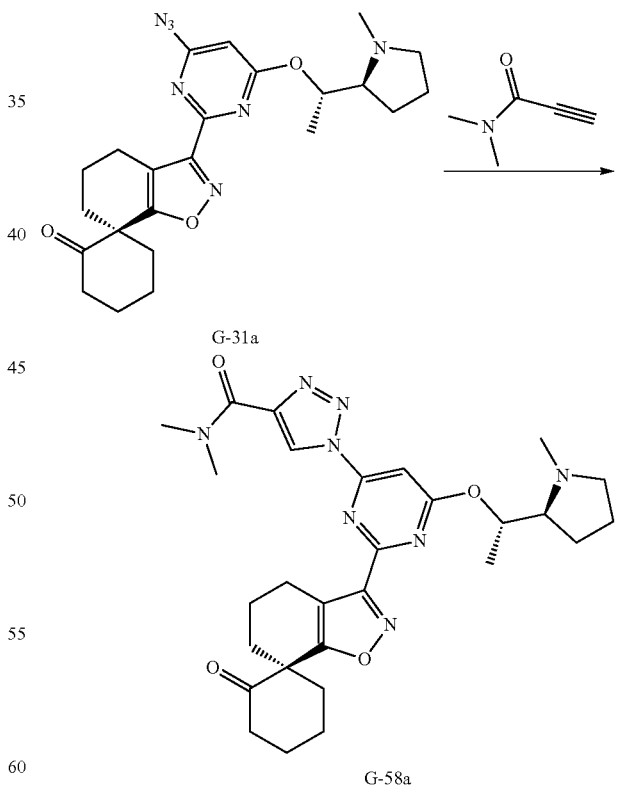

G-31a

G-58a

G-31a (150 mg, 0.28 mol, 1.0 equiv.) is dissolved in DCM, (2 mL), N,N-dimethylprop-2-ynamide (30.2 mg, 0.31 mmol, 1.1 equiv.), copper(I)iodide (10.8 mg, 0.06 mol, 0.2 equiv.) and DIPEA (98.9 µL, 0.56 mmol, 2 equiv.) are added. The reaction is stirred for 20 min at rt. After complete conversion, the reaction is extracted with DCM/NaHCO$_3$. The organic phase is concentrated under reduced pressure and purified by RP chromatography to yield G-58a.

The following intermediates G-58 (Table 43) are available in an analogous manner. The crude product is purified by chromatography if necessary.

TABLE 43

| # | structure | t$_{ret}$ [min] | [M + H]$^+$ | HPLC method |
|---|---|---|---|---|
| G-58a | 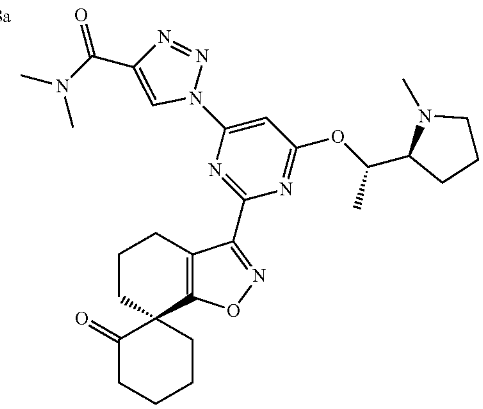 | 1.42 | 549 | A |
| G-58b | 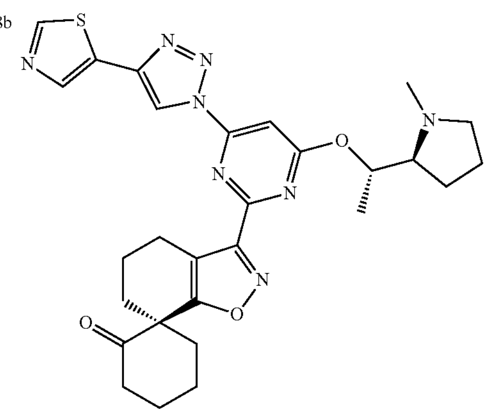 | 1.53 | 561 | A |
| G-58c | 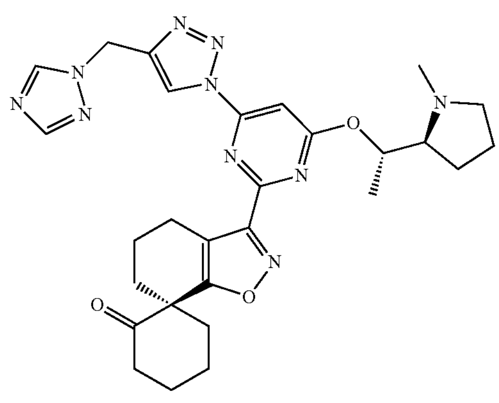 [SMILES: C[C@H](Oc1cc(-n2cc(Cn3cncn3)nn2)nc(-c2noc3c2CCC[C@@]32CCCCC2=O)n1)[C@@H]1CCCN1C] | 1.32 | 559 | A |

TABLE 43-continued

| # | structure | $t_{ret}$ [min] | [M + H]$^+$ | HPLC method |
|---|---|---|---|---|
| G-58d | 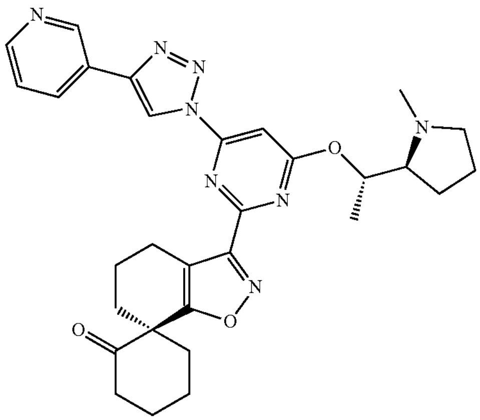 [SMILES: C[C@H](Oc1cc(-n2cc(-c3cccnc3)nn2)nc(-c2noc3c2CCC[C@@]32CCCCC2=O)n1)[C@@H]1CCCN1C] | 1.51 | 555 | A |
| G-58e | 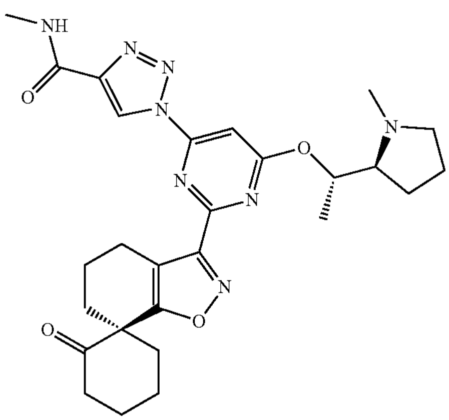 [SMILES: CNC(=O)c1cn(-c2cc(O[C@@H](C)[C@@H]3CCCN3C)nc(-c3noc4c3CCC[C@@]43CCCCC3=O)n2)nn1] | 1.37 | 535 | A |
| G-58f | 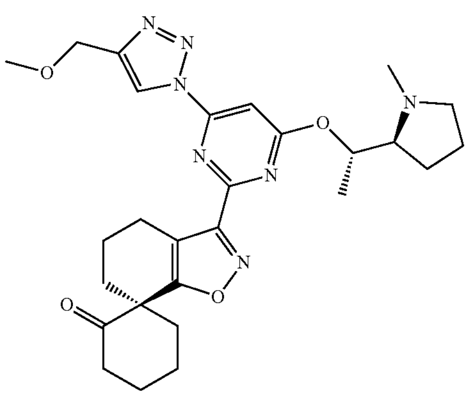 [SMILES: COCc1cn(-c2cc(O[C@@H](C)[C@@H]3CCCN3C)nc(-c3noc4c3CCC[C@@]43CCCCC3=O)n2)nn1] | 1.46 | 522 | A |
| G-58g | 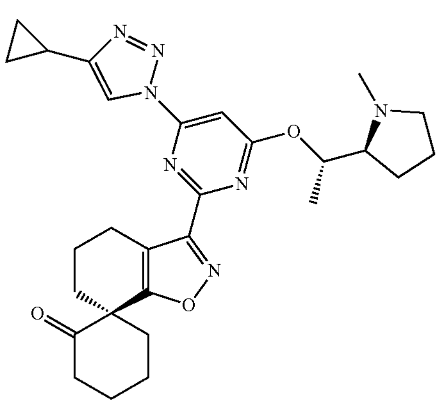 [SMILES: C[C@H](Oc1cc(-n2cc(C3CC3)nn2)nc(-c2noc3c2CCC[C@@]32CCCCC2=O)n1)[C@@H]1CCCN1C] | 1.60 | 518 | A |

TABLE 43-continued

| # | structure | $t_{ret}$ [min] | $[M + H]^+$ | HPLC method |
|---|---|---|---|---|
| G-58h | 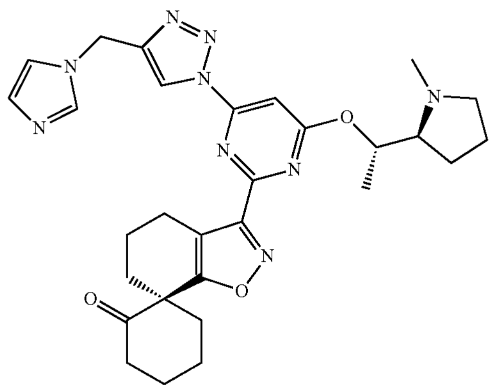 [SMILES: C[C@H](Oc1cc(-n2cc(Cn3ccnc3)nn2)nc(-c2noc3c2CCC[C@@]32CCCCC2=O)n1)[C@@H]1CCCN1C] | 1.35 | 558 | A |

Experimental Procedure for the Synthesis of G-59a

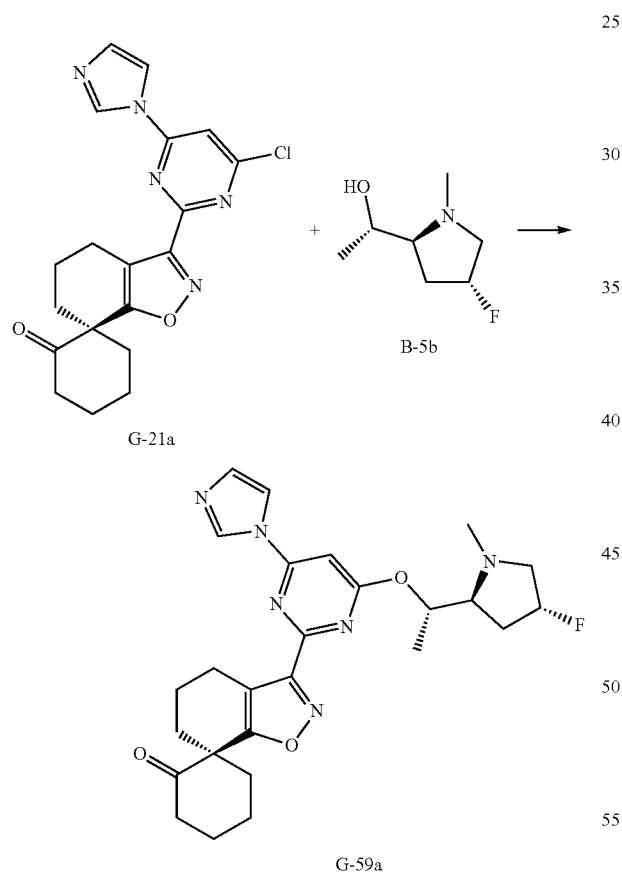

G-21a (144 mg, 0.36 mmol, 1.0 equiv.), B-5b (80.0 mg, 0.49 mmol, 1.37 equiv.) are dissolved in dioxane (1.4 mL) and degassed with argon. [BrettPhos Pd(crotyl)]OTf (24 mg, 0.03 mmol, 0.08 equiv.) is added and NaOtBu (222 µL, 0.44 mmol, 1.25 equiv.) is added at rt. The reaction is stirred at 60° C. for 30 min. After complete conversion, the solution is filtered and purified by RP chromatography to give the desired product G-59a.

The following intermediates G-59 (Table 44) are available in an analogous manner. The crude product is purified by chromatography if necessary.
TABLE 44
| # | structure | $t_{ret}$ [min] | $[M + H]^+$ | HPLC method |
|---|---|---|---|---|
| G-59a | 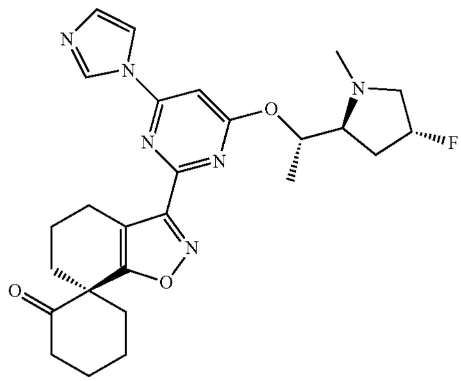 [SMILES: C[C@H](Oc1cc(-n2ccnc2)nc(-c2noc3c2CCC[C@@]32CCCCC2=O)n1)[C@@H]1C[C@@H](F)CN1C] | 0.70 | 495 | C |
| G-59b | 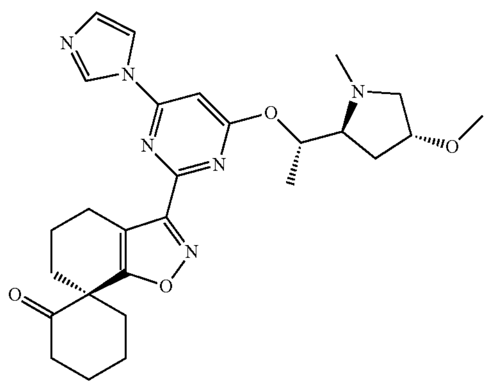 [SMILES: CO[C@@H]1C[C@@H]([C@H](C)Oc2cc(-n3ccnc3)nc(-c3noc4c3CCC[C@@]43CCCCC3=O)n2)N(C)C1] | 0.67 | 507 | C |
Experimental Procedure for the Synthesis of G-60a
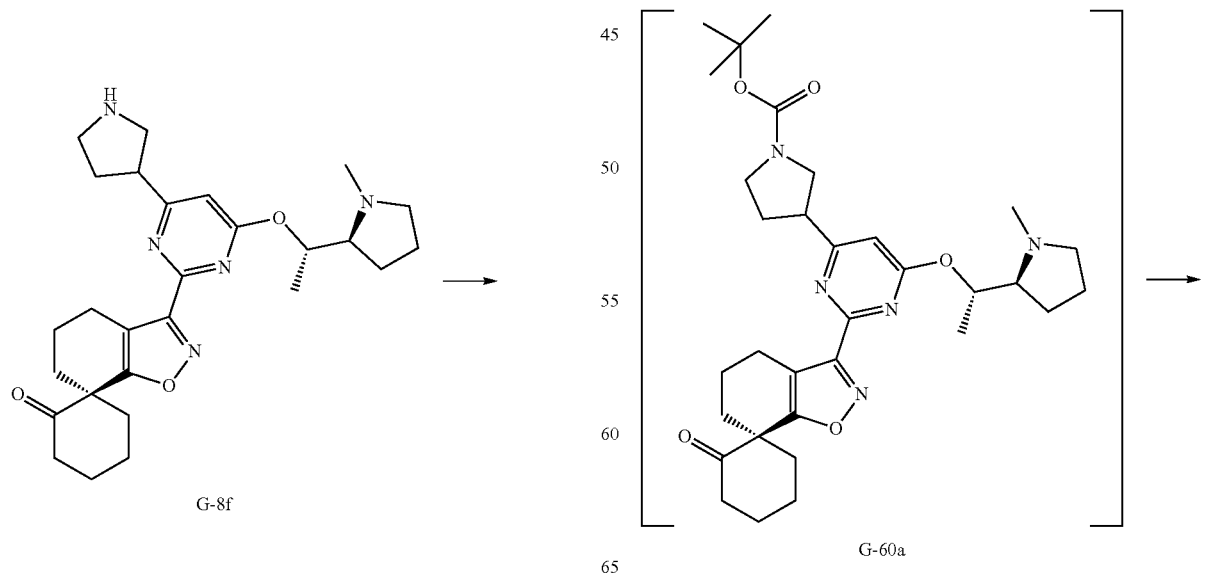

337
-continued

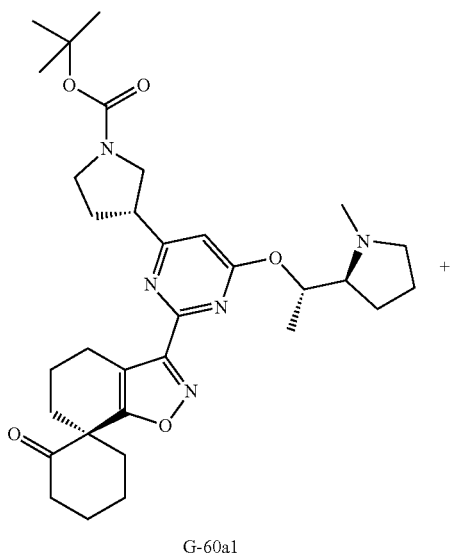

G-60a1

+

338
-continued

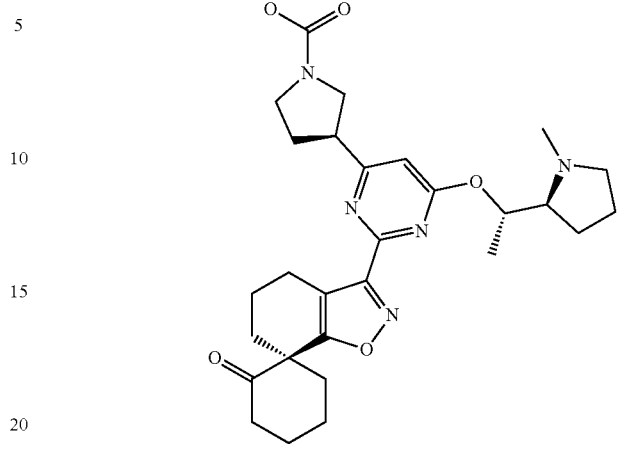

G-60a2

G-8f (2.4 g, 0.01 mol, 1 equiv.) is dissolved in THF (100 mL), triethylamine (2.09 mL, 0.02 mol, 3.0 equiv.) and dimethyl aminopyridine (122 mg, 1.0 mmol, 0.2 equiv.) are added and the reaction is stirred for 5 min at rt, the reaction is cooled down to 0° C. and Boc-anhydride (2.18 g, 0.01 mol, 2.0 equiv.) is added. The reaction is stirred for 16 h at rt. After full conversion, water is added, and the reaction is extracted with DCM. The combined organic phases are concentrated under reduced pressure and purified by NP chromatography yielding the desired product G-60a as a mixture of diastereomers. The diastereomeric mixture G-60a is separated via SFC (Column: (R,R)Whelk-01 (250×30, 5μ); 55% CO2, 45% cosolvent=0.5% i-propylamine in iso-propanol, flow: 100 g/min, temp: 30° C.)

yielding G-60a1 and G-60a2 (Table 45).

TABLE 45

| # | structure | [M + H]$^+$ | t$_{ret}$ [min] | HPLC method |
|---|---|---|---|---|
| G-60a1 | 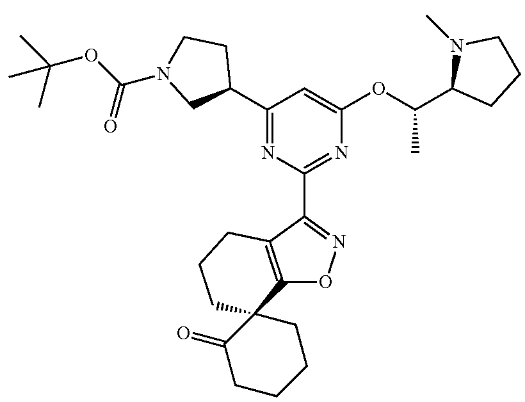 [SMILES: C[C@H](Oc1cc([C@@H]2CCN(C(=O)OC(C)(C)C)C2)nc(-c2noc3c2CCC[C@@]32CCCCC2=O)n1)[C@@H]1CCCN1C] | 580 | 2.20 | J |
| | | | 5.78 | SFC-2 |

TABLE 45-continued
| # | structure | [M + H]+ | t_ret [min] | HPLC method |
|---|---|---|---|---|
| G-60a2 | 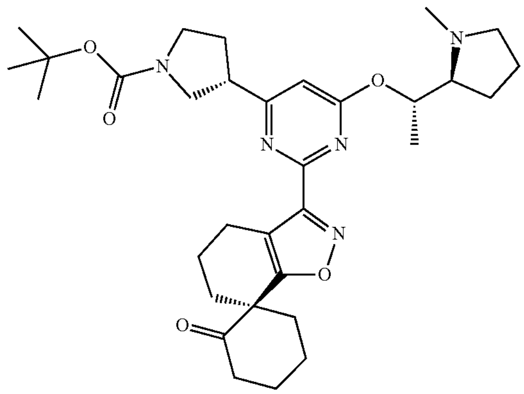 [SMILES: C[C@H](Oc1cc([C@H]2CCN(C(=O)OC(C)(C)C)C2)nc(-c2noc3c2CCC[C@@]32CCCCC2=O)n1)[C@@H]1CCCN1C] | 580 | 2.20<br>7.10 | J<br>SFC-2 |
Experimental Procedure for the Synthesis of G-61a
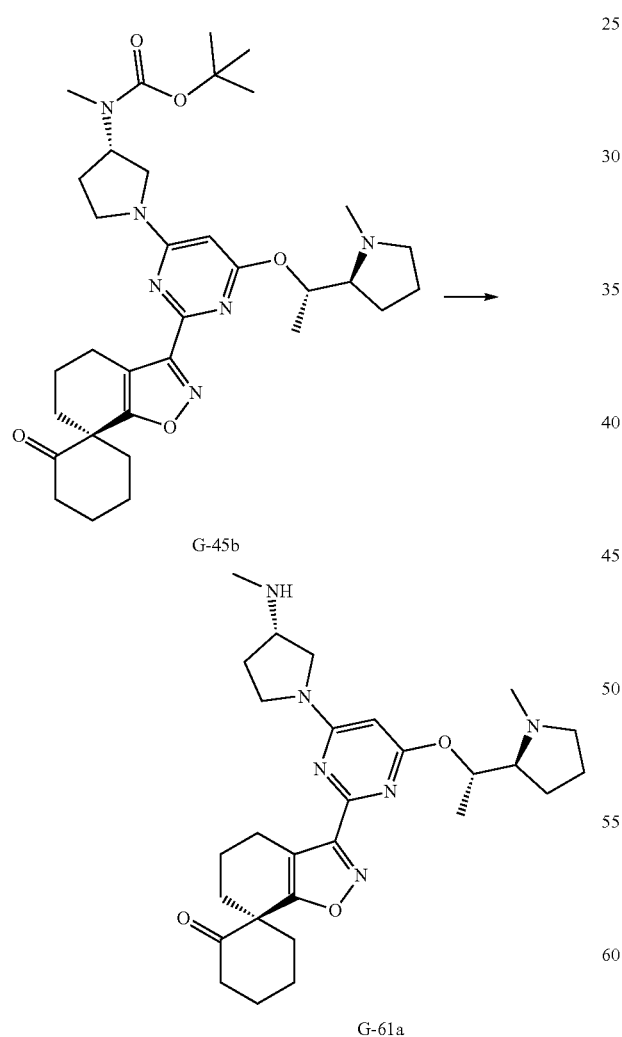
G-45b
G-61a G-45b (204 mg, 0.335 mmol, 1.0 equiv.) is dissolved in MeOH (1 mL) and 4M HCl (0.42 mL, 1.67 mmol, 5.0 equiv.) is added. Reaction stirred for 3 h at 60° C. After complete conversion, the reaction mixture is quenched by the addition of NaHCO$_3$ and extracted with DCM. The combined organic phases are filtered and concentrated under reduced pressure. The residue is purified by RP chromatography to give the desired product G-61a.

The following intermediates G-61 (Table 46) are available in an analogous manner. The crude product is purified by chromatography if necessary.

TABLE 46

| # | structure | t$_{ret}$ [min] | [M + H]$^+$ | HPLC method |
|---|---|---|---|---|
| G-61a | 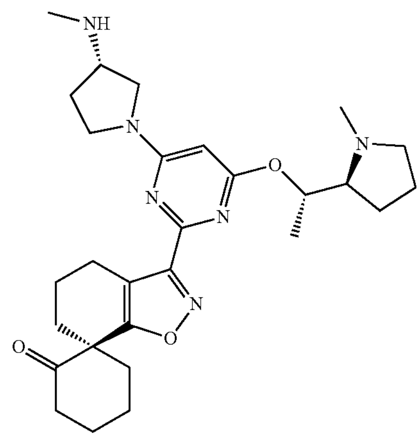 [SMILES: CN[C@H]1CCN(c2cc(O[C@@H](C)[C@@H]3CCCN3C)nc(-c3noc4c3CCC[C@@]43CCCCC3=O)n2)C1] | 1.34 | 509.0 | A |
| G-61b | 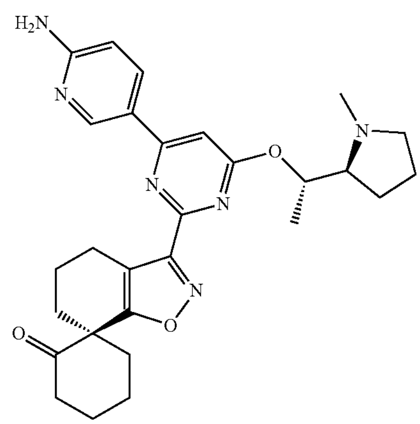 [SMILES: C[C@H](Oc1cc(-c2ccc(N)nc2)nc(-c2noc3c2CCC[C@@]32CCCCC2=O)n1)[C@@H]1CCCN1C] | 0.72 | 503 | C |
| G-61c | 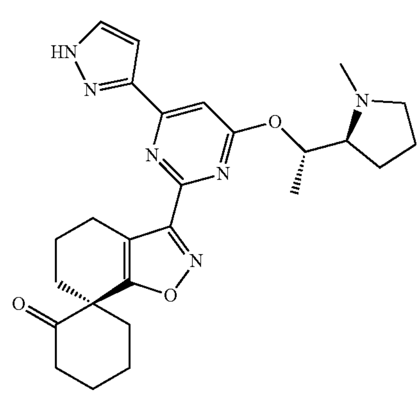 [SMILES: C[C@H](Oc1cc(-c2cc[nH]n2)nc(-c2noc3c2CCC[C@@]32CCCCC2=O)n1)[C@@H]1CCCN1C] | 1.40 | 477 | A |

TABLE 46-continued

| # | structure | t_ret [min] | [M + H]+ | HPLC method |
|---|---|---|---|---|
| G-61d | 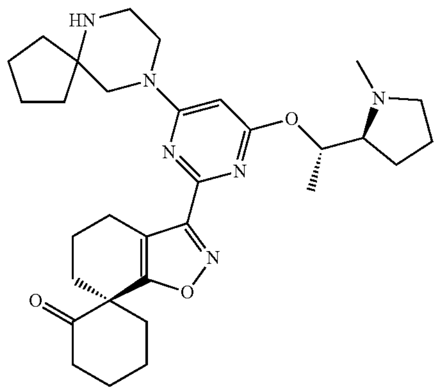 [SMILES: C[C@H](Oc1cc(N2CCNC3(CCCC3)C2)nc(-c2noc3c2CCC[C@@]32CCCCC2=O)n1)[C@@H]1CCCN1C] | 1.46 | 549 | A |
| G-61e | 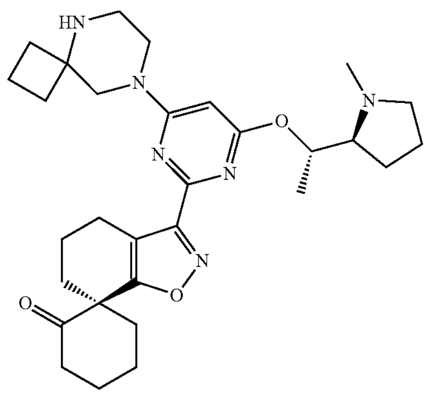 [SMILES: C[C@H](Oc1cc(N2CCNC3(CCC3)C2)nc(-c2noc3c2CCC[C@@]32CCCCC2=O)n1)[C@@H]1CCCN1C] | 1.41 | 535 | A |
| G-61f | 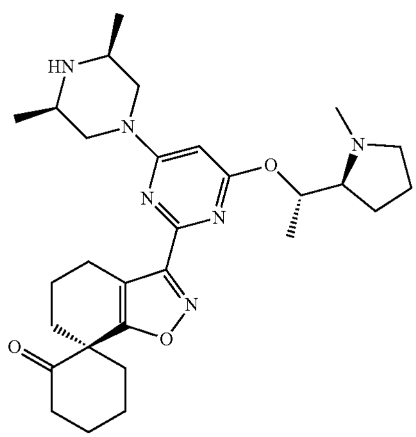 [SMILES: C[C@@H]1CN(c2cc(O[C@@H](C)[C@@H]3CCCN3C)nc(-c3noc4c3CCC[C@@]43CCCCC3=O)n2)C[C@H](C)N1] | 1.39 | 523 | A |
| G-61g | 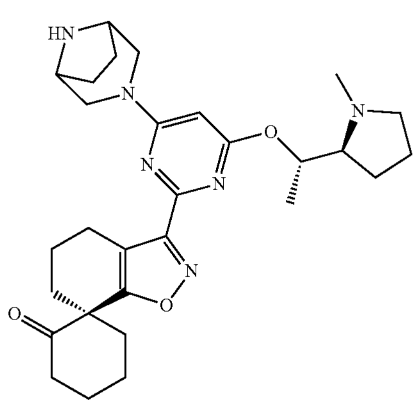 [SMILES: C[C@H](Oc1cc(N2CC3CCC(C2)N3)nc(-c2noc3c2CCC[C@@]32CCCCC2=O)n1)[C@@H]1CCCN1C] | 0.32 | 521 | F |

TABLE 46-continued
| # | structure | $t_{ret}$ [min] | $[M + H]^+$ | HPLC method |
|---|---|---|---|---|
| G-61h | 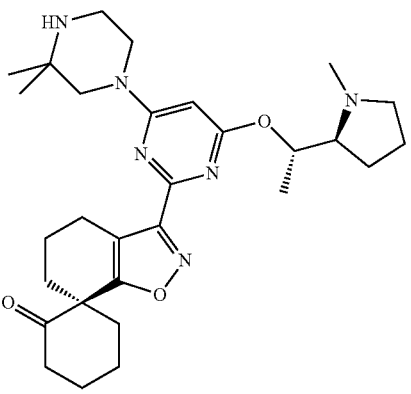 [SMILES: C[C@H](Oc1cc(N2CCNC(C)(C)C2)nc(-c2noc3c2CCC[C@@]32CCCCC2=O)n1)[C@@H]1CCCN1C] | 0.70 | 523 | E |
| G-61i | 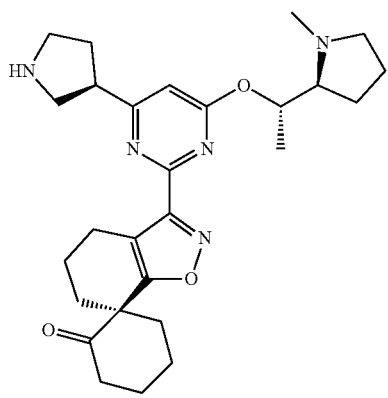 [SMILES: C[C@H](Oc1cc([C@@H]2CCNC2)nc(-c2noc3c2CCC[C@@]32CCCCC2=O)n1)[C@@H]1CCCN1C] | 0.61 | 480 | C |
| G-61j | 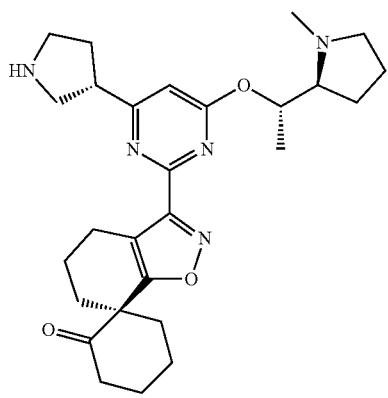 [SMILES: C[C@H](Oc1cc([C@H]2CCNC2)nc(-c2noc3c2CCC[C@@]32CCCCC2=O)n1)[C@@H]1CCCN1C] | 0.67 | 480 | C |

TABLE 46-continued

| # | structure | $t_{ret}$ [min] | [M + H]$^+$ | HPLC method |
|---|---|---|---|---|
| G-61k | 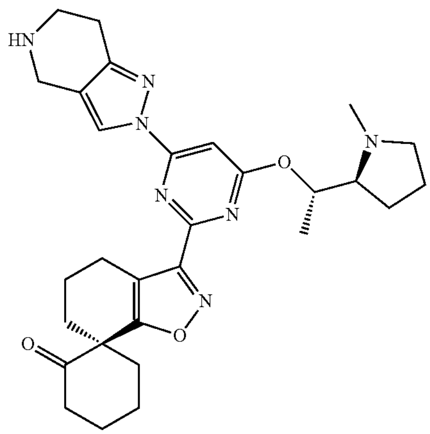 [SMILES: C[C@H](Oc1cc(-n2cc3c(n2)CCNC3)nc(-c2noc3c2CCC[C@@]32CCCCC2=O)n1)[C@@H]1CCCN1C] | 0.32 | 532 | D |
| G-61l | 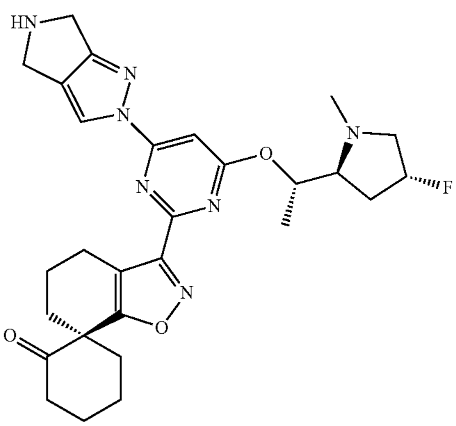 [SMILES: C[C@H](Oc1cc(-n2cc3c(n2)CNC3)nc(-c2noc3c2CCC[C@@]32CCCCC2=O)n1)[C@@H]1C[C@@H](F)CN1C] | 1.32 | 536 | A |
| G-61m | 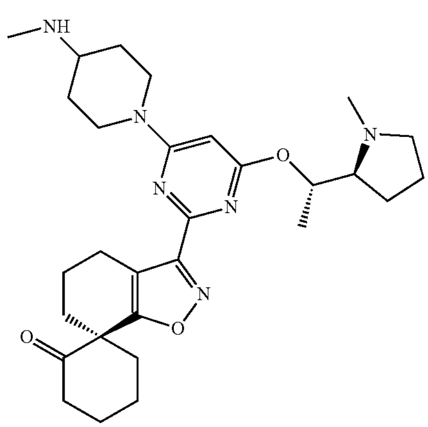 [SMILES: CNC1CCN(c2cc(O[C@@H](C)[C@@H]3CCCN3C)nc(-c3noc4c3CCC[C@@]43CCCCC3=O)n2)CC1] | 0.65 | 523 | C |

Experimental Procedure for the Synthesis of G-62a

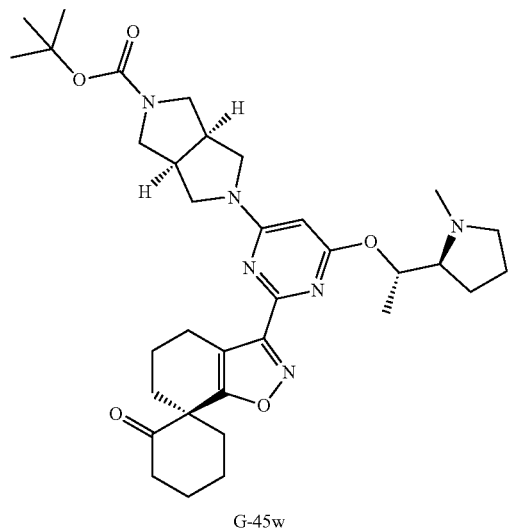

G-45w

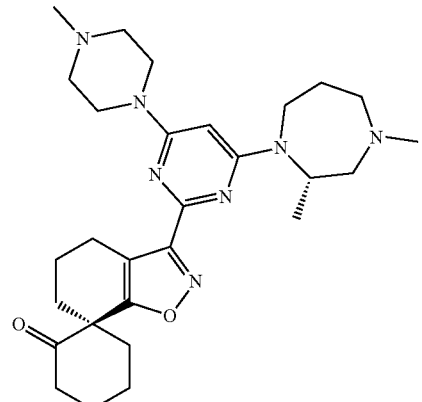

G-62a

G-45w (135 mg, 217 µmol, 1.0 equiv.) is dissolved in DCM (1.0 mL) and trifluoracetic acid (0.50 mL, 6.49 mmol, 30 equiv.). The reaction is stirred 1 h at rt. After complete conversion, the solvent is removed under reduced pressure. The residue is dissolved in DCM and extracted with aq. saturated $Na_2CO_3$. The combined organic phases are dried with magnesium sulfate and concentrated under reduced pressure. The residue is purified by RP chromatography to give G-62a (HPLC method: B; $t_{ret}$=0.93 min; [M+H]$^+$=521).

Experimental Procedure for the Synthesis of G-63a

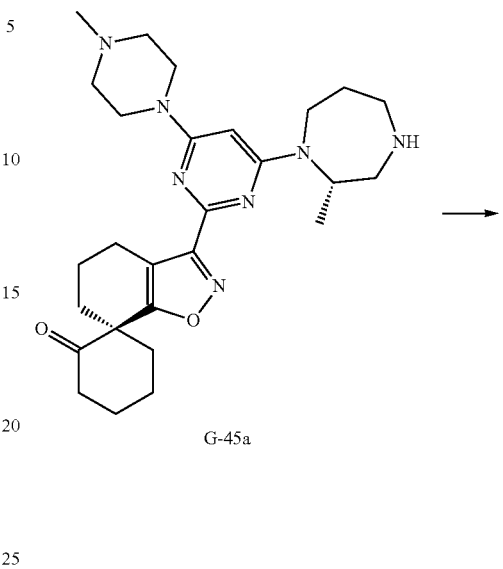

G-45a

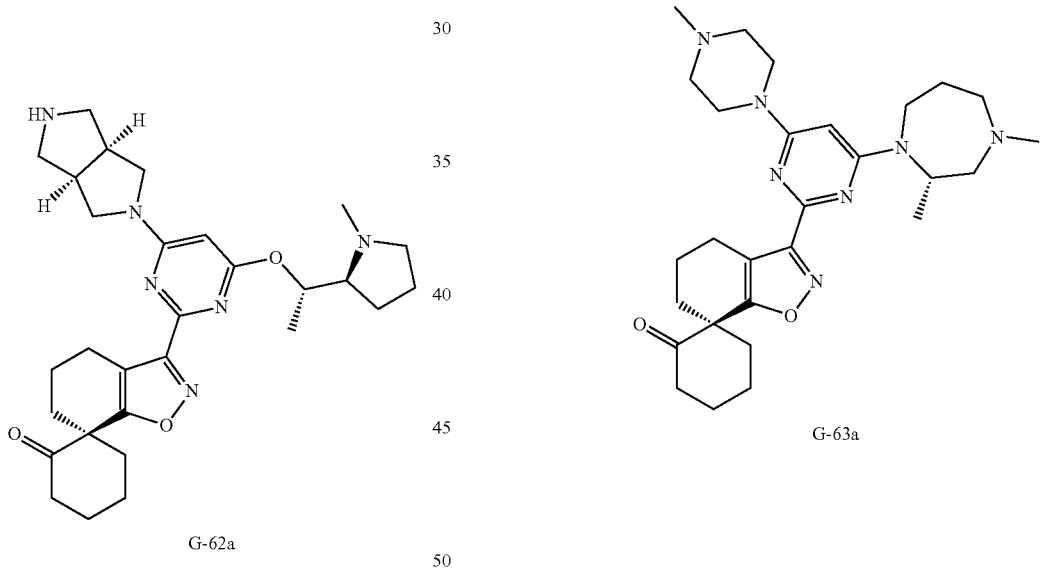

G-63a

G-45a (124 mg, 0.251 mmol, 1.0 equiv.) is dissolved in DCM (1 mL) under argon and cooled to 0° C. Formaldehyde (22.5 µL, 0.301 mmol, 1.2 equiv.) is added followed by the addition of sodium triacetoxyborohydride (224 mg, 1.01 mmol, 4.0 equiv.). The solution is stirred for 30 min at 0° C. After complete consumption of starting material, the reaction is quenched by the addition of water. The aqueous phase is extracted with DCM. The combined organic phases are dried, filtered, and concentrated under reduced pressure. The residue is purified by RP chromatography to give the desired product G-63a.

The following intermediates G-63 (Table 47) are available in an analogous manner. Deuterated intermediates G-63 are obtained analogously but sodium triacetoxyborohydride is exchanged by sodium triacetoxyborodeuteride. The crude product is purified by chromatography if necessary.

TABLE 47

| # | structure | $t_{ret}$ [min] | $[M + H]^+$ | HPLC method |
|---|---|---|---|---|
| G-63a | 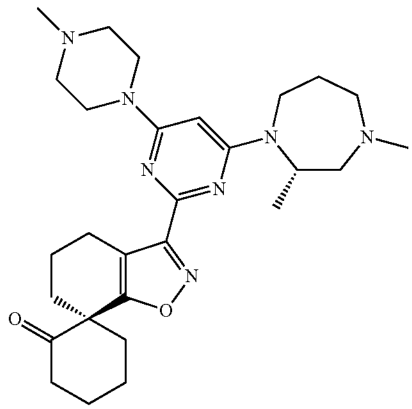 [SMILES: C[C@H]1CN(C)CCCN1c1cc(N2CCN(C)CC2)nc(-c2noc3c2CCC[C@@]32CCCCC2=O)n1] | 0.70 | 508 | C |
| G-63b | 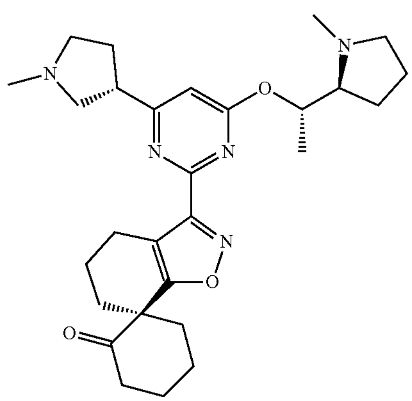 [SMILES: C[C@H](Oc1cc([C@H]2CCN(C)C2)nc(-c2noc3c2CCC[C@@]32CCCCC2=O)n1)[C@@H]1CCCN1C] | 1.40 | 494.0 | A |
| G-63c | 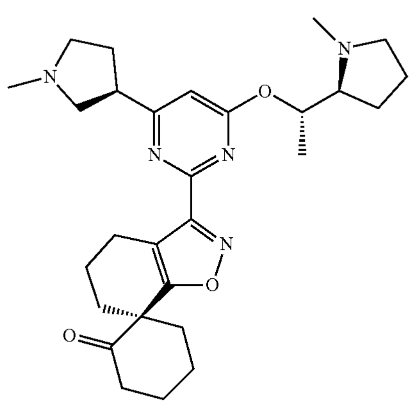 [SMILES: C[C@H](Oc1cc([C@@H]2CCN(C)C2)nc(-c2noc3c2CCC[C@@]32CCCCC2=O)n1)[C@@H]1CCCN1C] | 1.49 | 494 | A |

TABLE 47-continued

| # | structure | $t_{ret}$ [min] | [M + H]$^+$ | HPLC method |
|---|---|---|---|---|
| G-63d | 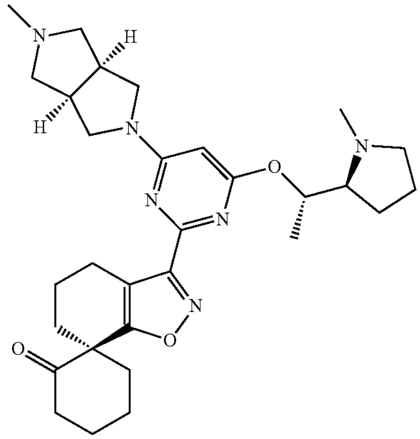 [SMILES: C[C@H](Oc1cc(N2C[C@H]3CN(C)C[C@H]3C2)nc(-c2noc3c2CCC[C@@]32CCCCC2=O)n1)[C@@H]1CCCN1C] | 1.03 | 535 | B |
| G-63e | 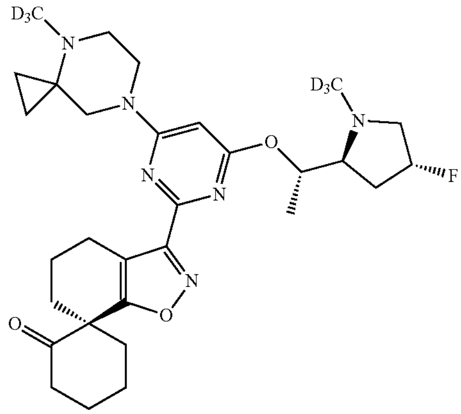 [SMILES: [2H]C([2H])([2H])N1C[C@H](F)C[C@H]1[C@H](C)Oc1cc(N2CCN(C([2H])([2H])[2H])C3(CC3)C2)nc(-c2noc3c2CCC[C@@]32CCCCC2=O)n1] | 1.04 | 558 | B |

Experimental Procedure for the Synthesis of G-64a

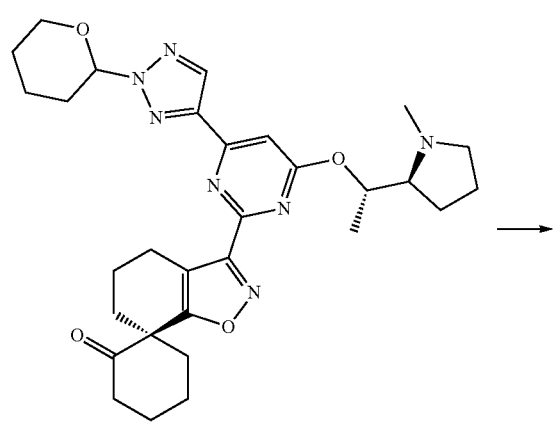

G-48af

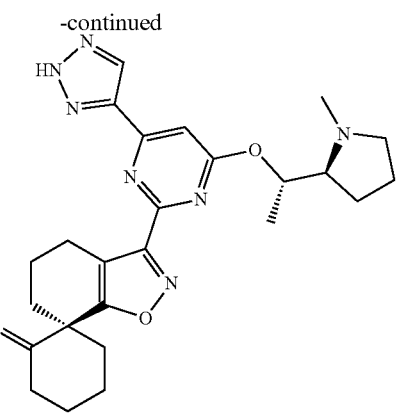

G-64a

G-48af (272 mg, 0.48 mmol, 1equiv.) is dissolved in MeOH (2 mL) and HCl (4 M in dioxane, 363 µL 1.45 mmol, 3.0 equiv.) are added. The reaction is stirred for 1.5 h at rt. After complete conversion, the reaction is filtered and extracted with NaHCO$_3$/DCM (3×). The combined organic phase is concentrated under reduced pressure and purified by RP chromatography to give the product G-64a (HPLC method: A; $t_{ret}$=1.10 min; [M+H]$^+$=478).

Experimental Procedure for the Synthesis of G-65a

Experimental Procedure for the Synthesis of G-66a

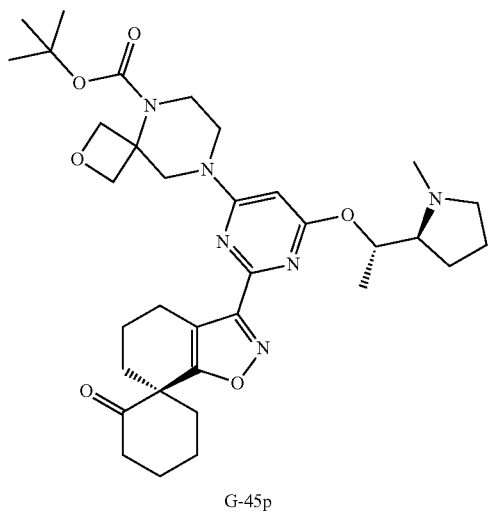

G-45p

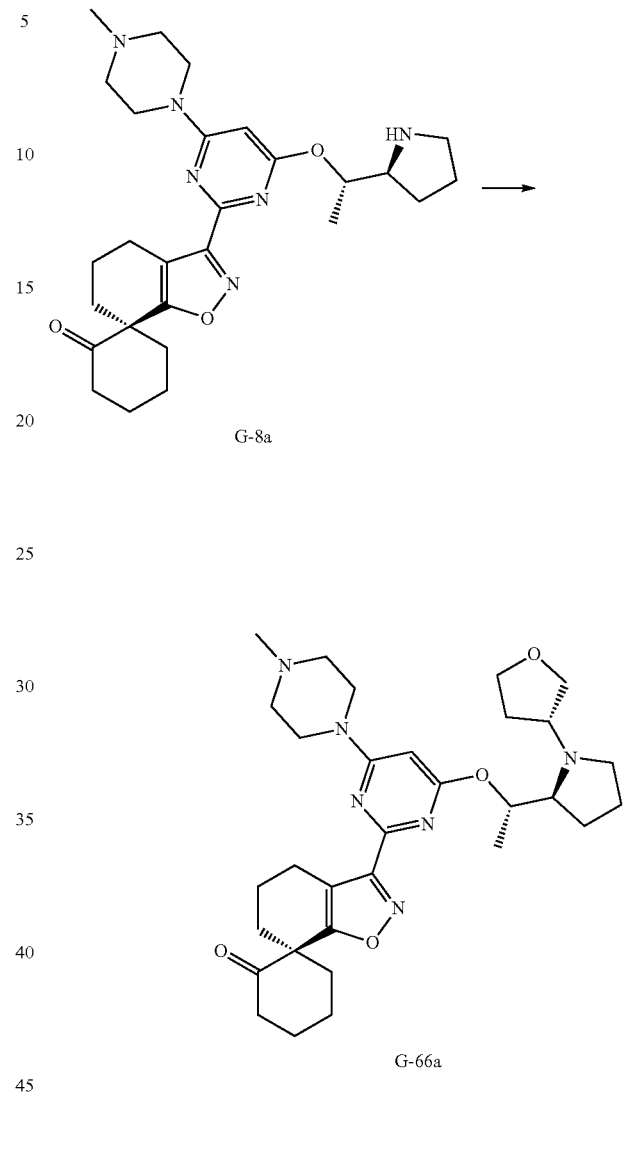

G-8a

G-65a

G-66a

G-45p (150 mg, 0.24 mmol, 1 equiv.) is dissolved in ACN (2 mL). The reaction is stirred for 4 h at 150° C. at the microwave. After complete conversion, reaction is concentrated under reduced pressure and purified by RP chromatography to give the desired product G-65a (HPLC method: C, $t_{ret}$=0.659; [M+H]$^+$=537).

G-8a (87.0 mg, 0.176 mmol, 1.0 equiv.) is dissolved in ACN (1 mL) and DIPEA (121.0 µL, 0.704 mmol, 4.0 equiv.) and [(3S)-tetrahydrofuran-3-yl] 4-methylbenzenesulfonate (139 mg, 0.528 mmol, 3.0 equiv.) is added. The reaction mixture is stirred at 70° C. until complete conversion is observed. The mixture is diluted with aq. saturated NaHCO$_3$ solution and extracted with DCM. The organic phases are combined, filtered and concentrated under reduced pressure. The resulting residue is dissolved in DMF and purified by RP chromatography to give the desired product G-66a (HPLC method: A, $t_{ret}$=1.48 min; [M+H]$^+$=565).

Experimental Procedure for the Synthesis of G-67a

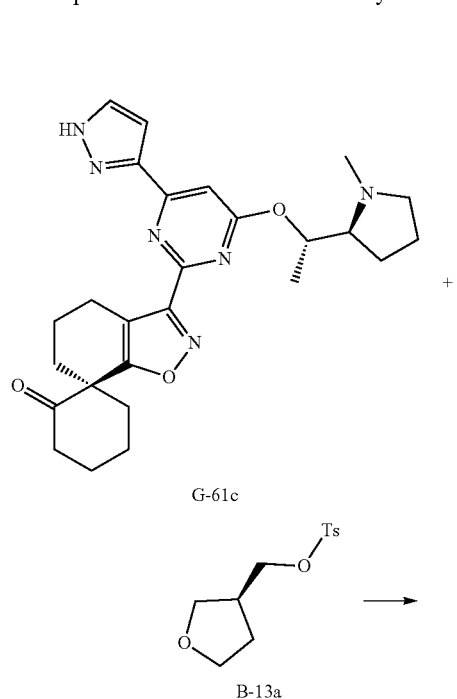

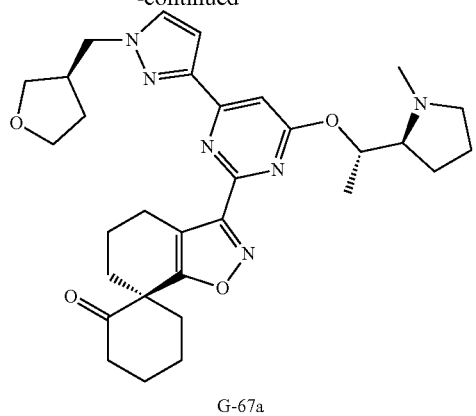

G-61c (60.0 mg, 0.13 mmol, 1.0 equiv.) is dissolved in ACN (0.5 mL), cesium carbonate (82.0 mg, 0.25 mmol, 2.0 equiv.) is added and the mixture is stirred for 30 min at rt. B-13a (65.9 mg, 0.25 mmol, 2.0 equiv.) is added. The reaction mixture is stirred at 85° C. for 2 h. After complete conversion, the reaction is extracted with DCM/water. The organic phase is concentrated under reduced pressure and purified by RP chromatography to give the desired product G-67a.

The following intermediates G-67 (Table 48) are available in an analogous manner. The crude product is purified by chromatography if necessary.

TABLE 48

| # | structure | $t_{ret}$ [min] | $[M + H]^+$ | HPLC method |
|---|---|---|---|---|
| G-67a | 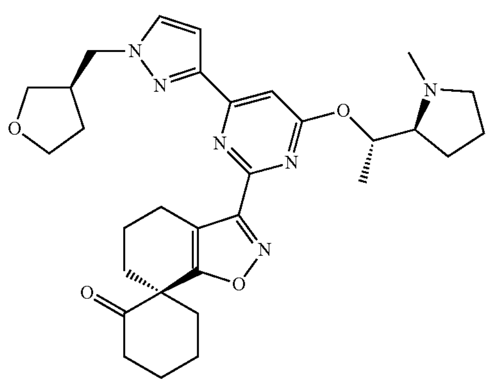 [SMILES: C[C@H](Oc1cc(-c2ccn(C[C@H]3CCOC3)n2)nc(-c2noc3c2CCC[C@@]32CCCCC2=O)n1)[C@@H]1CCCN1C] | 1.49 | 561 | A |
| G-67b | 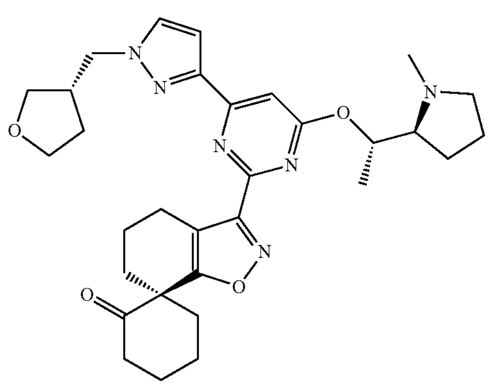 [SMILES: C[C@H](Oc1cc(-c2ccn(C[C@@H]3CCOC3)n2)nc(-c2noc3c2CCC[C@@]32CCCCC2=O)n1)[C@@H]1CCCN1C] | 1.54 | 561 | A |

TABLE 48-continued

| # | structure | $t_{ret}$ [min] | [M + H]$^+$ | HPLC method |
|---|---|---|---|---|
| G-67c | 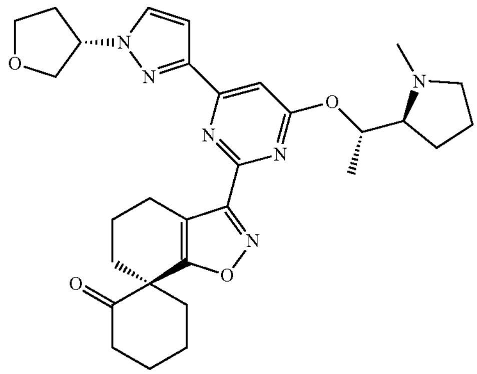 [SMILES: C[C@H](Oc1cc(-c2ccn([C@H]3CCOC3)n2)nc(-c2noc3c2CCC[C@@]32CCCCC2=O)n1)[C@@H]1CCCN1C] | 1.49 | 547 | A |
| G-67d | 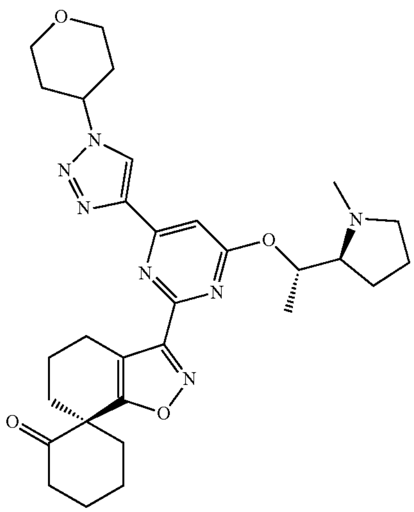 [SMILES: C[C@H](Oc1cc(-c2cn(C3CCOCC3)nn2)nc(-c2noc3c2CCC[C@@]32CCCCC2=O)n1)[C@@H]1CCCN1C] | 1.42 | 562 | A |
| G-67e | 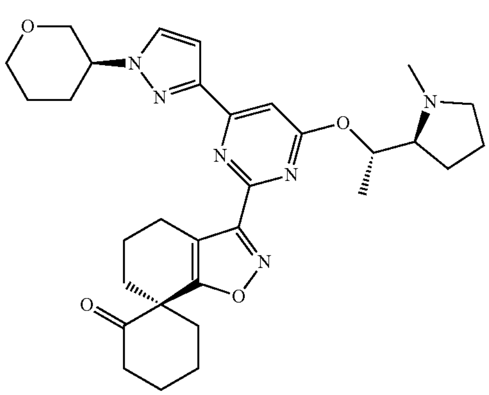 [SMILES: C[C@H](Oc1cc(-c2ccn([C@H]3CCCOC3)n2)nc(-c2noc3c2CCC[C@@]32CCCCC2=O)n1)[C@@H]1CCCN1C] | 1.54 | 561 | A |

TABLE 48-continued

| # | structure | $t_{ret}$ [min] | $[M + H]^+$ | HPLC method |
|---|---|---|---|---|
| G-67f | 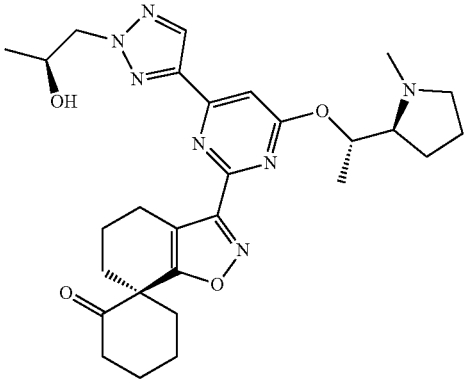 [SMILES: C[C@H](O)Cn1ncc(-c2cc(O[C@@H](C)[C@@H]3CCCN3C)nc(-c3noc4c3CCC[C@@]43CCCCC3=O)n2)n1] | 1.40 | 536 | A |

Experimental Procedure for the Synthesis of G-68a

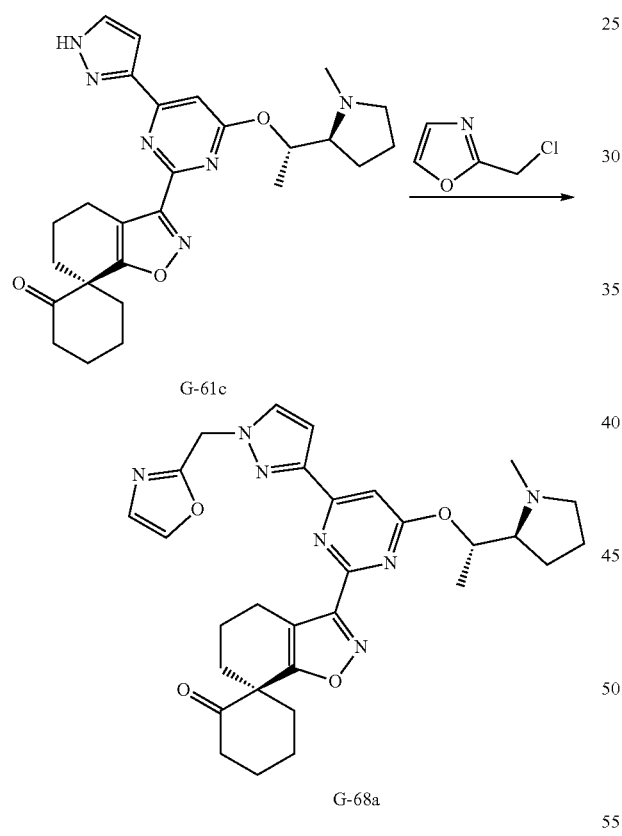

G-61c (60 mg, 0.13 mmol, 1 equiv.), 2-(chloromethyl) oxazole (23.4 mg, 0.19 mmol, 1.5 equiv.) and $K_2CO_3$ (34.8 mg, 0.25 mmol, 2.0 equiv.) are dissolved in DMF (0.5 mL) and stirred at 60° C. for 30 min. After complete conversion, the reaction mixture is extracted with DCM/water. The organic phase is concentrated under reduced pressure and purified by RP chromatography to give the desired product G-68a.

The following intermediates G-68 (Table 49) are available in an analogous manner using a suitable alkyl halide. The crude product is purified by chromatography if necessary.

TABLE 49

| # | structure | $t_{ret}$ [min] | $[M + H]^+$ | HPLC method |
|---|---|---|---|---|
| G-68a | 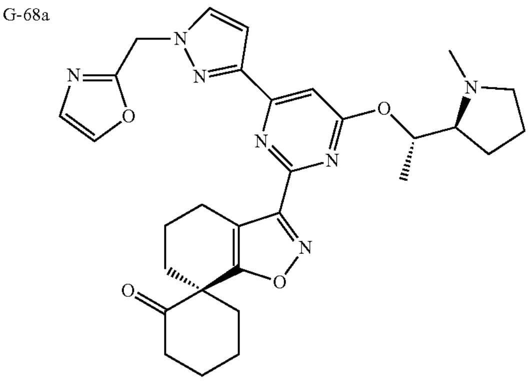 | 1.42 | 558 | A |
| G-68b | 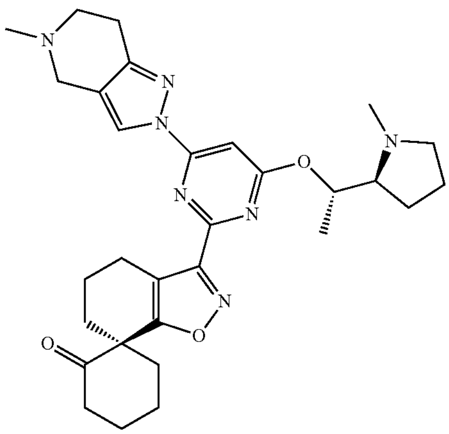 [SMILES: C[C@H](Oc1cc(-n2cc3c(n2)CCN(C)C3)nc(-c2noc3c2CCC[C@@]32CCCCC2=O)n1)[C@@H]1CCCN1C] | 0.85 | 546 | D |

Experimental Procedure for the Synthesis of G-69a

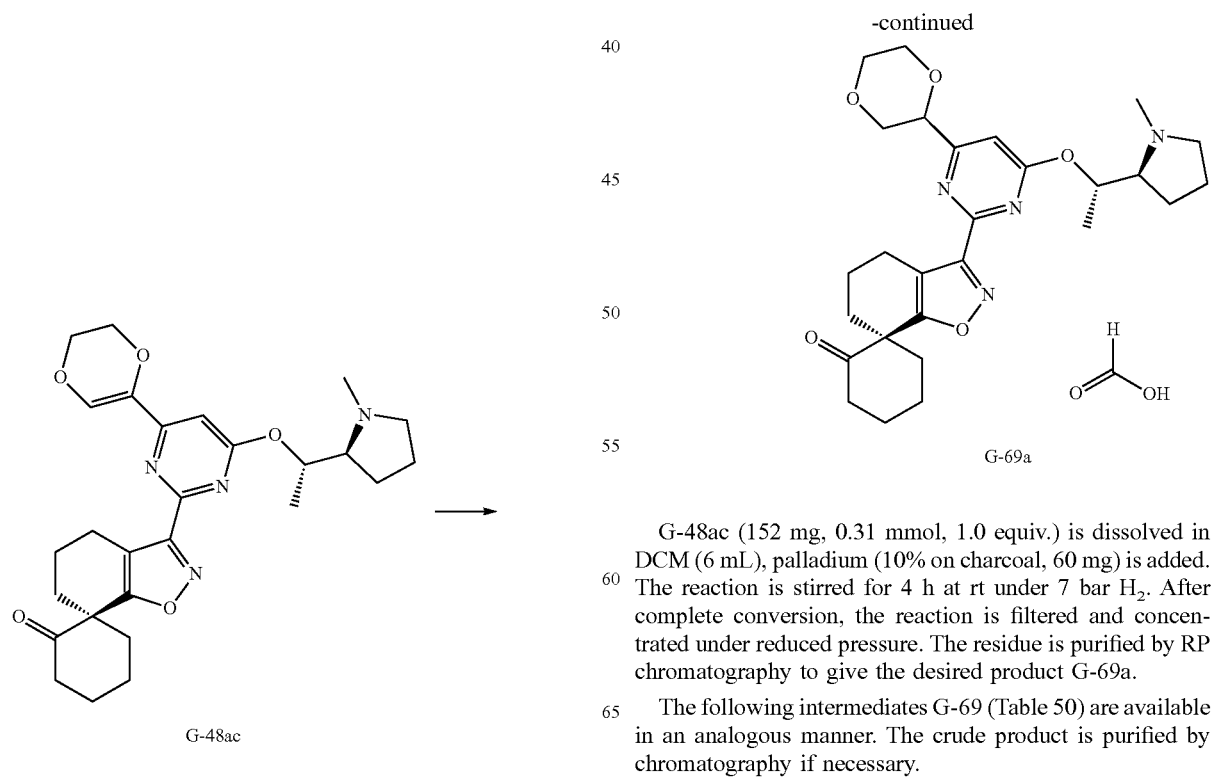

G-48ac

G-69a

G-48ac (152 mg, 0.31 mmol, 1.0 equiv.) is dissolved in DCM (6 mL), palladium (10% on charcoal, 60 mg) is added. The reaction is stirred for 4 h at rt under 7 bar $H_2$. After complete conversion, the reaction is filtered and concentrated under reduced pressure. The residue is purified by RP chromatography to give the desired product G-69a.

The following intermediates G-69 (Table 50) are available in an analogous manner. The crude product is purified by chromatography if necessary.

TABLE 50

| # | structure | $t_{ret}$ [min] | $[M + H]^+$ | HPLC method |
|---|---|---|---|---|
| G-69a | 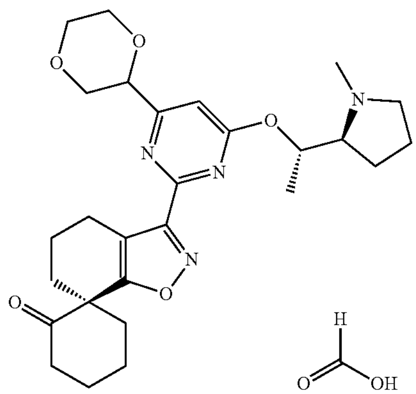 [SMILES: C[C@H](Oc1cc(C2COCCO2)nc(-c2noc3c2CCC[C@@]32CCCCC2=O)n1)[C@@H]1CCCN1C ; O=CO] | 0.80 | 497 | C |
| G-69b | 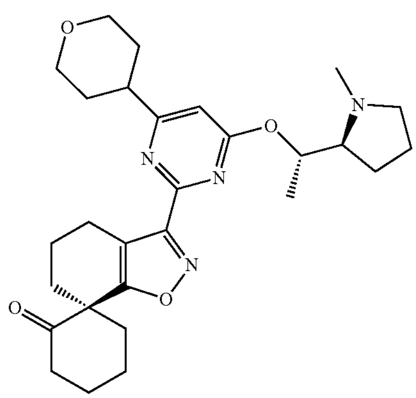 [SMILES: C[C@H](Oc1cc(C2CCOCC2)nc(-c2noc3c2CCC[C@@]32CCCCC2=O)n1)[C@@H]1CCCN1C] | 0.83 | 495 | C |
| G-69c | 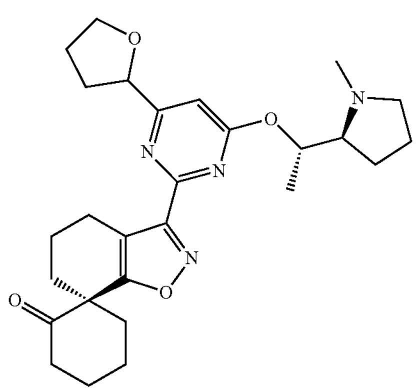 [SMILES: C[C@H](Oc1cc(C2CCCO2)nc(-c2noc3c2CCC[C@@]32CCCCC2=O)n1)[C@@H]1CCCN1C] | 0.84 | 481 | C |

Experimental Procedure for the Synthesis of G-85a

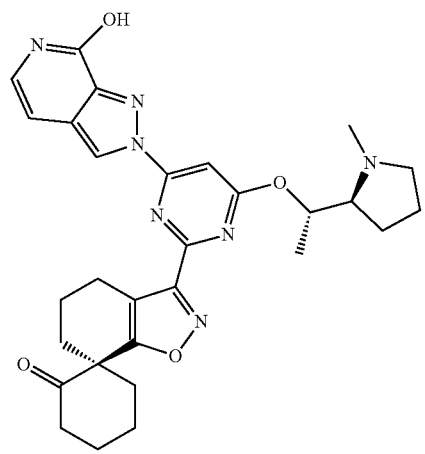

G-53k

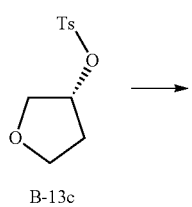

B-13c

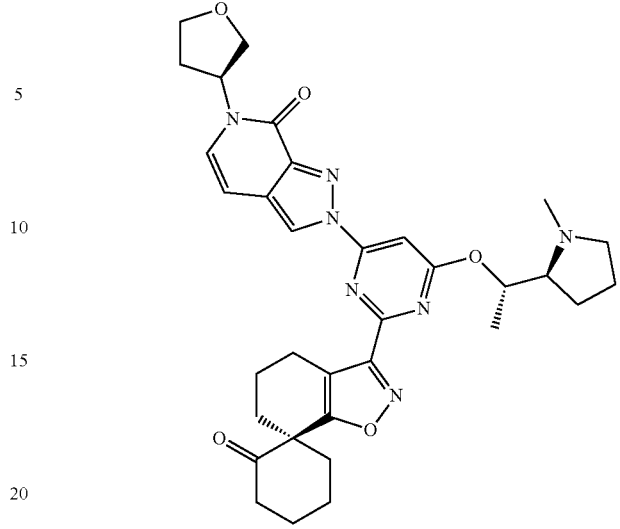

G-85a

G-53k (600 mg, 1.10 mmol, 1.0 equiv.) is dissolved in DMSO (4.0 mL), cesium carbonate (539 mg, 1.66 mmol, 1.5 equiv.) and B-13c (269 mg, 1.10 mmol, 1.0 equiv.) is added and the reaction mixture is stirred at 65° C. for 12 h. After complete conversion, the desired product is isolated by RP chromatography to obtain G-85a.

The following intermediates G-85 (Table 51) are available in an analogous manner. The crude product is purified by chromatography if necessary.

TABLE 51

| # | structure | $t_{ret}$ [min] | $[M + H]^+$ | HPLC method |
|---|---|---|---|---|
| G-85a | (see structure above) | 1.48 | 614 | A |

TABLE 51-continued

| # | structure | $t_{ret}$ [min] | [M + H]⁺ | HPLC method |
|---|---|---|---|---|
| G-85b | 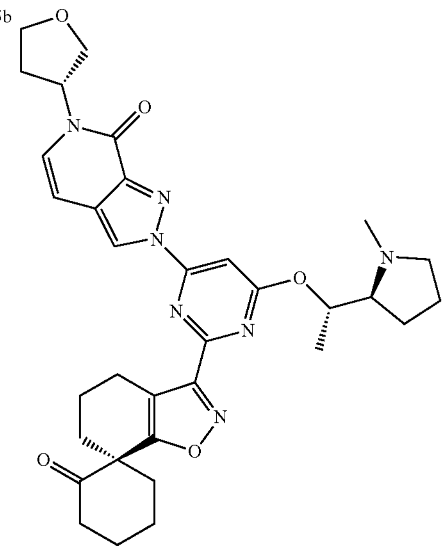 | 1.44 | 614 | A |
| G-85c | 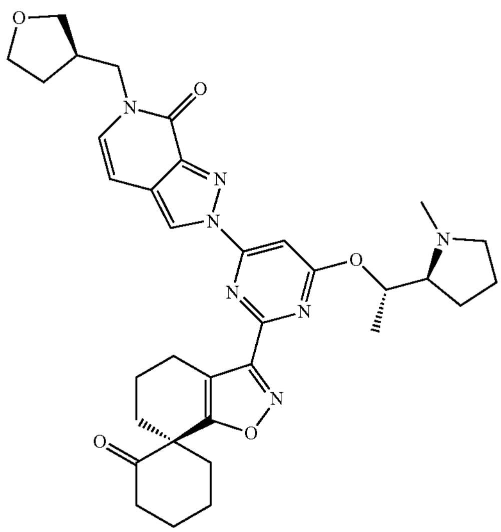 [SMILES: C[C@H](Oc1cc(-n2cc3ccn(C[C@H]4CCOC4)c(=O)c3n2)nc(-c2noc3c2CCC[C@@]32CCCCC2=O)n1)[C@@H]1CCCN1C] | 1.43 | 628 | A |
| G-85d | 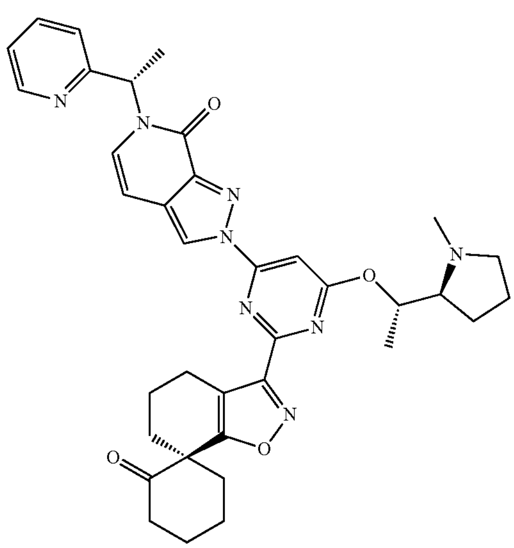 [SMILES: C[C@H](Oc1cc(-n2cc3ccn([C@@H](C)c4ccccn4)c(=O)c3n2)nc(-c2noc3c2CCC[C@@]32CCCCC2=O)n1)[C@@H]1CCCN1C] | 1.53 | 649 | A |

TABLE 51-continued

| # | structure | $t_{ret}$ [min] | $[M + H]^+$ | HPLC method |
|---|---|---|---|---|
| G-85e | 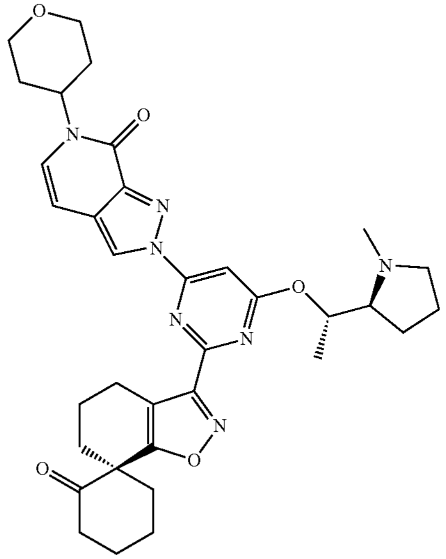 [SMILES: C[C@H](Oc1cc(-n2cc3ccn(C4CCOCC4)c(=O)c3n2)nc(-c2noc3c2CCC[C@@]32CCCCC2=O)n1)[C@@H]1CCCN1C] | 1.46 | 628 | A |

Experimental Procedure for the Synthesis of G-86a

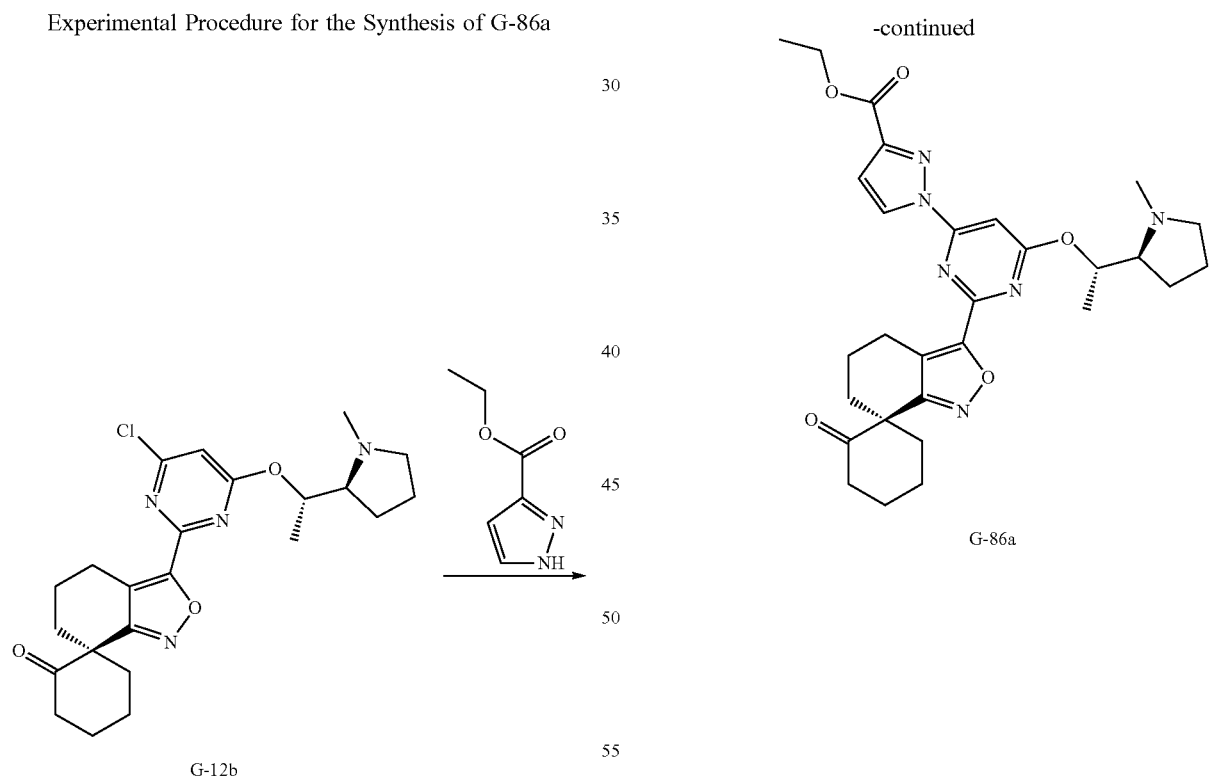

G-12b (2.00 g, 4.23 mmol, 1 equiv.), ethyl 1H-pyrazole-5-carboxylate (936 mg, 6.34 mmol, 1.5 equiv.) and cesium carbonate (4.59 g, 8.46 mmol, 2 equiv.) are dissolved in THF (20 mL). The reaction is stirred for 2 h at 70° C. After complete conversion, DCM is added, and the solution is washed with water. The organic phase is concentrated under reduced pressure and purified by RP chromatography to obtain G-86a.

The following intermediates G-86 (Table 52) are available in an analogous manner. The crude product is purified by chromatography if necessary.

TABLE 52

| # | structure | $t_{ret}$ [min] | $[M + H]^+$ | HPLC method |
|---|---|---|---|---|
| G-86a | 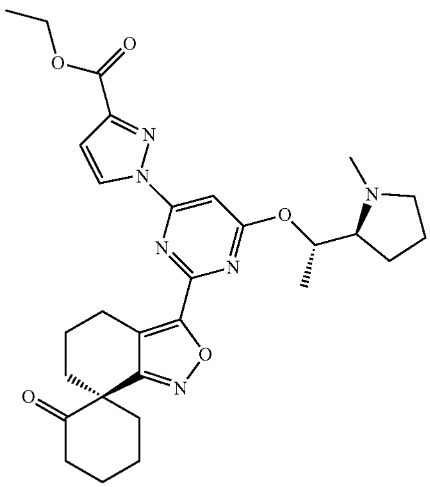 [SMILES: CCOC(=O)c1ccn(-c2cc(O[C@@H](C)[C@@H]3CCCN3C)nc(-c3onc4c3CCC[C@@]43CCCCC3=O)n2)n1] | 0.96 | 549 | C |
| G-86b | 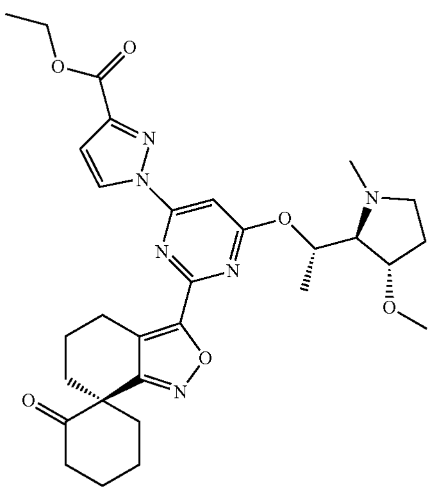 [SMILES: CCOC(=O)c1ccn(-c2cc(O[C@@H](C)[C@@H]3[C@@H](OC)CCN3C)nc(-c3onc4c3CCC[C@@]43CCCCC3=O)n2)n1] | 0.92 | 579 | C |
| G-86c | 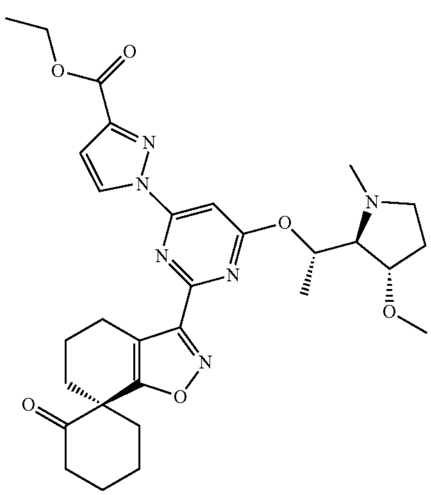 [SMILES: CCOC(=O)c1ccn(-c2cc(O[C@@H](C)[C@@H]3[C@@H](OC)CCN3C)nc(-c3noc4c3CCC[C@@]43CCCCC3=O)n2)n1] | 0.88 | 579 | C |

TABLE 52-continued
| # | structure | t_ret [min] | [M + H]+ | HPLC method |
|---|---|---|---|---|
| G-86d | 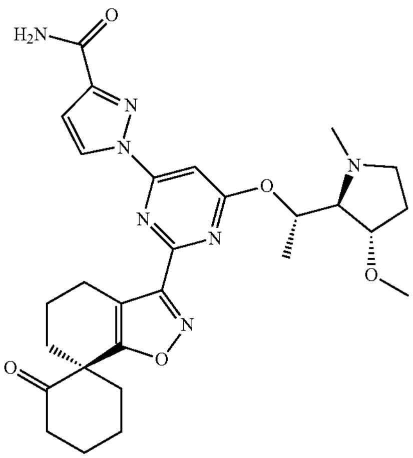 [SMILES: CO[C@H]1CCN(C)[C@@H]1[C@H](C)Oc1cc(-n2ccc(C(N)=O)n2)nc(-c2noc3c2CCC[C@@]32CCCCC2=O)n1] | 0.69 | 550 | C |
| G-86e | 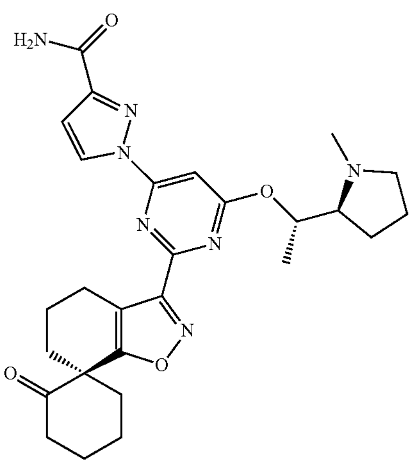 [SMILES: C[C@H](Oc1cc(-n2ccc(C(N)=O)n2)nc(-c2noc3c2CCC[C@@]32CCCCC2=O)n1)[C@@H]1CCCN1C] | 1.34 | 520 | A |
Experimental Procedure for the Synthesis of G-88a
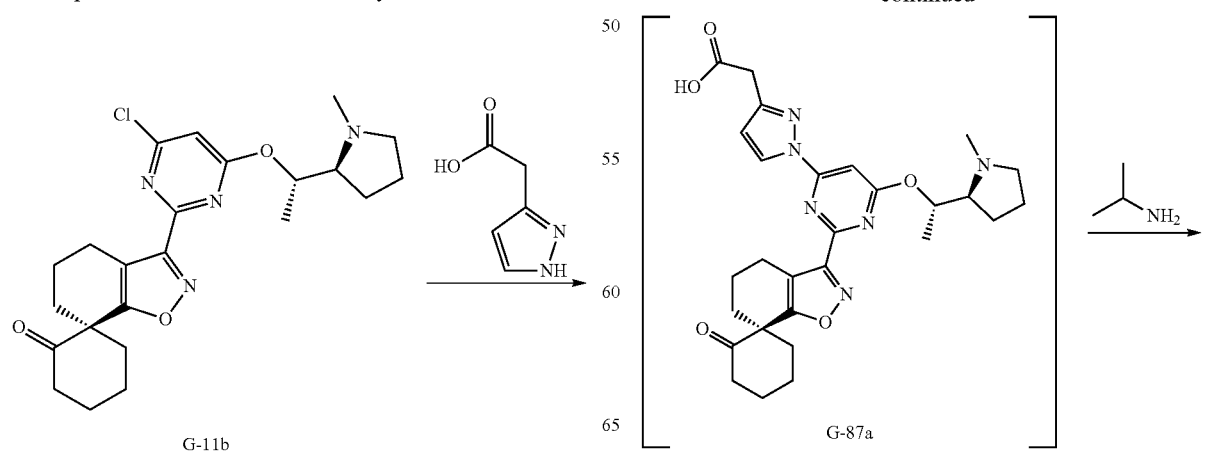

-continued

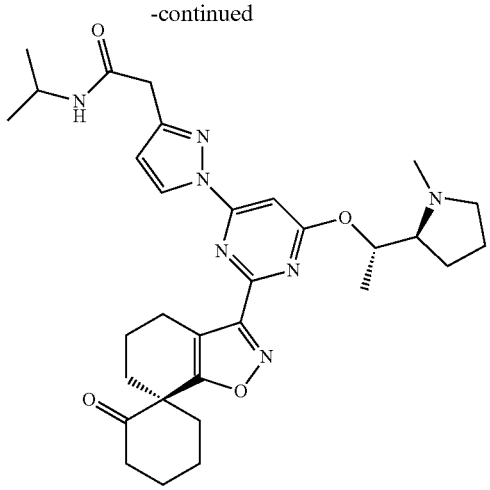

G-88a

G-11b (4.00 g, 8.99 mmol, 1 equiv.), 2-(1H-pyrazol-3-yl) acetic acid hydrochloride (1.73 g, 10.34 mmol, 1.15 equiv.) and cesium carbonate (8.79 g, 26.97 mmol, 3 equiv.) are dissolved in DMSO (20 mL). The reaction is stirred for 1.5 h at 90° C. After complete conversion to the desired intermediate, the reaction mixture is cooled to RT, isopropylamine (1.55 mL, 17.98 mmol, 2.0 equiv.), 1-methylimidazole (1.43 mL, 17.98 mmol, 2.0 equiv.), and chloro-N,N,N',N'-tetramethylformamidinium hexafluorophosphate (5.15 g, 17.98 mmol, 2.0 equiv.) are added and the mixture is stirred for 15 min. at RT. After complete conversion, DCM is added, and the solution is washed with water and brine. The organic phase is concentrated under reduced pressure and purified by RP chromatography to obtain G-88a.

The following intermediates G-88 (Table 53) are available in an analogous manner. The crude product is purified by chromatography if necessary.

TABLE 53

| # | structure | $t_{ret}$ [min] | $[M + H]^+$ | HPLC method |
|---|---|---|---|---|
| G-88a | 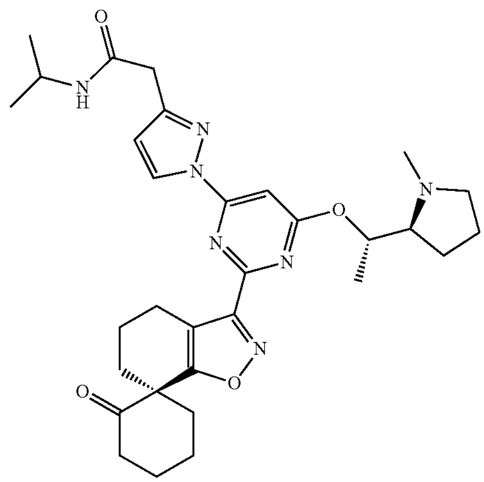 [SMILES: CC(C)NC(=O)Cc1ccn(-c2cc(O[C@@H](C)[C@@H]3CCCN3C)nc(-c3noc4c3CCC[C@@]43CCCCC3=O)n2)n1] | 0.78 | 576 | C |
| G-88b | 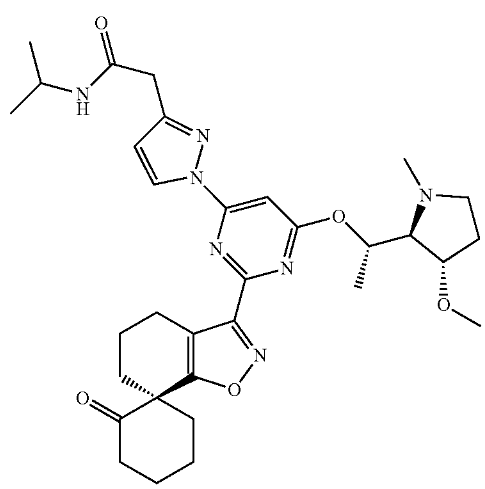 [SMILES: CO[C@H]1CCN(C)[C@@H]1[C@H](C)Oc1cc(-n2ccc(CC(=O)NC(C)C)n2)nc(-c2noc3c2CCC[C@@]32CCCCC2=O)n1] | 0.76 | 606 | C |

TABLE 53-continued

| # | structure | $t_{ret}$ [min] | $[M + H]^+$ | HPLC method |
|---|---|---|---|---|
| G-88c | 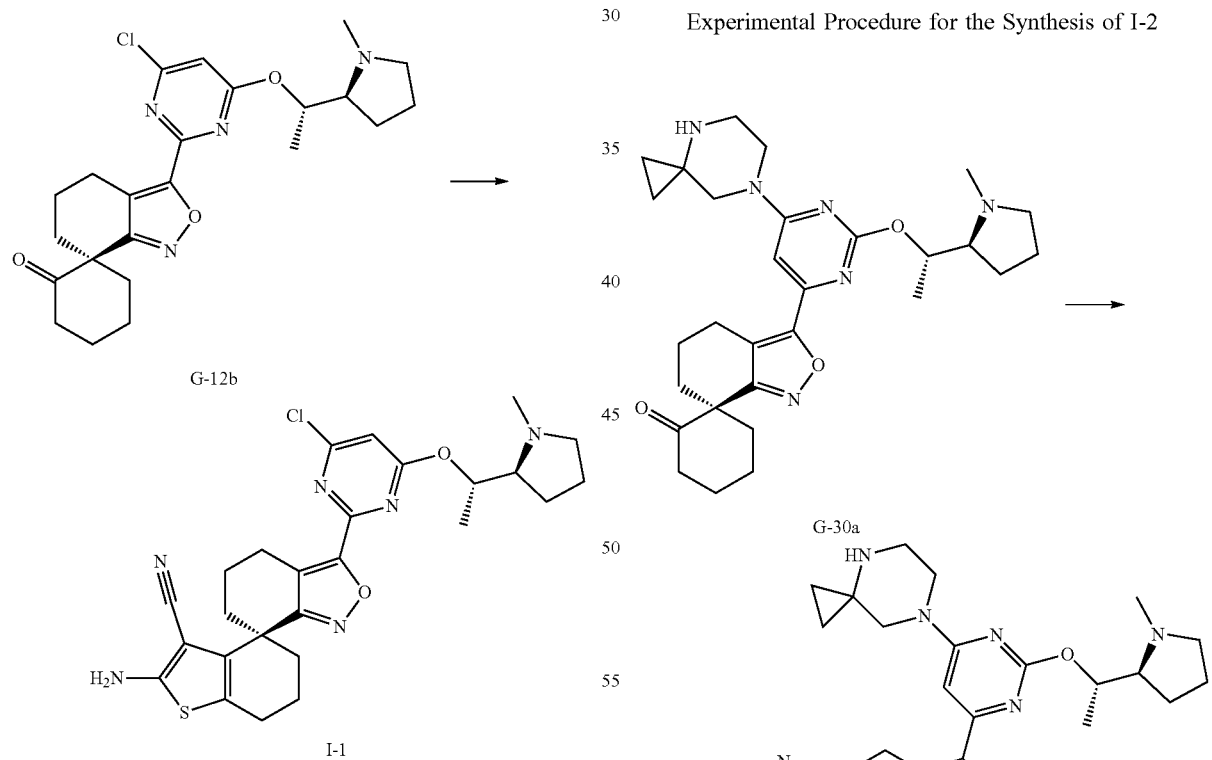 | 0.80 | 606 | C |

Synthesis of Aminocyanothiophenes I and II

Experimental Procedure for the Synthesis of I-1

To a solution of G-12b (76.1 mg, 0.157 mmol, 1.00 equiv.) and molecular sieves (3 Å) in MeOH (2 mL) under an argon atmosphere is added malononitrile (14.5 mg, 0.209 mmol, 1.33 equiv.), sulfur (10.1 mg, 0.312 mmol, 2.00 equiv.) and ß-Alanine (19.4 mg, 0.218 mmol, 1.40 equiv.). The reaction mixture is stirred at 80° C. overnight. After complete conversion, the reaction mixture is cooled to the rt, filtered and extracted with DCM and aq. saturated NaHCO₃ solution. The organic phases are combined and concentrated under reduced pressure. The residue is dissolved in ACN and water and purified by basic RP chromatography to give the desired product I-1 (HPLC method: A, $t_{ret}$=2.16 min; $[M+H]^+$=525).

Experimental Procedure for the Synthesis of I-2

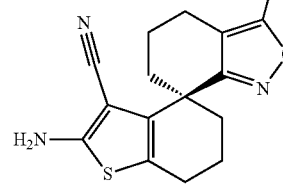

G-30a (80.0 mg, 154 µmol, 1.00 equiv.), malononitrile (64.2 mg, 953 µmol, 6.20 equiv.), sulfur (23.1 mg, 791 µmol, 4.70 equiv.) ß-Alanine (60.9 mg, 684 µmol, 4.50 equiv.) and magnesium sulfate (23.5 mg, 195 µmol, 1.30 equiv.) are suspended in EtOH (2.0 mL) and stirred at 80° C. for 18 h. The reaction mixture is diluted with EtOAc, filtered and washed with aq. saturated NaHCO₃. The organic phase is separated and the remaining aq. phase is extracted with EtOAc (2×). The combined organic phases are dried with magnesium sulfate, evaporated and the resulting residue is purified by RP chromatography to afford I-2.

The following final compounds I (Table 54) are available in an analogous manner. The crude product is purified by chromatography if necessary.

TABLE 54

| # | structure | $t_{ret}$ [min] | [M + H]⁺ | HPLC method |
|---|---|---|---|---|
| I-2 | 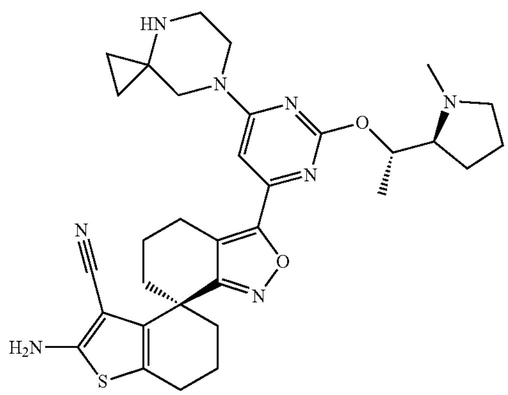 [SMILES: C[C@H](Oc1nc(-c2onc3c2CCC[C@@]32CCCc3sc(N)c(C#N)c32)cc(N2CCNC3(CC3)C2)n1)[C@@H]1CCCN1C] | 1.41 | 601 | A |
| I-3 | 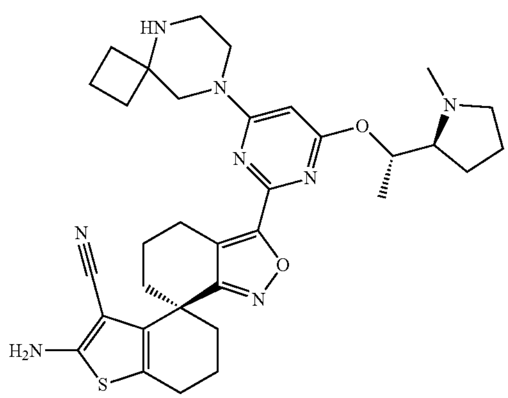 [SMILES: C[C@H](Oc1cc(N2CCNC3(CCC3)C2)nc(-c2onc3c2CCC[C@@]32CCCc3sc(N)c(C#N)c32)n1)[C@@H]1CCCN1C] | 1.58 | 615 | A |
| I-4 | 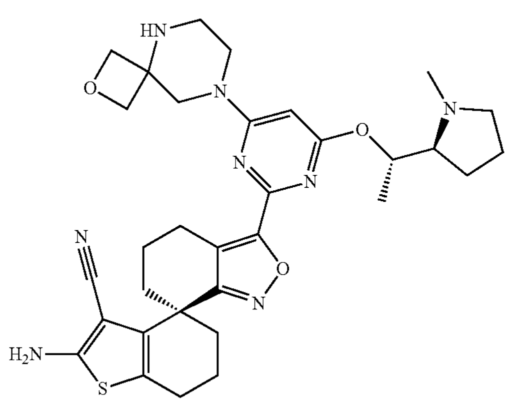 [SMILES: C[C@H](Oc1cc(N2CCNC3(COC3)C2)nc(-c2onc3c2CCC[C@@]32CCCc3sc(N)c(C#N)c32)n1)[C@@H]1CCCN1C] | 1.34 | 617 | A |

TABLE 54-continued

| # | structure | t_ret [min] | [M + H]+ | HPLC method |
|---|---|---|---|---|
| I-5 | 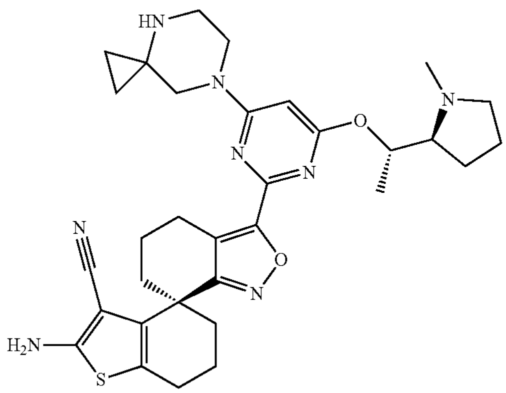 [SMILES: C[C@H](Oc1cc(N2CCNC3(CC3)C2)nc(-c2onc3c2CCC[C@@]32CCCc3sc(N)c(C#N)c32)n1)[C@@H]1CCCN1C] | 1.43 | 601 | A |
| I-6 | 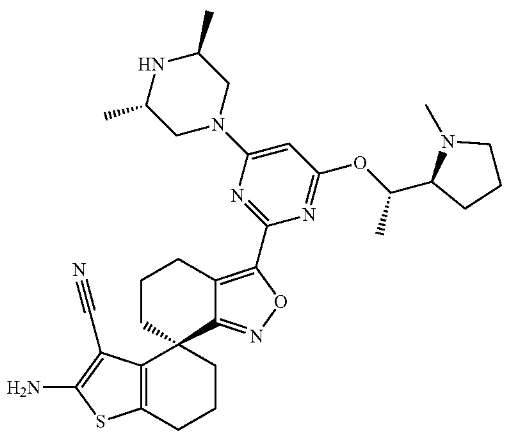 [SMILES: C[C@H](Oc1cc(N2C[C@H](C)N[C@@H](C)C2)nc(-c2onc3c2CCC[C@@]32CCCc3sc(N)c(C#N)c32)n1)[C@@H]1CCCN1C] | 1.45 | 603 | A |
| I-7 | 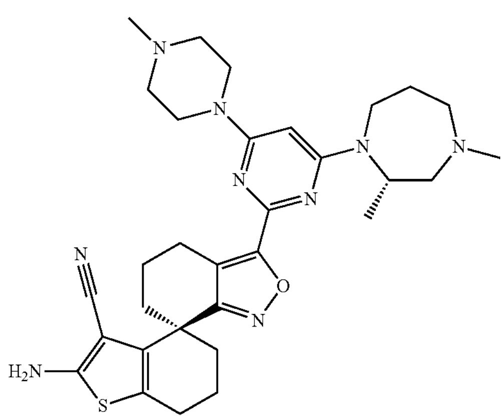 [SMILES: C[C@H]1CN(C)CCCN1c1cc(N2CCN(C)CC2)nc(-c2onc3c2CCC[C@@]32CCCc3sc(N)c(C#N)c32)n1] | 1.42 | 588 | A |

TABLE 54-continued

| # | structure | $t_{ret}$ [min] | [M + H]$^+$ | HPLC method |
|---|---|---|---|---|
| I-8 | 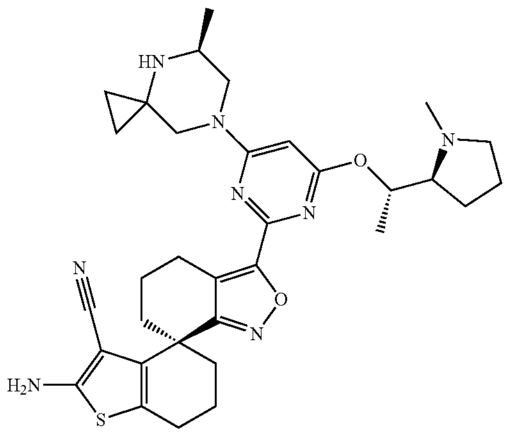 [SMILES: C[C@H](Oc1cc(N2C[C@H](C)NC3(CC3)C2)nc(-c2onc3c2CCC[C@@]32CCCc3sc(N)c(C#N)c32)n1)[C@@H]1CCCN1C] | 1.51 | 615 | A |
| I-9 | 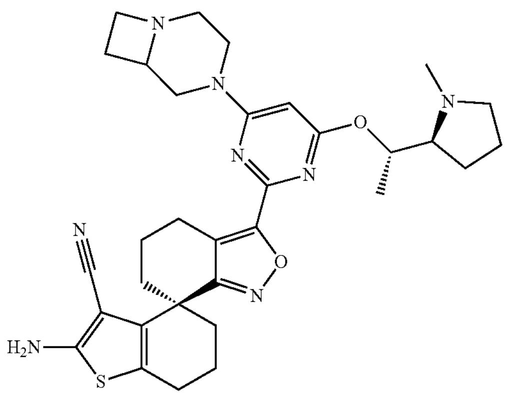 [SMILES: C[C@H](Oc1cc(N2CCN3CCC3C2)nc(-c2onc3c2CCC[C@@]32CCCc3sc(N)c(C#N)c32)n1)[C@@H]1CCCN1C] | 1.43 | 601 | A |
| I-10 | 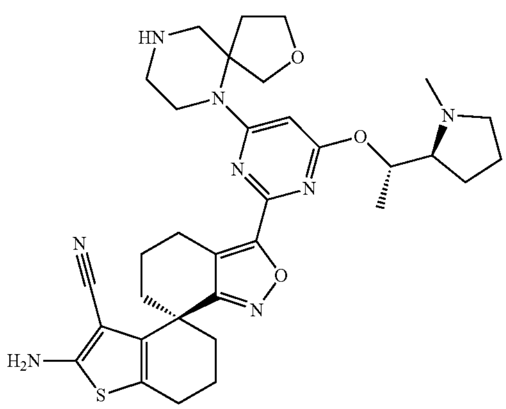 [SMILES: C[C@H](Oc1cc(N2CCNCC23CCOC3)nc(-c2onc3c2CCC[C@@]32CCCc3sc(N)c(C#N)c32)n1)[C@@H]1CCCN1C] | 1.40 | 631 | A |

TABLE 54-continued

| # | structure | $t_{ret}$ [min] | $[M + H]^+$ | HPLC method |
|---|---|---|---|---|
| I-11 | 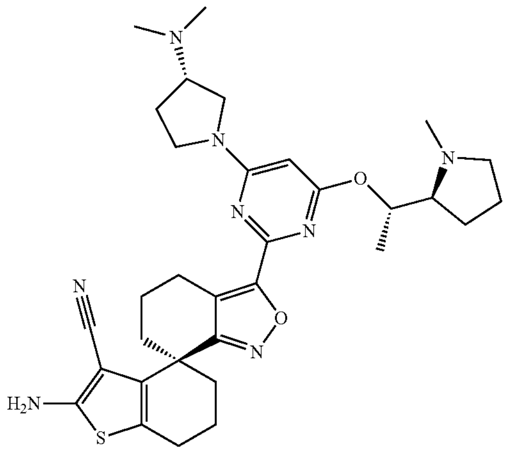 [SMILES: C[C@H](Oc1cc(N2CC[C@H](N(C)C)C2)nc(-c2onc3c2CCC[C@@]32CCCc3sc(N)c(C#N)c32)n1)[C@@H]1CCCN1C] | 1.64 | 603 | A |
| I-12 | 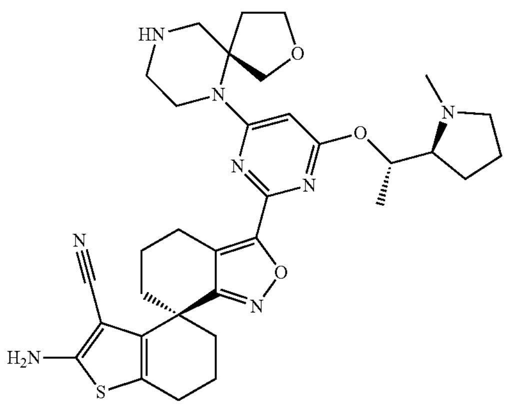 [SMILES: C[C@H](Oc1cc(N2CCNC[C@]23CCOC3)nc(-c2onc3c2CCC[C@@]32CCCc3sc(N)c(C#N)c32)n1)[C@@H]1CCCN1C] | 1.38 | 631 | A |
| I-13 | 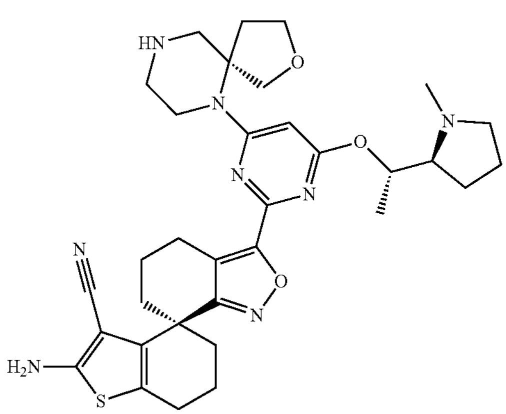 [SMILES: C[C@H](Oc1cc(N2CCNC[C@@]23CCOC3)nc(-c2onc3c2CCC[C@@]32CCCc3sc(N)c(C#N)c32)n1)[C@@H]1CCCN1C] | 1.39 | 631 | A |

TABLE 54-continued

| # | structure | $t_{ret}$ [min] | $[M + H]^+$ | HPLC method |
|---|---|---|---|---|
| I-14 | 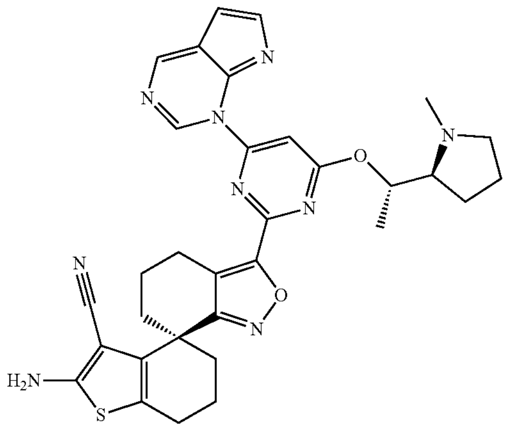 [SMILES: C[C@H](Oc1cc(-n2cncc3ccnc2-3)nc(-c2onc3c2CCC[C@@]32CCCc3sc(N)c(C#N)c32)n1)[C@@H]1CCCN1C] | 1.64 | 608 | A |
| I-15 | 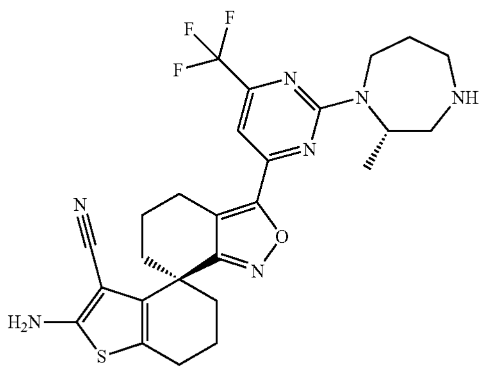 [SMILES: C[C@H]1CNCCCN1c1nc(-c2onc3c2CCC[C@@]32CCCc3sc(N)c(C#N)c32)cc(C(F)(F)F)n1] | 1.57 | 544 | A |
| I-16 | 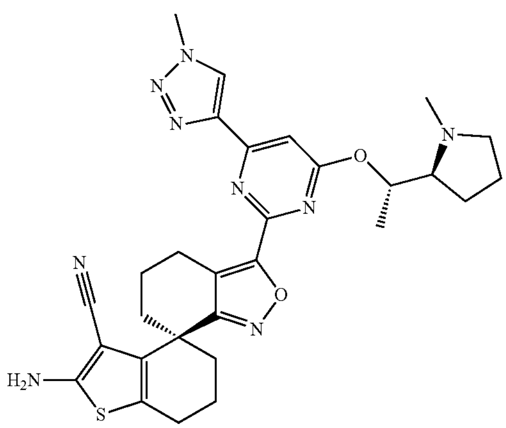 [SMILES: C[C@H](Oc1cc(-c2cn(C)nn2)nc(-c2onc3c2CCC[C@@]32CCCc3sc(N)c(C#N)c32)n1)[C@@H]1CCCN1C] | 1.45 | 572 | A |
| I-17 | 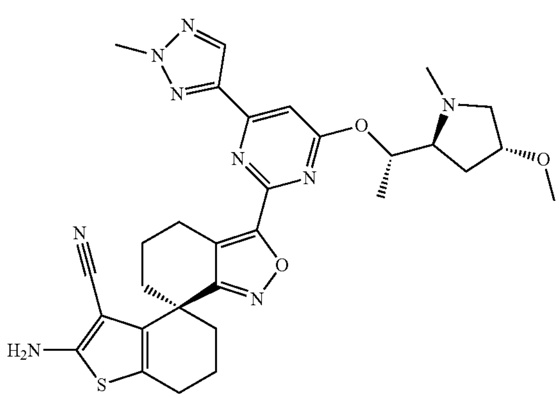 [SMILES: CO[C@@H]1C[C@@H]([C@H](C)Oc2cc(-c3cnn(C)n3)nc(-c3onc4c3CCC[C@@]43CCCc4sc(N)c(C#N)c43)n2)N(C)C1] | 1.51 | 602 | A |

TABLE 54-continued

| # | structure | t_ret [min] | [M + H]+ | HPLC method |
|---|---|---|---|---|
| I-18 | 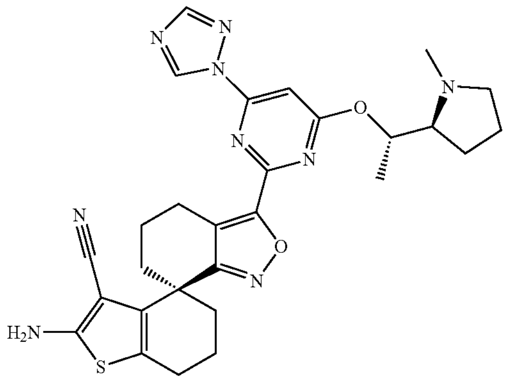 [SMILES: C[C@H](Oc1cc(-n2cncn2)nc(-c2onc3c2CCC[C@@]32CCCc3sc(N)c(C#N)c32)n1)[C@@H]1CCCN1C] | 1.48 | 558 | A |
| I-19 | 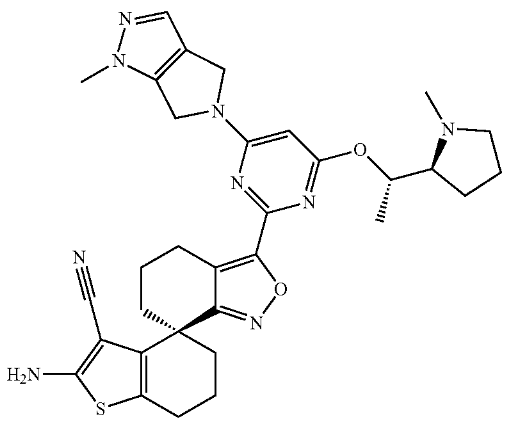 [SMILES: C[C@H](Oc1cc(N2Cc3cnn(C)c3C2)nc(-c2onc3c2CCC[C@@]32CCCc3sc(N)c(C#N)c32)n1)[C@@H]1CCCN1C] | 1.52 | 612 | A |
| I-20 | 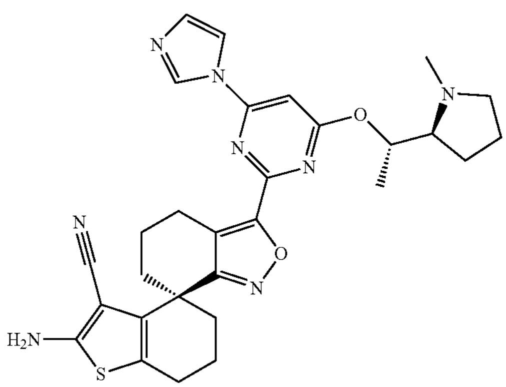 [SMILES: C[C@H](Oc1cc(-n2ccnc2)nc(-c2onc3c2CCC[C@@]32CCCc3sc(N)c(C#N)c32)n1)[C@@H]1CCCN1C] | 1.42 | 557 | A |
| I-21 | 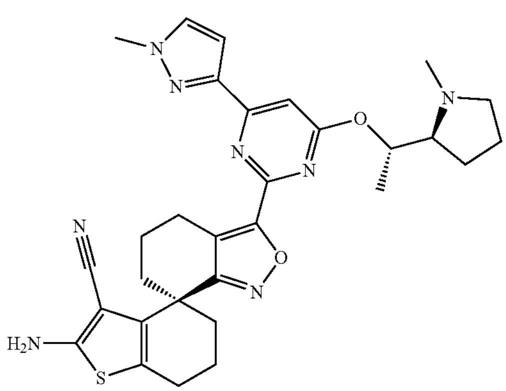 [SMILES: C[C@H](Oc1cc(-c2ccn(C)n2)nc(-c2onc3c2CCC[C@@]32CCCc3sc(N)c(C#N)c32)n1)[C@@H]1CCCN1C] | 1.53 | 571 | A |

TABLE 54-continued

| # | structure | $t_{ret}$ [min] | $[M + H]^+$ | HPLC method |
|---|---|---|---|---|
| I-22 | 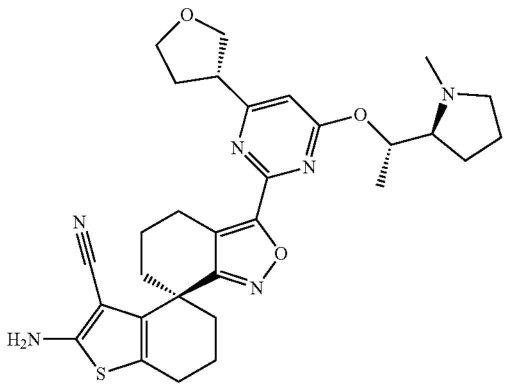 [SMILES: C[C@H](Oc1cc([C@@H]2CCOC2)nc(-c2onc3c2CCC[C@@]32CCCc3sc(N)c(C#N)c32)n1)[C@@H]1CCCN1C] | 1.51 | 561 | A |
| I-23 | 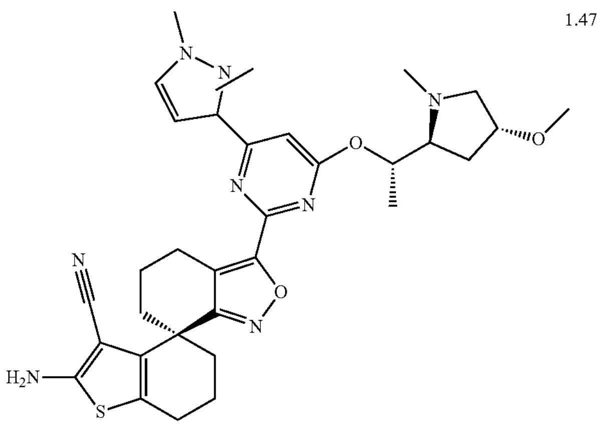 | 1.47 | 601 | A |
| I-24 | 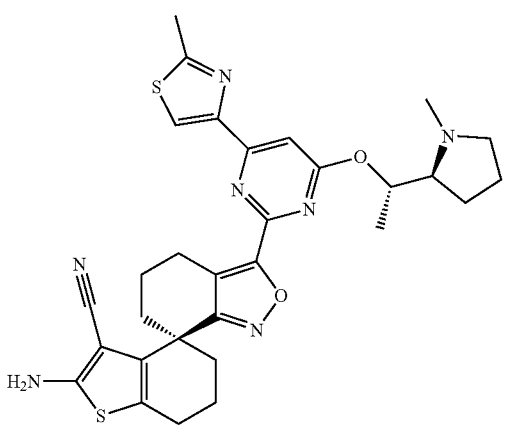 [SMILES: Cc1nc(-c2cc(O[C@@H](C)[C@@H]3CCCN3C)nc(-c3onc4c3CCC[C@@]43CCCc4sc(N)c(C#N)c43)n2)cs1] | 1.68 | 588 | A |

TABLE 54-continued

| # | structure | $t_{ret}$ [min] | $[M + H]^+$ | HPLC method |
|---|---|---|---|---|
| I-25 | 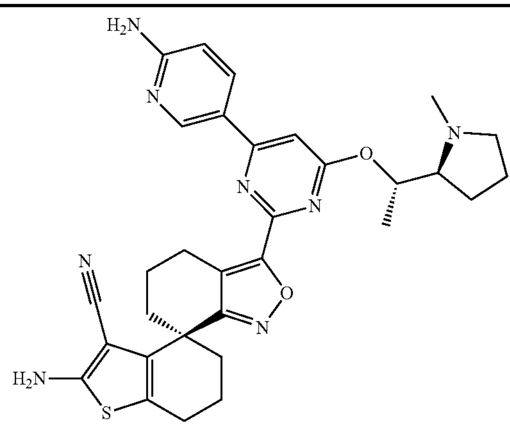 | 1.42 | 583 | A |
| I-26 | 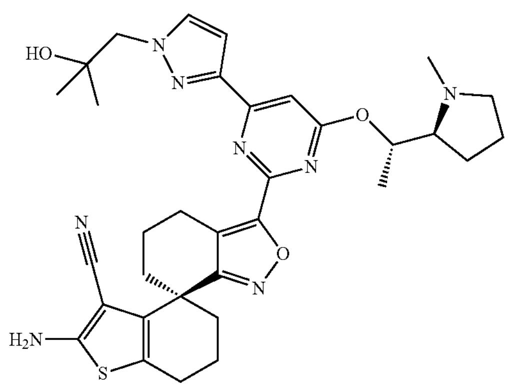 [SMILES: C[C@H](Oc1cc(-c2ccn(CC(C)(C)O)n2)nc(-c2onc3c2CCC[C@@]32CCCc3sc(N)c(C#N)c32)n1)[C@@H]1CCCN1C] | 1.51 | 629 | A |
| I-27 | 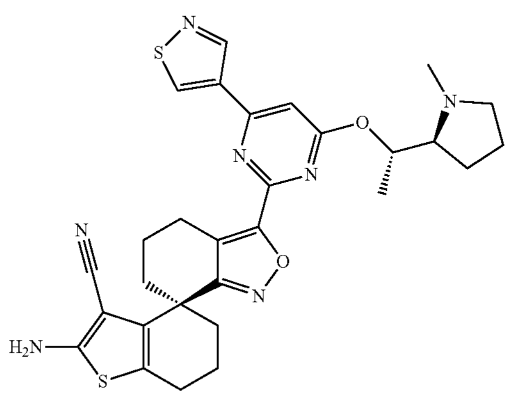 [SMILES: C[C@H](Oc1cc(-c2cnsc2)nc(-c2onc3c2CCC[C@@]32CCCc3sc(N)c(C#N)c32)n1)[C@@H]1CCCN1C] | 1.59 | 574 | A |
| I-28 | 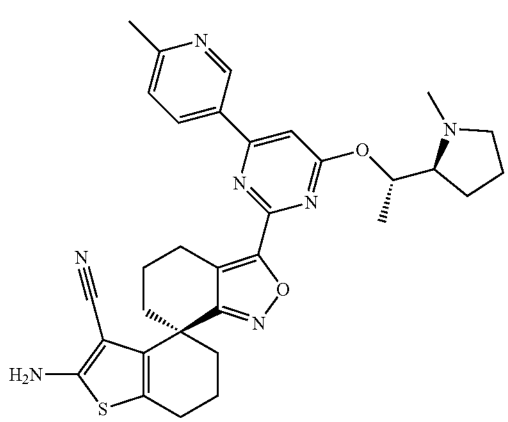 [SMILES: Cc1ccc(-c2cc(O[C@@H](C)[C@@H]3CCCN3C)nc(-c3onc4c3CCC[C@@]43CCCc4sc(N)c(C#N)c43)n2)cn1] | 1.56 | 582 | A |

TABLE 54-continued

| # | structure | $t_{ret}$ [min] | $[M + H]^+$ | HPLC method |
|---|---|---|---|---|
| I-29 | 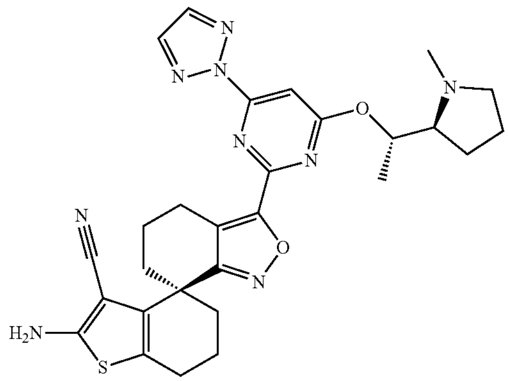 [SMILES: C[C@H](Oc1cc(-n2nccn2)nc(-c2onc3c2CCC[C@@]32CCCc3sc(N)c(C#N)c32)n1)[C@@H]1CCCN1C] | 1.54 | 558 | A |
| I-30 | 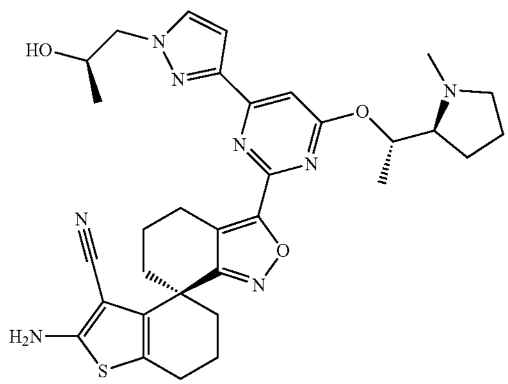 [SMILES: C[C@H](Oc1cc(-c2ccn(C[C@@H](C)O)n2)nc(-c2onc3c2CCC[C@@]32CCCc3sc(N)c(C#N)c32)n1)[C@@H]1CCCN1C] | 1.45 | 615 | A |
| I-31 | 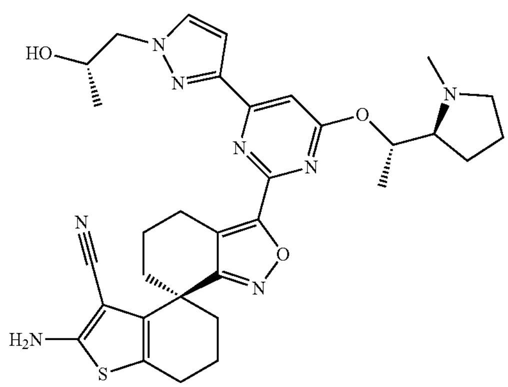 [SMILES: C[C@H](O)Cn1ccc(-c2cc(O[C@@H](C)[C@@H]3CCCN3C)nc(-c3onc4c3CCC[C@@]43CCCc4sc(N)c(C#N)c43)n2)n1] | 1.44 | 615 | A |
| I-32 | 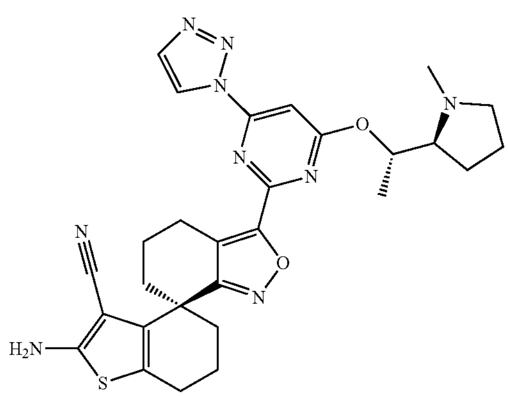 [SMILES: C[C@H](Oc1cc(-n2ccnn2)nc(-c2onc3c2CCC[C@@]32CCCc3sc(N)c(C#N)c32)n1)[C@@H]1CCCN1C] | 1.51 | 558 | A |

TABLE 54-continued

| # | structure | t_ret [min] | [M + H]+ | HPLC method |
|---|-----------|-------------|----------|-------------|
| I-33 | 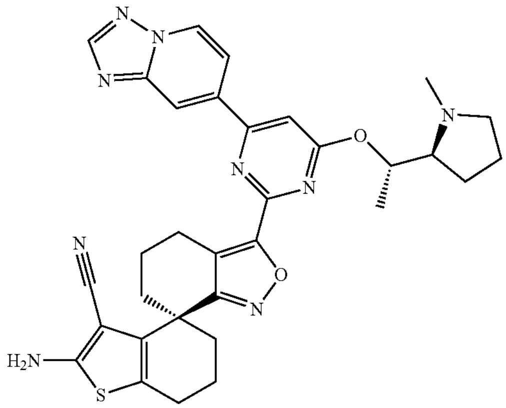 [SMILES: C[C@H](Oc1cc(-c2ccn3ncnc3c2)nc(-c2onc3c2CCC[C@@]32CCCc3sc(N)c(C#N)c32)n1)[C@@H]1CCCN1C] | 1.46 | 608 | A |
| I-34 | 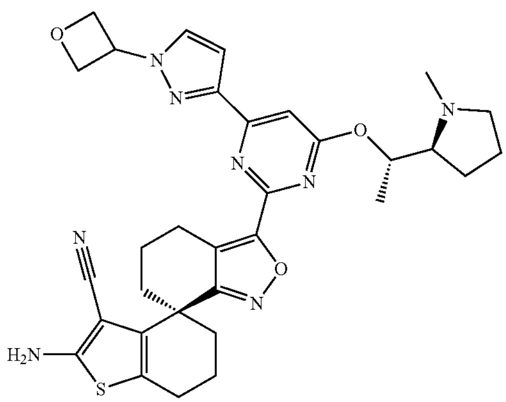 [SMILES: C[C@H](Oc1cc(-c2ccn(C3COC3)n2)nc(-c2onc3c2CCC[C@@]32CCCc3sc(N)c(C#N)c32)n1)[C@@H]1CCCN1C] | 1.51 | 613 | A |
| I-35 | 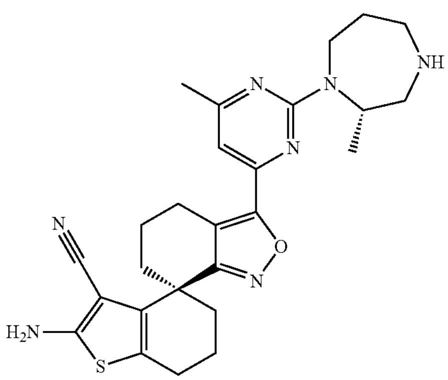 [SMILES: Cc1cc(-c2onc3c2CCC[C@@]32CCCc3sc(N)c(C#N)c32)nc(N2CCCNC[C@@H]2C)n1] | 1.42 | 490 | A |
| I-36 | 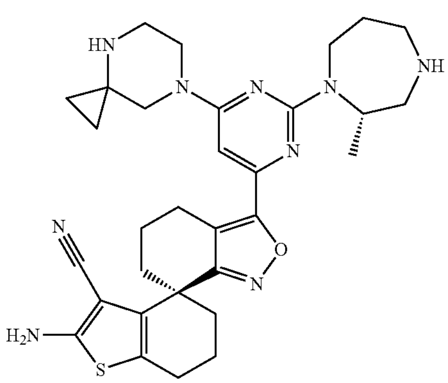 [SMILES: C[C@H]1CNCCCN1c1nc(-c2onc3c2CCC[C@@]32CCCc3sc(N)c(C#N)c32)cc(N2CCNC3(CC3)C2)n1] | 1.42 | 490 | A |

TABLE 54-continued

| # | structure | $t_{ret}$ [min] | $[M + H]^+$ | HPLC method |
|---|---|---|---|---|
| I-61 | 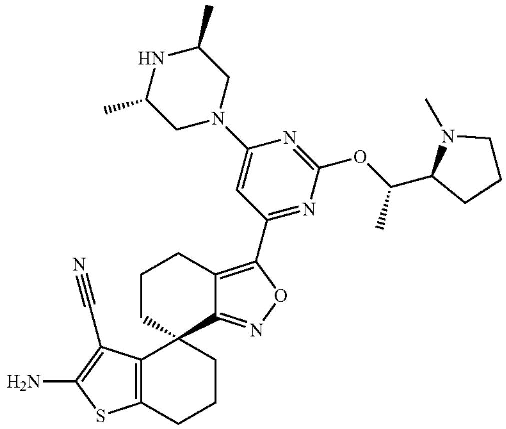 [SMILES: C[C@H](Oc1nc(-c2onc3c2CCC[C@@]32CCCc3sc(N)c(C#N)c32)cc(N2C[C@H](C)N[C@@H](C)C2)n1)[C@@H]1CCCN1C] | 1.46 | 603 | A |

Experimental Procedure for the Synthesis of I-37

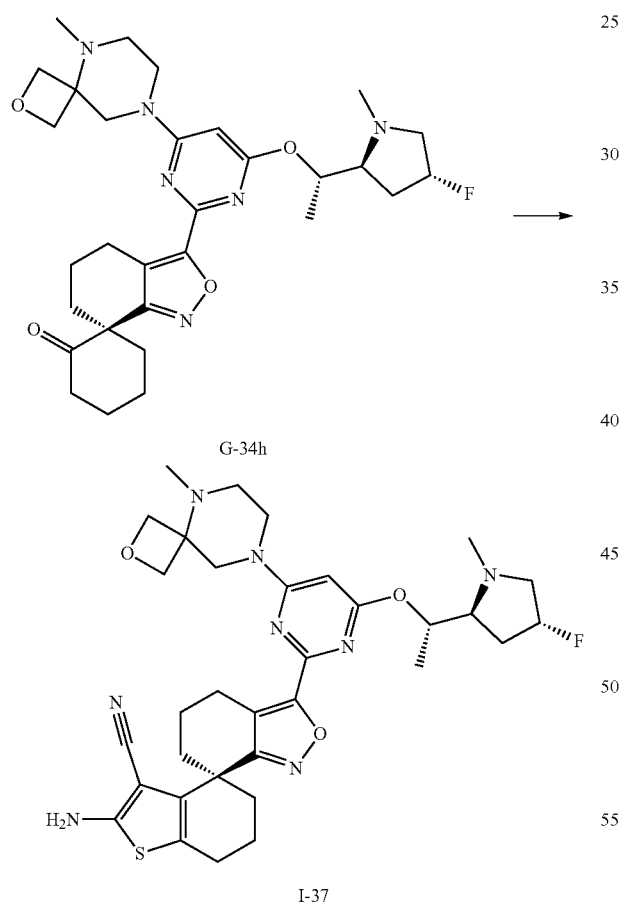

G-34h

I-37

G-34 h (91.0 mg, 0.160 mmol, 1.00 equiv.), ammonium acetate (26.3 mg, 0.320 mmol, 2.00 equiv.) and sulfur (10.3 mg, 0.320 mmol, 2.00 equiv.) is suspended in EtOH (1.0 mL) and stirred at 60° C. for 15 min Malonitrile (22.3 mg, 0.320 mmol, 2.00 equiv.) is added. The reaction is stirred for 5 h at 80° C. After full conversion the mixture is diluted with DMSO, filtered and purified with RP chromatography to afford I-37.

The following final compounds I (Table 55) are available in an analogous manner. The crude product is purified by chromatography if necessary.

TABLE 55

| # | structure | t_ret [min] | [M + H]+ | HPLC method |
|---|---|---|---|---|
| I-37 | 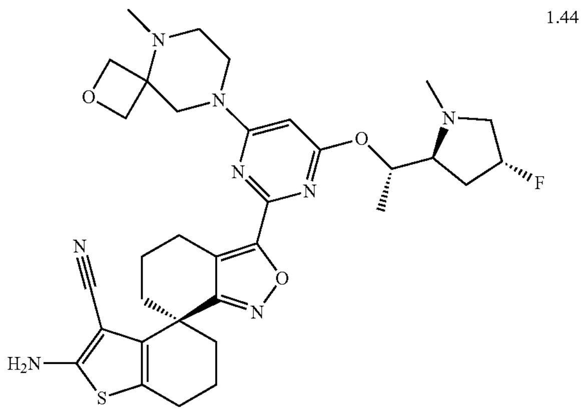 | 1.44 | 649 | A |
| I-38 | 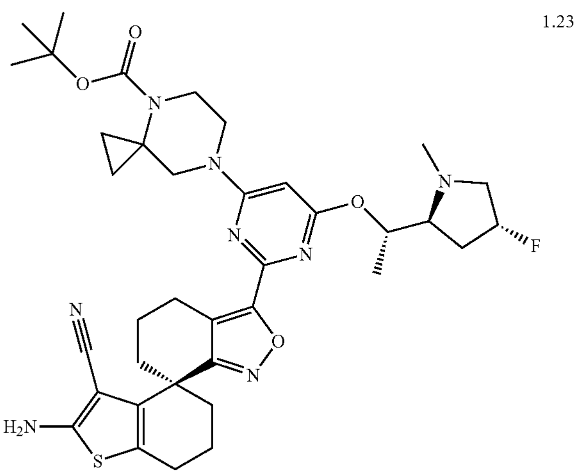 | 1.23 | 719 | B |
| I-39 | 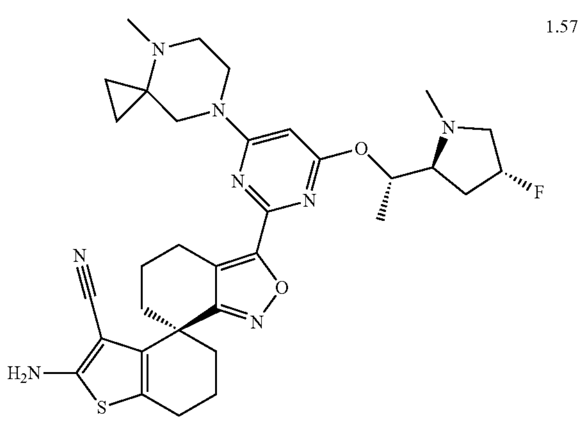 | 1.57 | 633 | A |

TABLE 55-continued

| # | structure | $t_{ret}$ [min] | $[M + H]^+$ | HPLC method |
|---|---|---|---|---|
| I-46 | 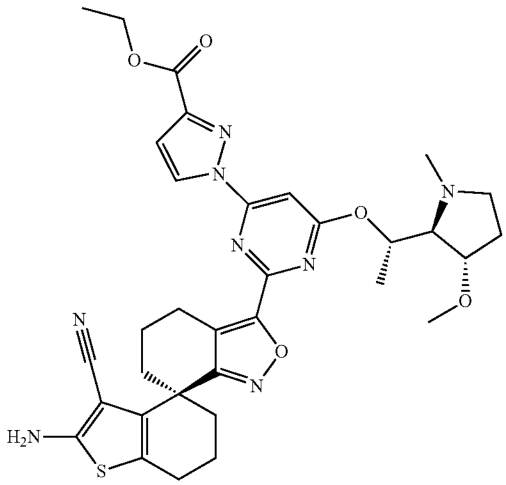 [SMILES: CCOC(=O)c1ccn(-c2cc(O[C@@H](C)[C@@H]3[C@@H](OC)CCN3C)nc(-c3onc4c3CCC[C@@]43CCCc4sc(N)c(C#N)c43)n2)n1] | 0.92 | 659 | C |
| I-47 | 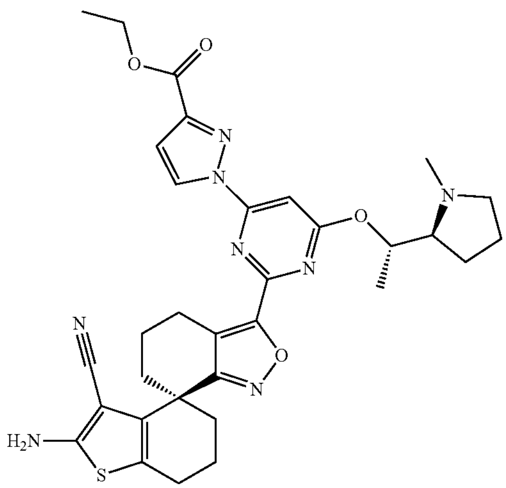 [SMILES: CCOC(=O)c1ccn(-c2cc(O[C@@H](C)[C@@H]3CCCN3C)nc(-c3onc4c3CCC[C@@]43CCCc4sc(N)c(C#N)c43)n2)n1] | 0.94 | 629 | C |
| I-48 | 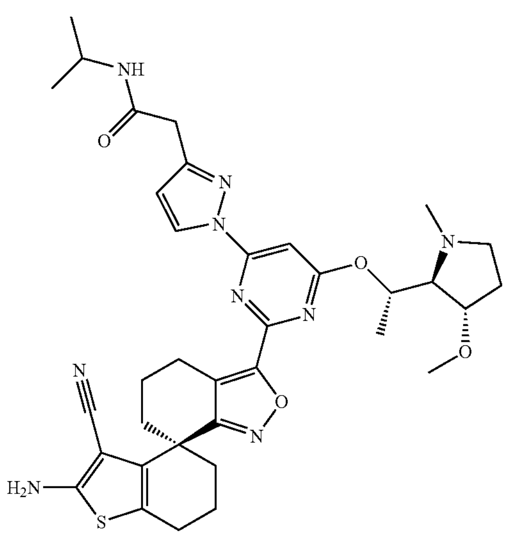 [SMILES: CO[C@H]1CCN(C)[C@@H]1[C@H](C)Oc1cc(-n2ccc(CC(=O)NC(C)C)n2)nc(-c2onc3c2CCC[C@@]32CCCc3sc(N)c(C#N)c32)n1] | 1.48 | 686 | A |

TABLE 55-continued

| # | structure | $t_{ret}$ [min] | $[M + H]^+$ | HPLC method |
|---|---|---|---|---|
| I-49 | 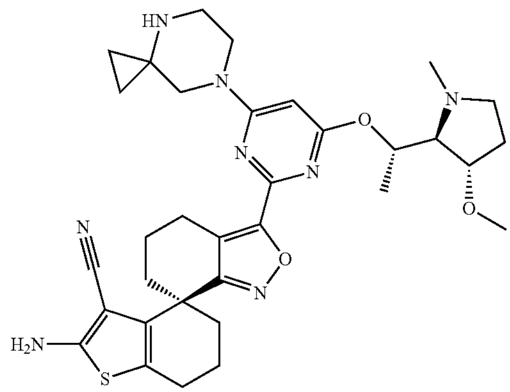 [SMILES: CO[C@H]1CCN(C)[C@@H]1[C@H](C)Oc1cc(N2CCNC3(CC3)C2)nc(-c2onc3c2CCC[C@@]32CCCc3sc(N)c(C#N)c32)n1] | 1.45 | 631 | 4 |
| I-50 | 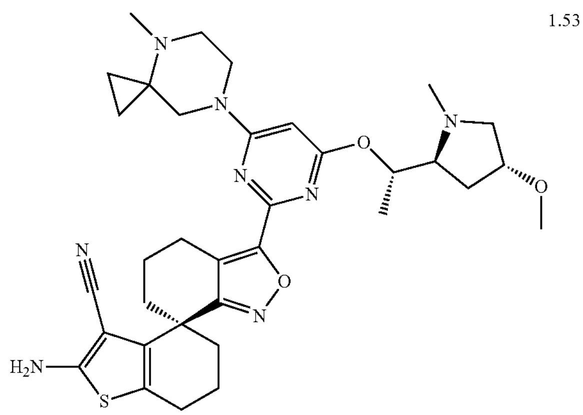 | 1.53 | 645 | A |

Experimental Procedure for the Synthesis of I-40

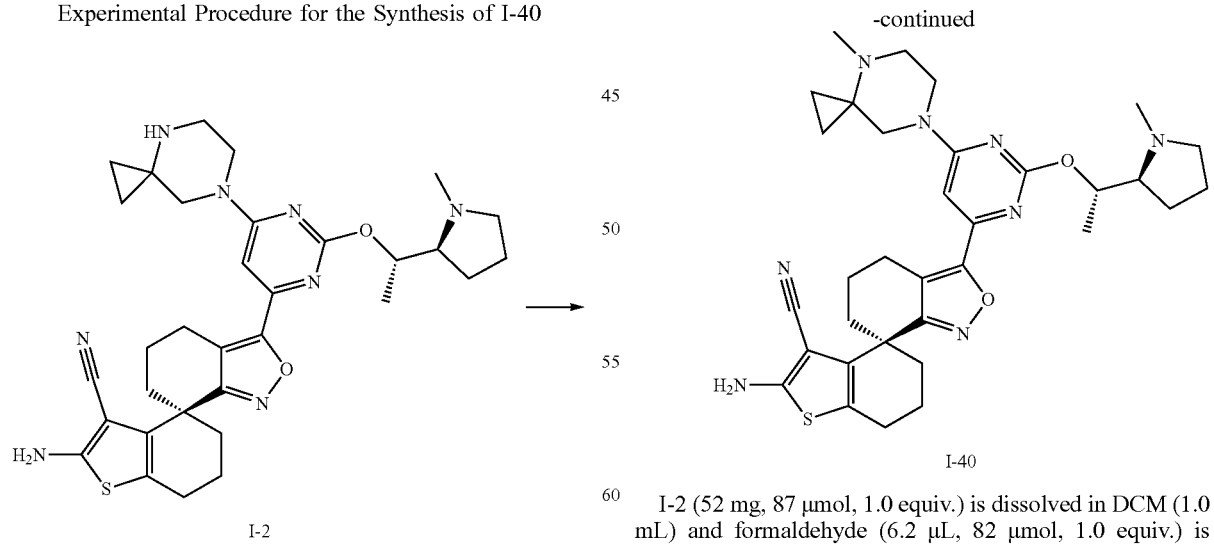

I-2 (52 mg, 87 µmol, 1.0 equiv.) is dissolved in DCM (1.0 mL) and formaldehyde (6.2 µL, 82 µmol, 1.0 equiv.) is added. The solution is stirred at rt for 4 h, then sodium triacetoxyborohydride (23 mg, 0.10 mmol, 1.2 equiv.) is added and the suspension is stirred for 2 h. The reaction mixture is quenched with water, diluted with DCM and washed with water. The organic phase is separated and the remaining aq. phase is extracted with DCM (2×). The combined organic phases are washed with brine, dried with magnesium sulfate, evaporated and the resulting residue is purified by RP chromatography to afford I-40.
The following final compounds I (Table 56) are available in an analogous manner. The crude product is purified by chromatography if necessary.
TABLE 56
| # | structure | $t_{ret}$ [min] | $[M + H]^+$ | HPLC method |
|---|---|---|---|---|
| I-40 | 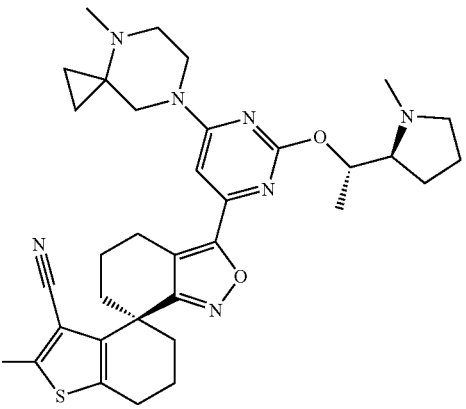 | 1.51 | 615 | A |
| I-41 | 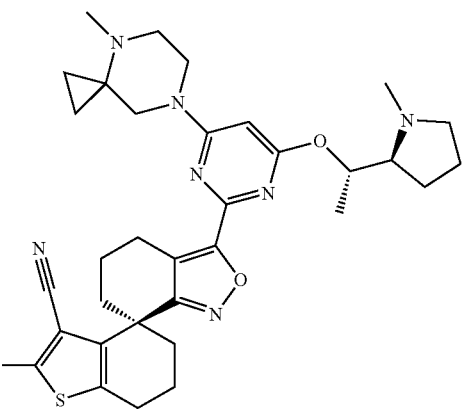 | 1.55 | 615 | A |
| I-42 | 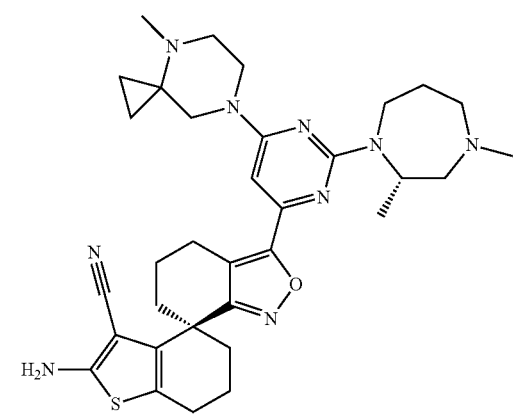 [SMILES: C[C@H]1CN(C)CCCN1c1nc(-c2onc3c2CCC[C@@]32CCCc3sc(N)c(C#N)c32)cc(N2CCN(C)C3(CC3)C2)n1] | 1.58 | 614 | A |

TABLE 56-continued

| # | structure | $t_{ret}$ [min] | $[M + H]^+$ | HPLC method |
|---|---|---|---|---|
| I-43 | 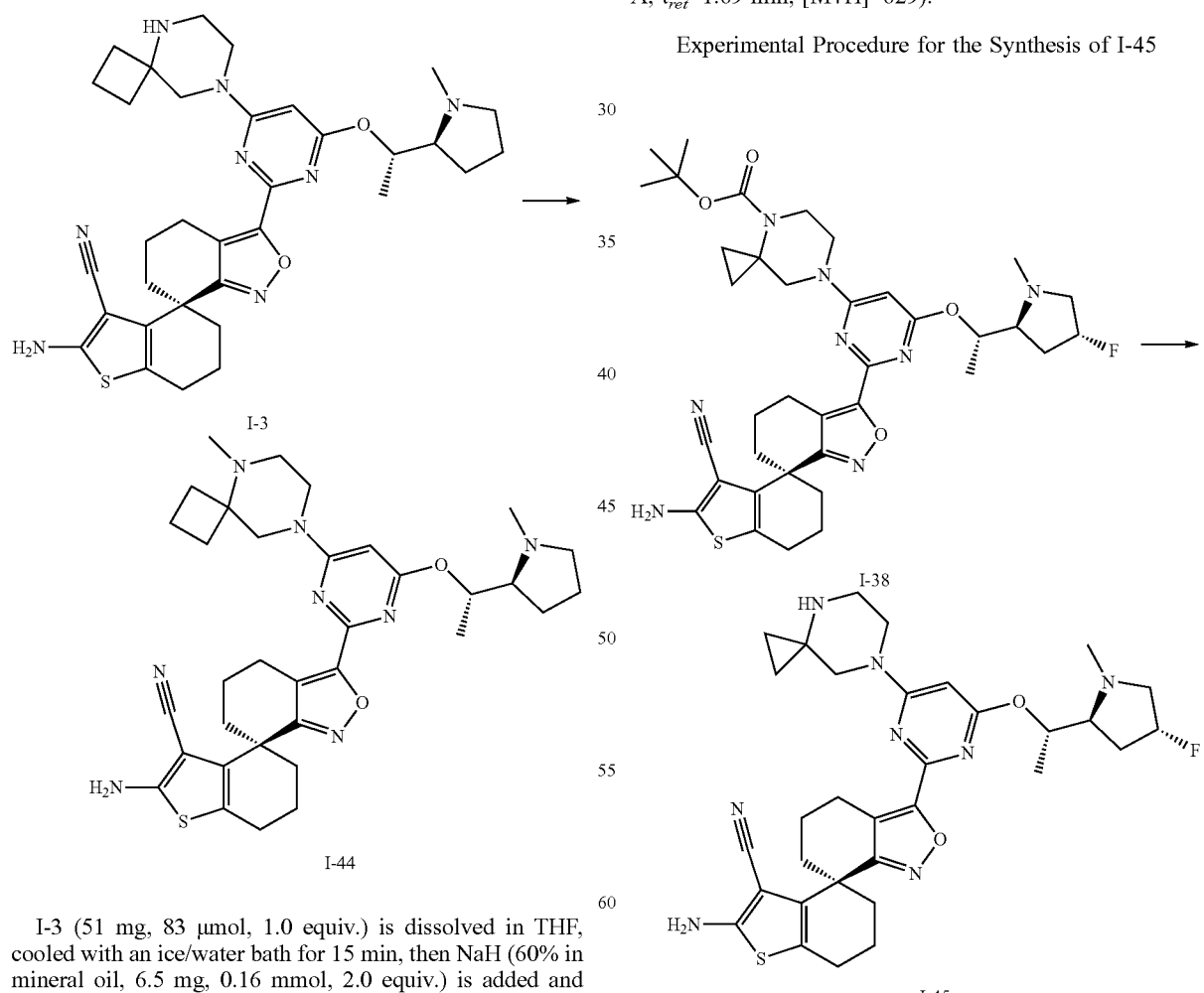 | 1.60 | 617 | A |

Experimental Procedure for the Synthesis of I-44

I-3 (51 mg, 83 μmol, 1.0 equiv.) is dissolved in THF, cooled with an ice/water bath for 15 min, then NaH (60% in mineral oil, 6.5 mg, 0.16 mmol, 2.0 equiv.) is added and stirred for 10 min. Methyl iodide (5.7 μL, 9.2 μmol, 1.1 equiv.) is added, the reaction is warmed to rt and stirred for 18 h at rt. After complete conversion, the reaction mixture is extracted with EtOAc (3×). The combined organic phases are filtered and concentrated under reduced pressure. The residue is dissolved in DMSO and purified by RP chromatography to give the desired product I-44 (HPLC-Method: A, $t_{ret}$=1.69 min, [M+H]=629).

Experimental Procedure for the Synthesis of I-45

I-38 (225 mg, 0.31 mmol, 1.0 equiv.) is dissolved in DCM/TFA (1:1, 2.0 mL) and the reaction is stirred at rt for 3 h. After complete conversion, the reaction mixture is concentrated under vacuum and purified with RP chromatography yielding I-45 (HPLC-Method: A, $t_{ret}$=1.47 min; [M+H]=619).

Experimental Procedure for the Synthesis of I-51

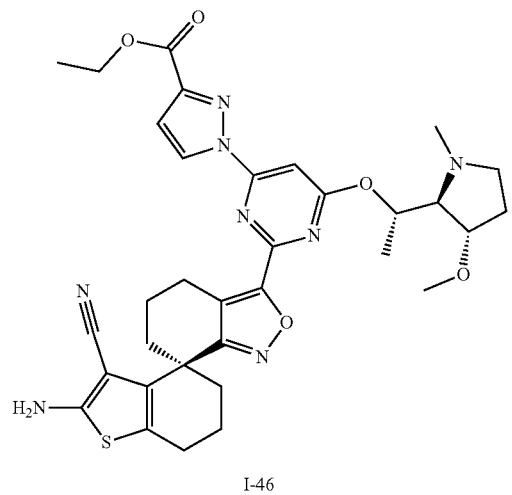

I-46

→

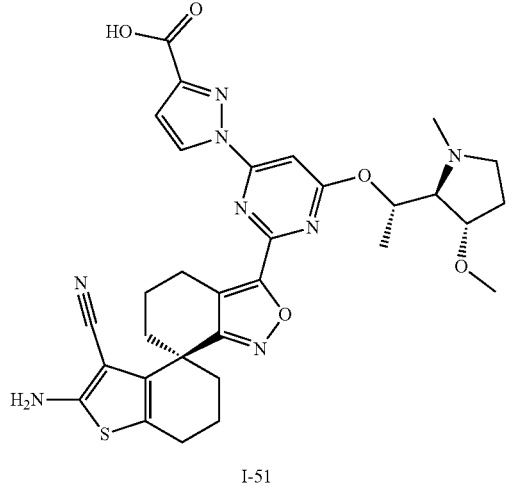

I-51

To a suspension of I-46 (2.73 g, 4.14 mmol, 1.0 equiv.) in ethanol (47 mL) is added potassium hydroxide (1.91 g, 29.0 mmol, 7.0 equiv.) dissolved in water (53 mL) and the mixture is stirred for 2 h at rt. After complete conversion the mixture is acidified to pH6, ethanol is removed under reduced pressure and the resulting precipitate is collected by repeated centrifuging and washing with water and dried under reduced pressure to give the desired product I-51. The crude product is used without further purification.

The following final compounds I (Table 57) are available in an analogous manner. The crude product is purified by chromatography if necessary.

TABLE 57

| # | structure | $t_{ret}$ [min] | [M + H]⁺ | HPLC method |
|---|---|---|---|---|
| I-51 | ![structure] | 0.56 | 631 | C |

TABLE 57-continued

| # | structure | $t_{ret}$ [min] | $[M + H]^+$ | HPLC method |
|---|---|---|---|---|
| I-52 | 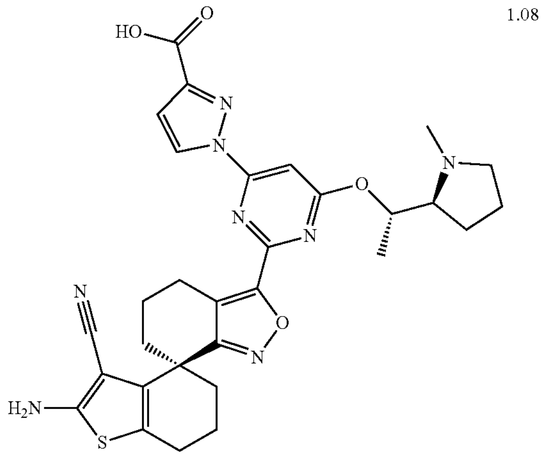 | 1.08 | 601 | A |

Experimental Procedure for the Synthesis of I-53

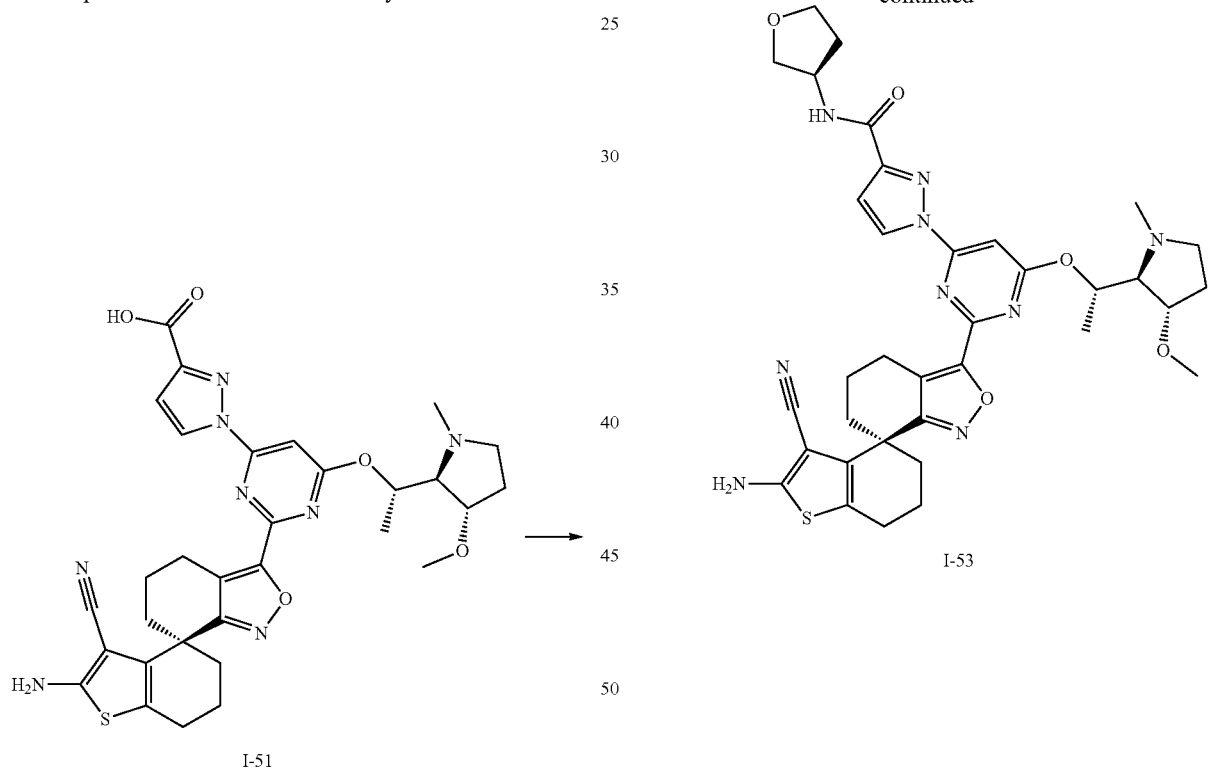

To a solution of I-51 (90.1 mg, 0.14 mmol, 1.0 equiv.) in DMSO (0.7 mL) is added (R)-tetrahydrofuran-3-amine hydrochloride (21.9 mg, 0.17 mmol, 1.2 equiv.), 1-methylimidazole (45.6 µL, 0.57 mmol, 4.0 equiv.) and chlor-N,N,N',N'-tetramethylformamidinium-hexafluorophosphat (57.3 mg, 0.20 mmol, 1.4 equiv.) and the mixture is stirred for 1 h at rt. After complete conversion, the mixture is diluted with ACN and the product is isolated via RP chromatography to give the desired product I-53.

The following final compounds I (Table 58) are available in an analogous manner. The crude product is purified by chromatography if necessary.

TABLE 58

| # | structure | t_ret [min] | [M + H]+ | HPLC method |
|---|---|---|---|---|
| I-53 | 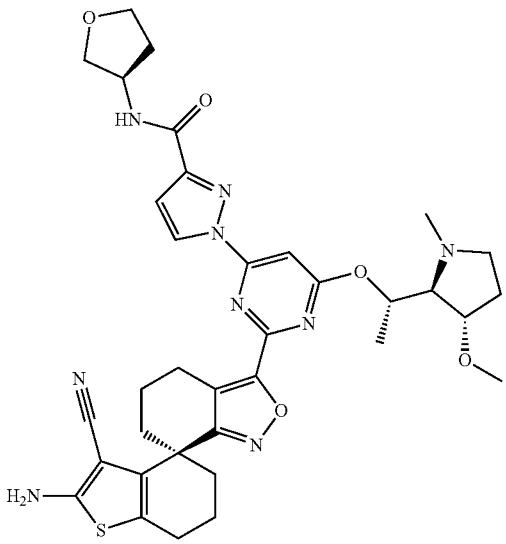 [SMILES: CO[C@H]1CCN(C)[C@@H]1[C@H](C)Oc1cc(-n2ccc(C(=O)N[C@@H]3CCOC3)n2)nc(-c2onc3c2CCC[C@@]32CCCc3sc(N)c(C#N)c32)n1] | 1.46 | 700 | A |
| I-54 | 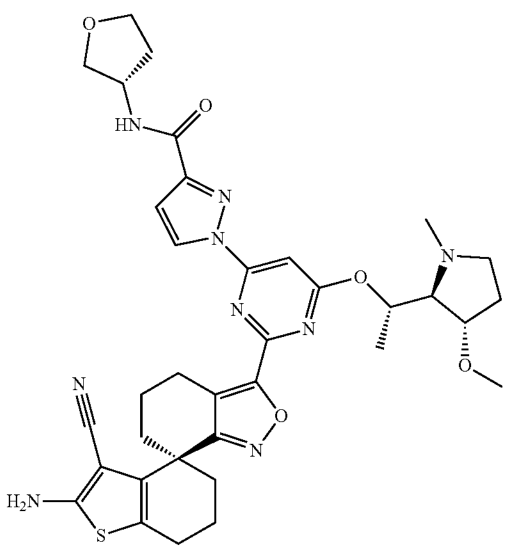 [SMILES: CO[C@H]1CCN(C)[C@@H]1[C@H](C)Oc1cc(-n2ccc(C(=O)N[C@H]3CCOC3)n2)nc(-c2onc3c2CCC[C@@]32CCCc3sc(N)c(C#N)c32)n1] | 1.45 | 700 | A |
| I-55 | 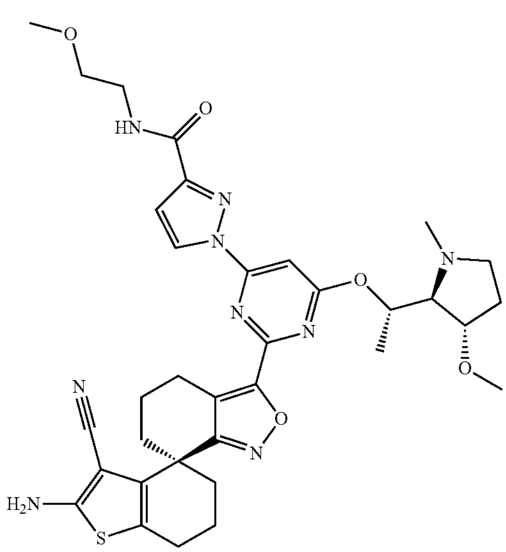 | 1.47 | 688 | A |

TABLE 58-continued
| # | structure | $t_{ret}$ [min] | $[M + H]^+$ | HPLC method |
|---|---|---|---|---|
| I-56 | 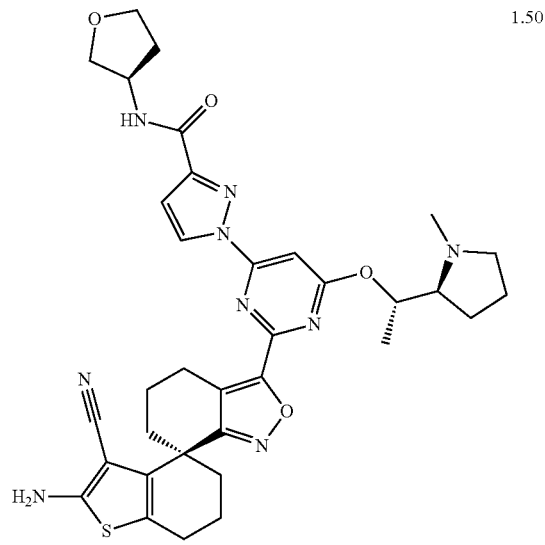 | 1.50 | 670 | A |
| I-57 | 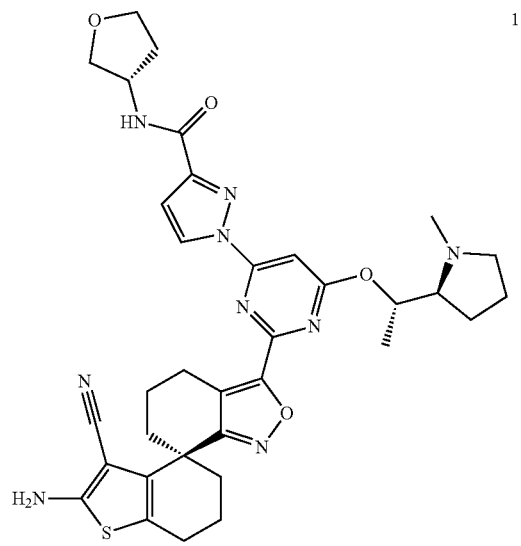 | 1.50 | 670 | A |

TABLE 58-continued

| # | structure | $t_{ret}$ [min] | $[M + H]^+$ | HPLC method |
|---|---|---|---|---|
| I-58 | 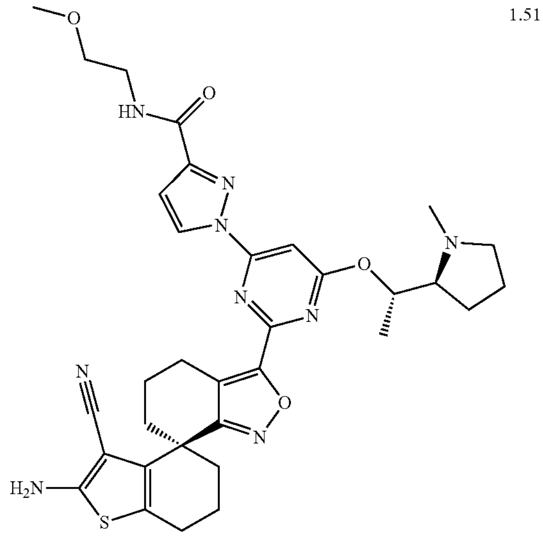 | 1.51 | 658 | A |
| I-59 | 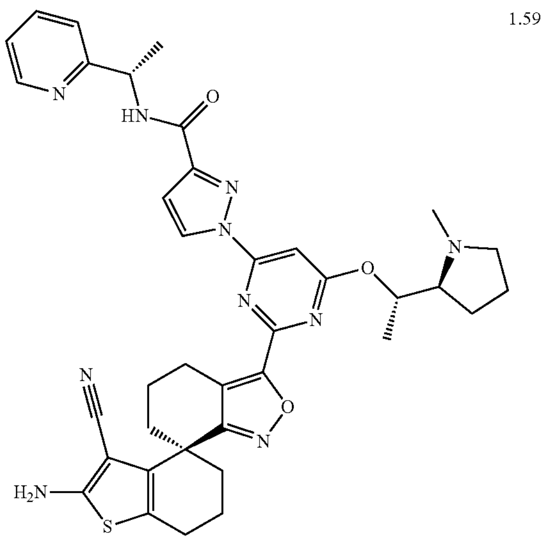 | 1.59 | 705 | A |
| I-60 | 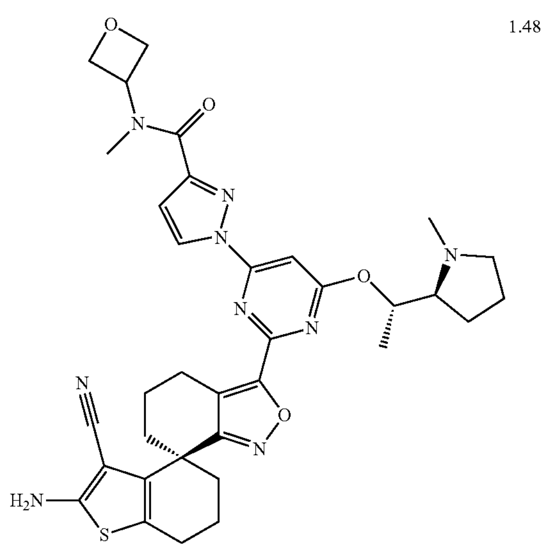 | 1.48 | 670 | A |

Experimental Procedure for the Synthesis of II-1

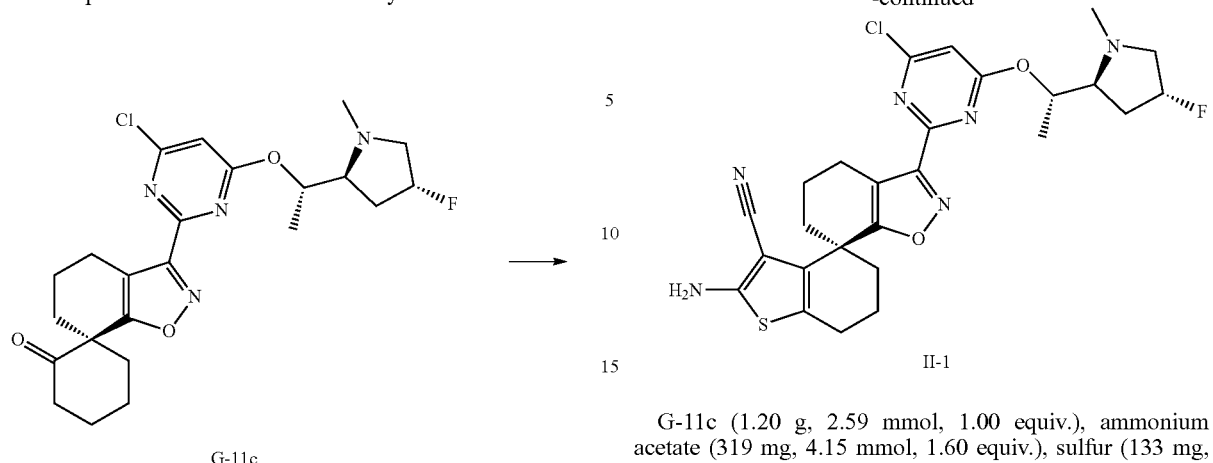

G-11c (1.20 g, 2.59 mmol, 1.00 equiv.), ammonium acetate (319 mg, 4.15 mmol, 1.60 equiv.), sulfur (133 mg, 4.15 mmol, 1.60 equiv.) is dissolved in EtOH (12 mL) and stirred at 60° C. for 15 min. Malonitrile as a solution in EtOH (3.77 mL, 4.28 mmol, 1.65 equiv.) is added slowly dropwise (8 mL/h). Reaction is stirred for 5 h at 80° C. After full conversion reaction is concentrated and purified by NP chromatography. Product fractions are concentrated and extracted with DCM and saturated $NaHCO_3$. The organic phase is concentrated under reduced pressure to obtain II-1.

The following final compounds II (Table 59) are available in an analogous manner. The crude product is purified by chromatography if necessary.

TABLE 59

| # | structure | $t_{ret}$ [min] | $[M + H]^+$ | HPLC method |
|---|---|---|---|---|
| II-1 | 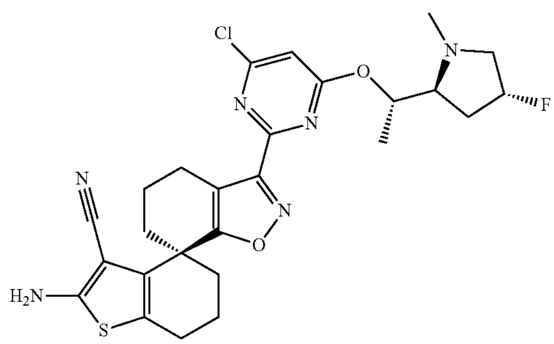 [SMILES: C[C@H](Oc1cc(Cl)nc(-c2noc3c2CCC[C@@]32CCCc3sc(N)c(C#N)c32)n1)[C@@H]1C[C@@H](F)CN1C] | 1.59 | 543 | A |
| II-2 | 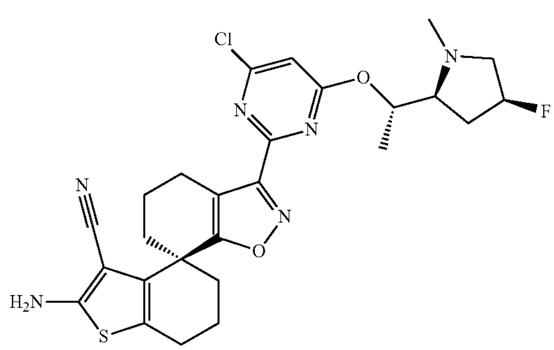 [SMILES: C[C@H](Oc1cc(Cl)nc(-c2noc3c2CCC[C@@]32CCCc3sc(N)c(C#N)c32)n1)[C@@H]1C[C@H](F)CN1C] | 1.55 | 543 | A |

TABLE 59-continued

| # | structure | $t_{ret}$ [min] | $[M + H]^+$ | HPLC method |
|---|---|---|---|---|
| II-3 | 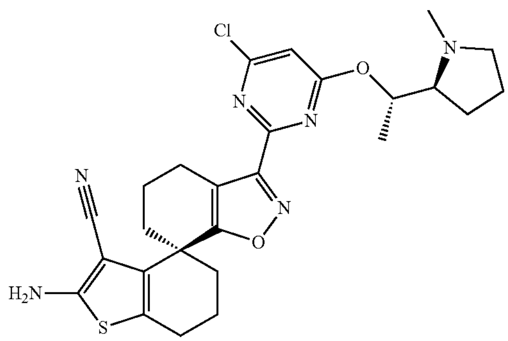 [SMILES: C[C@H](Oc1cc(Cl)nc(-c2noc3c2CCC[C@@]32CCCc3sc(N)c(C#N)c32)n1)[C@@H]1CCCN1C] | 0.83 | 525 | E |
| II-4 | 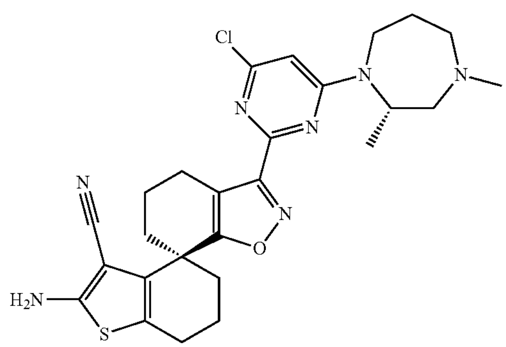 [SMILES: C[C@H]1CN(C)CCCN1c1cc(Cl)nc(-c2noc3c2CCC[C@@]32CCCc3sc(N)c(C#N)c32)n1] | 0.89 | 525 | E |
| II-179 | 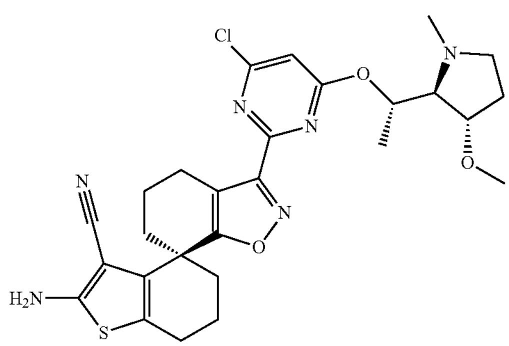 [SMILES: CO[C@H]1CCN(C)[C@@H]1[C@H](C)Oc1cc(Cl)nc(-c2noc3c2CCC[C@@]32CCCc3sc(N)c(C#N)c32)n1] | 1.11 | 556 | B |
| II-180 | 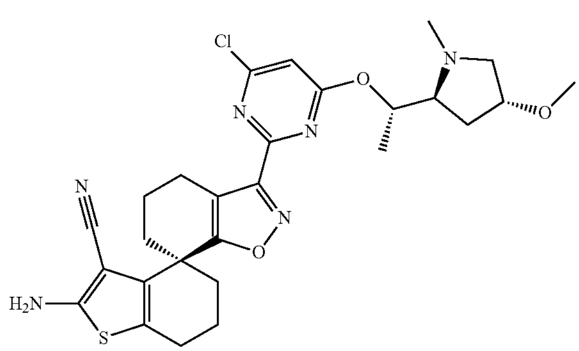 [SMILES: CO[C@@H]1C[C@@H]([C@H](C)Oc2cc(Cl)nc(-c3noc4c3CCC[C@@]43CCCc4sc(N)c(C#N)c43)n2)N(C)C1] | 1.54 | 556 | A |

TABLE 59-continued

| # | structure | $t_{ret}$ [min] | $[M + H]^+$ | HPLC method |
|---|---|---|---|---|
| II-181 | 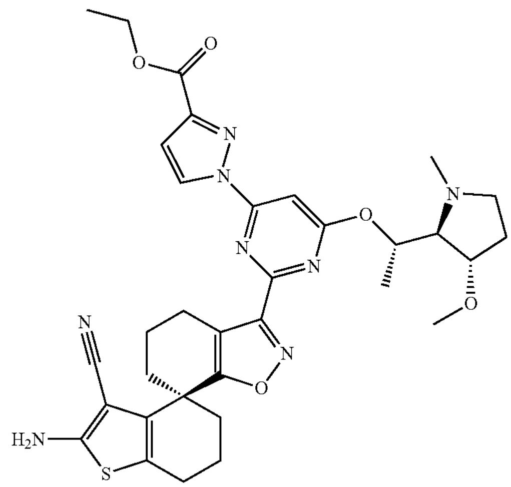 [SMILES: CCOC(=O)c1ccn(-c2cc(O[C@@H](C)[C@@H]3[C@@H](OC)CCN3C)nc(-c3noc4c3CCC[C@@]43CCCc4sc(N)c(C#N)c43)n2)n1] | 0.91 | 659 | C |
| II-182 | 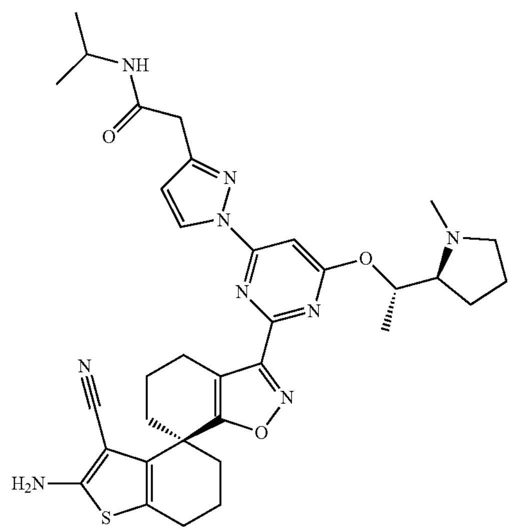 [SMILES: CC(C)NC(=O)Cc1ccn(-c2cc(O[C@@H](C)[C@@H]3CCCN3C)nc(-c3noc4c3CCC[C@@]43CCCc4sc(N)c(C#N)c43)n2)n1] | 1.50 | 656 | A |
| II-183 | 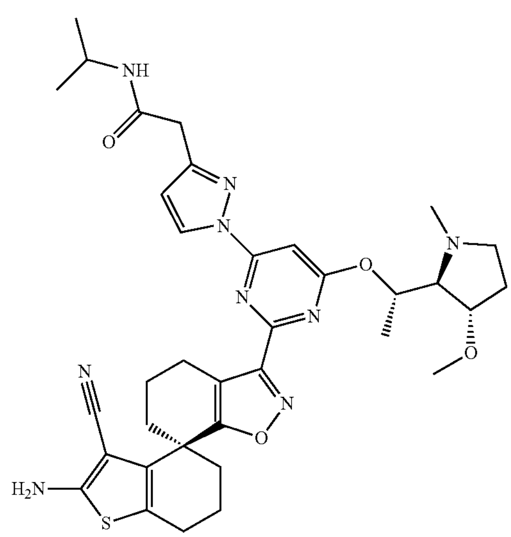 [SMILES: CO[C@H]1CCN(C)[C@@H]1[C@H](C)Oc1cc(-n2ccc(CC(=O)NC(C)C)n2)nc(-c2noc3c2CCC[C@@]32CCCc3sc(N)c(C#N)c32)n1] | 1.46 | 686 | A |

Experimental Procedure for the Synthesis of II-5

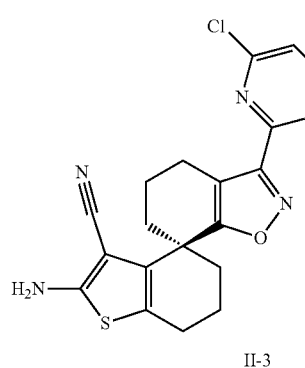

II-3

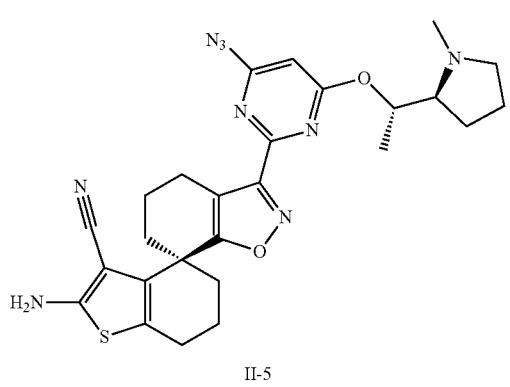

II-5

II-3 (100 mg, 0.152 mmol, 1.00 equiv.) is dissolved in DMF (1 mL) and sodium azide (17.8 mg 0.274 mmol, 1.80 equiv.) is added the reaction is stirred 16 h at 50° C. After complete conversion, the reaction is extracted with DCM/water. The organic phase is concentrated under reduced pressure to provide II-5 (HPLC method: A, $t_{ret}$=1.63 min; [M+H]$^+$=532).

Experimental Procedure for the Synthesis of II-6

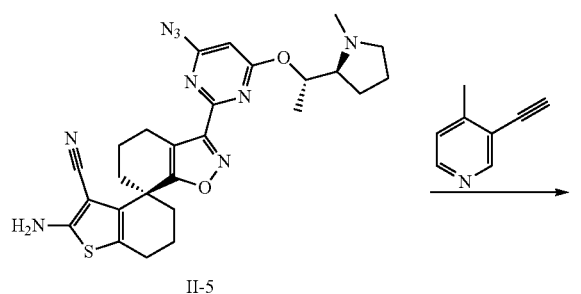

II-5

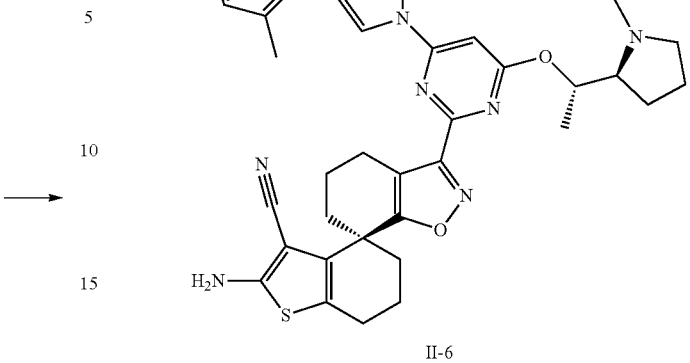

II-6

II-5 (40 mg, 0.068 mmol, 1.0 equiv.), 3-ethynyl-4-methylpyridine (10 mg, 0.088 mmol, 1.3 equiv.) and copper(I) iodide (2.6 mg, 0.01 mmol, 0.20 equiv.) are dissolved in DCM (500 µL) and DIPEA (24 µL, 0.14 mmol, 2.0 equiv.) is added. The brown solution is stirred at rt. After 30 min, more 3-ethynyl-4-methylpyridine (10 mg, 0.088 mmol, 1.3 equiv.) is added. The reaction mixture is stirred for 18 h at rt. After full conversion, the reaction mixture is extracted with DCM and ammonium chloride solution, dried, filtered, and concentrated. The residue obtained is purified by RP chromatography to give the desired final product II-6 (HPLC method: A, $t_{ret}$=1.56 min; [M+H]$^+$=649).

Experimental Procedure for the Synthesis of II-7

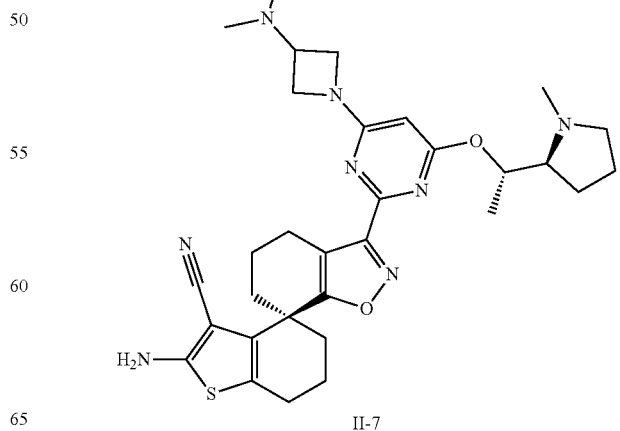

II-3

II-7

II-3 (100 mg, 0.190 mmol, 1.00 equiv.) is suspended in EtOH (700 μl). DIPEA (116 μL, 0.667 mmol, 3.00 equiv.) and N,N-dimethylazetidin-3-amine dihydrochloride (41.6 mg, 0.229 mmol, 1.20 equiv.) is added and the reaction mixture is stirred overnight at 80° C. After full conversion the reaction mixture is filtered and purified with RP chromatography to give the desired final product II-7.

The following final compounds II (Table 60) are available in an analogous manner. The crude product is purified by chromatography if necessary.

TABLE 60

| # | structure | $t_{ret}$ [min] | $[M + H]^+$ | HPLC method |
|---|---|---|---|---|
| II-7 | 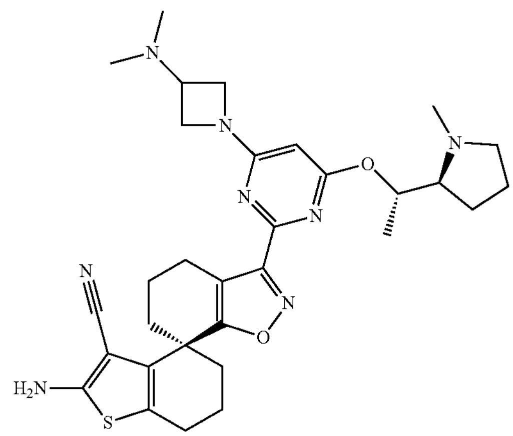 [SMILES: C[C@H](Oc1cc(N2CC(N(C)C)C2)nc(-c2noc3c2CCC[C@@]32CCCc3sc(N)c(C#N)c32)n1)[C@@H]1CCCN1C] | 1.50 | 589 | A |
| II-8 | 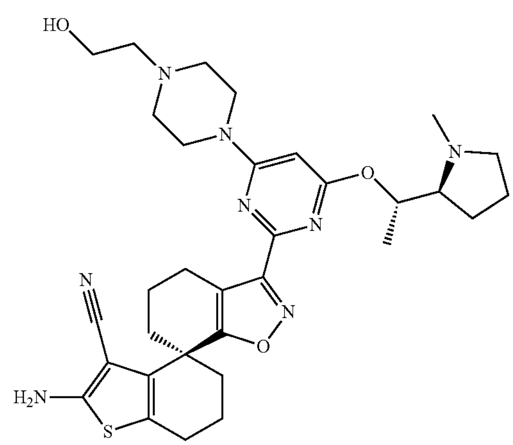 [SMILES: C[C@H](Oc1cc(N2CCN(CCO)CC2)nc(-c2noc3c2CCC[C@@]32CCCc3sc(N)c(C#N)c32)n1)[C@@H]1CCCN1C] | 1.33 | 619 | A |
| II-9 | 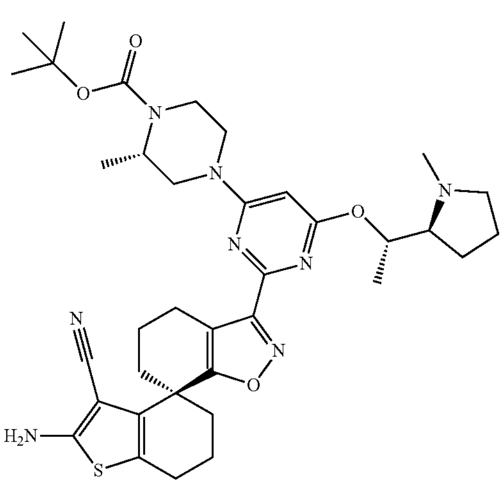 [SMILES: C[C@H](Oc1cc(N2CCN(C(=O)OC(C)(C)C)[C@@H](C)C2)nc(-c2noc3c2CCC[C@@]32CCCc3sc(N)c(C#N)c32)n1)[C@@H]1CCCN1C] | 1.75 | 689 | A |

TABLE 60-continued

| # | structure | t_ret [min] | [M + H]+ | HPLC method |
|---|---|---|---|---|
| II-10 | 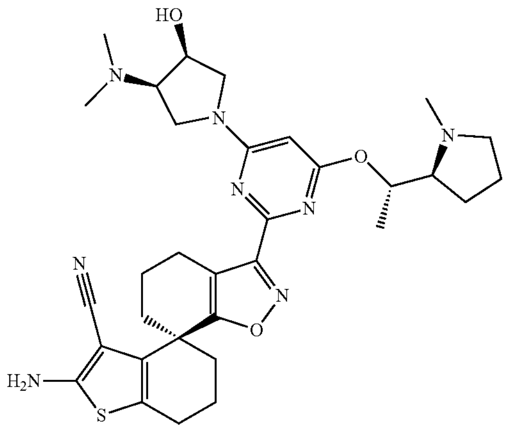 [SMILES: C[C@H](Oc1cc(N2C[C@@H](N(C)C)[C@@H](O)C2)nc(-c2noc3c2CCC[C@@]32CCCc3sc(N)c(C#N)c32)n1)[C@@H]1CCCN1C] | 1.49 | 619 | A |
| II-11 | 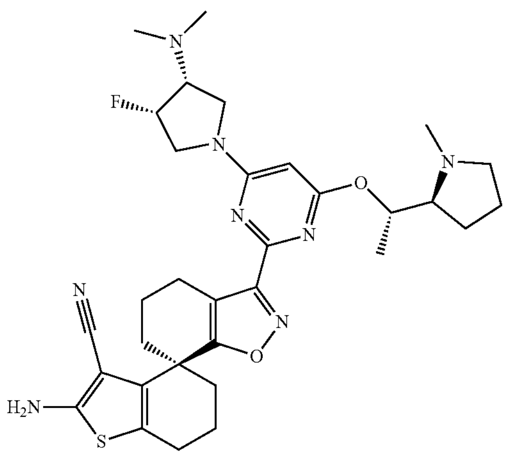 [SMILES: C[C@H](Oc1cc(N2C[C@@H](N(C)C)[C@@H](F)C2)nc(-c2noc3c2CCC[C@@]32CCCc3sc(N)c(C#N)c32)n1)[C@@H]1CCCN1C] | 1.48 | 621 | A |
| II-12 | 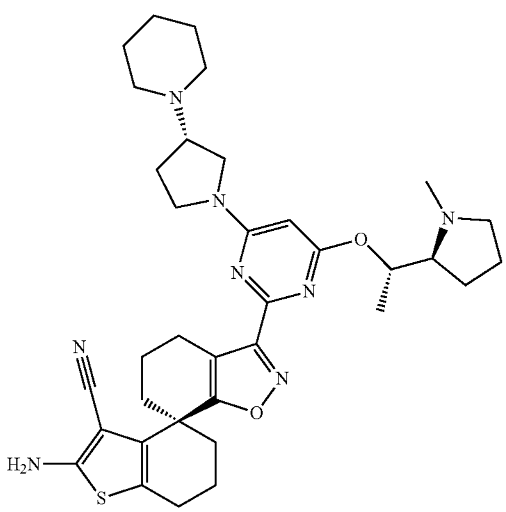 [SMILES: C[C@H](Oc1cc(N2CC[C@H](N3CCCCC3)C2)nc(-c2noc3c2CCC[C@@]32CCCc3sc(N)c(C#N)c32)n1)[C@@H]1CCCN1C] | 1.66 | 643 | A |

TABLE 60-continued

| # | structure | t_ret [min] | [M + H]+ | HPLC method |
|---|---|---|---|---|
| II-13 | 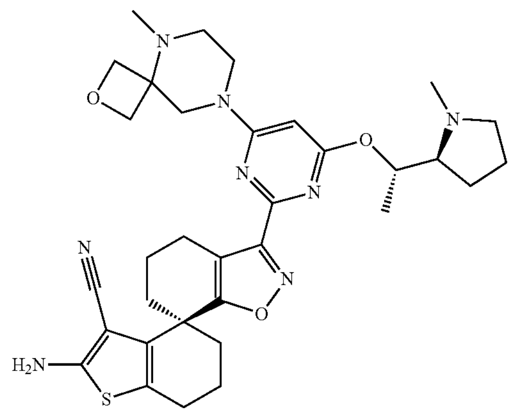 [SMILES: C[C@H](Oc1cc(N2CCN(C)C3(COC3)C2)nc(-c2noc3c2CCC[C@@]32CCCc3sc(N)c(C#N)c32)n1)[C@@H]1CCCN1C] | 1.40 | 631 | A |
| II-14 | 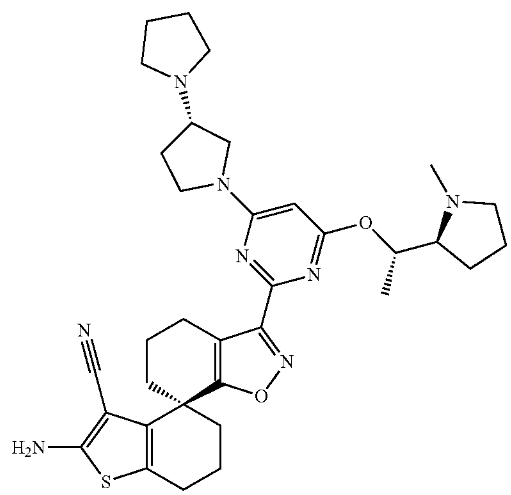 [SMILES: C[C@H](Oc1cc(N2CC[C@H](N3CCCC3)C2)nc(-c2noc3c2CCC[C@@]32CCCc3sc(N)c(C#N)c32)n1)[C@@H]1CCCN1C] | 1.63 | 629 | A |
| II-15 | 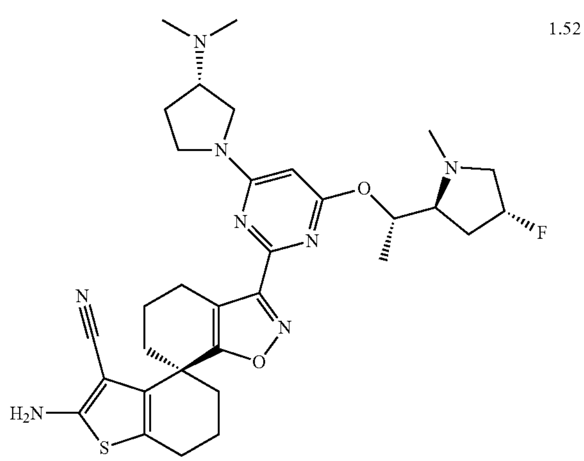 | 1.52 | 621 | A |

TABLE 60-continued

| # | structure | $t_{ret}$ [min] | $[M + H]^+$ | HPLC method |
|---|---|---|---|---|
| II-16 | 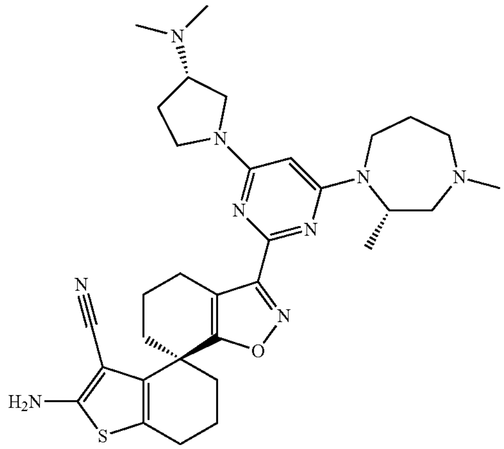 [SMILES: C[C@H]1CN(C)CCCN1c1cc(N2CC[C@H](N(C)C)C2)nc(-c2noc3c2CCC[C@@]32CCCc3sc(N)c(C#N)c32)n1] | 1.43 | 602 | A |

Experimental Procedure for the Synthesis of II-17

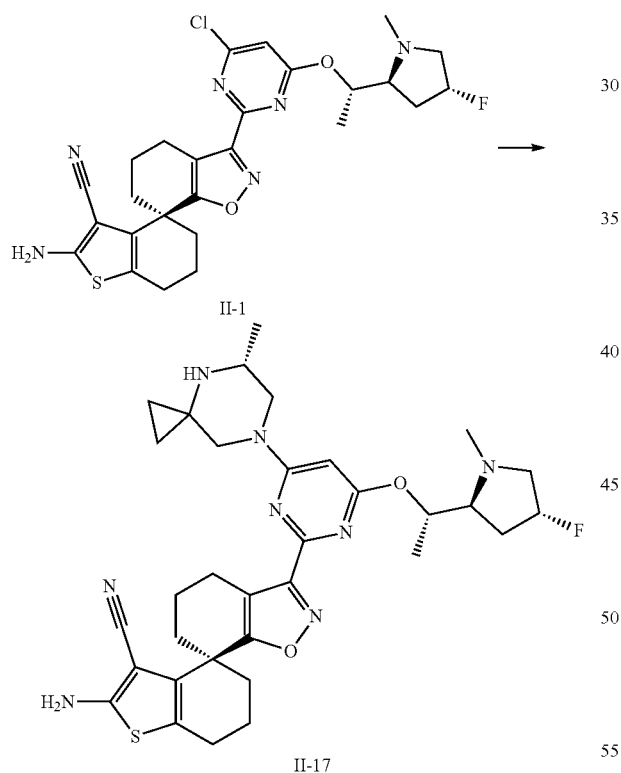

II-1 (0.10 g, 0.18 mmol, 1.0 equiv.) is suspended in DMSO (0.50 ml). DIPEA (0.11 mL, 0.57 mmol, 3.1 equiv.) and (R)-5-methyl-4,7-diazaspiro[2.5]octane dihydrochloride (42 mg, 0.20 mmol, 1.1 equiv.) is added and the reaction mixture is stirred for 2 h at 80° C. After full conversion the reaction mixture is purified with RP chromatography.

The following final compounds II (Table 61) are available in an analogous manner. The crude product is purified by chromatography if necessary.

TABLE 61
| # | structure | t_ret [min] | [M + H]+ | HPLC method |
|---|---|---|---|---|
| II-17 | 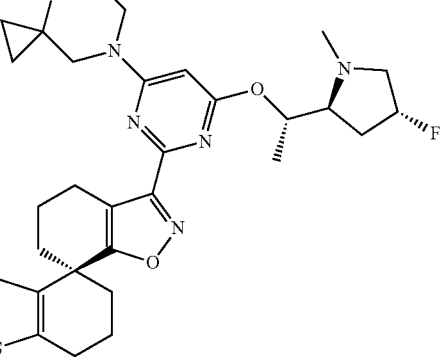 | 1.50 | 633 | A |
| II-18 | 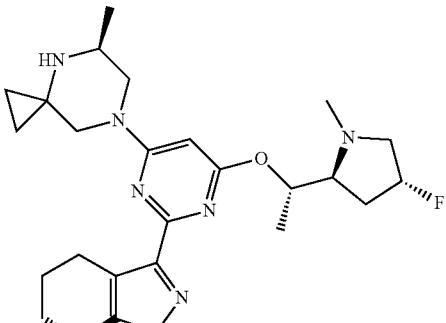 | 1.50 | 633 | A |
| II-184 | 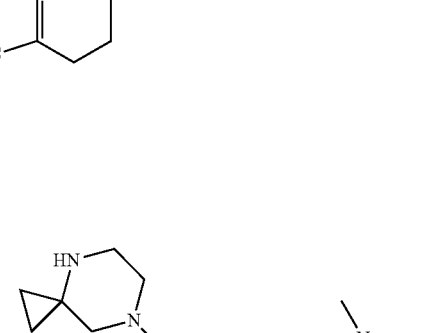 | 1.43 | 631 | A |

TABLE 61-continued
| # | structure | $t_{ret}$ [min] | $[M + H]^+$ | HPLC method |
|---|---|---|---|---|
| II-185 | 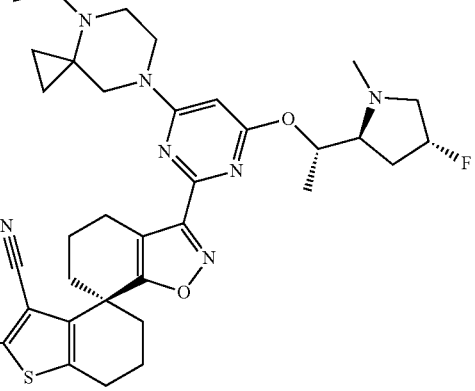 | 1.63 | 647 | A |
| II-186 | 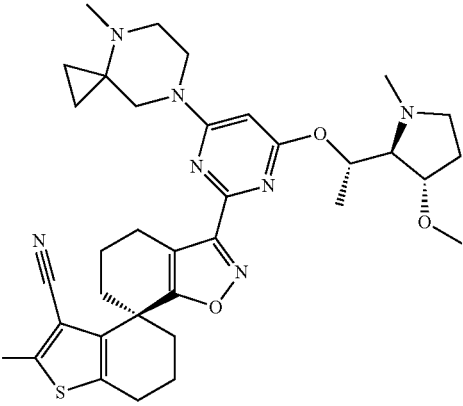 | 1.54 | 645 | A |
| II-187 | 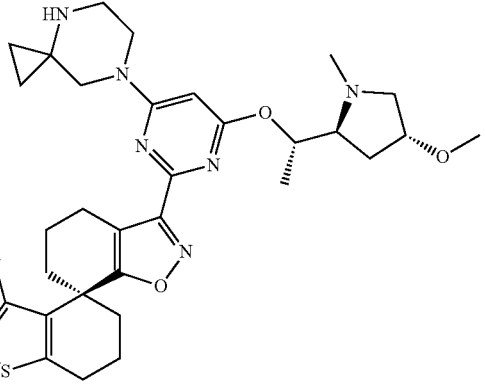 | 1.41 | 631 | A |

Experimental Procedure for the Synthesis of II-19

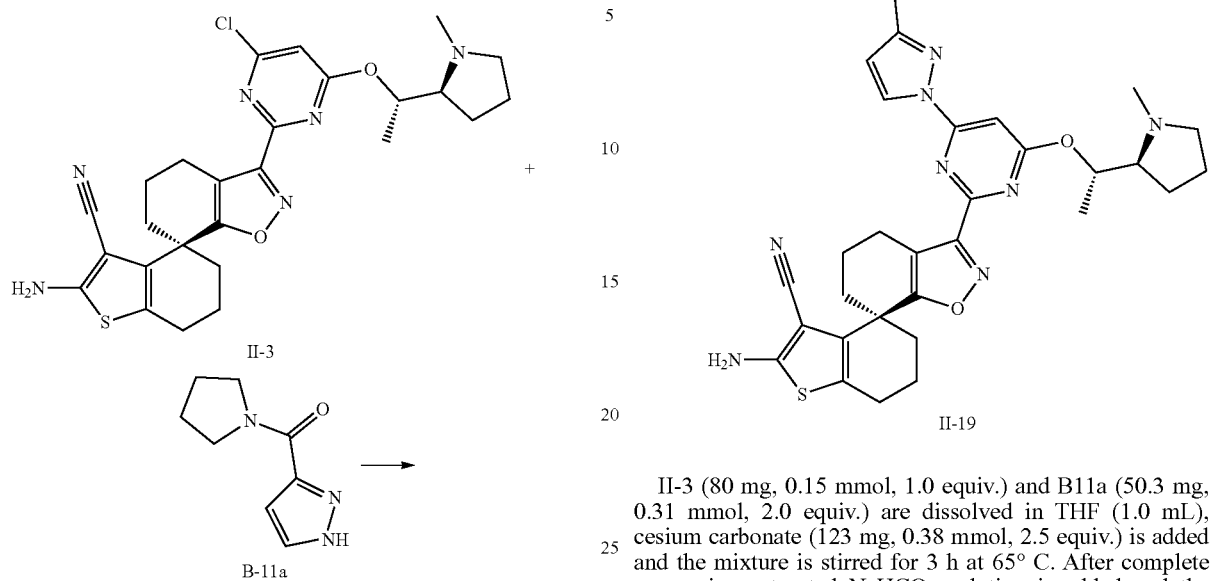

II-3 (80 mg, 0.15 mmol, 1.0 equiv.) and B11a (50.3 mg, 0.31 mmol, 2.0 equiv.) are dissolved in THF (1.0 mL), cesium carbonate (123 mg, 0.38 mmol, 2.5 equiv.) is added and the mixture is stirred for 3 h at 65° C. After complete conversion saturated NaHCO₃ solution is added and the product is extracted with DCM. The organic phase is dried, filtered and concentrated under reduced pressure. The crude product is purified by RP chromatography to yield the desired final product II-19.

The following final compounds II (Table 62) are available in an analogous manner. The crude product is purified by chromatography if necessary.

TABLE 62

| # | structure | $t_{ret}$ [min] | [M + H]⁺ | HPLC method |
|---|---|---|---|---|
| II-19 | 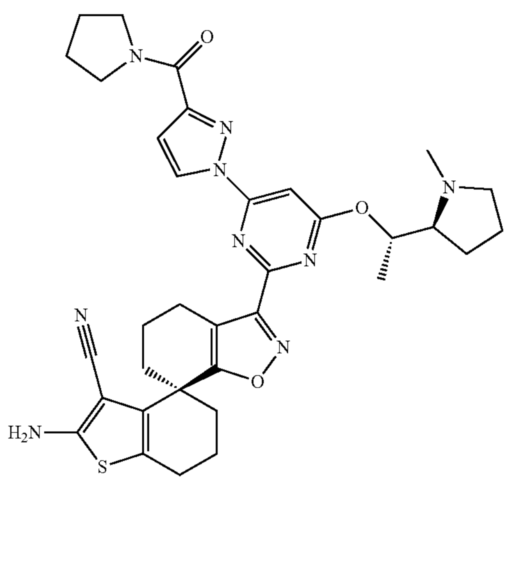 [SMILES: C[C@H](Oc1cc(-n2ccc(C(=O)N3CCCC3)n2)nc(-c2noc3c2CCC[C@@]32CCCc3sc(N)c(C#N)c32)n1)[C@@H]1CCCN1C] | 1.58 | 654 | A |

TABLE 62-continued

| # | structure | $t_{ret}$ [min] | [M + H]$^+$ | HPLC method |
|---|---|---|---|---|
| II-20 | 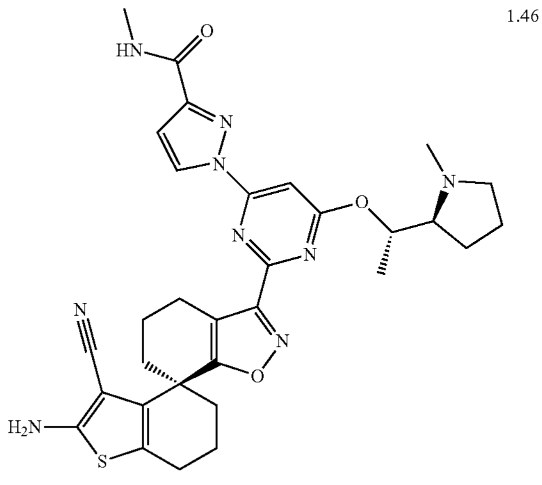 | 1.46 | 614 | A |
| II-21 | 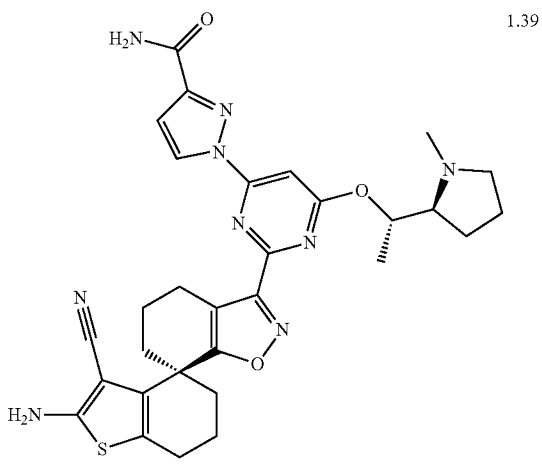 | 1.39 | 600 | A |
| II-22 | 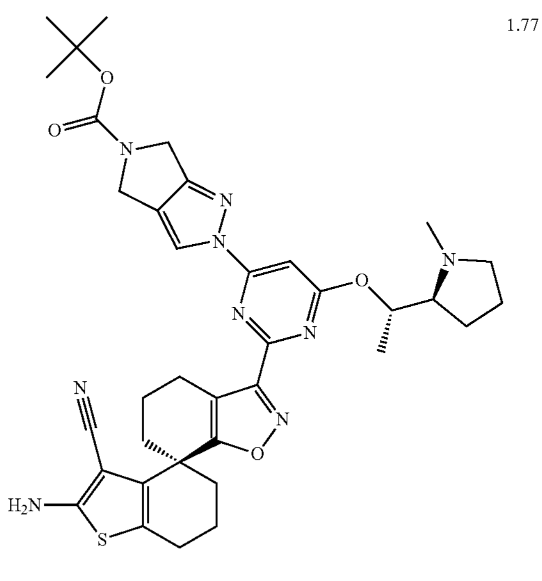 | 1.77 | 698 | A |

TABLE 62-continued

| # | structure | $t_{ret}$ [min] | $[M + H]^+$ | HPLC method |
|---|---|---|---|---|
| II-23 | 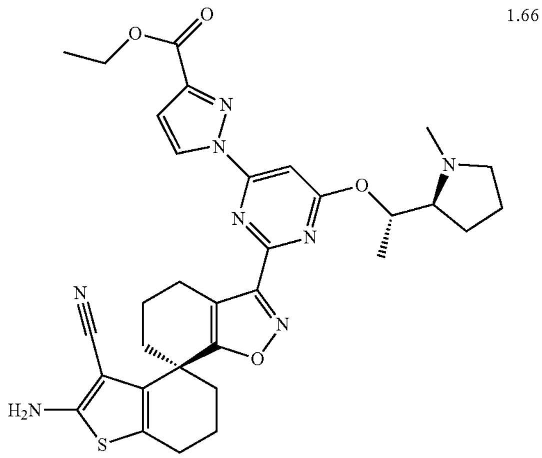 | 1.66 | 629 | A |
| II-188 | 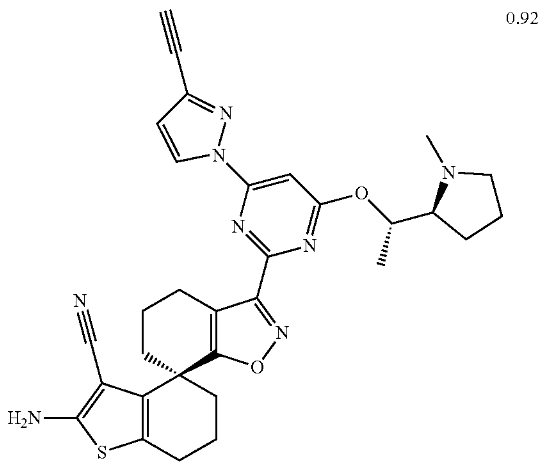 | 0.92 | 581 | C |
| II-189 | 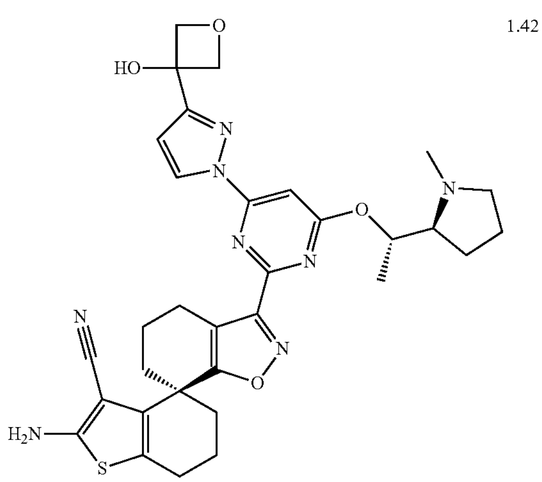 | 1.42 | 629 | A |

Experimental Procedure for the Synthesis of II-24

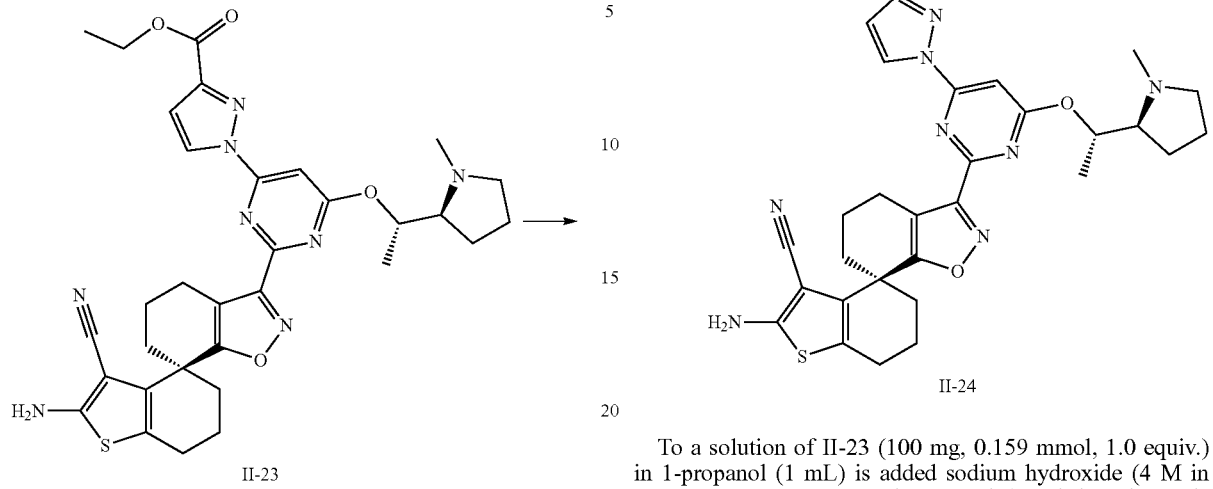

To a solution of II-23 (100 mg, 0.159 mmol, 1.0 equiv.) in 1-propanol (1 mL) is added sodium hydroxide (4 M in water, 99.4 µL, 0.40 mmol, 2.5 equiv.) and the mixture is stirred for 30 min at rt. After complete conversion, saturated NaHCO$_3$ is added, the mixture is washed with DCM, then the aqueous phase is acidified with HCl and extracted with DCM. The organic phases are dried, filtered and concentrated and the crude product is purified via RP chromatography to give the desired product II-24.

The following final compounds II (Table 63) are available in an analogous manner. The crude

TABLE 63

| # | structure | t$_{ret}$ [min] | [M + H]$^+$ | HPLC method |
|---|-----------|-----------------|-------------|-------------|
| II-24 | 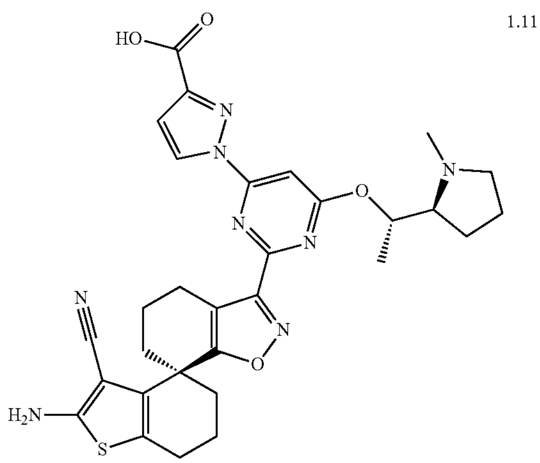 | 1.11 | 601 | A |

TABLE 63-continued

| # | structure | $t_{ret}$ [min] | [M + H]⁺ | HPLC method |
|---|---|---|---|---|
| II-190 | 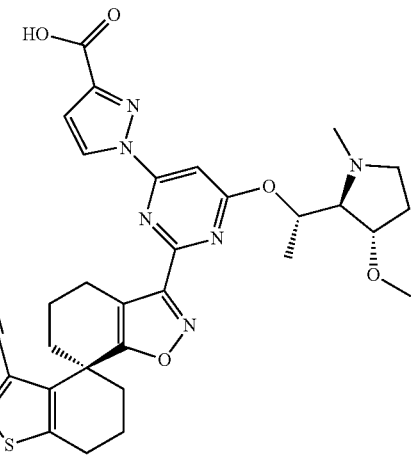 | 0.56 | 631 | C |

Experimental Procedure for the Synthesis of II-25

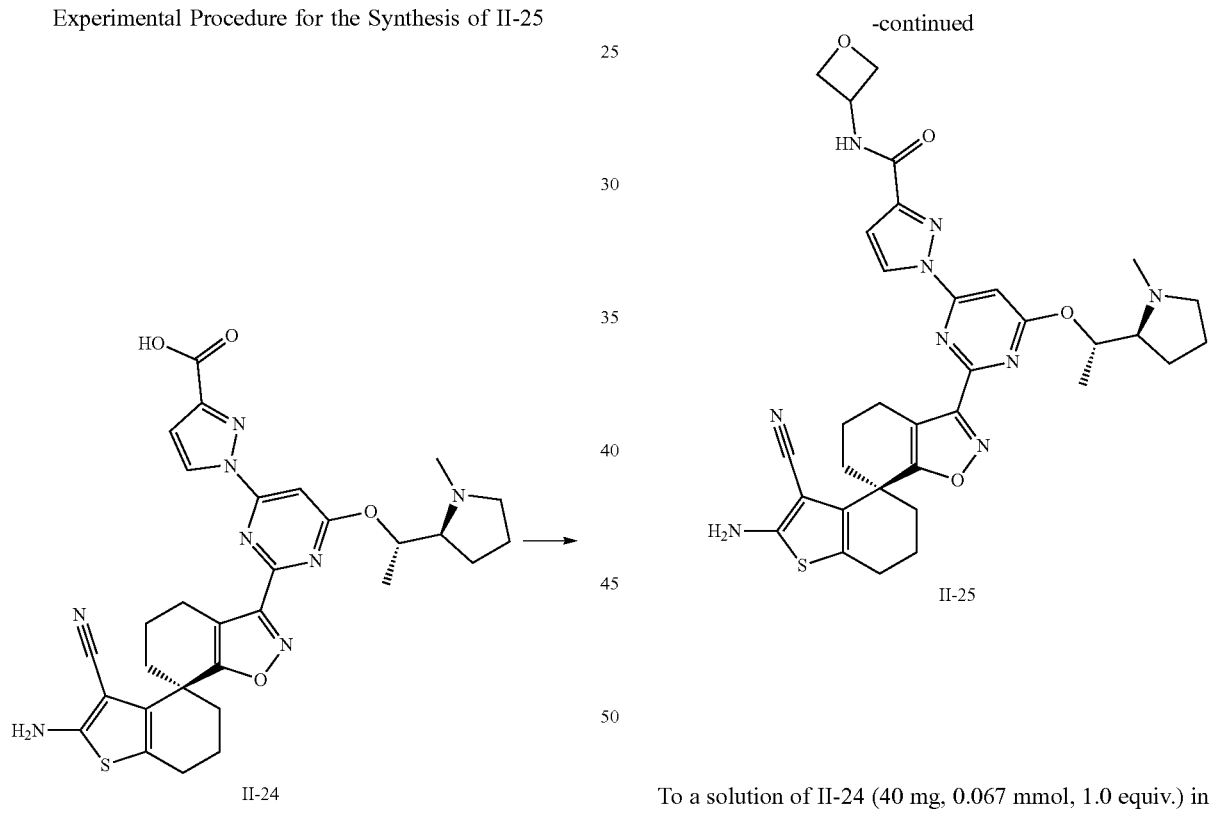

To a solution of II-24 (40 mg, 0.067 mmol, 1.0 equiv.) in DMF (0.4 mL) is added oxetan-3-amine hydrochloride (15 mg, 0.133 mmol, 2.0 equiv.), DIPEA (22.3 µL, 0.166 mmol, 2.5 equiv.) and 1-propanephosphonic anhydride (29.7 µL, 1.00 mmol, 1.5 equiv.) and the mixture is stirred for 3 h at rt. After complete conversion, saturated $NaHCO_3$ is added and the mixture is extracted with DCM. The organic phases are dried, filtered and concentrated and the crude product is purified via RP chromatography to give the desired product II-25.

The following final compounds II (Table 64) are available in an analogous manner. The crude product is purified by chromatography if necessary.

TABLE 64

| # | structure | $t_{ret}$ [min] | [M + H]⁺ | HPLC method |
|---|---|---|---|---|
| II-25 | 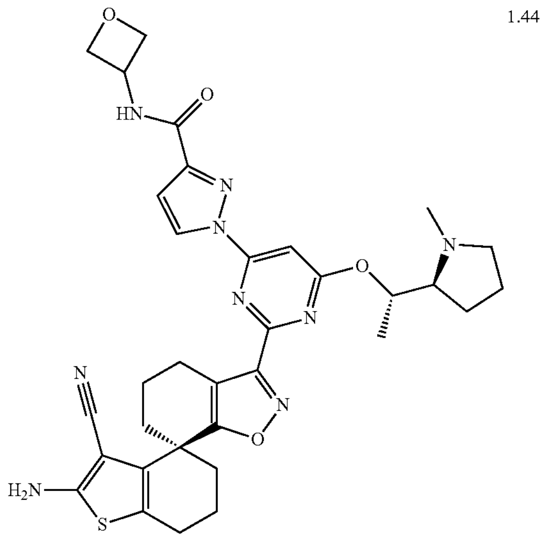 | 1.44 | 656 | A |
| II-26 | 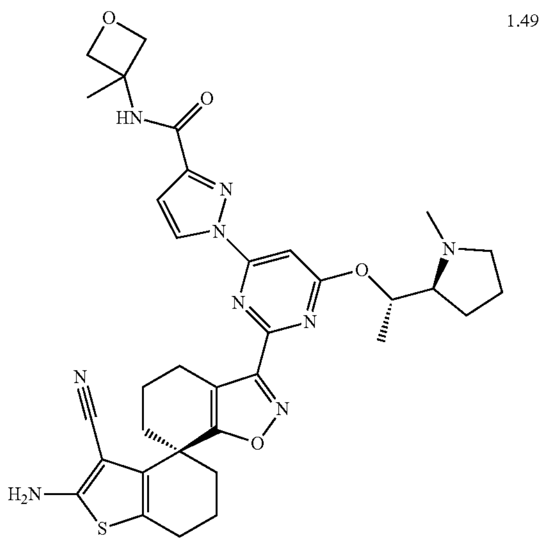 | 1.49 | 670 | A |
| II-191 | 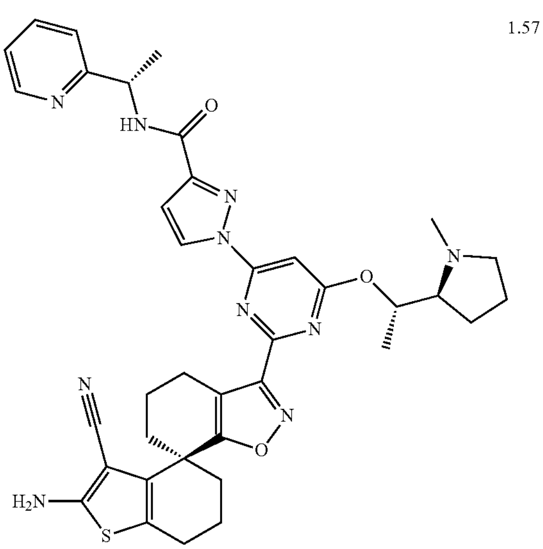 | 1.57 | 705 | A |

TABLE 64-continued
| # | structure | $t_{ret}$ [min] | [M + H]+ | HPLC method |
|---|---|---|---|---|
| II-192 | 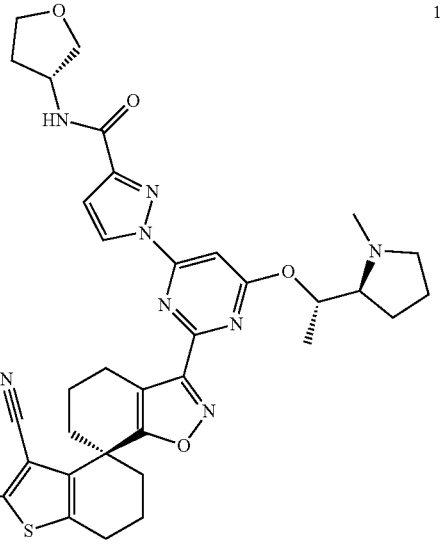 | 1.48 | 670 | A |
| II-193 | 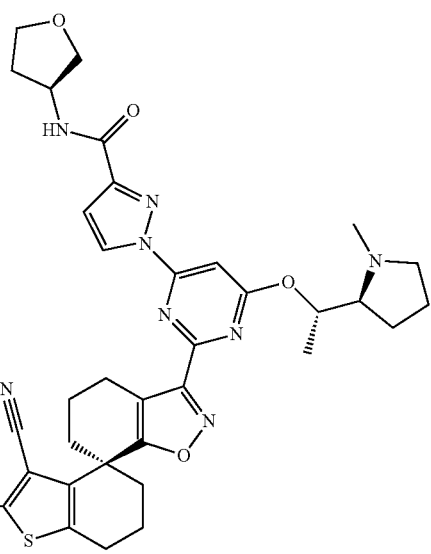 | 1.47 | 670 | A |
| II-194 | 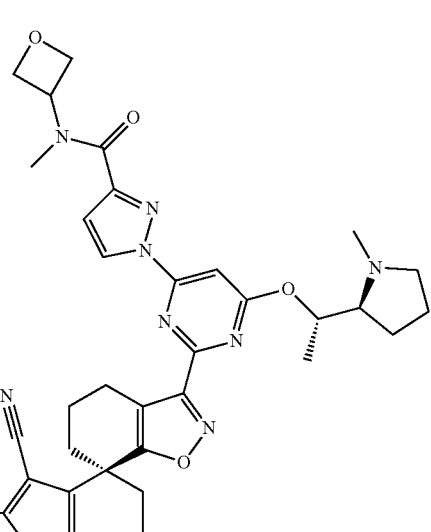 | 1.46 | 670 | A |

TABLE 64-continued
| # | structure | $t_{ret}$ [min] | $[M + H]^+$ | HPLC method |
|---|---|---|---|---|
| II-195 | 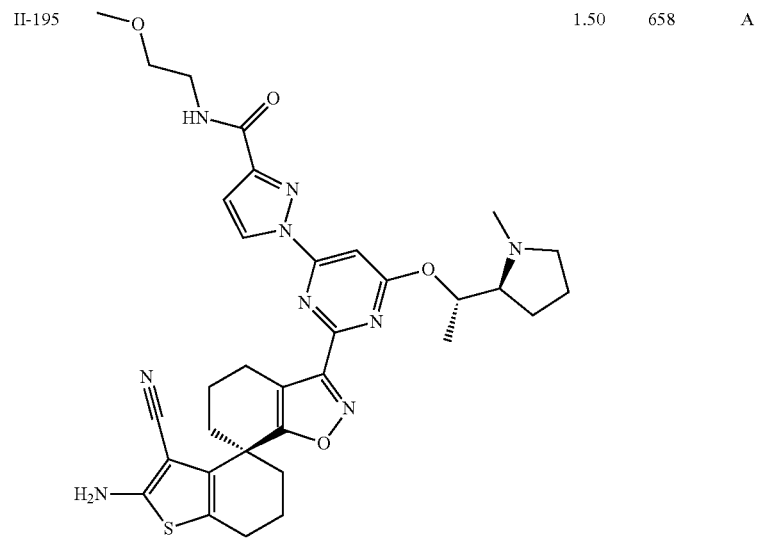 | 1.50 | 658 | A |
| II-196 | 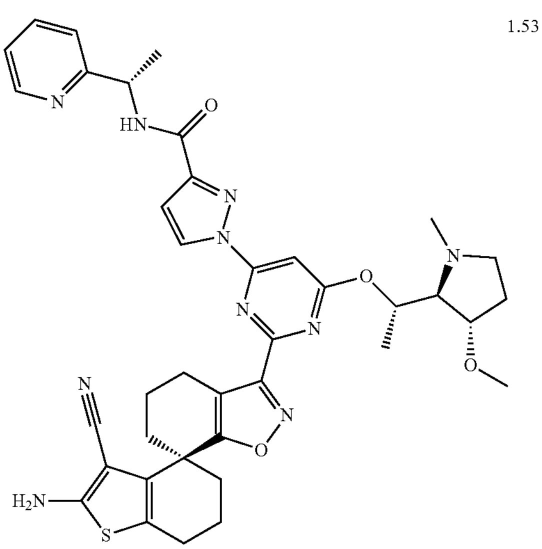 | 1.53 | 735 | A |

TABLE 64-continued

| # | structure | $t_{ret}$ [min] | [M + H]$^+$ | HPLC method |
|---|---|---|---|---|
| II-197 | 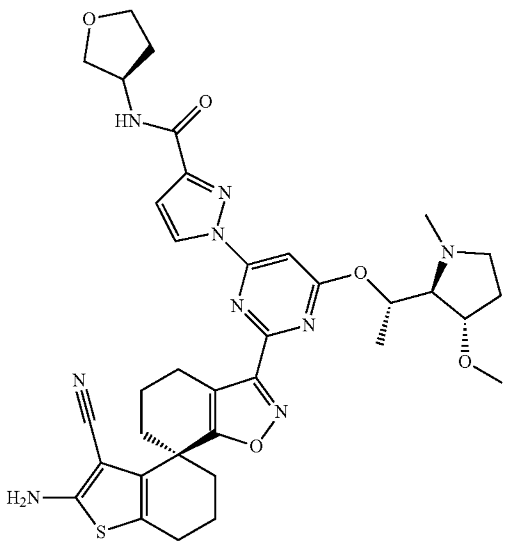 [SMILES: CO[C@H]1CCN(C)[C@@H]1[C@H](C)Oc1cc(-n2ccc(C(=O)N[C@@H]3CCOC3)n2)nc(-c2noc3c2CCC[C@@]32CCCc3sc(N)c(C#N)c32)n1] | 1.44 | 700 | A |
| II-198 | 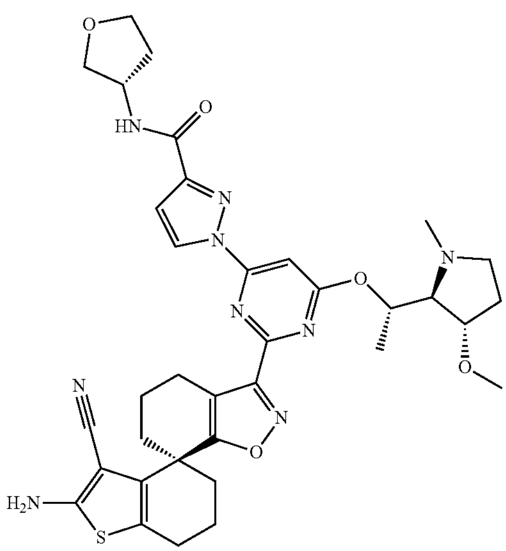 [SMILES: CO[C@H]1CCN(C)[C@@H]1[C@H](C)Oc1cc(-n2ccc(C(=O)N[C@H]3CCOC3)n2)nc(-c2noc3c2CCC[C@@]32CCCc3sc(N)c(C#N)c32)n1] | 1.44 | 700 | A |
| II-199 | 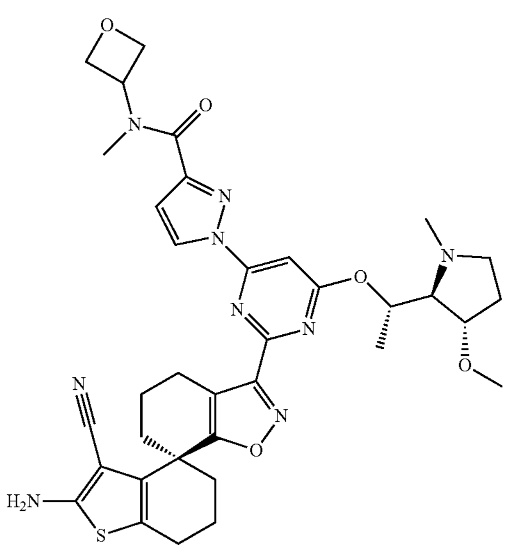 [SMILES: CO[C@H]1CCN(C)[C@@H]1[C@H](C)Oc1cc(-n2ccc(C(=O)N(C)C3COC3)n2)nc(-c2noc3c2CCC[C@@]32CCCc3sc(N)c(C#N)c32)n1] | 1.43 | 700 | A |

TABLE 64-continued
| # | structure | $t_{ret}$ [min] | $[M + H]^+$ | HPLC method |
|---|---|---|---|---|
| II-200 | 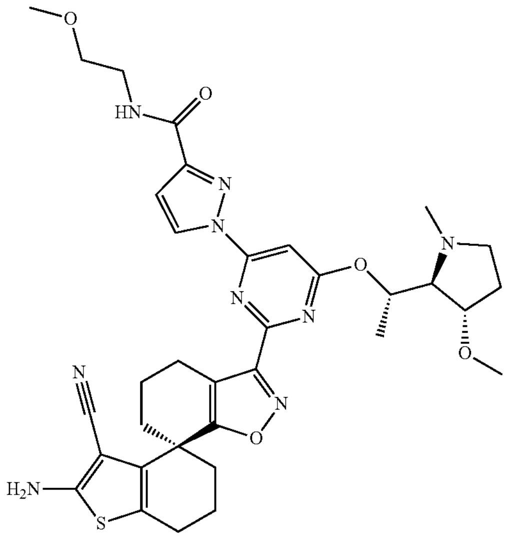 | 1.46 | 688 | A |
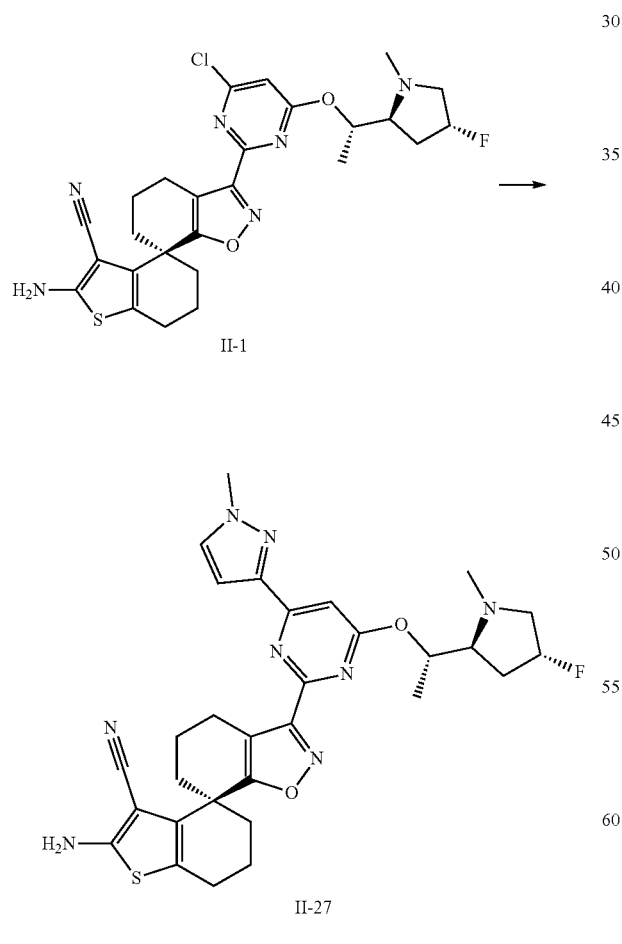
Experimental Procedure for the Synthesis of II-27

II-1 (70 mg, 0.1 mmol, 1.0 equiv.) is dissolved in dioxane (1 mL) cesium carbonate (2 M, 131 μL, 0.26 mmol, 2.5 equiv.) is added and the resulting suspension is stirred for 10 min at 80° C. 1-methyl-3-(4,4,5,5,-tetramethyl-1,3,2-dioxaborolan-2-yl)-1H-pyrazole (32.7 mg, 0.16 mmol, 1.5 equiv.) and XPhos-Pd-G3 (9.34 mg, 0.01 mmol, 0.1 equiv.) is added. The reaction is stirred under argon for 10 min, before the reaction mixture is heated for 18 h at 80° C. After complete conversion, the reaction mixture is extracted with NaHCO₃ and DCM. The organic phase is concentrated under reduced pressure, dissolved in DMSO and purified by RP chromatography to give the desired product II-27.

The following final compounds II (Table 65) are available in an analogous manner. The crude product is purified by chromatography if necessary.

TABLE 65

| # | structure | $t_{ret}$ [min] | [M + H]⁺ | HPLC method |
|---|---|---|---|---|
| II-27 | 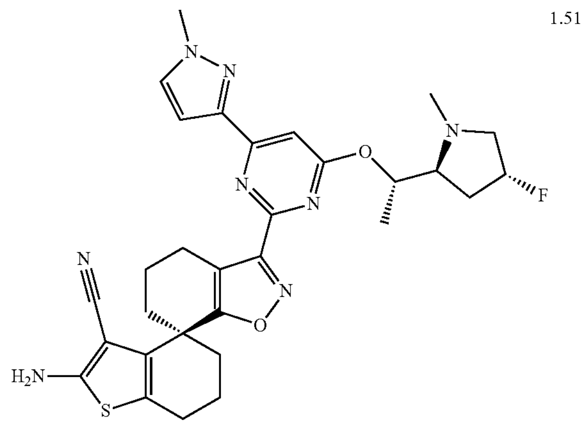 | 1.51 | 589 | A |
| II-28 | 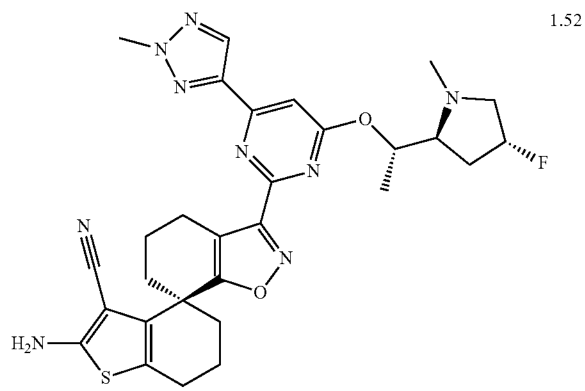 | 1.52 | 590 | A |
| II-29 | 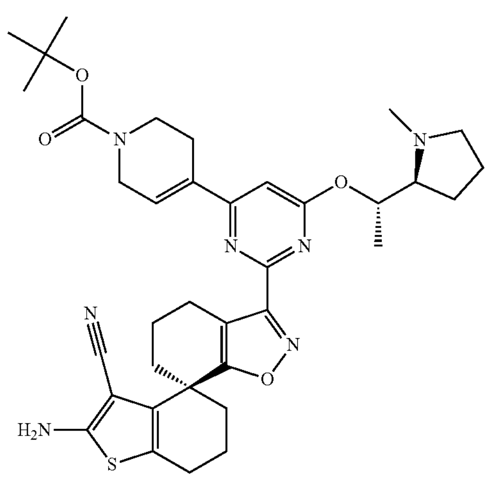 [SMILES: C[C@H](Oc1cc(C2=CCN(C(=O)OC(C)(C)C)CC2)nc(-c2noc3c2CCC[C@@]32CCCc3sc(N)c(C#N)c32)n1)[C@@H]1CCCN1C] | 1.79 | 672 | A |

Experimental Procedure for the Synthesis of II-30

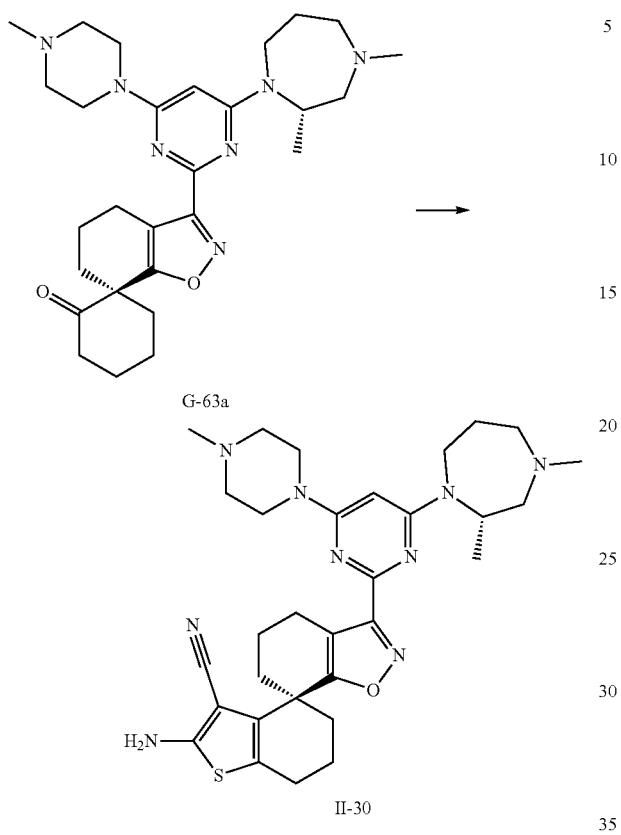

G-63a

II-30

To a solution of G-63a (94.0 mg, 0.18 mmol, 1.0 equiv.) and molecular sieves (3 Å) in anhydrous EtOH (2 mL) under an argon atmosphere are added malononitrile (64.4 mg, 0.97 mmol, 5.0 equiv.), sulfur (23.8 mg, 0.74 mmol, 4.0 equiv.) and ß-Alanine (69.5 mg, 0.78 mmol, 4.0 equiv.). The reaction mixture is stirred at 80° C. overnight. After complete conversion, the mixture is cooled to the rt, filtered and extracted with DCM and aq. sat. NaHCO$_3$. The organic phases are combined and concentrated under reduced pressure. The residue is dissolved in ACN and water and purified by basic RP chromatography to give the desired product II-30.

The following final compounds II (Table 66) are available in an analogous manner. The crude product is purified by chromatography if necessary. In the case of II-87, Boc-deprotection is observed during the reaction using G-48r as the starting material.

TABLE 66

| # | structure | $t_{ret}$ [min] | $[M + H]^+$ | HPLC method |
|---|---|---|---|---|
| II-30 | 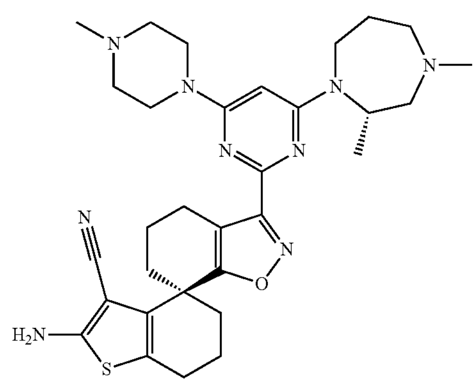 [SMILES: C[C@H]1CN(C)CCCN1c1cc(N2CCN(C)CC2)nc(-c2noc3c2CCC[C@@]32CCCc3sc(N)c(C#N)c32)n1] | 1.39 | 588 | A |

TABLE 66-continued

| # | structure | t_ret [min] | [M + H]+ | HPLC method |
|---|---|---|---|---|
| II-31 | 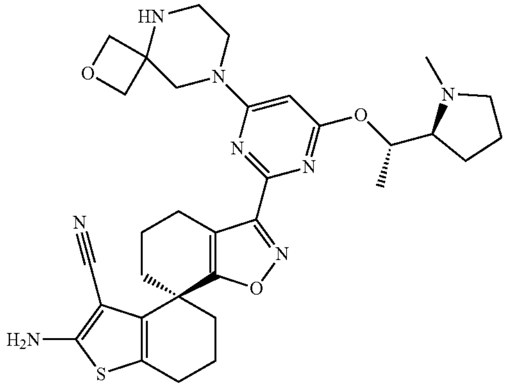 [SMILES: C[C@H](Oc1cc(N2CCNC3(COC3)C2)nc(-c2noc3c2CCC[C@@]32CCCc3sc(N)c(C#N)c32)n1)[C@@H]1CCCN1C] | 1.33 | 617 | A |
| II-32 | 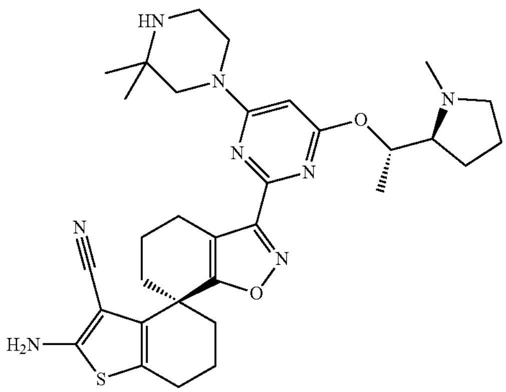 [SMILES: C[C@H](Oc1cc(N2CCNC(C)(C)C2)nc(-c2noc3c2CCC[C@@]32CCCc3sc(N)c(C#N)c32)n1)[C@@H]1CCCN1C] | 1.48 | 603 | A |
| II-33 | 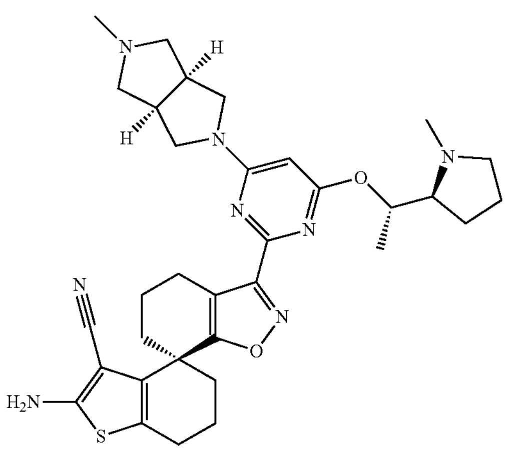 [SMILES: C[C@H](Oc1cc(N2C[C@H]3CN(C)C[C@H]3C2)nc(-c2noc3c2CCC[C@@]32CCCc3sc(N)c(C#N)c32)n1)[C@@H]1CCCN1C] | 1.59 | 615 | A |
| II-34 | 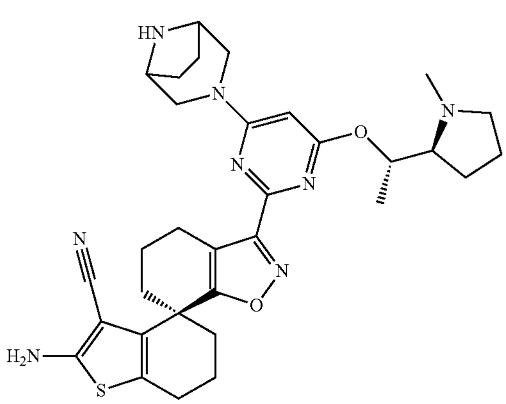 [SMILES: C[C@H](Oc1cc(N2CC3CCC(C2)N3)nc(-c2noc3c2CCC[C@@]32CCCc3sc(N)c(C#N)c32)n1)[C@@H]1CCCN1C] | 1.42 | 601 | A |

TABLE 66-continued

| # | structure | $t_{ret}$ [min] | $[M + H]^+$ | HPLC method |
|---|---|---|---|---|
| II-35 | 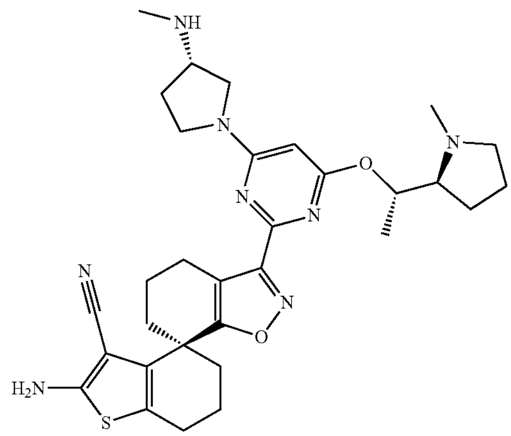 [SMILES: CN[C@H]1CCN(c2cc(O[C@@H](C)[C@@H]3CCCN3C)nc(-c3noc4c3CCC[C@@]43CCCc4sc(N)c(C#N)c43)n2)C1] | 1.49 | 589 | A |
| II-36 | 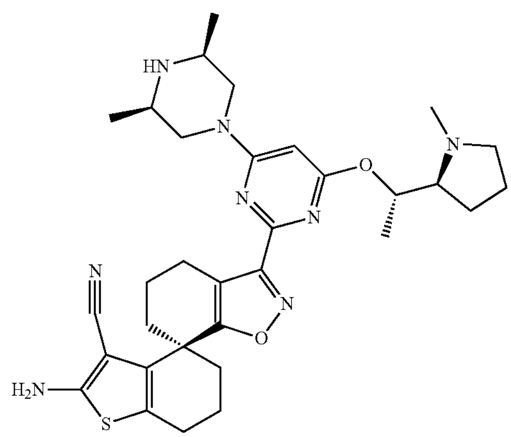 [SMILES: C[C@@H]1CN(c2cc(O[C@@H](C)[C@@H]3CCCN3C)nc(-c3noc4c3CCC[C@@]43CCCc4sc(N)c(C#N)c43)n2)C[C@H](C)N1] | 1.44 | 603 | A |
| II-37 | 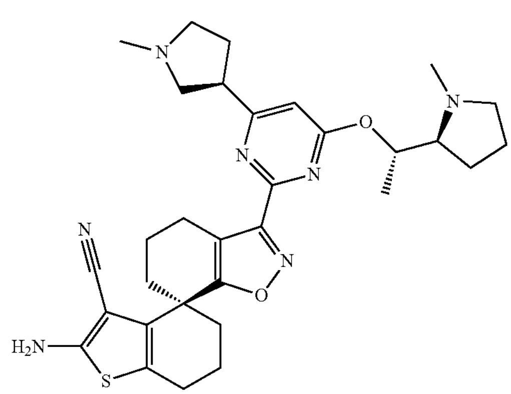 [SMILES: C[C@H](Oc1cc([C@@H]2CCN(C)C2)nc(-c2noc3c2CCC[C@@]32CCCc3sc(N)c(C#N)c32)n1)[C@@H]1CCCN1C] | 1.46 | 574 | A |

TABLE 66-continued

| # | structure | $t_{ret}$ [min] | $[M + H]^+$ | HPLC method |
|---|---|---|---|---|
| II-38 | 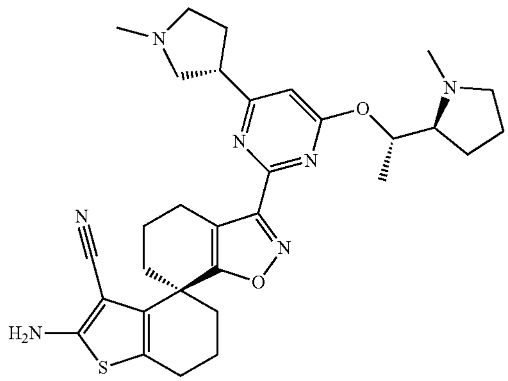 [SMILES: C[C@H](Oc1cc([C@H]2CCN(C)C2)nc(-c2noc3c2CCC[C@@]32CCCc3sc(N)c(C#N)c32)n1)[C@@H]1CCCN1C] | 1.52 | 574 | A |
| II-39 | 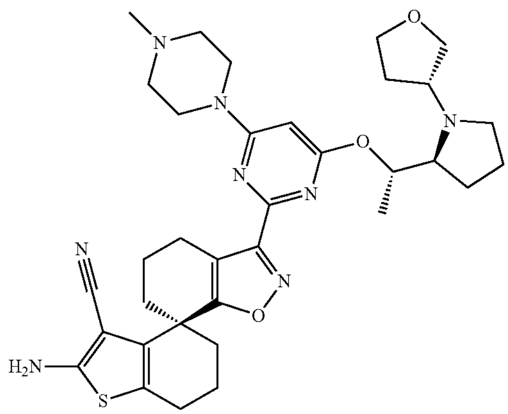 [SMILES: C[C@H](Oc1cc(N2CCN(C)CC2)nc(-c2noc3c2CCC[C@@]32CCCc3sc(N)c(C#N)c32)n1)[C@@H]1CCCN1[C@@H]1CCOC1] | 1.49 | 645 | A |
| II-40 | 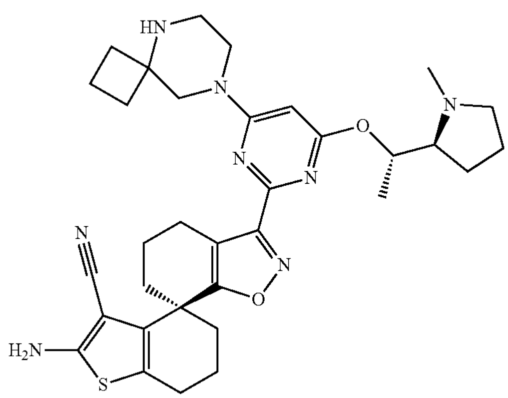 | 1.48 | 615 | A |
| II-41 | 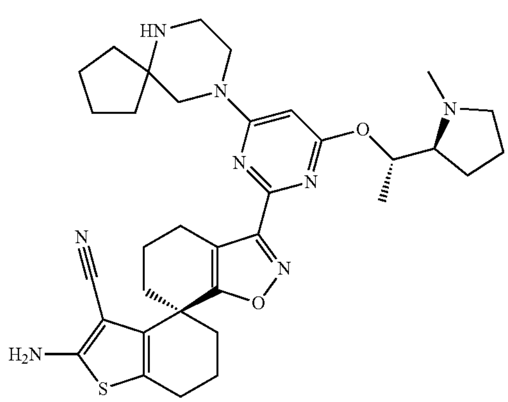 [SMILES: C[C@H](Oc1cc(N2CCNC3(CCCC3)C2)nc(-c2noc3c2CCC[C@@]32CCCc3sc(N)c(C#N)c32)n1)[C@@H]1CCCN1C] | 1.57 | 629 | A |

TABLE 66-continued

| # | structure | $t_{ret}$ [min] | $[M + H]^+$ | HPLC method |
|---|---|---|---|---|
| II-42 | 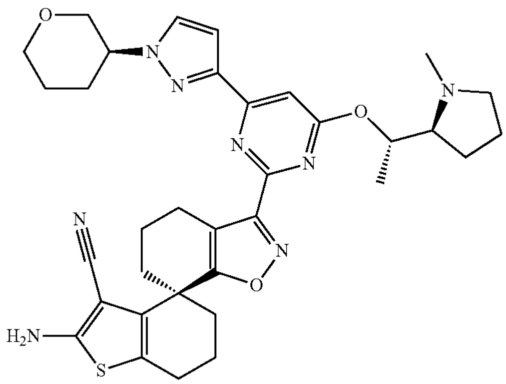 [SMILES: C[C@H](Oc1cc(-c2ccn([C@H]3CCCOC3)n2)nc(-c2noc3c2CCC[C@@]32CCCc3sc(N)c(C#N)c32)n1)[C@@H]1CCCN1C] | 1.57 | 641 | A |
| II-43 | 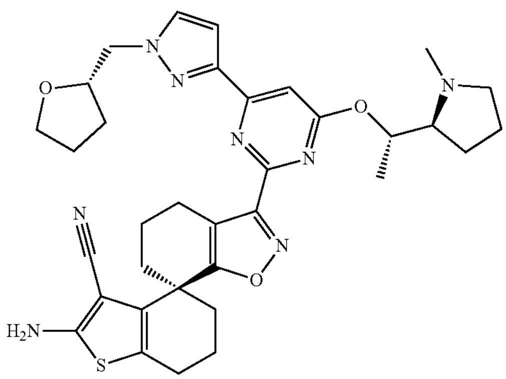 [SMILES: C[C@H](Oc1cc(-c2ccn(C[C@@H]3CCCO3)n2)nc(-c2noc3c2CCC[C@@]32CCCc3sc(N)c(C#N)c32)n1)[C@@H]1CCCN1C] | 1.57 | 64 | A |
| II-44 | 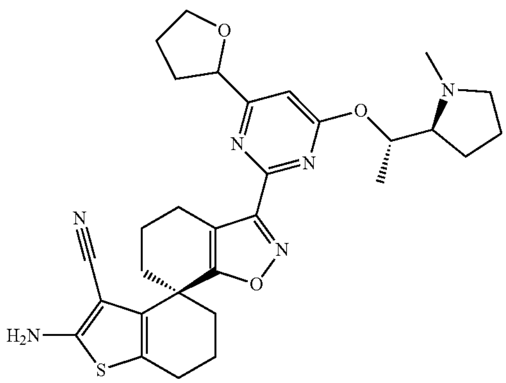 [SMILES: C[C@H](Oc1cc(C2CCCO2)nc(-c2noc3c2CCC[C@@]32CCCc3sc(N)c(C#N)c32)n1)[C@@H]1CCCN1C] | 1.58 | 561 | A |
| II-45 | 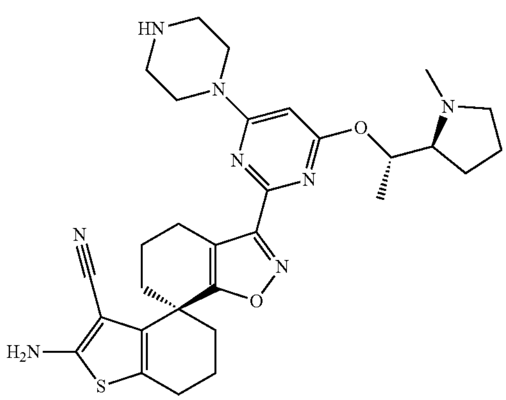 [SMILES: C[C@H](Oc1cc(N2CCNCC2)nc(-c2noc3c2CCC[C@@]32CCCc3sc(N)c(C#N)c32)n1)[C@@H]1CCCN1C] | 1.51 | 575 | A |

TABLE 66-continued

| # | structure | $t_{ret}$ [min] | $[M + H]^+$ | HPLC method |
|---|---|---|---|---|
| II-46 | 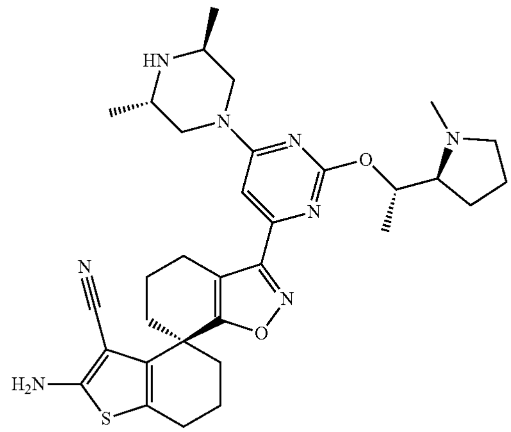 [SMILES: C[C@H](Oc1nc(-c2noc3c2CCC[C@@]32CCCc3sc(N)c(C#N)c32)cc(N2C[C@H](C)N[C@@H](C)C2)n1)[C@@H]1CCCN1C] | 1.43 | 603 | A |
| II-47 | 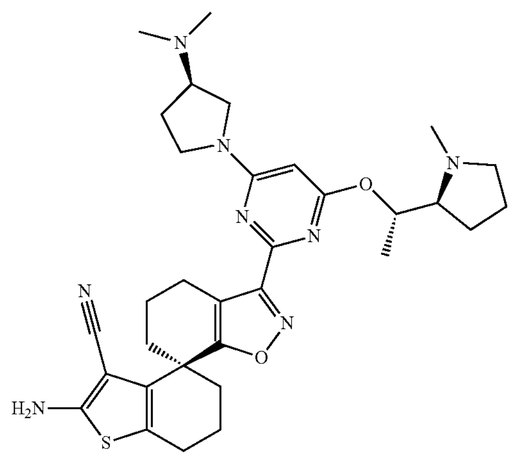 [SMILES: C[C@H](Oc1cc(N2CC[C@@H](N(C)C)C2)nc(-c2noc3c2CCC[C@@]32CCCc3sc(N)c(C#N)c32)n1)[C@@H]1CCCN1C] | 1.55 | 603.0 | A |
| II-48 | 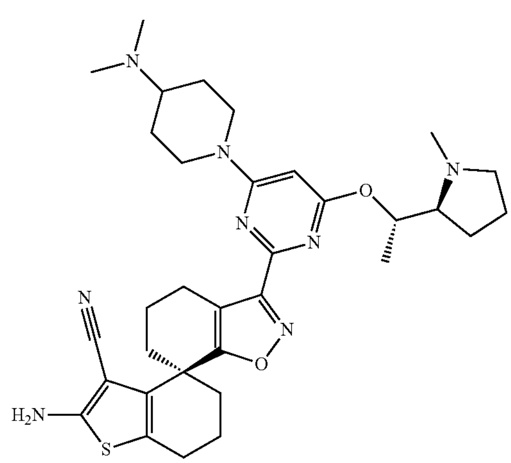 [SMILES: C[C@H](Oc1cc(N2CCC(N(C)C)CC2)nc(-c2noc3c2CCC[C@@]32CCCc3sc(N)c(C#N)c32)n1)[C@@H]1CCCN1C] | 1.57 | 617 | A |

TABLE 66-continued

| # | structure | $t_{ret}$ [min] | $[M + H]^+$ | HPLC method |
|---|---|---|---|---|
| II-49 | 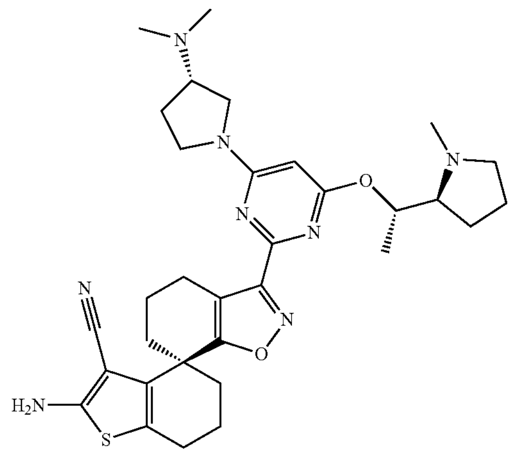 [SMILES: C[C@H](Oc1cc(N2CC[C@H](N(C)C)C2)nc(-c2noc3c2CCC[C@@]32CCCc3sc(N)c(C#N)c32)n1)[C@@H]1CCCN1C] | 1.56 | 603 | A |
| II-50 | 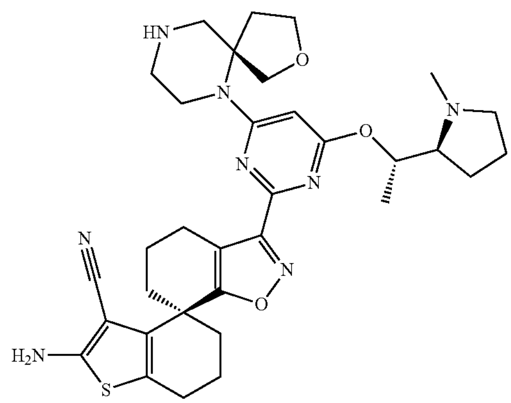 [SMILES: C[C@H](Oc1cc(N2CCNC[C@]23CCOC3)nc(-c2noc3c2CCC[C@@]32CCCc3sc(N)c(C#N)c32)n1)[C@@H]1CCCN1C] | 1.36 | 631.0 | A |
| II-51 | 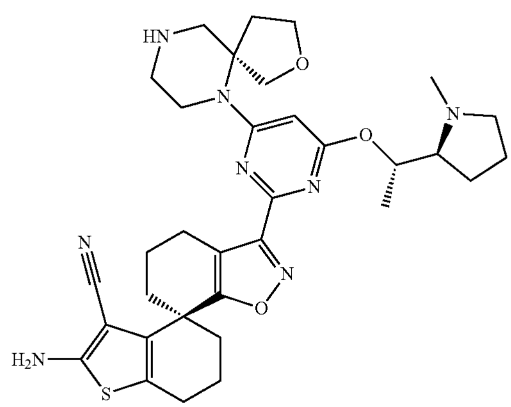 [SMILES: C[C@H](Oc1cc(N2CCNC[C@@]23CCOC3)nc(-c2noc3c2CCC[C@@]32CCCc3sc(N)c(C#N)c32)n1)[C@@H]1CCCN1C] | 1.33 | 631.0 | A |

TABLE 66-continued

| # | structure | $t_{ret}$ [min] | [M + H]$^+$ | HPLC method |
|---|---|---|---|---|
| II-52 | 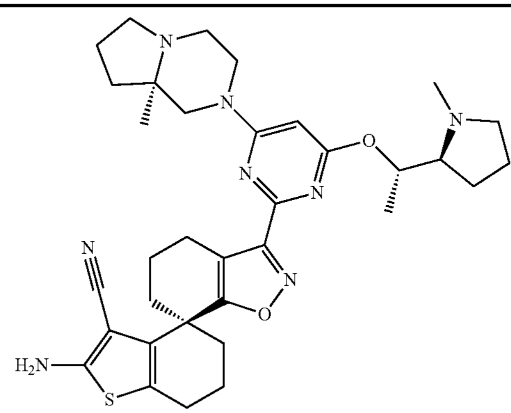 | 1.71 | 629.0 | A |
| II-53 | 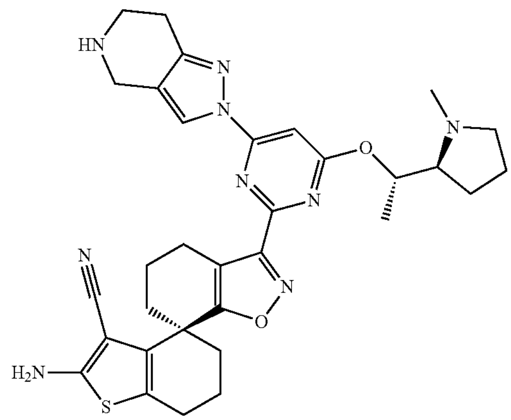 [SMILES: C[C@H](Oc1cc(-n2cc3c(n2)CCNC3)nc(-c2noc3c2CCC[C@@]32CCCc3sc(N)c(C#N)c32)n1)[C@@H]1CCCN1C] | 1.45 | 612 | A |
| II-54 | 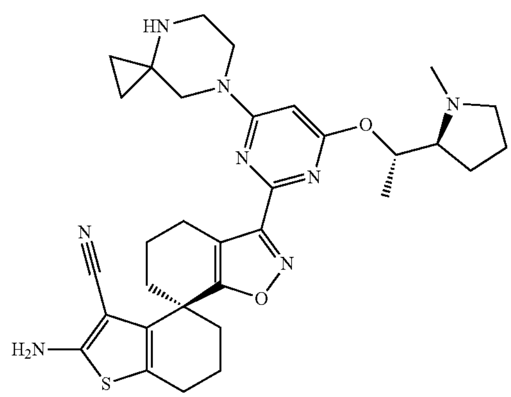 [SMILES: C[C@H](Oc1cc(N2CCNC3(CC3)C2)nc(-c2noc3c2CCC[C@@]32CCCc3sc(N)c(C#N)c32)n1)[C@@H]1CCCN1C] | 1.40 | 601 | A |
| II-55 | 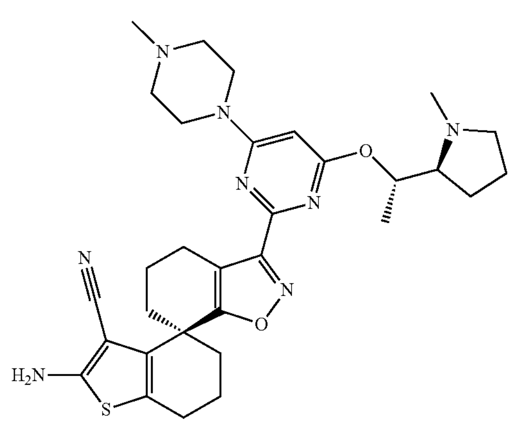 [SMILES: C[C@H](Oc1cc(N2CCN(C)CC2)nc(-c2noc3c2CCC[C@@]32CCCc3sc(N)c(C#N)c32)n1)[C@@H]1CCCN1C] | 1.44 | 589.0 | A |

TABLE 66-continued
| # | structure | $t_{ret}$ [min] | $[M + H]^+$ | HPLC method |
|---|---|---|---|---|
| II-56 | 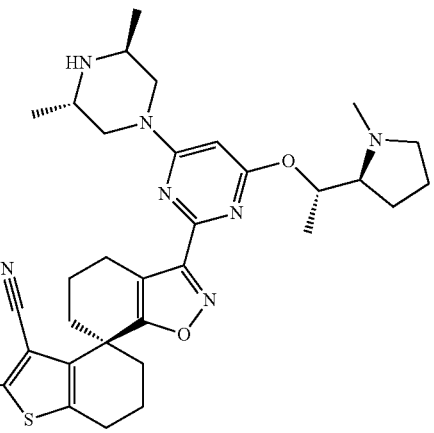 | 1.47 | 603.0 | A |
| II-57 | 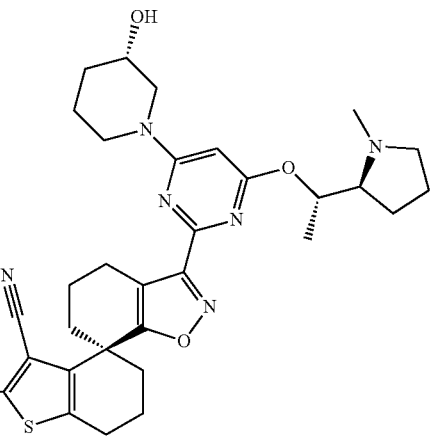 | 1.41 | 590 | A |
| II-58 | 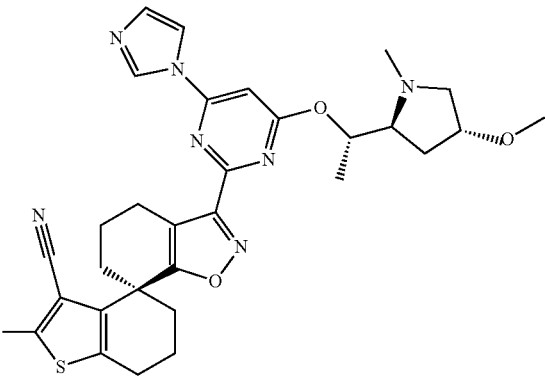 | 1.36 | 587 | A |

TABLE 66-continued

| # | structure | $t_{ret}$ [min] | $[M + H]^+$ | HPLC method |
|---|---|---|---|---|
| II-59 | 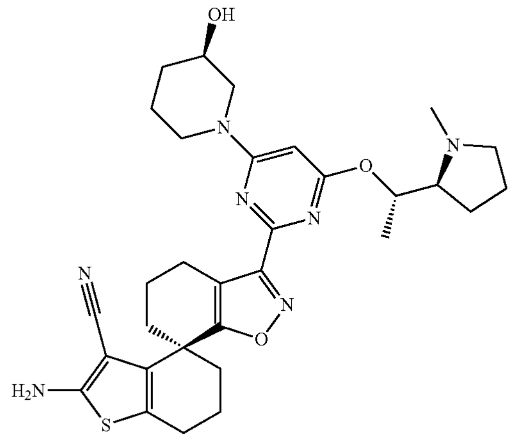 [SMILES: C[C@H](Oc1cc(N2CCC[C@@H](O)C2)nc(-c2noc3c2CCC[C@@]32CCCc3sc(N)c(C#N)c32)n1)[C@@H]1CCCN1C] | 1.42 | 590 | A |
| II-60 | 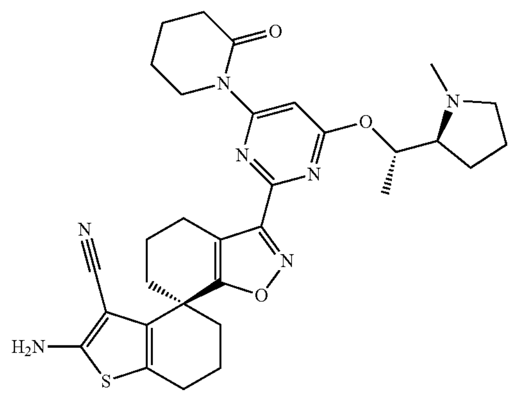 [SMILES: C[C@H](Oc1cc(N2CCCCC2=O)nc(-c2noc3c2CCC[C@@]32CCCc3sc(N)c(C#N)c32)n1)[C@@H]1CCCN1C] | 1.54 | 620 | A |
| II-61 | 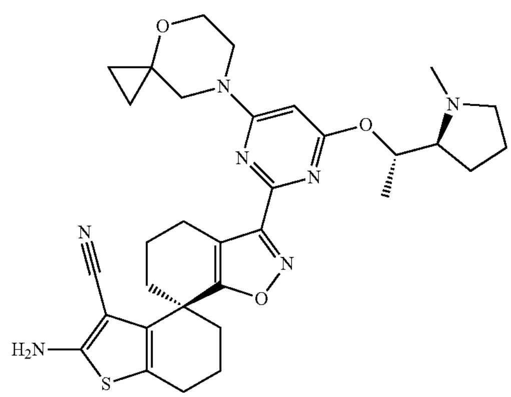 [SMILES: C[C@H](Oc1cc(N2CCOC3(CC3)C2)nc(-c2noc3c2CCC[C@@]32CCCc3sc(N)c(C#N)c32)n1)[C@@H]1CCCN1C] | 1.60 | 602 | A |
| II-62 | 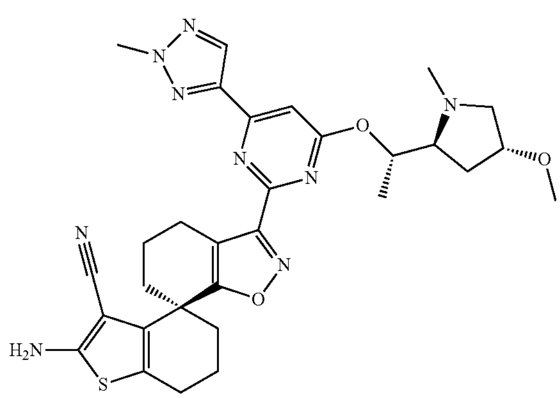 [SMILES: CO[C@@H]1C[C@@H]([C@H](C)Oc2cc(-c3cnn(C)n3)nc(-c3noc4c3CCC[C@@]43CCCc4sc(N)c(C#N)c43)n2)N(C)C1] | 1.49 | 602 | A |

TABLE 66-continued

| # | structure | $t_{ret}$ [min] | $[M + H]^+$ | HPLC method |
|---|---|---|---|---|
| II-63 | 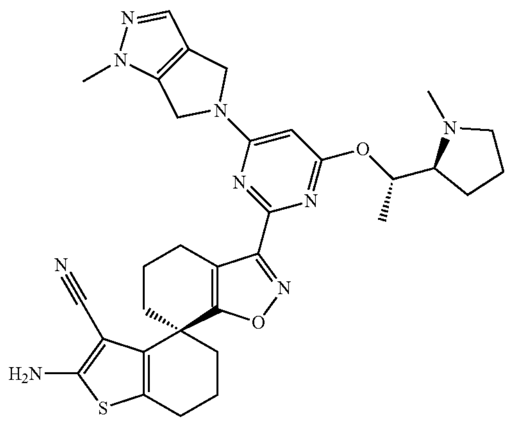 [SMILES: C[C@H](Oc1cc(N2Cc3cnn(C)c3C2)nc(-c2noc3c2CCC[C@@]32CCCc3sc(N)c(C#N)c32)n1)[C@@H]1CCCN1C] | 1.54 | 612 | A |
| II-64 | 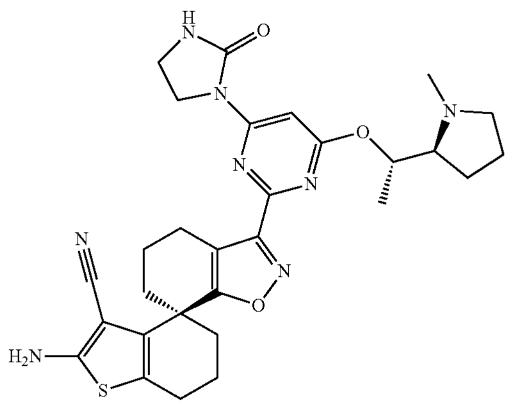 [SMILES: C[C@H](Oc1cc(N2CCNC2=O)nc(-c2noc3c2CCC[C@@]32CCCc3sc(N)c(C#N)c32)n1)[C@@H]1CCCN1C] | 1.38 | 575 | A |
| II-65 | 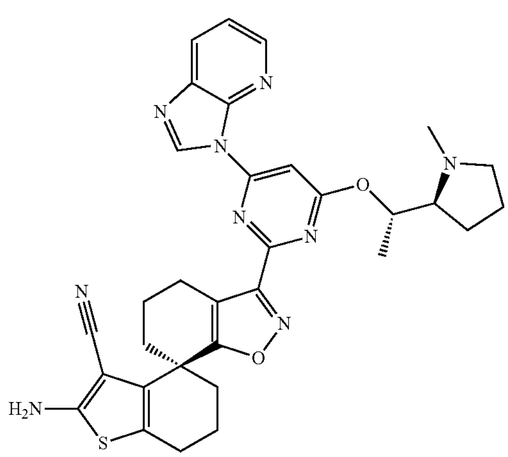 [SMILES: C[C@H](Oc1cc(-n2cnc3cccnc32)nc(-c2noc3c2CCC[C@@]32CCCc3sc(N)c(C#N)c32)n1)[C@@H]1CCCN1C] | 1.59 | 608 | A |

TABLE 66-continued
| # | structure | t_ret [min] | [M + H]+ | HPLC method |
|---|---|---|---|---|
| II-66 | 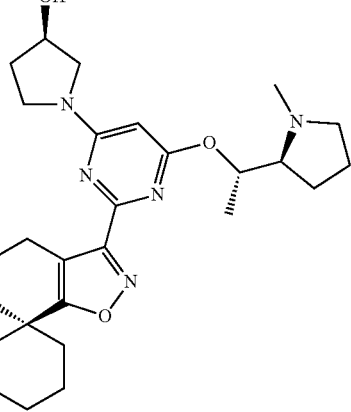 | 1.37 | 576 | A |
| II-67 | 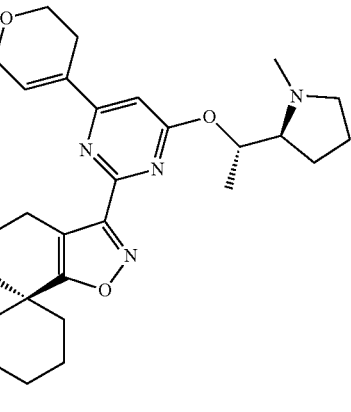 | 1.54 | 573 | A |
| II-68 | 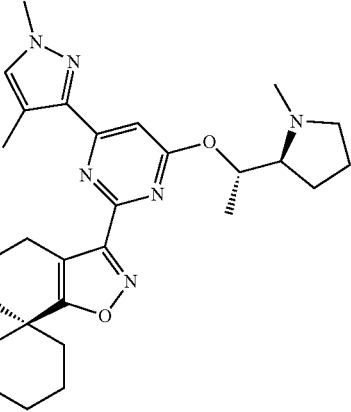 | 1.58 | 585 | A |

TABLE 66-continued
| # | structure | $t_{ret}$ [min] | $[M + H]^+$ | HPLC method |
|---|---|---|---|---|
| II-69 | 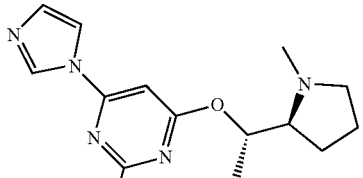 | 1.4 | 557 | A |
| II-70 | 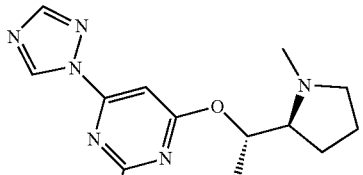 | 1.46 | 558 | A |
| II-71 | 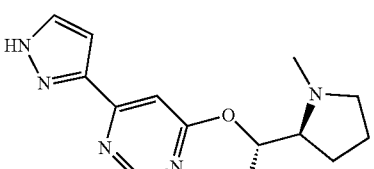 | 1.43 | 557 | A |
| II-72 | 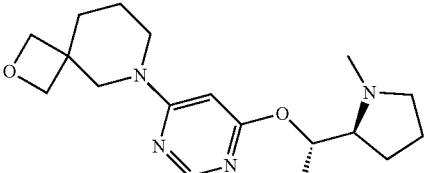 | 1.51 | 616 | A |

TABLE 66-continued
| # | structure | $t_{ret}$ [min] | $[M + H]^+$ | HPLC method |
|---|---|---|---|---|
| II-73 | 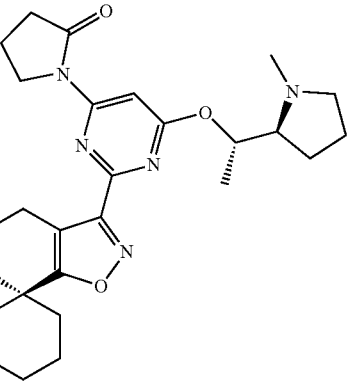 | 1.52 | 574 | A |
| II-74 | 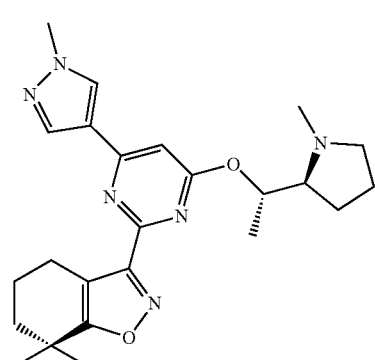 | 1.47 | 571 | A |
| II-75 | 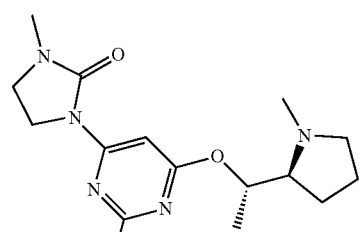 | 1.48 | 589 | A |
| II-76 | 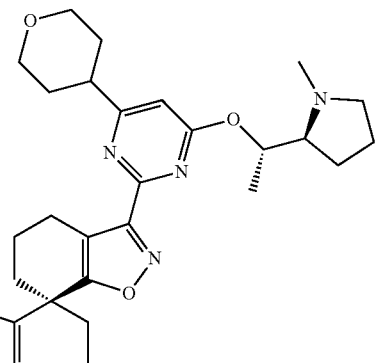 | 1.53 | 575 | A |

TABLE 66-continued

| # | structure | t_ret [min] | [M + H]+ | HPLC method |
|---|---|---|---|---|
| II-77 | 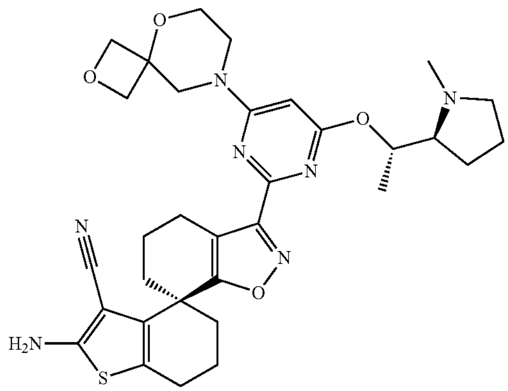 | 1.44 | 618 | A |
| II-78 | 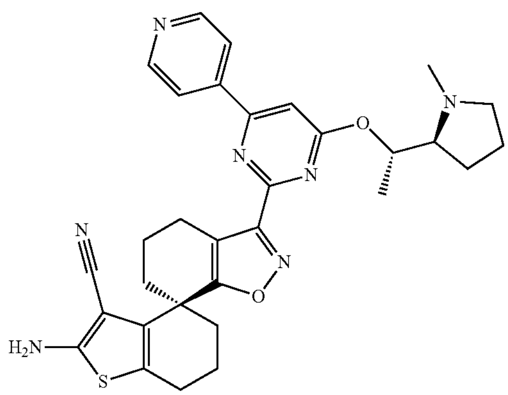 [SMILES: C[C@H](Oc1cc(-c2ccncc2)nc(-c2noc3c2CCC[C@@]32CCCc3sc(N)c(C#N)c32)n1)[C@@H]1CCCN1C] | 1.47 | 568 | A |
| II-79 | 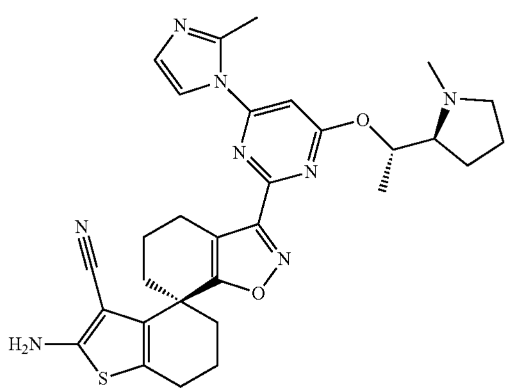 [SMILES: Cc1nccn1-c1cc(O[C@@H](C)[C@@H]2CCCN2C)nc(-c2noc3c2CCC[C@@]32CCCc3sc(N)c(C#N)c32)n1] | 1.73 | 571 | A |
| II-80 | 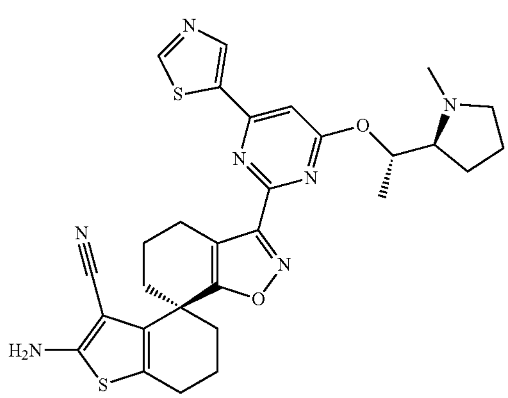 [SMILES: C[C@H](Oc1cc(-c2cncs2)nc(-c2noc3c2CCC[C@@]32CCCc3sc(N)c(C#N)c32)n1)[C@@H]1CCCN1C] | 1.49 | 574 | A |

TABLE 66-continued

| # | structure | $t_{ret}$ [min] | $[M + H]^+$ | HPLC method |
|---|---|---|---|---|
| II-81 | 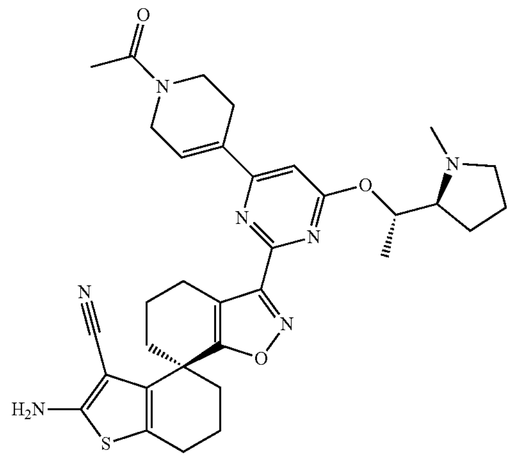 [SMILES: CC(=O)N1CC=C(c2cc(O[C@@H](C)[C@@H]3CCCN3C)nc(-c3noc4c3CCC[C@@]43CCCc4sc(N)c(C#N)c43)n2)CC1] | 1.41 | 614 | A |
| II-82 | 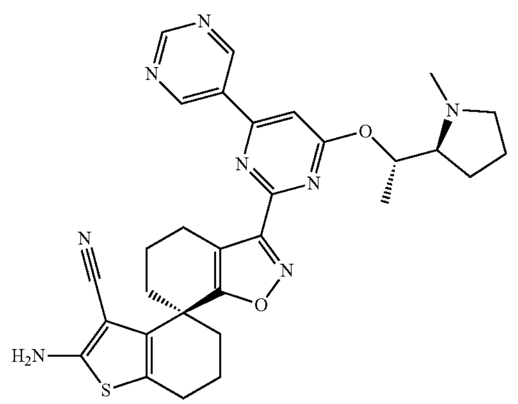 [SMILES: C[C@H](Oc1cc(-c2cncnc2)nc(-c2noc3c2CCC[C@@]32CCCc3sc(N)c(C#N)c32)n1)[C@@H]1CCCN1C] | 1.42 | 569 | A |
| II-83 | 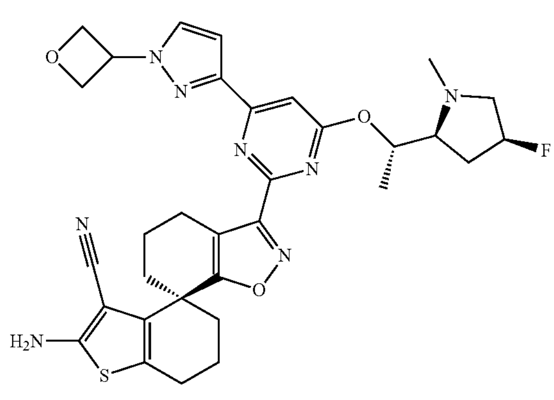 [SMILES: C[C@H](Oc1cc(-c2ccn(C3COC3)n2)nc(-c2noc3c2CCC[C@@]32CCCc3sc(N)c(C#N)c32)n1)[C@@H]1C[C@H](F)CN1C] | 1.44 | 631 | A |

TABLE 66-continued

| # | structure | t_ret [min] | [M + H]+ | HPLC method |
|---|-----------|-------------|----------|-------------|
| II-84 | 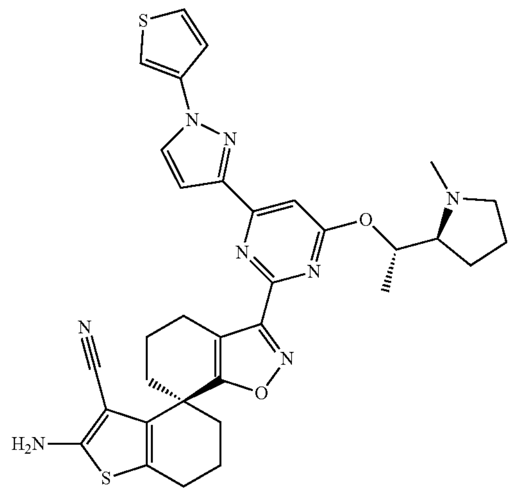 [SMILES: C[C@H](Oc1cc(-c2ccn(-c3ccsc3)n2)nc(-c2noc3c2CCC[C@@]32CCCc3sc(N)c(C#N)c32)n1)[C@@H]1CCCN1C] | 1.73 | 639 | A |
| II-85 | 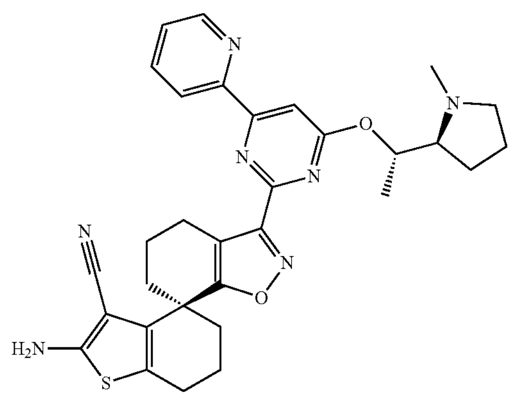 [SMILES: C[C@H](Oc1cc(-c2ccccn2)nc(-c2noc3c2CCC[C@@]32CCCc3sc(N)c(C#N)c32)n1)[C@@H]1CCCN1C] | 1.59 | 568 | A |
| II-86 | 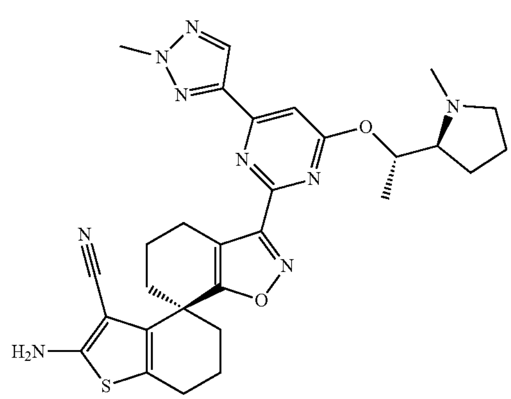 [SMILES: C[C@H](Oc1cc(-c2cnn(C)n2)nc(-c2noc3c2CCC[C@@]32CCCc3sc(N)c(C#N)c32)n1)[C@@H]1CCCN1C] | 1.55 | 572 | A |

TABLE 66-continued

| # | structure | $t_{ret}$ [min] | [M + H]⁺ | HPLC method |
|---|---|---|---|---|
| II-87 | 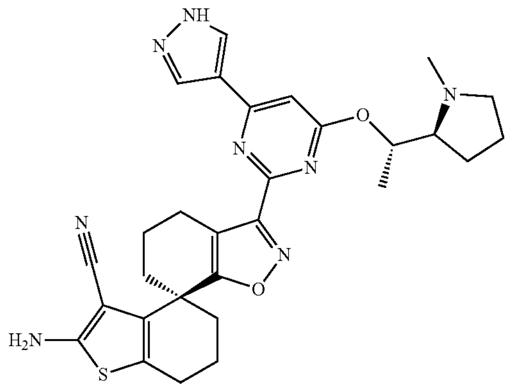 [SMILES: C[C@H](Oc1cc(-c2cn[nH]c2)nc(-c2noc3c2CCC[C@@]32CCCc3sc(N)c(C#N)c32)n1)[C@@H]1CCCN1C] | 1.36 | 557 | A |
| II-88 | 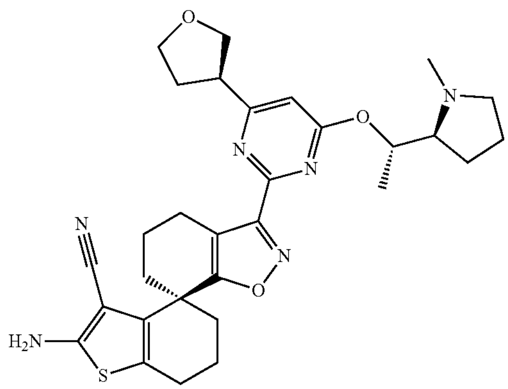 [SMILES: C[C@H](Oc1cc([C@H]2CCOC2)nc(-c2noc3c2CCC[C@@]32CCCc3sc(N)c(C#N)c32)n1)[C@@H]1CCCN1C] | 2.41 | 561 | A |
| II-89 | 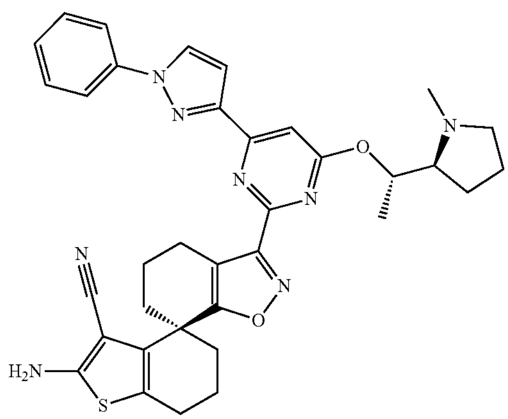 [SMILES: C[C@H](Oc1cc(-c2ccn(-c3ccccc3)n2)nc(-c2noc3c2CCC[C@@]32CCCc3sc(N)c(C#N)c32)n1)[C@@H]1CCCN1C] | 1.80 | 633 | A |
| II-90 | 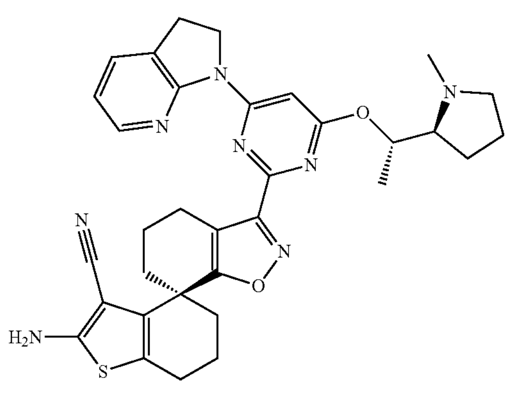 [SMILES: C[C@H](Oc1cc(N2CCc3cccnc32)nc(-c2noc3c2CCC[C@@]32CCCc3sc(N)c(C#N)c32)n1)[C@@H]1CCCN1C] | 1.77 | 609 | A |

TABLE 66-continued
| # | structure | $t_{ret}$ [min] | $[M + H]^+$ | HPLC method |
|---|---|---|---|---|
| II-91 | 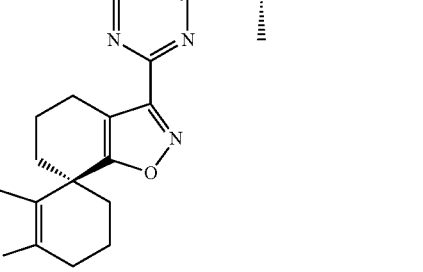 | 1.45 | 601 | A |
| II-92 | 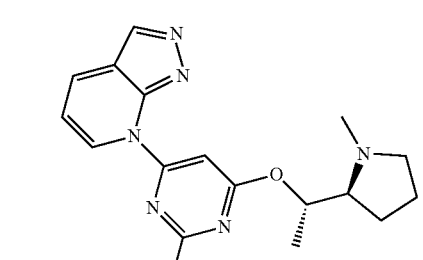 | 1.59 | 608 | A |
| II-93 | 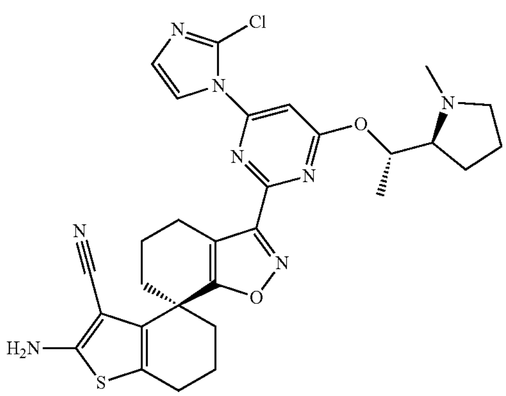 [SMILES: C[C@H](Oc1cc(-n2ccnc2Cl)nc(-c2noc3c2CCC[C@@]32CCCc3sc(N)c(C#N)c32)n1)[C@@H]1CCCN1C] | 1.52 | 591 | A |
| II-94 | 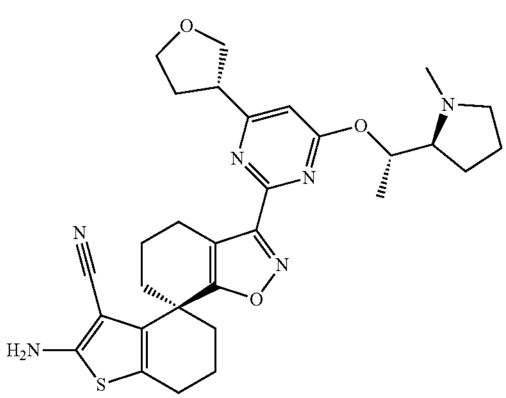 [SMILES: C[C@H](Oc1cc([C@@H]2CCOC2)nc(-c2noc3c2CCC[C@@]32CCCc3sc(N)c(C#N)c32)n1)[C@@H]1CCCN1C] | 1.50 | 561 | A |

TABLE 66-continued
| # | structure | t_ret [min] | [M + H]+ | HPLC method |
|---|---|---|---|---|
| II-95 | 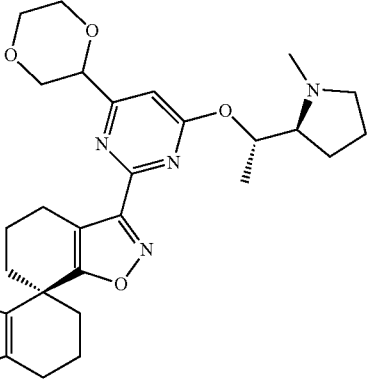 | 1.52 | 577 | A |
| II-96 | 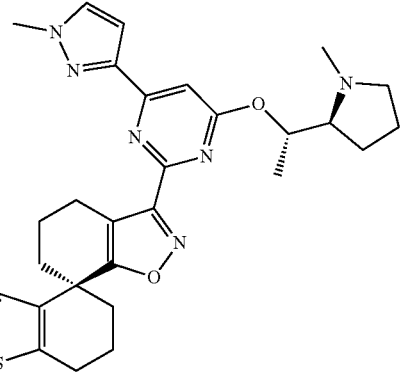 | 1.49 | 571 | A |
| II-97 | 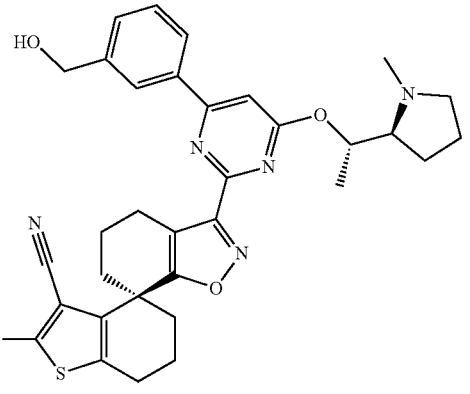 | 1.52 | 597 | A |

TABLE 66-continued
| # | structure | t_ret [min] | [M + H]+ | HPLC method |
|---|---|---|---|---|
| II-98 | 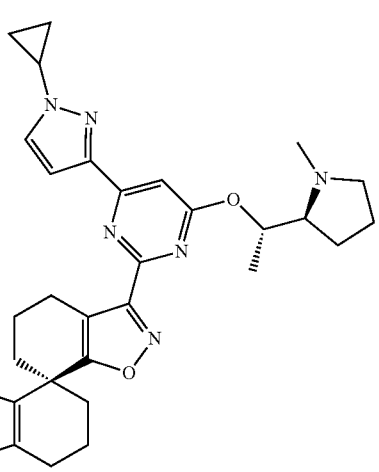 | 1.61 | 597 | A |
| II-99 | 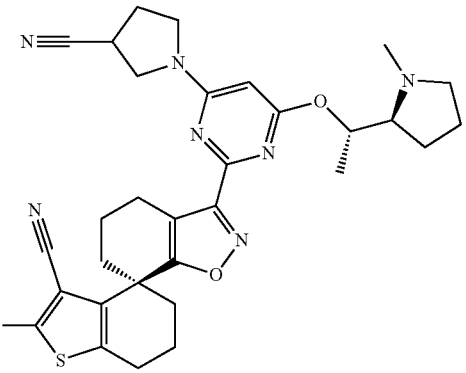 | 1.47 | 585 | A |
| II-100 | 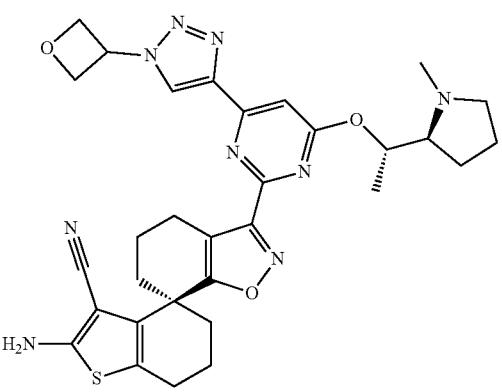 [SMILES: C[C@H](Oc1cc(-c2cn(C3COC3)nn2)nc(-c2noc3c2CCC[C@@]32CCCc3sc(N)c(C#N)c32)n1)[C@@H]1CCCN1C] | 1.49 | 614 | A |

TABLE 66-continued

| # | structure | $t_{ret}$ [min] | $[M + H]^+$ | HPLC method |
|---|---|---|---|---|
| II-101 | 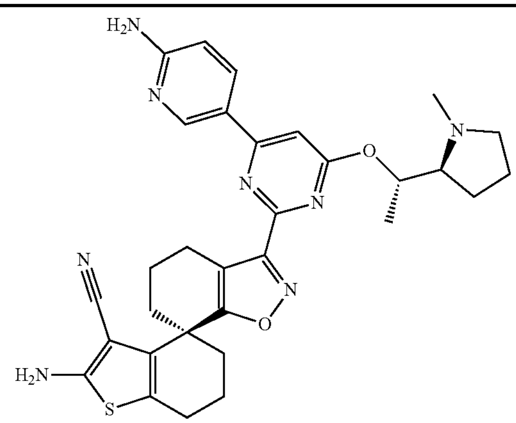 | 1.39 | 583 | A |
| II-102 | 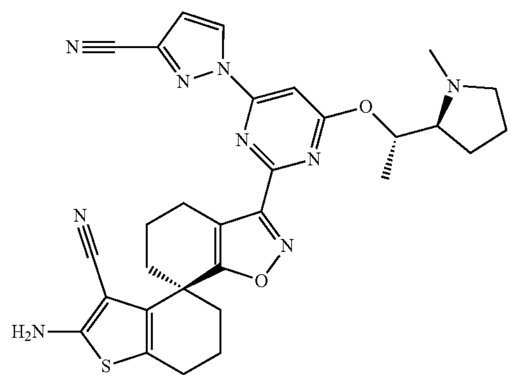 [SMILES: C[C@H](Oc1cc(-n2ccc(C#N)n2)nc(-c2noc3c2CCC[C@@]32CCCc3sc(N)c(C#N)c32)n1)[C@@H]1CCCN1C] | 1.63 | 582 | A |
| II-103 | 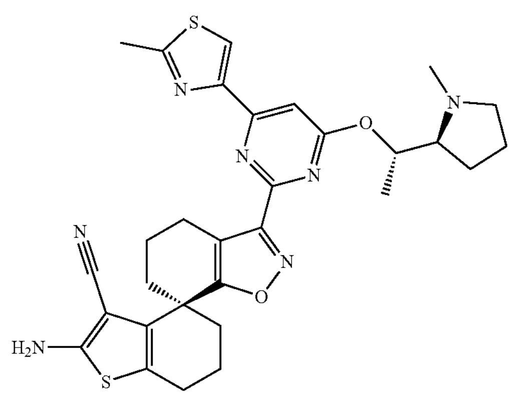 [SMILES: Cc1nc(-c2cc(O[C@@H](C)[C@@H]3CCCN3C)nc(-c3noc4c3CCC[C@@]43CCCc4sc(N)c(C#N)c43)n2)cs1] | 1.64 | 588 | A |
| II-104 | 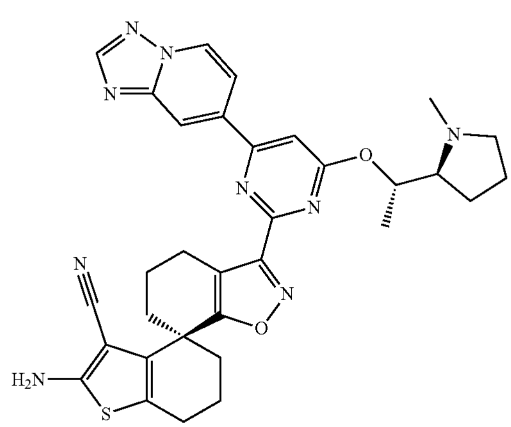 [SMILES: C[C@H](Oc1cc(-c2ccn3ncnc3c2)nc(-c2noc3c2CCC[C@@]32CCCc3sc(N)c(C#N)c32)n1)[C@@H]1CCCN1C] | 1.44 | 608 | A |

TABLE 66-continued

| # | structure | $t_{ret}$ [min] | $[M + H]^+$ | HPLC method |
|---|---|---|---|---|
| II-105 | 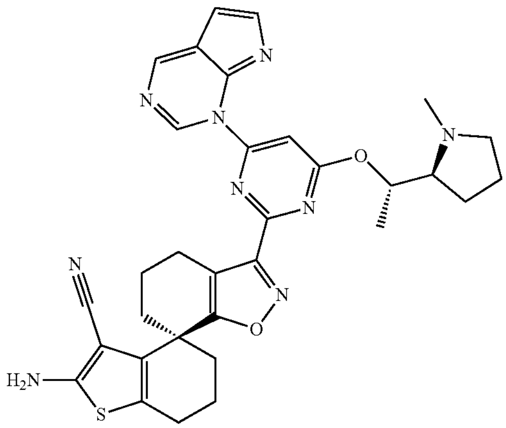 [SMILES: C[C@H](Oc1cc(-n2cncc3ccnc2-3)nc(-c2noc3c2CCC[C@@]32CCCc3sc(N)c(C#N)c32)n1)[C@@H]1CCCN1C] | 1.59 | 608 | A |
| II-106 | 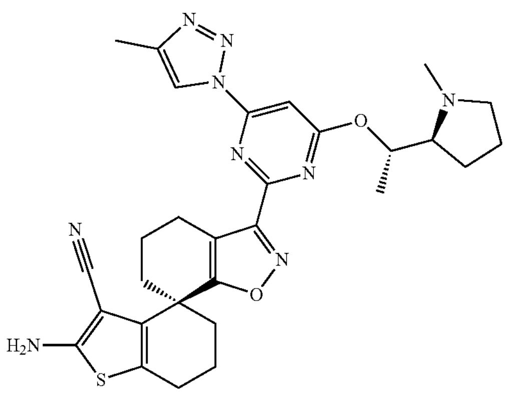 [SMILES: Cc1cn(-c2cc(O[C@@H](C)[C@@H]3CCCN3C)nc(-c3noc4c3CCC[C@@]43CCCc4sc(N)c(C#N)c43)n2)nn1] | 1.58 | 572 | A |
| II-107 | 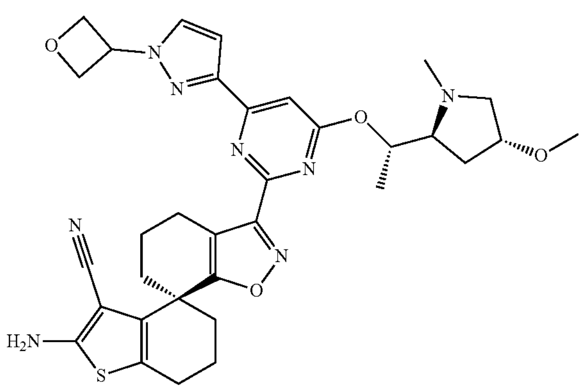 [SMILES: CO[C@@H]1C[C@@H]([C@H](C)Oc2cc(-c3ccn(C4COC4)n3)nc(-c3noc4c3CCC[C@@]43CCCc4sc(N)c(C#N)c43)n2)N(C)C1] | 1.44 | 643 | A |
| II-108 | 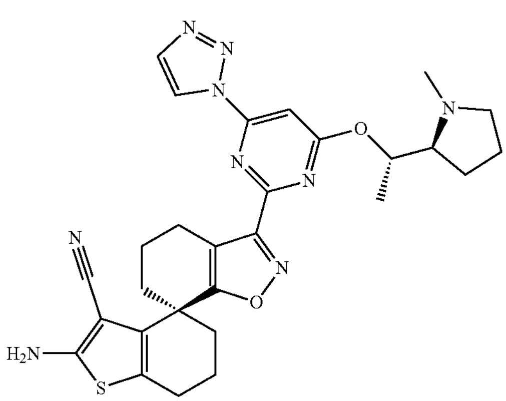 [SMILES: C[C@H](Oc1cc(-n2ccnn2)nc(-c2noc3c2CCC[C@@]32CCCc3sc(N)c(C#N)c32)n1)[C@@H]1CCCN1C] | 1.48 | 558 | A |

TABLE 66-continued

| # | structure | $t_{ret}$ [min] | [M + H]⁺ | HPLC method |
|---|---|---|---|---|
| II-109 | 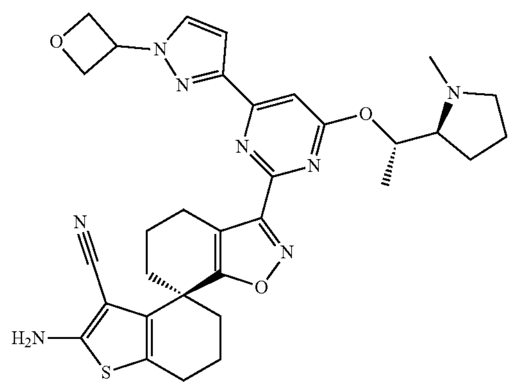 [SMILES: C[C@H](Oc1cc(-c2ccn(C3COC3)n2)nc(-c2noc3c2CCC[C@@]32CCCc3sc(N)c(C#N)c32)n1)[C@@H]1CCCN1C] | 1.48 | 613 | A |
| II-110 | 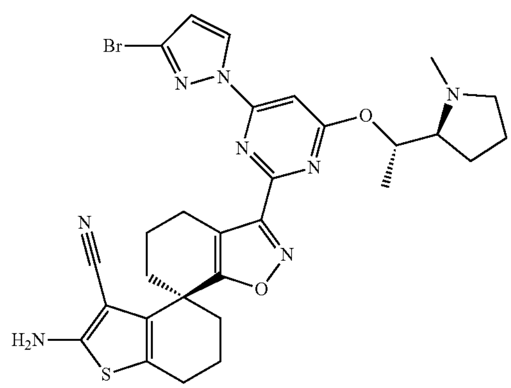 [SMILES: C[C@H](Oc1cc(-n2ccc(Br)n2)nc(-c2noc3c2CCC[C@@]32CCCc3sc(N)c(C#N)c32)n1)[C@@H]1CCCN1C] | 1.35 | 635 | A |
| II-111 | 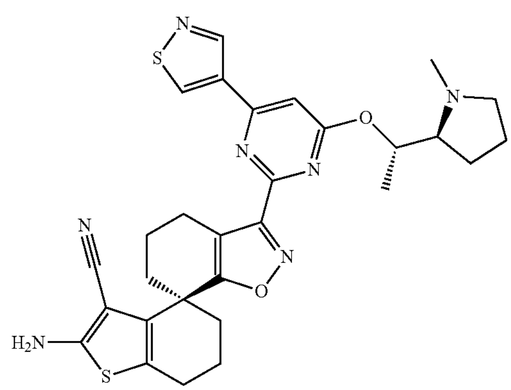 [SMILES: C[C@H](Oc1cc(-c2cnsc2)nc(-c2noc3c2CCC[C@@]32CCCc3sc(N)c(C#N)c32)n1)[C@@H]1CCCN1C] | 1.56 | 574 | A |
| II-112 | 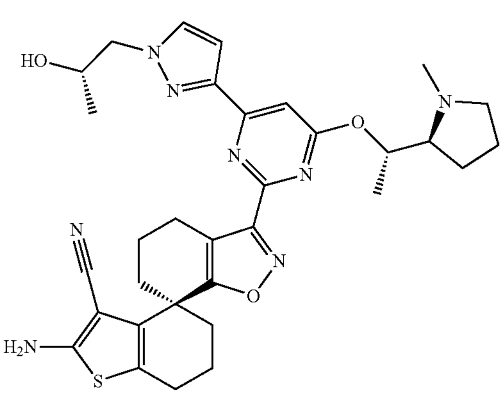 [SMILES: C[C@H](O)Cn1ccc(-c2cc(O[C@@H](C)[C@@H]3CCCN3C)nc(-c3noc4c3CCC[C@@]43CCCc4sc(N)c(C#N)c43)n2)n1] | 1.43 | 615 | A |

TABLE 66-continued

| # | structure | t_ret [min] | [M + H]+ | HPLC method |
|---|---|---|---|---|
| II-113 | 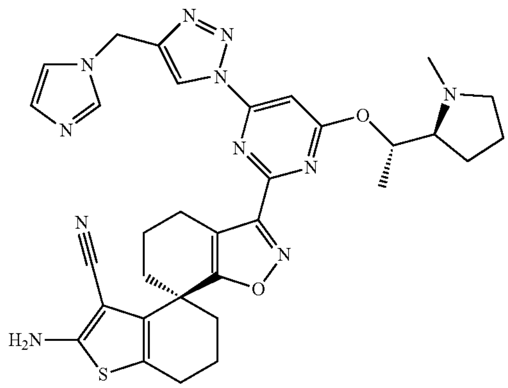 [SMILES: C[C@H](Oc1cc(-n2cc(Cn3ccnc3)nn2)nc(-c2noc3c2CCC[C@@]32CCCc3sc(N)c(C#N)c32)n1)[C@@H]1CCCN1C] | 1.40 | 638 | A |
| II-114 | 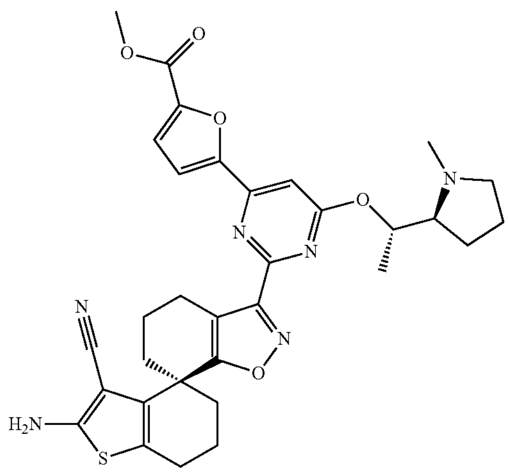 [SMILES: COC(=O)c1ccc(-c2cc(O[C@@H](C)[C@@H]3CCCN3C)nc(-c3noc4c3CCC[C@@]43CCCc4sc(N)c(C#N)c43)n2)o1] | 1.64 | 615 | A |
| II-115 | 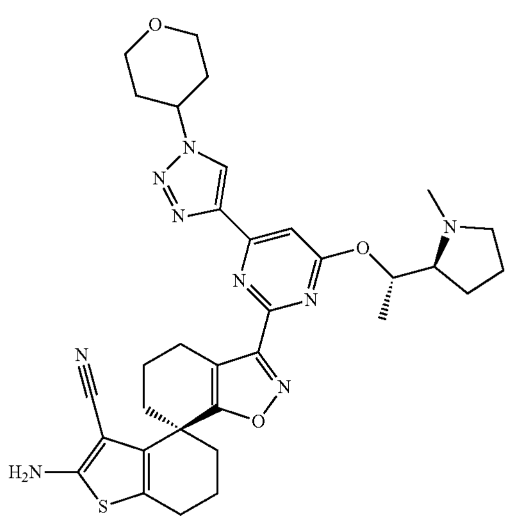 [SMILES: C[C@H](Oc1cc(-c2cn(C3CCOCC3)nn2)nc(-c2noc3c2CCC[C@@]32CCCc3sc(N)c(C#N)c32)n1)[C@@H]1CCCN1C] | 1.46 | 642 | A |

TABLE 66-continued

| # | structure | t_ret [min] | [M + H]+ | HPLC method |
|---|---|---|---|---|
| II-116 | 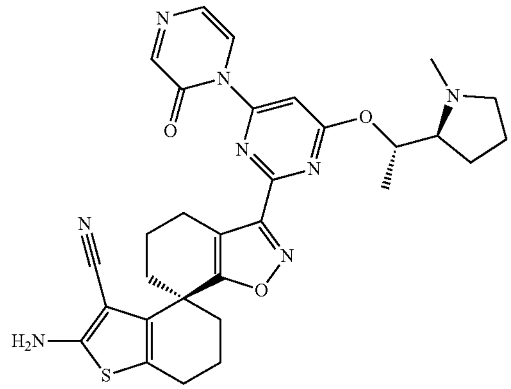 [SMILES: C[C@H](Oc1cc(-n2ccncc2=O)nc(-c2noc3c2CCC[C@@]32CCCc3sc(N)c(C#N)c32)n1)[C@@H]1CCCN1C] | 1.42 | 585 | A |
| II-117 | 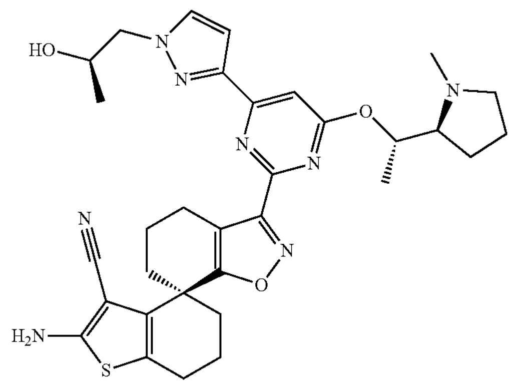 [SMILES: C[C@H](Oc1cc(-c2ccn(C[C@@H](C)O)n2)nc(-c2noc3c2CCC[C@@]32CCCc3sc(N)c(C#N)c32)n1)[C@@H]1CCCN1C] | 1.43 | 615 | A |
| II-118 | 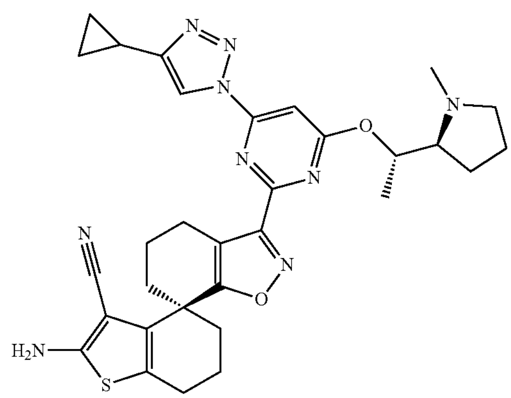 [SMILES: C[C@H](Oc1cc(-n2cc(C3CC3)nn2)nc(-c2noc3c2CCC[C@@]32CCCc3sc(N)c(C#N)c32)n1)[C@@H]1CCCN1C] | 1.63 | 598 | A |
| II-119 | 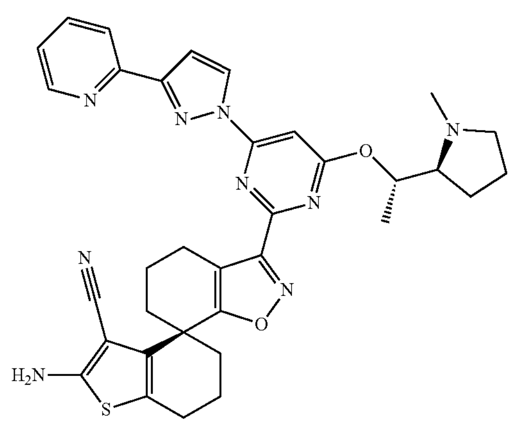 [SMILES: C[C@H](Oc1cc(-n2ccc(-c3ccccn3)n2)nc(-c2noc3c2CCC[C@@]32CCCc3sc(N)c(C#N)c32)n1)[C@@H]1CCCN1C] | 1.69 | 634 | A |

TABLE 66-continued

| # | structure | t_ret [min] | [M + H]+ | HPLC method |
|---|---|---|---|---|
| II-120 | 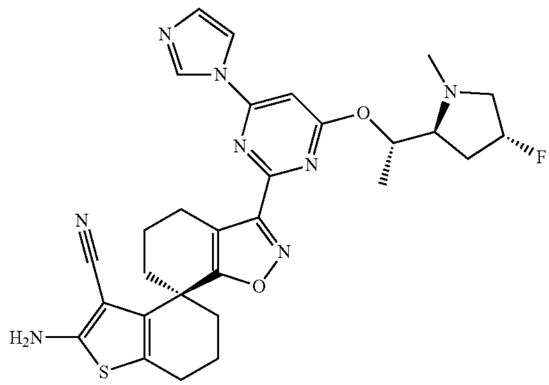 [SMILES: C[C@H](Oc1cc(-n2ccnc2)nc(-c2noc3c2CCC[C@@]32CCCc3sc(N)c(C#N)c32)n1)[C@@H]1C[C@@H](F)CN1C] | 1.39 | 575 | A |
| II-121 | 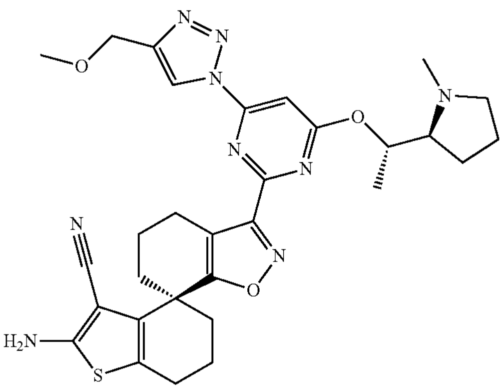 [SMILES: COCc1cn(-c2cc(O[C@@H](C)[C@@H]3CCCN3C)nc(-c3noc4c3CCC[C@@]43CCCc4sc(N)c(C#N)c43)n2)nn1] | 1.51 | 602 | A |
| II-122 | 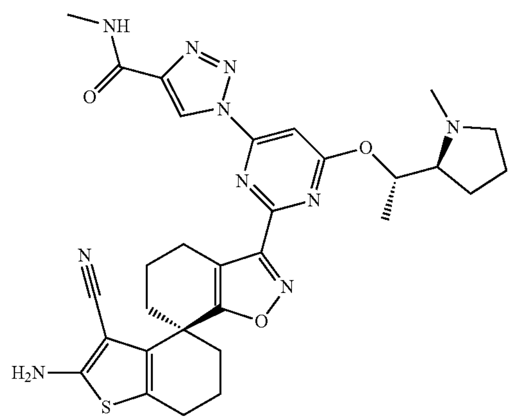 [SMILES: CNC(=O)c1cn(-c2cc(O[C@@H](C)[C@@H]3CCCN3C)nc(-c3noc4c3CCC[C@@]43CCCc4sc(N)c(C#N)c43)n2)nn1] | 1.42 | 615 | A |
| II-123 | 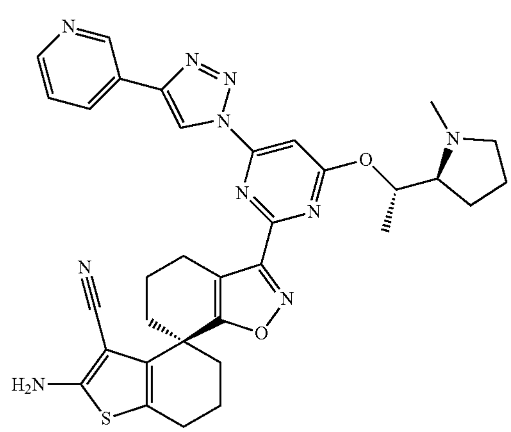 [SMILES: C[C@H](Oc1cc(-n2cc(-c3cccnc3)nn2)nc(-c2noc3c2CCC[C@@]32CCCc3sc(N)c(C#N)c32)n1)[C@@H]1CCCN1C] | 1.55 | 635 | A |

TABLE 66-continued

| # | structure | $t_{ret}$ [min] | [M + H]$^+$ | HPLC method |
|---|---|---|---|---|
| II-124 | 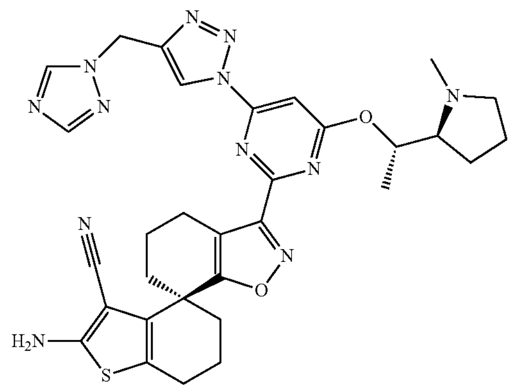 [SMILES: C[C@H](Oc1cc(-n2cc(Cn3cncn3)nn2)nc(-c2noc3c2CCC[C@@]32CCCc3sc(N)c(C#N)c32)n1)[C@@H]1CCCN1C] | 1.38 | 639 | A |
| II-125 | 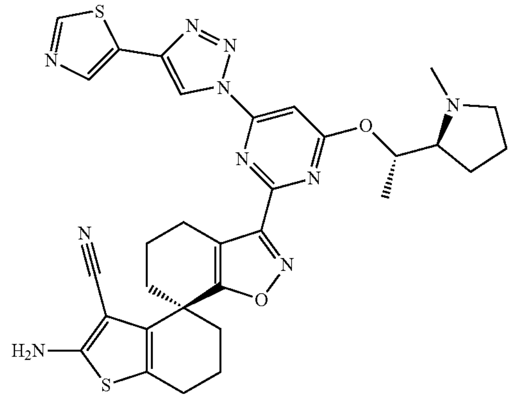 [SMILES: C[C@H](Oc1cc(-n2cc(-c3cncs3)nn2)nc(-c2noc3c2CCC[C@@]32CCCc3sc(N)c(C#N)c32)n1)[C@@H]1CCCN1C] | 1.56 | 641 | A |
| II-126 | 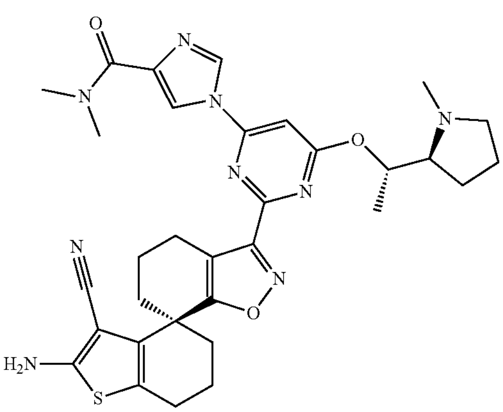 [SMILES: C[C@H](Oc1cc(-n2cnc(C(=O)N(C)C)c2)nc(-c2noc3c2CCC[C@@]32CCCc3sc(N)c(C#N)c32)n1)[C@@H]1CCCN1C] | 1.38 | 628 | A |
| II-127 | 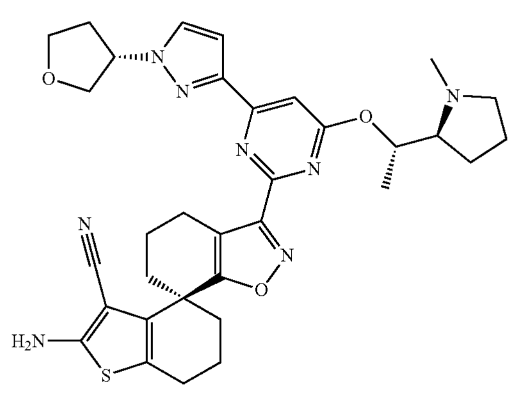 [SMILES: C[C@H](Oc1cc(-c2ccn([C@H]3CCOC3)n2)nc(-c2noc3c2CCC[C@@]32CCCc3sc(N)c(C#N)c32)n1)[C@@H]1CCCN1C] | 1.53 | 627 | A |

TABLE 66-continued
| # | structure | $t_{ret}$ [min] | [M + H]⁺ | HPLC method |
|---|-----------|-----------------|----------|-------------|
| II-128 | 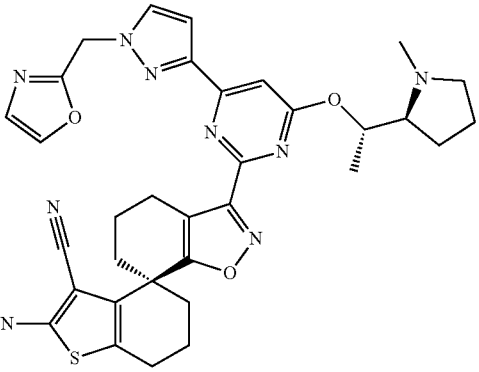 | 1.47 | 638 | A |
| II-129 | 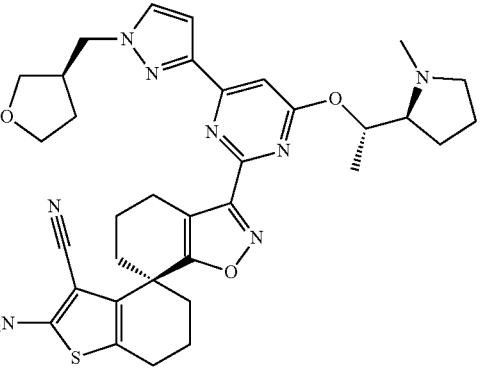 | 1.54 | 641 | A |
| II-130 | 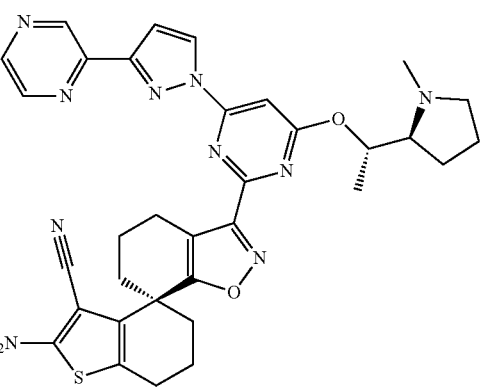 | 1.63 | 635 | A |
| II-131 | 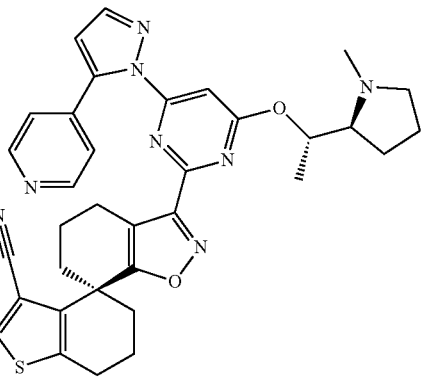 | 1.62 | 634 | A |

TABLE 66-continued

| # | structure | $t_{ret}$ [min] | [M + H]+ | HPLC method |
|---|---|---|---|---|
| II-132 | 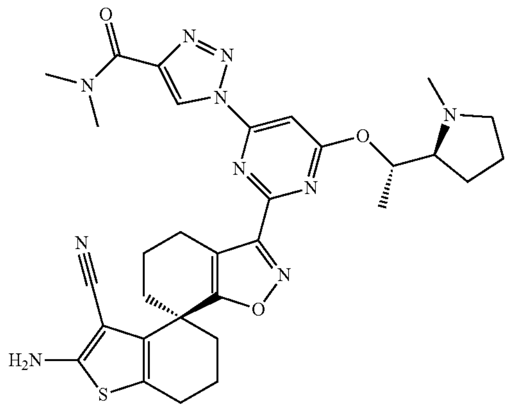 [SMILES: C[C@H](Oc1cc(-n2cc(C(=O)N(C)C)nn2)nc(-c2noc3c2CCC[C@@]32CCCc3sc(N)c(C#N)c32)n1)[C@@H]1CCCN1C] | 1.47 | 629 | A |
| II-133 | 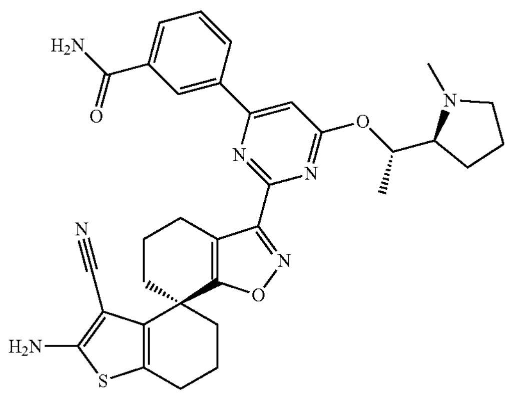 [SMILES: C[C@H](Oc1cc(-c2cccc(C(N)=O)c2)nc(-c2noc3c2CCC[C@@]32CCCc3sc(N)c(C#N)c32)n1)[C@@H]1CCCN1C] | 1.41 | 610 | A |
| II-134 | 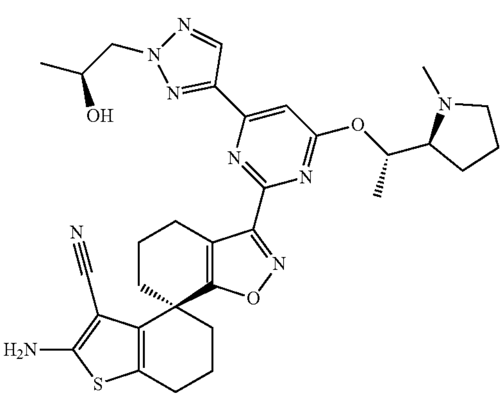 [SMILES: C[C@H](O)Cn1ncc(-c2cc(O[C@@H](C)[C@@H]3CCCN3C)nc(-c3noc4c3CCC[C@@]43CCCc4sc(N)c(C#N)c43)n2)n1] | 1.46 | 616 | A |
| II-135 | 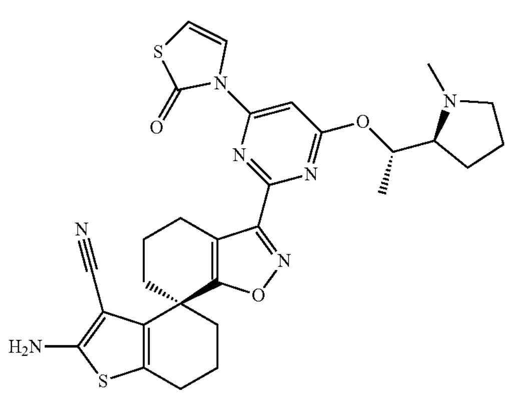 [SMILES: C[C@H](Oc1cc(-n2ccsc2=O)nc(-c2noc3c2CCC[C@@]32CCCc3sc(N)c(C#N)c32)n1)[C@@H]1CCCN1C] | 1.61 | 590 | A |

TABLE 66-continued

| # | structure | $t_{ret}$ [min] | $[M + H]^+$ | HPLC method |
|---|---|---|---|---|
| II-136 | 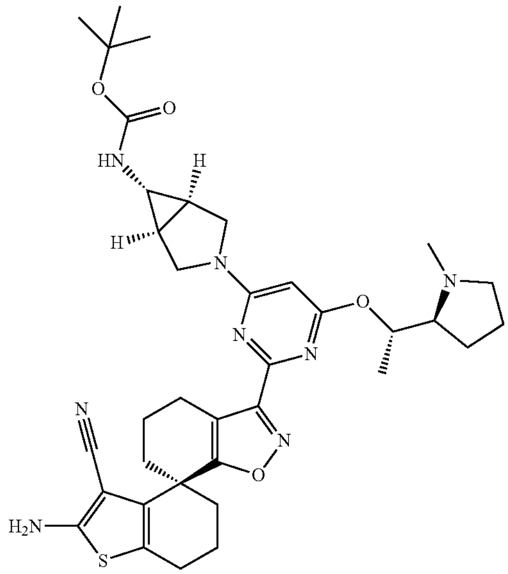 [SMILES: C[C@H](Oc1cc(N2C[C@@H]3[C@H](C2)[C@H]3NC(=O)OC(C)(C)C)nc(-c2noc3c2CCC[C@@]32CCCc3sc(N)c(C#N)c32)n1)[C@@H]1CCCN1C] | 0.9 | 687 | E |
| II-137 | 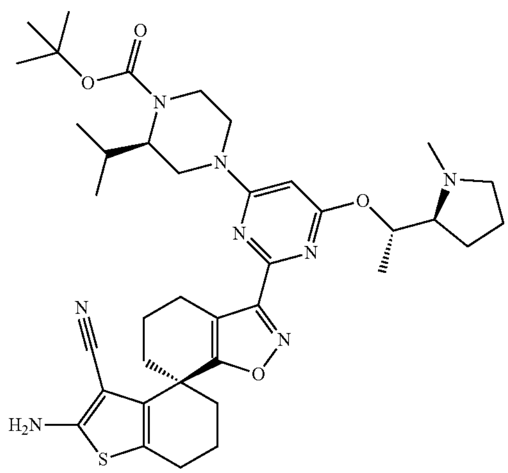 [SMILES: CC(C)[C@@H]1CN(c2cc(O[C@@H](C)[C@@H]3CCCN3C)nc(-c3noc4c3CCC[C@@]43CCCc4sc(N)c(C#N)c43)n2)CCN1C(=O)OC(C)(C)C] | 1.86 | 717 | A |
| II-138 | 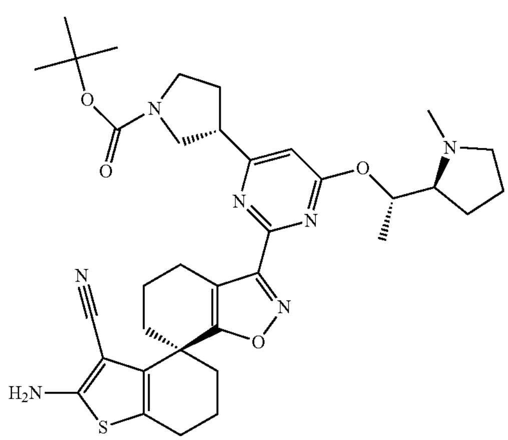 [SMILES: C[C@H](Oc1cc([C@H]2CCN(C(=O)OC(C)(C)C)C2)nc(-c2noc3c2CCC[C@@]32CCCc3sc(N)c(C#N)c32)n1)[C@@H]1CCCN1C] | 0.96 | 660 | C |

TABLE 66-continued

| # | structure | $t_{ret}$ [min] | $[M + H]^+$ | HPLC method |
|---|---|---|---|---|
| II-139 | 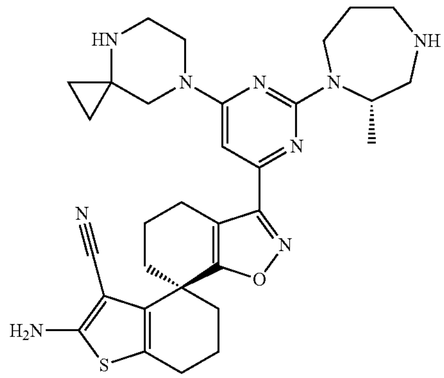 [SMILES: C[C@H]1CNCCCN1c1nc(-c2noc3c2CCC[C@@]32CCCc3sc(N)c(C#N)c32)cc(N2CCNC3(CC3)C2)n1] | 0.72 | 586 | C |
| II-140 | 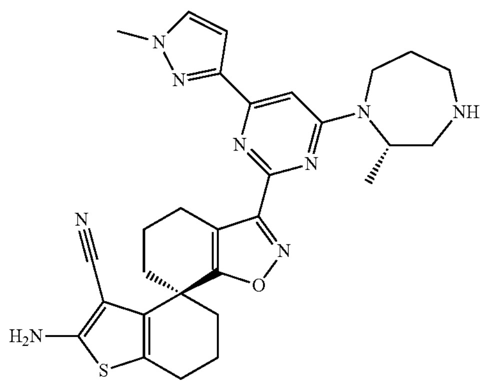 [SMILES: C[C@H]1CNCCCN1c1cc(-c2ccn(C)n2)nc(-c2noc3c2CCC[C@@]32CCCc3sc(N)c(C#N)c32)n1] | 1.30 | 556 | A |
| II-141 | 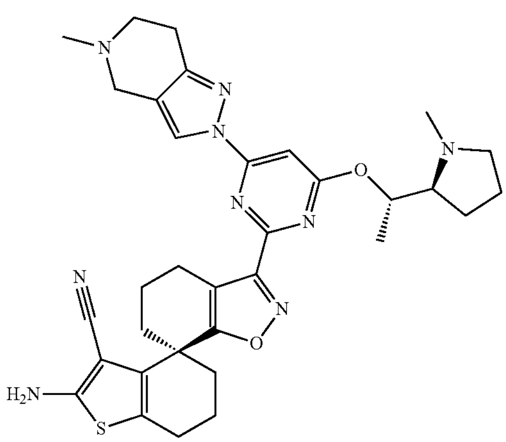 [SMILES: C[C@H](Oc1cc(-n2cc3c(n2)CCN(C)C3)nc(-c2noc3c2CCC[C@@]32CCCc3sc(N)c(C#N)c32)n1)[C@@H]1CCCN1C] | 1.55 | 626 | A |
| II-142 | 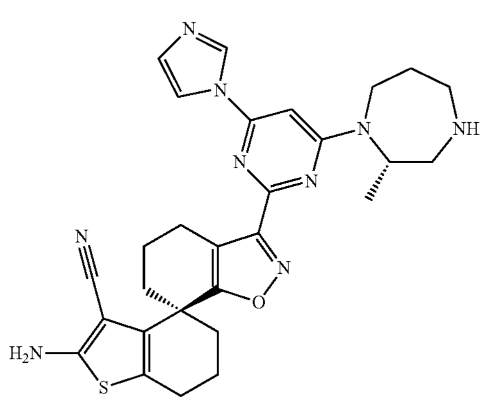 [SMILES: C[C@H]1CNCCCN1c1cc(-n2ccnc2)nc(-c2noc3c2CCC[C@@]32CCCc3sc(N)c(C#N)c32)n1] | 1.28 | 542 | A |

| # | structure | $t_{ret}$ [min] | [M + H]⁺ | HPLC method |
|---|---|---|---|---|
| II-214 | 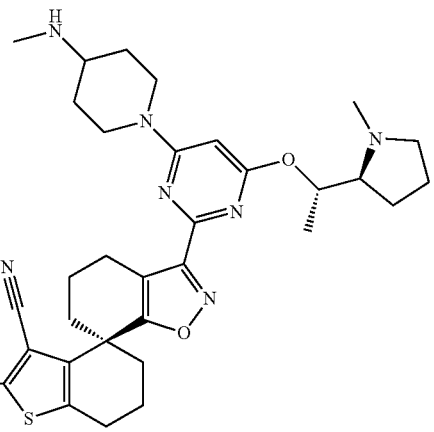 | 1.41 | 603 | A |

Experimental Procedure for the Synthesis of II-143

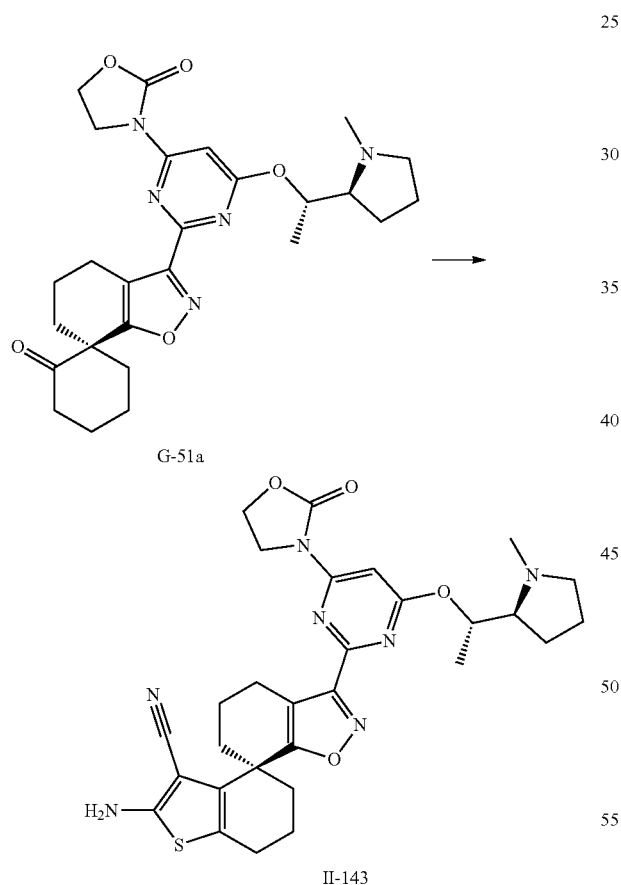

G-51a (90 mg, 0.18 mmol, 1.0 equiv.), ammonium acetate (22.4 mg, 0.29 mmol, 1.6 equiv.), and sulfur (9.32 mg, 0.29 mmol, 1.6 equiv.) are dissolved in EtOH (1.20 mL) and stirred at 60° C. for 15 min. Malonitrile as a solution in EtOH (0.26 mL, 0.3 mmol, 1.65 equiv.) is added slowly, dropwise. The reaction is stirred for 5 h at 80° C. After full conversion, DCM is added and extracted 3 times with water. The combined organic phases are concentrated under reduced pressure, dissolved in DMF/ACN/water and purified with RP chromatography to afford II-143.

The following final compounds II (Table 67) are available in an analogous manner. The crude product is purified by chromatography if necessary.

TABLE 67

| # | structure | t_ret [min] | [M + H]+ | HPLC method |
| --- | --- | --- | --- | --- |
| II-143 | 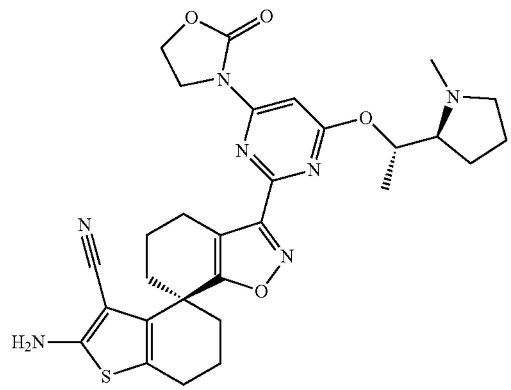 | 1.45 | 576 | A |
| II-144 | 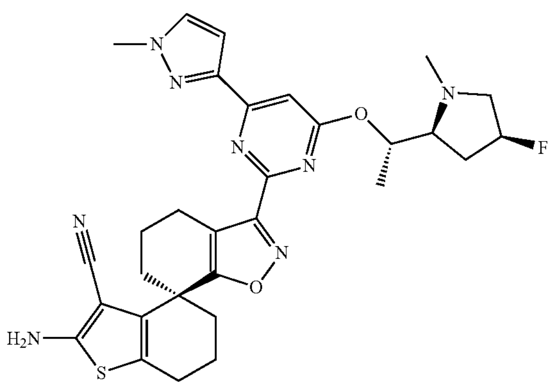 [SMILES: C[C@H](Oc1cc(-c2ccn(C)n2)nc(-c2noc3c2CCC[C@@]32CCCc3sc(N)c(C#N)c32)n1)[C@@H]1C[C@H](F)CN1C] | 1.46 | 589 | A |
| II-145 | 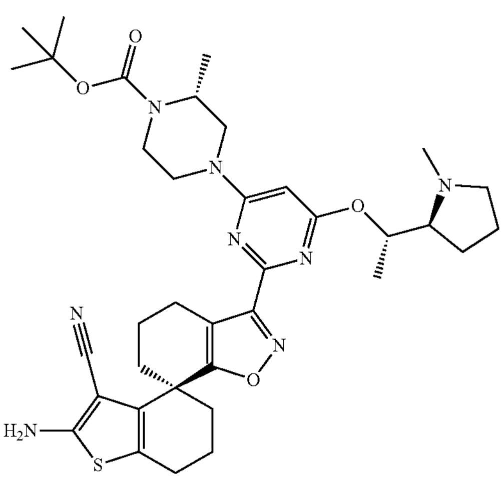 [SMILES: C[C@H](Oc1cc(N2CCN(C(=O)OC(C)(C)C)[C@H](C)C2)nc(-c2noc3c2CCC[C@@]32CCCc3sc(N)c(C#N)c32)n1)[C@@H]1CCCN1C] | 1.02 | 689 | E |

TABLE 67-continued

| # | structure | $t_{ret}$ [min] | [M + H]⁺ | HPLC method |
|---|---|---|---|---|
| II-146 | 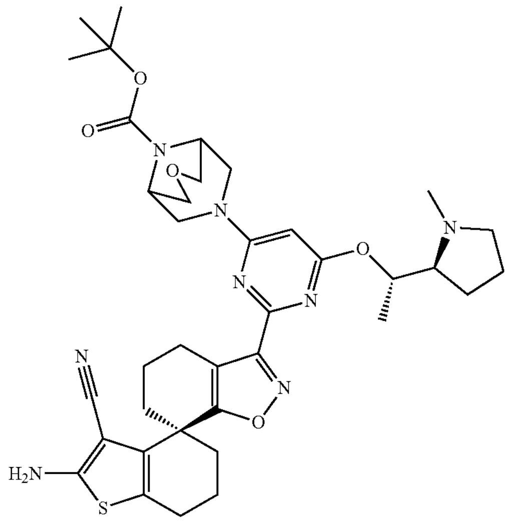 [SMILES: C[C@H](Oc1cc(N2CC3COCC(C2)N3C(=O)OC(C)(C)C)nc(-c2noc3c2CCC[C@@]32CCCc3sc(N)c(C#N)c32)n1)[C@@H]1CCCN1C] | 1.60 | 717 | A |
| II-147 | 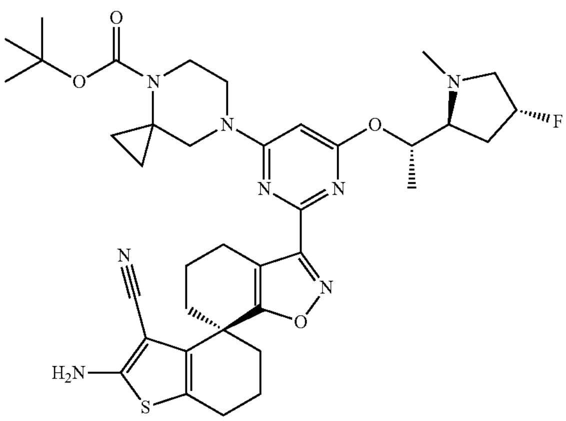 [SMILES: C[C@H](Oc1cc(N2CCN(C(=O)OC(C)(C)C)C3(CC3)C2)nc(-c2noc3c2CCC[C@@]32CCCc3sc(N)c(C#N)c32)n1)[C@@H]1C[C@@H](F)CN1C] | 1.21 | 719 | B |
| II-148 | 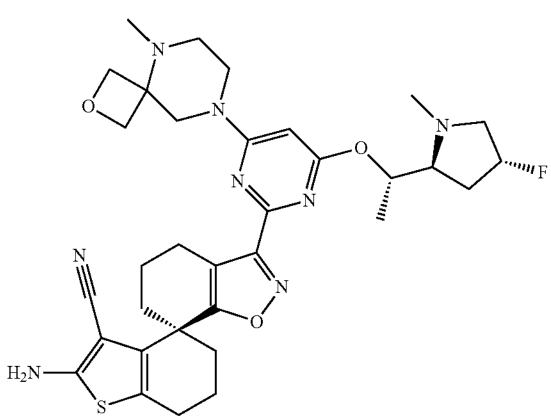 [SMILES: C[C@H](Oc1cc(N2CCN(C)C3(COC3)C2)nc(-c2noc3c2CCC[C@@]32CCCc3sc(N)c(C#N)c32)n1)[C@@H]1C[C@@H](F)CN1C] | 1.42 | 649 | A |

TABLE 67-continued

| # | structure | $t_{ret}$ [min] | $[M + H]^+$ | HPLC method |
|---|---|---|---|---|
| II-149 | 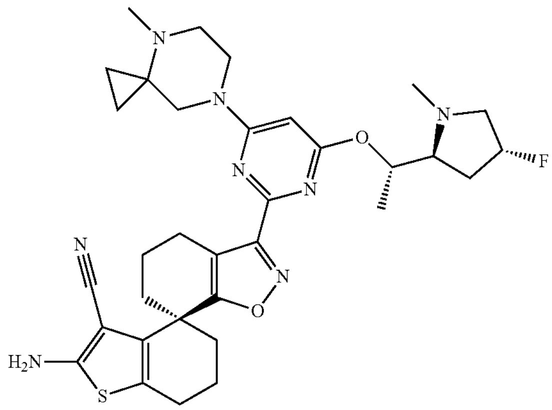 [SMILES: C[C@H](Oc1cc(N2CCN(C)C3(CC3)C2)nc(-c2noc3c2CCC[C@@]32CCCc3sc(N)c(C#N)c32)n1)[C@@H]1C[C@@H](F)CN1C] | 1.56 | 633 | A |
| II-150 | 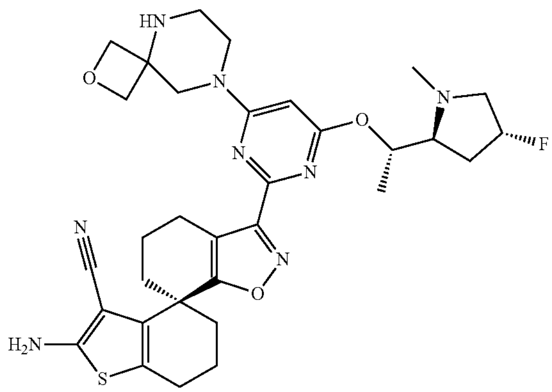 [SMILES: C[C@H](Oc1cc(N2CCNC3(COC3)C2)nc(-c2noc3c2CCC[C@@]32CCCc3sc(N)c(C#N)c32)n1)[C@@H]1C[C@@H](F)CN1C] | 1.35 | 635 | A |
| II-151 | 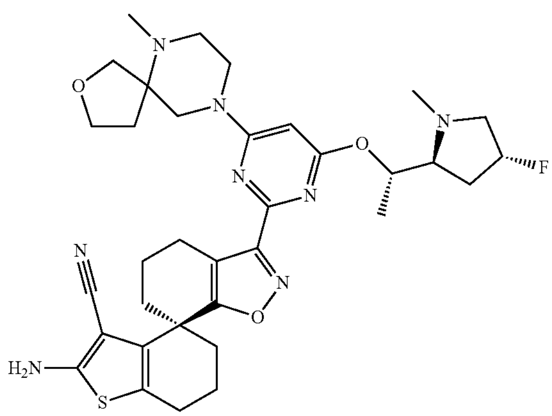 [SMILES: C[C@H](Oc1cc(N2CCN(C)C3(CCOC3)C2)nc(-c2noc3c2CCC[C@@]32CCCc3sc(N)c(C#N)c32)n1)[C@@H]1C[C@@H](F)CN1C] | 1.46 | 663 | A |
| II-152 | 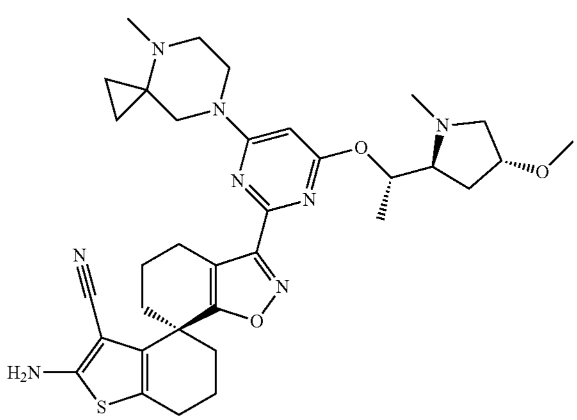 [SMILES: CO[C@@H]1C[C@@H]([C@H](C)Oc2cc(N3CCN(C)C4(CC4)C3)nc(-c3noc4c3CCC[C@@]43CCCc4sc(N)c(C#N)c43)n2)N(C)C1] | 1.52 | 645 | A |

TABLE 67-continued

| # | structure | $t_{ret}$ [min] | $[M + H]^+$ | HPLC method |
|---|---|---|---|---|
| II-153 | 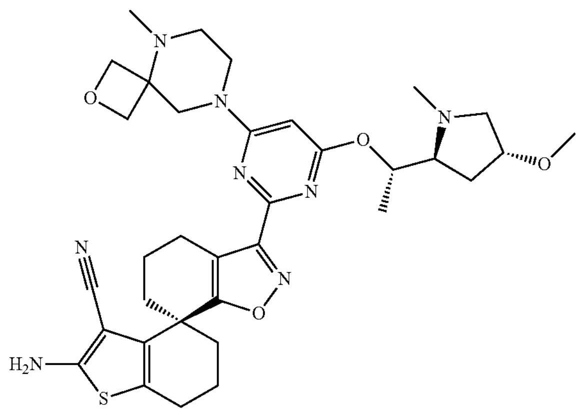 [SMILES: CO[C@@H]1C[C@@H]([C@H](C)Oc2cc(N3CCN(C)C4(COC4)C3)nc(-c3noc4c3CCC[C@@]43CCCc4sc(N)c(C#N)c43)n2)N(C)C1] | 1.40 | 661 | A |
| II-154 | 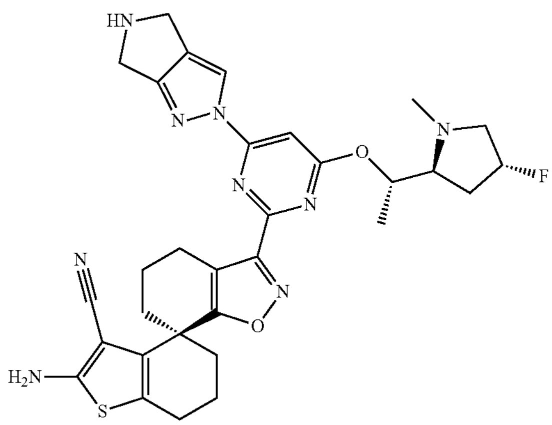 [SMILES: C[C@H](Oc1cc(-n2cc3c(n2)CNC3)nc(-c2noc3c2CCC[C@@]32CCCc3sc(N)c(C#N)c32)n1)[C@@H]1C[C@@H](F)CN1C] | 1.39 | 616 | A |
| II-155 | 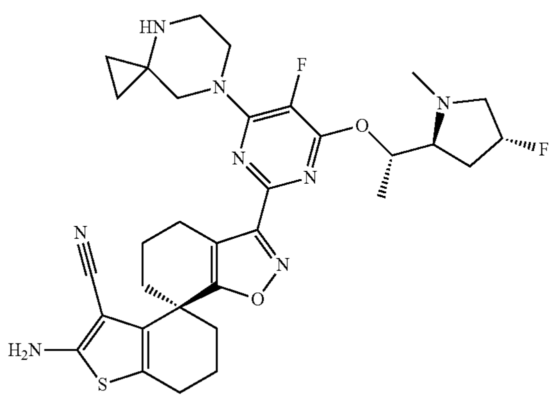 [SMILES: C[C@H](Oc1nc(-c2noc3c2CCC[C@@]32CCCc3sc(N)c(C#N)c32)nc(N2CCNC3(CC3)C2)c1F)[C@@H]1C[C@@H](F)CN1C] | 1.50 | 637 | A |

TABLE 67-continued
| # | structure | t_ret [min] | [M + H]+ | HPLC method |
|---|---|---|---|---|
| II-156 | 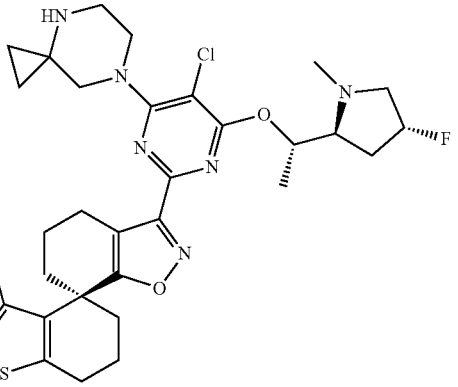 | 1.07 | 653 | B |
| II-157 | 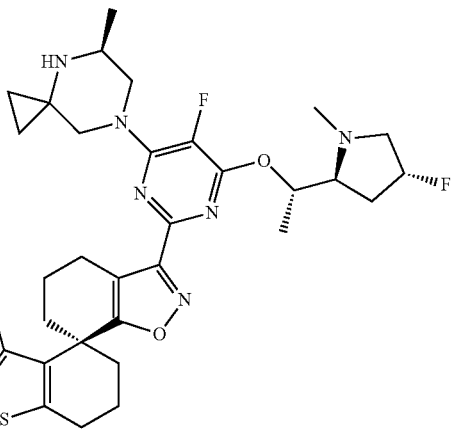 | 1.56 | 651 | A |
| II-158 | 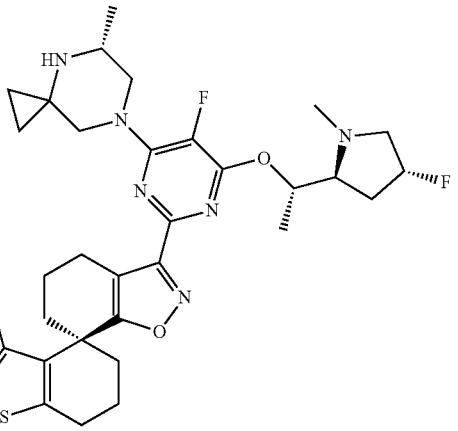 | 1.56 | 651 | A |

TABLE 67-continued

| # | structure | $t_{ret}$ [min] | $[M + H]^+$ | HPLC method |
|---|---|---|---|---|
| II-159 | 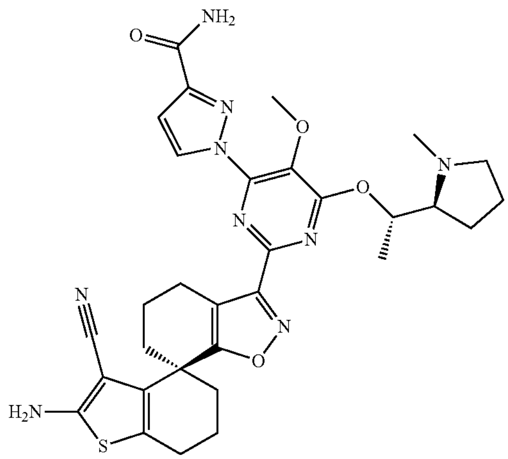 [SMILES: COc1c(O[C@@H](C)[C@@H]2CCCN2C)nc(-c2noc3c2CCC[C@@]32CCCc3sc(N)c(C#N)c32)nc1-n1ccc(C(N)=O)n1] | 1.40 | 630 | A |
| II-201 | 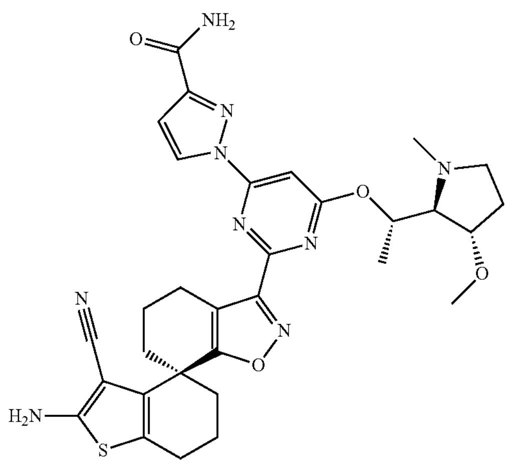 [SMILES: CO[C@H]1CCN(C)[C@@H]1[C@H](C)Oc1cc(-n2ccc(C(N)=O)n2)nc(-c2noc3c2CCC[C@@]32CCCc3sc(N)c(C#N)c32)n1] | 1.38 | 630 | A |
| II-202 | 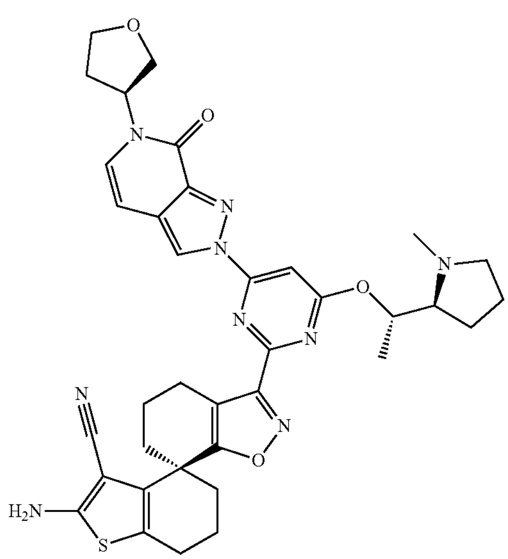 [SMILES: C[C@H](Oc1cc(-n2cc3ccn([C@H]4CCOC4)c(=O)c3n2)nc(-c2noc3c2CCC[C@@]32CCCc3sc(N)c(C#N)c32)n1)[C@@H]1CCCN1C] | 1.51 | 694 | A |

TABLE 67-continued

| # | structure | t_ret [min] | [M + H]+ | HPLC method |
|---|---|---|---|---|
| II-203 | 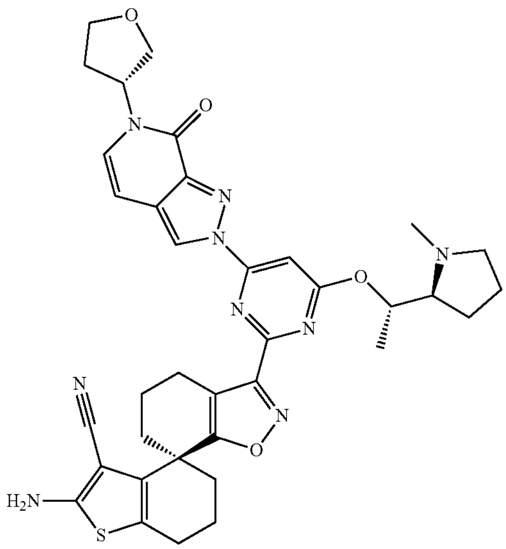 [SMILES: C[C@H](Oc1cc(-n2cc3ccn([C@@H]4CCOC4)c(=O)c3n2)nc(-c2noc3c2CCC[C@@]32CCCc3sc(N)c(C#N)c32)n1)[C@@H]1CCCN1C] | 1.49 | 694 | A |
| II-204 | 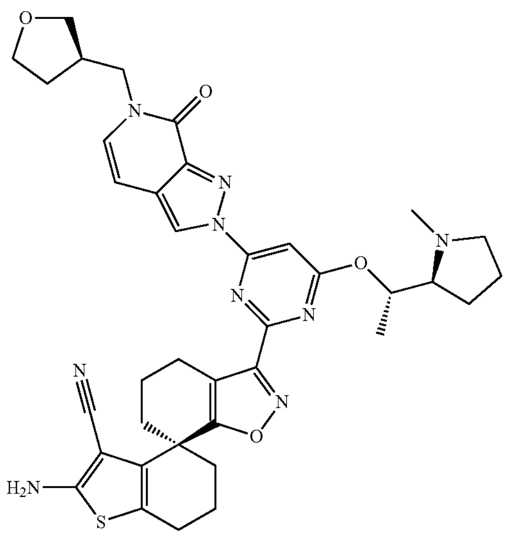 [SMILES: C[C@H](Oc1cc(-n2cc3ccn(C[C@H]4CCOC4)c(=O)c3n2)nc(-c2noc3c2CCC[C@@]32CCCc3sc(N)c(C#N)c32)n1)[C@@H]1CCCN1C] | 1.48 | 708 | A |
| II-205 | 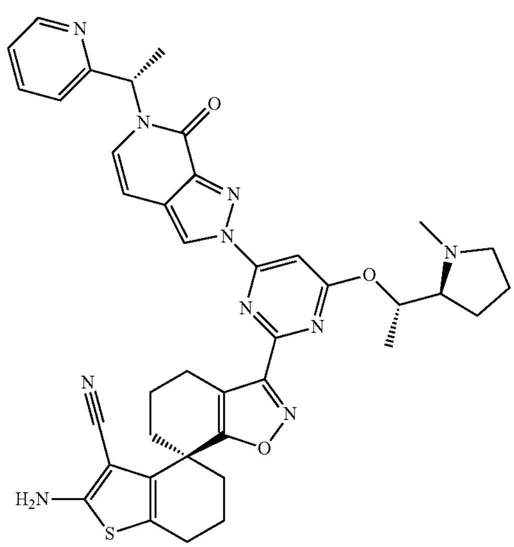 [SMILES: C[C@H](Oc1cc(-n2cc3ccn([C@@H](C)c4ccccn4)c(=O)c3n2)nc(-c2noc3c2CCC[C@@]32CCCc3sc(N)c(C#N)c32)n1)[C@@H]1CCCN1C] | 1.56 | 729 | A |

TABLE 67-continued

| # | structure | $t_{ret}$ [min] | [M + H]$^+$ | HPLC method |
|---|---|---|---|---|
| II-206 | 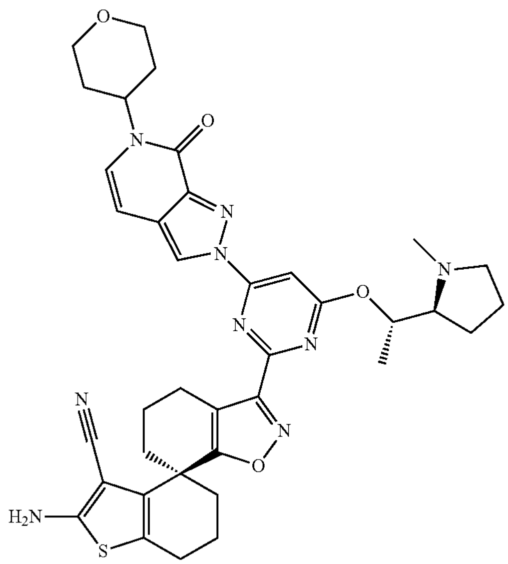 [SMILES: C[C@H](Oc1cc(-n2cc3ccn(C4CCOCC4)c(=O)c3n2)nc(-c2noc3c2CCC[C@@]32CCCc3sc(N)c(C#N)c32)n1)[C@@H]1CCCN1C] | 1.49 | 708 | A |
| II-207 | 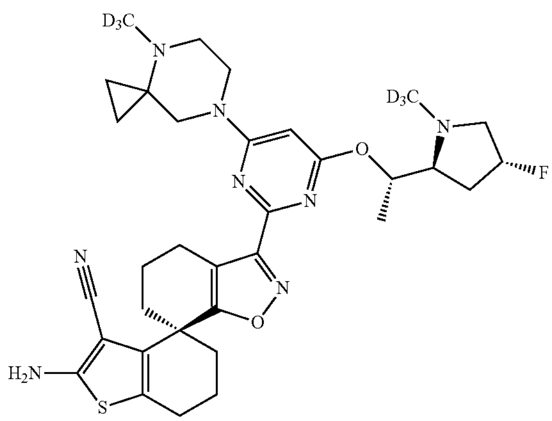 [SMILES: [2H]C([2H])([2H])N1C[C@H](F)C[C@H]1[C@H](C)Oc1cc(N2CCN(C([2H])([2H])[2H])C3(CC3)C2)nc(-c2noc3c2CCC[C@@]32CCCc3sc(N)c(C#N)c32)n1] | 1.51 | 639 | A |
| II-208 | 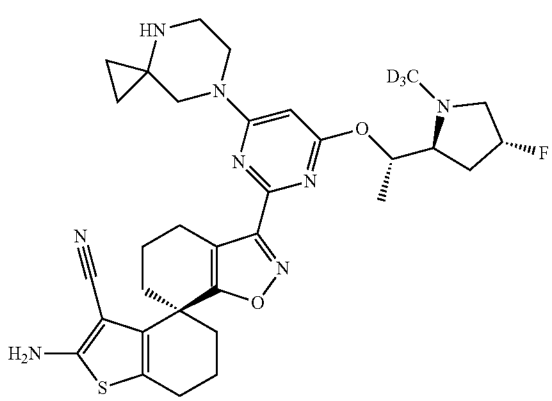 [SMILES: [2H]C([2H])([2H])N1C[C@H](F)C[C@H]1[C@H](C)Oc1cc(N2CCNC3(CC3)C2)nc(-c2noc3c2CCC[C@@]32CCCc3sc(N)c(C#N)c32)n1] | 1.45 | 622 | A |

TABLE 67-continued
| # | structure | $t_{ret}$ [min] | $[M + H]^+$ | HPLC method |
|---|---|---|---|---|
| II-209 | 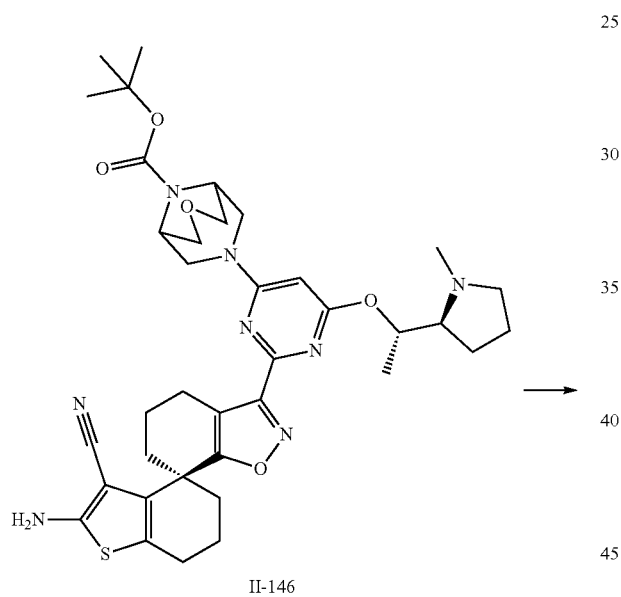 | 1.55 | 636 | A |
Experimental Procedure for the Synthesis of II-160
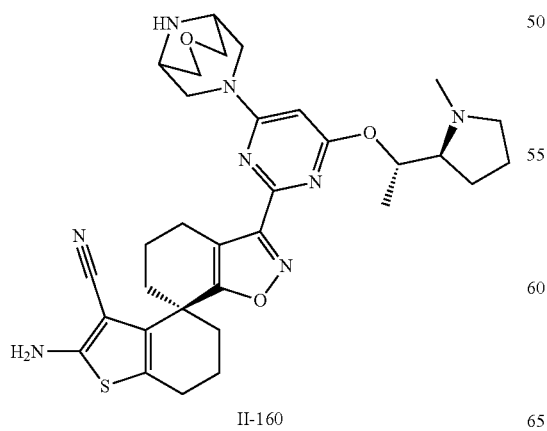

To a solution of II-146 (210 mg, 0.29 mmol, 1.0 equiv.) in dioxane (3 mL), HCl (4 M in dioxane, 0.29 mL, 1.17 mmol, 4.0 eq) is added and the reaction mixture is stirred for 18 h at rt. The reaction mixture is heated to 50° C. and stirred for 6 h. The solvent is removed, and the residue is purified by RP chromatography to obtain II-160.

The following final compounds II (Table 68) are available in an analogous manner. The crude product is purified by chromatography if necessary.

TABLE 68

| # | structure | $t_{ret}$ [min] | [M + H]$^+$ | HPLC method |
|---|---|---|---|---|
| II-160 | 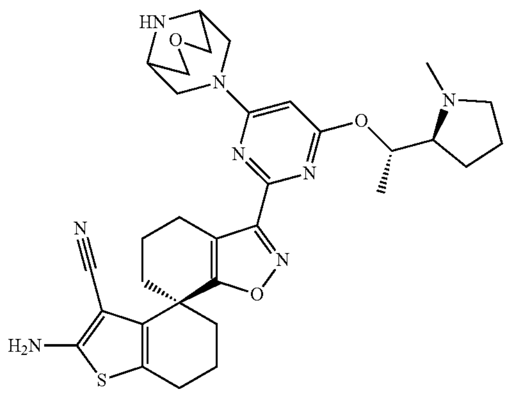 [SMILES: C[C@H](Oc1cc(N2CC3COCC(C2)N3)nc(-c2noc3c2CCC[C@@]32CCCc3sc(N)c(C#N)c32)n1)[C@@H]1CCCN1C] | 1.30 | 617 | A |
| II-161 | 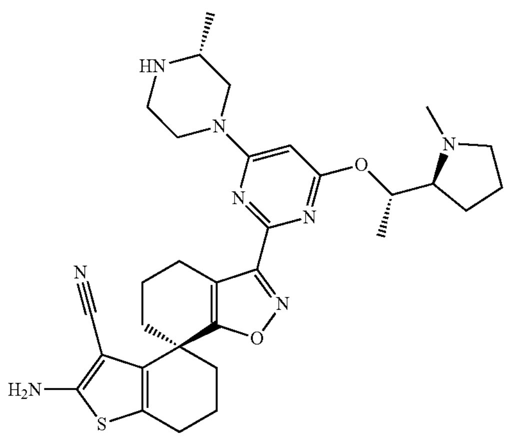 [SMILES: C[C@@H]1CN(c2cc(O[C@@H](C)[C@@H]3CCCN3C)nc(-c3noc4c3CCC[C@@]43CCCc4sc(N)c(C#N)c43)n2)CCN1] | 1.56 | 589 | A |
| II-162 | 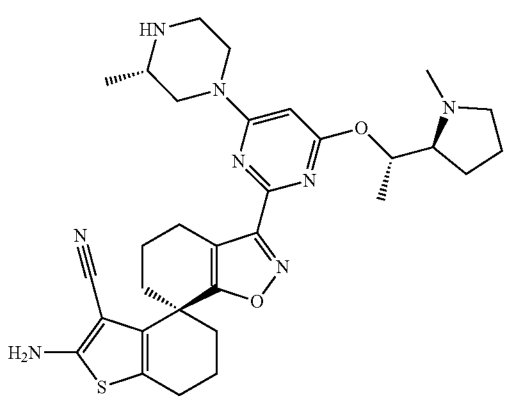 [SMILES: C[C@H](Oc1cc(N2CCN[C@@H](C)C2)nc(-c2noc3c2CCC[C@@]32CCCc3sc(N)c(C#N)c32)n1)[C@@H]1CCCN1C] | 1.38 | 589 | A |

TABLE 68-continued
| # | structure | t_ret [min] | [M + H]+ | HPLC method |
|---|---|---|---|---|
| II-163 | 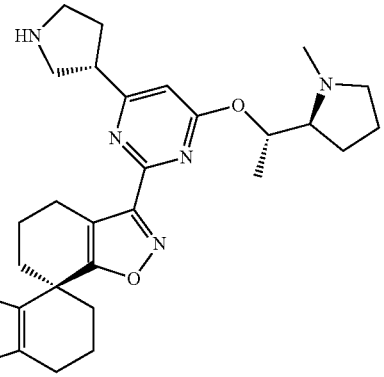 | 1.39 | 560 | A |
| II-164 | 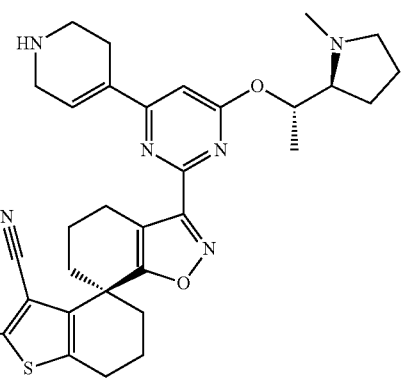 | 1.55 | 572 | A |
| II-165 | 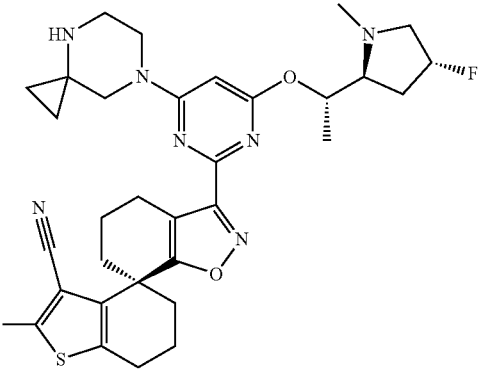 | 1.44 | 619 | A |

Experimental Procedure for the Synthesis of II-166

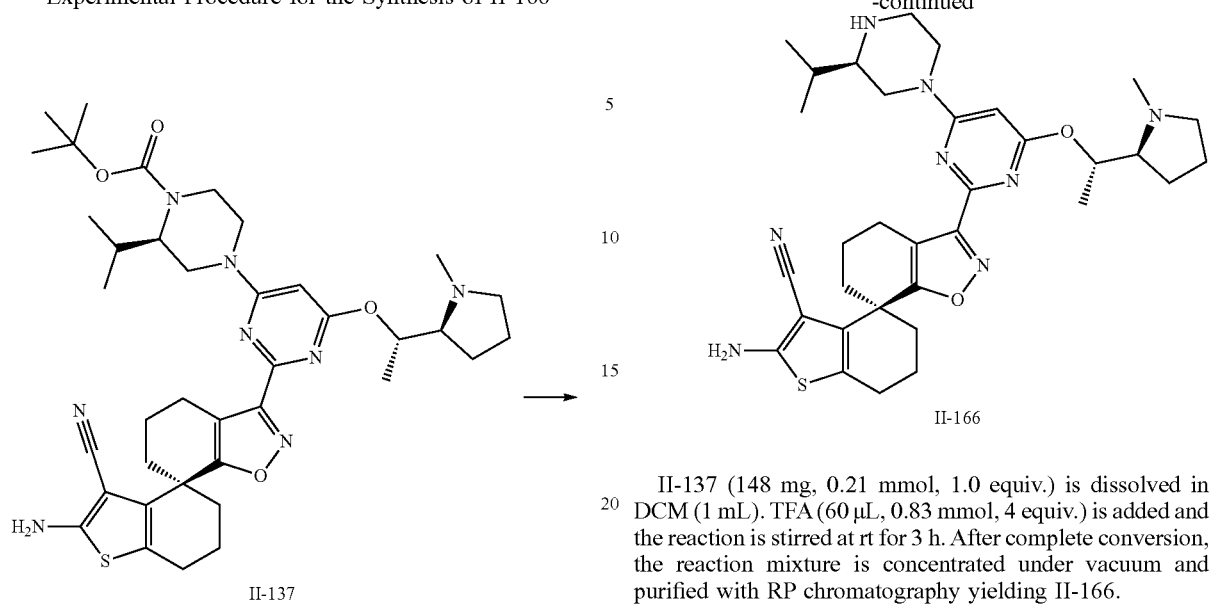

II-137 (148 mg, 0.21 mmol, 1.0 equiv.) is dissolved in DCM (1 mL). TFA (60 µL, 0.83 mmol, 4 equiv.) is added and the reaction is stirred at rt for 3 h. After complete conversion, the reaction mixture is concentrated under vacuum and purified with RP chromatography yielding II-166.

The following final compounds II (Table 69) are available in an analogous manner. The crude product is purified by chromatography if necessary.

TABLE 69

| # | structure | $t_{ret}$ [min] | $[M + H]^+$ | HPLC method |
|---|---|---|---|---|
| II-166 | 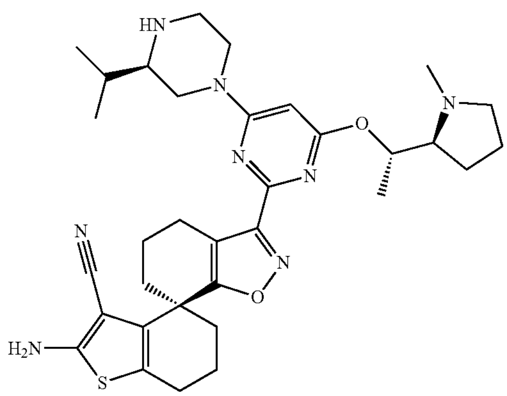 [SMILES: CC(C)[C@@H]1CN(c2cc(O[C@@H](C)[C@@H]3CCCN3C)nc(-c3noc4c3CCC[C@@]43CCCc4sc(N)c(C#N)c43)n2)CCN1] | 1.52 | 617 | A |
| II-167 | 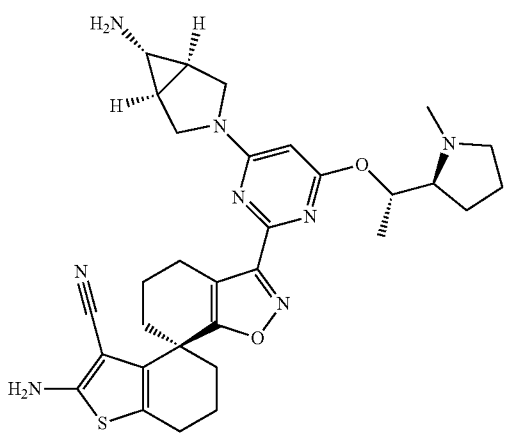 [SMILES: C[C@H](Oc1cc(N2C[C@@H]3[C@@H](N)[C@@H]3C2)nc(-c2noc3c2CCC[C@@]32CCCc3sc(N)c(C#N)c32)n1)[C@@H]1CCCN1C] | 1.36 | 587 | A |

TABLE 69-continued

| # | structure | $t_{ret}$ [min] | $[M + H]^+$ | HPLC method |
|---|---|---|---|---|
| II-168 | 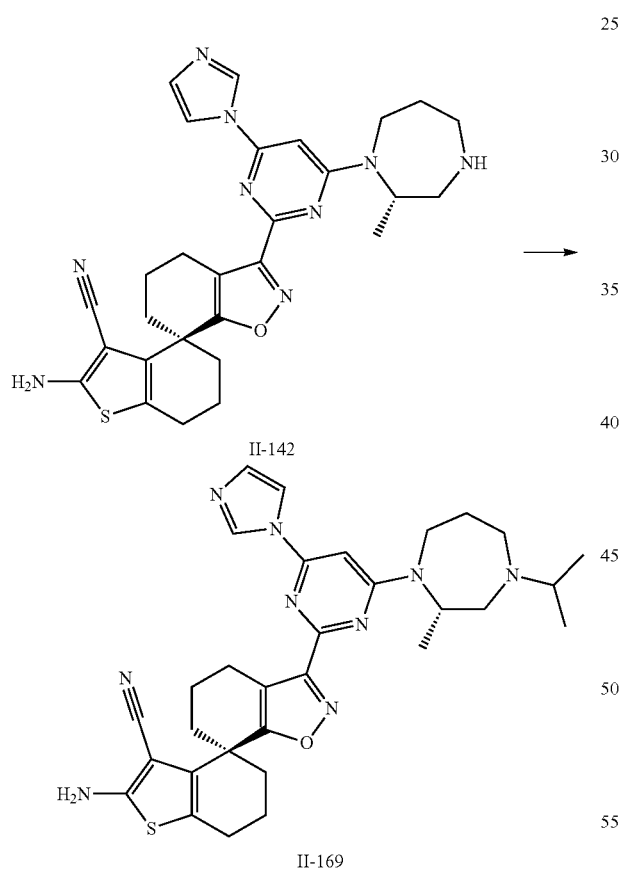 | 1.36 | 598 | A |

Experimental Procedure for the Synthesis of II-169

II-142 (70 mg, 0.129 mmol, 1.0 equiv.) is dissolved in DCM (1.0 mL), acetone (100 μL, 1.36 mmol, 10.5 equiv.) and acetic acid (1.48 μL, 0.03 mmol, 0.2 equiv.) is added. The resulting solution is cooled to 0° C. and stirred for 10 min. Then sodium triacetoxyborohydride (115 mg, 0.52 mmol, 4.0 equiv.) is added and the suspension is stirred for 1 h. The reaction mixture is quenched with water and the aq. phase is extracted with DCM. The combined organic phases are evaporated and the resulting residue is purified by RP chromatography to afford II-169.

The intermediates II (Table 70) are available in an analogous manner. The crude product is purified by chromatography if necessary.

TABLE 70

| # | structure | $t_{ret}$ [min] | $[M + H]^+$ | HPLC method |
|---|---|---|---|---|
| II-169 | 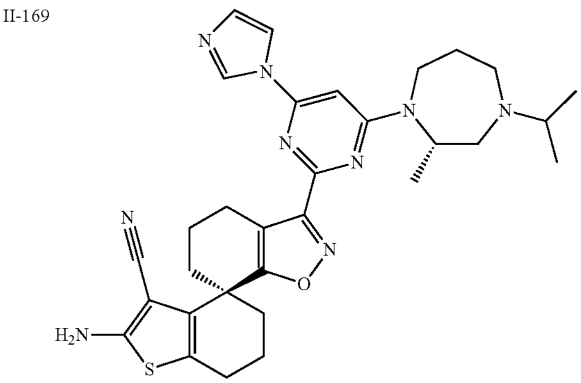 | 1.51 | 584 | A |
| II-170 | 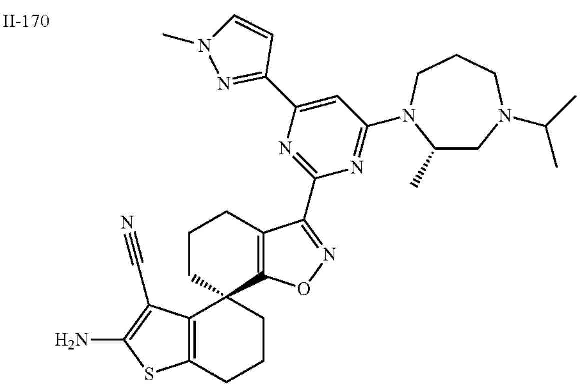 | 1.55 | 598 | A |

Experimental Procedure for the Synthesis of II-171

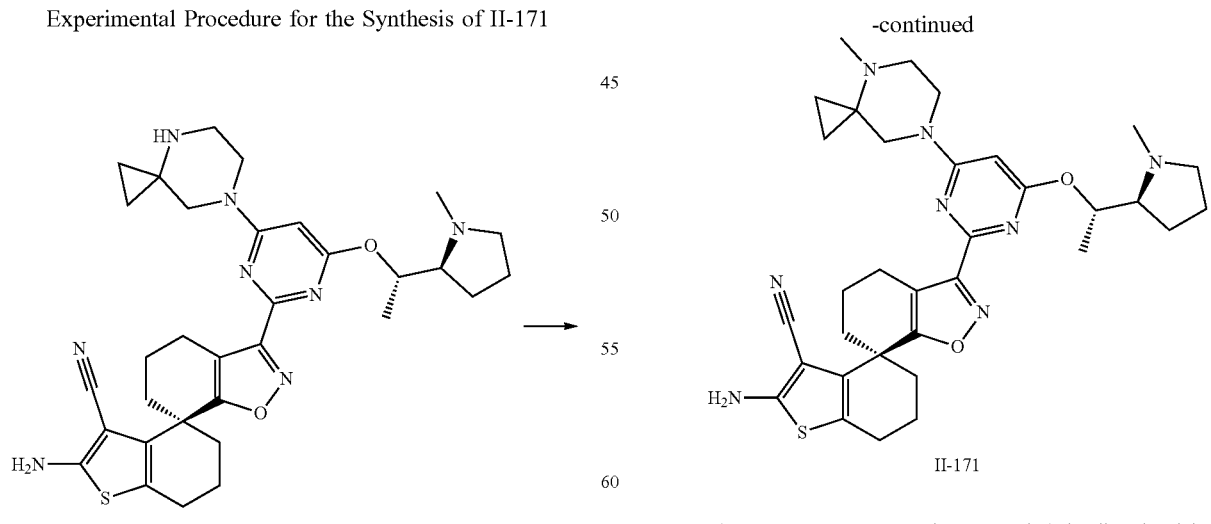

II-171

II-54 (50.0 mg, 0.083 mmol, 1.0 equiv.) is dissolved in DCM (1 mL) under Argon and cooled down to −30° C. Formaldehyde (7.48 μL, 0.100 mmol, 1.3 equiv.) is added, followed by the addition of sodium triacetoxyborohydride (74.2 mg, 0.333 mmol, 4.0 equiv.). The solution is stirred for 30 min at −30° C. After complete consumption of starting material, the reaction is quenched by the addition of water. The aqueous phase is extracted with DCM (3×). The combined organic phases are filtered and concentrated under reduced pressure. The residue is dissolved in ACN and purified by RP chromatography (gradient elution: 60% to 98% ACN in water) to give the desired product II-171.

The following final products II (Table 71) are available in an analogous manner. The crude product is purified by chromatography if necessary.

TABLE 71

| # | structure | $t_{ret}$ [min] | $[M + H]^+$ | HPLC method |
|---|---|---|---|---|
| II-171 | 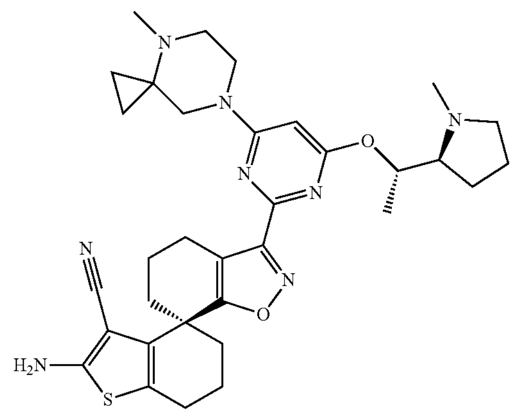 [SMILES: C[C@H](Oc1cc(N2CCN(C)C3(CC3)C2)nc(-c2noc3c2CCC[C@@]32CCCc3sc(N)c(C#N)c32)n1)[C@@H]1CCCN1C] | 1.52 | 615 | A |
| II-172 | 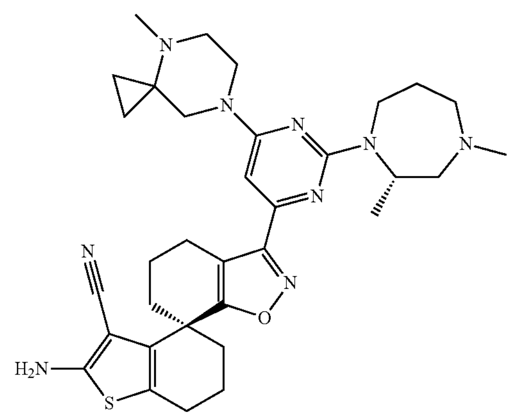 [SMILES: C[C@H]1CN(C)CCCN1c1nc(-c2noc3c2CCC[C@@]32CCCc3sc(N)c(C#N)c32)cc(N2CCN(C)C3(CC3)C2)n1] | 1.59 | 614 | A |
| II-173 | 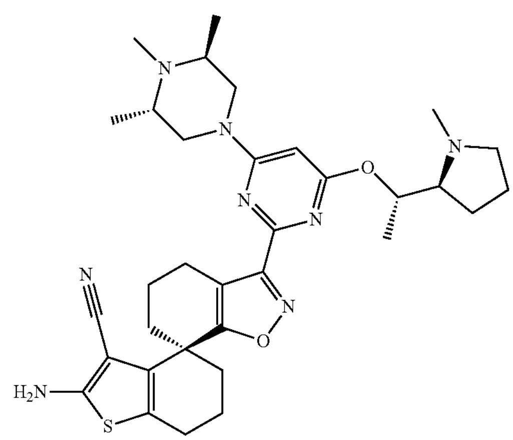 [SMILES: C[C@H](Oc1cc(N2C[C@H](C)N(C)[C@@H](C)C2)nc(-c2noc3c2CCC[C@@]32CCCc3sc(N)c(C#N)c32)n1)[C@@H]1CCCN1C] | 1.60 | 617 | A |

TABLE 71-continued
| # | structure | $t_{ret}$ [min] | [M + H]$^+$ | HPLC method |
|---|---|---|---|---|
| II-174 | 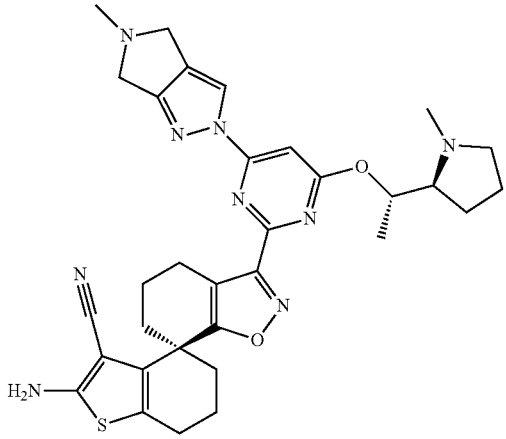 [SMILES: C[C@H](Oc1cc(-n2cc3c(n2)CN(C)C3)nc(-c2noc3c2CCC[C@@]32CCCc3sc(N)c(C#N)c32)n1)[C@@H]1CCCN1C] | 1.66 | 612 | A |
| II-175 | 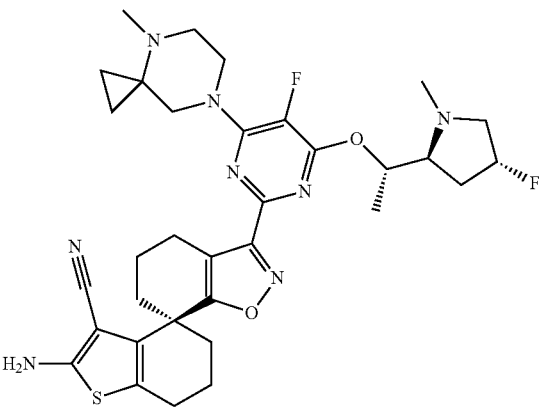 [SMILES: C[C@H](Oc1nc(-c2noc3c2CCC[C@@]32CCCc3sc(N)c(C#N)c32)nc(N2CCN(C)C3(CC3)C2)c1F)[C@@H]1C[C@@H](F)CN1C] | 1.61 | 649 | A |
| II-176 | 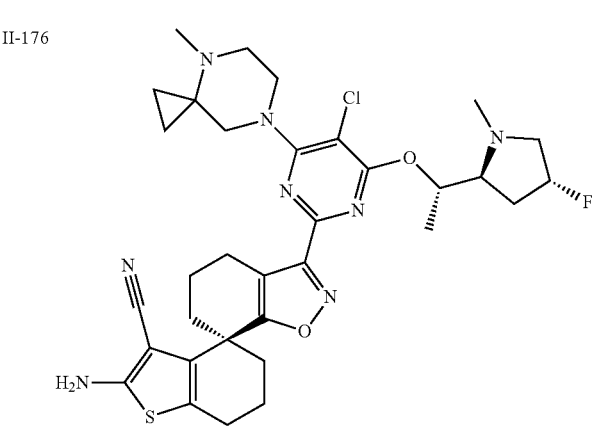 | 1.67 | 667 | A |

Experimental Procedure for the Synthesis of II-177

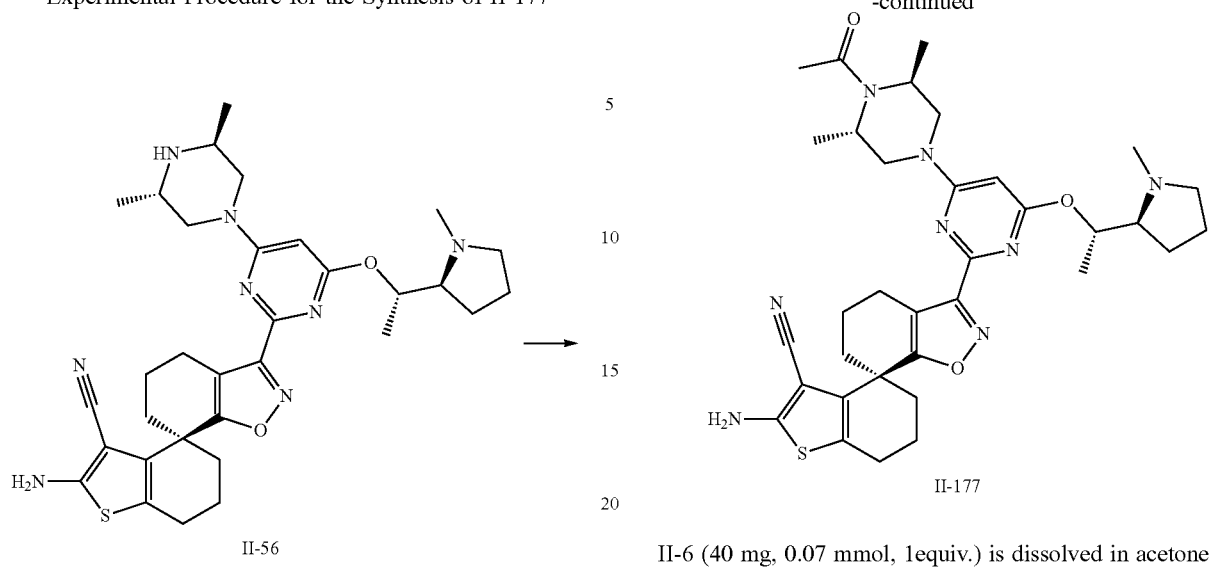

II-6 (40 mg, 0.07 mmol, 1equiv.) is dissolved in acetone (720 µL) and an aqueous solution of potassium carbonate (27.5 mg, 0.2 mmol, 3.0 equiv.) in water (280 µL) is added. Acetyl chloride (1 M in acetone, 51.8 mg, 0.07 mmol, 1 eq) is added to the reaction and the reaction mixture is stirred for 3 h at rt. After complete conversion, the reaction mixture is concentrated under reduced pressure, dissolved in DMF/water and purified by RP chromatography yielding II-177.

The following final compounds II (Table 72) are available in an analogous manner. The crude product is purified by chromatography if necessary.

TABLE 72

| # | structure | $t_{ret}$ [min] | $[M + H]^+$ | HPLC method |
|---|-----------|-----------------|-------------|-------------|
| II-177 | 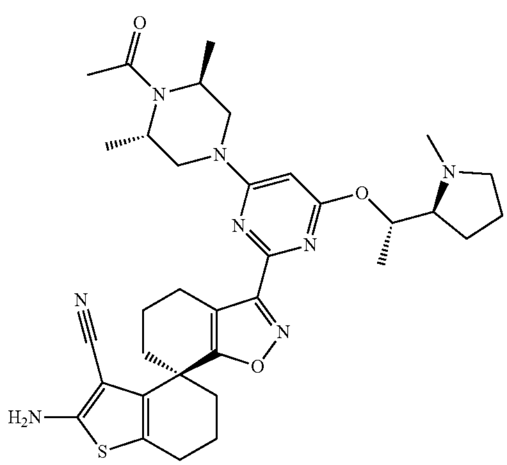 [SMILES: CC(=O)N1[C@@H](C)CN(c2cc(O[C@@H](C)[C@@H]3CCCN3C)nc(-c3noc4c3CCC[C@@]43CCCc4sc(N)c(C#N)c43)n2)C[C@@H]1C] | 1.41 | 545 | A |

TABLE 72-continued

| # | structure | $t_{ret}$ [min] | $[M + H]^+$ | HPLC method |
|---|---|---|---|---|
| II-178 | 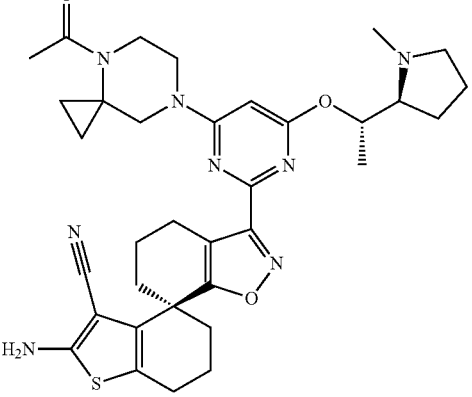 | 1.46 | 643 | A |

Experimental Procedure for the Synthesis of II-210

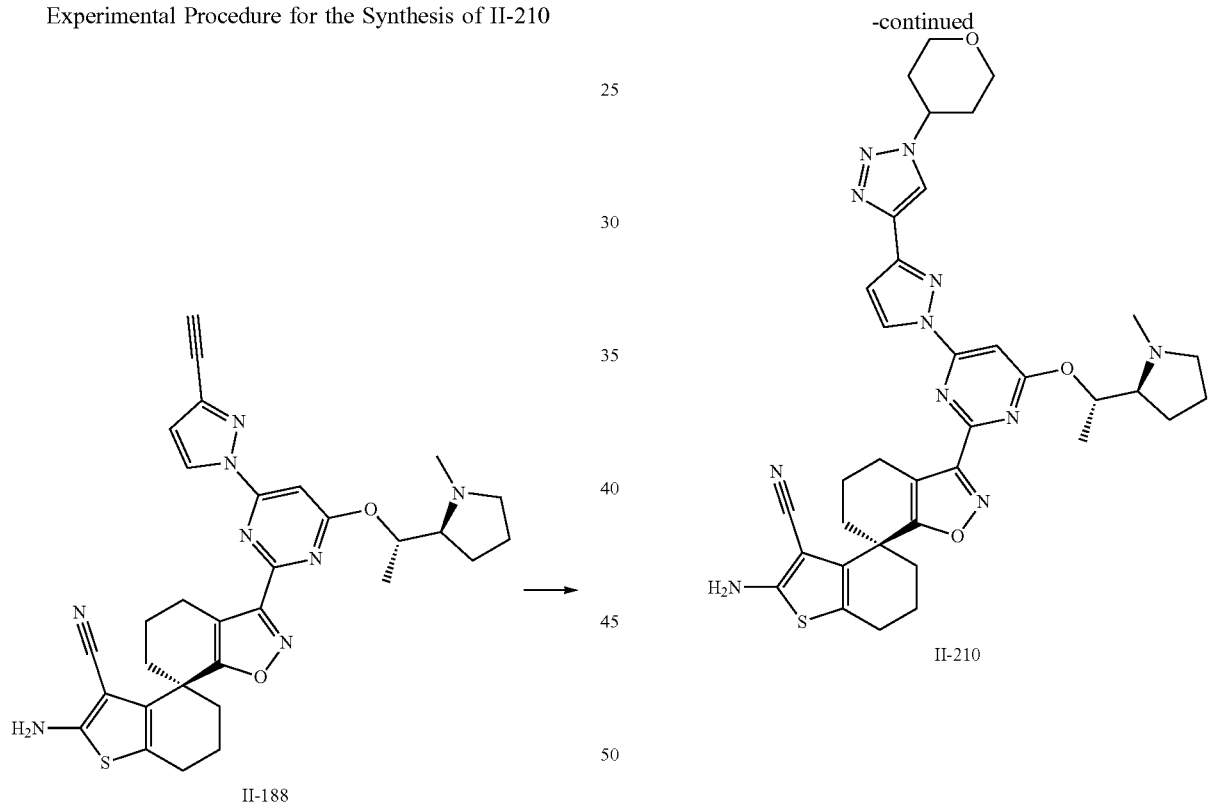

II-188 (76 mg, 0.13 mmol, 1 equiv.), 4-azidooxane (19.8 mg, 0.15 mmol, 1.1 equiv.) and CuI (2.6 mg, 0.013 mmol, 0.1 equiv.) are suspended in DCM (2.0 mL). DIPEA (53.2 mg, 0.27 mmol, 2.0 equiv.) is added and the reaction mixture is stirred for 12 h at 40° C. After complete conversion, the reaction mixture is concentrated under reduced pressure, dissolved in DMF, filtered and purified by RP chromatography yielding II-210.

The following final compounds II (Table 73) are available in an analogous manner. The crude product is purified by chromatography if necessary.

TABLE 73
| # | structure | t_ret [min] | [M + H]+ | HPLC method |
|---|---|---|---|---|
| II-210 | 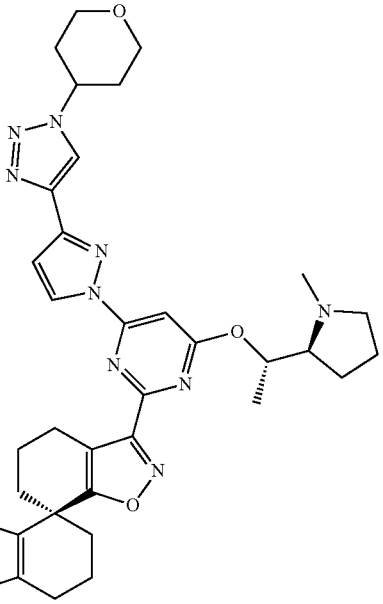 | 1.53 | 708 | A |
| II-211 | 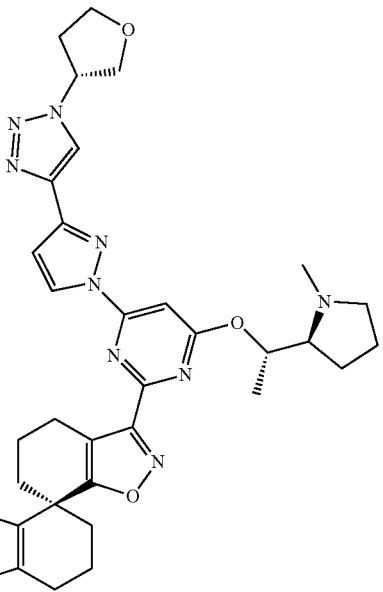 | 1.50 | 694 | A |

TABLE 73-continued

| # | structure | $t_{ret}$ [min] | $[M + H]^+$ | HPLC method |
|---|---|---|---|---|
| II-212 | 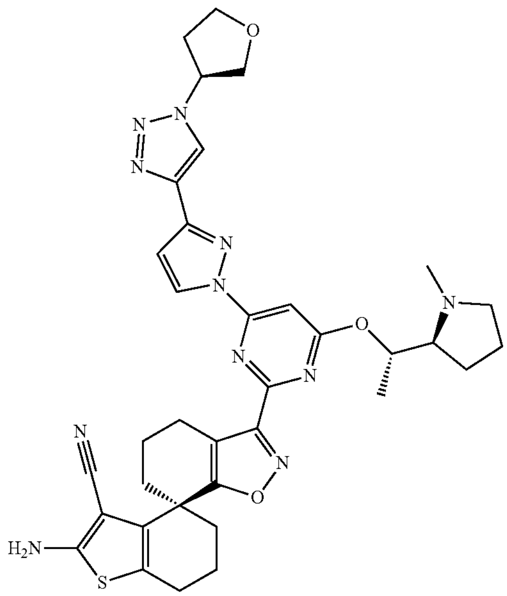 [SMILES: C[C@H](Oc1cc(-n2ccc(-c3cn([C@H]4CCOC4)nn3)n2)nc(-c2noc3c2CCC[C@@]32CCCc3sc(N)c(C#N)c32)n1)[C@@H]1CCCN1C] | 1.52 | 694 | A |
| II-213 | 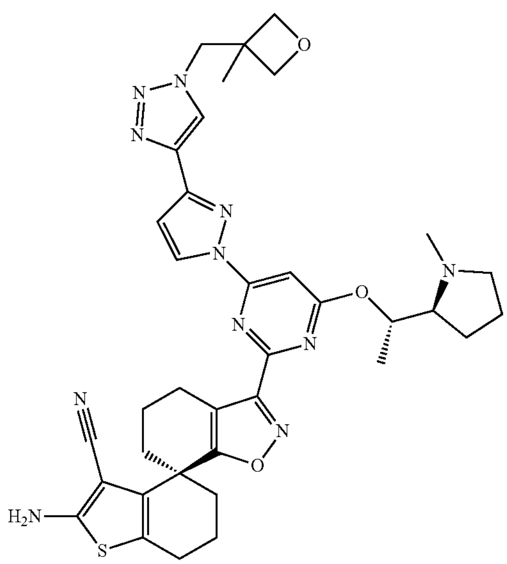 [SMILES: C[C@H](Oc1cc(-n2ccc(-c3cn(CC4(C)COC4)nn3)n2)nc(-c2noc3c2CCC[C@@]32CCCc3sc(N)c(C#N)c32)n1)[C@@H]1CCCN1C] | 1.50 | 708 | A |

The following Examples describe the biological activity of the compounds according to the invention, without restricting the invention to these Examples.

KRAS:SOS1 AlphaScreen Binding Assay

This assay can be used to examine the potency with which compounds according to the invention binding to (mutated) KRAS inhibit the protein-protein interaction between SOS1 and (mutated) KRAS e.g., KRAS WT, KRAS G12C, KRAS G12D, KRAS G12V, KRAS G13D. This inhibits the GEF functionality of SOS1 and locks the corresponding (mutated) KRAS protein in its inactive, GDP-bound state. Low $IC_{50}$ values in this assay setting are indicative of strong inhibition of protein-protein interaction between SOS1 and KRAS:

Description of the Assay:

These assays measure the inhibitory effect of compounds on KRAS mutant protein-protein interactions using the Alpha Screen technology by Perkin Elmer.

The following (mutant) enzyme forms of KRAS and interacting proteins are used in these assays at the given concentrations:

KRAS (G12D) 1-169, N-terminal 6His-tag, C-terminal avi-tag (Xtal BioStructures, Inc.); final assay concentration 10 nM and SOS1 564-1049, N-terminal 229 GST-tag, TEV cleavage site (Viva Biotech Ltd); final assay concentration 5 nM;

KRAS (G12C) 1-169, N-terminal 6His-tag for purification, cleaved off, C-terminal avi-tag, biotinylated, mutations: C51S, C80L, C118S (in house); final assay concentration 7.5 nM and SOS1 564-1049, N-terminal 229 GST-tag, TEV cleavage site (Viva Biotech Ltd); final assay concentration 5 nM;

KRAS (G12V) 1-169, N-terminal 6His-tag for purification, cleaved off, C-terminal avi-tag, biotinylated, TEV cleavage site, mutation: C118S, GDP loaded (in house);

final assay concentration 10 nM and SOS1 564-1049, N-terminal 229 GST-tag, TEV cleavage site (Viva Biotech Ltd); final assay concentration 10 nM;

KRAS (G13D) 1-169, N-terminal 6His-tag for purification, cleaved off, C-terminal avi-tag, biotinylated, TEV cleavage site, mutation: C118S, GDP loaded (in house); final assay concentration 10 nM and SOS1 564-1049, N-terminal 229 GST-tag, TEV cleavage site (Viva Biotech Ltd); final assay concentration 10 nM;

KRAS (WT) 1-169, N-terminal 6His-tag for purification, cleaved off, C-terminal avi-tag, biotinylated, TEV cleavage site, mutation: C118S, GDP loaded (in house); final assay concentration 10 nM and SOS1 564-1049, N-terminal 229 GST-tag, TEV cleavage site (Viva Biotech Ltd); final assay concentration 10 nM.

Test compounds dissolved in DMSO are dispensed onto assay plates (Proxiplate 384 PLUS, white, PerkinElmer; 6008289) using an Access Labcyte Workstation with the Labcyte Echo 55x. For the chosen highest assay concentration of 100 µM, 150 nL of compound solution are transferred from a 10 mM DMSO compound stock solution. A series of eleven fivefold dilutions per compound are transferred to the assay plate, compound dilutions are tested in duplicates. DMSO are added as backfill to a total volume of 150 nL.

The assays run on a fully automated robotic system in a darkened room below 100 Lux. To 150 nl of compound dilution 10 µl of a mix including KRAS mutant protein, SOS1 (final assay concentrations see above) and GDP nucleotide (Sigma G7127; final assay concentration 10 µM) in assay buffer (1×PBS, 0.1% BSA, 0.05% Tween 20) are added into columns 1-24.

After 30 minutes incubation time 5 µl of Alpha Screen bead mix in assay buffer are added into columns 1-23. Bead mix consists of AlphaLISA Glutathione Acceptor Beads (PerkinElmer, Cat No AL109) and AlphaScreen Streptavidin Donor Beads (PerkinElmer Cat No 6760002) in assay buffer at a final assay concentration of 10 µg/ml each.

Plates are kept at room temperature in a darkened incubator. After an additional 60 minutes incubation time the signal is measured in a PerkinElmer Envision HTS Multi-label Reader using the AlphaScreen specs from PerkinElmer.

Each plate contains up to 16 wells of a negative control depending on the dilution procedure (platewise or serial) (DMSO instead of test compound; with KRAS mutant: SOS1 GDP mix and bead mix; column 23) and 16 wells of a positive control (DMSO instead of test compound; with KRAS mutant:SOS1 GDP mix w/o bead mix; column 24).

As internal control known inhibitors of KRAS mutant: SOS1 interaction can be measured on each compound plate.

IC50 values are calculated and analyzed with Boehringer Ingelheim's MEGALAB IC50 application using a 4 parametric logistic model.

Tables of example compounds disclosed herein contain $IC_{50}$ values determined using the above assays (see Table 74).

TABLE 74

| Ex # | KRAS G12D IC50 (nM) | KRAS G12C IC50 (nM) | KRAS G12V IC50 (nM) | KRAS G13D IC50 (nM) | KRAS WT IC50 (nM) |
|---|---|---|---|---|---|
| I-1 | 3 | 2 | | | |
| I-2 | 2 | 45 | | | 42 |
| I-3 | 1 | 3 | | | 7 |
| I-4 | 1 | 2 | 8 | 20 | 3 |
| I-5 | 1 | 2 | | | 4 |
| I-6 | 1 | 5 | | | |
| I-7 | 3 | 23 | | | |
| I-8 | 1 | 4 | | | |
| I-9 | 2 | 5 | | | |
| I-10 | 1 | 3 | | | |
| I-11 | 1 | 7 | | | |
| I-12 | 1 | 2 | | | |
| I-13 | 1 | 7 | | | |
| I-14 | 3 | 2 | | | |
| I-15 | 348 | 299 | | | |
| I-16 | 2 | 2 | | | |
| I-17 | 15 | 4 | | | |
| I-18 | 3 | 2 | | | |
| I-19 | 12 | 2 | | | |
| I-20 | 2 | 2 | | | |
| I-21 | 4 | 2 | | | |
| I-22 | 1 | 2 | | | 3 |
| I-23 | 7 | 3 | | | |
| I-24 | 2 | 2 | | | |
| I-25 | 5 | 2 | | | |
| I-26 | 3 | 2 | | | |
| I-27 | 3 | 2 | | | |
| I-28 | 10 | 3 | 3 | | 18 |
| I-29 | 6 | 3 | | | |
| I-30 | 2 | 2 | | | 3 |
| I-31 | 3 | 2 | | | |
| I-32 | 2 | 2 | | | |
| I-33 | 6 | 2 | | | |
| I-34 | 4 | 2 | | | 4 |
| I-35 | 21 | 32 | | | |
| I-37 | 1 | 2 | | | 4 |
| I-39 | 1 | 10 | | 146 | 11 |
| I-40 | 6 | 88 | | | |
| I-41 | 1 | 6 | | | 5 |
| I-42 | 35 | 606 | | | |
| I-43 | 1 | 6 | 8 | | |
| I-44 | 2 | 13 | | | |
| I-45 | 1 | 4 | 8 | | 6 |
| I-48 | 1 | 2 | | | |
| I-49 | 1 | 3 | | | |
| I-50 | 1 | 5 | | | |
| I-53 | 1 | 1 | | | |
| I-54 | 1 | 1 | | | |
| I-55 | 1 | 1 | | | |
| I-56 | 2 | 2 | | | |
| I-57 | 2 | 2 | | | |
| I-58 | 1 | 1 | | | |
| I-59 | 1 | 1 | | | |
| I-60 | 1 | 1 | | | |
| II-6 | 2 | 2 | | | |
| II-7 | 1 | 5 | | | |
| II-8 | 1 | 3 | | | |
| II-10 | 2 | 7 | | | |
| II-11 | 1 | 6 | | | 4 |
| II-12 | 1 | 8 | | | 15 |
| II-13 | 1 | 2 | 3 | 8 | 3 |
| II-14 | 1 | 4 | | | 15 |
| II-15 | 1 | 7 | 39 | 71 | 11 |
| II-16 | 1 | 74 | | | |
| II-17 | 2 | 3 | | | 5 |
| II-18 | 2 | 3 | | | 6 |
| II-19 | 1 | 1 | | 9 | |
| II-20 | 2 | 1 | 2 | | 4 |
| II-21 | 2 | 2 | 1 | 12 | 3 |
| II-23 | 2 | 1 | | | |
| II-24 | 3 | 2 | | | |
| II-25 | 2 | 1 | 7 | 11 | 16 |
| II-26 | 2 | 1 | 2 | 8 | 3 |
| II-27 | 8 | 2 | | | |
| II-28 | 22 | 7 | 12 | | |
| II-30 | 4 | 19 | | | |
| II-31 | 1 | 2 | | 8 | |
| II-32 | 1 | 2 | | | |
| II-33 | 2 | 8 | | | |

TABLE 74-continued

| Ex # | KRAS G12D IC50 (nM) | KRAS G12C IC50 (nM) | KRAS G12V IC50 (nM) | KRAS G13D IC50 (nM) | KRAS WT IC50 (nM) |
|---|---|---|---|---|---|
| II-34 | 1 | 3 | 17 | 38 | 8 |
| II-35 | 2 | 7 | | | 13 |
| II-36 | 1 | 2 | | | |
| II-37 | 1 | 3 | | | |
| II-38 | 1 | 2 | | | |
| II-39 | 1 | 6 | | | |
| II-40 | 1 | 3 | | | |
| II-41 | 1 | 9 | | | |
| II-42 | 2 | 2 | 2 | | 5 |
| II-43 | 2 | 1 | | | |
| II-44 | 2 | 2 | | | |
| II-45 | 1 | 3 | | | |
| II-46 | 1 | 37 | | | 53 |
| II-47 | 1 | 4 | | | |
| II-48 | 1 | 7 | | | 34 |
| II-49 | 1 | 9 | 54 | 173 | 20 |
| II-50 | 1 | 2 | | | |
| II-51 | 1 | 4 | | | |
| II-53 | 1 | | | | 5 |
| II-54 | 1 | 2 | 9 | 33 | 3 |
| II-55 | 1 | 4 | 11 | 47 | 10 |
| II-56 | 1 | 2 | | | |
| II-57 | 2 | 2 | | | |
| II-58 | 3 | 2 | | | |
| II-59 | 2 | 2 | | | |
| II-60 | 2 | 2 | | | |
| II-61 | 3 | 2 | | | |
| II-62 | 7 | 3 | | | |
| II-63 | 12 | 3 | | | |
| II-64 | 1 | 2 | | | 2 |
| II-65 | 9 | 4 | | | |
| II-66 | 1 | 2 | | | |
| II-67 | 3 | 2 | | | |
| II-68 | 9 | 2 | | | |
| II-69 | 2 | 2 | | | 3 |
| II-70 | 2 | 2 | | 19 | |
| II-71 | 2 | 2 | | | |
| II-72 | 2 | 2 | | 9 | |
| II-73 | 2 | 3 | | | |
| II-74 | 6 | 3 | | | |
| II-75 | 1 | 2 | | | |
| II-76 | 3 | 2 | | 41 | |
| II-77 | 1 | 2 | | 8 | 4 |
| II-78 | 4 | 2 | 3 | | 7 |
| II-79 | 2 | 2 | | | |
| II-80 | 7 | 7 | | | |
| II-81 | 5 | 3 | | | |
| II-82 | 6 | 3 | 9 | | 36 |
| II-83 | 20 | 5 | | | |
| II-84 | 6 | 3 | | | |
| II-85 | 2 | 2 | 2 | | 5 |
| II-86 | 5 | 2 | | | 5 |
| II-87 | 3 | 3 | | | |
| II-88 | 1 | 2 | | | |
| II-89 | 12 | 3 | | | |
| II-90 | 21 | 7 | 8 | | 33 |
| II-91 | 4 | 2 | | | |
| II-92 | 14 | 5 | | | |
| II-93 | 3 | 3 | | | |
| II-94 | 1 | 1 | 2 | 9 | 3 |
| II-95 | 2 | 2 | | | |
| II-96 | 2 | 2 | 2 | | 5 |
| II-97 | 13 | 3 | | | |
| II-98 | 4 | 2 | | | |
| II-99 | 4 | 3 | | | |
| II-100 | 6 | 3 | | | |
| II-101 | 4 | 2 | 2 | | 8 |
| II-102 | 3 | 2 | | | |
| II-103 | 2 | 2 | | | |
| II-104 | 5 | 2 | | | 4 |
| II-105 | 2 | 2 | 2 | | 4 |
| II-106 | 9 | 4 | | | |
| II-107 | 4 | 2 | | | |
| II-109 | 3 | 2 | | | |
| II-110 | 3 | 2 | 3 | | 7 |
| II-111 | 3 | 2 | | | 4 |
| II-112 | 1 | 1 | | | |
| II-113 | 2 | 2 | | | |
| II-114 | 3 | 2 | | | |
| II-115 | 13 | 8 | | | |
| II-116 | 2 | 2 | | 17 | |
| II-117 | 2 | 1 | | | |
| II-118 | 4 | 2 | | | |
| II-119 | 2 | 2 | 2 | | 6 |
| II-120 | 9 | 2 | 5 | | |
| II-121 | 3 | 2 | | | |
| II-122 | 4 | 2 | | | 10 |
| II-123 | 8 | 2 | | | 11 |
| II-124 | 2 | 2 | | | |
| II-125 | 6 | 2 | | | 9 |
| II-126 | 7 | 2 | | | |
| II-127 | 3 | 2 | | | |
| II-128 | 2 | 2 | | | |
| II-129 | 3 | 2 | | | |
| II-130 | 2 | 2 | 2 | | 5 |
| II-131 | 6 | 4 | | | |
| II-132 | 3 | 2 | | | |
| II-133 | 6 | 2 | 2 | | 8 |
| II-134 | 4 | 2 | | | |
| II-140 | 22 | 5 | | | |
| II-141 | 2 | 2 | | | 3 |
| II-142 | 25 | 5 | | | |
| II-143 | 1 | 2 | | | |
| II-144 | 14 | 3 | | | |
| II-148 | 1 | 2 | 3 | | 5 |
| II-149 | 1 | 8 | | | 12 |
| II-150 | 1 | 2 | | | 3 |
| II-151 | 2 | 8 | | | 8 |
| II-152 | 3 | 7 | | | 14 |
| II-153 | 2 | 3 | | | |
| II-154 | 1 | 2 | | | |
| II-155 | 1 | 2 | | | 4 |
| II-156 | 1 | 2 | | | 6 |
| II-157 | 1 | 2 | | | 5 |
| II-158 | 2 | 2 | | | 4 |
| II-159 | 6 | 2 | | | |
| II-160 | 2 | 7 | | | |
| II-161 | 2 | 5 | | | |
| II-162 | 1 | 3 | | | 8 |
| II-163 | 1 | 2 | | | |
| II-164 | 1 | 2 | | | 8 |
| II-165 | 1 | 3 | 15 | 48 | 5 |
| II-166 | 1 | 8 | | | |
| II-167 | 2 | 5 | | | |
| II-168 | 1 | 2 | | | 3 |
| II-169 | 9 | 3 | | | |
| II-170 | 9 | 3 | | | |
| II-171 | 1 | 5 | 50 | 64 | 7 |
| II-172 | 36 | 888 | | | |
| II-173 | 1 | 5 | | | |
| II-174 | 1 | 2 | | | 4 |
| II-175 | 2 | 8 | | | 7 |
| II-176 | 2 | 15 | | | 31 |
| II-177 | 2 | 2 | | | |
| II-178 | 2 | 2 | | | |
| II-182 | 1 | 1 | | 8 | |
| II-183 | 1 | 2 | | | |
| II-184 | 1 | 2 | 2 | | |
| II-185 | 1 | 21 | | | |
| II-186 | 1 | 3 | | | |
| II-187 | 1 | 2 | | | |
| II-189 | 2 | 2 | 3 | | 4 |
| II-191 | 1 | 2 | | | |
| II-192 | 1 | 1 | 1 | 7 | 5 |
| II-193 | 1 | 1 | 2 | 9 | 6 |
| II-194 | 1 | 1 | | | |
| II-195 | 1 | 1 | 1 | 7 | 3 |
| II-196 | 1 | 1 | 2 | | 6 |
| II-197 | 1 | 1 | | | |
| II-198 | 1 | 1 | | | |

TABLE 74-continued

| Ex # | KRAS G12D IC50 (nM) | KRAS G12C IC50 (nM) | KRAS G12V IC50 (nM) | KRAS G13D IC50 (nM) | KRAS WT IC50 (nM) |
|---|---|---|---|---|---|
| II-199 | 1 | 1 | | | |
| II-200 | 1 | 1 | | | |
| II-201 | 2 | 1 | | 27 | |
| II-202 | 1 | 1 | | | |
| II-203 | 2 | 2 | | | |
| II-204 | 2 | 1 | | | |
| II-205 | 8 | 2 | | | |
| II-206 | 1 | 2 | | | |
| II-207 | 1 | 6 | | | |
| II-208 | 0 | 1 | | | 4 |
| II-209 | 0 | 4 | | | |
| II-210 | 1 | 2 | 2 | | 7 |
| II-211 | 1 | 2 | | | |
| II-212 | 1 | 2 | | | |
| II-213 | 1 | 2 | | | |
| II-214 | 1 | 9 | | | |

Ba/F3 Cell Model Generation and Proliferation Assay

Ba/F3 cells are ordered from DSMZ (ACC300, Lot17) and grown in RPMI-1640 (ATCC 30-2001)+10% FCS+10 ng/mL IL-3 at 37° C. in 5% $CO_2$ atmosphere. Plasmids containing KRASG12 mutants (i.e. G121D, G12C, G12V) are obtained from GeneScript. To generate KRASG12-dependent Ba/F3 models, Ba/F3 cells are transduced with retroviruses containing vectors that harbor KRASG12 isoforms. Platinum-E cells (Cell Biolabs) are used for retrovirus packaging. Retrovirus is added to Ba/F3 cells. To ensure infection, 4 µg/mL polybrene is added and cells are infected. Infection efficiency is confirmed by measuring GFP-positive cells using a cell analyzer. Cells with an infection efficiency of 10% to 20% are further cultivated and puromycin selection with 1 µg/mL is initiated. As a control, parental Ba/F3 cells are used to show selection status. Selection is considered successful when parental Ba/F3 cells cultures died. To evaluate the transforming potential of KRASG12 mutations, the growth medium is no longer supplemented with IL-3. Ba/F3 cells harboring the empty vector are used as a control. Approximately ten days before conducting the experiments, puromycin is left out.

For proliferation assays, Ba/F3 cells are seeded into 384-well plates at 1 0.5×10³ cells/60 µL in growth media (RPMI-1640+10% FCS). Compounds are added using an Access Labcyte Workstation with a Labcyte Echo 550 or 555 acoustic dispenser. All treatments are performed in technical duplicates. Treated cells are incubated for 72 h at 37° C. with 5% $CO_2$. AlamarBlue™ (ThermoFisher), a viability stain, is added and fluorescence measured in the PerkinElmer Envision HTS Multilabel Reader. The raw data are imported into and analyzed with the Boehringer Ingelheim proprietary software MegaLab (curve fitting based on the program PRISM, GraphPad Inc.).

$IC_{50}$ values of representative compounds according to the invention measured with this assay are presented in table 75.

TABLE 75

| Ex # | KRAS G12D Ba/F3 IC50 (nM) | KRAS G12C Ba/F3 IC50 (nM) | KRAS G12V Ba/F3 IC50 (nM) |
|---|---|---|---|
| I-1 | 178 | 77 | 43 |
| I-2 | 124 | 493 | |
| I-3 | 5 | 345 | 351 |
| I-4 | 9 | 69 | 134 |
| I-5 | 3 | 124 | 253 |
| I-6 | 14 | 253 | 316 |
| I-7 | 190 | 608 | |
| I-8 | 4 | 106 | 258 |
| I-9 | 92 | 264 | 496 |
| I-10 | 9 | 218 | 247 |
| I-11 | 24 | 331 | 416 |
| I-12 | 4 | 224 | 343 |
| I-13 | 49 | 1542 | 821 |
| I-14 | 18 | 15 | 7 |
| I-15 | 1133 | 930 | |
| I-16 | 32 | 21 | 9 |
| I-17 | 77 | 40 | 23 |
| I-18 | 22 | 11 | 8 |
| I-19 | 165 | 76 | 23 |
| I-20 | 30 | 14 | 10 |
| I-21 | 14 | 6 | 6 |
| I-22 | 14 | 9 | 9 |
| I-23 | 27 | 10 | 7 |
| I-24 | 24 | 9 | 5 |
| I-25 | 261 | 92 | 57 |
| I-26 | 48 | 17 | 13 |
| I-27 | 64 | 18 | 7 |
| I-28 | 250 | 67 | 41 |
| I-29 | 71 | 18 | 15 |
| I-30 | 42 | 9 | 8 |
| I-31 | 43 | 9 | 9 |
| I-32 | 14 | 3 | 3 |
| I-33 | 81 | 14 | 14 |
| I-34 | 38 | 7 | 14 |
| I-35 | | 289 | |
| I-37 | 78 | 1184 | 1340 |
| I-39 | 34 | 613 | 895 |
| I-40 | 243 | 913 | |
| I-41 | 11 | 233 | 445 |
| I-42 | 440 | 867 | |
| I-43 | 63 | 170 | 302 |
| I-44 | 91 | 509 | 1053 |
| I-45 | 11 | 280 | 453 |
| I-48 | 24 | 4 | 4 |
| I-49 | 3 | 130 | 184 |
| I-50 | 41 | 448 | 811 |
| I-53 | 12 | 2 | 1 |
| I-54 | 7 | 1 | 1 |
| I-55 | 12 | 2 | 1 |
| I-56 | 16 | 3 | 4 |
| I-57 | 8 | 1 | 1 |
| I-58 | 11 | 4 | 6 |
| I-59 | 13 | 2 | 1 |
| I-60 | 22 | 5 | 4 |
| II-6 | 4 | 6 | 5 |
| II-7 | 94 | 277 | 196 |
| II-8 | 144 | 301 | 316 |
| II-10 | 116 | 844 | 957 |
| II-11 | 85 | 241 | 324 |
| II-12 | 20 | 438 | 549 |
| II-13 | 24 | 120 | 247 |
| II-14 | 10 | 293 | 771 |
| II-15 | 14 | 323 | 340 |
| II-16 | 183 | 1572 | 1643 |
| II-17 | 39 | 373 | 422 |
| II-18 | 20 | 429 | 438 |
| II-19 | 10 | 5 | 3 |
| II-20 | 16 | 2 | 2 |
| II-21 | 23 | 4 | 3 |
| II-23 | 53 | 8 | 4 |
| II-24 | >25000 | 9221 | 8108 |
| II-25 | 25 | 3 | 4 |
| II-26 | 37 | 5 | 3 |
| II-27 | 49 | 18 | 16 |
| II-28 | 90 | 35 | 27 |
| II-30 | 273 | 1051 | |
| II-31 | 4 | 69 | 65 |
| II-32 | 3 | 474 | 1219 |
| II-33 | 82 | 527 | 657 |
| II-34 | 51 | 527 | 681 |

TABLE 75-continued

| Ex # | KRAS G12D Ba/F3 IC50 (nM) | KRAS G12C Ba/F3 IC50 (nM) | KRAS G12V Ba/F3 IC50 (nM) |
|---|---|---|---|
| II-35 | 82 | 1292 | 1683 |
| II-36 | 64 | 330 | 390 |
| II-37 | 26 | 132 | 177 |
| II-38 | 11 | 66 | 56 |
| II-39 | 68 | 193 | |
| II-40 | 7 | 381 | 456 |
| II-41 | 26 | 490 | 980 |
| II-42 | 26 | 34 | 5 |
| II-43 | 34 | 37 | 8 |
| II-44 | 32 | 28 | 14 |
| II-45 | 58 | 606 | 642 |
| II-46 | 116 | 50 | |
| II-47 | 40 | 240 | 164 |
| II-48 | 70 | 724 | 581 |
| II-49 | 16 | 329 | 304 |
| II-50 | 7 | 270 | 393 |
| II-51 | 37 | 314 | 693 |
| II-52 | 72 | 403 | 401 |
| II-53 | 57 | 292 | 285 |
| II-54 | 1 | 74 | 157 |
| II-55 | 63 | 297 | 302 |
| II-56 | 20 | 233 | 166 |
| II-57 | 40 | 38 | 45 |
| II-58 | 45 | 41 | 9 |
| II-59 | 35 | 31 | 31 |
| II-60 | 24 | 21 | 17 |
| II-61 | 55 | 47 | 38 |
| II-62 | 39 | 34 | 17 |
| II-63 | 266 | 114 | 49 |
| II-64 | 11 | 9 | 5 |
| II-65 | 122 | 97 | 40 |
| II-66 | 71 | 54 | 29 |
| II-67 | 38 | 28 | 15 |
| II-68 | 77 | 56 | 23 |
| II-69 | 26 | 18 | 7 |
| II-70 | 47 | 25 | 5 |
| II-71 | 41 | 28 | 8 |
| II-72 | 39 | 22 | 21 |
| II-73 | 16 | 10 | 17 |
| II-74 | 81 | 50 | 11 |
| II-75 | 83 | 26 | 14 |
| II-76 | 30 | 18 | 19 |
| II-77 | 28 | 14 | 11 |
| II-78 | 87 | 37 | 14 |
| II-79 | 45 | 24 | 18 |
| II-80 | 41 | 21 | 10 |
| II-81 | 103 | 49 | 13 |
| II-82 | 200 | 82 | 44 |
| II-83 | 33 | 15 | 18 |
| II-84 | 79 | 36 | 17 |
| II-85 | 72 | 19 | 8 |
| II-86 | 59 | 25 | 14 |
| II-87 | 150 | 47 | 25 |
| II-88 | 15 | 6 | 6 |
| II-89 | 199 | 57 | 18 |
| II-90 | 397 | 157 | 115 |
| II-91 | 65 | 15 | 8 |
| II-92 | 120 | 47 | 27 |
| II-93 | 43 | 16 | 45 |
| II-94 | 11 | 5 | 3 |
| II-95 | 81 | 30 | 27 |
| II-96 | 23 | 8 | 5 |
| II-97 | 198 | 58 | 26 |
| II-98 | 69 | 23 | 14 |
| II-99 | 83 | 28 | 35 |
| II-100 | 56 | 19 | 52 |
| II-101 | 155 | 51 | 28 |
| II-102 | 14 | 4 | 4 |
| II-103 | 21 | 7 | |
| II-104 | 78 | 24 | 12 |
| II-105 | 37 | 12 | 6 |
| II-106 | 107 | 31 | 23 |
| II-107 | 19 | 5 | 8 |
| II-108 | 54 | 15 | 8 |
| II-109 | 80 | 13 | 18 |
| II-110 | 51 | 14 | 13 |
| II-111 | 46 | 10 | 4 |
| II-112 | 42 | 11 | 6 |
| II-113 | 106 | 25 | 33 |
| II-114 | 99 | 16 | 7 |
| II-115 | 131 | 29 | 34 |
| II-116 | 30 | 6 | 8 |
| II-117 | 36 | 7 | 6 |
| II-118 | 133 | 25 | 26 |
| II-119 | 51 | 8 | 6 |
| II-120 | 149 | 27 | 13 |
| II-121 | 77 | 13 | 11 |
| II-122 | 132 | 21 | 10 |
| II-123 | 93 | 15 | 24 |
| II-124 | 58 | 9 | 12 |
| II-125 | 109 | 17 | 16 |
| II-126 | 211 | 32 | 26 |
| II-127 | 109 | 13 | 13 |
| II-128 | 83 | 10 | 31 |
| II-129 | 92 | 11 | 9 |
| II-130 | 45 | 6 | 6 |
| II-131 | 145 | 16 | 19 |
| II-132 | 99 | 10 | 6 |
| II-133 | 248 | 33 | 19 |
| II-134 | 1172 | 41 | 28 |
| II-135 | 1044 | 4 | 4 |
| II-140 | 2242 | 1023 | |
| II-141 | 14 | 134 | 170 |
| II-142 | 5858 | 2205 | 1774 |
| II-143 | 3 | 5 | 2 |
| II-144 | 4 | 2 | |
| II-148 | 14 | 99 | 162 |
| II-149 | 18 | 333 | 412 |
| II-150 | 3 | 55 | 77 |
| II-151 | 53 | 393 | 655 |
| II-152 | 68 | 1291 | 1192 |
| II-153 | 126 | 1561 | 2379 |
| II-154 | 82 | 245 | 135 |
| II-155 | 6 | 169 | 185 |
| II-156 | 16 | 353 | 271 |
| II-157 | 17 | 244 | 258 |
| II-158 | 24 | 135 | 108 |
| II-159 | 366 | 147 | 93 |
| II-160 | 429 | 1723 | 2008 |
| II-161 | 250 | 910 | 971 |
| II-162 | 41 | 526 | 574 |
| II-163 | 97 | 373 | 322 |
| II-164 | 66 | 240 | 133 |
| II-165 | 3 | 109 | 121 |
| II-166 | 154 | 386 | 430 |
| II-167 | 614 | 884 | 879 |
| II-168 | 27 | 62 | 26 |
| II-169 | 285 | 107 | 61 |
| II-170 | 89 | 26 | 17 |
| II-171 | 10 | 232 | 426 |
| II-172 | | 830 | |
| II-173 | 51 | 296 | 678 |
| II-174 | 16 | 103 | 71 |
| II-175 | 30 | 196 | 183 |
| II-176 | 112 | 1314 | 1206 |
| II-177 | 81 | 66 | 54 |
| II-178 | 85 | 31 | 32 |
| II-182 | 16 | 5 | 3 |
| II-183 | 12 | 2 | 3 |
| II-184 | 1 | 98 | 155 |
| II-185 | 47 | 305 | 334 |
| II-186 | 12 | 192 | 321 |
| II-187 | 3 | 133 | 225 |
| II-189 | 28 | 9 | 8 |
| II-191 | 11 | 3 | <0 |
| II-192 | 13 | 2 | 2 |
| II-193 | 9 | 2 | 2 |
| II-194 | 22 | 4 | 4 |
| II-195 | 14 | 2 | 2 |
| II-196 | 9 | 1 | 1 |
| II-197 | 6 | 2 | 1 |
| II-198 | 4 | 1 | 1 |

TABLE 75-continued

| Ex # | KRAS G12D Ba/F3 IC50 (nM) | KRAS G12C Ba/F3 IC50 (nM) | KRAS G12V Ba/F3 IC50 (nM) |
|---|---|---|---|
| II-199 | 16 | 3 | 3 |
| II-200 | 8 | 1 | 1 |
| II-201 | 18 | 3 | 1 |
| II-202 | 56 | 18 | 6 |
| II-203 | 59 | 6 | 4 |
| II-204 | 62 | 11 | 7 |
| II-205 | 85 | 19 | 6 |
| II-206 | 63 | 7 | 3 |
| II-207 | 18 | 283 | 387 |
| II-208 | 3 | 112 | 166 |
| II-209 | 18 | 271 | 389 |
| II-210 | 23 | 2 | 2 |
| II-211 | 28 | 6 | 3 |
| II-212 | 10 | 2 | 0 |
| II-213 | 43 | 11 | 6 |
| II-214 | 1706 | 1900 | 1364 |

Additional Proliferation Assays with Mutant Cancer Cell Lines

NCI-H358 CTG Proliferation Assay (120 h) (NSCLC, G12C)

NCI-H358 cells (ATCC No. CRL-5807) are dispensed into white bottom opaque 96 well plates (Perkin Elmer cat no. 5680) at a density of 2000 cells per well in 100 µL RPMI-1640 ATCC-Formulation (Gibco #A10491)+10% FCS (fetal calf serum) (assay 1) or into black 384-well plates, flat and clear bottom (Greiner, PNr. 781091) at a density of 200 cells per well in 60 µl RPMI-1640 ATCC-Formulation (Gibco #A10491)+10% FCS (fetal calf serum) (assay 2). Cells are incubated overnight at 37° C. in a humidified tissue culture incubator at 5% $CO_2$. Compounds (10 mM stock in DMSO) are added at logarithmic dose series using the HP Digital Dispenser D300 (Tecan) (assay 1) or the ECHO acoustic liquid handler system (Beckman Coulter) (assay 2), normalizing for added DMSO and including DMSO controls. For the T0 time point measurement, untreated cells are analyzed at the time of compound addition. Plates are incubated for 120 h, and cell viability is measured using CellTiter-Glo luminescent cell viability reagent (Promega product code G7570). Viability (stated as percent of control) is defined as relative luminescence units RLU of each well divided by the RLU of cells in DMSO controls. $IC_{50}$ values are determined from viability measurements by non-linear regression using a four parameter model.

NCI-H2122 CTG Proliferation Assay (120 h) (NSCLC, G12C)

The CTG assay is designed to measure quantitatively the proliferation of NCI-H2122 cells (ATCC CRL-5985), using the CellTiter Glow Assay Kit (Promega G7571). Cells are grown in RPMI medium (ATCC) supplemented with Fetal Calf Serum (Life Technologies, Gibco BRL, Cat. No. 10270-106). On "day 0" 200 NCI-H2122 cells are seeded in 60 µL RPMI ATCC+10% FCS+ Penstrep in a black 384-well plate, flat and clear bottom (Greiner, PNr. 781091). Cells are then incubated in the plates at 37° C. in a $CO_2$ incubator overnight. On day 1, compounds (10 mM stock in DMSO) are added with the ECHO acoustic liquid handler system (Beckman Coulter), including DMSO controls. Plates are incubated for 120 h, and cell viability is measured using CellTiter-Glo luminescent cell viability reagent (Promega product code G7570). Viability (stated as percent of control) is defined as relative luminescence units RLU of each well divided by the RLU of cells in DMSO controls. $IC_{50}$ values are determined from viability measurements by non-linear regression using a four parameter model.

AsPC-1 CTG Proliferation Assay (120 h) (Pancreatic Cancer, G12D)

The CTG assay is designed to measure quantitatively the proliferation of AsPC-1 cells (ATCC CRL-5985), using the CellTiter Glow Assay Kit (Promega G7571). Cells are grown in RPMI medium (ATCC) supplemented with Fetal Calf Serum (Life Technologies, Gibco BRL, Cat. No. 10270-106). On "day 0" 2000 AsPC-1 cells are seeded in 60 µL RPMI ATCC+10% FCS+Penstrep in a 384-well plate, flat and clear bottom (Greiner, PNr. 781091). Cells are then incubated in the plates at 37° C. in a $CO_2$ incubator overnight. On day 1, compounds (10 mM stock in DMSO) are added with the ECHO acoustic liquid handler system (Beckman Coulter), including DMSO controls. Plates are incubated for 120 h, and cell viability is measured using CellTiter-Glo luminescent cell viability reagent (Promega product code G7570). Viability (stated as percent of control) is defined as relative luminescence units RLU of each well divided by the RLU of cells in DMSO controls. $IC_{50}$ values are determined from viability measurements by non-linear regression using a four-parameter model.

GP2D Proliferation Assay (120 h) (Colorectal Cancer, G12D)

GP2D cells (ATCC No. CRL-5807) are dispensed into white 384-well plates, flat and white bottom (Perkin Elmer, 6007680) at a density of 500 cells per well in 40 µl DMEM (Sigma, D6429)+1× GlutaMAX (Gibco, 35050038)+10% FCS (fetal calf serum). Cells are incubated overnight at 37° C. in a humidified tissue culture incubator at 5% $CO_2$. Compounds (10 mM stock in DMSO) are added at logarithmic dose series using the HP Digital Dispenser D300 (Tecan), including DMSO controls and normalizing for added DMSO. For the T0 time point measurement, untreated cells are analyzed at the time of compound addition. Plates are incubated for 120 h, and cell viability is measured using CellTiter-Glo luminescent cell viability reagent (Promega product code G7570). Viability (stated as percent of control) is defined as relative luminescence units RLU of each well divided by the RLU of cells in DMSO controls. $IC_{50}$ values are determined from viability measurements by non-linear regression using a four parameter model.

SAS CTG Proliferation Assay (120 h) (HNSCC, Wt Amplified)

SAS cells (JCRB0260) are dispensed into 384-well plates, flat and clear bottom (Greiner, PNr. 781091) at a density of 300 cells per well in 60 µL DMEM:F12 (Gibco 31330-038)+ 10% Fetal Calf Serum (HyClone, PNr.: SH30084.03) and incubated at 37° C. in a $CO_2$ incubator overnight. The next day, compounds (10 mM stock in DMSO) are added with the ECHO acoustic liquid handler system (Beckman Coulter), including DMSO controls. Plates are incubated for 120 h, and cell viability is measured using CellTiter-Glo luminescent cell viability reagent (Promega product code G7570). Viability (stated as percent of control) is defined as relative luminescence units RLU of each well divided by the RLU of cells in DMSO controls. $IC_{50}$ values are determined from viability measurements by non-linear regression using a four-parameter model.

MKN1 CTG Proliferation Assay (120 h) (Gastric Cancer, Wt Amplified)

MKN1 cells (JCRB0252) are dispensed into white 384-well plates, flat and white bottom (Corning Costar, PNr.: 3570) at a density of 400 cells per well in 50 µL RPMI 1640 (PAN-Biotech, PNr.: P04-18047)+10% FCS (HyClone, PNr.: SH30084.03) (assay 1) or into white 384-well plates, flat and white bottom (Perkin Elmer, 6007680) at a density of 500 cells per well in 40 µl RPMI (Gibco, PNr.: 21875034)+10% FCS (HyClone, PNr.: SH30084.03) (assay 2) or into black 384-well plates, flat and clear bottom (Greiner, PNr. 781091) at a density of 200 cells per well in 60 µl RPMI-1640 (Gibco #A10491)+10% FCS (HyClone, PNr.: SH30084.03)+PenStrep (Gibco, PNr.15140-122) (assay 3). Cells are incubated overnight at 37° C. in a humidified tissue culture incubator at 5% $CO_2$. Compounds (10 mM stock in DMSO) are added at logarithmic dose series using the HP Digital Dispenser D300 (Tecan) (assay 1+2) or the ECHO acoustic liquid handler system (Beckman Coulter) (assay 3), including DMSO controls and normalizing for added DMSO. Plates are incubated for 120 h, and cell viability is measured using CellTiter-Glo luminescent cell viability reagent (Promega product code G7570). Viability (stated as percent of control) is defined as relative luminescence units RLU of each well divided by the RLU of cells in DMSO controls. $IC_{50}$ values are determined from viability measurements by non-linear regression using a four-parameter model.

SK-CO-1 CTG Proliferation Assay (120 h) (CRC, G12V)

SK-CO-1 cells (ATCC HTB-39) are dispensed into 384-well plates, flat and clear bottom (Greiner, PNr. 781091) at a density of 500 cells per well in 60 µL EMEM (Sigma M5650)+10% Fetal Calf Serum (HyClone, PNr.: SH30084.03) and incubated at 37° C. in a $CO_2$ incubator overnight. The next day, compounds (10 mM stock in DMSO) are added with the ECHO acoustic liquid handler system (Beckman Coulter), including DMSO controls. Plates are incubated for 120 h, and cell viability is measured using CellTiter-Glo luminescent cell viability reagent (Promega product code G7570). Viability (stated as percent of control) is defined as relative luminescence units RLU of each well divided by the RLU of cells in DMSO controls. $IC_{50}$ values are determined from viability measurements by non-linear regression using a four-parameter model.

LOVO CTG Proliferation Assay (120 h) (CRC, G13D)

LOVO cells (ATCC CCL-229) are dispensed into 384-well plates, flat and clear bottom (Greiner, PNr. 781091) at a density of 1000 cells per well in 60 µL DMEM (Sigma D6429)+10% Fetal Calf Serum (HyClone, PNr.: SH30084.03) and incubated at 37° C. in a $CO_2$ incubator overnight. The next day, compounds (10 mM stock in DMSO) are added with the ECHO acoustic liquid handler system (Beckman Coulter), including DMSO controls. Plates are incubated for 120 h, and cell viability is measured using CellTiter-Glo luminescent cell viability reagent (Promega product code G7570). Viability (stated as percent of control) is defined as relative luminescence units RLU of each well divided by the RLU of cells in DMSO controls. $IC_{50}$ values are determined from viability measurements by non-linear regression using a four-parameter model.

A375 CTG Proliferation Assay (120 h) (Melanoma, Wt, B-Raf Mutant, Negative Control)

A375 cells (ATCC CRL-1619) are dispensed into 384-well plates, flat and clear bottom (Greiner, PNr. 781091) at a density of 300 cells per well in 60 µL DMEM (Sigma 06429)+10% Fetal Calf Serum (HyClone, PNr.: SH30084.03) and incubated at 37° C. in a $OO_2$ incubator overnight. The next day, compounds (10 mM stock in DMSO) are added at logarithmic dose series using the HP Digital Dispenser D300 (Tecan), including DMSO controls. Plates are incubated for 120 h, and cell viability is measured using CellTiter-Glo luminescent cell viability reagent (Promega product code G7570). Viability (stated as percent of control) is defined as relative luminescence units RLU of each well divided by the RLU of cells in DMSO controls. $IC_{50}$ values are determined from viability measurements by non-linear regression using a four-parameter model.

$IC_{50}$ values of representative compounds according to the invention measured with these assays in the indicated cell lines are presented in table 76 and 77.

TABLE 76

| Ex # | H2122 IC50 (nM) | H358 (assay 1) IC50 (nM) | H358 (assay 2) IC50 (nM) | AsPC-1 IC50 (nM) | GP2D IC50 (nM) | SAS IC50 (nM) |
|---|---|---|---|---|---|---|
| I-1 | 4119 | | 577 | 5899 | | 2876 |
| I-3 | 3373 | | 1322 | 273 | 2 | 4889 |
| I-4 | 3750 | | 740 | 64 | 1 | 395 |
| I-5 | 2422 | 813 | 852 | 86 | 1 | 2038 |
| I-6 | 3376 | 809 | | 1695 | | 3439 |
| I-7 | 3456 | | | 2370 | | 472 |
| I-8 | 3043 | 874 | | 512 | 6 | 131 |
| I-9 | 3339 | | 1306 | 2852 | | 20226 |
| I-10 | | | 200 | | | |
| I-11 | 2555 | | 1980 | 565 | | 651 |
| I-12 | 3285 | | 3122 | 235 | 1 | 218 |
| I-13 | 6467 | | 4284 | 1546 | | 294 |
| I-14 | 2873 | | | 3410 | | 25 |
| I-16 | | | 204 | | 673 | 77 |
| I-17 | 4231 | | | 9846 | | 241 |
| I-18 | 1762 | | 179 | 7069 | | 72 |
| I-19 | 2714 | | 2161 | 3000 | | 217 |
| I-20 | 1360 | | 287 | 5424 | | 35 |
| I-21 | 1434 | | | 2975 | 546 | 40 |
| I-22 | 10156 | 31 | 10 | 650 | 27 | 33 |
| I-23 | 8831 | 1 | | 8157 | 1174 | 24 |
| I-24 | 930 | | 163 | 3452 | | 77 |
| I-25 | 1646 | | 188 | 3451 | | 285 |
| I-26 | 1068 | | 140 | 2239 | | 89 |
| I-27 | 599 | | 121 | 2123 | | 109 |
| I-28 | 2603 | | 240 | 3424 | | 934 |
| I-29 | 3133 | | 2757 | 10287 | | 97 |
| I-30 | 837 | | 205 | 4573 | 811 | 50 |
| I-31 | | | 266 | | 588 | 57 |
| I-32 | 1507 | | 303 | 4442 | | 52 |
| I-33 | 1423 | | | 3711 | | 81 |
| I-34 | 1074 | | 76 | 4153 | 872 | 185 |
| I-37 | | | 3892 | 609 | 24 | 412 |
| I-39 | | | 1451 | 149 | 17 | 1198 |
| I-41 | 3559 | | | 297 | 8 | 4186 |
| I-43 | 1408 | | | 1005 | 143 | 1797 |
| I-44 | 1274 | | 2326 | 980 | | 1195 |
| I-45 | | | 470 | 32 | 2 | 1190 |
| I-48 | | | 4 | 384 | | 13 |
| I-49 | | | 145 | 20 | 1 | 905 |
| I-50 | | | 733 | 115 | 10 | 2901 |
| I-53 | | | 1 | 414 | | 13 |
| I-54 | | | 4 | 266 | | 17 |
| I-55 | | | 5 | 565 | | 10 |
| I-56 | | | 2 | 695 | | 25 |
| I-57 | | | 6 | 278 | | |
| I-58 | | | 5 | 696 | | 45 |
| I-59 | | | 2 | 444 | | 15 |
| I-60 | | | 4 | 779 | | 40 |
| II-6 | 1159 | | | 1323 | | 10 |
| II-7 | 3497 | | | 1636 | | 1189 |
| II-8 | 933 | | | 2730 | | 534 |
| II-10 | 8444 | | 570 | 811 | 11 | 3542 |
| II-11 | 3510 | | | 1428 | 78 | 1321 |
| II-12 | 1387 | | | 544 | 9 | 1925 |
| II-13 | 5018 | | | 251 | 9 | 450 |
| II-14 | 1393 | | | 245 | 6 | 1667 |
| II-15 | 2423 | | | 220 | 9 | 1296 |
| II-16 | 3531 | | | 1919 | 56 | 3867 |
| II-17 | | | 134 | 251 | 6 | 1029 |
| II-18 | | | 160 | 45 | 2 | 293 |
| II-19 | 19 | 17 | 2 | 870 | 136 | 132 |
| II-20 | 2041 | 6 | 2 | 1031 | 57 | 86 |
| II-21 | 128 | 10 | 4 | 694 | 57 | 35 |
| II-23 | 2953 | | 4 | 1637 | | 222 |

TABLE 76-continued

| Ex # | H2122 IC50 (nM) | H358 (assay 1) IC50 (nM) | H358 (assay 2) IC50 (nM) | AsPC-1 IC50 (nM) | GP2D IC50 (nM) | SAS IC50 (nM) |
|---|---|---|---|---|---|---|
| II-24 | 5328 | | | >25000 | | 15616 |
| II-25 | 33 | | <0 | 891 | | 9 |
| II-26 | 143 | | 4 | 1380 | | 5 |
| II-27 | 898 | 112 | 44 | 4105 | 408 | 151 |
| II-28 | 9477 | | | 5068 | | 203 |
| II-30 | 3550 | | | 2385 | | 10607 |
| II-31 | 2546 | | 143 | 42 | 1 | 208 |
| II-32 | 3299 | | | 385 | 5 | 8310 |
| II-33 | 4122 | | | 1414 | | 597 |
| II-34 | 9006 | | | 1416 | 49 | 1949 |
| II-35 | 4799 | | 457 | 713 | 31 | 4733 |
| II-36 | 3478 | | | 990 | | 179 |
| II-37 | 5495 | | | 1454 | | 1246 |
| II-38 | 2586 | | | 213 | 4 | 47 |
| II-39 | 3597 | | | 1762 | | 2937 |
| II-40 | 1416 | | 1302 | 261 | 5 | 979 |
| II-41 | 1654 | | 1522 | 269 | | 2108 |
| II-42 | 357 | | 136 | 1886 | | 264 |
| II-43 | 102 | | 117 | 2051 | | 24 |
| II-44 | 1585 | | 398 | 2163 | | 6000 |
| II-45 | 10593 | 969 | >25000 | 2306 | | 530 |
| II-46 | 900 | | | 2739 | | 399 |
| II-47 | 2015 | | 2046 | 991 | 105 | 2619 |
| II-48 | 3099 | | 2162 | 1494 | 65 | 3878 |
| II-49 | 2836 | | 1906 | 511 | 6 | 1185 |
| II-50 | 2677 | | 2707 | 142 | 3 | 41 |
| II-51 | 2559 | | 3362 | 903 | | 70 |
| II-52 | | | 1716 | | | |
| II-53 | 3692 | | 230 | 825 | 29 | 1715 |
| II-54 | 1773 | 298 | 908 | 67 | 1 | 234 |
| II-55 | 4906 | | 588 | 748 | 46 | 968 |
| II-56 | 3193 | 587 | 173 | 378 | 13 | 1426 |
| II-57 | 916 | | 286 | 1844 | 164 | 54 |
| II-58 | 904 | | 562 | 6424 | | 342 |
| II-59 | 1347 | | 337 | 2243 | | 31 |
| II-60 | 6946 | | | 3368 | | 61 |
| II-61 | 2342 | | 1424 | 1548 | | 169 |
| II-62 | 4791 | | | 9192 | | 50 |
| II-63 | 3386 | | 66 | 3295 | | 1308 |
| II-64 | 6360 | 36 | | 1073 | 22 | 16 |
| II-65 | 2548 | | 3225 | 3560 | | 173 |
| II-66 | 5006 | | 586 | 3970 | | 60 |
| II-67 | 1299 | | 1038 | 2795 | | 8 |
| II-68 | 1233 | | 111 | 3242 | | 623 |
| II-69 | 515 | | 290 | 1729 | 585 | 102 |
| II-70 | 891 | | 131 | 1942 | | 41 |
| II-71 | 933 | | 209 | 1673 | | 47 |
| II-72 | 2251 | | 9 | 783 | | 206 |
| II-73 | 1612 | | | 1813 | 33 | |
| II-74 | 2859 | | 1682 | 3213 | | 192 |
| II-75 | 3132 | 49 | 10 | 1561 | 111 | 31 |
| II-76 | 1299 | | 507 | 3968 | | 66 |
| II-77 | 1775 | 51 | 9 | 738 | 37 | 152 |
| II-78 | 2145 | | 170 | 2117 | | 318 |
| II-79 | 1272 | | | 2829 | | 2586 |
| II-80 | 1670 | | | 5080 | | >25000 |
| II-81 | 1678 | | 1200 | 4863 | | 51 |
| II-82 | 2683 | | 807 | 5451 | | 990 |
| II-83 | 3818 | | | 5128 | | 18 |
| II-84 | 583 | | >25000 | 3057 | | 52 |
| II-85 | 1120 | | 23 | 1291 | | 26 |
| II-86 | 2081 | | 993 | 4137 | 824 | 502 |
| II-87 | 1989 | | 106 | 3062 | | 107 |
| II-88 | 434 | | 126 | 1983 | | 2223 |
| II-89 | 1530 | | 220 | 3037 | | 246 |
| II-90 | 1864 | | 3251 | 3809 | | 4386 |
| II-91 | 1094 | 78 | 19 | 2256 | 394 | 70 |
| II-92 | 1812 | | 3395 | 3916 | | 275 |
| II-93 | 1564 | | 872 | 4645 | | 366 |
| II-94 | 834 | 20 | 20 | 985 | 26 | 82 |
| II-95 | 1422 | | 400 | 3320 | | 5181 |
| II-96 | 307 | | 98 | 2237 | 809 | 148 |
| II-97 | 2018 | | 242 | 2359 | | 646 |
| II-98 | 1019 | | 242 | 3336 | | 30 |
| II-99 | 1165 | | 1339 | 3238 | | 88 |
| II-100 | 2142 | | | 9772 | | 3185 |
| II-101 | 1518 | | 195 | 2994 | | 130 |
| II-102 | 84 | | | 2770 | | 71 |
| II-104 | | | 391 | | 510 | 114 |
| II-105 | 847 | | 46 | 1324 | 463 | 55 |
| II-106 | 2861 | | 2250 | 9452 | | 96 |
| II-107 | 5720 | | | 7270 | | 7 |
| II-108 | | | 134 | | | |
| II-109 | 441 | | 78 | 3828 | | 20 |
| II-110 | 953 | | 217 | 2822 | | 68 |
| II-111 | 858 | | 139 | 2806 | 443 | 57 |
| II-112 | 197 | | 141 | 2252 | 248 | 54 |
| II-113 | 661 | | 128 | 2014 | | 381 |
| II-114 | 680 | | 123 | 2299 | | 28 |
| II-116 | 1123 | | | 6521 | | 2007 |
| II-117 | 47 | | 98 | 1656 | 276 | 22 |
| II-118 | 1007 | | 295 | 3174 | | 931 |
| II-119 | 251 | | 42 | 1325 | | 39 |
| II-120 | 1090 | | 190 | 3509 | | 488 |
| II-121 | 580 | | 268 | 3066 | | 560 |
| II-122 | 961 | | 823 | 3352 | | 889 |
| II-123 | 878 | | 439 | 1536 | | 113 |
| II-124 | 901 | | 114 | 2104 | | 68 |
| II-125 | 768 | | 255 | 1371 | | 182 |
| II-126 | 2687 | | 1685 | 10187 | | 189 |
| II-127 | 189 | | 400 | 2760 | | 18 |
| II-128 | 361 | | 417 | 2105 | | 46 |
| II-129 | 198 | | 295 | 2075 | | 18 |
| II-130 | 221 | 25 | 28 | 1085 | 233 | 176 |
| II-131 | 672 | | 277 | 3520 | | 623 |
| II-132 | 188 | | 324 | 5113 | | 319 |
| II-133 | 180 | 74 | 9 | 2700 | 301 | 202 |
| II-134 | 4119 | | | 9668 | | 35 |
| II-135 | 112 | | | 1387 | | 69 |
| II-140 | 8237 | | 702 | 21550 | | 128 |
| II-141 | 2826 | | | 244 | 4 | 873 |
| II-142 | 10530 | | 10772 | 10131 | | 6106 |
| II-143 | 584 | 25 | | 1506 | 59 | 48 |
| II-144 | 3692 | | | 7097 | >1000 | 302 |
| II-148 | 2218 | | | 376 | 11 | 421 |
| II-149 | 2546 | | | 257 | 8 | 849 |
| II-150 | 2509 | | 115 | 27 | 1 | 91 |
| II-151 | 3582 | | | 714 | 32 | 161 |
| II-152 | | | 926 | 526 | 13 | 4229 |
| II-153 | | | 2850 | 577 | 14 | 199 |
| II-154 | | | 374 | 1014 | 39 | 747 |
| II-155 | 929 | | 77 | 11 | 1 | 471 |
| II-156 | | | 230 | 86 | 1 | 440 |
| II-157 | | | 151 | 129 | 2 | 1189 |
| II-158 | | | 58 | 256 | 9 | 585 |
| II-159 | | | 31 | 1888 | | 70 |
| II-160 | 3186 | | | 3217 | | 821 |
| II-161 | 4850 | | | 1602 | | 1575 |
| II-162 | 3316 | | | 922 | 30 | 2120 |
| II-163 | 4505 | | | 935 | | 274 |
| II-164 | 4577 | | 40 | 483 | 23 | 1502 |
| II-165 | 1787 | | 166 | 25 | 1 | 437 |
| II-166 | 1254 | | | 1276 | | 1184 |
| II-167 | 9787 | | | 4231 | | 1392 |
| II-168 | 1773 | | | 778 | 12 | 441 |
| II-169 | 2282 | | 595 | 3731 | 1868 | 4410 |
| II-170 | 942 | | 623 | 3590 | | 1048 |
| II-171 | 3059 | | | 295 | 5 | 1100 |
| II-173 | 1456 | | | 1206 | 107 | 751 |
| II-174 | | | 112 | 103 | 3 | 248 |
| II-175 | 2740 | | | 434 | 21 | 118 |
| II-176 | | | 1640 | 851 | 50 | 4937 |
| II-177 | 2245 | | 583 | 2761 | | 221 |
| II-178 | 948 | | 129 | 814 | | 2568 |
| II-182 | | | 3 | 188 | | 32 |
| II-183 | | | <0 | 162 | | 6 |
| II-184 | | | 95 | 8 | 0 | 882 |
| II-185 | | | 510 | 190 | 15 | 2421 |
| II-186 | | | 273 | 38 | 2 | 532 |
| II-187 | | | 135 | 30 | 1 | 1148 |

TABLE 76-continued

| Ex # | H2122 IC50 (nM) | H358 (assay 1) IC50 (nM) | H358 (assay 2) IC50 (nM) | AsPC-1 IC50 (nM) | GP2D IC50 (nM) | SAS IC50 (nM) |
|---|---|---|---|---|---|---|
| II-189 | | | 19 | 1149 | | 51 |
| II-191 | | | 3 | 425 | | 10 |
| II-192 | | | 2 | 305 | 31 | 25 |
| II-193 | | | 1 | 176 | | 10 |
| II-194 | | | 3 | 411 | | 37 |
| II-195 | | | 4 | 282 | | 37 |
| II-196 | | | 2 | 248 | | 9 |
| II-197 | | | 1 | 226 | | 8 |
| II-198 | | | 1 | 143 | | 8 |
| II-199 | | | 5 | 446 | | 17 |
| II-200 | | | 3 | 340 | | 8 |
| II-201 | | | 6 | 651 | | 20 |
| II-202 | | | 5 | 380 | | 21 |
| II-203 | | | 5 | 483 | 137 | 18 |
| II-204 | | | 5 | 508 | 122 | 17 |
| II-205 | | | 18 | 1313 | | 20 |
| II-206 | | | 4 | 194 | | 25 |
| II-207 | | | 287 | 82 | | 1085 |
| II-208 | | | 99 | 15 | 0 | 718 |
| II-209 | | | 136 | 59 | | 737 |
| II-210 | | | 2 | 210 | | 14 |
| II-211 | | | 1 | 297 | | 17 |
| II-212 | | | 1 | 170 | | 19 |
| II-213 | | | 1 | 275 | | 13 |
| II-214 | | | | 3517 | | |

TABLE 77

| Ex # | MKN1 (assay 1) IC50 (nM) | MKN1 (assay 2) IC50 (nM) | MKN1 (assay 3) IC50 (nM) | SK-CO-1 IC50 (nM) | LOVO IC50 (nM) | A375 IC50 (nM) |
|---|---|---|---|---|---|---|
| I-1 | | | 1731 | 418 | 1271 | |
| I-3 | | | | 2086 | 2159 | |
| I-4 | | | 75 | 541 | 205 | |
| I-5 | | 499 | | 987 | 1639 | |
| I-6 | | | | 2081 | 1219 | |
| I-7 | | | | 1489 | 2812 | |
| I-8 | | | 395 | 532 | 296 | |
| I-9 | | | | 10823 | 649 | |
| I-11 | | | | 530 | 1708 | |
| I-12 | | | | 710 | 824 | |
| I-13 | | | 679 | 2156 | 1512 | |
| I-14 | | | | 71 | 1350 | |
| I-17 | | | | 357 | 730 | |
| I-18 | | | | 236 | 260 | |
| I-19 | | | | 56 | 479 | |
| I-20 | | | | 185 | 298 | |
| I-21 | | | 149 | 30 | 128 | |
| I-22 | | | 68 | 20 | 31 | >3000 |
| I-23 | | | | 139 | 79 | |
| I-24 | | | | 67 | 101 | |
| I-25 | | | | 357 | 1056 | |
| I-26 | | | | 118 | 281 | |
| I-27 | | | 396 | 52 | 265 | |
| I-28 | | | 1284 | 131 | 390 | |
| I-29 | | | | 381 | 1646 | |
| I-30 | | | | 31 | 66 | |
| I-32 | | | | 111 | 159 | |
| I-33 | | | | 181 | 574 | |
| I-34 | | | 693 | 84 | 161 | |
| I-37 | | | | 1081 | 165 | |
| I-39 | | 621 | | 2072 | 354 | |
| I-41 | | | | 2759 | 304 | |
| I-43 | | | | 892 | 554 | |
| I-44 | | | | 1206 | 925 | |
| I-45 | | 510 | | 763 | 315 | |
| I-48 | | | 17 | 14 | 23 | |
| I-49 | | 335 | 152 | 515 | 223 | |
| I-50 | | 785 | 627 | 2048 | 439 | |
| I-53 | | | 48 | 7 | 29 | |

TABLE 77-continued

| Ex # | MKN1 (assay 1) IC50 (nM) | MKN1 (assay 2) IC50 (nM) | MKN1 (assay 3) IC50 (nM) | SK-CO-1 IC50 (nM) | LOVO IC50 (nM) | A375 IC50 (nM) |
|---|---|---|---|---|---|---|
| I-54 | | | 26 | 7 | 32 | |
| I-55 | | | 39 | 9 | 39 | |
| I-56 | | | | 8 | 23 | |
| I-57 | | | 19 | 4 | 8 | |
| I-58 | 25 | | 17 | 14 | 29 | |
| I-59 | | | 26 | 5 | 22 | |
| I-60 | | | 32 | 21 | 49 | |
| II-6 | | | | 62 | 323 | |
| II-7 | | | | 1241 | 835 | |
| II-8 | | | | 692 | 680 | |
| II-10 | | | 1265 | 1665 | 972 | |
| II-11 | | | | 800 | 383 | |
| II-12 | | | 460 | 819 | 401 | |
| II-13 | | | | 896 | 61 | |
| II-14 | | | | 771 | 674 | |
| II-15 | | | | 1247 | 867 | |
| II-16 | | | | 1872 | 1339 | |
| II-17 | | | | 617 | 186 | |
| II-18 | | 279 | | 444 | 49 | |
| II-19 | | | 47 | 11 | 21 | 1115 |
| II-20 | 24 | | | 9 | 158 | >3000 |
| II-21 | 20 | 27 | 24 | 6 | 29 | >3000 |
| II-23 | | | 172 | 31 | 124 | |
| II-24 | | | | 9249 | 7420 | |
| II-25 | | | | 3 | 63 | |
| II-26 | | | | 3 | 109 | |
| II-27 | | | 116 | 115 | 345 | >3000 |
| II-28 | | | | 433 | 720 | |
| II-30 | | | | 9067 | >25000 | |
| II-31 | | | 30 | 365 | 182 | |
| II-32 | | | | 704 | 8323 | |
| II-33 | | | | 1049 | 737 | |
| II-34 | | | 453 | 1239 | 2403 | |
| II-35 | | | | 5734 | 1686 | |
| II-36 | | | | 1123 | 16620 | |
| II-37 | | | | 562 | 692 | |
| II-38 | | | | 174 | 74 | |
| II-39 | | | | 1239 | 2924 | |
| II-40 | | | | 488 | 508 | |
| II-41 | | | | 910 | 703 | |
| II-42 | | | | 38 | 149 | |
| II-43 | | | | 46 | 120 | |
| II-44 | | | | 193 | 92 | |
| II-45 | | | 1485 | 1786 | 6602 | |
| II-46 | | | | 655 | 1218 | |
| II-47 | | | | 600 | 459 | |
| II-48 | | | | 1068 | 736 | |
| II-49 | | >3000 | | 501 | 872 | 651 |
| II-50 | | | | 802 | 1634 | |
| II-51 | | | | 772 | 772 | |
| II-53 | | | 994 | 566 | 495 | |
| II-54 | | | | 464 | 531 | |
| II-55 | | | 876 | 754 | 1094 | |
| II-56 | | | 660 | 554 | 661 | |
| II-57 | | | | 87 | 500 | |
| II-58 | | | | 90 | 113 | |
| II-59 | | | | 67 | 72 | |
| II-60 | | | | 216 | 255 | |
| II-61 | | | | 192 | 276 | |
| II-62 | | | | 280 | 2322 | |
| II-63 | | | 578 | 134 | 640 | |
| II-64 | | | | 24 | 96 | 2579 |
| II-65 | | | | 360 | 289 | |
| II-66 | | | | 76 | 3676 | |
| II-67 | | | | 60 | 49 | |
| II-68 | | | | 5570 | 894 | |
| II-69 | | | | 115 | 52 | |
| II-70 | | | 387 | 28 | 77 | |
| II-71 | | | | 18 | 50 | |
| II-72 | | | 68 | 71 | 55 | |
| II-73 | | | | 43 | 250 | |
| II-74 | | | | 52 | 319 | |
| II-75 | | | 108 | 23 | 279 | 2536 |
| II-76 | | | | 120 | 51 | |
| II-77 | | | 18 | 40 | 39 | >3000 |

TABLE 77-continued

| Ex # | MKN1 (assay 1) IC50 (nM) | MKN1 (assay 2) IC50 (nM) | MKN1 (assay 3) IC50 (nM) | SK-CO-1 IC50 (nM) | LOVO IC50 (nM) | A375 IC50 (nM) |
|---|---|---|---|---|---|---|
| II-78 | | | 533 | 84 | 175 | |
| II-79 | | | | 188 | 106 | |
| II-80 | | | | 148 | 561 | |
| II-81 | | | | 32 | 289 | |
| II-82 | | | 712 | 170 | 728 | |
| II-83 | | | | 447 | 2200 | |
| II-84 | | | | 116 | 286 | |
| II-85 | | | 266 | 51 | 209 | |
| II-86 | | | | 121 | 77 | |
| II-87 | | | 302 | 71 | 427 | |
| II-88 | | | | 47 | 62 | |
| II-89 | | | 625 | 198 | 453 | |
| II-90 | | | | 451 | 735 | |
| II-91 | | | 247 | 78 | 136 | 1138 |
| II-92 | | | | 279 | 467 | |
| II-93 | | | | 140 | 136 | |
| II-94 | 32 | | 51 | 19 | 51 | >3000 |
| II-95 | | | | 341 | 149 | |
| II-96 | | | | 67 | 231 | |
| II-97 | | | 598 | 212 | 683 | |
| II-98 | | | | 137 | 608 | |
| II-99 | | | | 159 | 286 | |
| II-100 | | | | 257 | 83 | |
| II-101 | | | | 257 | 1016 | |
| II-102 | | | | 37 | 76 | |
| II-105 | | | 426 | 31 | 150 | |
| II-106 | | | | 491 | 993 | |
| II-107 | | | | 181 | 1009 | |
| II-109 | | | | 106 | 76 | |
| II-110 | | | | 126 | 92 | |
| II-111 | | | | 51 | 309 | |
| II-112 | | | | 34 | 58 | |
| II-113 | | | | 64 | 123 | |
| II-114 | | | 358 | 64 | 142 | |
| II-116 | | | | 64 | 8 | |
| II-117 | | | | 24 | 58 | |
| II-118 | | | | 3865 | 295 | |
| II-119 | | | 252 | 37 | 152 | |
| II-120 | | | 234 | 126 | 401 | |
| II-121 | | | | 57 | 129 | |
| II-122 | | | | 52 | 180 | 761 |
| II-123 | | | | 96 | 72 | 259 |
| II-124 | | | | 38 | 128 | |
| II-125 | | | | 121 | 97 | 324 |
| II-126 | | | | 137 | 251 | |
| II-127 | | | | 90 | 131 | |
| II-128 | | | | 47 | 91 | |
| II-129 | | | | 66 | 69 | |
| II-130 | 216 | | 297 | 29 | 190 | 1314 |
| II-131 | | | | 90 | 225 | |
| II-132 | | | | 18 | 120 | |
| II-133 | | | 391 | 89 | 459 | 1378 |
| II-134 | | | | 225 | 3242 | |
| II-135 | | | | 29 | 51 | |
| II-140 | | | | 292 | 5489 | |
| II-141 | | | | 436 | 284 | |
| II-142 | | | | 2186 | 2645 | |
| II-143 | | | | 9 | 96 | >3000 |
| II-144 | | | | 130 | 2844 | |
| II-148 | | | | 779 | 109 | |
| II-149 | | 467 | | 1976 | 270 | |
| II-150 | | 32 | | 325 | 81 | |
| II-151 | | | | 1358 | 1065 | |
| II-152 | | | | 955 | 650 | |
| II-153 | | | | 872 | 283 | |
| II-154 | | | | 2122 | 904 | |
| II-155 | | 284 | 633 | 263 | 107 | |
| II-156 | | | | 390 | 226 | |
| II-157 | | | | 339 | 136 | |
| II-158 | | | | 374 | 84 | |
| II-159 | | | | 131 | 356 | |
| II-160 | | | | 6852 | 7606 | |
| II-161 | | | | 1022 | 472 | |
| II-162 | | 411 | | 980 | 401 | |
| II-163 | | | | 649 | 1087 | |
| II-164 | | | 1072 | 287 | 246 | |
| II-165 | | 427 | | 529 | 303 | |
| II-166 | | | | 551 | 863 | |
| II-167 | | | | 1337 | 6428 | |
| II-168 | | | 176 | 154 | 193 | |
| II-169 | | | | 316 | 553 | |
| II-170 | | | | 121 | 270 | |
| II-171 | | | | 1534 | 593 | |
| II-173 | | | | 805 | 1228 | |
| II-174 | | 341 | | 385 | 139 | |
| II-175 | | | | 936 | 823 | |
| II-176 | | | | 2061 | 2683 | |
| II-177 | | | | 45 | 694 | |
| II-178 | | | | 149 | 624 | |
| II-182 | 24 | | 12 | 9 | 38 | |
| II-183 | | | 41 | 7 | 9 | |
| II-184 | | 227 | 68 | 249 | 325 | |
| II-185 | | >949 | 1901 | 1290 | 714 | |
| II-186 | | 313 | 260 | 880 | 357 | |
| II-187 | | 383 | 357 | 457 | 429 | |
| II-189 | 19 | | 18 | 45 | 39 | |
| II-191 | | | | 3 | 13 | |
| II-192 | 25 | 26 | 9 | 4 | 32 | |
| II-193 | | | 17 | 3 | 12 | |
| II-194 | 20 | | 25 | 11 | 13 | |
| II-195 | | | 22 | 4 | 12 | |
| II-196 | | | 17 | 4 | 15 | |
| II-197 | | | 16 | 4 | 14 | |
| II-198 | | | 15 | 3 | 25 | |
| II-199 | | | 51 | 17 | 34 | |
| II-200 | | | 11 | 5 | 15 | |
| II-201 | 20 | | 14 | 9 | 33 | |
| II-202 | | | 27 | 6 | 103 | |
| II-203 | | 41 | 63 | 12 | 70 | |
| II-204 | | 33 | 48 | 14 | 46 | |
| II-205 | | | 33 | 31 | 22 | |
| II-206 | | | 34 | 11 | 31 | |
| II-207 | | | 785 | 1256 | 310 | |
| II-208 | | 451 | 245 | 398 | 334 | |
| II-209 | | | 670 | 1391 | 493 | |
| II-210 | | | 37 | 3 | 35 | |
| II-211 | | | 22 | 4 | 40 | |
| II-212 | | | 17 | 4 | 35 | |
| II-213 | | | 12 | 7 | 117 | |
| II-214 | | | 5353 | | | |

ERK Phosphorylation Assay

ERK phosphorylation assays are used to examine the potency with which compounds inhibit the KRAS G12C-mediated signal transduction in a KRAS G12C mutant human cancer cell line in vitro. This demonstrates the molecular mode of action of compounds according to the invention by interfering with the RAS G12C protein signal transduction cascade. Low $IC_{50}$ values in this assay setting are indicative of high potency of the compounds according to the invention. It is observed that compounds according to the invention demonstrate an inhibitory effect on ERK phosphorylation in a KRAS G12C mutant human cancer cell line, thus confirming the molecular mode of action of the compounds on RAS G12C protein signal transduction.

ERK phosphorylation assays are performed using the following human cell lines: NCI-H358 (ATCC (ATCC CRL-5807): human lung cancer with a KRAS G12C mutation (→assay 1) and NCI-H358_Cas9_SOS2, i.e. the same cell line, in which SOS2 is knocked (→assay 2). Vectors containing the designed DNA sequences for the production of gRNA for SOS2 protein knock-out are obtained from Sigma-Aldrich. To generate the NCI-H358 SOS2 knock-out cell line, NCI-H358 cells expressing Cas9 endonuclease are transfected with XtremeGene9 reagent and the correspondent plasmids. Transfection efficiency is confirmed by measuring GFP-positive cells using a cell analyzer. GFP positive cells are collected and further expanded. These GFP-positive cell pools are single-cell diluted and SOS2 knock-out clones are identified via Western-blot and genomic DNA sequencing analysis.

Materials Used for the Assay:
RPMI-1640 Medium (ATCC@ 30-2001™)
Fetal Bovine Serum (FBS) from HyClone (SH30071.03)
Non-essential amino acids from Thermo Fischer Scientific (11140035)
Pyruvate from Thermo Fischer Scientific (11360039)
Glutamax from Thermo Fischer Scientific (35050061)
384 plates from Greiner Bio-One (781182)
Proxiplate™ 384 from PerkinElmer Inc. (6008280)
AlphaLISA SureFire Ultra p-ERK1/2 (Thr202/Tyr204) Assay Kit (ALSU-PERK-A500)
EGF from Sigma (E4127)
Acceptor Mix: Protein A Acceptor Beads from PerkinElmer (6760137M)
Donor Mix: AlphaScreen Streptavidin-coated Donor Beads from PerkinElmer (6760002)
Trametinib
Staurosporine from Sigma Aldrich (S6942)

Assay Setup:
Cells are seeded at 40,000 cells per well in/60 µL of RPMI with 10% FBS, non-essential amino acids, pyruvate and glutamax in Greiner TC 384 plates. The cells are incubated for 1 h at room temperature and then incubated overnight in an incubator at 37° C. and 5% $CO_2$ in a humidified atmosphere. 60 nL compound solution (10 mM DMSO stock solution) is then added using a Labcyte Echo 550 device. After a 1 h incubation in the aforementioned incubator the medium is removed after centrifugation and the cells lysed by addition of 20 µL of 1.6-fold lysis buffer from the AlphaLISA SureFire Ultra pERK1/2 (Thr202/Tyr204) Assay Kit with added protease inhibitors, 100 nM trametinib+100 nM staurosporine. After 20 min of incubation at room temperature with shaking, 6 µL of each lysate sample is transferred to a 384-well Proxiplate and analyzed for pERK (Thr202/Tyr204) with the AlphaLISA SureFire Ultra pERK1/2 (Thr202/Tyr204) Assay Kit. 3 µL Acceptor Mix and 3 µL Donor Mix are added under subdued light and incubated for 2 h at room temperature in the dark, before the signal is measured on a PerkinElmer Envision HTS Multi-label Reader. The raw data are imported into and analyzed with the Boehringer Ingelheim proprietary software MegaLab (curve fitting based on the program PRISM, GraphPad Inc.).

Analogously the described assay (pERK reduction; SureFire) can be performed on additional cell lines, carrying various KRAS mutations or KRAS wildtype, allowing the measurement and determination of the activity of compounds on various additional KRAS alleles in a cellular background.

Metabolic (Microsomal) Stability Assay

The metabolic degradation of the test compound is assayed at 37° C. with pooled liver microsomes (mouse (MLM), rat (RLM) or human (HLM)). The final incubation volume of 48 µL per time point contains TRIS buffer (pH 7.5; 0.1 M), magnesium chloride (6.5 mM), microsomal protein (0.5 mg/mL for mouse/rat, 1 mg/mL for human specimens) and the test compound at a final concentration of 1 µM. Following a short preincubation period at 37° C., the reactions are initiated by addition of 12 µL beta-nicotinamide adenine dinucleotide phosphate, reduced form (NADPH, 10 mM) and terminated by transferring an aliquot into solvent after different time points (0, 5, 15, 30, 60 min). Additionally, the NADPH-independent degradation is monitored in incubations without NADPH, terminated at the last time point by addition of acetonitrile. The quenched incubations are pelleted by centrifugation (4,000 rpm, 15 min). An aliquot of the supernatant is assayed by LC-MS/MS to quantify the concentration of parent compound in the individual samples.

In vitro intrinsic clearance ($CL_{int,\ in\ vitro}$) is calculated from the time course of the disappearance of the test drug during the microsomal incubation. Each plot is fitted to the first-order elimination rate constant as $C(t)=C_0*exp(-ke*t)$, where $C(t)$ and $C_0$ are the concentration of unchanged test drug at incubation time t and that at preincubation and ke is the disappearance rate constant of the unchanged drug. Subsequently, $CL_{int\ in\ vitro}$ (µL $min^{-1}$·amount protein) values are converted to predicted $CL_{int,in\ vivo}$ (mL $min^{-1}$·$kg^{-1}$) from incubation parameters according to the equation $CL_{int,\ in\ vivo}=CL_{int,\ invitro}\times$(incubation volume (ml)/amount protein (mg))×(amount protein (mg)/g liver tissue)×(liver weight/body wt.).

For better across species comparison the predicted clearance is expressed as percent of the liver blood flow [% QH] (mL $min^{-1}$·$kg^{-1}$) in the individual species. In general, high stability (corresponding to low % QH) of the compounds across species is desired.

Table 78 shows metabolic stability data obtained with the disclosed assay in HLM for a selection of compounds (1) according to the invention.

TABLE 78

| Ex # | HLM QH [%] |
|---|---|
| I-1 | 79 |
| I-2 | 44 |
| I-3 | <24 |
| I-4 | <24 |
| I-5 | <24 |
| I-6 | <24 |
| I-7 | <24 |
| I-8 | <24 |
| I-9 | <24 |
| I-10 | 30 |
| I-11 | <24 |
| I-12 | 36 |
| I-13 | <24 |
| I-15 | 38 |
| I-16 | 31 |
| I-17 | 56 |
| I-18 | 48 |
| I-19 | <24 |
| I-20 | 30 |
| I-21 | 44 |
| I-22 | 37 |
| I-23 | 45 |
| I-24 | <24 |
| I-25 | <24 |
| I-26 | <24 |
| I-27 | <24 |
| I-28 | <24 |
| I-29 | 27 |
| I-30 | <24 |
| I-31 | <24 |
| I-32 | 45 |
| I-33 | <24 |
| I-34 | <24 |
| I-35 | 32 |
| I-37 | 51 |
| I-39 | 39 |
| I-40 | 42 |
| I-41 | <24 |

TABLE 78-continued

| Ex # | HLM QH [%] |
|---|---|
| I-42 | 42 |
| I-43 | <24 |
| I-44 | <24 |
| I-45 | 45 |
| I-48 | 51 |
| I-49 | 40 |
| I-50 | 44 |
| I-53 | 56 |
| I-54 | 52 |
| I-55 | 56 |
| I-56 | 25 |
| I-58 | 34 |
| I-59 | <24 |
| I-60 | <24 |
| II-6 | <24 |
| II-7 | <24 |
| II-8 | <24 |
| II-10 | <24 |
| II-11 | <24 |
| II-12 | <24 |
| II-13 | <24 |
| II-14 | <24 |
| II-15 | <24 |
| II-16 | <24 |
| II-17 | 63 |
| II-18 | 58 |
| II-19 | 30 |
| II-20 | <24 |
| II-21 | <24 |
| II-23 | <24 |
| II-24 | <24 |
| II-25 | <24 |
| II-26 | <24 |
| II-27 | 44 |
| II-28 | 51 |
| II-30 | <24 |
| II-31 | 42 |
| II-32 | <24 |
| II-33 | <24 |
| II-34 | <24 |
| II-35 | <24 |
| II-36 | <24 |
| II-37 | <24 |
| II-38 | <24 |
| II-39 | 52 |
| II-40 | <24 |
| II-41 | <24 |
| II-42 | <24 |
| II-43 | <24 |
| II-44 | 31 |
| II-46 | 27 |
| II-47 | <24 |
| II-48 | <24 |
| II-49 | <24 |
| II-50 | 52 |
| II-51 | 37 |
| II-52 | <24 |
| II-53 | 46 |
| II-54 | 28 |
| II-55 | <24 |
| II-56 | <24 |
| II-57 | <24 |
| II-58 | 46 |
| II-59 | <24 |
| II-60 | 27 |
| II-61 | <24 |
| II-62 | 58 |
| II-63 | <24 |
| II-64 | 27 |
| II-65 | <24 |
| II-66 | <24 |
| II-67 | <24 |
| II-68 | <24 |
| II-69 | <24 |
| II-70 | 61 |
| II-71 | <24 |
| II-72 | 41 |
| II-73 | 53 |
| II-74 | <24 |
| II-75 | 38 |
| II-76 | 31 |
| II-77 | 34 |
| II-78 | 35 |
| II-79 | 45 |
| II-80 | 30 |
| II-81 | <24 |
| II-82 | <24 |
| II-83 | 72 |
| II-84 | <24 |
| II-85 | 47 |
| II-86 | 35 |
| II-87 | <24 |
| II-88 | 26 |
| II-89 | <24 |
| II-90 | <24 |
| II-91 | 46 |
| II-92 | <24 |
| II-93 | 44 |
| II-94 | 48 |
| II-95 | 37 |
| II-96 | <24 |
| II-97 | <24 |
| II-98 | <24 |
| II-99 | <24 |
| II-100 | 28 |
| II-101 | 31 |
| II-102 | 51 |
| II-103 | <24 |
| II-104 | <24 |
| II-106 | 44 |
| II-107 | 45 |
| II-108 | 59 |
| II-109 | <24 |
| II-110 | 47 |
| II-111 | <24 |
| II-112 | <24 |
| II-113 | 43 |
| II-114 | 34 |
| II-115 | <24 |
| II-116 | 75 |
| II-117 | <24 |
| II-118 | 25 |
| II-119 | <24 |
| II-120 | 47 |
| II-121 | 39 |
| II-122 | 35 |
| II-123 | 28 |
| II-124 | 37 |
| II-125 | <24 |
| II-126 | 25 |
| II-127 | <24 |
| II-128 | <24 |
| II-129 | <24 |
| II-130 | <24 |
| II-131 | <24 |
| II-132 | 36 |
| II-133 | <24 |
| II-134 | 34 |
| II-135 | 54 |
| II-140 | <24 |
| II-141 | 28 |
| II-143 | 57 |
| II-144 | 75 |
| II-148 | 52 |
| II-149 | 45 |
| II-150 | 64 |
| II-151 | 59 |
| II-152 | 58 |
| II-153 | 58 |
| II-154 | 76 |
| II-155 | 70 |
| II-156 | 65 |
| II-157 | 69 |
| II-158 | 73 |

TABLE 78-continued

| Ex # | HLM QH [%] |
|---|---|
| II-159 | 40 |
| II-160 | 31 |
| II-161 | <24 |
| II-162 | <24 |
| II-164 | <24 |
| II-165 | 61 |
| II-166 | <24 |
| II-167 | <24 |
| II-168 | 62 |
| II-169 | 39 |
| II-170 | 33 |
| II-171 | 32 |
| II-172 | 51 |
| II-173 | <24 |
| II-174 | 39 |
| II-175 | 63 |
| II-176 | 63 |
| II-177 | <24 |
| II-178 | <24 |
| II-182 | 35 |
| II-183 | 75 |
| II-184 | 60 |
| II-186 | 49 |
| II-187 | 46 |
| II-189 | <24 |
| II-191 | 32 |
| II-192 | 30 |
| II-193 | 31 |
| II-194 | 30 |
| II-195 | 44 |
| II-196 | 75 |
| II-197 | 69 |
| II-198 | 63 |
| II-199 | 67 |
| II-200 | 65 |
| II-201 | 41 |
| II-202 | <24 |
| II-203 | <24 |
| II-204 | <24 |
| II-205 | <24 |
| II-206 | <24 |
| II-207 | 40 |
| II-208 | 48 |
| II-209 | 40 |
| II-210 | <24 |
| II-211 | <24 |
| II-212 | <24 |
| II-213 | <24 |
| II-214 | <24 |

Plasma Protein Binding Assay (PPB)

Binding of test compounds to plasma was determined using equilibrium dialysis (ED) and quantitative mass spectrometry interfaced with liquid chromatography (LC-MS). In brief, ED was performed with dialysis devices consisting of two chambers separated by a semipermeable membrane with a molecular weight cut-off of 5-10 kg/mol. One chamber was filled with 10% FCS in PBS containing 1-10 µmol/L test compound and the other chamber was filled with phosphate-buffer saline (PBS) with or without dextran. The dialysis chamber was incubated for 3-5 hours at 37° C. After incubation, protein was precipitated from aliquots of each chamber and the concentration of test compound in the supernatant of the plasma-containing compartment ($C_{serum}$) and of the buffer-containing compartment ($C_{buffer}$) was determined by LC-MS. The fraction of unbound test compound (not bound to plasma) (fQ was calculated according to the following equation:

$$f_u[\%] = \frac{c_{buffer}}{c_{plasma}} \times 100$$

Table 79 shows metabolic stability data obtained with the disclosed assay for a selection of compounds (1) according to the invention.

TABLE 79

| Ex # | PPB 10% FCS (% fu) |
|---|---|
| I-1 | 53 |
| I-2 | 69 |
| I-3 | 68 |
| I-5 | 51 |
| I-6 | 94 |
| I-7 | 36 |
| I-8 | 77 |
| I-9 | 80 |
| I-10 | 70 |
| I-11 | 33 |
| I-12 | 46 |
| I-13 | 21 |
| I-14 | 10 |
| I-15 | 8 |
| I-16 | 55 |
| I-17 | 24 |
| I-18 | 61 |
| I-19 | 48 |
| I-20 | 58 |
| I-21 | 83 |
| I-22 | 38 |
| I-23 | 20 |
| I-24 | 19 |
| I-25 | 35 |
| I-26 | 23 |
| I-27 | 21 |
| I-28 | 30 |
| I-29 | 54 |
| I-30 | 46 |
| I-31 | 53 |
| I-32 | 48 |
| I-33 | 31 |
| I-34 | 54 |
| I-37 | 26 |
| I-39 | 7 |
| I-40 | 51 |
| I-43 | 73 |
| I-44 | 22 |
| I-45 | 14 |
| I-48 | 12 |
| I-49 | 15 |
| I-50 | 14 |
| I-53 | 5 |
| I-54 | 9 |
| I-55 | 6 |
| I-56 | 32 |
| I-58 | 28 |
| I-59 | 4 |
| I-60 | 10 |
| II-6 | 5 |
| II-7 | 43 |
| II-8 | 17 |
| II-10 | 69 |
| II-11 | 89 |
| II-12 | 20 |
| II-13 | 24 |
| II-14 | 16 |
| II-15 | 64 |
| II-16 | 16 |
| II-17 | 9 |
| II-18 | 11 |
| II-19 | 4 |
| II-20 | 14 |
| II-21 | 24 |
| II-23 | 3 |
| II-24 | 48 |
| II-25 | 15 |

TABLE 79-continued

| Ex # | PPB 10% FCS (% fu) |
|---|---|
| II-26 | 24 |
| II-27 | 5 |
| II-28 | 9 |
| II-30 | 64 |
| II-31 | 63 |
| II-32 | 31 |
| II-33 | 68 |
| II-34 | 37 |
| II-35 | 77 |
| II-36 | 57 |
| II-37 | 71 |
| II-38 | 54 |
| II-39 | 17 |
| II-40 | 53 |
| II-41 | 10 |
| II-42 | 10 |
| II-43 | 11 |
| II-44 | 39 |
| II-45 | 61 |
| II-47 | 34 |
| II-48 | 62 |
| II-49 | 36 |
| II-50 | 38 |
| II-51 | 39 |
| II-52 | 48 |
| II-53 | 29 |
| II-54 | 30 |
| II-55 | 26 |
| II-56 | 48 |
| II-57 | 50 |
| II-58 | 31 |
| II-59 | 64 |
| II-60 | 20 |
| II-61 | 26 |
| II-62 | 18 |
| II-63 | 6 |
| II-64 | 23 |
| II-65 | 3 |
| II-66 | 41 |
| II-67 | 23 |
| II-68 | 9 |
| II-69 | 45 |
| II-70 | 44 |
| II-71 | 59 |
| II-72 | 10 |
| II-73 | 22 |
| II-74 | 48 |
| II-75 | 16 |
| II-76 | 61 |
| II-77 | 16 |
| II-78 | 49 |
| II-79 | 15 |
| II-80 | 23 |
| II-81 | 52 |
| II-82 | 66 |
| II-83 | 18 |
| II-84 | 0 |
| II-85 | 8 |
| II-86 | 34 |
| II-87 | 26 |
| II-88 | 20 |
| II-89 | 0 |
| II-90 | 1 |
| II-91 | 8 |
| II-92 | 9 |
| II-93 | 5 |
| II-94 | 31 |
| II-95 | 53 |
| II-96 | 25 |
| II-97 | 13 |
| II-98 | 1 |
| II-99 | 11 |
| II-100 | 28 |
| II-101 | 23 |
| II-102 | 4 |
| II-103 | 7 |
| II-104 | 18 |
| II-105 | 7 |
| II-106 | 20 |
| II-107 | 24 |
| II-108 | 42 |
| II-109 | 18 |
| II-110 | 1 |
| II-111 | 11 |
| II-112 | 41 |
| II-113 | 39 |
| II-114 | 7 |
| II-115 | 43 |
| II-116 | 35 |
| II-117 | 19 |
| II-118 | 8 |
| II-119 | 4 |
| II-120 | 24 |
| II-121 | 40 |
| II-122 | 44 |
| II-123 | 11 |
| II-124 | 40 |
| II-125 | 13 |
| II-126 | 38 |
| II-127 | 8 |
| II-128 | 6 |
| II-129 | 23 |
| II-130 | 3 |
| II-131 | 1 |
| II-132 | 31 |
| II-133 | 4 |
| II-134 | 31 |
| II-135 | 6 |
| II-141 | 60 |
| II-143 | 18 |
| II-144 | 11 |
| II-148 | 25 |
| II-149 | 17 |
| II-150 | 13 |
| II-151 | 24 |
| II-152 | 8 |
| II-153 | 14 |
| II-154 | 10 |
| II-155 | 4 |
| II-156 | 4 |
| II-157 | 3 |
| II-158 | 4 |
| II-159 | 21 |
| II-160 | 53 |
| II-161 | 37 |
| II-162 | 69 |
| II-163 | 61 |
| II-164 | 54 |
| II-165 | 16 |
| II-166 | 22 |
| II-167 | 26 |
| II-168 | 47 |
| II-170 | 32 |
| II-171 | 23 |
| II-173 | 41 |
| II-174 | 17 |
| II-175 | 2 |
| II-176 | 1 |
| II-177 | 56 |
| II-178 | 46 |
| II-182 | 13 |
| II-183 | 4 |
| II-184 | 10 |
| II-185 | 2 |
| II-186 | 8 |
| II-187 | 14 |
| II-189 | 16 |
| II-191 | 3 |
| II-192 | 24 |
| II-193 | 20 |
| II-194 | 8 |
| II-195 | 24 |
| II-196 | 1 |
| II-197 | 4 |

TABLE 79-continued

| Ex # | PPB 10% FCS (% fu) |
|---|---|
| II-198 | 6 |
| II-199 | 7 |
| II-200 | 3 |
| II-201 | 7 |
| II-202 | 5 |
| II-203 | 4 |
| II-204 | 3 |
| II-205 | 6 |
| II-206 | 5 |
| II-207 | 9 |
| II-208 | 15 |
| II-209 | 6 |
| II-210 | 2 |
| II-211 | 2 |
| II-212 | 5 |
| II-213 | 2 |
| II-214 | 81 |

Mechanism Based Inhibition of CYP3A4 Assay (MBI 3A4):

The time dependent inhibition towards CYP3A4 is assayed in human liver microsomes (0.02 mg/mL) with midazolam (15 µM) as a substrate. The test compounds and water control (wells w/o test compound) are preincubated in presence of NADPH (1 mM) with human liver microsomes (0.2 mg/mL) at a concentration of 25 uM for 0 min and 30 min. After preincubation, the incubate is diluted 1:10 and the substrate midazolam is added for the main incubation (15 min). The main incubation is quenched with acetonitrile and the formation of hydroxy-midazolam is quantified via LC/MS-MS. The formation of hydroxy-midazolam from the 30 min preincubation relative to the formation from the 0 min preincubation is used as a readout. Values of less than 100% mean that the substrate midazolam is metabolized to a lower extent upon 30 min preincubation compared to 0 min preincubation. In general low effects upon 30 min preincubation are desired (corresponding to values close to 100%/ not different to the values determined with water control).

Table 80 shows data obtained with the disclosed assay for a selection of compounds (1) according to the invention.

TABLE 80

| Ex # | MBI 3A4 [%] |
|---|---|
| I-2 | 36 |
| I-3 | 51 |
| I-4 | 64 |
| I-5 | 34 |
| I-6 | 79 |
| I-8 | 25 |
| I-10 | 72 |
| I-11 | 78 |
| I-12 | 56 |
| I-13 | 48 |
| I-14 | 83 |
| I-18 | 58 |
| I-20 | 85 |
| I-21 | 40 |
| I-23 | 57 |
| I-24 | 73 |
| I-26 | 71 |
| I-27 | 50 |
| I-28 | 77 |
| I-30 | 77 |
| I-31 | 67 |
| I-32 | 41 |
| I-33 | 73 |
| I-34 | 67 |
| I-37 | 45 |
| I-39 | 37 |
| I-40 | 37 |
| I-41 | 68 |
| I-43 | 64 |
| II-6 | 54 |
| II-10 | 80 |
| II-12 | 78 |
| II-13 | 70 |
| II-14 | 83 |
| II-15 | 76 |
| II-20 | 63 |
| II-21 | 77 |
| II-25 | 77 |
| II-26 | 58 |
| II-27 | 71 |
| II-31 | 65 |
| II-32 | 79 |
| II-34 | 83 |
| II-37 | 81 |
| II-42 | 63 |
| II-43 | 70 |
| II-44 | 71 |
| II-46 | 91 |
| II-48 | 84 |
| II-49 | 75 |
| II-50 | 54 |
| II-53 | 80 |
| II-54 | 31 |
| II-55 | 88 |
| II-56 | 73 |
| II-57 | 61 |
| II-58 | 68 |
| II-59 | 80 |
| II-62 | 53 |
| II-63 | 74 |
| II-66 | 71 |
| II-67 | 72 |
| II-68 | 74 |
| II-69 | 94 |
| II-70 | 64 |
| II-71 | 79 |
| II-73 | 52 |
| II-74 | 81 |
| II-75 | 57 |
| II-76 | 73 |
| II-78 | 48 |
| II-81 | 62 |
| II-82 | 73 |
| II-85 | 52 |
| II-86 | 68 |
| II-87 | 64 |
| II-88 | 77 |
| II-89 | 73 |
| II-91 | 68 |
| II-94 | 71 |
| II-95 | 68 |
| II-96 | 85 |
| II-97 | 76 |
| II-98 | 74 |
| II-99 | 78 |
| II-103 | 53 |
| II-104 | 78 |
| II-105 | 79 |
| II-106 | 61 |
| II-107 | 58 |
| II-109 | 63 |
| II-110 | 67 |
| II-111 | 76 |
| II-112 | 81 |
| II-114 | 85 |
| II-117 | 77 |
| II-118 | 45 |
| II-119 | 52 |
| II-120 | 71 |
| II-121 | 56 |
| II-122 | 68 |
| II-123 | 64 |

TABLE 80-continued

| Ex # | MBI 3A4 [%] |
|---|---|
| II-125 | 68 |
| II-126 | 56 |
| II-127 | 74 |
| II-128 | 60 |
| II-129 | 74 |
| II-130 | 67 |
| II-132 | 70 |
| II-134 | 76 |
| II-141 | 88 |
| II-144 | 60 |
| II-148 | 55 |
| II-149 | 42 |
| II-150 | 49 |
| II-153 | 49 |
| II-162 | 84 |
| II-169 | 66 |
| II-170 | 70 |
| II-171 | 63 |
| II-173 | 82 |
| II-177 | 72 |
| II-192 | 49 |
| II-193 | 61 |
| II-195 | 56 |

Solubility Measurement (DMSO Solution Precipitation Method)

A 10 mM DMSO stock solution of a test compound is used to determine its aqueous solubility. The DMSO solution is diluted with an aqueous medium (McIlvaine buffer with pH=4.5 or 6.8) to a final concentration of 250 µM. After 24 h of shaking at ambient temperature a potentially formed precipitate is removed by filtration. The concentration of the test compound in the filtrate is determined by LC-UV methods by calibrating the signal to the signal of a reference solution with complete dissolution of the test compound in acetonitrile/water (1:1) with known concentration.

Table 81 shows data obtained with the disclosed assay for a selection of compounds (1) according to the invention.

TABLE 81

| Ex # | solubility [µg/ml] pH 4,5 | solubility [µg/ml] pH 6,8 |
|---|---|---|
| I-1 | >125 | 101 |
| I-2 | >142 | >131 |
| I-3 | >173 | >176 |
| I-4 | >148 | >140 |
| I-5 | >138 | >123 |
| I-6 | >147 | >144 |
| I-7 | >139 | >133 |
| I-8 | >146 | 116 |
| I-9 | >149 | >147 |
| I-10 | >141 | >136 |
| I-11 | >141 | 112 |
| I-12 | >152 | 125 |
| I-13 | >148 | >150 |
| I-14 | 41 | <1 |
| I-15 | 1 | <1 |
| I-16 | >118 | 82 |
| I-18 | >121 | 91 |
| I-19 | 48 | 14 |
| I-20 | >157 | 98 |
| I-21 | 110 | 33 |
| I-22 | 112 | 104 |
| I-23 | 106 | <1 |
| I-24 | 68 | <1 |
| I-25 | >170 | 44 |
| I-27 | 67 | 1 |
| I-28 | 93 | 8 |
| I-29 | >114 | 82 |
| I-30 | >150 | >141 |
| I-31 | >128 | 118 |
| I-32 | 100 | 14 |
| I-33 | 8 | 4 |
| I-34 | >135 | 92 |
| I-35 | 3 | <1 |
| I-37 | >149 | 17 |
| I-39 | >147 | <1 |
| I-41 | >137 | 118 |
| I-42 | >141 | 99 |
| I-43 | >346 | >306 |
| I-45 | >148 | >86 |
| I-48 | >161 | 7 |
| I-49 | >154 | 43 |
| I-50 | >139 | 95 |
| I-53 | >152 | 5 |
| I-54 | 16 | <1 |
| I-55 | >162 | 5 |
| I-56 | 108 | 97 |
| I-58 | >128 | 94 |
| I-59 | >150 | 15 |
| I-60 | >158 | >161 |
| II-6 | <1 | <1 |
| II-7 | >141 | >134 |
| II-8 | >141 | >132 |
| II-10 | >143 | >135 |
| II-11 | >150 | >141 |
| II-12 | >143 | >137 |
| II-13 | >139 | >147 |
| II-14 | >151 | 123 |
| II-15 | >144 | >130 |
| II-16 | >147 | >132 |
| II-17 | >147 | 20 |
| II-18 | >146 | 8 |
| II-19 | 89 | <1 |
| II-20 | 83 | 33 |
| II-21 | 80 | 34 |
| II-23 | 75 | <1 |
| II-24 | <1 | <1 |
| II-25 | 124 | 73 |
| II-26 | >194 | 62 |
| II-27 | 108 | <1 |
| II-28 | >133 | <1 |
| II-30 | >136 | >125 |
| II-31 | >151 | >133 |
| II-32 | >121 | 117 |
| II-34 | >146 | 114 |
| II-36 | >146 | >140 |
| II-37 | >152 | >152 |
| II-40 | >140 | >133 |
| II-41 | >138 | >130 |
| II-42 | 119 | 9 |
| II-43 | 121 | 9 |
| II-44 | >115 | 104 |
| II-45 | >135 | >118 |
| II-46 | >150 | >150 |
| II-47 | >162 | >145 |
| II-48 | >164 | >149 |
| II-49 | >141 | 114 |
| II-50 | >144 | >135 |
| II-51 | >138 | >133 |
| II-54 | >134 | >122 |
| II-55 | >172 | >161 |
| II-56 | >144 | >146 |
| II-57 | 109 | 101 |
| II-58 | >124 | 2 |
| II-59 | >133 | >123 |
| II-60 | >140 | 102 |
| II-61 | 111 | 41 |
| II-62 | >129 | <1 |
| II-63 | <1 | <1 |
| II-64 | 40 | 8 |
| II-65 | 7 | <1 |
| II-66 | >117 | 112 |
| II-67 | 98 | 41 |
| II-68 | 79 | 5 |

TABLE 81-continued

| Ex # | solubility [μg/ml] pH 4,5 | solubility [μg/ml] pH 6,8 |
|---|---|---|
| II-69 | 108 | 76 |
| II-70 | 109 | 94 |
| II-71 | >112 | 82 |
| II-72 | >146 | 89 |
| II-73 | >124 | 88 |
| II-74 | 57 | 29 |
| II-75 | >122 | 91 |
| II-76 | >122 | 104 |
| II-77 | >143 | >134 |
| II-78 | 41 | 3 |
| II-79 | >154 | 102 |
| II-81 | 114 | 84 |
| II-82 | 102 | 72 |
| II-83 | <1 | <1 |
| II-84 | <1 | <1 |
| II-85 | 38 | 3 |
| II-86 | 112 | 60 |
| II-89 | 2 | <1 |
| II-91 | 118 | <1 |
| II-93 | 97 | 20 |
| II-94 | >126 | >122 |
| II-95 | >134 | >121 |
| II-96 | 107 | 2 |
| II-97 | 40 | <1 |
| II-98 | 83 | <1 |
| II-99 | 115 | 84 |
| II-100 | 120 | 57 |
| II-101 | 88 | 2 |
| II-102 | 24 | <1 |
| II-103 | 53 | <1 |
| II-104 | 3 | <1 |
| II-105 | 3 | <1 |
| II-106 | 107 | 13 |
| II-107 | >162 | <1 |
| II-109 | 117 | 61 |
| II-110 | 3 | <1 |
| II-111 | 22 | <1 |
| II-112 | >139 | 121 |
| II-113 | >173 | 107 |
| II-114 | 41 | <1 |
| II-117 | >183 | >147 |
| II-118 | 32 | <1 |
| II-119 | <1 | <1 |
| II-120 | 106 | <1 |
| II-121 | 109 | 69 |
| II-122 | 122 | 98 |
| II-123 | <1 | <1 |
| II-124 | >148 | 108 |
| II-125 | <1 | <1 |
| II-126 | 123 | 104 |
| II-127 | >127 | 39 |
| II-128 | >130 | 42 |
| II-129 | >130 | 15 |
| II-130 | <1 | <1 |
| II-132 | 117 | 100 |
| II-133 | 3 | <1 |
| II-134 | 116 | 105 |
| II-135 | 19 | <1 |
| II-140 | 82 | 8 |
| II-141 | 123 | 83 |
| II-142 | 86 | 10 |
| II-143 | >123 | 91 |
| II-144 | 105 | <1 |
| II-148 | >146 | <1 |
| II-149 | >164 | <1 |
| II-150 | >149 | 57 |
| II-151 | >161 | <1 |
| II-152 | >132 | 61 |
| II-153 | >135 | 103 |
| II-154 | >144 | 17 |
| II-155 | >153 | 3 |
| II-156 | >142 | <1 |
| II-157 | >147 | <1 |
| II-158 | >150 | <1 |
| II-159 | 125 | 125 |
| II-162 | >140 | >137 |
| II-163 | >137 | >133 |
| II-164 | >164 | >137 |
| II-165 | >142 | 49 |
| II-166 | >152 | >147 |
| II-167 | >153 | >142 |
| II-168 | >139 | >128 |
| II-169 | >124 | 13 |
| II-170 | 118 | 24 |
| II-171 | >150 | >148 |
| II-173 | >144 | >146 |
| II-174 | >149 | 115 |
| II-175 | >158 | <1 |
| II-176 | >140 | <1 |
| II-177 | >130 | 125 |
| II-178 | 127 | 110 |
| II-182 | >148 | 86 |
| II-183 | 113 | 4 |
| II-184 | >158 | >147 |
| II-185 | >147 | 8 |
| II-186 | >140 | 22 |
| II-187 | >140 | 119 |
| II-189 | >152 | 103 |
| II-191 | 73 | 12 |
| II-192 | 124 | 59 |
| II-193 | 15 | <1 |
| II-194 | 116 | 31 |
| II-195 | 131 | 71 |
| II-196 | 94 | <1 |
| II-197 | >173 | 5 |
| II-198 | 12 | <1 |
| II-199 | >163 | 9 |
| II-200 | >163 | 4 |
| II-201 | >128 | 6 |
| II-202 | >166 | 58 |
| II-203 | >159 | 65 |
| II-204 | 4 | 5 |
| II-206 | 17 | 2 |
| II-207 | >134 | <1 |
| II-209 | >150 | <1 |
| II-210 | 5 | <1 |
| II-211 | 20 | 4 |
| II-212 | 16 | <1 |
| II-213 | 23 | 2 |
| II-214 | >121 | >151 |

Caco-2 Assay

The assay provides information on the potential of a compound to pass the cell membrane, on the extent of oral absorption as well as on whether the compound is actively transported by uptake and/or efflux transporters. Permeability measurements across polarized, confluent Caco-2 cell monolayers grown on permeable filter supports (Corning, catalog #3391) are used. 10 μM test compound solution in assay buffer (128.13 mM NaCl, 5.36 mM KCl, 1 mM MgSO$_4$, 1.8 mM CaCl$_2$, 4.17 mM NaHCO$_3$, 1.19 mM Na$_2$HPO$_4$, 0.41 mM NaH$_2$PO$_4$, 15 mM 2-[4-(2-hydroxyethyl)piperazin-1-yl]ethanesulfonic acid (HEPES), 20 mM glucose, pH 7.4) was added to the donor compartment of the cell chamber containing a monolayer of Caco-2 cells in between the donor and the receiver compartment. The receiver and donor compartments contain 0.25% bovine serum albumine (BSA) in assay buffer. Passive diffusion and/or active transport of compounds across the monolayer is measured in both apical to basolateral (a-b) and basolateral to apical (b-a) direction. a-b permeability (PappAB) represents drug absorption from the intestine into the blood and b-a permeability (PappBA) drug secretion from the blood back into the intestine via both passive permeability as well as active transport mechanisms mediated by efflux and uptake transporters that are expressed on the Caco-2 cells.

After a pre-incubation of 25-30 min at 37° C., at predefined time points (0, 30, 60 and 90 min), samples were taken from the receiver and donor compartment, respectively. Concentrations of test compounds in samples were measured by HPLC/MS/MS, samples from the donor compartment were diluted 1:50 (v:v) with assay buffer, samples from receiver compartment were measured without dilution.

Apparent permeabilities in a-b (PappAB) and b-a (PappBA) directions are calculated according to the formula:

$$Papp[cm/s] = \frac{1}{A \cdot C_{don}} \cdot \frac{Vrec \cdot \Delta Crec}{\Delta t}$$

Vrec [mL]: buffer volume in receiver compartment
Cdon [µmol/mL]: concentration of test compound in donor compartment at t=0
ΔCrec: difference between concentrations of test compound in receiver compartment at start and end of incubation time
Δt: Incubation time
Vrec·ΔCrec/Δt [µmol/min]: Amount of compound transferred to receiver compartment per time
A [cm²]: filter surface
Caco-2 efflux ratios (ER) are calculated as the ratio of PappBA/PappAB.

Table 82 shows data obtained with the disclosed assay for a selection of compounds (1) according to the invention.

TABLE 82

| Ex # | Caco ER | Caco PappAB (×10⁻⁶ cm/sec) |
|---|---|---|
| I-2 | 17.5 | 1.2 |
| I-3 | 20.8 | 1.2 |
| I-4 |  | <4.8 |
| I-5 | 29.0 | 1.1 |
| I-6 | 15.0 | 2.9 |
| I-10 |  | <2.1 |
| I-11 |  | <4.1 |
| I-12 | 70.2 | 0.5 |
| I-13 | 49.8 | 0.4 |
| I-14 | 0.8 |  |
| I-18 | 1.2 | 17.0 |
| I-20 | 4.9 | 4.3 |
| I-21 | 6.8 | 5.1 |
| I-22 | 1.9 | 18.0 |
| I-23 | 1.5 | 9.2 |
| I-26 | 10.7 | 3.0 |
| I-27 | 1.1 |  |
| I-30 | 18.5 | 2.0 |
| I-31 | 13.9 | 2.3 |
| I-34 | 9.2 | 3.6 |
| I-37 | 2.0 | 12.0 |
| I-39 | 0.6 |  |
| I-43 | 6.7 | 2.6 |
| I-45 | 3.1 | 11.0 |
| I-49 | 2.9 | 10.0 |
| I-50 | 1.7 |  |
| I-56 | 10.4 |  |
| I-58 | 3.4 | 14.0 |
| II-6 | 3.8 |  |
| II-7 | 21.5 | 1.3 |
| II-8 | 12.7 | 1.1 |
| II-10 | 68.0 | 0.3 |
| II-12 | 12.1 |  |
| II-13 | 21.4 | 1.4 |
| II-14 | 32.3 | 1.0 |
| II-15 | 5.3 |  |
| II-16 | 33.3 | 0.5 |

TABLE 82-continued

| Ex # | Caco ER | Caco PappAB (×10⁻⁶ cm/sec) |
|---|---|---|
| II-20 | 3.3 | 11.1 |
| II-21 | 6.6 | 3.5 |
| II-25 | 22.7 | 1.1 |
| II-26 | 5.8 | 11.0 |
| II-27 | 0.7 | 11.0 |
| II-31 |  | <0.1 |
| II-32 | 76.6 | 0.3 |
| II-33 | 52.3 | 0.4 |
| II-34 | 37.8 | 0.4 |
| II-35 |  | <0.5 |
| II-37 | 121.1 | 0.2 |
| II-38 | 104.5 | 0.2 |
| II-40 | 39.7 | 0.8 |
| II-42 | 2.0 |  |
| II-43 | 1.2 | 10.0 |
| II-44 | 1.5 | 15.0 |
| II-46 | 28.8 | 0.8 |
| II-48 | 32.2 | 0.6 |
| II-49 | 10.8 | 4.7 |
| II-50 | 111.1 | 0.3 |
| II-53 | 22.0 | 1.5 |
| II-54 |  | <1.1 |
| II-55 | 5.4 | 3.5 |
| II-56 | 2.3 | 7.5 |
| II-57 | 43.3 | 0.7 |
| II-58 | 1.2 | 13.0 |
| II-59 | 37.2 | 0.9 |
| II-62 | 0.3 | 19.0 |
| II-66 |  | <2.9 |
| II-68 | 1.2 | 5.8 |
| II-69 | 5.4 | 4.1 |
| II-70 | 1.4 | 17.0 |
| II-71 | 63.3 | 0.5 |
| II-75 | 5.0 | 5.0 |
| II-76 | 3.7 | 6.5 |
| II-81 | 23.0 | 2.0 |
| II-82 | 9.2 | 2.5 |
| II-85 | 1.2 |  |
| II-86 | 0.8 | 12.0 |
| II-87 |  | <1.7 |
| II-88 | 1.8 | 12.0 |
| II-89 |  | <10.0 |
| II-91 | 1.6 | 9.0 |
| II-94 | 2.1 | 13.0 |
| II-95 | 2.2 | 12.0 |
| II-96 | 7.3 | 6.5 |
| II-97 |  | <9.7 |
| II-98 | 1.5 |  |
| II-99 | 23.6 | 1.1 |
| II-101 | 7.0 | 2.0 |
| II-104 | 4.2 |  |
| II-105 | 1.1 | <10.0 |
| II-106 | 1.1 | 15.0 |
| II-107 | 2.4 | 10.0 |
| II-109 | 7.4 | 3.5 |
| II-110 | 0.5 |  |
| II-111 | 1.5 |  |
| II-112 | 5.6 | 5.9 |
| II-113 | 30.9 | 1.1 |
| II-114 | 0.9 |  |
| II-117 | 20.7 | 1.4 |
| II-118 | 0.7 |  |
| II-119 | 1.1 | 1.0 |
| II-120 | 1.5 | 8.0 |
| II-121 | 3.7 | 6.3 |
| II-122 | 3.2 | 7.9 |
| II-123 | 4.6 |  |
| II-124 | 33.7 | 1.0 |
| II-125 | 1.3 |  |
| II-126 | 11.0 | 2.0 |
| II-127 | 4.1 | 5.9 |
| II-129 | 5.2 | 4.2 |
| II-130 | 1.4 |  |
| II-131 | 0.9 |  |
| II-132 | 4.9 | 6.8 |

TABLE 82-continued

| Ex # | Caco ER | Caco PappAB ($\times 10^{-6}$ cm/sec) |
|---|---|---|
| II-134 | 8.0 | 4.0 |
| II-141 | 7.9 | |
| II-143 | 7.3 | 4.5 |
| II-144 | 0.7 | 15.0 |
| II-148 | 3.3 | 12.0 |
| II-149 | 1.2 | |
| II-150 | 11.6 | 2.5 |
| II-151 | 2.0 | |
| II-152 | 16.8 | 3.1 |
| II-153 | 30.0 | 1.2 |
| II-155 | 2.9 | |
| II-156 | 1.8 | |
| II-157 | 0.7 | |
| II-158 | 0.4 | |
| II-161 | 47.6 | 0.4 |
| II-162 | 57.6 | 0.3 |
| II-164 | 138.5 | 0.1 |
| II-165 | 2.5 | |
| II-167 | 82.1 | 0.3 |
| II-168 | 39.5 | 1.0 |
| II-169 | 9.6 | |
| II-170 | 7.0 | 3.3 |
| II-171 | 8.2 | 3.0 |
| II-173 | 19.9 | 8.7 |
| II-174 | 5.8 | |
| II-175 | 0.6 | |
| II-177 | 51.9 | 0.5 |
| II-182 | 5.5 | 7.1 |
| II-184 | 2.3 | |
| II-186 | 0.8 | 21.0 |
| II-187 | 4.6 | 5.4 |
| II-189 | 5.8 | 7.9 |
| II-191 | 2.5 | |
| II-192 | 2.5 | 10.0 |
| II-193 | 8.1 | 3.7 |
| II-194 | 2.6 | 11.0 |
| II-195 | 4.5 | 6.2 |
| II-201 | 1.8 | 18.0 |
| II-202 | 3.6 | 4.4 |
| II-206 | 16.8 | |
| II-208 | 1.8 | |
| II-209 | 0.8 | |
| II-210 | 2.6 | |
| II-211 | 2.2 | |
| II-212 | 2.9 | |
| II-213 | 2.6 | |

The formulation examples which follow illustrate the present invention without restricting its scope:

Examples of Pharmaceutical Formulations

A)

| Tablets | per tablet |
|---|---|
| active substance according to formula (I) | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

B)

| Tablets | per tablet |
|---|---|
| active substance according to formula (I) | 80 mg |
| lactose | 55 mg |
| corn starch | 190 mg |
| microcrystalline cellulose | 35 mg |
| polyvinylpyrrolidone | 15 mg |
| sodiumcarboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

C)

| Tablets | per tablet |
|---|---|
| active substance according to formula (I) | 25 mg |
| lactose | 50 mg |
| microcrystalline cellulose | 24 mg |
| magnesium stearate | 1 mg |
| | 100 mg |

The active substance, lactose and cellulose are mixed together. The mixture is screened, then either moistened with water, kneaded, wet-granulated and dried or dry-granulated or directly final blend with the magnesium stearate and compressed to tablets of suitable shape and size. When wet-granulated, additional lactose or cellulose and magnesium stearate is added and the mixture is compressed to produce tablets of suitable shape and size.

D)

| Ampoule solution | |
|---|---|
| active substance according to formulae (I) | 50 mg |
| sodium chloride | 50 mg |
| water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:

1. A compound of the formula (I)

[Structure (I)]

wherein $R^{1a}$ and $R^{1b}$ are both independently selected from the group consisting of hydrogen, $C_{1-4}$alkyl, $C_{1-4}$haloalkyl, $C_{1-4}$alkoxy, $C_{1-4}$haloalkoxy, halogen, $-NH_2$, $-NH(C_{1-4}$alkyl), $-N(C_{1-4}$alkyl)$_2$, $C_{3-5}$cycloalkyl and 3-5 membered heterocyclyl;

$R^{2a}$ and $R^{2b}$ are both independently selected from the group consisting of hydrogen, $C_{1-4}$alkyl, $C_{1-4}$haloalkyl, $C_{1-4}$alkoxy, $C_{1-4}$haloalkoxy, halogen, $-NH_2$, $-NH(C_{1-4}$alkyl), $-N(C_{1-4}$alkyl)$_2$, $C_{3-5}$ cycloalkyl and 3-5 membered heterocyclyl;

and/or, optionally, one of $R^{1a}$ or $R^{1b}$ and one of $R^{2a}$ or $R^{2b}$ together with the carbon atoms they are attached form a cyclopropane ring;

Z is $-(CR^{6a}R^{6b})_n-$;

each $R^{6a}$ and $R^{6b}$ is independently selected from the group consisting of hydrogen, $C_{1-4}$alkyl, $C_{1-4}$haloalkyl, $C_{1-4}$alkoxy, $C_{1-4}$haloalkoxy, halogen, $-NH_2$, $-NH(C_{1-4}$alkyl), $-N(C_{1-4}$alkyl)$_2$, $C_{3-5}$ cycloalkyl and 3-5 membered heterocyclyl;

or $R^{6a}$ and $R^{6b}$ together with the carbon atom they are attached to form a cyclopropane ring;

n is selected from the group consisting of 0, 1 and 2;

$R^3$ is selected from the group consisting of halogen, $C_{1-6}$alkyl, $C_{1-6}$haloalkyl, $-N_3$, $C_{3-10}$cycloalkyl, 3-11 membered heterocyclyl, $C_{6-10}$aryl and 5-10 membered heteroaryl, wherein the $C_{1-6}$alkyl, $C_{1-6}$haloalkyl, $C_{3-10}$cycloalkyl, 3-11 membered heterocyclyl, $C_{6-10}$aryl and 5-10 membered heteroaryl are all optionally and independently substituted with one or more, identical or different $R^7$ and/or $R^8$;

each $R^7$ is independently selected from the group consisting of $-OR^8$, $-NR^8R^8$, halogen, $-CN$, $-C(=O)R^8$, $-C(=O)OR^8$, $-C(=O)NR^8R^8$, $-NHC(=O)OR^8$ and the bivalent substituent $=O$;

each $R^8$ is independently selected from the group consisting of hydrogen, $C_{1-6}$ alkyl, $C_{3-10}$cycloalkyl, 3-11 membered heterocyclyl, $C_{6-10}$aryl and 5-10 membered heteroaryl, wherein the $C_{1-6}$alkyl, $C_{3-10}$cycloalkyl, 3-11 membered heterocyclyl, $C_{6-10}$aryl and 5-10 membered heteroaryl are all optionally substituted with one or more, identical or different $R^9$ and/or $R^{10}$;

each $R^9$ is independently selected from the group consisting of $-OR^{10}$, $-NR^{10}R^{10}$ and $-C(O)NR^{10}R^{10}$;

each $R^{10}$ is independently selected from the group consisting of hydrogen, $C_{1-6}$ alkyl, $C_{3-10}$cycloalkyl, 3-11 membered heterocyclyl and 5-10 membered heteroaryl, wherein the $C_{1-6}$ alkyl is optionally substituted with a substituent selected from the group consisting of $C_{1-6}$ alkoxy, $C_{3-10}$cycloalkyl and 3-11 membered heterocyclyl optionally substituted with $C_{1-6}$ alkyl;

W is nitrogen ($-N=$) or $-CH=$;

V is nitrogen ($-N=$) or $-CH=$;

U is nitrogen ($-N=$) or $-C(R^{11})=$;

$R^{11}$ is selected from hydrogen, halogen and $C_{1-4}$alkoxy;

ring A is a ring selected from the group consisting of pyrrole, furan, thiophene, imidazole, pyrazole, oxazole, isoxazole, thiazole, isothiazole and triazole;

each $R^4$, if present, is independently selected from the group consisting of $C_{1-6}$ alkyl, $C_{1-6}$haloalkyl, $C_{1-6}$alkoxy, $C_{1-6}$ haloalkoxy, cyano-$C_{1-6}$alkyl, halogen, $-OH$, $-NH_2$, $-NH(C_{1-4}$alkyl), $-N(C_{1-4}$alkyl)$_2$, $-CN$, $C_{3-5}$ cycloalkyl and 3-5 membered heterocyclyl;

p is selected from the group consisting of 0, 1, 2 and 3;

$R^5$ is a 3-11 membered heterocyclyl optionally substituted with one or more identical or different $C_{1-6}$alkyl, $C_{1-6}$alkoxy or a 5-6 membered heterocyclyl, wherein the $C_{1-6}$ alkyl is optionally substituted with cyclopropyl;

or $R^5$ is $-O-C_{1-6}$alkyl substituted with a 3-11 membered heterocyclyl, wherein the 3-11 membered heterocyclyl is optionally substituted with one or more, identical or different $R^{12}$, each $R^{12}$ is selected from the group consisting of $C_{1-6}$ alkyl, $C_{1-6}$ alkoxy, halogen and 3-11 membered heterocyclyl;

or a salt thereof.

2. A compound according to claim 1 of the formula (Ia) or its salt

[Structure (Ia)]

wherein

A, V, U, W, $R^3$ and $R^5$ are defined as in claim 1.

3. A compound according to claim 1 of the formula (Ib) or its salt

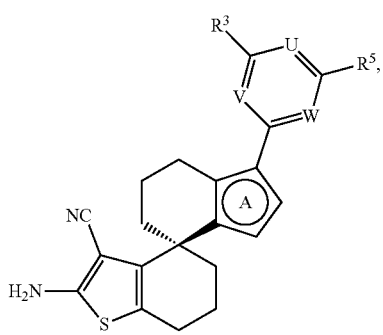

wherein
A, V, U, W, R³ and R⁵ are defined as in claim 1.

4. The compound or its salt according to claim 1, wherein ring A is selected from

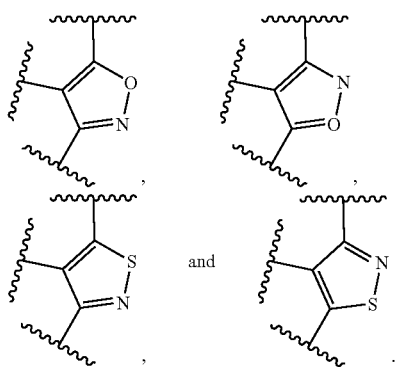

5. The compound or its salt according to claim 1, wherein R³ is selected from the group consisting of 3-11 membered heterocyclyl, $C_{6-10}$aryl and 5-10 membered heteroaryl, wherein the 3-11 membered heterocyclyl, $C_{6-10}$aryl and 5-10 membered heteroaryl are all optionally and independently substituted with one or more, identical or different R⁷ and/or R⁸;
  each R⁷ is independently selected from the group consisting of —OH, $C_{1-6}$ alkoxy, —NR⁸R⁸, halogen, —CN, —C(=O)R⁸, —C(=O)OR⁸, —C(=O)NR⁸R⁸, —NHC(=O)OR⁸ and the bivalent substituent =O;
  each R⁸ is independently selected from the group consisting of hydrogen, $C_{1-6}$ alkyl, $C_{3-10}$cycloalkyl, 3-11 membered heterocyclyl, $C_{6-10}$aryl and 5-10 membered heteroaryl, wherein the $C_{1-6}$ alkyl, $C_{3-10}$cycloalkyl, 3-11 membered heterocyclyl, $C_{6-10}$aryl and 5-10 membered heteroaryl are all optionally substituted with one or more, identical or different R⁹ and/or R¹⁰;
  each R⁹ is independently selected from the group consisting of —OR¹⁰, —NR¹⁰R¹⁰ and —C(O)NR¹⁰R¹⁰;
  each R¹⁰ is independently selected from the group consisting of hydrogen, $C_{1-6}$ alkyl, $C_{3-10}$cycloalkyl, 3-11 membered heterocyclyl and 5-10 membered heteroaryl, wherein the $C_{1-6}$ alkyl is optionally substituted with a substituent selected from the group consisting of $C_{1-6}$ alkoxy, $C_{3-10}$cycloalkyl and 3-11 membered heterocyclyl optionally substituted with $C_{1-6}$ alkyl.

6. The compound or its salt according to claim 1, wherein R³ is selected from the group consisting of 3-11 membered heterocyclyl and 5-10 membered heteroaryl, wherein the 3-11 membered heterocyclyl and 5-10 membered heteroaryl are all optionally and independently substituted with one or more, identical or different R⁷ and/or R⁸;
  each R⁷ is independently selected from the group consisting of —OR⁸, —NR⁸R⁸, halogen, —CN, —C(=O)R⁸, —C(=O)OR⁸, —C(=O)NR⁸R⁸, —NHC(=O)OR⁸ and the bivalent substituent =O;
  each R⁸ is independently selected from the group consisting of hydrogen, $C_{1-6}$ alkyl, $C_{3-10}$cycloalkyl, 3-11 membered heterocyclyl, $C_{6-10}$aryl and 5-10 membered heteroaryl, wherein the $C_{1-6}$ alkyl, $C_{3-10}$cycloalkyl, 3-11 membered heterocyclyl, $C_{6-10}$aryl and 5-10 membered heteroaryl are all optionally substituted with one or more, identical or different R⁹ and/or R¹⁰;
  each R⁹ is —OH or $C_{1-6}$ alkoxy;
  each R¹⁰ is independently selected from the group consisting of $C_{1-6}$ alkyl, 3-11 membered heterocyclyl and 5-10 membered heteroaryl.

7. The compound or its salt according to claim 1, wherein R⁵ is selected from the group consisting of

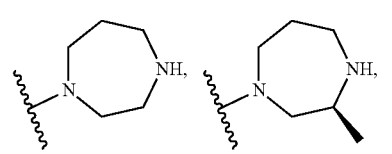

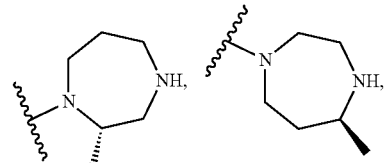

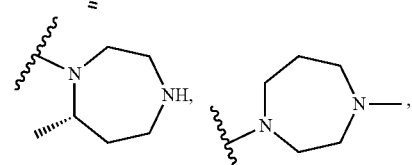

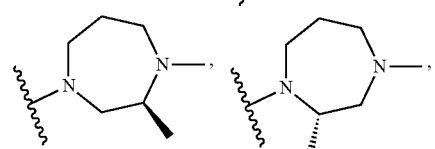

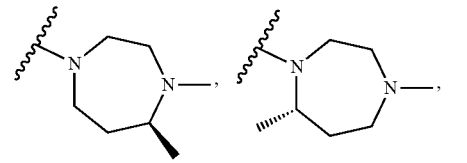

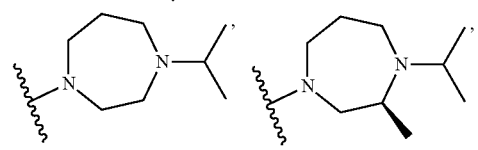

611
-continued
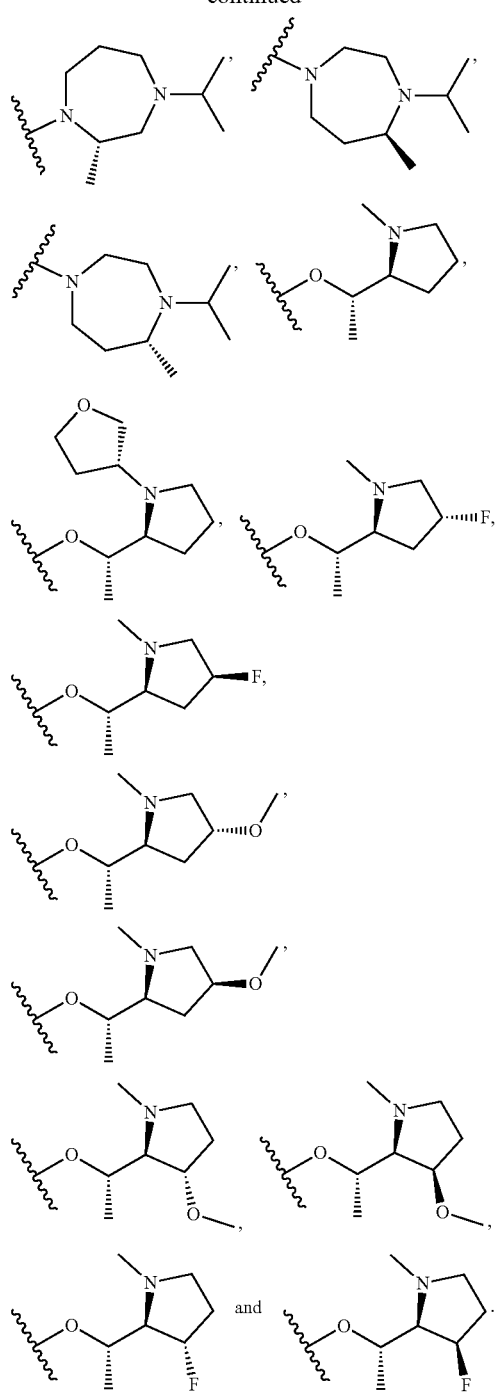
8. The compound or its salt according to claim 7, wherein R⁵ is selected from the group consisting of
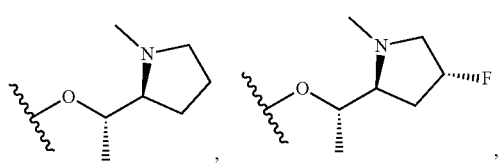
612
-continued
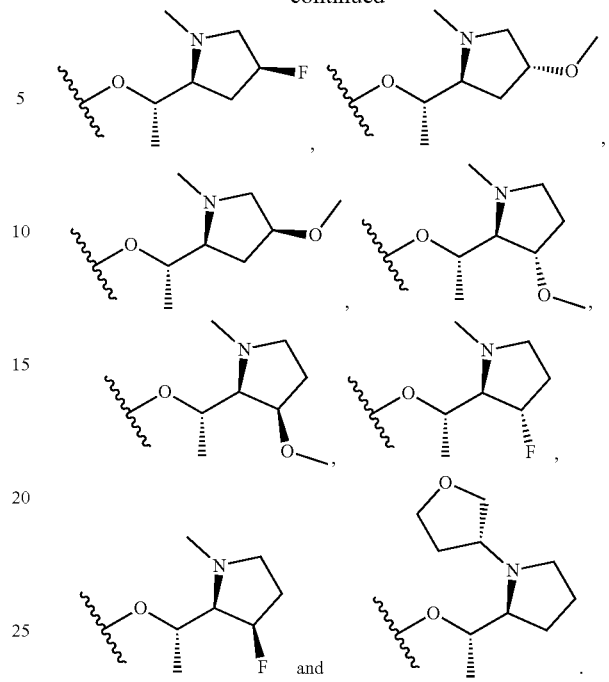
9. The compound or its salt according to claim 1, wherein
W is nitrogen (—N═);
V is nitrogen (—N═)
U is ═C(R$^{11}$)—;
R$^{11}$ is selected from hydrogen, halogen and C$_{1-4}$alkoxy.
10. The compound or its salt according to claim 1, wherein
R³ is selected from the group consisting of
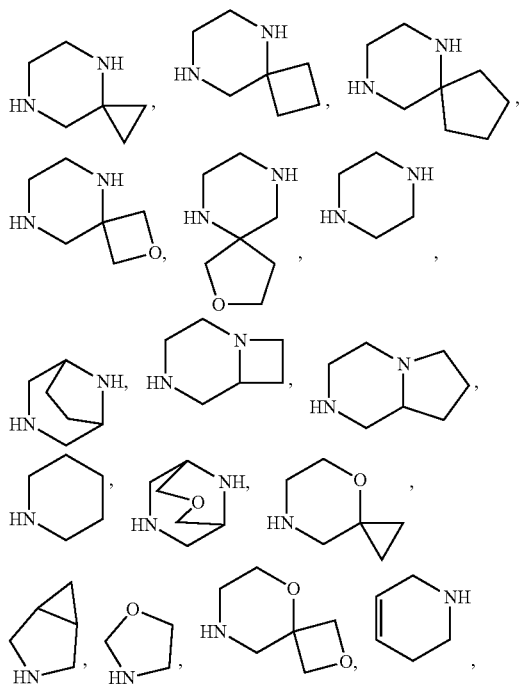

613
-continued

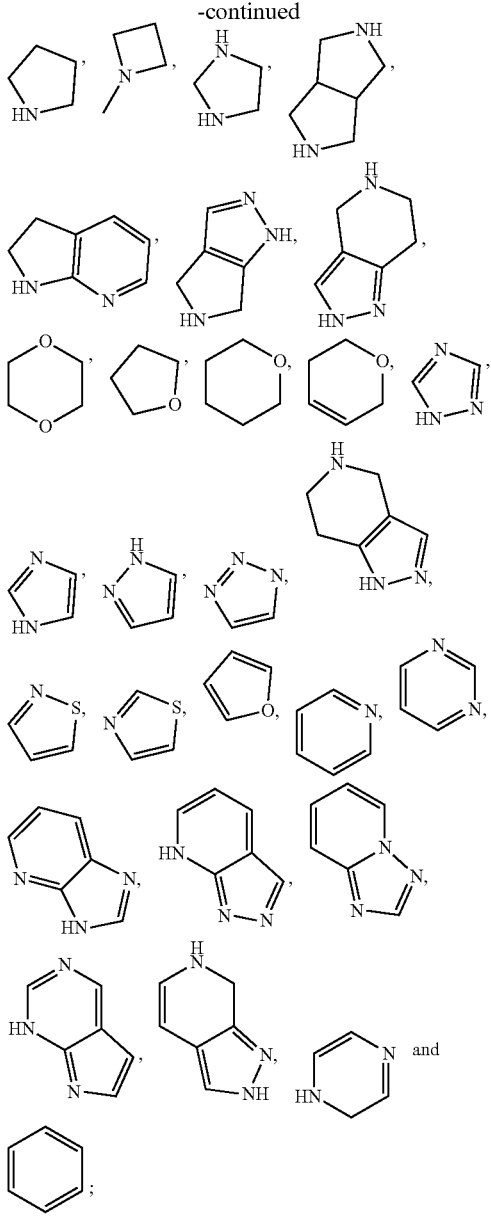

each of which groups is bound to formula (I) at any ring position by removal of a hydrogen atom and is optionally and independently substituted with one or more, identical or different $R^7$ and/or $R^8$, wherein
each $R^7$ is independently selected from the group consisting of —$OR^8$, —$NR^8R^8$, halogen, —CN, —C(=O)$R^8$, —C(=O)$OR^8$, —C(=O)$NR^8R^8$, —NHC(=O)$OR^8$ and the bivalent substituent =O;
each $R^8$ is independently selected from the group consisting of hydrogen, $C_{1-6}$ alkyl, $C_{3-10}$cycloalkyl, 3-11 membered heterocyclyl, $C_{6-10}$aryl and 5-10 membered heteroaryl, wherein the $C_{1-6}$ alkyl, $C_{3-10}$cycloalkyl, 3-11 membered heterocyclyl, $C_{6-10}$aryl and 5-10 membered heteroaryl are all optionally substituted with one or more, identical or different $R^9$ and/or $R^{10}$;
each $R^9$ is —OH or $C_{1-6}$alkoxy;
each $R^{10}$ is independently selected from the group consisting of $C_{1-6}$ alkyl, 3-11 membered heterocyclyl and 5-10 membered heteroaryl.

614

11. The compound or its salt according to claim 1, wherein
$R^3$ is selected from the group consisting of

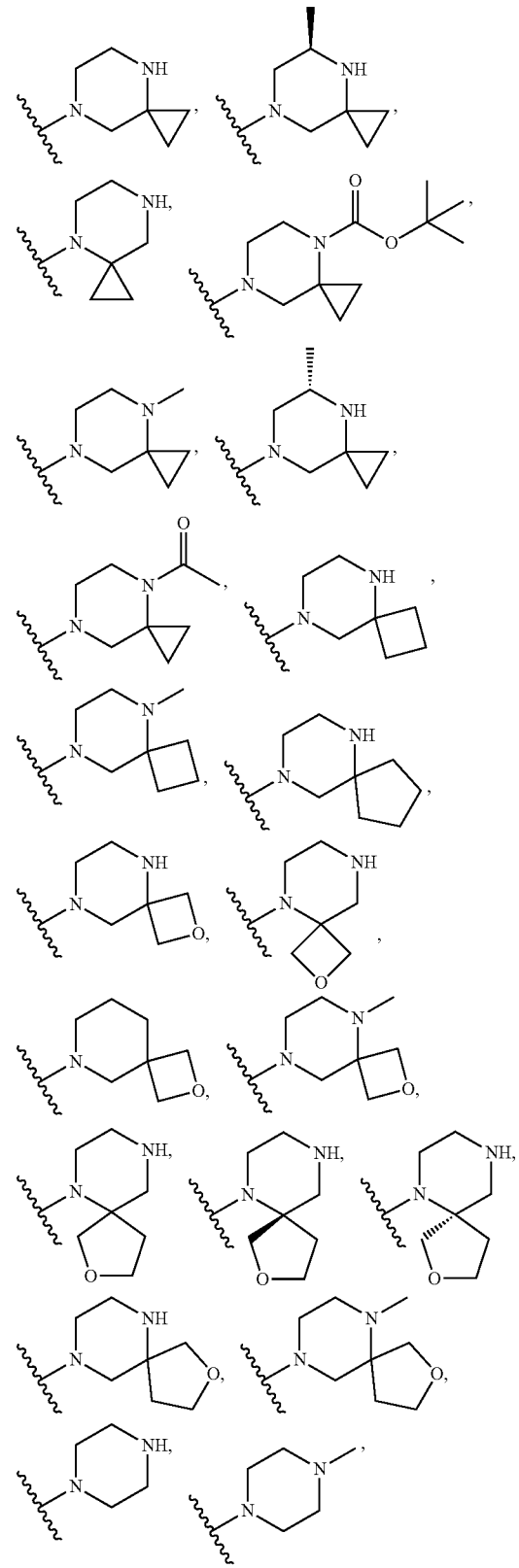

615
-continued
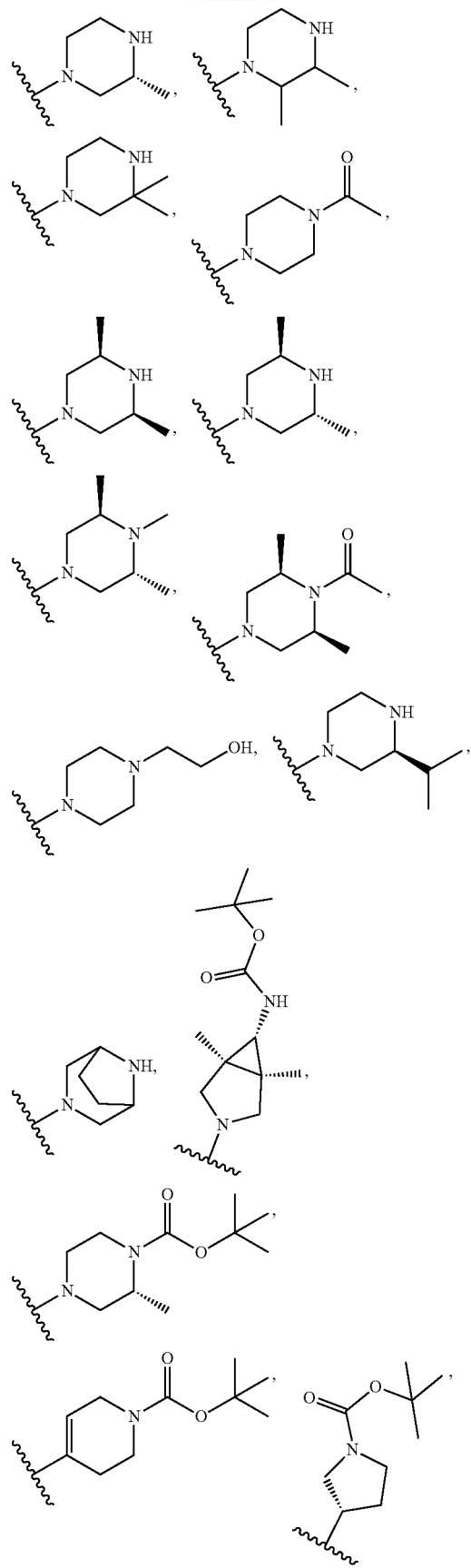
616
-continued
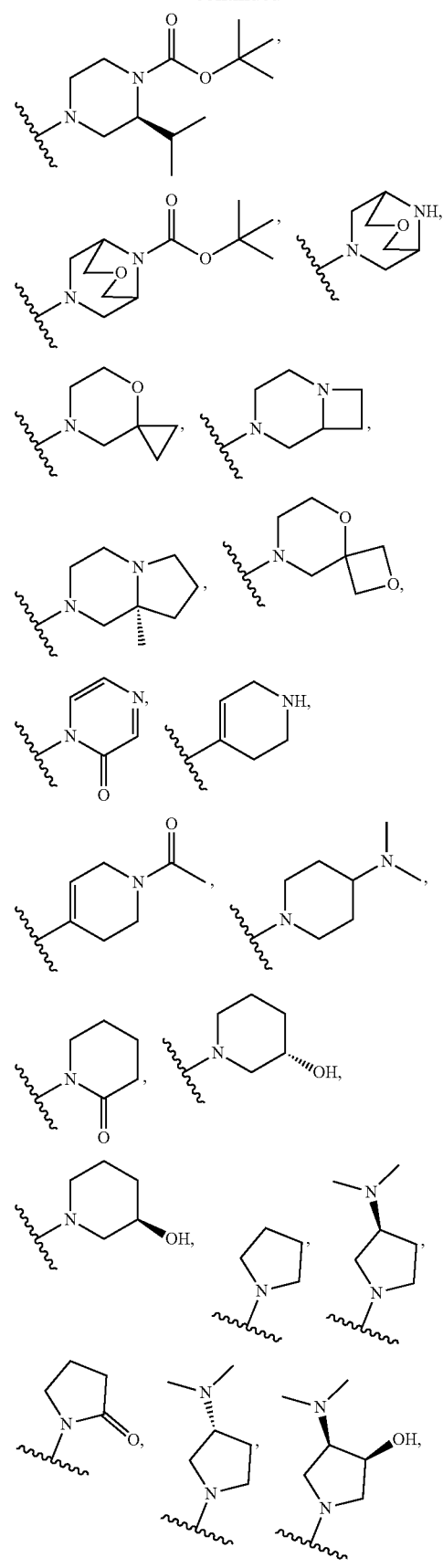

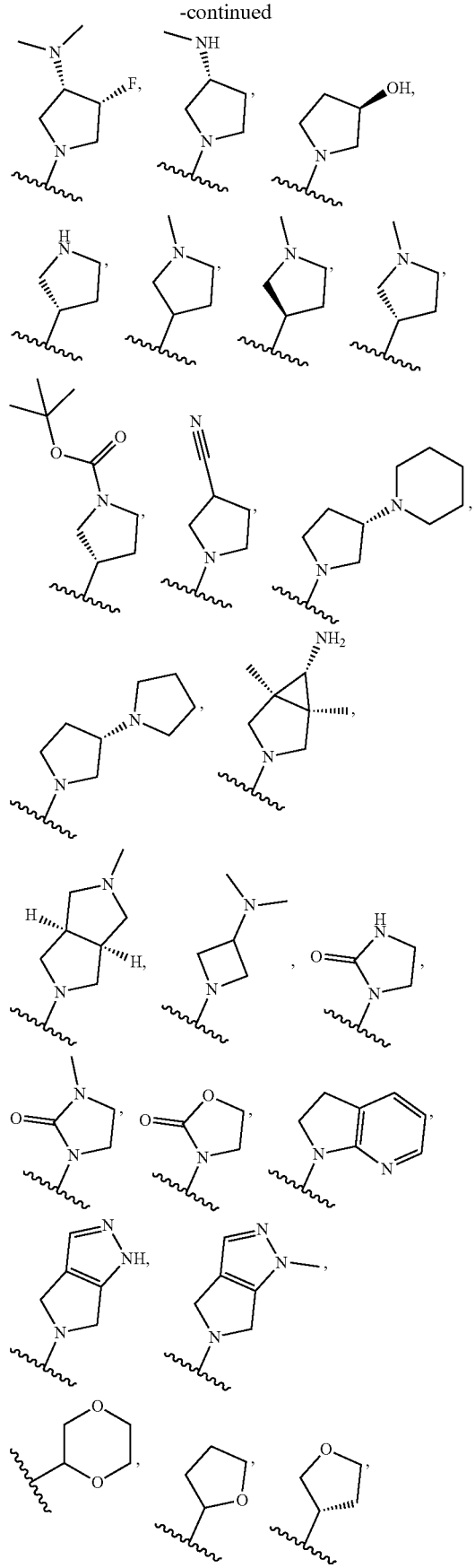
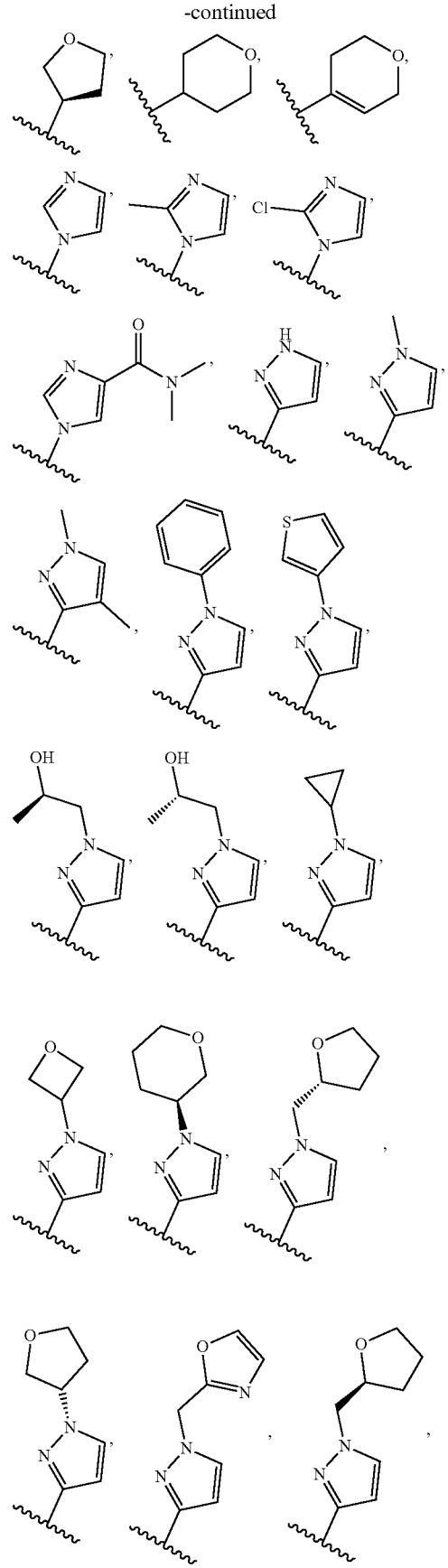

619
-continued
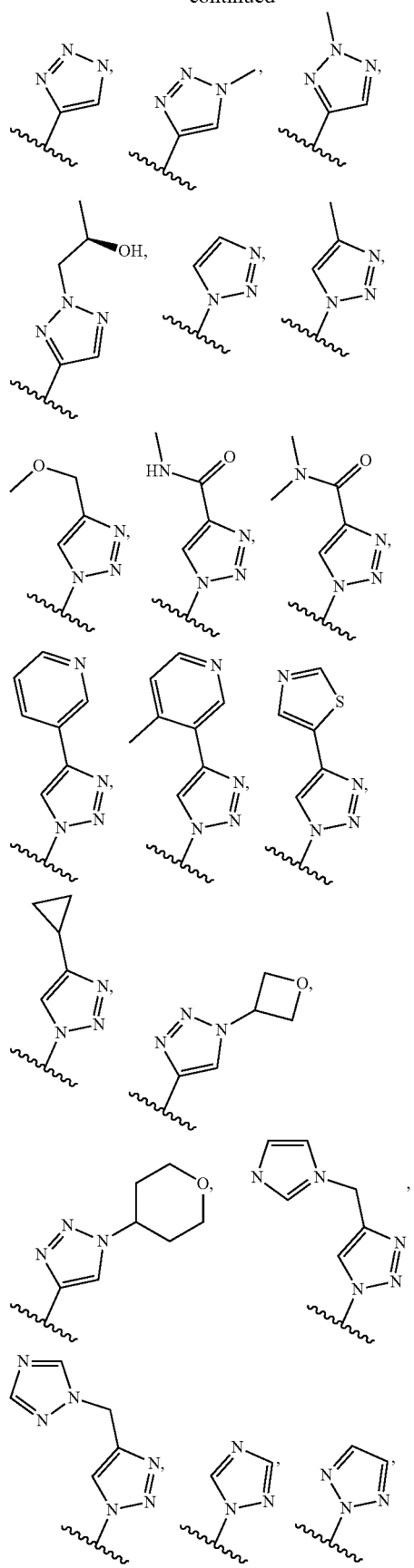
620
-continued
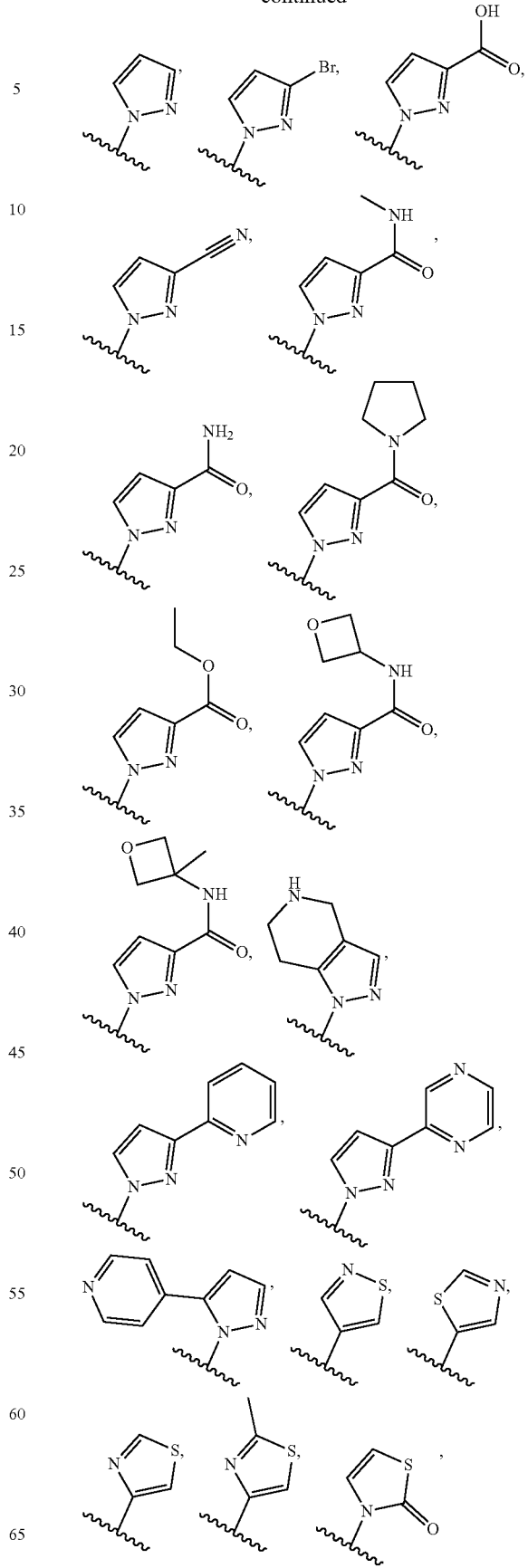

621
-continued
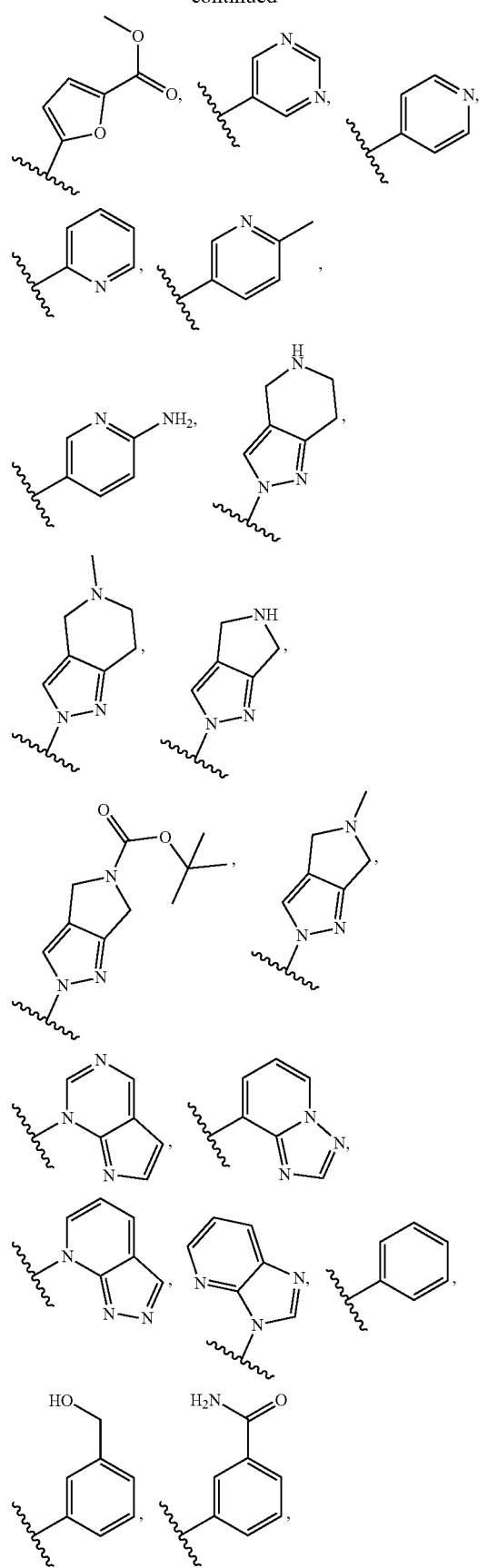
622
-continued
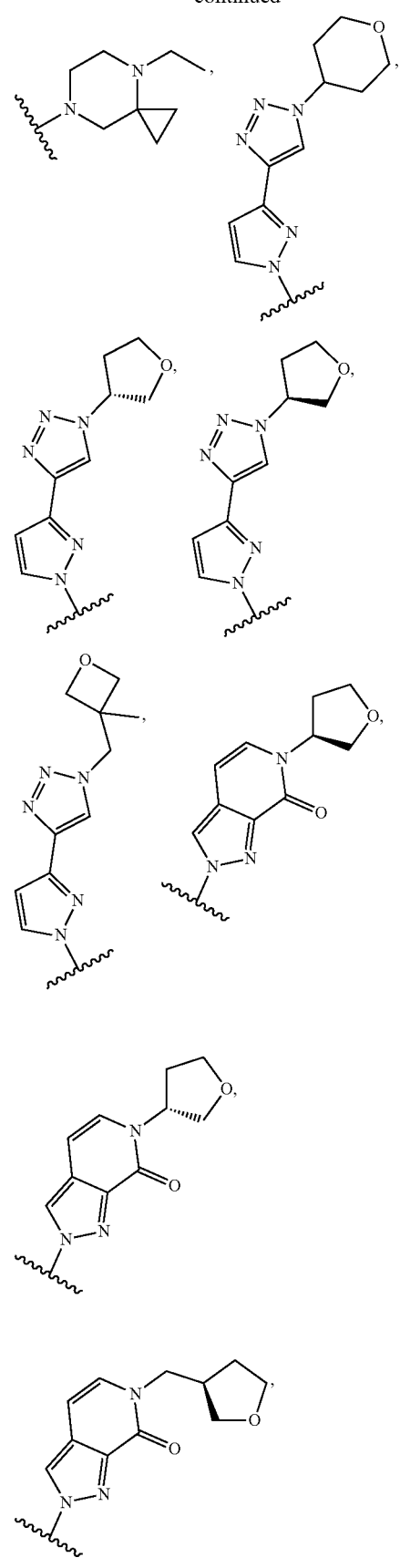

623
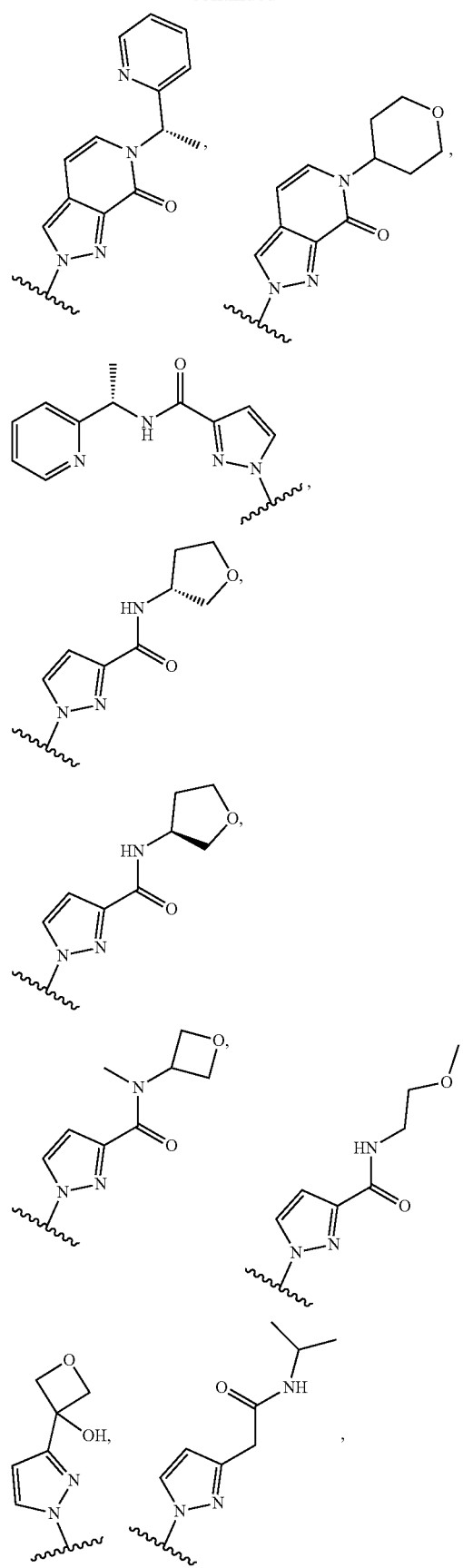
624
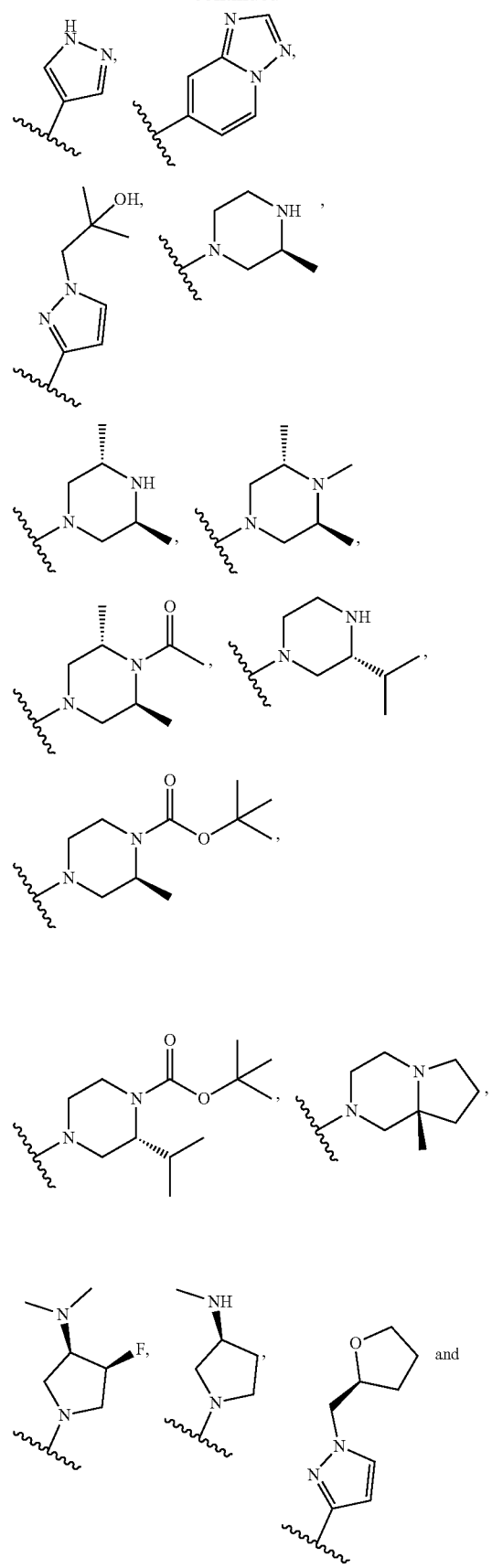

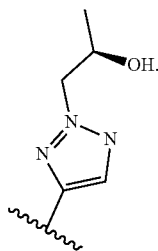

12. A method for the treatment and/or prevention of cancer comprising administering a therapeutically effective amount of a compound according to claim 1, or a pharmaceutically acceptable salt thereof, to a human being.

13. The method according to claim 12, wherein said compound or salt is administered in combination with one or more other pharmacologically active substance(s).

14. The method according to claim 12, wherein the cancer is selected from the group consisting of pancreatic cancer, lung cancer, colorectal cancer, cholangiocarcinoma, appendiceal cancer, multiple myeloma, melanoma, uterine cancer, endometrial cancer, thyroid cancer, acute myeloid leukaemia, bladder cancer, urothelial cancer, gastric cancer, cervical cancer, head and neck squamous cell carcinoma, diffuse large B cell lymphoma, oesophageal cancer, gastroesophageal cancer, chronic lymphocytic leukaemia, hepatocellular cancer, breast cancer, ovarian cancer, prostate cancer, glioblastoma, renal cancer and sarcoma.

15. The method according to claim 12, wherein the cancer comprises tumor cells harbouring a KRAS mutation or an amplification of KRAS wildtype.

16. The method according to claim 15, wherein the KRAS mutation is selected from the group consisting of: KRAS G12C, KRAS G12D, KRAS G12V and KRAS G13D.

17. A pharmaceutical composition comprising a compound according to claim 1, or a pharmaceutically acceptable salt thereof, and one or more other pharmacologically active substance(s).

18. A compound selected from the compounds in the following table, or a salt thereof:

| # | structure |
| --- | --- |
| I-1 | 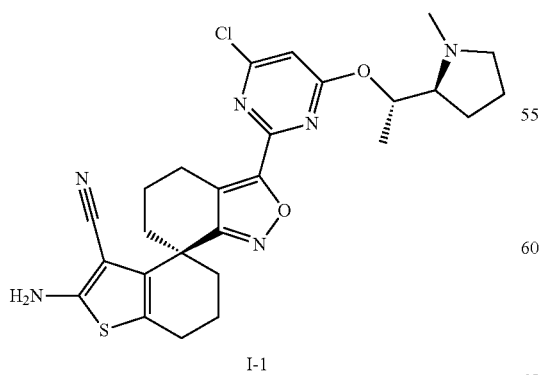 |
| I-2 | 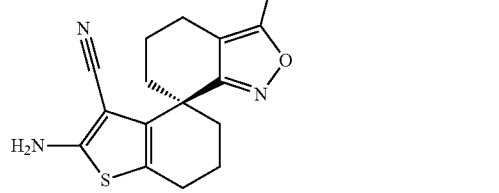 |
| I-3 | 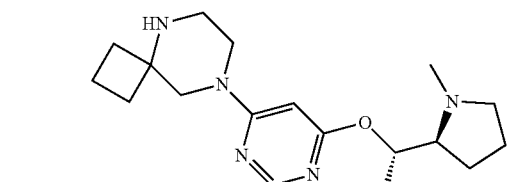 |
| I-4 | 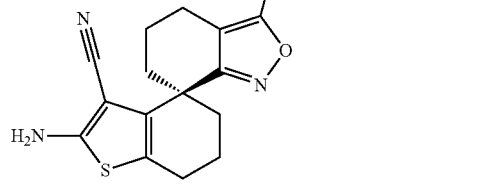 |
| I-5 | 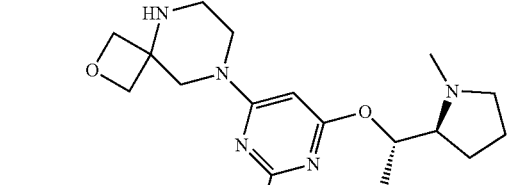 |

-continued

| # | structure |
|---|---|
| I-6 | 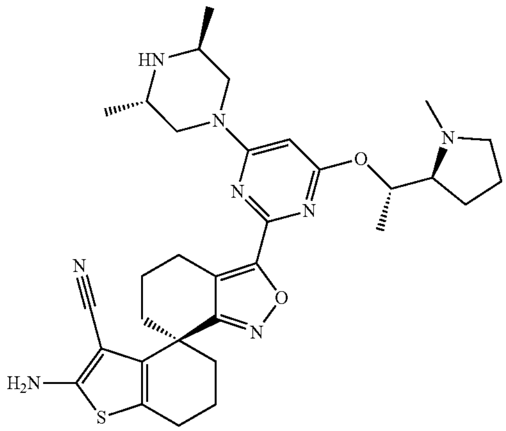 [SMILES: C[C@H](Oc1cc(N2C[C@H](C)N[C@@H](C)C2)nc(-c2onc3c2CCC[C@@]32CCCc3sc(N)c(C#N)c32)n1)[C@@H]1CCCN1C] |
| I-7 | 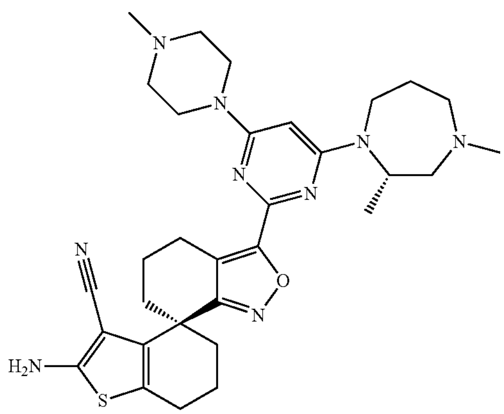 [SMILES: C[C@H]1CN(C)CCCN1c1cc(N2CCN(C)CC2)nc(-c2onc3c2CCC[C@@]32CCCc3sc(N)c(C#N)c32)n1] |
| I-8 | 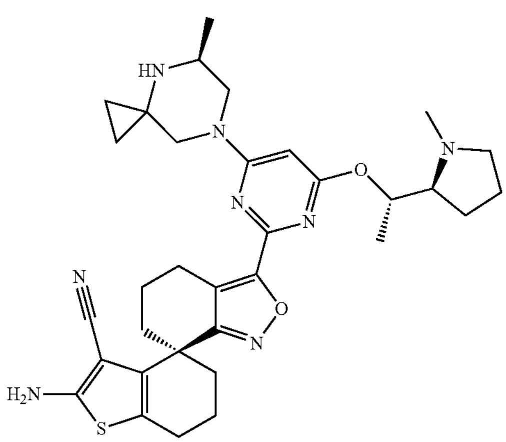 [SMILES: C[C@H](Oc1cc(N2C[C@H](C)NC3(CC3)C2)nc(-c2onc3c2CCC[C@@]32CCCc3sc(N)c(C#N)c32)n1)[C@@H]1CCCN1C] |

-continued

| # | structure |
|---|---|
| I-9 | 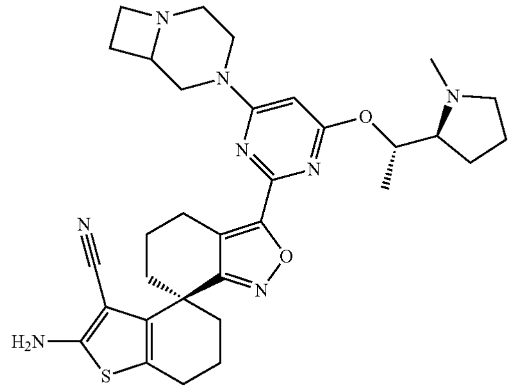 [SMILES: C[C@H](Oc1cc(N2CCN3CCC3C2)nc(-c2onc3c2CCC[C@@]32CCCc3sc(N)c(C#N)c32)n1)[C@@H]1CCCN1C] |
| I-10 | 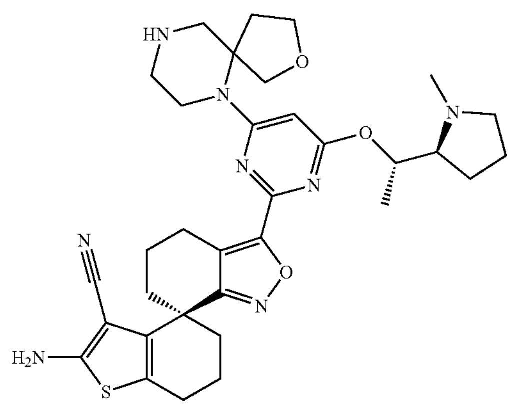 [SMILES: C[C@H](Oc1cc(N2CCNCC23CCOC3)nc(-c2onc3c2CCC[C@@]32CCCc3sc(N)c(C#N)c32)n1)[C@@H]1CCCN1C] |
| I-11 | 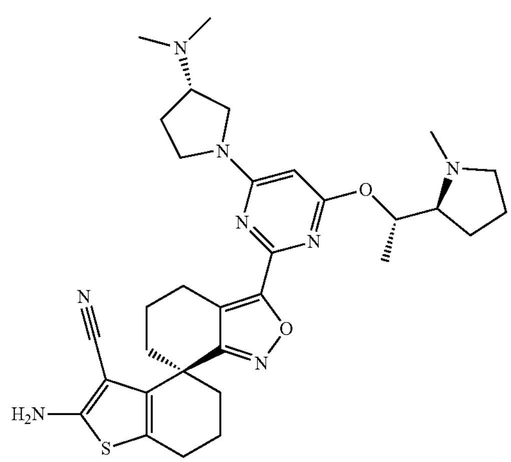 [SMILES: C[C@H](Oc1cc(N2CC[C@H](N(C)C)C2)nc(-c2onc3c2CCC[C@@]32CCCc3sc(N)c(C#N)c32)n1)[C@@H]1CCCN1C] |

-continued
| # | structure |
|---|---|
| I-12 | 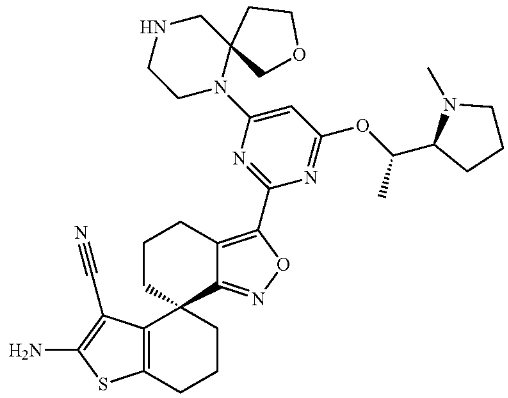 [SMILES: C[C@H](Oc1cc(N2CCNC[C@]23CCOC3)nc(-c2onc3c2CCC[C@@]32CCCc3sc(N)c(C#N)c32)n1)[C@@H]1CCCN1C] |
| I-13 | 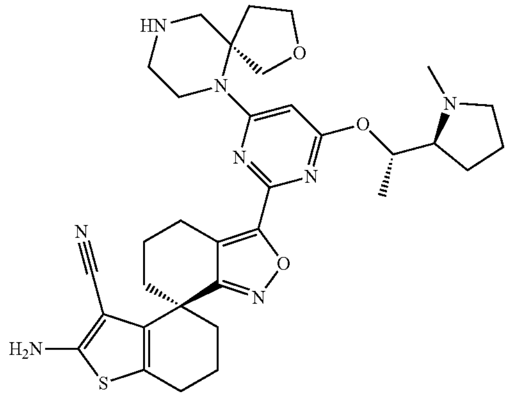 [SMILES: C[C@H](Oc1cc(N2CCNC[C@@]23CCOC3)nc(-c2onc3c2CCC[C@@]32CCCc3sc(N)c(C#N)c32)n1)[C@@H]1CCCN1C] |
| I-14 | 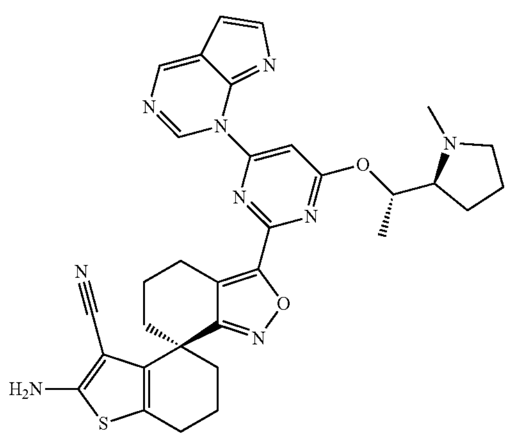 [SMILES: C[C@H](Oc1cc(-n2cncc3ccnc2-3)nc(-c2onc3c2CCC[C@@]32CCCc3sc(N)c(C#N)c32)n1)[C@@H]1CCCN1C] |
| I-15 | 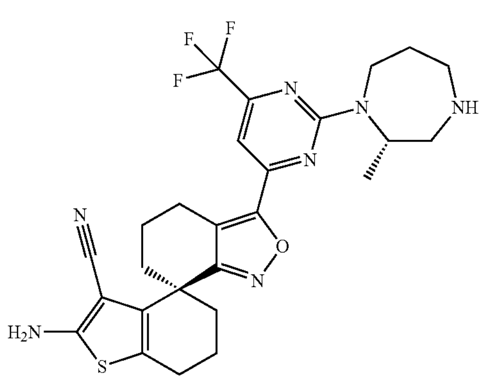 [SMILES: C[C@H]1CNCCCN1c1nc(-c2onc3c2CCC[C@@]32CCCc3sc(N)c(C#N)c32)cc(C(F)(F)F)n1] |
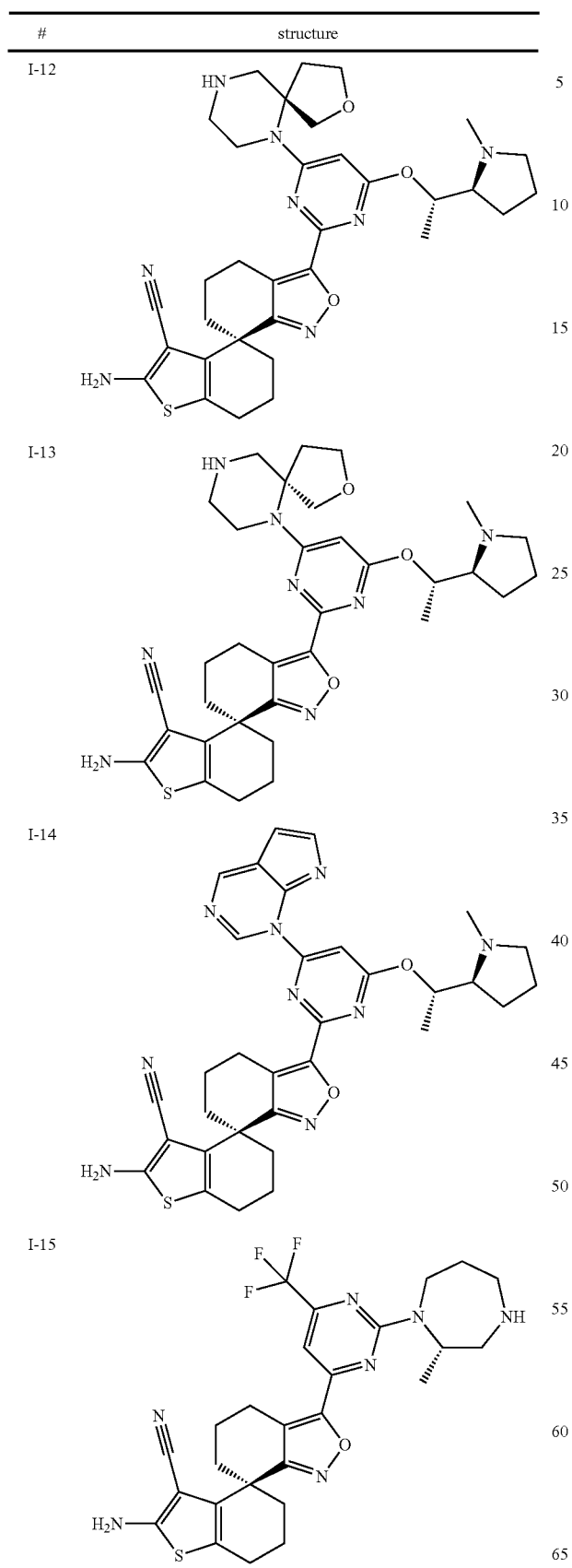
-continued
| # | structure |
|---|---|
| I-16 | 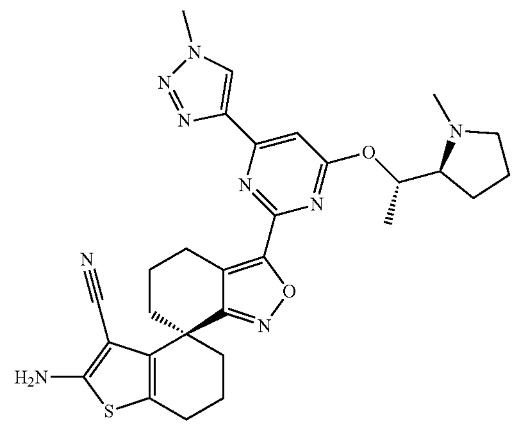 [SMILES: C[C@H](Oc1cc(-c2cn(C)nn2)nc(-c2onc3c2CCC[C@@]32CCCc3sc(N)c(C#N)c32)n1)[C@@H]1CCCN1C] |
| I-17 | 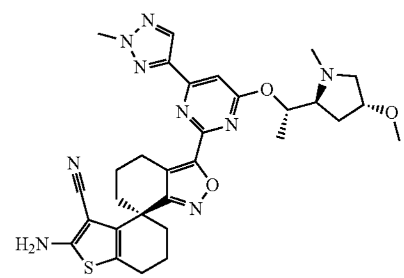 [SMILES: CO[C@@H]1C[C@@H]([C@H](C)Oc2cc(-c3cnn(C)n3)nc(-c3onc4c3CCC[C@@]43CCCc4sc(N)c(C#N)c43)n2)N(C)C1] |
| I-18 | 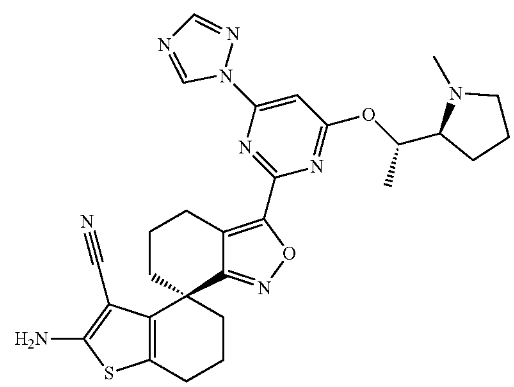 [SMILES: C[C@H](Oc1cc(-n2cncn2)nc(-c2onc3c2CCC[C@@]32CCCc3sc(N)c(C#N)c32)n1)[C@@H]1CCCN1C] |
| I-19 | 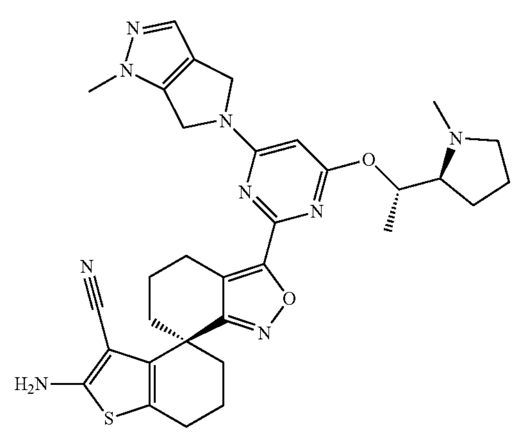 [SMILES: C[C@H](Oc1cc(N2Cc3cnn(C)c3C2)nc(-c2onc3c2CCC[C@@]32CCCc3sc(N)c(C#N)c32)n1)[C@@H]1CCCN1C] |
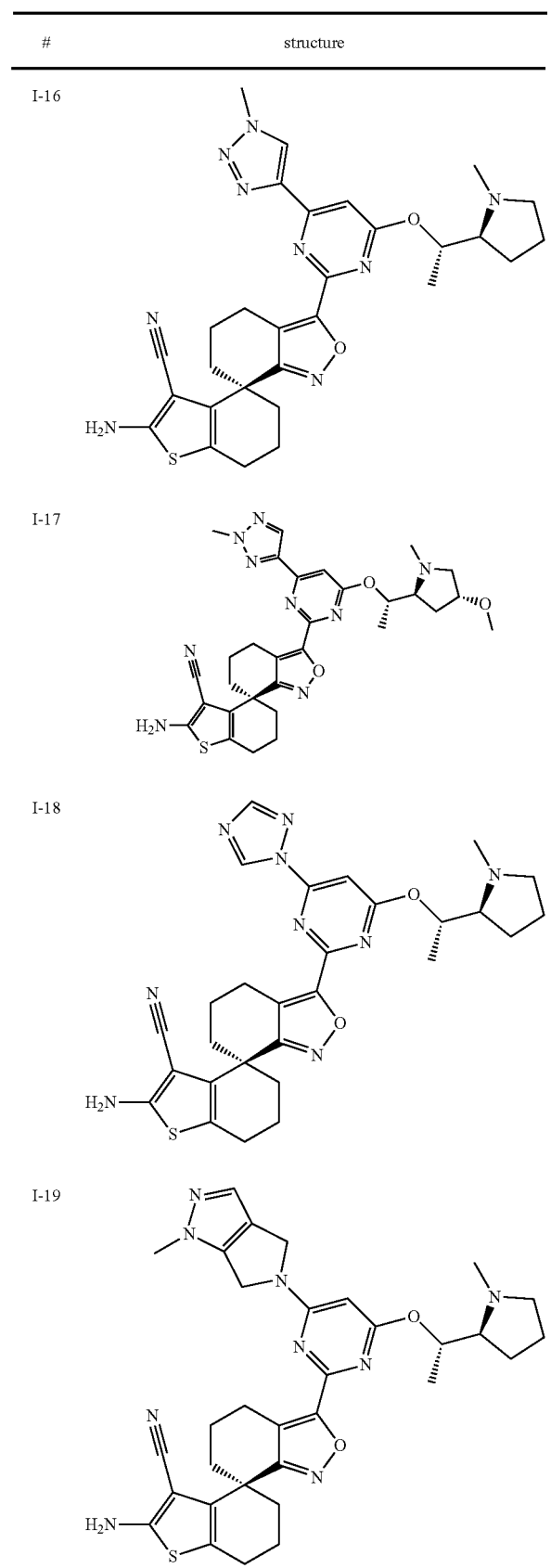

-continued
| # | structure |
|---|---|
| I-20 | 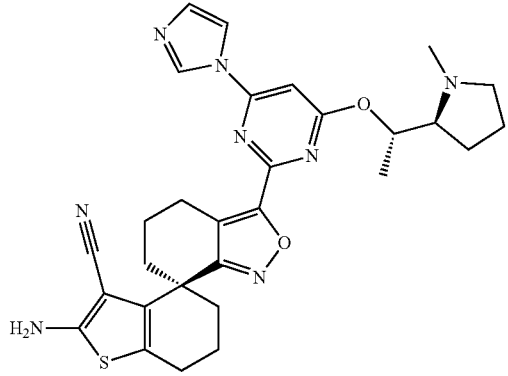 [SMILES: C[C@H](Oc1cc(-n2ccnc2)nc(-c2onc3c2CCC[C@@]32CCCc3sc(N)c(C#N)c32)n1)[C@@H]1CCCN1C] |
| I-21 | 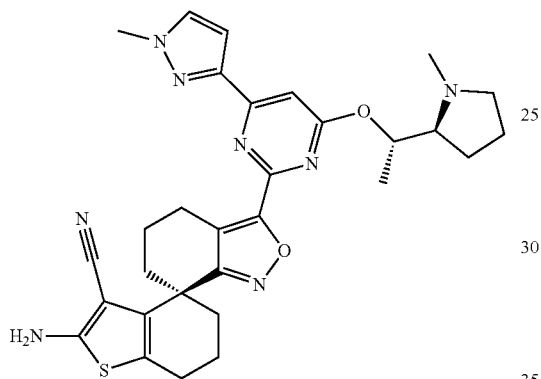 |
| I-22 | 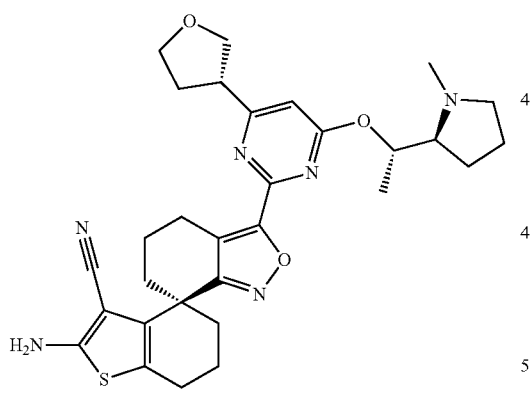 |
| I-23 | 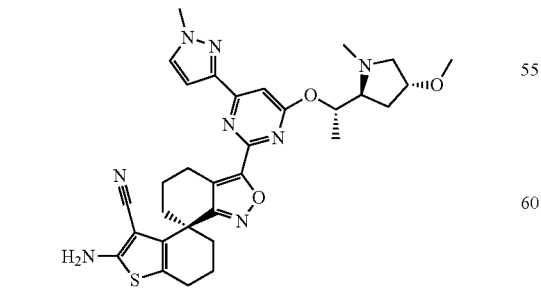 |
-continued
| # | structure |
|---|---|
| I-24 | 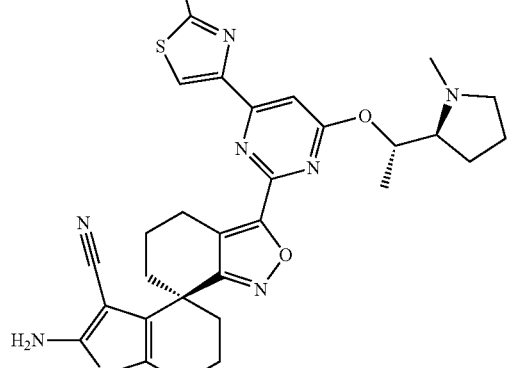 |
| I-25 | 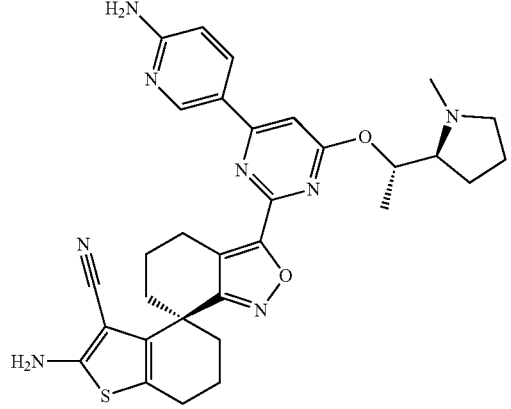 [SMILES: C[C@H](Oc1cc(-c2ccc(N)nc2)nc(-c2onc3c2CCC[C@@]32CCCc3sc(N)c(C#N)c32)n1)[C@@H]1CCCN1C] |
| I-26 | 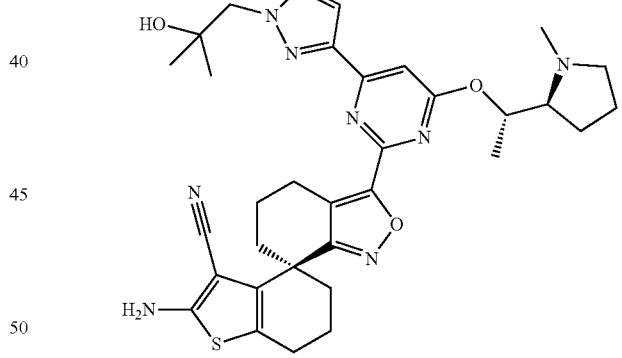 |
| I-27 | 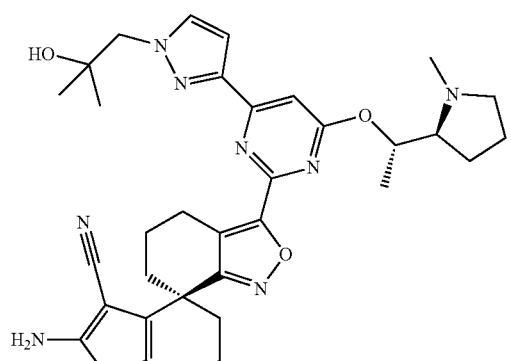 |

-continued
| # | structure |
|---|---|
| I-28 | 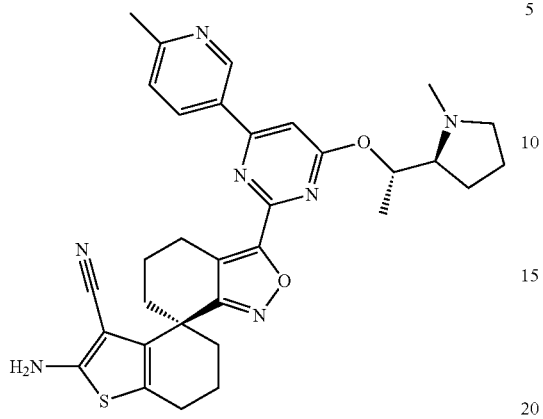 |
| I-29 | 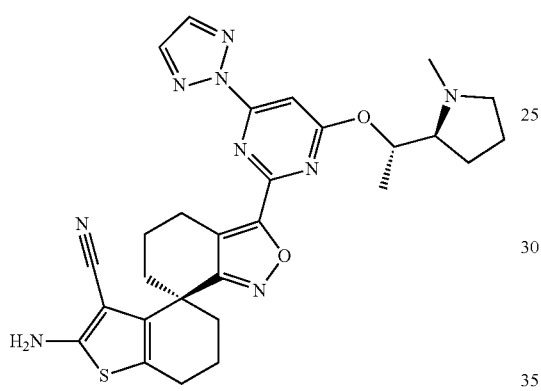 |
| I-30 | 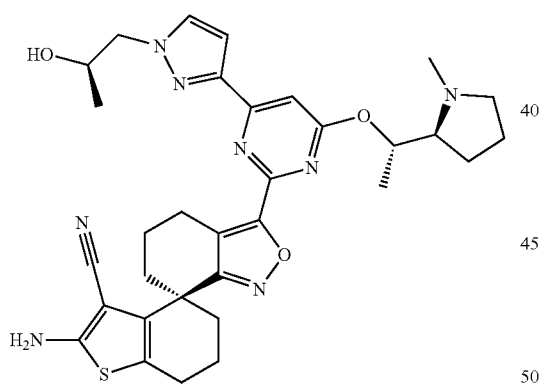 |
| I-31 | 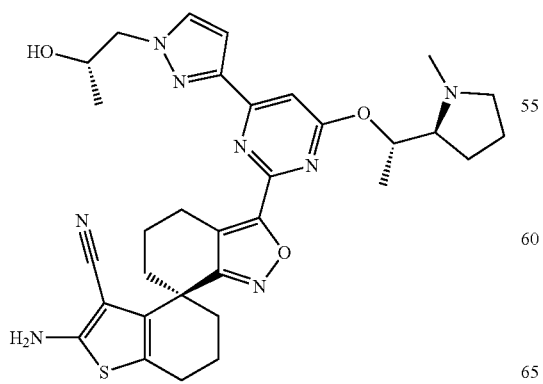 |
| I-32 | 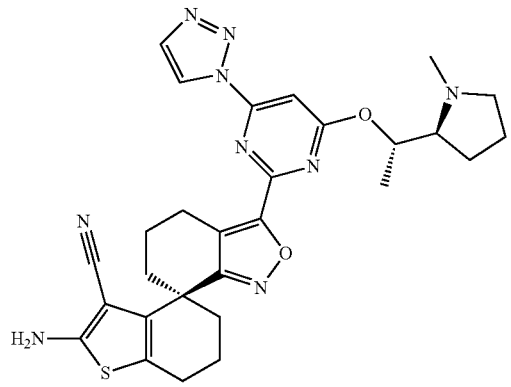 [SMILES: C[C@H](Oc1cc(-n2ccnn2)nc(-c2onc3c2CCC[C@@]32CCCc3sc(N)c(C#N)c32)n1)[C@@H]1CCCN1C] |
| I-33 | 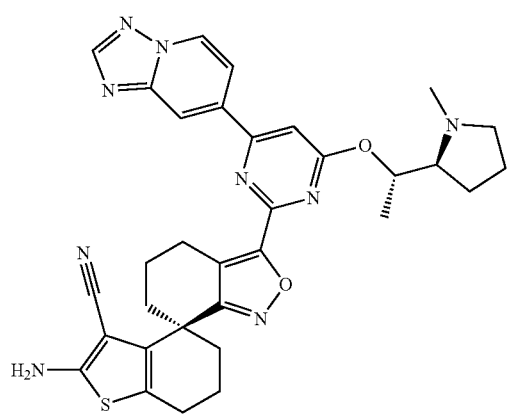 [SMILES: C[C@H](Oc1cc(-c2ccn3ncnc3c2)nc(-c2onc3c2CCC[C@@]32CCCc3sc(N)c(C#N)c32)n1)[C@@H]1CCCN1C] |
| I-34 | 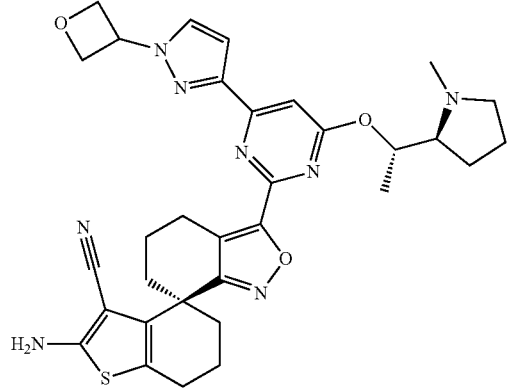 [SMILES: C[C@H](Oc1cc(-c2ccn(C3COC3)n2)nc(-c2onc3c2CCC[C@@]32CCCc3sc(N)c(C#N)c32)n1)[C@@H]1CCCN1C] |
| I-35 | 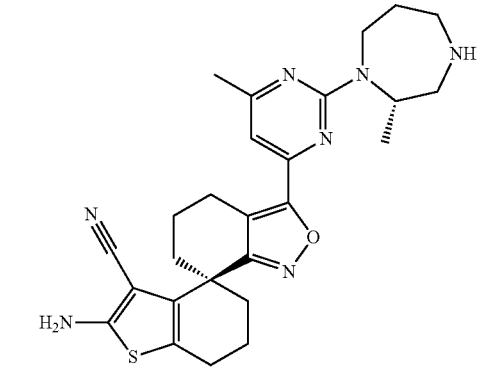 [SMILES: Cc1cc(-c2onc3c2CCC[C@@]32CCCc3sc(N)c(C#N)c32)nc(N2CCCNC[C@@H]2C)n1] |

635
-continued
| # | structure |
|---|---|
| I-36 | 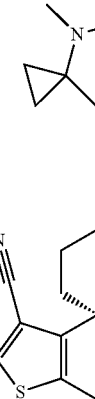 |
| I-37 | 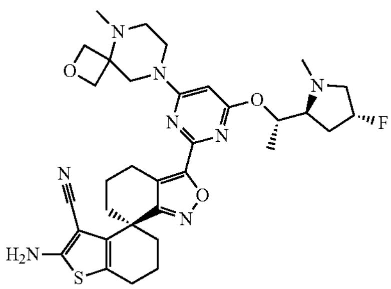 [SMILES: C[C@H](Oc1cc(N2CCN(C)C3(COC3)C2)nc(-c2onc3c2CCC[C@@]32CCCc3sc(N)c(C#N)c32)n1)[C@@H]1C[C@@H](F)CN1C] |
| I-38 | 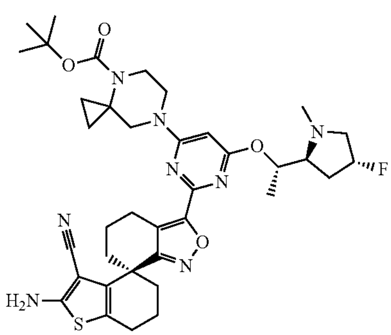 [SMILES: C[C@H](Oc1cc(N2CCN(C(=O)OC(C)(C)C)C3(CC3)C2)nc(-c2onc3c2CCC[C@@]32CCCc3sc(N)c(C#N)c32)n1)[C@@H]1C[C@@H](F)CN1C] |
| I-39 | 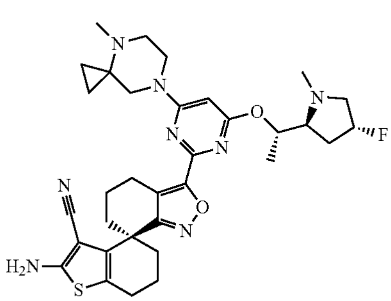 [SMILES: C[C@H](Oc1cc(N2CCN(C)C3(CC3)C2)nc(-c2onc3c2CCC[C@@]32CCCc3sc(N)c(C#N)c32)n1)[C@@H]1C[C@@H](F)CN1C] |
636
-continued
| # | structure |
|---|---|
| I-40 | 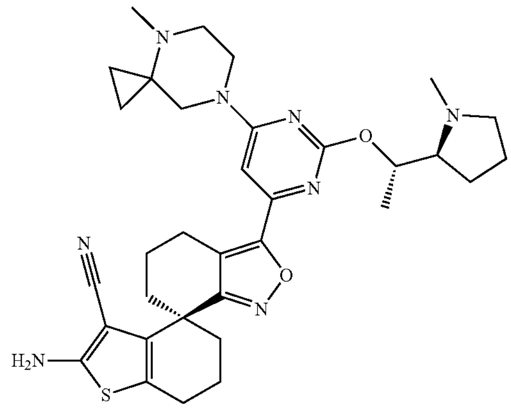 [SMILES: C[C@H](Oc1nc(-c2onc3c2CCC[C@@]32CCCc3sc(N)c(C#N)c32)cc(N2CCN(C)C3(CC3)C2)n1)[C@@H]1CCCN1C] |
| I-41 | 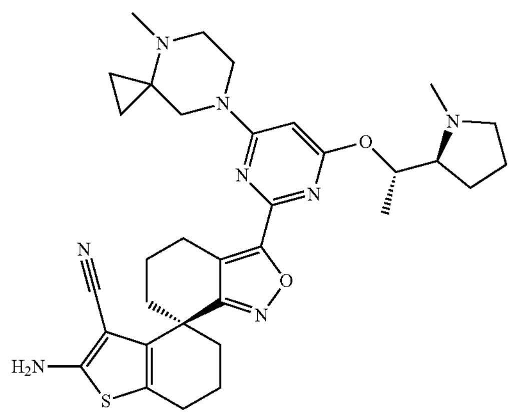 [SMILES: C[C@H](Oc1cc(N2CCN(C)C3(CC3)C2)nc(-c2onc3c2CCC[C@@]32CCCc3sc(N)c(C#N)c32)n1)[C@@H]1CCCN1C] |
| I-42 | 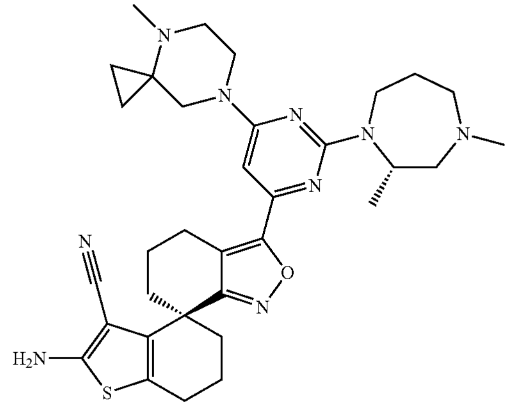 [SMILES: C[C@H]1CN(C)CCCN1c1nc(-c2onc3c2CCC[C@@]32CCCc3sc(N)c(C#N)c32)cc(N2CCN(C)C3(CC3)C2)n1] |

| # | structure |
|---|---|
| I-43 | 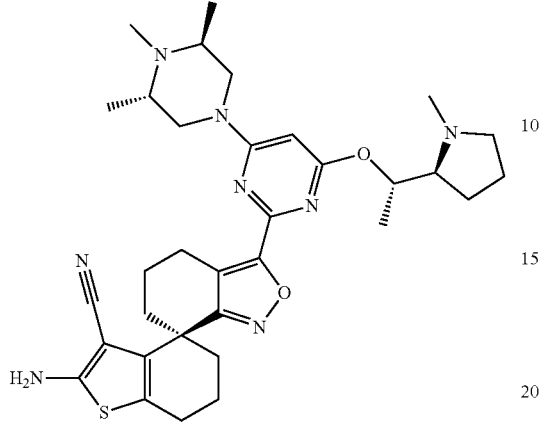 |
| I-44 | 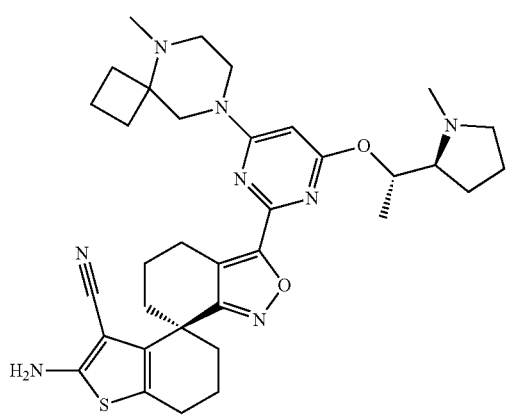 |
| I-45 | 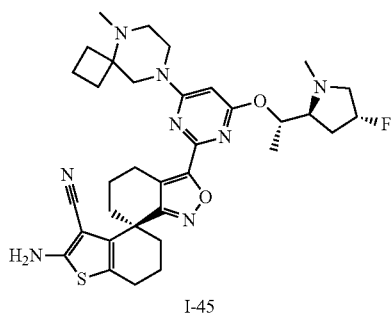 |
| # | structure |
|---|---|
| I-46 | 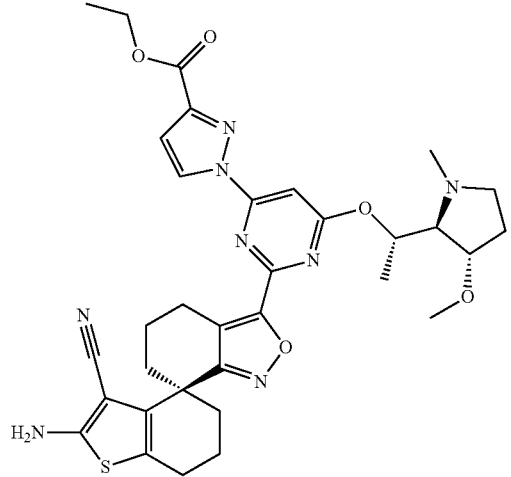 [SMILES: CCOC(=O)c1ccn(-c2cc(O[C@@H](C)[C@@H]3[C@@H](OC)CCN3C)nc(-c3onc4c3CCC[C@@]43CCCc4sc(N)c(C#N)c43)n2)n1] |
| I-47 | 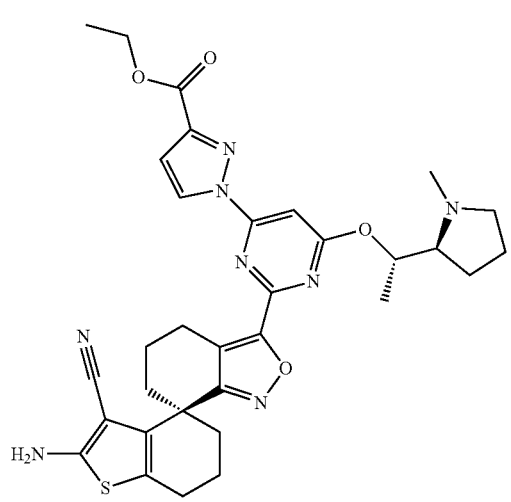 [SMILES: CCOC(=O)c1ccn(-c2cc(O[C@@H](C)[C@@H]3CCCN3C)nc(-c3onc4c3CCC[C@@]43CCCc4sc(N)c(C#N)c43)n2)n1] |
| I-48 | 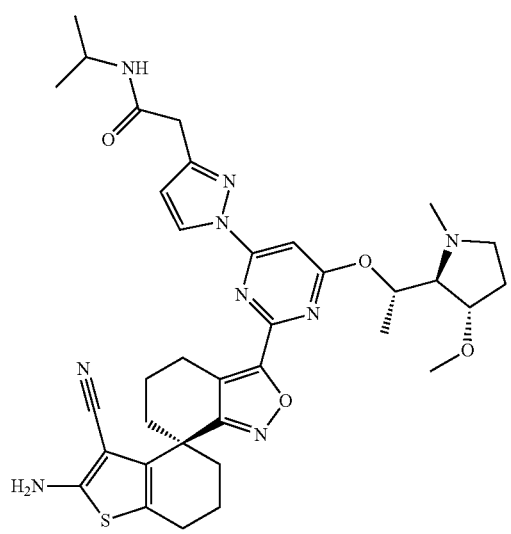 [SMILES: CO[C@H]1CCN(C)[C@@H]1[C@H](C)Oc1cc(-n2ccc(CC(=O)NC(C)C)n2)nc(-c2onc3c2CCC[C@@]32CCCc3sc(N)c(C#N)c32)n1] |

| # | structure |
|---|---|
| I-49 | 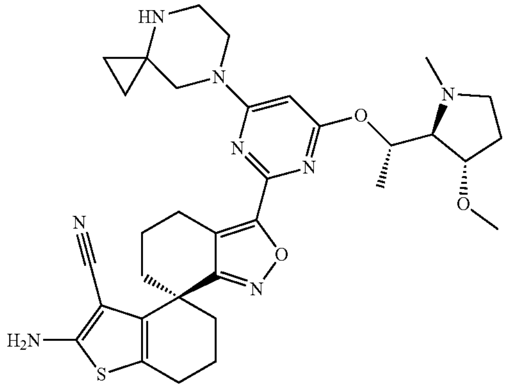 [SMILES: CO[C@H]1CCN(C)[C@@H]1[C@H](C)Oc1cc(N2CCNC3(CC3)C2)nc(-c2onc3c2CCC[C@@]32CCCc3sc(N)c(C#N)c32)n1] |
| I-50 | 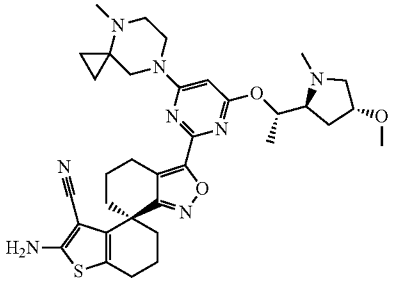 [SMILES: CO[C@@H]1C[C@@H]([C@H](C)Oc2cc(N3CCN(C)C4(CC4)C3)nc(-c3onc4c3CCC[C@@]43CCCc4sc(N)c(C#N)c43)n2)N(C)C1] |
| I-51 | 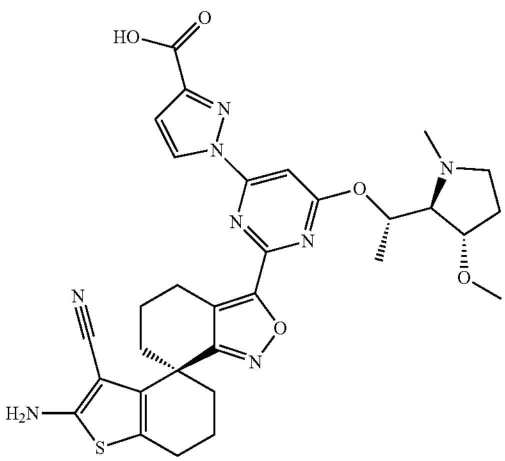 [SMILES: CO[C@H]1CCN(C)[C@@H]1[C@H](C)Oc1cc(-n2ccc(C(=O)O)n2)nc(-c2onc3c2CCC[C@@]32CCCc3sc(N)c(C#N)c32)n1] |
| I-52 | 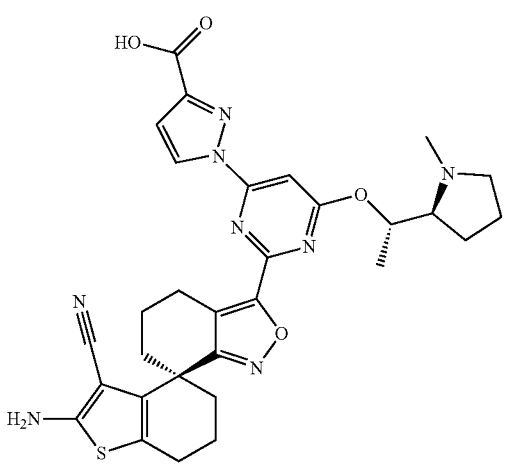 [SMILES: C[C@H](Oc1cc(-n2ccc(C(=O)O)n2)nc(-c2onc3c2CCC[C@@]32CCCc3sc(N)c(C#N)c32)n1)[C@@H]1CCCN1C] |

| # | structure |
|---|---|
| I-53 | 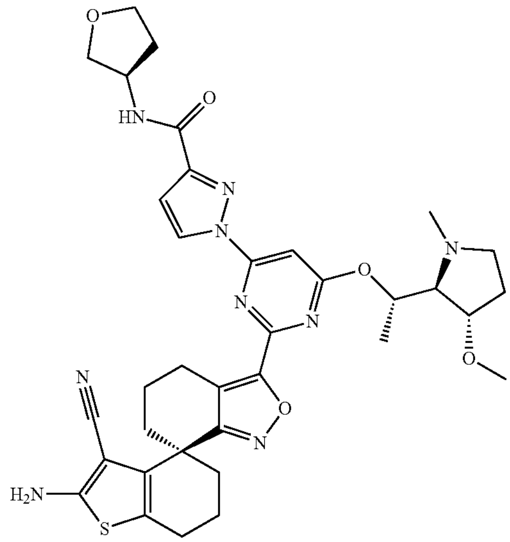 [SMILES: CO[C@H]1CCN(C)[C@@H]1[C@H](C)Oc1cc(-n2ccc(C(=O)N[C@@H]3CCOC3)n2)nc(-c2onc3c2CCC[C@@]32CCCc3sc(N)c(C#N)c32)n1] |
| I-54 | 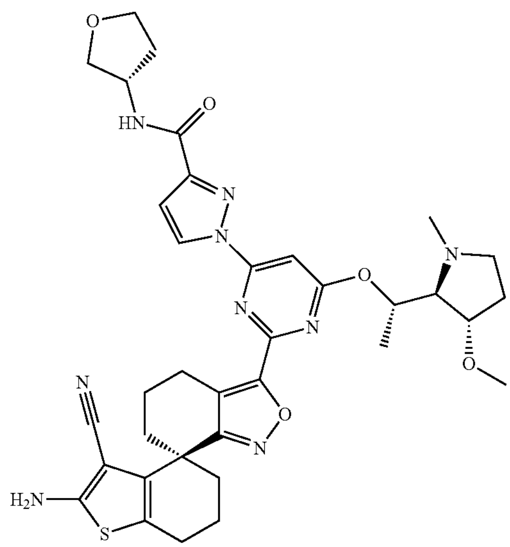 [SMILES: CO[C@H]1CCN(C)[C@@H]1[C@H](C)Oc1cc(-n2ccc(C(=O)N[C@H]3CCOC3)n2)nc(-c2onc3c2CCC[C@@]32CCCc3sc(N)c(C#N)c32)n1] |
| I-55 | 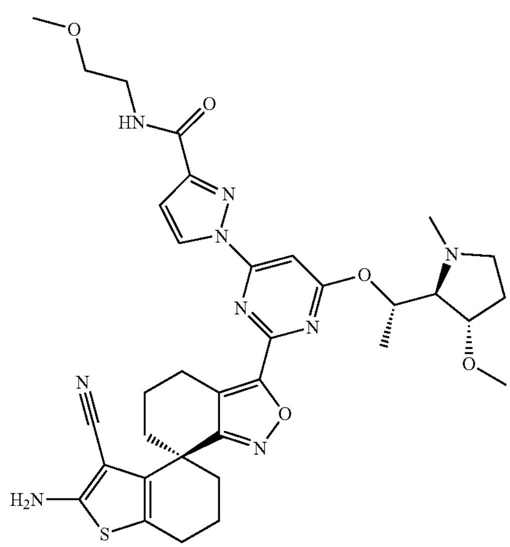 |

-continued
| # | structure |
|---|---|
| I-56 | 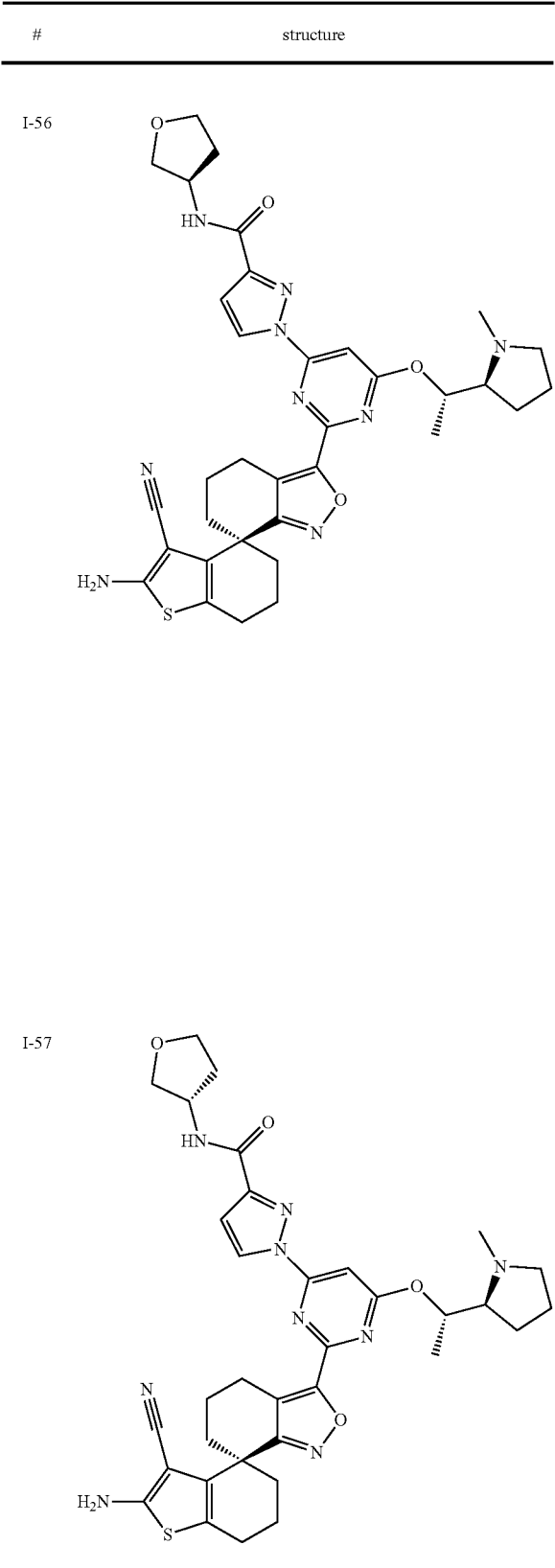 |
| I-57 | 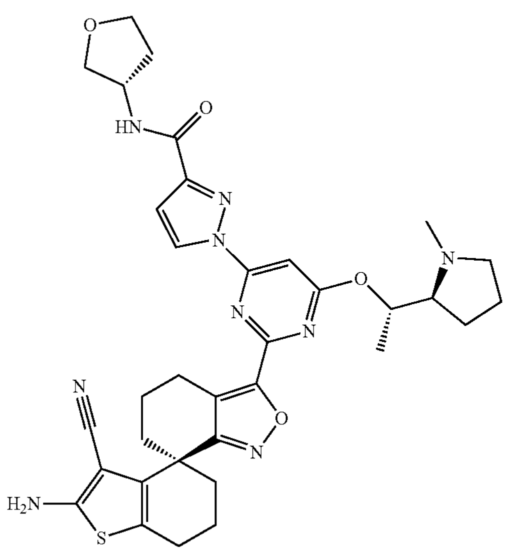 [SMILES: C[C@H](Oc1cc(-n2ccc(C(=O)N[C@H]3CCOC3)n2)nc(-c2onc3c2CCC[C@@]32CCCc3sc(N)c(C#N)c32)n1)[C@@H]1CCCN1C] |
-continued
| # | structure |
|---|---|
| I-58 | 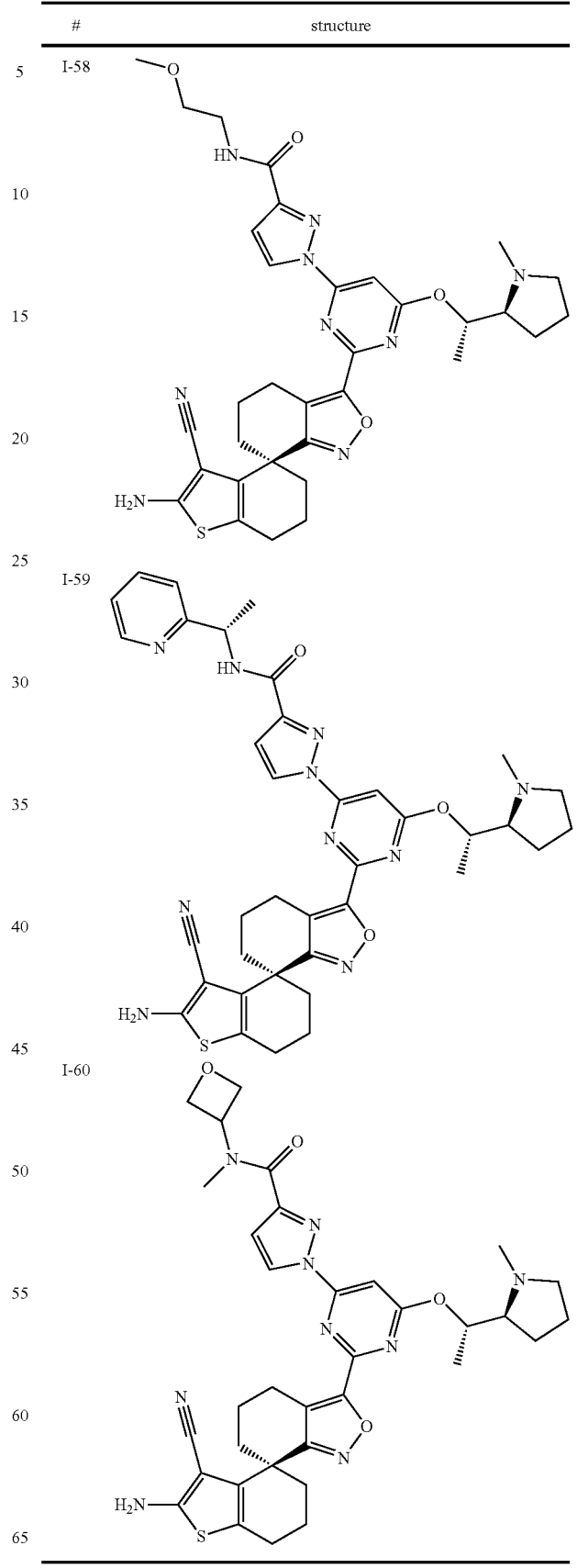 |
| I-59 | 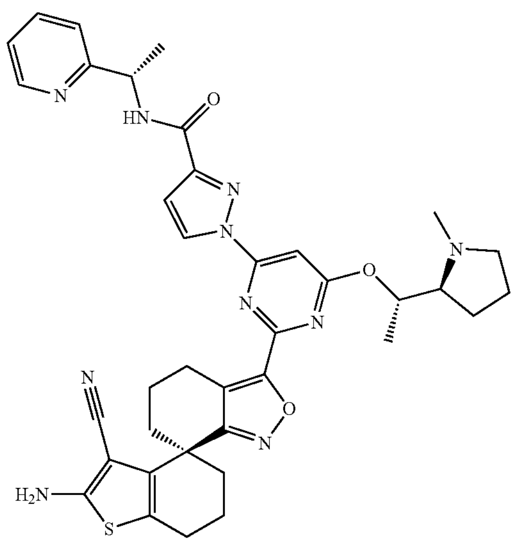 [SMILES: C[C@H](NC(=O)c1ccn(-c2cc(O[C@@H](C)[C@@H]3CCCN3C)nc(-c3onc4c3CCC[C@@]43CCCc4sc(N)c(C#N)c43)n2)n1)c1ccccn1] |
| I-60 | 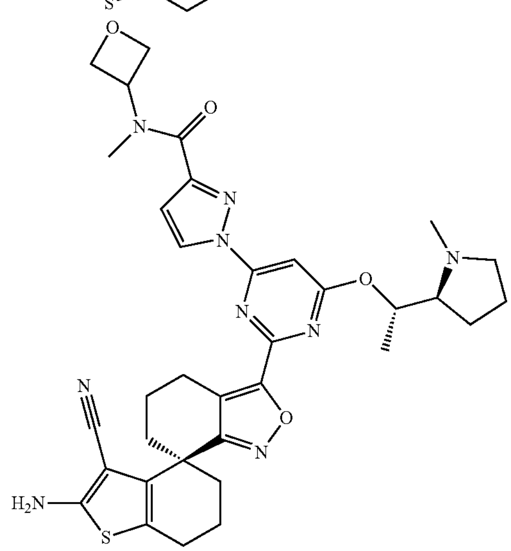 |

19. A compound according to claim 18 in the form of its pharmaceutically acceptable salt.

20. A compound selected from the compounds in the following table, or a salt thereof:

| # | structure |
|---|---|
| II-1 | 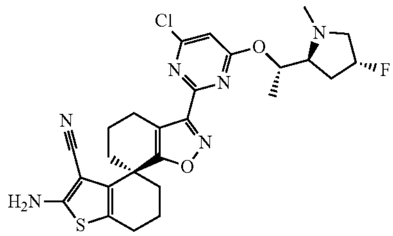 [SMILES: C[C@H](Oc1cc(Cl)nc(-c2noc3c2CCC[C@@]32CCCc3sc(N)c(C#N)c32)n1)[C@@H]1C[C@@H](F)CN1C] |
| II-2 | 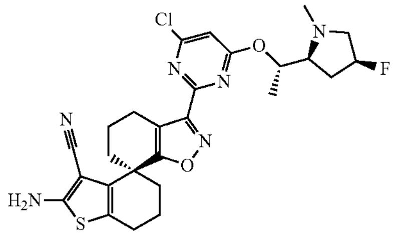 [SMILES: C[C@H](Oc1cc(Cl)nc(-c2noc3c2CCC[C@@]32CCCc3sc(N)c(C#N)c32)n1)[C@@H]1C[C@H](F)CN1C] |
| II-3 | 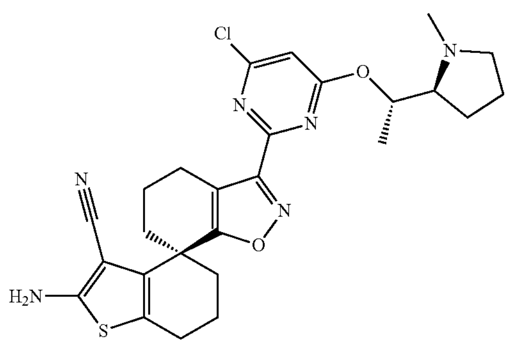 [SMILES: C[C@H](Oc1cc(Cl)nc(-c2noc3c2CCC[C@@]32CCCc3sc(N)c(C#N)c32)n1)[C@@H]1CCCN1C] |
| II-4 | 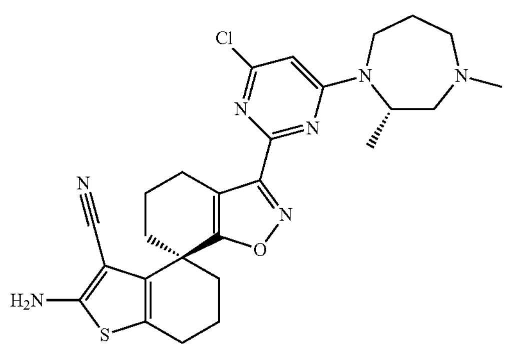 [SMILES: C[C@H]1CN(C)CCCN1c1cc(Cl)nc(-c2noc3c2CCC[C@@]32CCCc3sc(N)c(C#N)c32)n1] |
| II-5 | 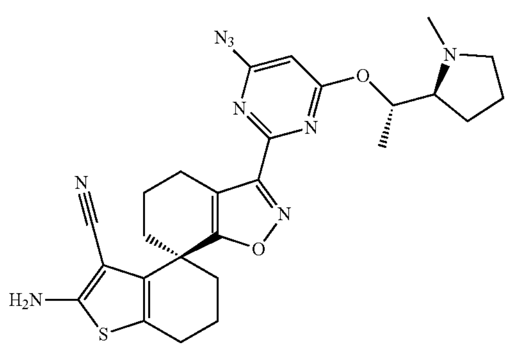 [SMILES: C[C@H](Oc1cc(N=[N+]=[N-])nc(-c2noc3c2CCC[C@@]32CCCc3sc(N)c(C#N)c32)n1)[C@@H]1CCCN1C] |

-continued

| # | structure |
|---|---|
| II-6 | 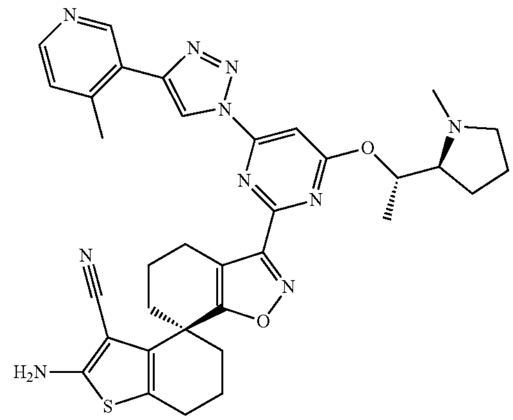 [SMILES: Cc1ccncc1-c1cn(-c2cc(O[C@@H](C)[C@@H]3CCCN3C)nc(-c3noc4c3CCC[C@@]43CCCc4sc(N)c(C#N)c43)n2)nn1] |
| II-7 | 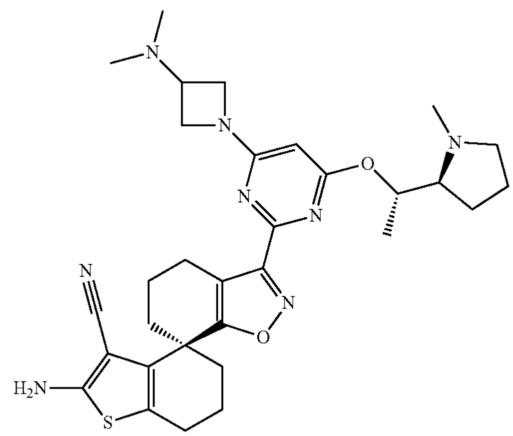 [SMILES: C[C@H](Oc1cc(N2CC(N(C)C)C2)nc(-c2noc3c2CCC[C@@]32CCCc3sc(N)c(C#N)c32)n1)[C@@H]1CCCN1C] |
| II-8 | 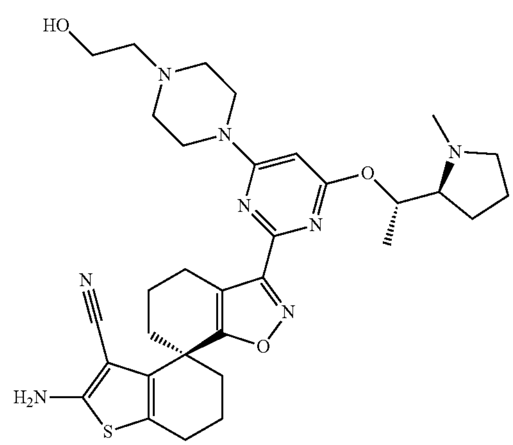 [SMILES: C[C@H](Oc1cc(N2CCN(CCO)CC2)nc(-c2noc3c2CCC[C@@]32CCCc3sc(N)c(C#N)c32)n1)[C@@H]1CCCN1C] |

645
-continued
| # | structure |
|---|---|
| II-9 | 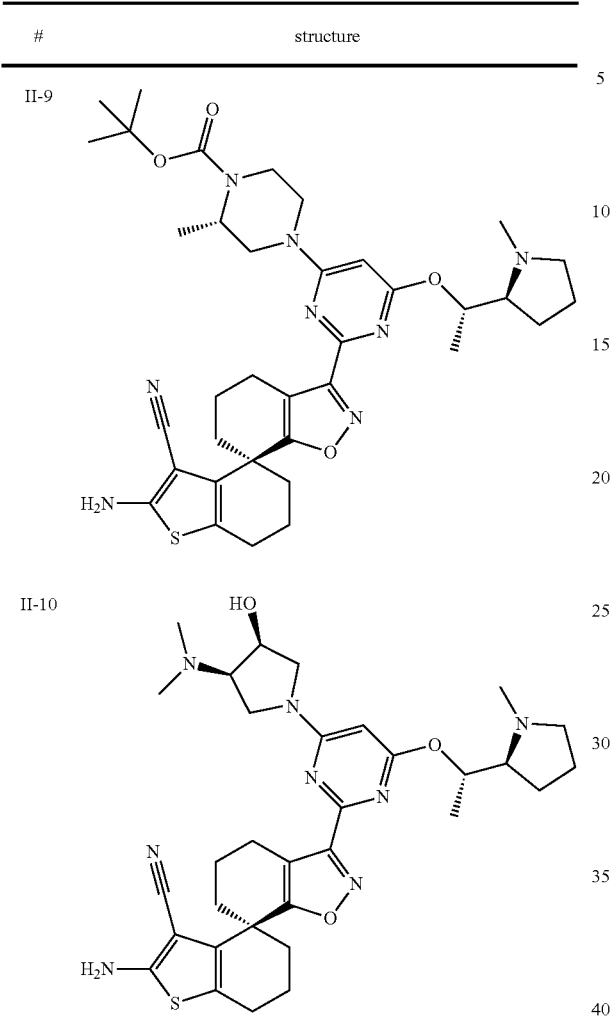 |
| II-10 | 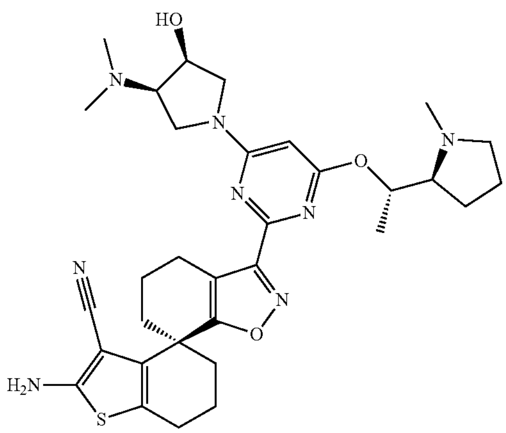 [SMILES: C[C@H](Oc1cc(N2C[C@@H](N(C)C)[C@@H](O)C2)nc(-c2noc3c2CCC[C@@]32CCCc3sc(N)c(C#N)c32)n1)[C@@H]1CCCN1C] |
| II-11 | 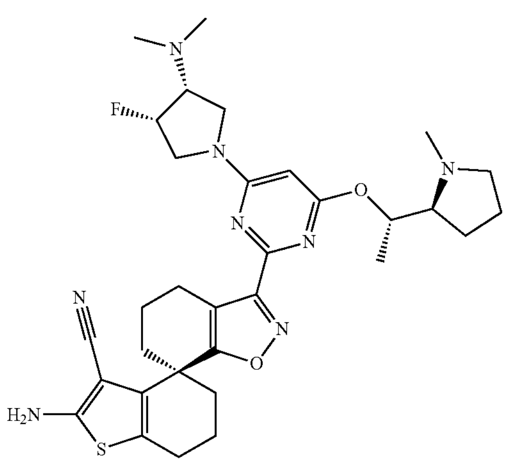 [SMILES: C[C@H](Oc1cc(N2C[C@@H](N(C)C)[C@@H](F)C2)nc(-c2noc3c2CCC[C@@]32CCCc3sc(N)c(C#N)c32)n1)[C@@H]1CCCN1C] |
646
-continued
| # | structure |
|---|---|
| II-12 | 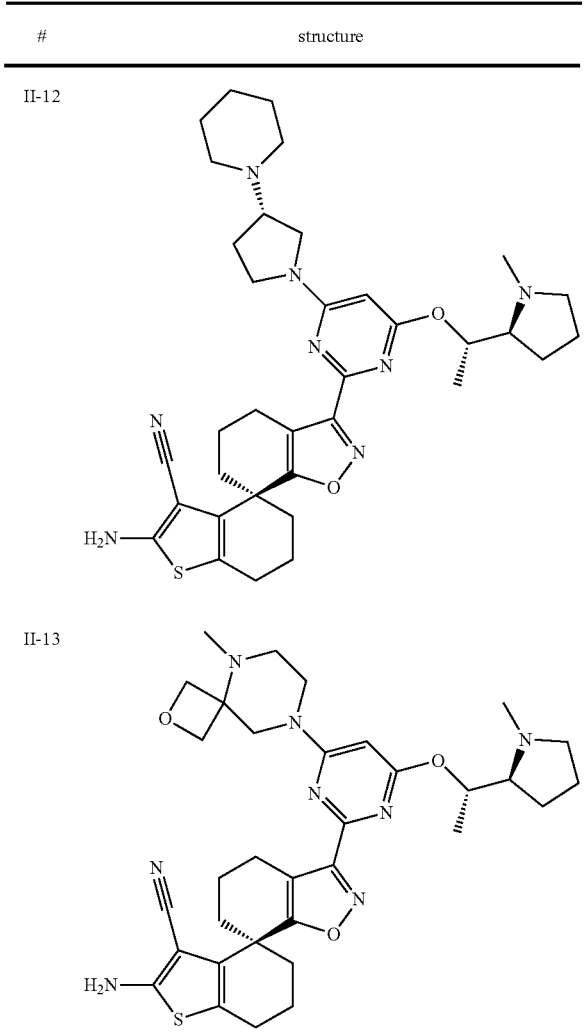 |
| II-13 | 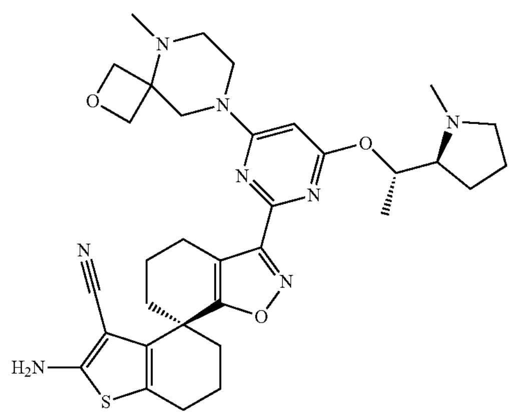 [SMILES: C[C@H](Oc1cc(N2CCN(C)C3(COC3)C2)nc(-c2noc3c2CCC[C@@]32CCCc3sc(N)c(C#N)c32)n1)[C@@H]1CCCN1C] |
| II-14 | 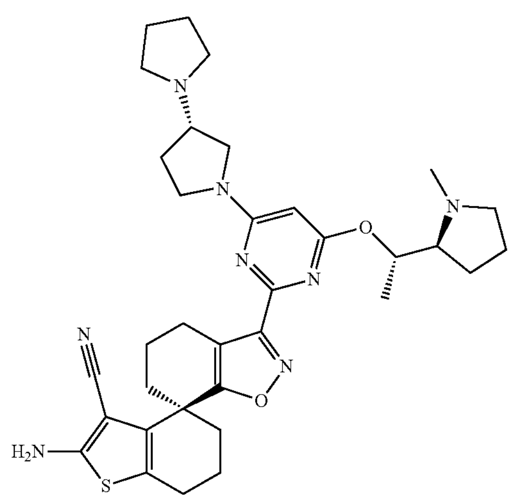 [SMILES: C[C@H](Oc1cc(N2CC[C@H](N3CCCC3)C2)nc(-c2noc3c2CCC[C@@]32CCCc3sc(N)c(C#N)c32)n1)[C@@H]1CCCN1C] |

-continued
| # | structure |
|---|---|
| II-15 | 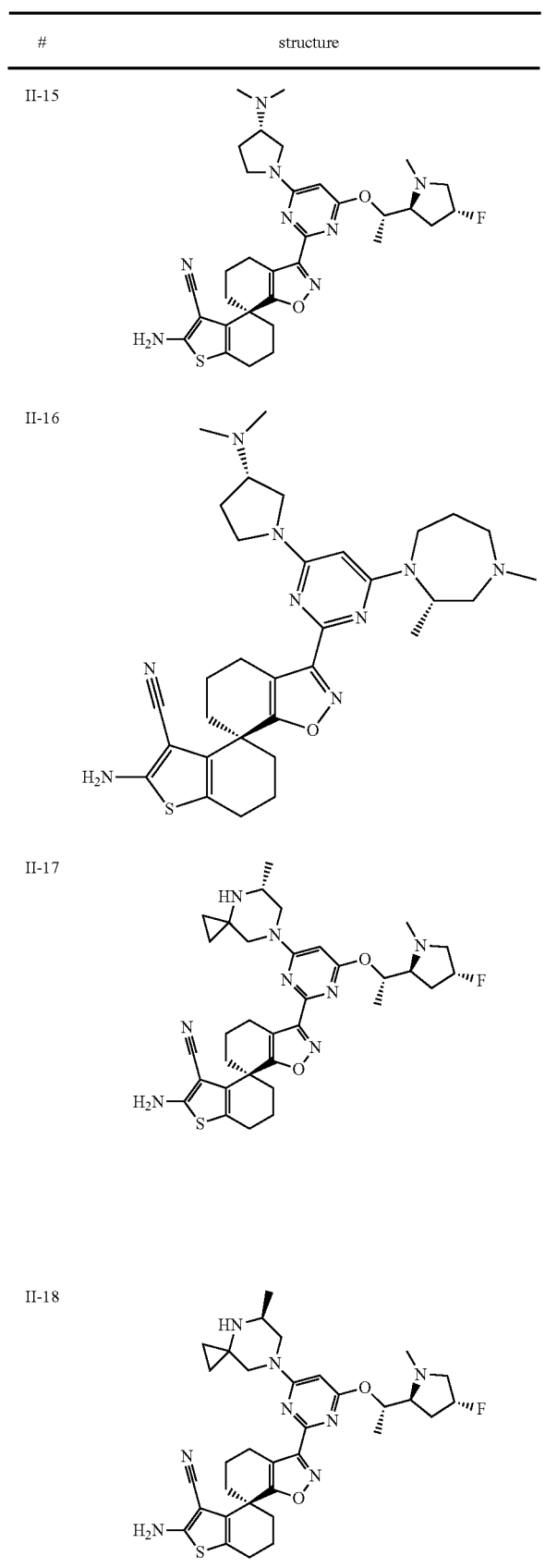 |
| II-16 | 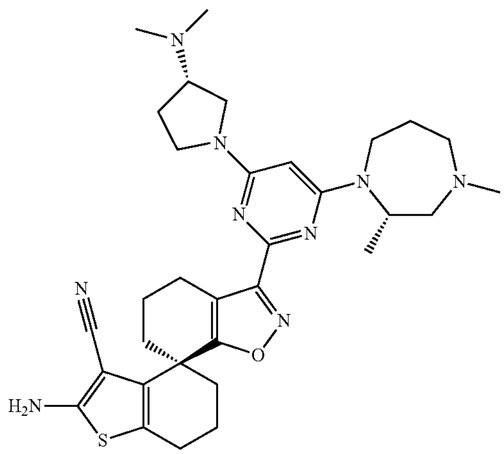 [SMILES: C[C@H]1CN(C)CCCN1c1cc(N2CC[C@H](N(C)C)C2)nc(-c2noc3c2CCC[C@@]32CCCc3sc(N)c(C#N)c32)n1] |
| II-17 | 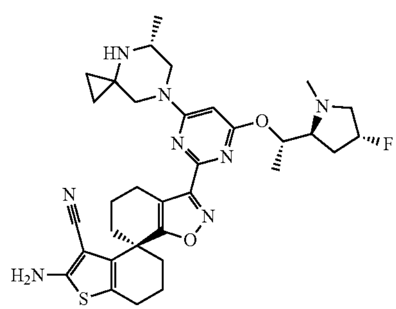 [SMILES: C[C@@H]1CN(c2cc(O[C@@H](C)[C@@H]3C[C@@H](F)CN3C)nc(-c3noc4c3CCC[C@@]43CCCc4sc(N)c(C#N)c43)n2)CC2(CC2)N1] |
| II-18 | 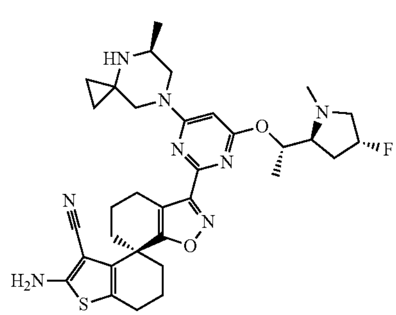 [SMILES: C[C@H](Oc1cc(N2C[C@H](C)NC3(CC3)C2)nc(-c2noc3c2CCC[C@@]32CCCc3sc(N)c(C#N)c32)n1)[C@@H]1C[C@@H](F)CN1C] |
-continued
| # | structure |
|---|---|
| II-19 | 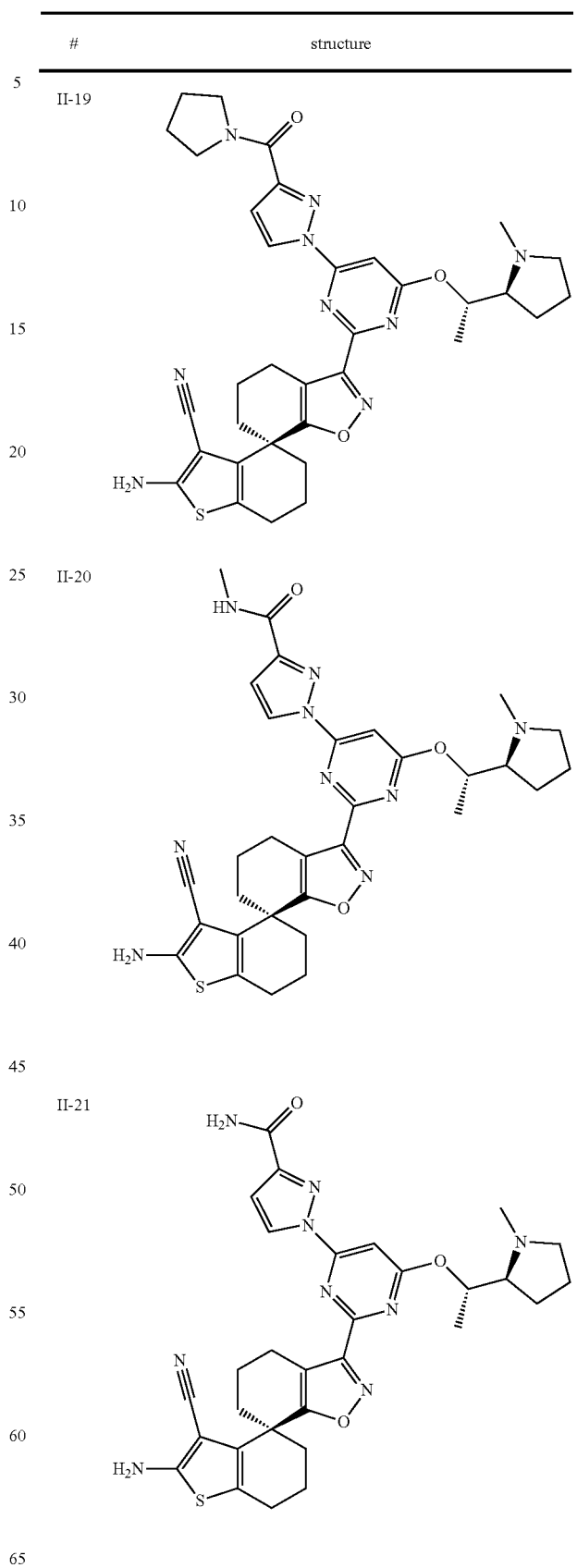 |
| II-20 | |
| II-21 | |

| # | structure |
|---|---|
| II-22 | 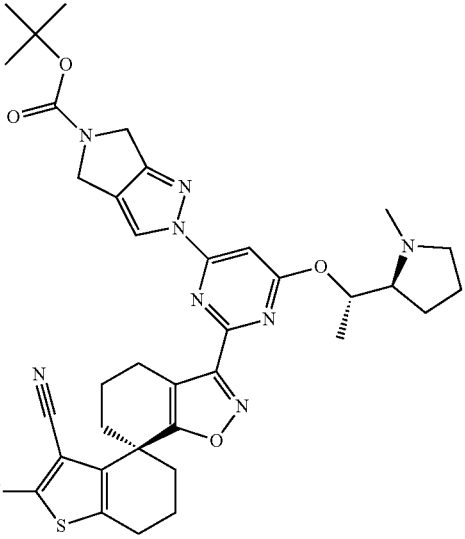 |
| II-23 | 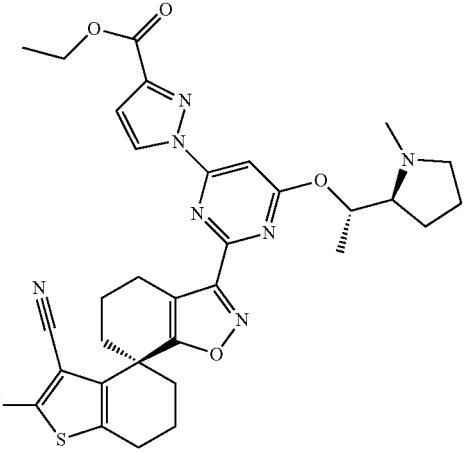 |
| II-24 | 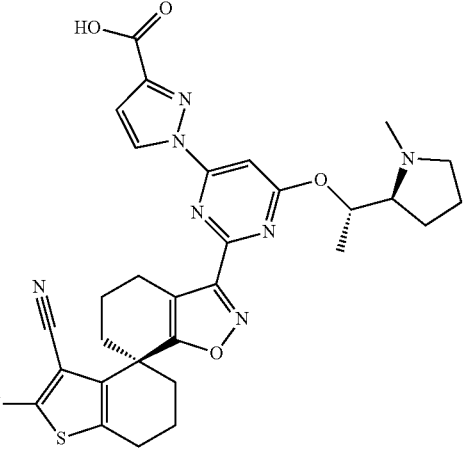 |
| # | structure |
|---|---|
| II-25 | 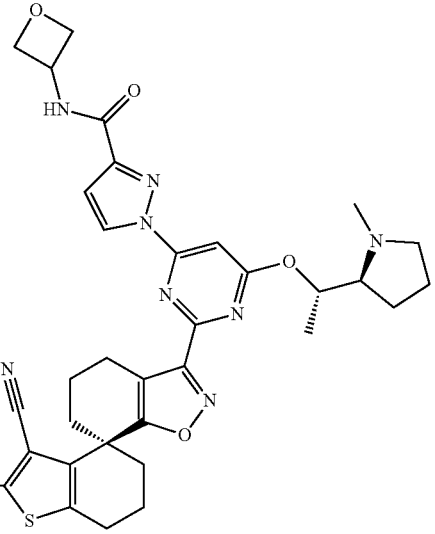 |
| II-26 | 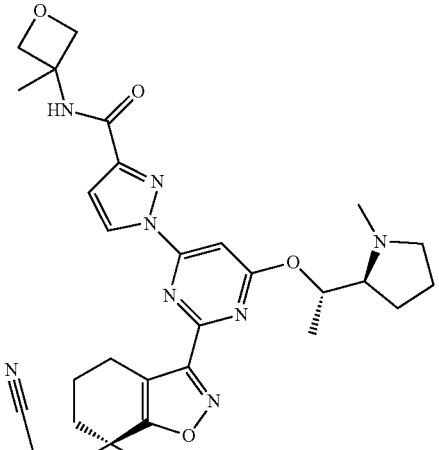 |
| II-27 | 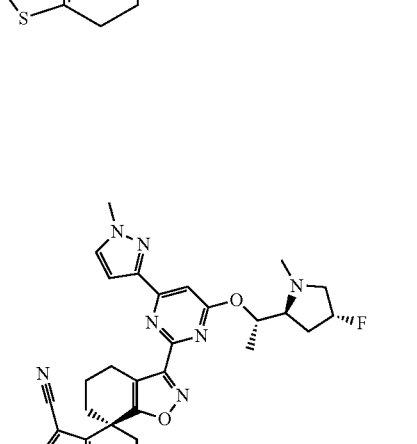 |

| # | structure |
|---|---|
| II-28 | 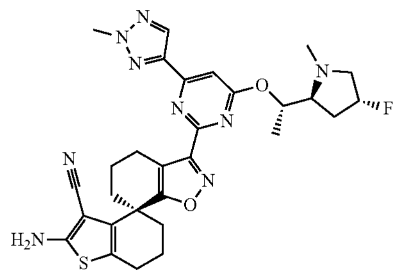 [SMILES: C[C@H](Oc1cc(-c2cnn(C)n2)nc(-c2noc3c2CCC[C@@]32CCCc3sc(N)c(C#N)c32)n1)[C@@H]1C[C@@H](F)CN1C] |
| II-29 | 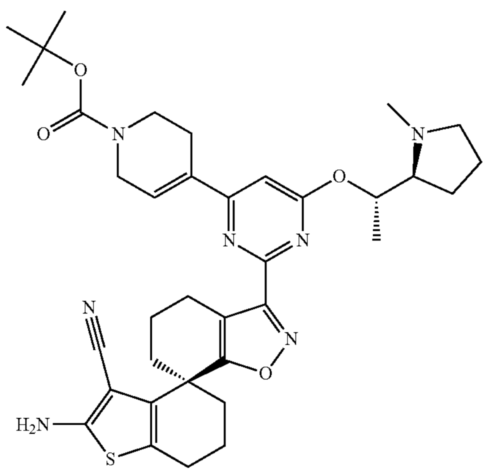 [SMILES: C[C@H](Oc1cc(C2=CCN(C(=O)OC(C)(C)C)CC2)nc(-c2noc3c2CCC[C@@]32CCCc3sc(N)c(C#N)c32)n1)[C@@H]1CCCN1C] |
| II-30 | 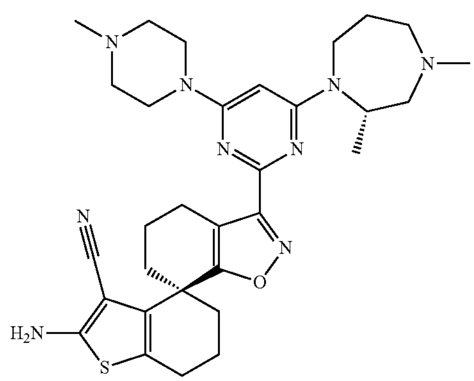 [SMILES: C[C@H]1CN(C)CCCN1c1cc(N2CCN(C)CC2)nc(-c2noc3c2CCC[C@@]32CCCc3sc(N)c(C#N)c32)n1] |
| II-31 | 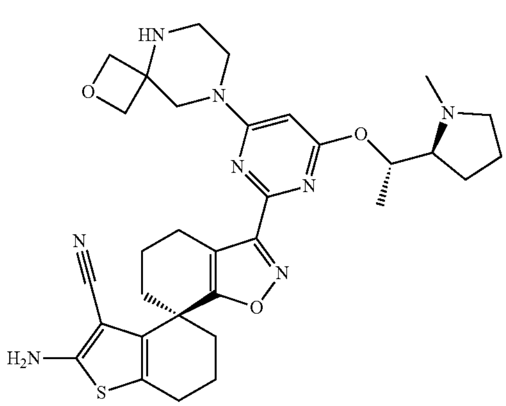 [SMILES: C[C@H](Oc1cc(N2CCNC3(COC3)C2)nc(-c2noc3c2CCC[C@@]32CCCc3sc(N)c(C#N)c32)n1)[C@@H]1CCCN1C] |

| # | structure |
|---|---|
| II-32 | 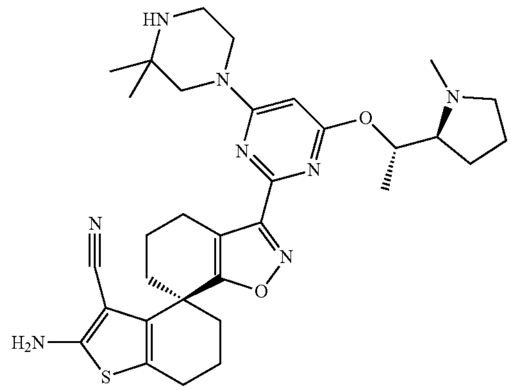 [SMILES: C[C@H](Oc1cc(N2CCNC(C)(C)C2)nc(-c2noc3c2CCC[C@@]32CCCc3sc(N)c(C#N)c32)n1)[C@@H]1CCCN1C] |
| II-33 | 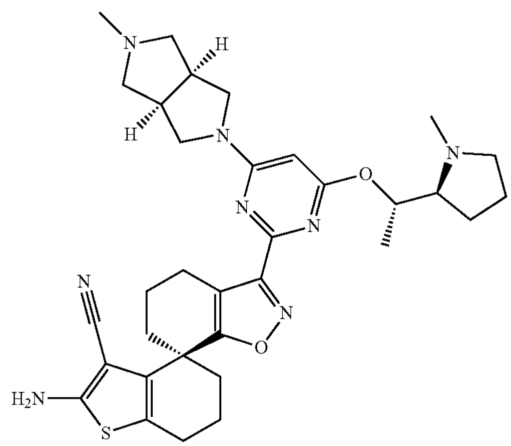 [SMILES: C[C@H](Oc1cc(N2C[C@H]3CN(C)C[C@H]3C2)nc(-c2noc3c2CCC[C@@]32CCCc3sc(N)c(C#N)c32)n1)[C@@H]1CCCN1C] |
| II-34 | 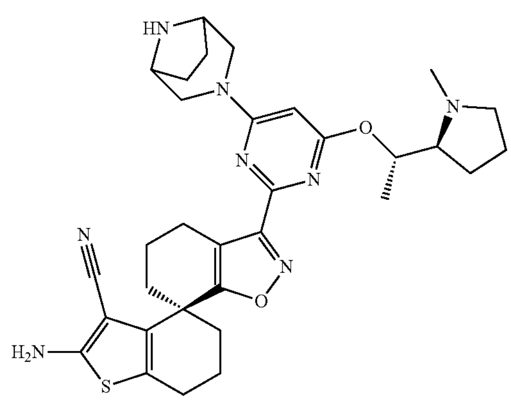 [SMILES: C[C@H](Oc1cc(N2CC3CCC(C2)N3)nc(-c2noc3c2CCC[C@@]32CCCc3sc(N)c(C#N)c32)n1)[C@@H]1CCCN1C] |

653
-continued
| # | structure |
|---|---|
| II-35 | 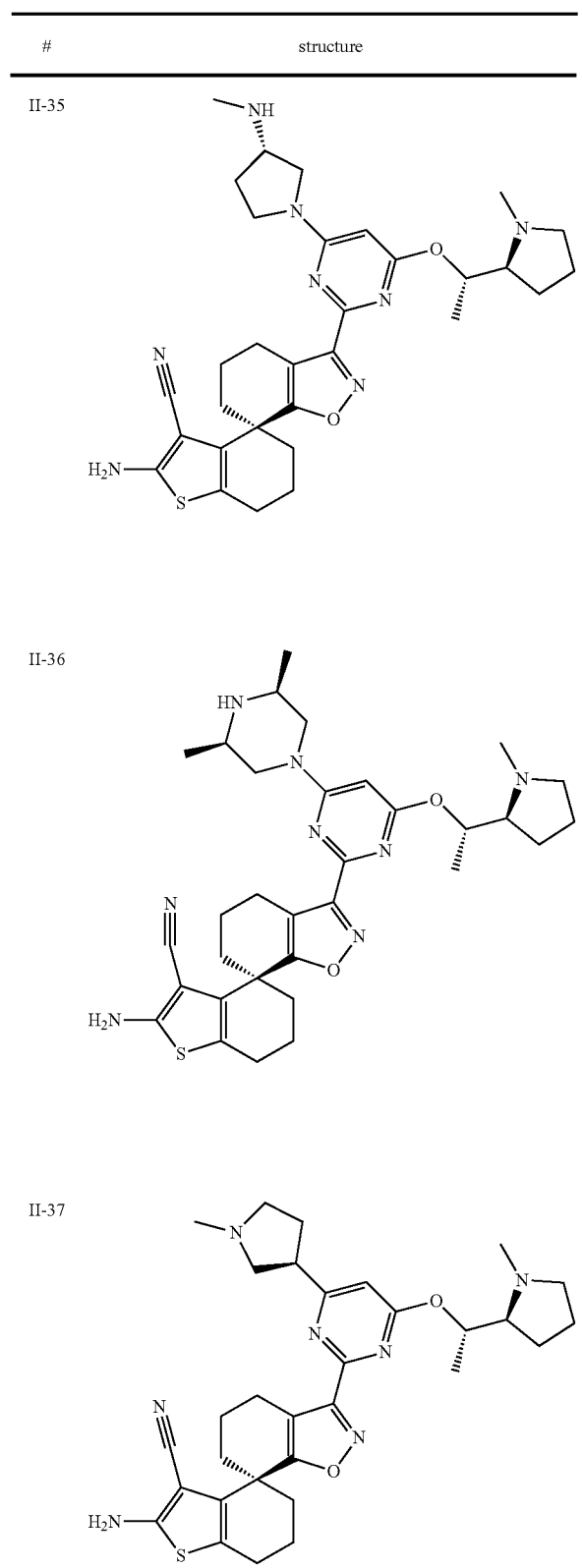 |
| II-36 | 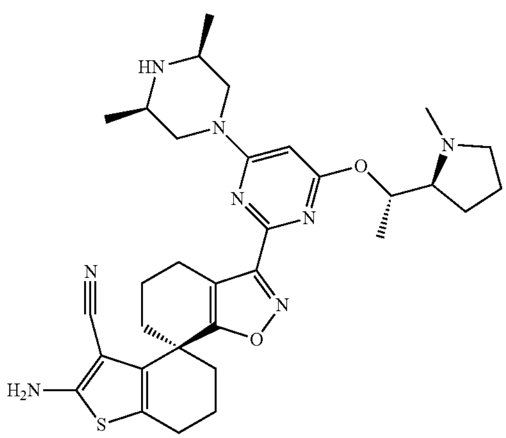 [SMILES: C[C@@H]1CN(c2cc(O[C@@H](C)[C@@H]3CCCN3C)nc(-c3noc4c3CCC[C@@]43CCCc4sc(N)c(C#N)c43)n2)C[C@H](C)N1] |
| II-37 | 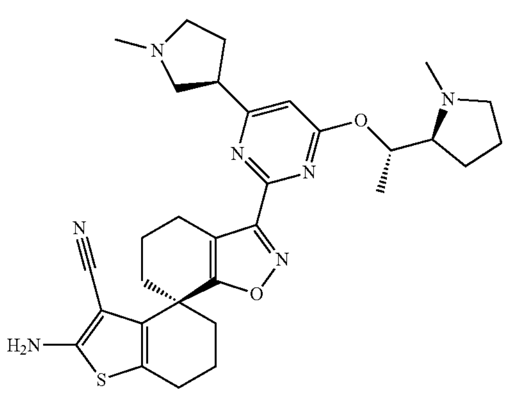 [SMILES: C[C@H](Oc1cc([C@@H]2CCN(C)C2)nc(-c2noc3c2CCC[C@@]32CCCc3sc(N)c(C#N)c32)n1)[C@@H]1CCCN1C] |
654
-continued
| # | structure |
|---|---|
| II-38 | 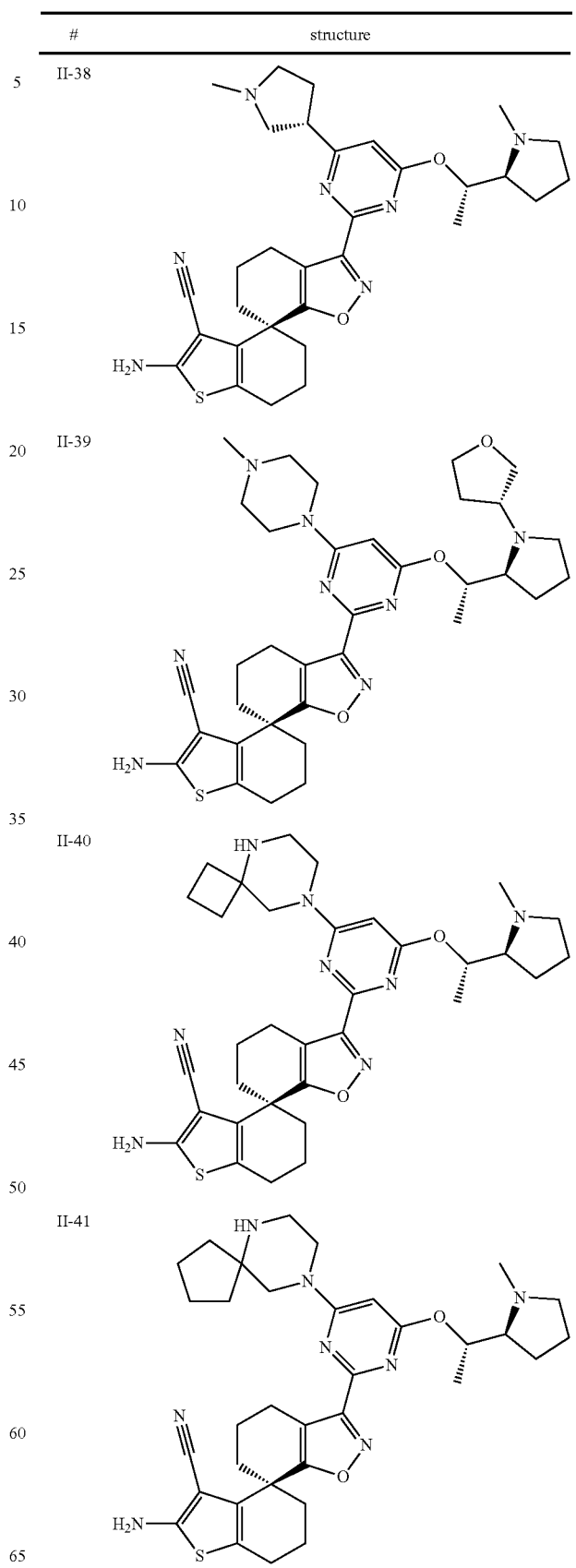 |
| II-39 | 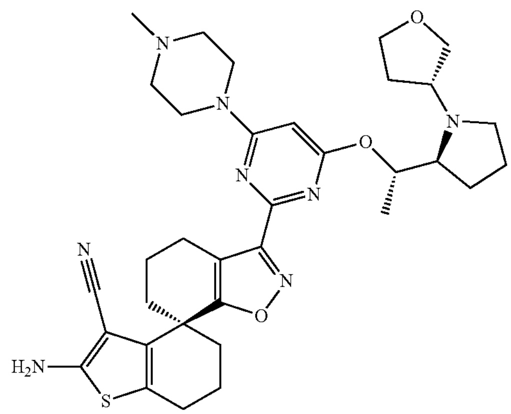 [SMILES: C[C@H](Oc1cc(N2CCN(C)CC2)nc(-c2noc3c2CCC[C@@]32CCCc3sc(N)c(C#N)c32)n1)[C@@H]1CCCN1[C@@H]1CCOC1] |
| II-40 | 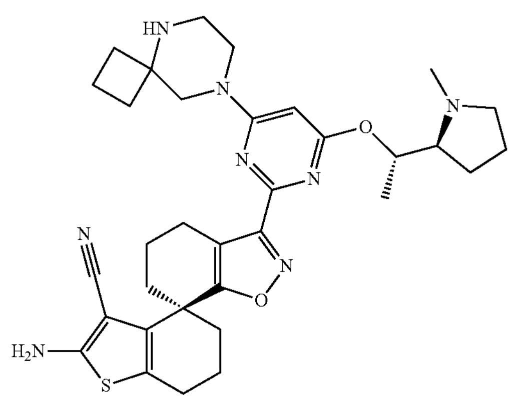 |
| II-41 | 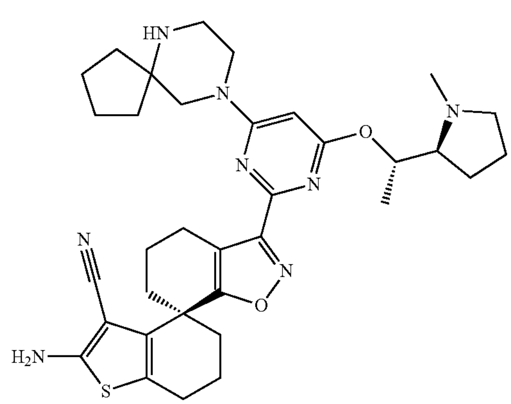 [SMILES: C[C@H](Oc1cc(N2CCNC3(CCCC3)C2)nc(-c2noc3c2CCC[C@@]32CCCc3sc(N)c(C#N)c32)n1)[C@@H]1CCCN1C] |

| # | structure |
|---|---|
| II-42 | 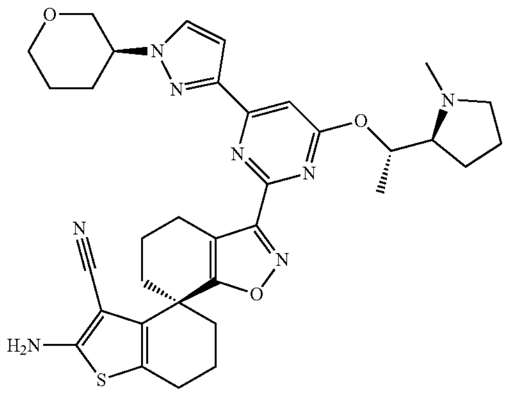 [SMILES: C[C@H](Oc1cc(-c2ccn([C@H]3CCCOC3)n2)nc(-c2noc3c2CCC[C@@]32CCCc3sc(N)c(C#N)c32)n1)[C@@H]1CCCN1C] |
| II-43 | 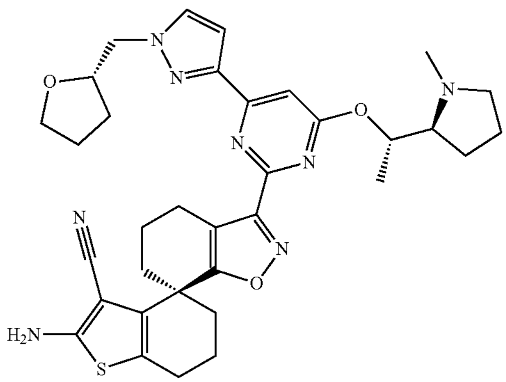 [SMILES: C[C@H](Oc1cc(-c2ccn(C[C@@H]3CCCO3)n2)nc(-c2noc3c2CCC[C@@]32CCCc3sc(N)c(C#N)c32)n1)[C@@H]1CCCN1C] |
| II-44 | 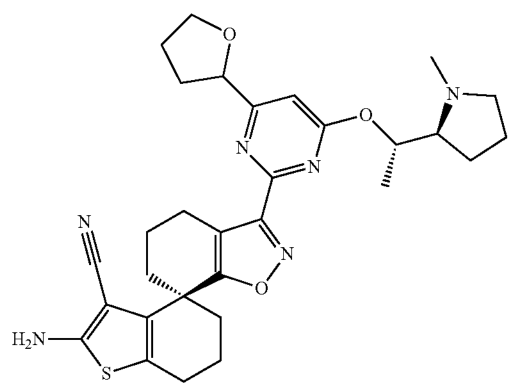 [SMILES: C[C@H](Oc1cc(C2CCCO2)nc(-c2noc3c2CCC[C@@]32CCCc3sc(N)c(C#N)c32)n1)[C@@H]1CCCN1C] |
| II-45 | 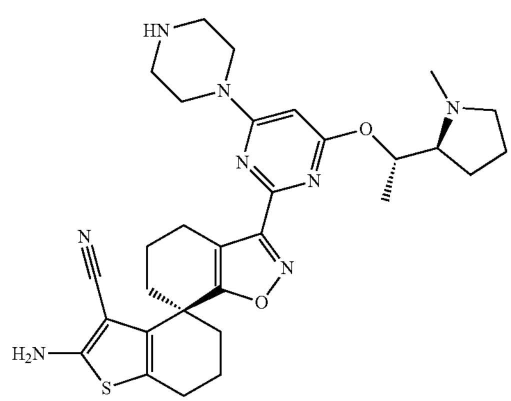 |

| # | structure |
|---|---|
| II-46 | 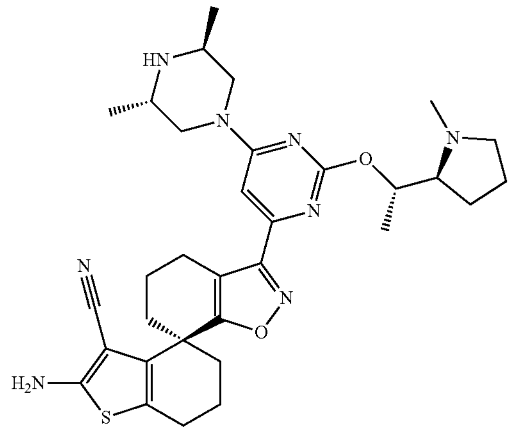 |
| II-47 | 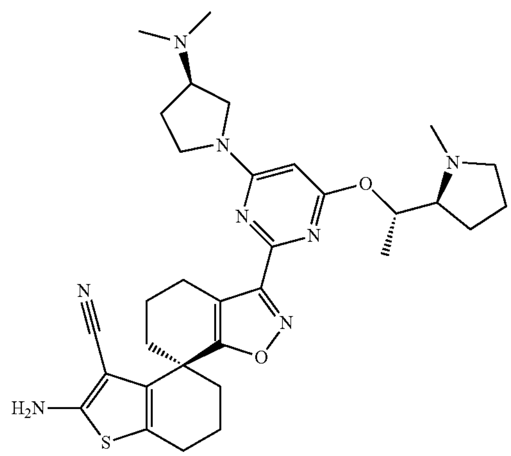 [SMILES: C[C@H](Oc1cc(N2CC[C@@H](N(C)C)C2)nc(-c2noc3c2CCC[C@@]32CCCc3sc(N)c(C#N)c32)n1)[C@@H]1CCCN1C] |
| II-48 | 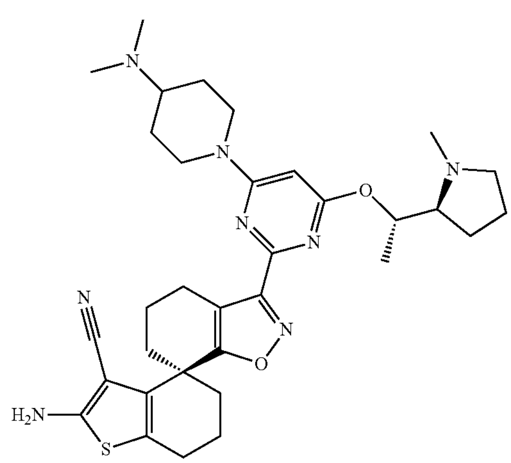 [SMILES: C[C@H](Oc1cc(N2CCC(N(C)C)CC2)nc(-c2noc3c2CCC[C@@]32CCCc3sc(N)c(C#N)c32)n1)[C@@H]1CCCN1C] |

| # | structure |
|---|---|
| II-49 | 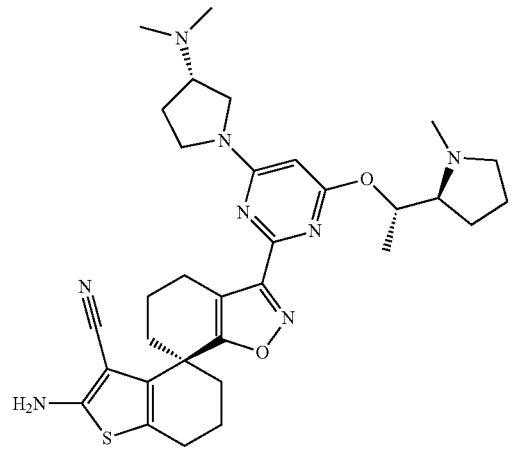 [SMILES: C[C@H](Oc1cc(N2CC[C@H](N(C)C)C2)nc(-c2noc3c2CCC[C@@]32CCCc3sc(N)c(C#N)c32)n1)[C@@H]1CCCN1C] |
| II-50 | 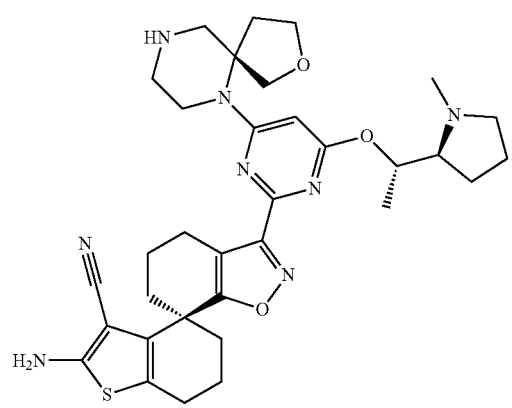 [SMILES: C[C@H](Oc1cc(N2CCNC[C@]23CCOC3)nc(-c2noc3c2CCC[C@@]32CCCc3sc(N)c(C#N)c32)n1)[C@@H]1CCCN1C] |
| II-51 | 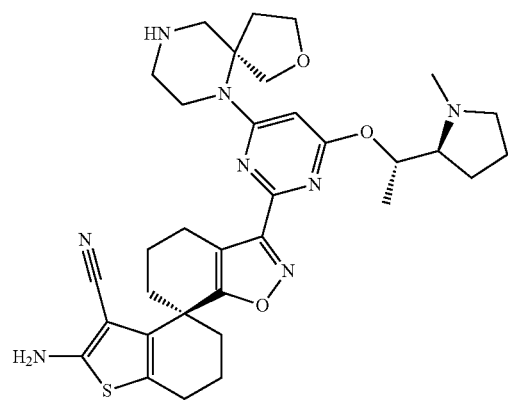 [SMILES: C[C@H](Oc1cc(N2CCNC[C@@]23CCOC3)nc(-c2noc3c2CCC[C@@]32CCCc3sc(N)c(C#N)c32)n1)[C@@H]1CCCN1C] |
| # | structure |
|---|---|
| II-52 | 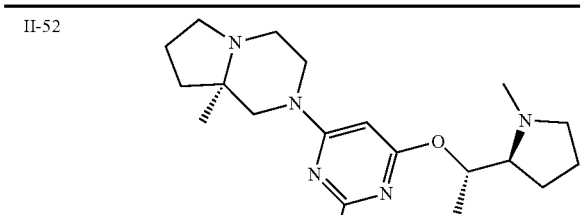 |
| II-53 | 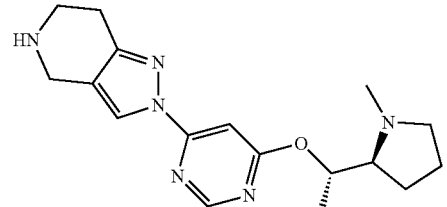 |
| II-54 | 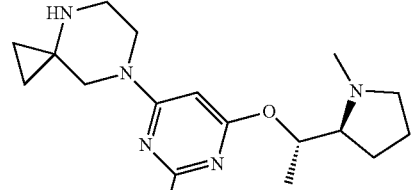 |
| II-55 | 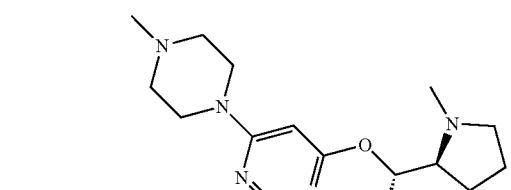 |

-continued
| # | structure |
|---|---|
| II-56 | 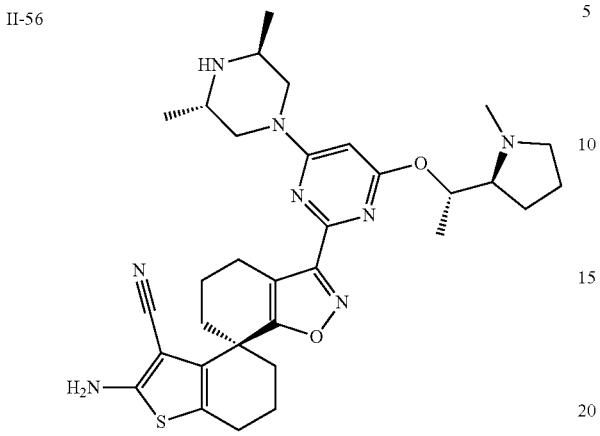 |
| II-57 | 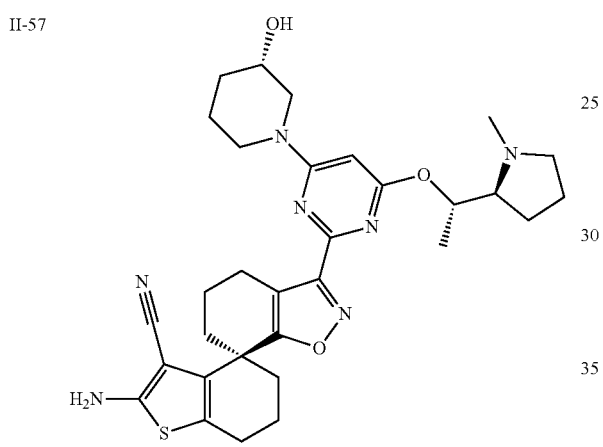 |
| II-58 | 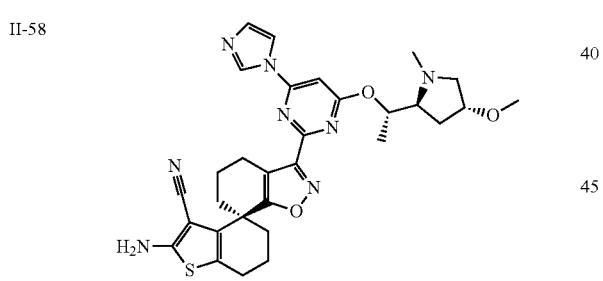 |
| II-59 | 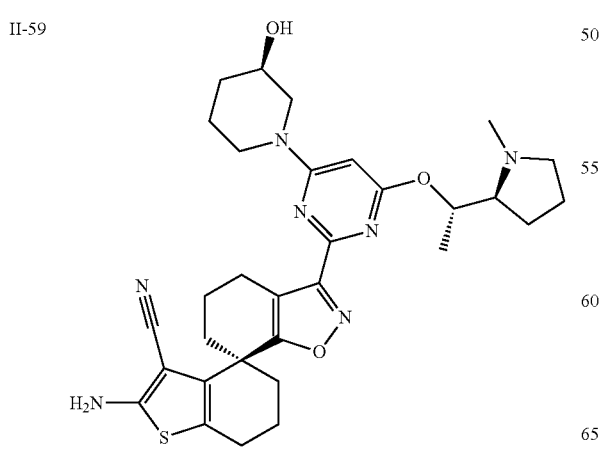 |
-continued
| # | structure |
|---|---|
| II-60 | 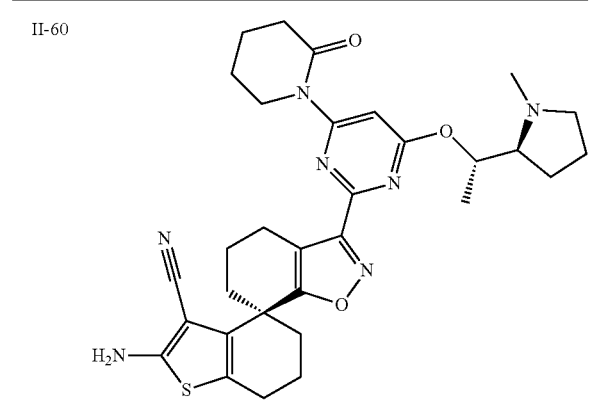 |
| II-61 | 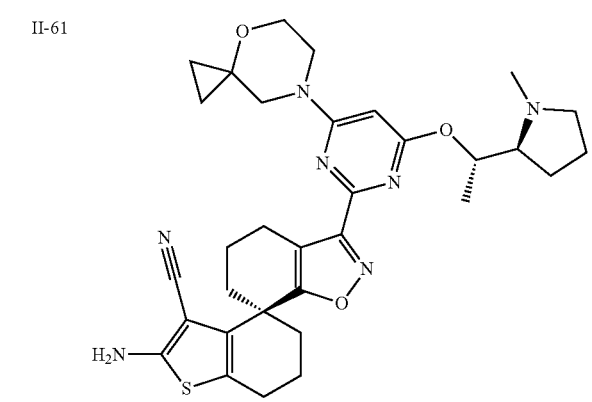 |
| II-62 | 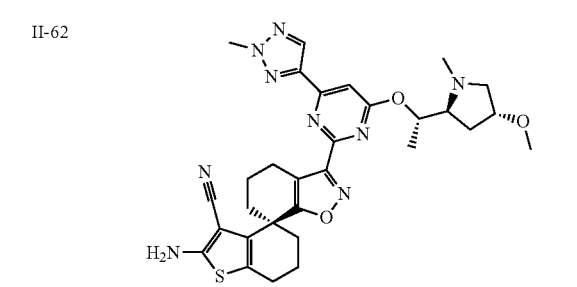 |
| II-63 | 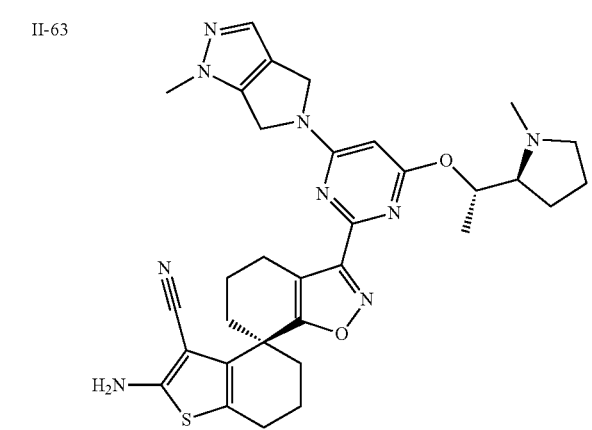 |

661
-continued
| # | structure |
|---|---|
| II-64 | 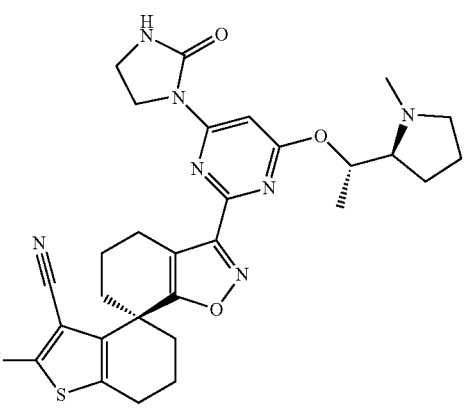 |
| II-65 | 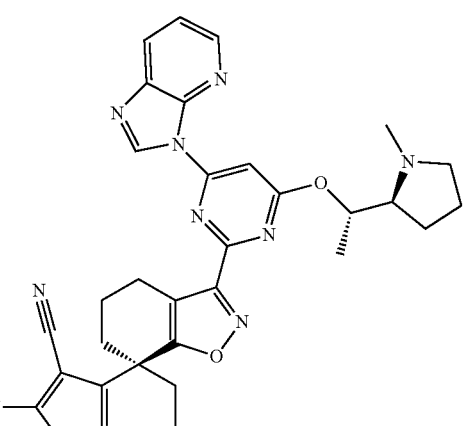 |
| II-66 | 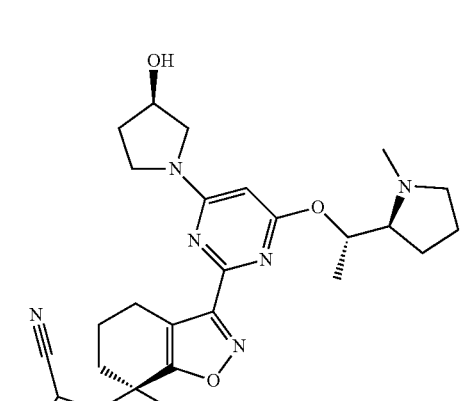 |
662
-continued
| # | structure |
|---|---|
| II-67 | 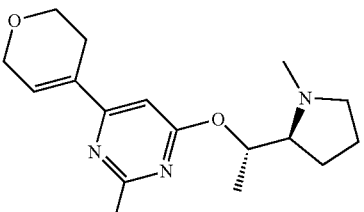 |
| II-68 | 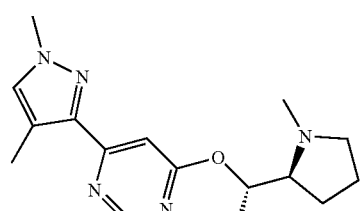 |
| II-69 | 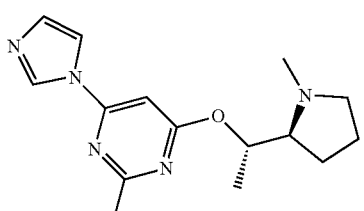 |
| II-70 | 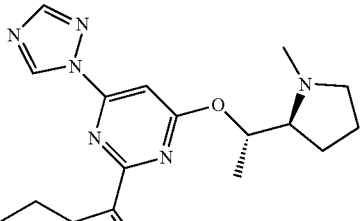 |

| # | structure |
|---|---|
| II-71 | 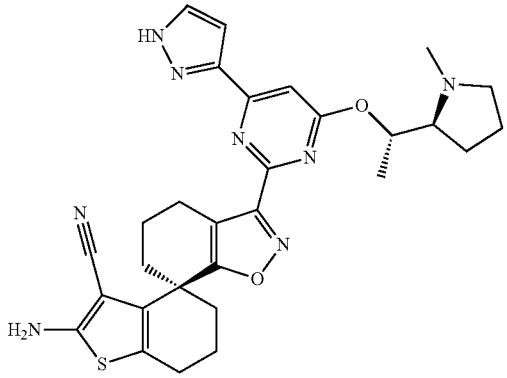 [SMILES: C[C@H](Oc1cc(-c2cc[nH]n2)nc(-c2noc3c2CCC[C@@]32CCCc3sc(N)c(C#N)c32)n1)[C@@H]1CCCN1C] |
| II-72 | 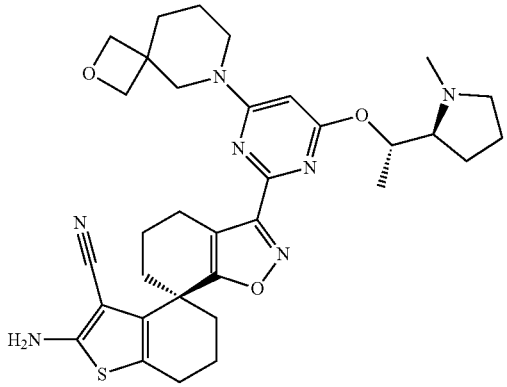 [SMILES: C[C@H](Oc1cc(N2CCCC3(COC3)C2)nc(-c2noc3c2CCC[C@@]32CCCc3sc(N)c(C#N)c32)n1)[C@@H]1CCCN1C] |
| II-73 | 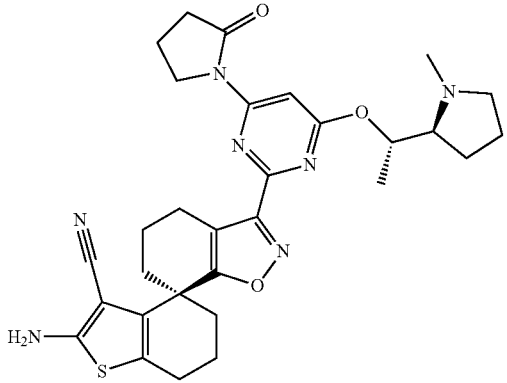 |
| II-74 | 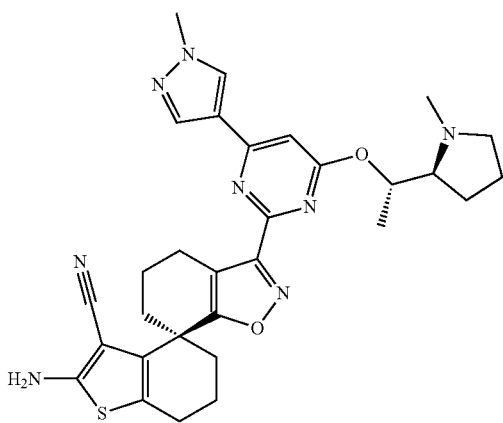 [SMILES: C[C@H](Oc1cc(-c2cnn(C)c2)nc(-c2noc3c2CCC[C@@]32CCCc3sc(N)c(C#N)c32)n1)[C@@H]1CCCN1C] |
| II-75 | 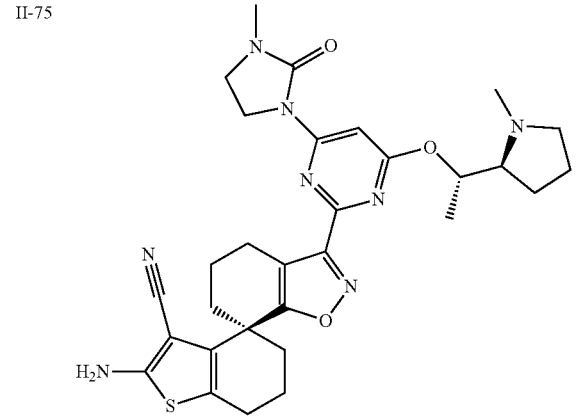 |
| II-76 | 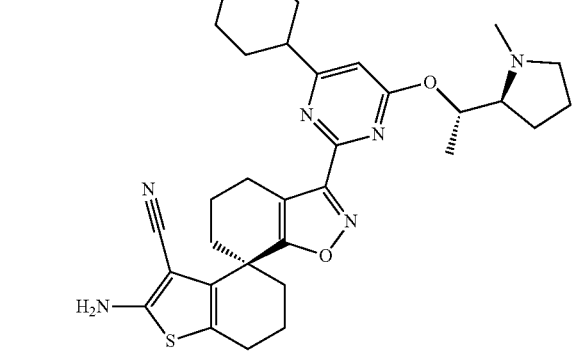 |
| II-77 | 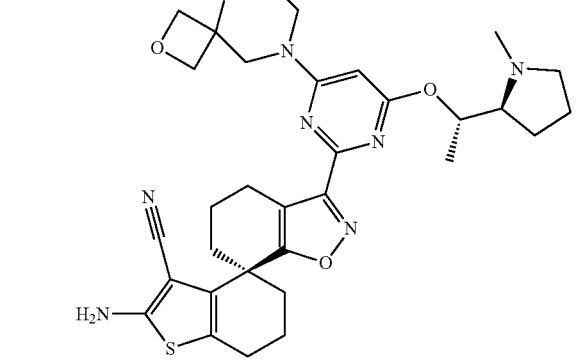 |
| II-78 | 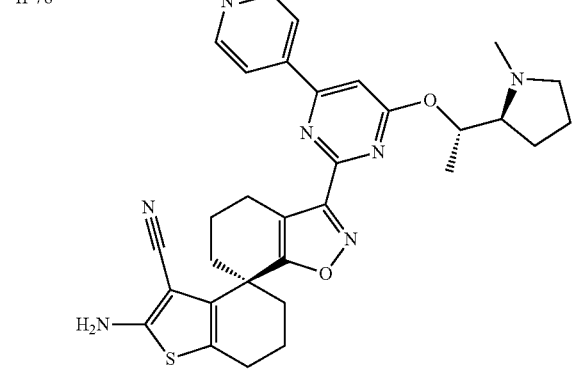 |

-continued
| # | structure |
|---|---|
| II-79 | 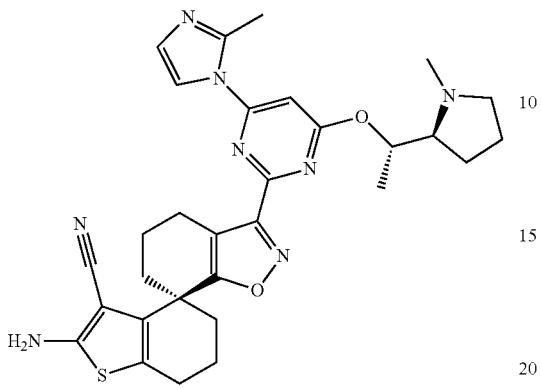 |
| II-80 | 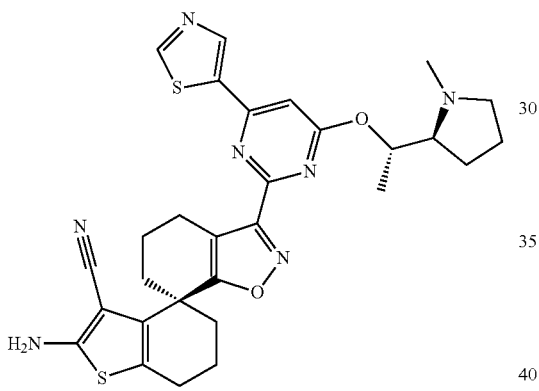 |
| II-81 | 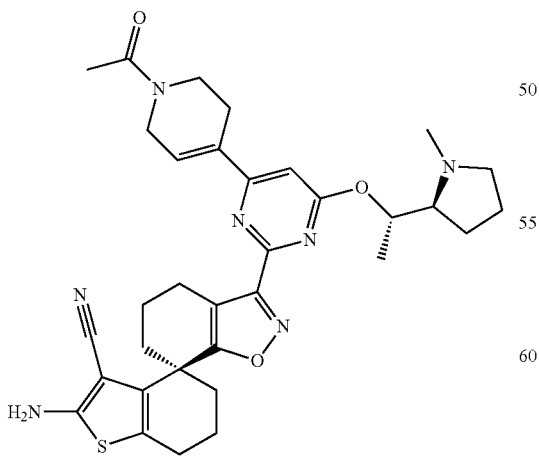 |
-continued
| # | structure |
|---|---|
| II-82 | 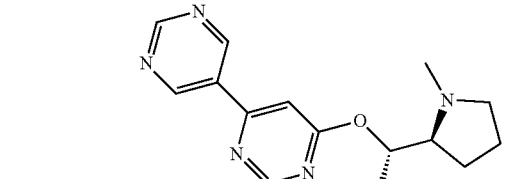 |
| II-83 | 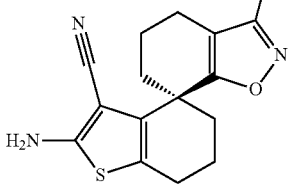 |
| II-84 | 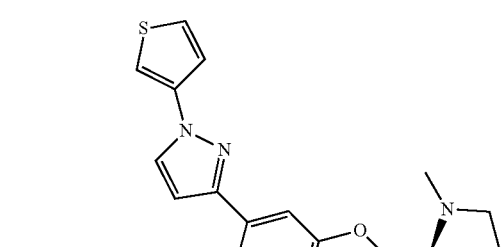 |
| II-85 | 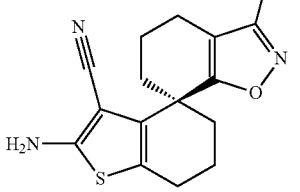 |

-continued

| # | structure |
|---|---|
| II-86 | 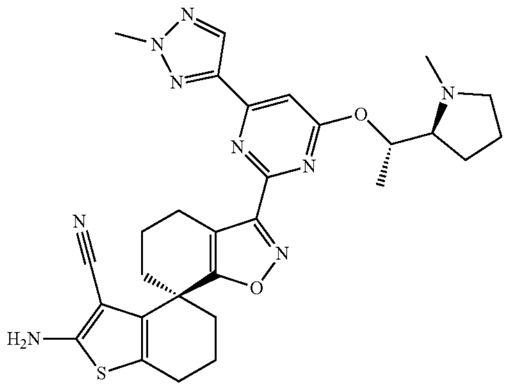 [SMILES: C[C@H](Oc1cc(-c2cnn(C)n2)nc(-c2noc3c2CCC[C@@]32CCCc3sc(N)c(C#N)c32)n1)[C@@H]1CCCN1C] |
| II-87 | 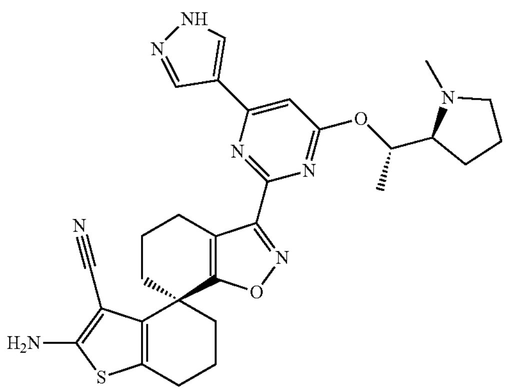 [SMILES: C[C@H](Oc1cc(-c2cn[nH]c2)nc(-c2noc3c2CCC[C@@]32CCCc3sc(N)c(C#N)c32)n1)[C@@H]1CCCN1C] |
| II-88 | 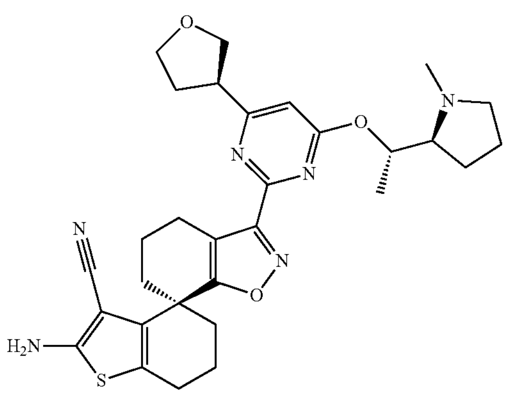 [SMILES: C[C@H](Oc1cc([C@H]2CCOC2)nc(-c2noc3c2CCC[C@@]32CCCc3sc(N)c(C#N)c32)n1)[C@@H]1CCCN1C] |
| II-89 | 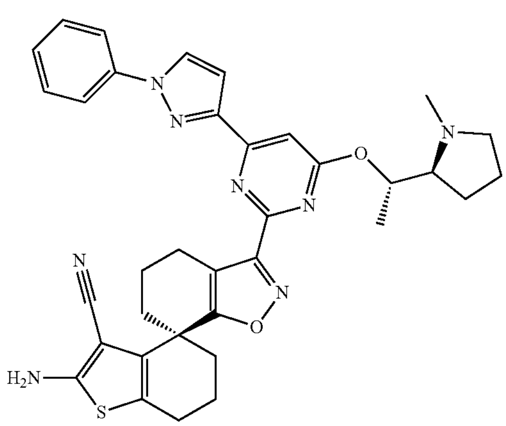 [SMILES: C[C@H](Oc1cc(-c2ccn(-c3ccccc3)n2)nc(-c2noc3c2CCC[C@@]32CCCc3sc(N)c(C#N)c32)n1)[C@@H]1CCCN1C] |

-continued

| # | structure |
|---|---|
| II-90 | 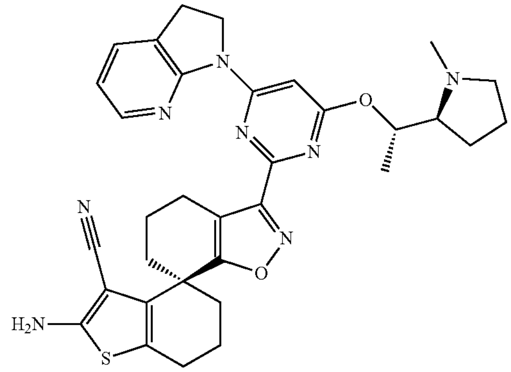 [SMILES: C[C@H](Oc1cc(N2CCc3cccnc32)nc(-c2noc3c2CCC[C@@]32CCCc3sc(N)c(C#N)c32)n1)[C@@H]1CCCN1C] |
| II-91 | 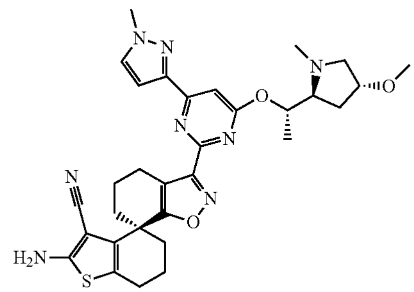 [SMILES: CO[C@@H]1C[C@@H]([C@H](C)Oc2cc(-c3ccn(C)n3)nc(-c3noc4c3CCC[C@@]43CCCc4sc(N)c(C#N)c43)n2)N(C)C1] |
| II-92 | 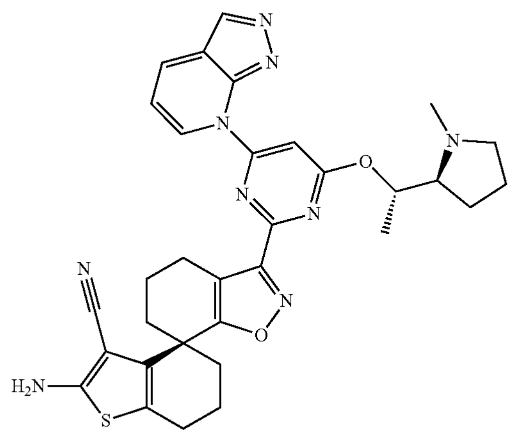 [SMILES: C[C@H](Oc1cc(-n2cccc3cnnc2-3)nc(-c2noc3c2CCC[C@@]32CCCc3sc(N)c(C#N)c32)n1)[C@@H]1CCCN1C] |
| II-93 | 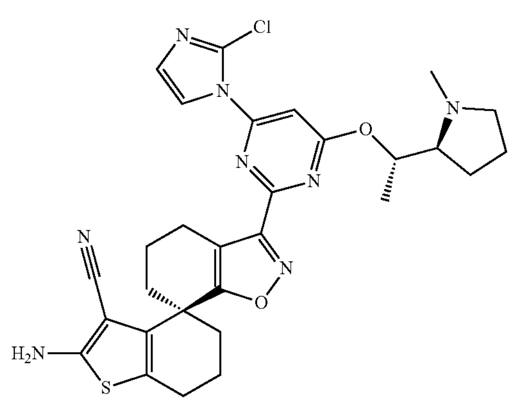 [SMILES: C[C@H](Oc1cc(-n2ccnc2Cl)nc(-c2noc3c2CCC[C@@]32CCCc3sc(N)c(C#N)c32)n1)[C@@H]1CCCN1C] |

US 12,060,367 B2
669
-continued
| # | structure |
|---|---|
| II-94 | 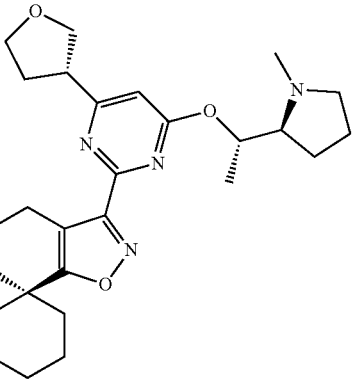 |
| II-95 | 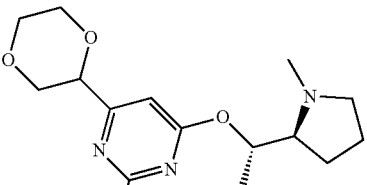 |
| II-96 | 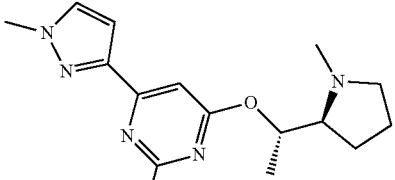 |
| II-97 | 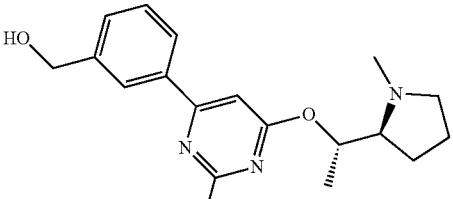 |
670
-continued
| # | structure |
|---|---|
| II-98 | 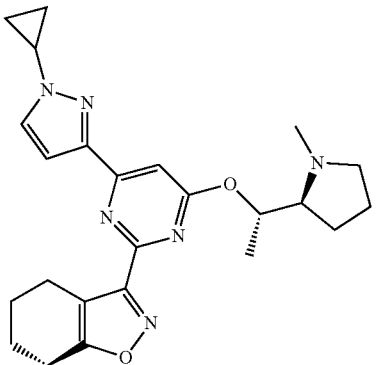 |
| II-99 | 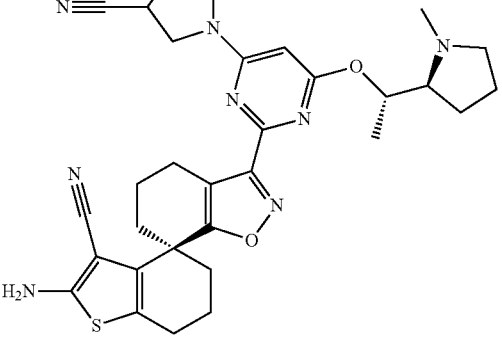 |
| II-100 | 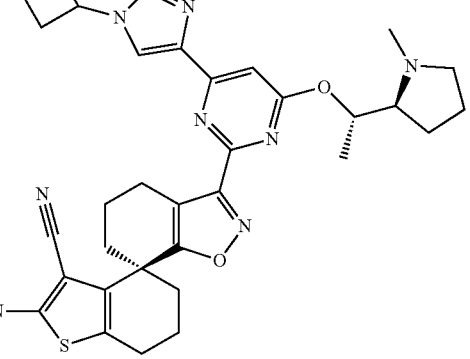 |

-continued
| # | structure |
|---|---|
| II-101 | 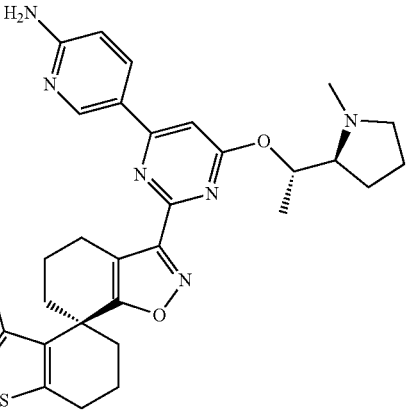 |
| II-102 | 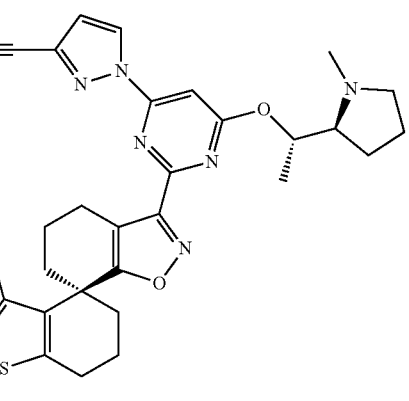 |
| II-103 | 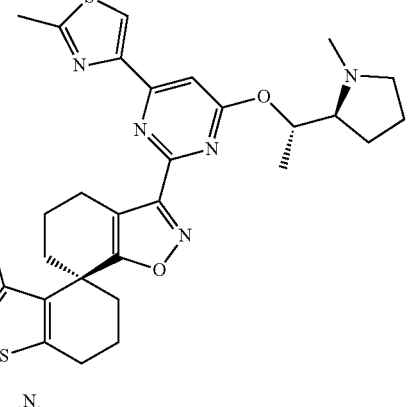 |
| II-104 | 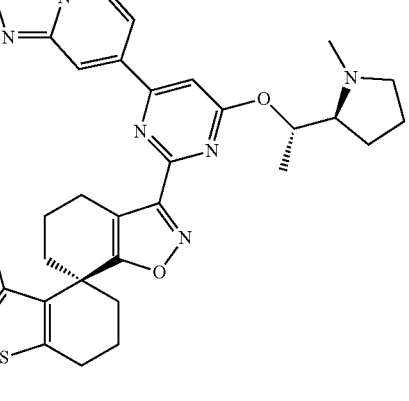 |
-continued
| # | structure |
|---|---|
| II-105 | 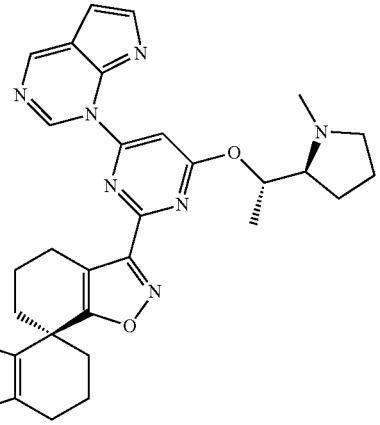 |
| II-106 | 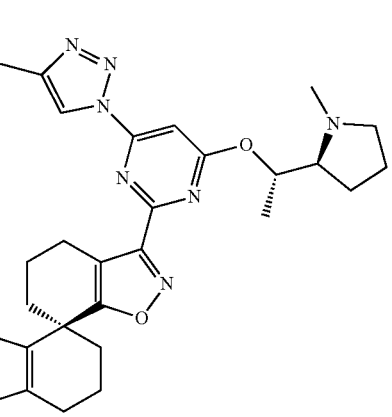 |
| II-107 | 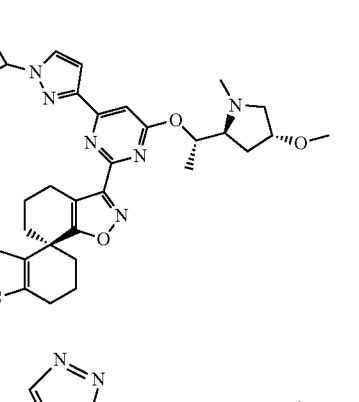 |
| II-108 | 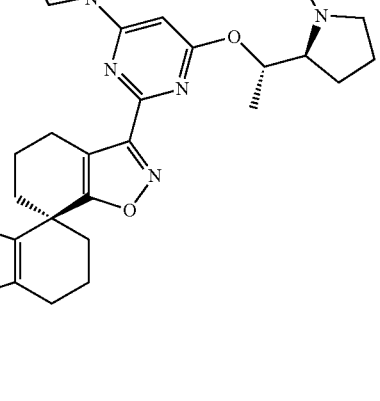 |

673
-continued
| # | structure |
|---|---|
| II-109 | 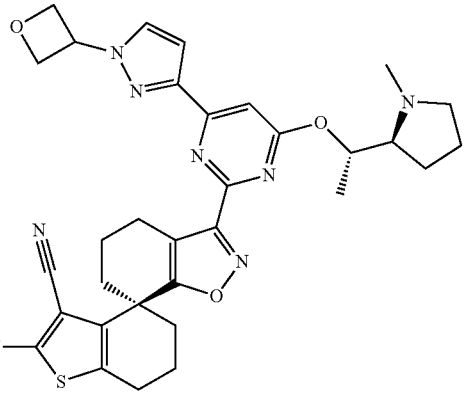 |
| II-110 | 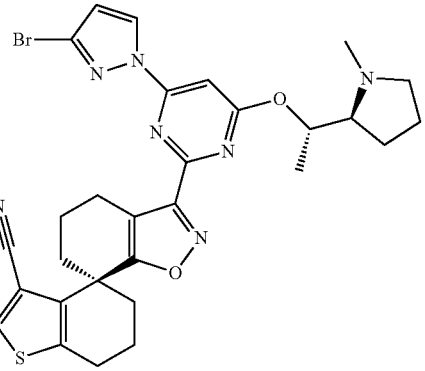 |
| II-111 | 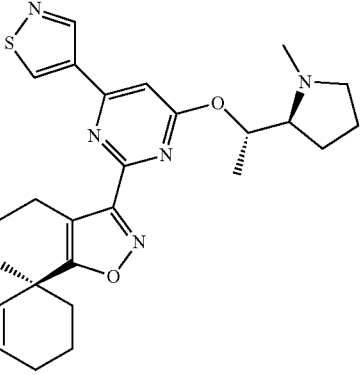 |
| II-112 | 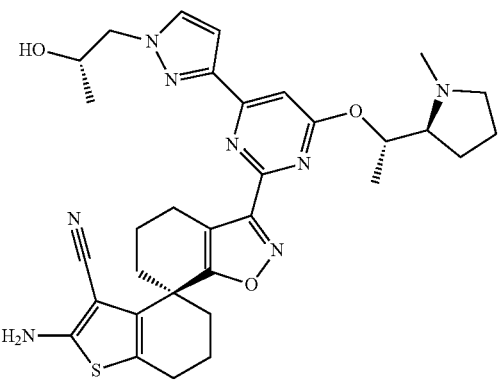 [SMILES: C[C@H](O)Cn1ccc(-c2cc(O[C@@H](C)[C@@H]3CCCN3C)nc(-c3noc4c3CCC[C@@]43CCCc4sc(N)c(C#N)c43)n2)n1] |
674
-continued
| # | structure |
|---|---|
| II-113 | 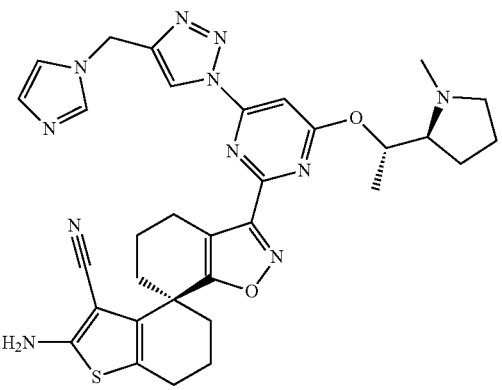 [SMILES: C[C@H](Oc1cc(-n2cc(Cn3ccnc3)nn2)nc(-c2noc3c2CCC[C@@]32CCCc3sc(N)c(C#N)c32)n1)[C@@H]1CCCN1C] |
| II-114 | 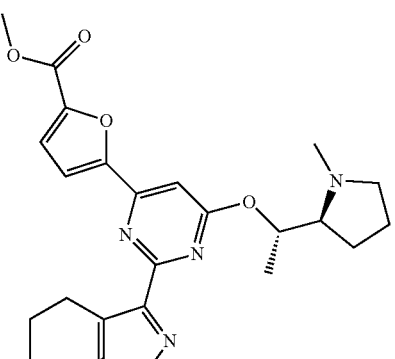 |
| II-115 | 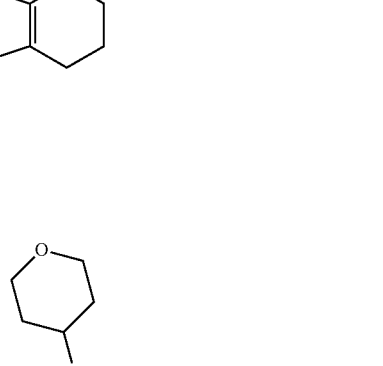 |

| # | structure |
|---|---|
| II-116 | 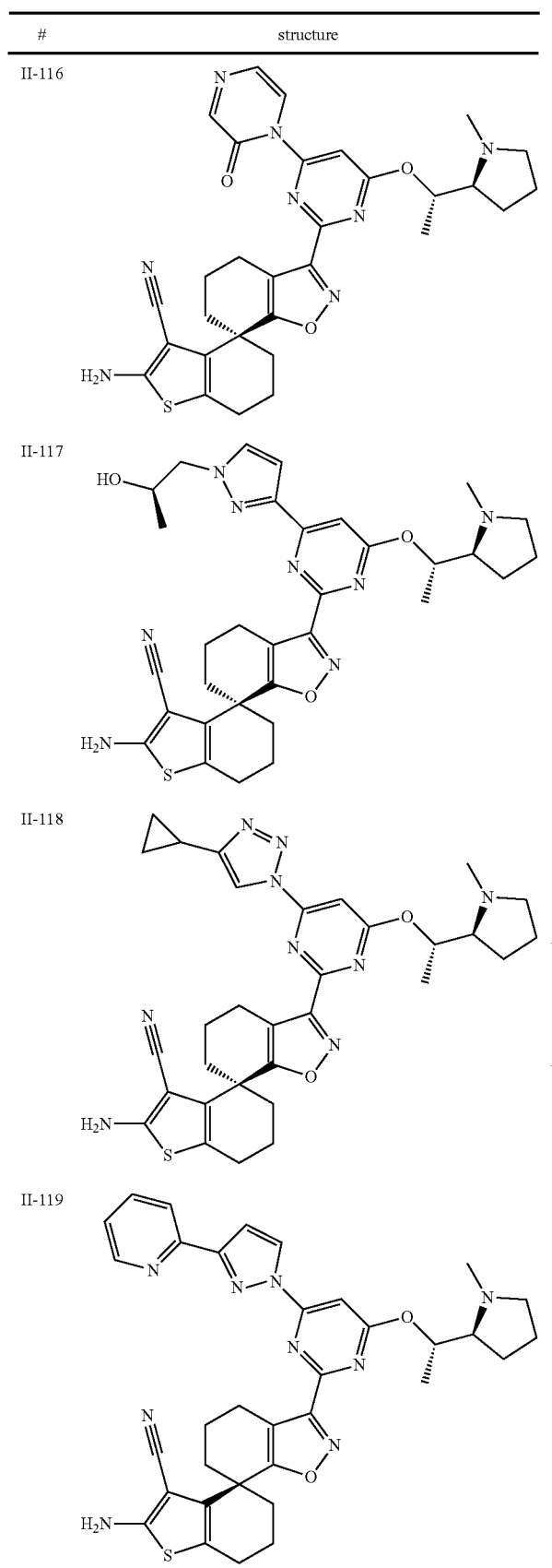 |
| II-117 | |
| II-118 | |
| II-119 | |
| # | structure |
|---|---|
| II-120 | 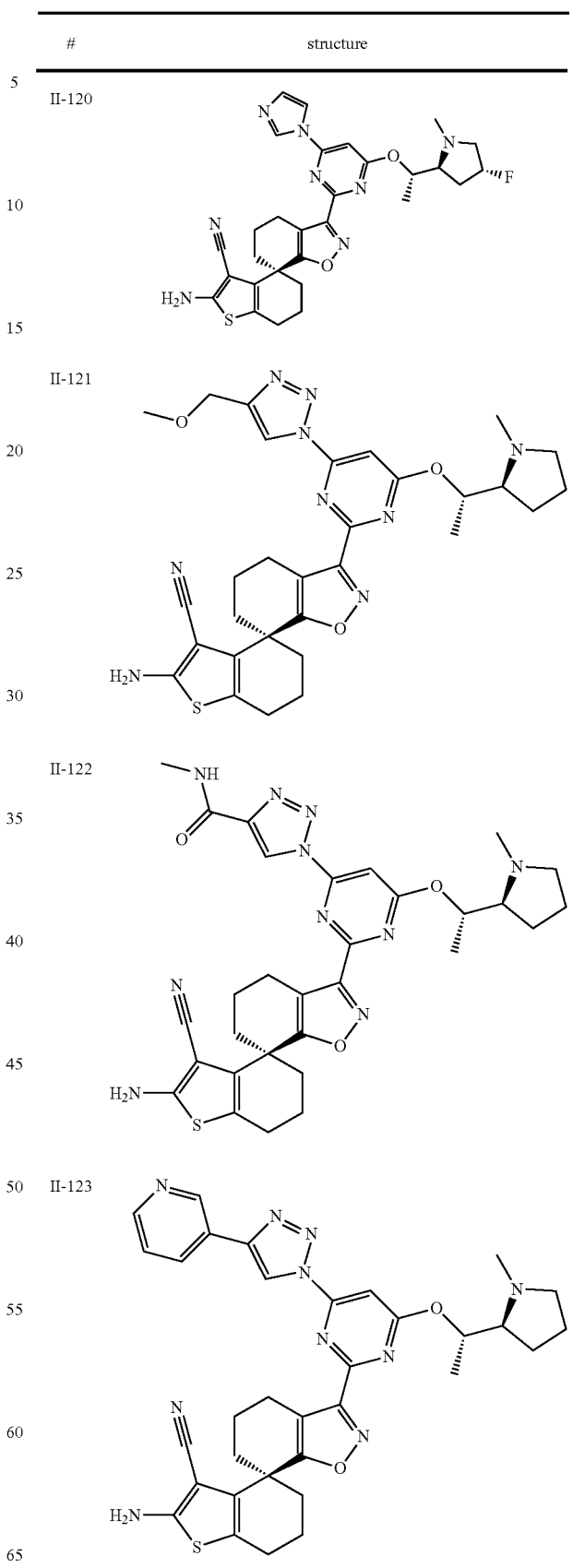 |
| II-121 | |
| II-122 | |
| II-123 | |

| # | structure |
|---|---|
| II-124 | 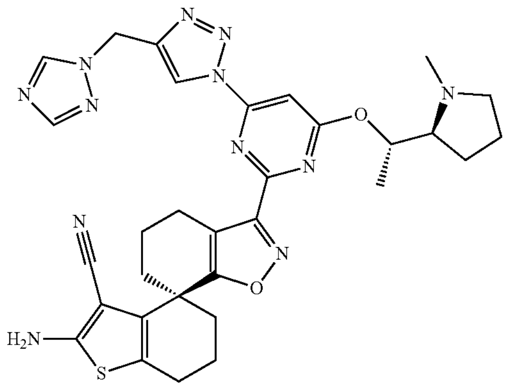 [SMILES: C[C@H](Oc1cc(-n2cc(Cn3cncn3)nn2)nc(-c2noc3c2CCC[C@@]32CCCc3sc(N)c(C#N)c32)n1)[C@@H]1CCCN1C] |
| II-125 | 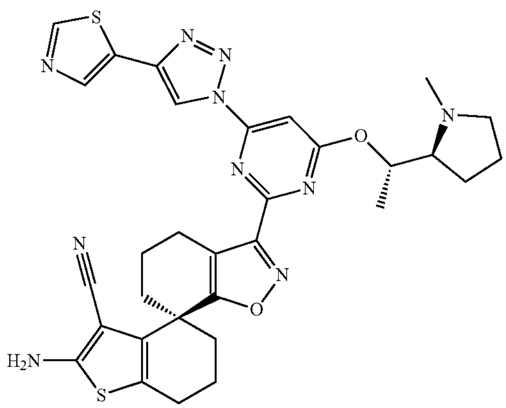 [SMILES: C[C@H](Oc1cc(-n2cc(-c3cncs3)nn2)nc(-c2noc3c2CCC[C@@]32CCCc3sc(N)c(C#N)c32)n1)[C@@H]1CCCN1C] |
| II-126 | 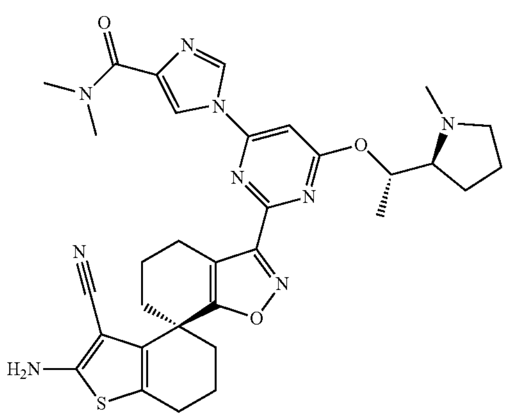 [SMILES: C[C@H](Oc1cc(-n2cnc(C(=O)N(C)C)c2)nc(-c2noc3c2CCC[C@@]32CCCc3sc(N)c(C#N)c32)n1)[C@@H]1CCCN1C] |
| II-127 | 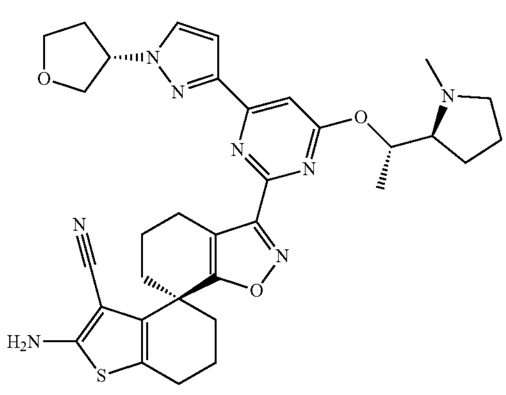 [SMILES: C[C@H](Oc1cc(-c2ccn([C@H]3CCOC3)n2)nc(-c2noc3c2CCC[C@@]32CCCc3sc(N)c(C#N)c32)n1)[C@@H]1CCCN1C] |
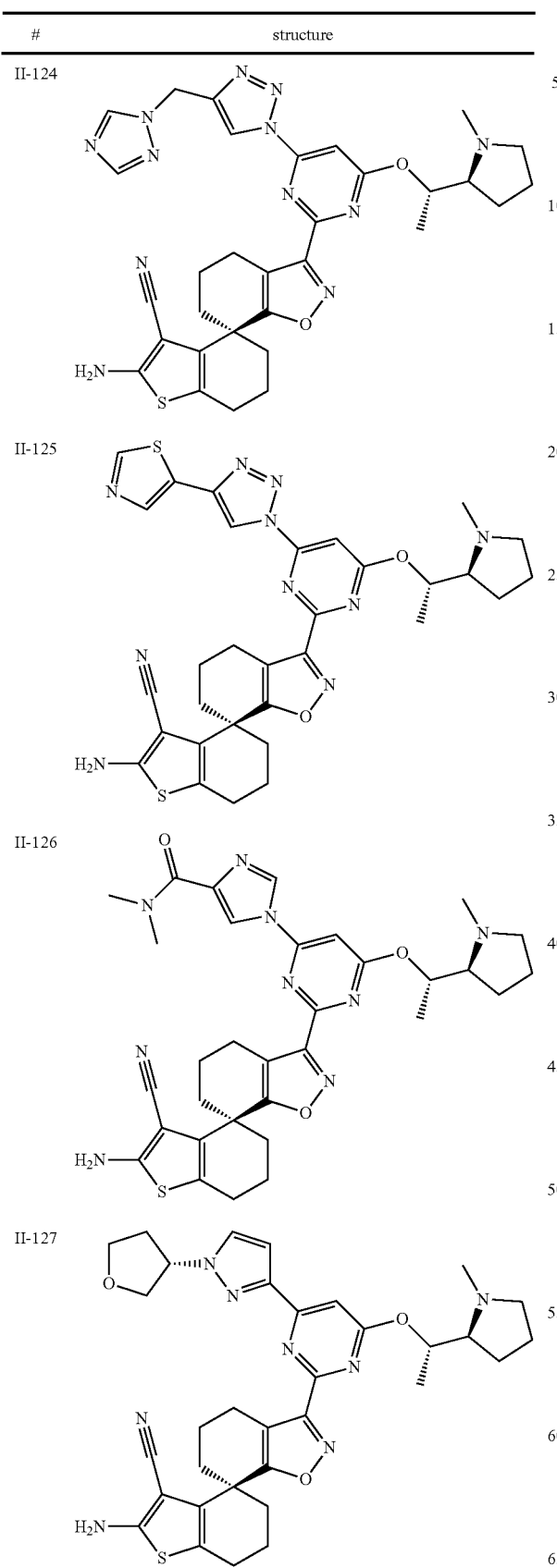
| # | structure |
|---|---|
| II-128 | |
| II-129 | |
| II-130 | |
| II-131 | |
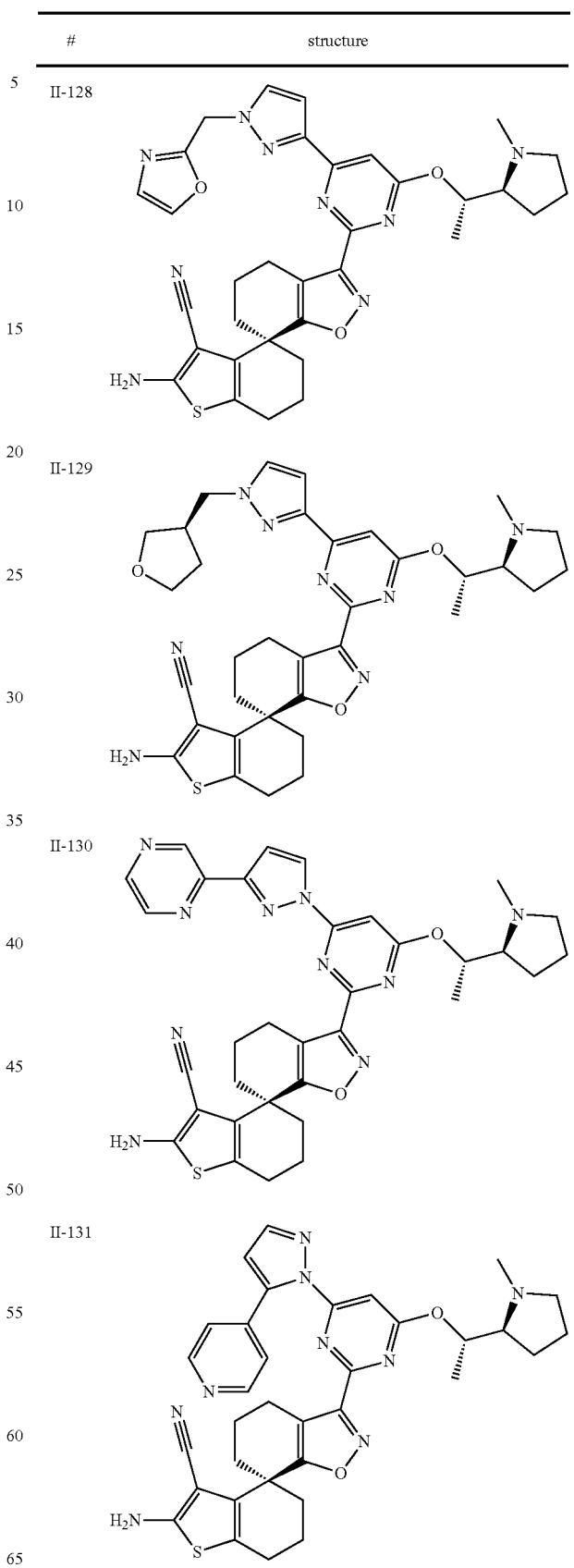

679
-continued
| # | structure |
|---|---|
| II-132 | 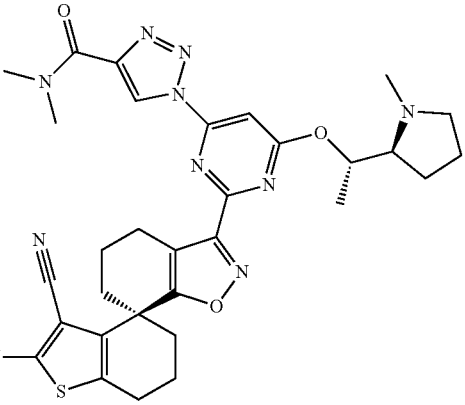 |
| II-133 | 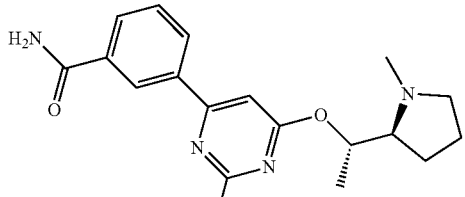 |
| II-134 | 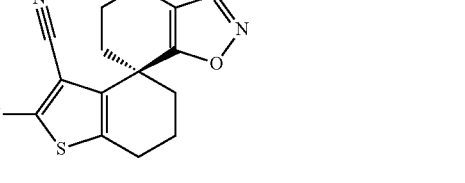 |
| II-135 | 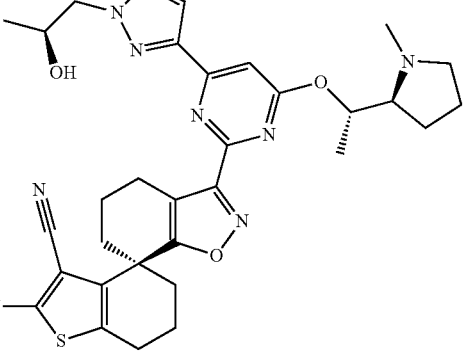 |
680
-continued
| # | structure |
|---|---|
| II-136 | 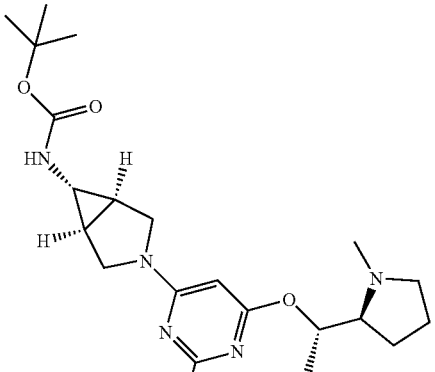 |
| II-137 | 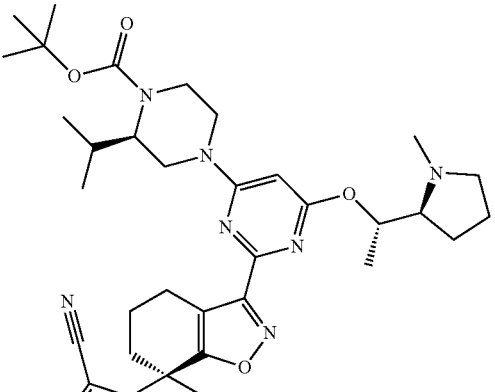 |
| II-138 | 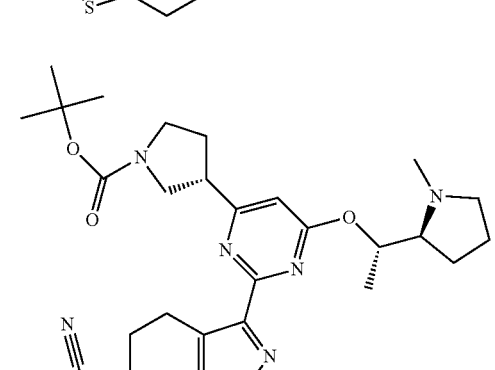 |

| # | structure |
|---|---|
| II-139 | 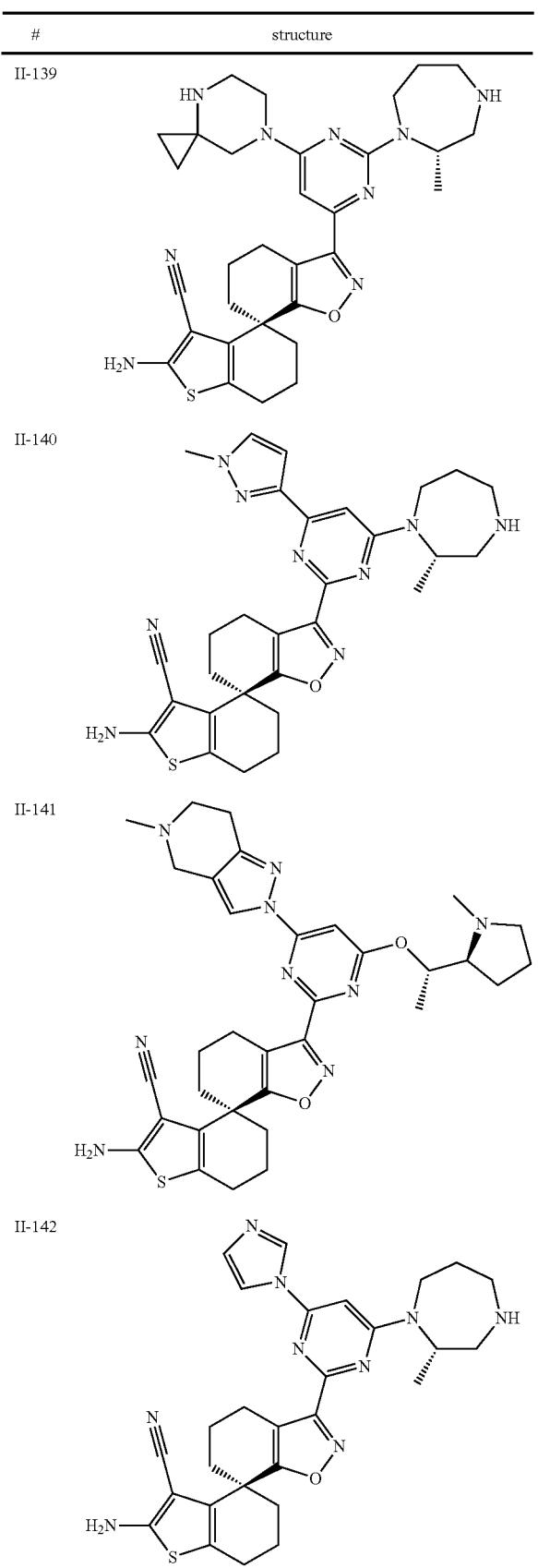 |
| II-140 | |
| II-141 | |
| II-142 | |
| # | structure |
|---|---|
| II-143 | 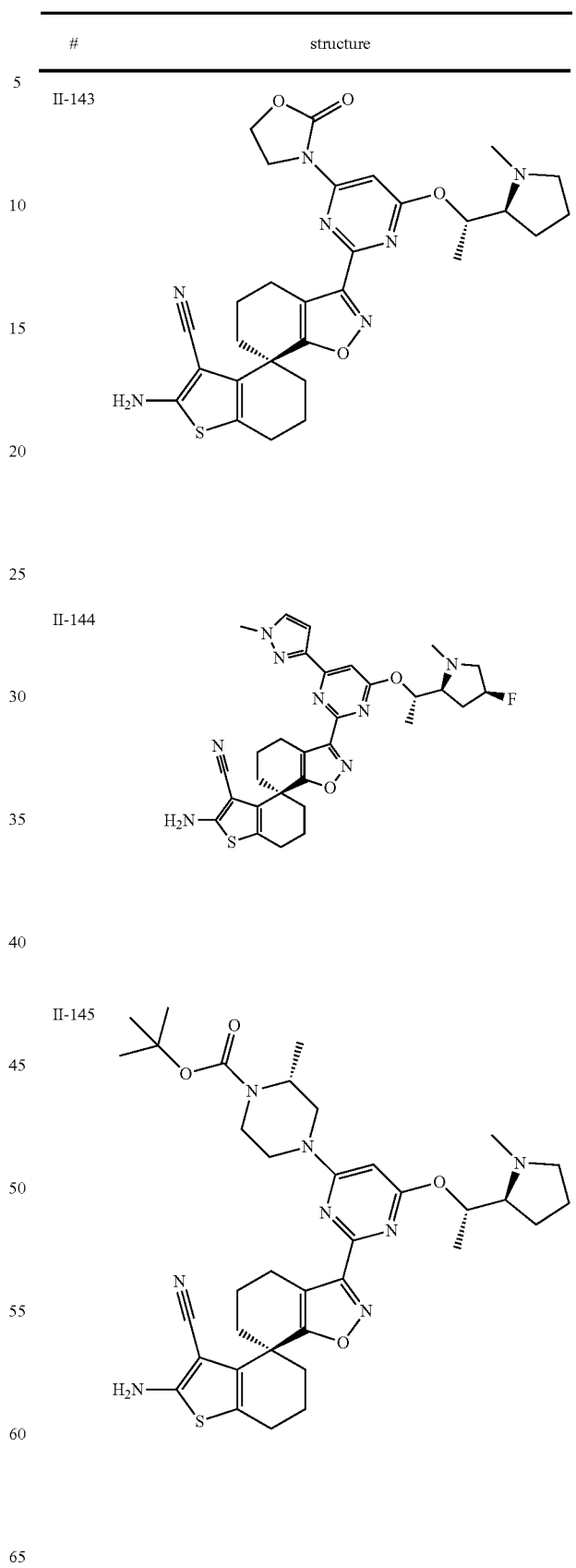 |
| II-144 | |
| II-145 | |

-continued

| # | structure |
|---|---|
| II-146 | 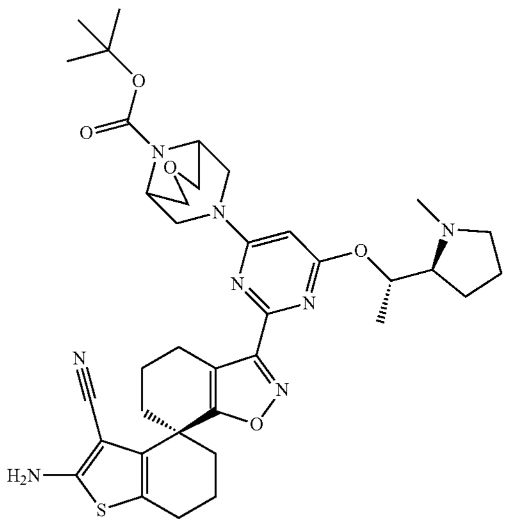 [SMILES: C[C@H](Oc1cc(N2CC3COCC(C2)N3C(=O)OC(C)(C)C)nc(-c2noc3c2CCC[C@@]32CCCc3sc(N)c(C#N)c32)n1)[C@@H]1CCCN1C] |
| II-147 | 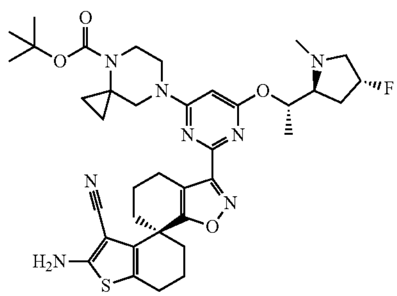 [SMILES: C[C@H](Oc1cc(N2CCN(C(=O)OC(C)(C)C)C3(CC3)C2)nc(-c2noc3c2CCC[C@@]32CCCc3sc(N)c(C#N)c32)n1)[C@@H]1C[C@@H](F)CN1C] |
| II-148 | 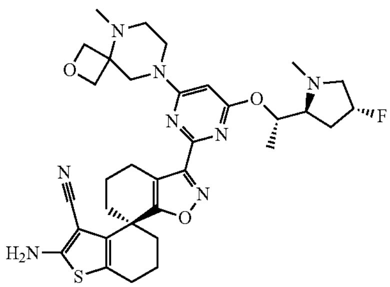 [SMILES: C[C@H](Oc1cc(N2CCN(C)C3(COC3)C2)nc(-c2noc3c2CCC[C@@]32CCCc3sc(N)c(C#N)c32)n1)[C@@H]1C[C@@H](F)CN1C] |
| II-149 | 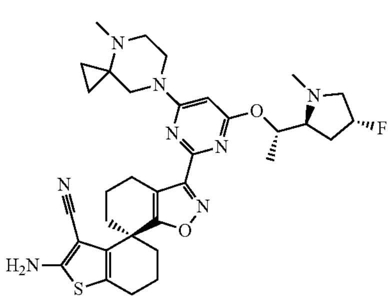 [SMILES: C[C@H](Oc1cc(N2CCN(C)C3(CC3)C2)nc(-c2noc3c2CCC[C@@]32CCCc3sc(N)c(C#N)c32)n1)[C@@H]1C[C@@H](F)CN1C] |

-continued

| # | structure |
|---|---|
| II-150 | 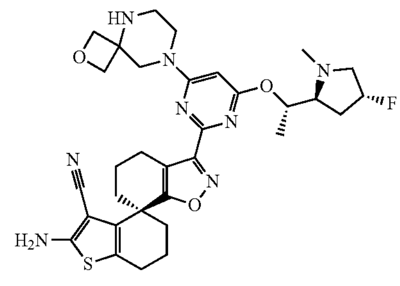 [SMILES: C[C@H](Oc1cc(N2CCNC3(COC3)C2)nc(-c2noc3c2CCC[C@@]32CCCc3sc(N)c(C#N)c32)n1)[C@@H]1C[C@@H](F)CN1C] |
| II-151 | 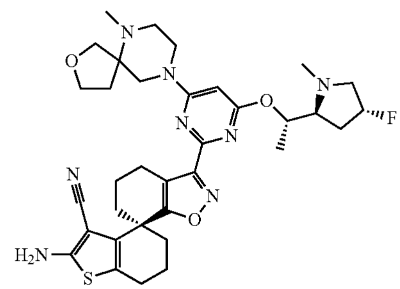 [SMILES: C[C@H](Oc1cc(N2CCN(C)C3(CCOC3)C2)nc(-c2noc3c2CCC[C@@]32CCCc3sc(N)c(C#N)c32)n1)[C@@H]1C[C@@H](F)CN1C] |
| II-152 | 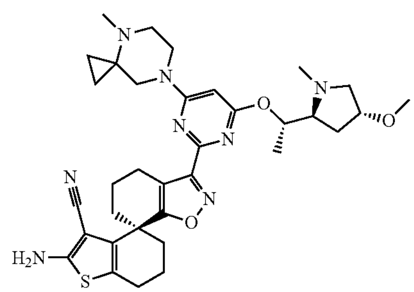 [SMILES: CO[C@@H]1C[C@@H]([C@H](C)Oc2cc(N3CCN(C)C4(CC4)C3)nc(-c3noc4c3CCC[C@@]43CCCc4sc(N)c(C#N)c43)n2)N(C)C1] |
| II-153 | 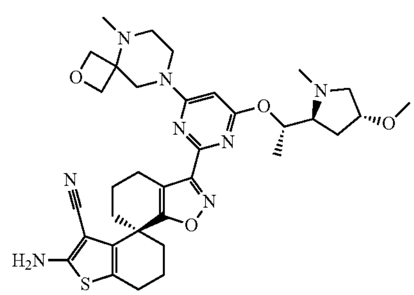 [SMILES: CO[C@@H]1C[C@@H]([C@H](C)Oc2cc(N3CCN(C)C4(COC4)C3)nc(-c3noc4c3CCC[C@@]43CCCc4sc(N)c(C#N)c43)n2)N(C)C1] |
| II-154 | 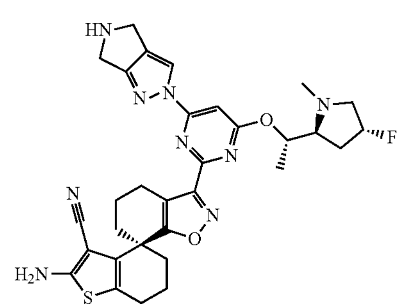 [SMILES: C[C@H](Oc1cc(-n2cc3c(n2)CNC3)nc(-c2noc3c2CCC[C@@]32CCCc3sc(N)c(C#N)c32)n1)[C@@H]1C[C@@H](F)CN1C] |

-continued
| # | structure |
|---|---|
| II-155 | 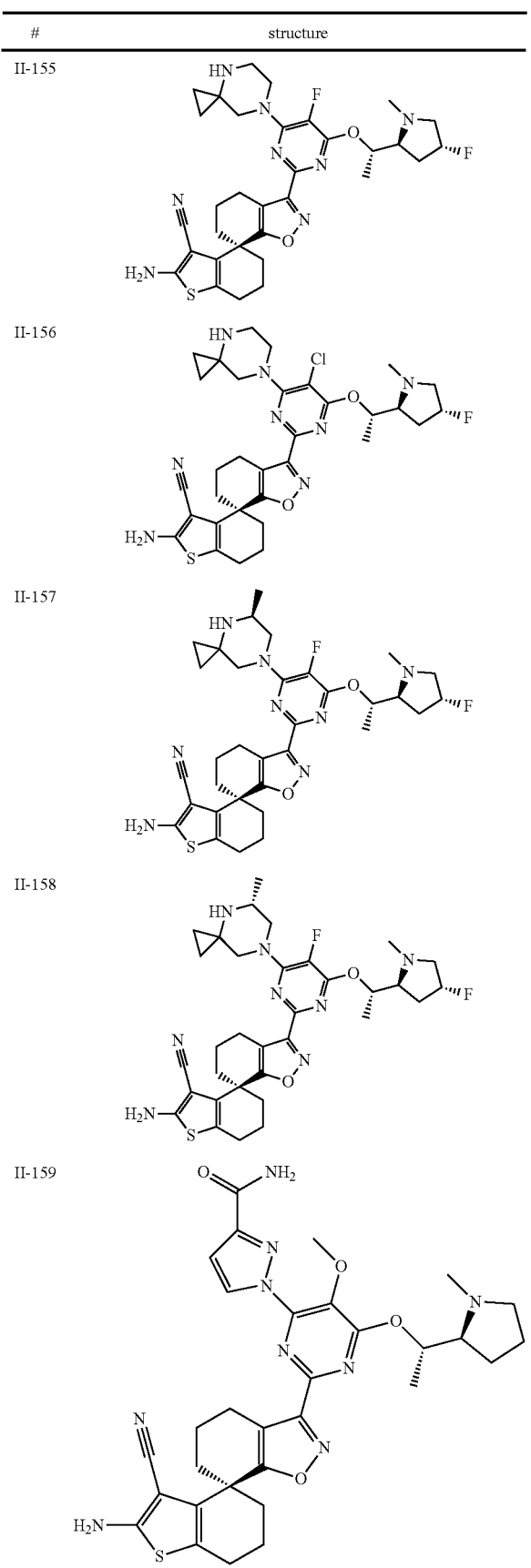 |
| II-156 | 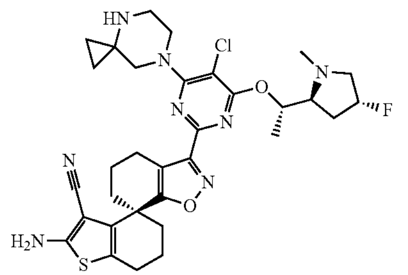 [SMILES: C[C@H](Oc1nc(-c2noc3c2CCC[C@@]32CCCc3sc(N)c(C#N)c32)nc(N2CCNC3(CC3)C2)c1Cl)[C@@H]1C[C@@H](F)CN1C] |
| II-157 | 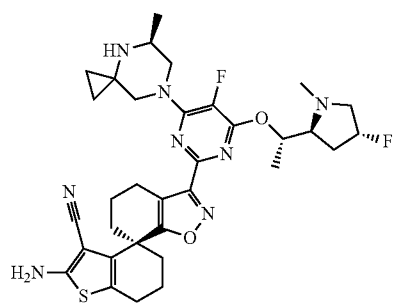 [SMILES: C[C@H](Oc1nc(-c2noc3c2CCC[C@@]32CCCc3sc(N)c(C#N)c32)nc(N2C[C@H](C)NC3(CC3)C2)c1F)[C@@H]1C[C@@H](F)CN1C] |
| II-158 | 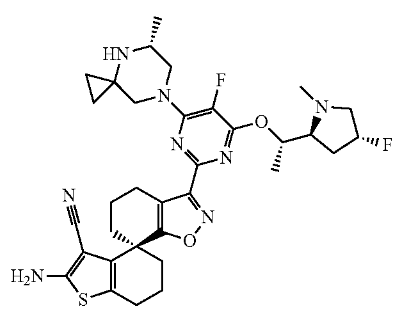 [SMILES: C[C@@H]1CN(c2nc(-c3noc4c3CCC[C@@]43CCCc4sc(N)c(C#N)c43)nc(O[C@@H](C)[C@@H]3C[C@@H](F)CN3C)c2F)CC2(CC2)N1] |
| II-159 | 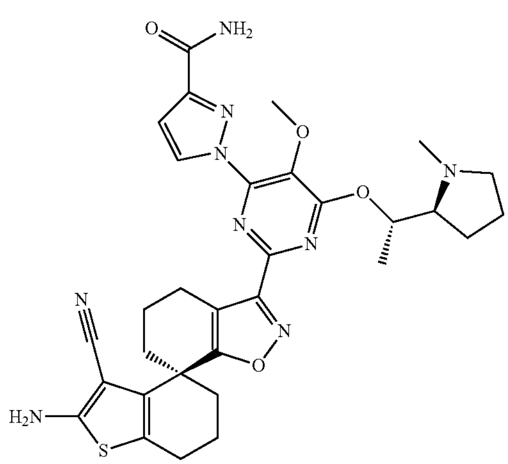 [SMILES: COc1c(O[C@@H](C)[C@@H]2CCCN2C)nc(-c2noc3c2CCC[C@@]32CCCc3sc(N)c(C#N)c32)nc1-n1ccc(C(N)=O)n1] |
-continued
| # | structure |
|---|---|
| II-160 | 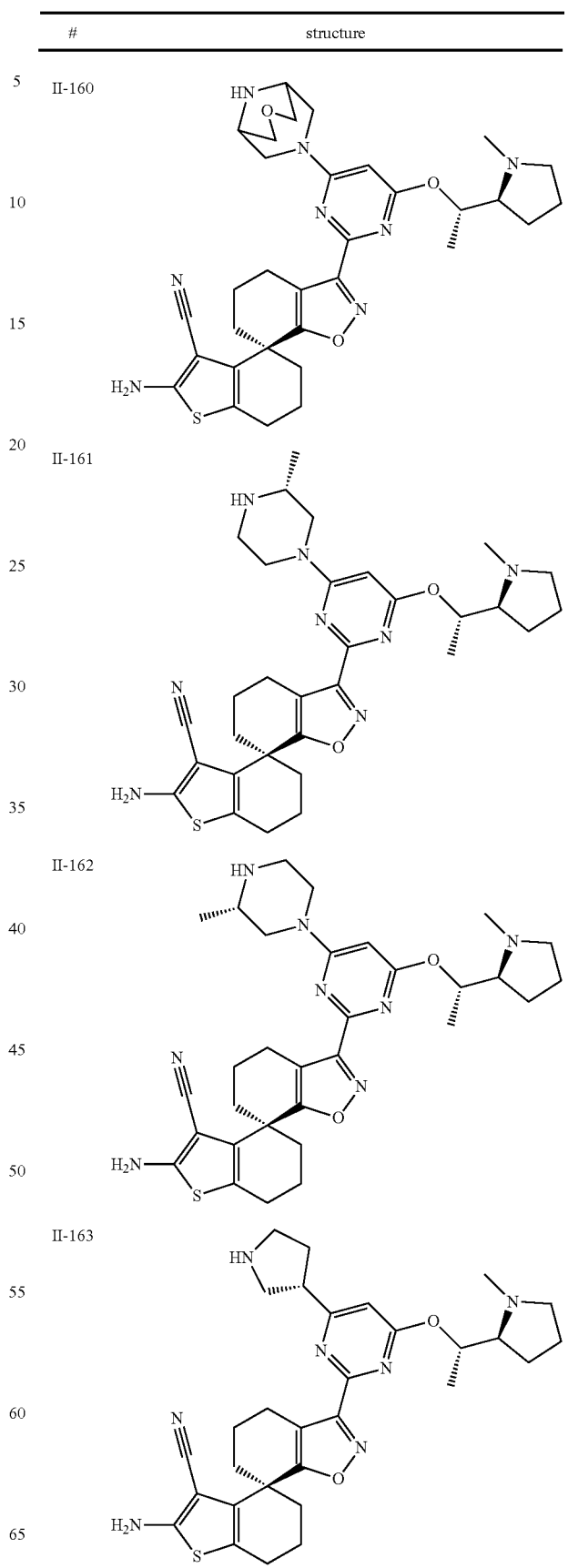 |
| II-161 | 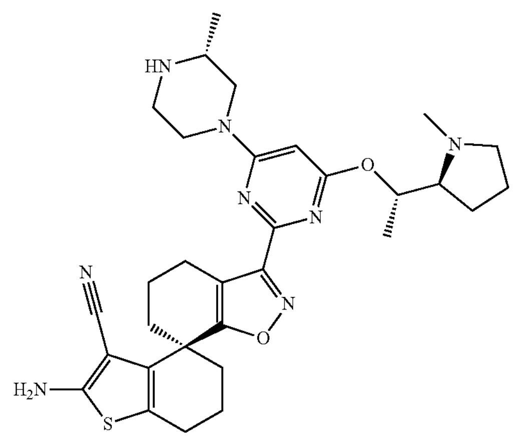 [SMILES: C[C@@H]1CN(c2cc(O[C@@H](C)[C@@H]3CCCN3C)nc(-c3noc4c3CCC[C@@]43CCCc4sc(N)c(C#N)c43)n2)CCN1] |
| II-162 | 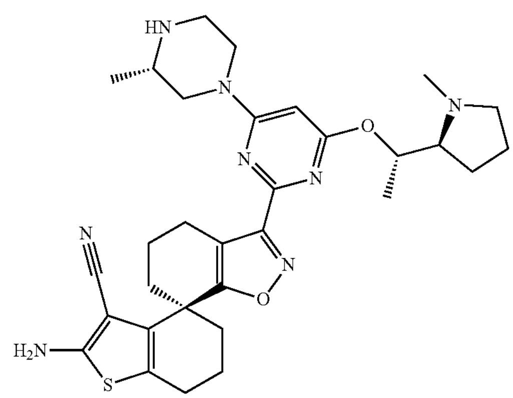 [SMILES: C[C@H](Oc1cc(N2CCN[C@@H](C)C2)nc(-c2noc3c2CCC[C@@]32CCCc3sc(N)c(C#N)c32)n1)[C@@H]1CCCN1C] |
| II-163 | 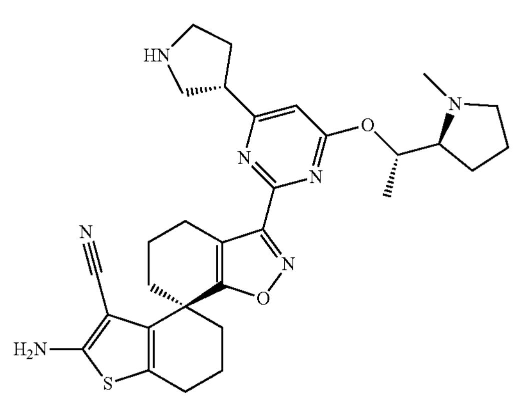 [SMILES: C[C@H](Oc1cc([C@H]2CCNC2)nc(-c2noc3c2CCC[C@@]32CCCc3sc(N)c(C#N)c32)n1)[C@@H]1CCCN1C] |

-continued
| # | structure |
|---|---|
| II-164 | 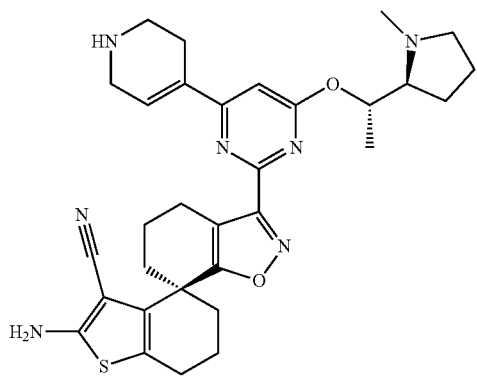 [SMILES: C[C@H](Oc1cc(C2=CCNCC2)nc(-c2noc3c2CCC[C@@]32CCCc3sc(N)c(C#N)c32)n1)[C@@H]1CCCN1C] |
| II-165 | 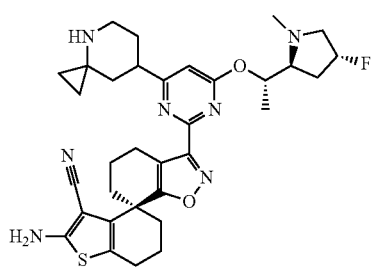 [SMILES: C[C@H](Oc1cc(C2CCNC3(CC3)C2)nc(-c2noc3c2CCC[C@@]32CCCc3sc(N)c(C#N)c32)n1)[C@@H]1C[C@@H](F)CN1C] |
| II-166 | 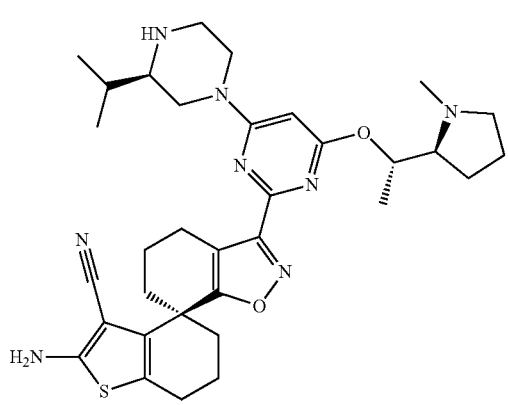 [SMILES: CC(C)[C@@H]1CN(c2cc(O[C@@H](C)[C@@H]3CCCN3C)nc(-c3noc4c3CCC[C@@]43CCCc4sc(N)c(C#N)c43)n2)CCN1] |
| II-167 | 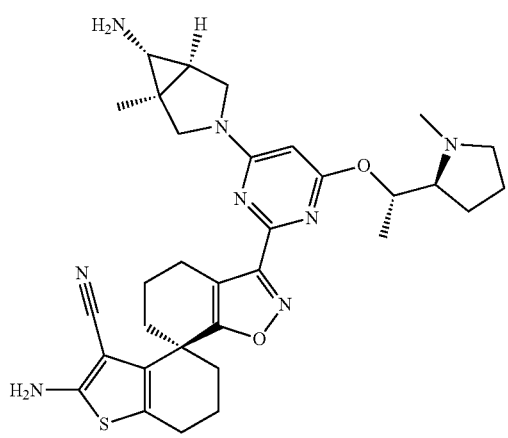 [SMILES: C[C@H](Oc1cc(N2C[C@@H]3[C@@H](N)[C@]3(C)C2)nc(-c2noc3c2CCC[C@@]32CCCc3sc(N)c(C#N)c32)n1)[C@@H]1CCCN1C] |
-continued
| # | structure |
|---|---|
| II-168 | 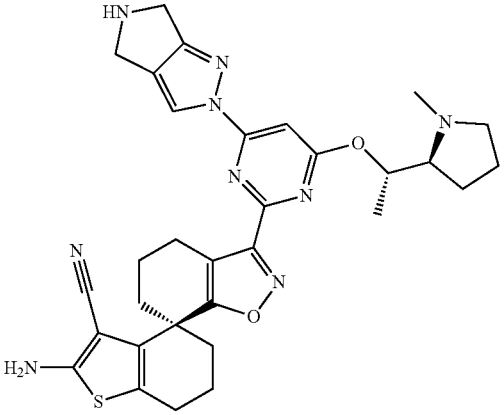 [SMILES: C[C@H](Oc1cc(-n2cc3c(n2)CNC3)nc(-c2noc3c2CCC[C@@]32CCCc3sc(N)c(C#N)c32)n1)[C@@H]1CCCN1C] |
| II-169 | 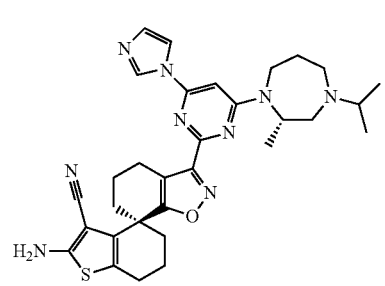 [SMILES: CC(C)N1CCCN(c2cc(-n3ccnc3)nc(-c3noc4c3CCC[C@@]43CCCc4sc(N)c(C#N)c43)n2)[C@@H](C)C1] |
| II-170 | 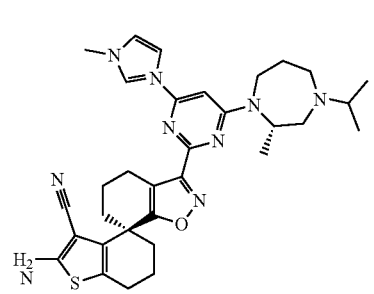 |
| II-171 | 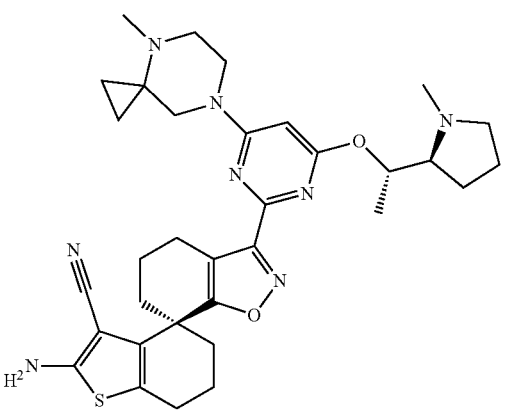 [SMILES: C[C@H](Oc1cc(N2CCN(C)C3(CC3)C2)nc(-c2noc3c2CCC[C@@]32CCCc3sc(N)c(C#N)c32)n1)[C@@H]1CCCN1C] |

| # | structure |
|---|---|
| II-172 | 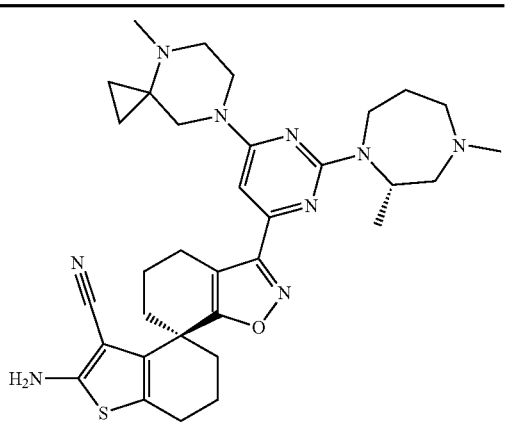 |
| II-173 | 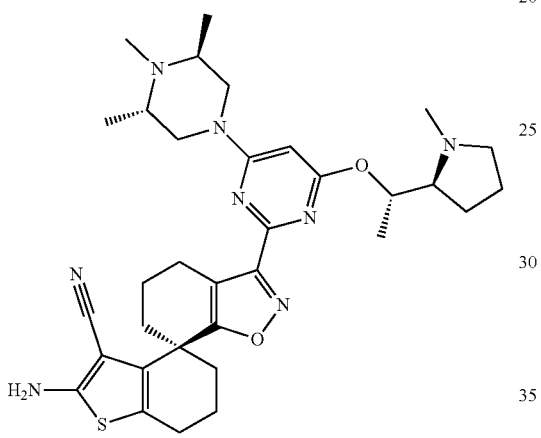 |
| II-174 | 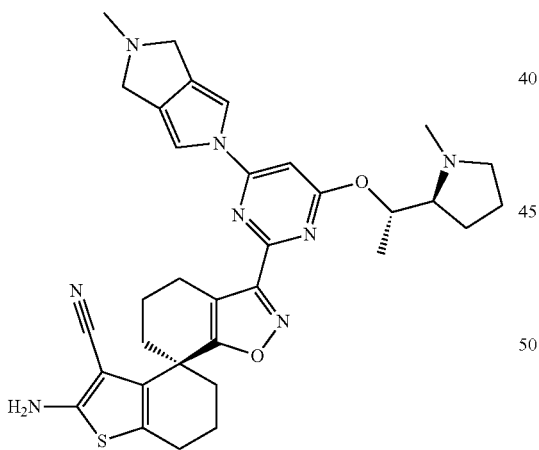 |
| II-175 | 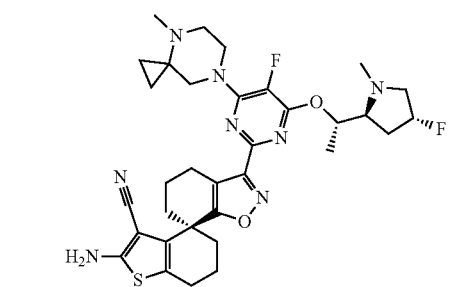 |
| # | structure |
|---|---|
| II-176 | 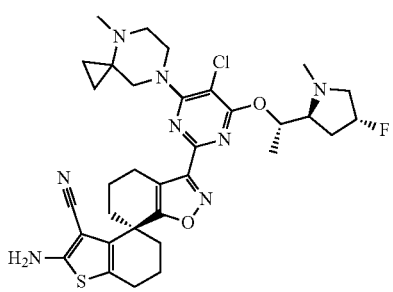 [SMILES: C[C@H](Oc1nc(-c2noc3c2CCC[C@@]32CCCc3sc(N)c(C#N)c32)nc(N2CCN(C)C3(CC3)C2)c1Cl)[C@@H]1C[C@@H](F)CN1C] |
| II-177 | 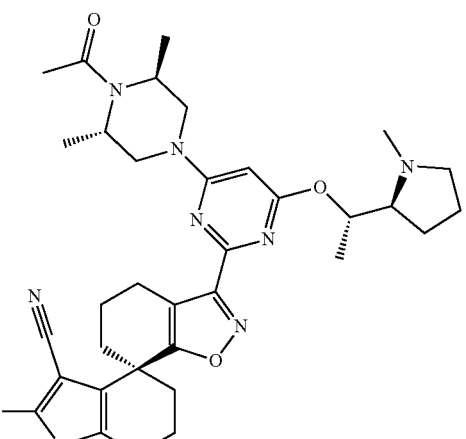 |
| II-178 | 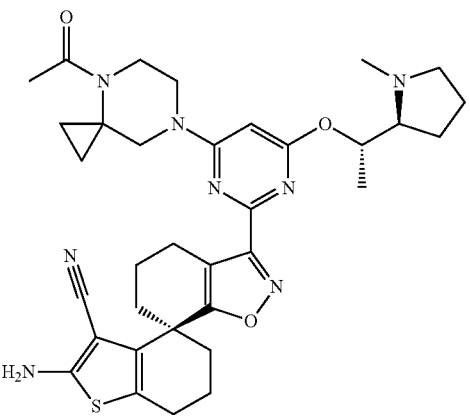 [SMILES: CC(=O)N1CCN(c2cc(O[C@@H](C)[C@@H]3CCCN3C)nc(-c3noc4c3CCC[C@@]43CCCc4sc(N)c(C#N)c43)n2)CC12CC2] |
| II-179 | 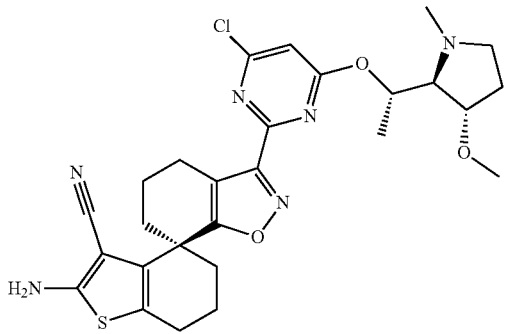 [SMILES: CO[C@H]1CCN(C)[C@@H]1[C@H](C)Oc1cc(Cl)nc(-c2noc3c2CCC[C@@]32CCCc3sc(N)c(C#N)c32)n1] |

691
-continued
| # | structure |
|---|---|
| II-180 | 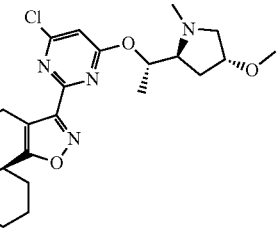 |
| II-181 | 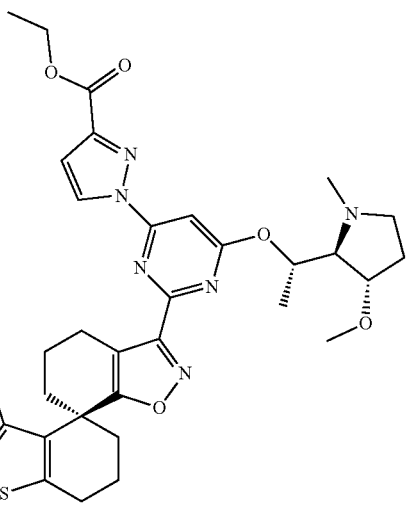 |
| II-182 | 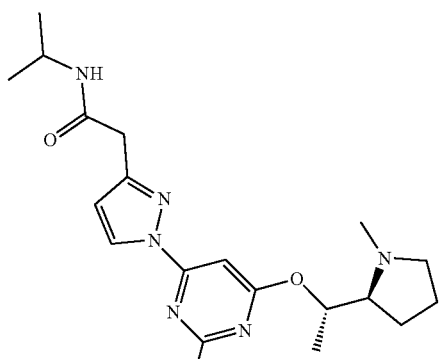 |
692
-continued
| # | structure |
|---|---|
| II-183 | 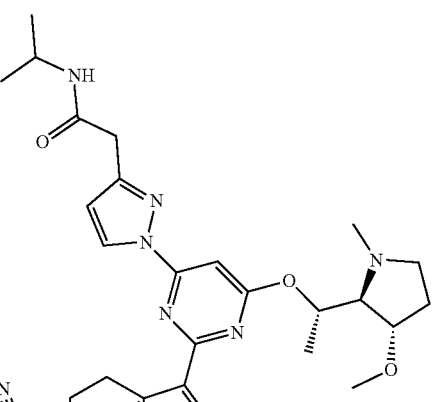 |
| II-184 | 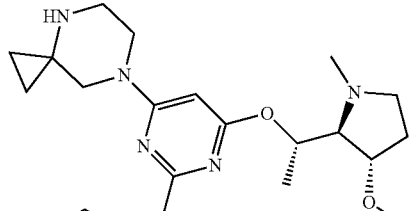 |
| II-185 | 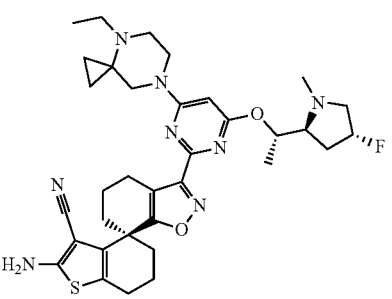 [SMILES: CCN1CCN(c2cc(O[C@@H](C)[C@@H]3C[C@@H](F)CN3C)nc(-c3noc4c3CCC[C@@]43CCCc4sc(N)c(C#N)c43)n2)CC12CC2] |

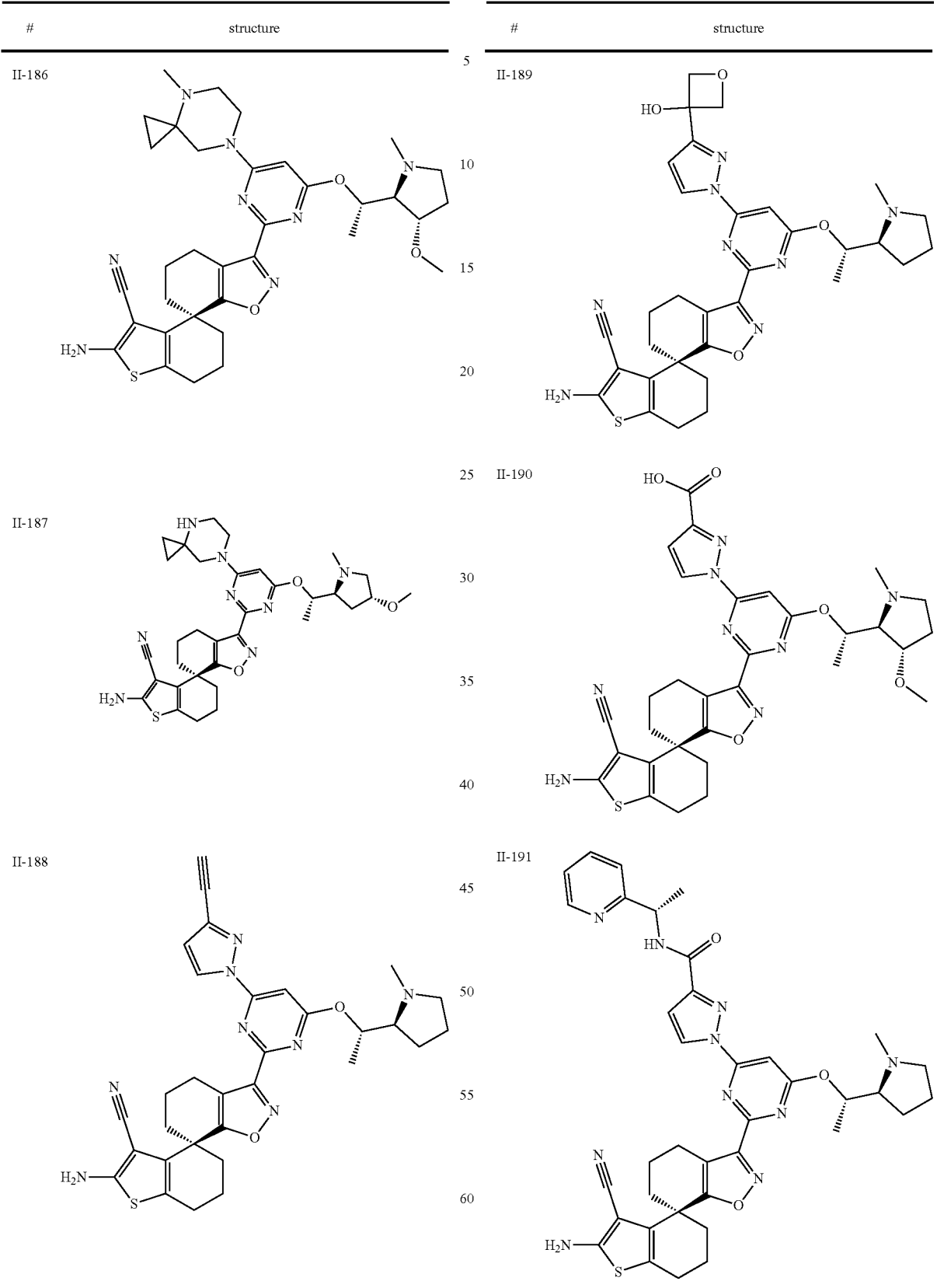

695
-continued
| # | structure |
|---|---|
| II-192 | 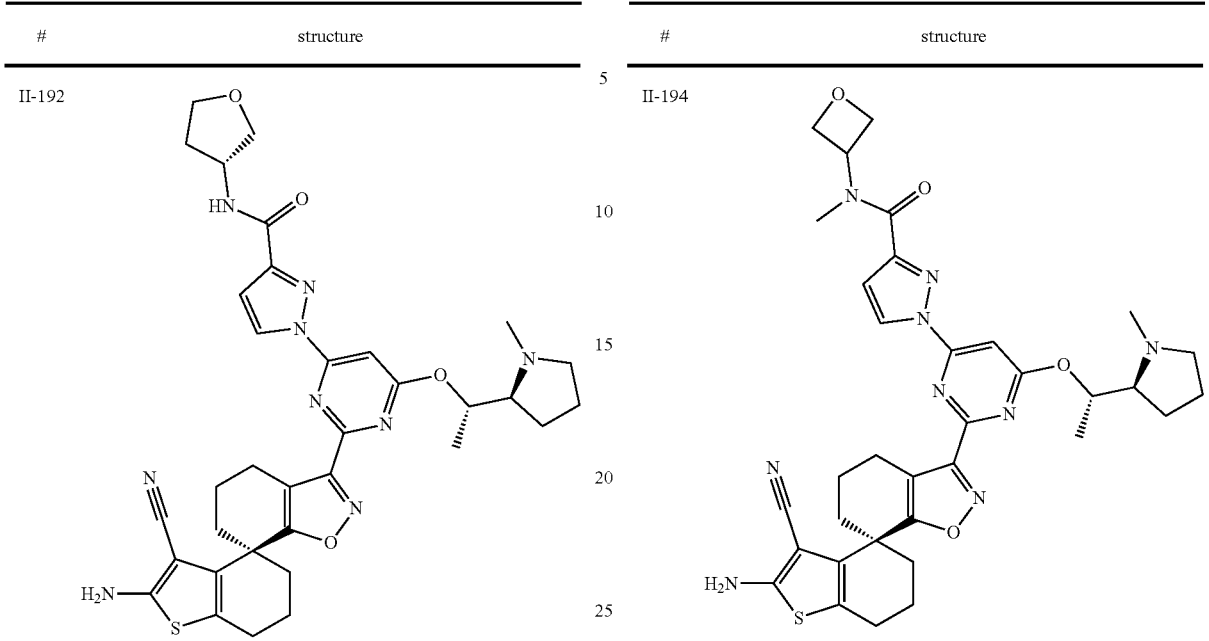 |
| II-193 | 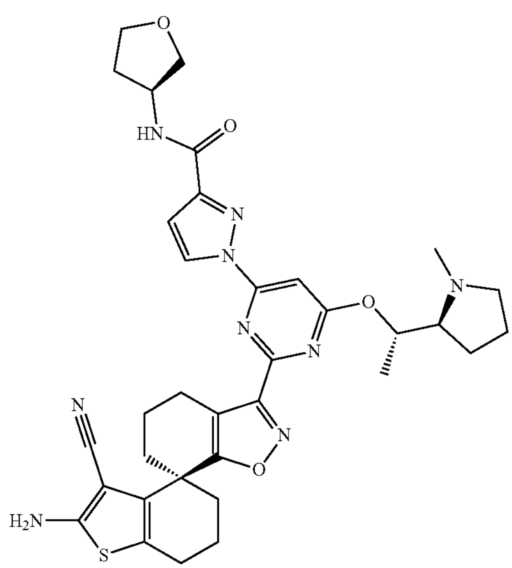 [SMILES: C[C@H](Oc1cc(-n2ccc(C(=O)N[C@H]3CCOC3)n2)nc(-c2noc3c2CCC[C@@]32CCCc3sc(N)c(C#N)c32)n1)[C@@H]1CCCN1C] |
696
-continued
| # | structure |
|---|---|
| II-194 | 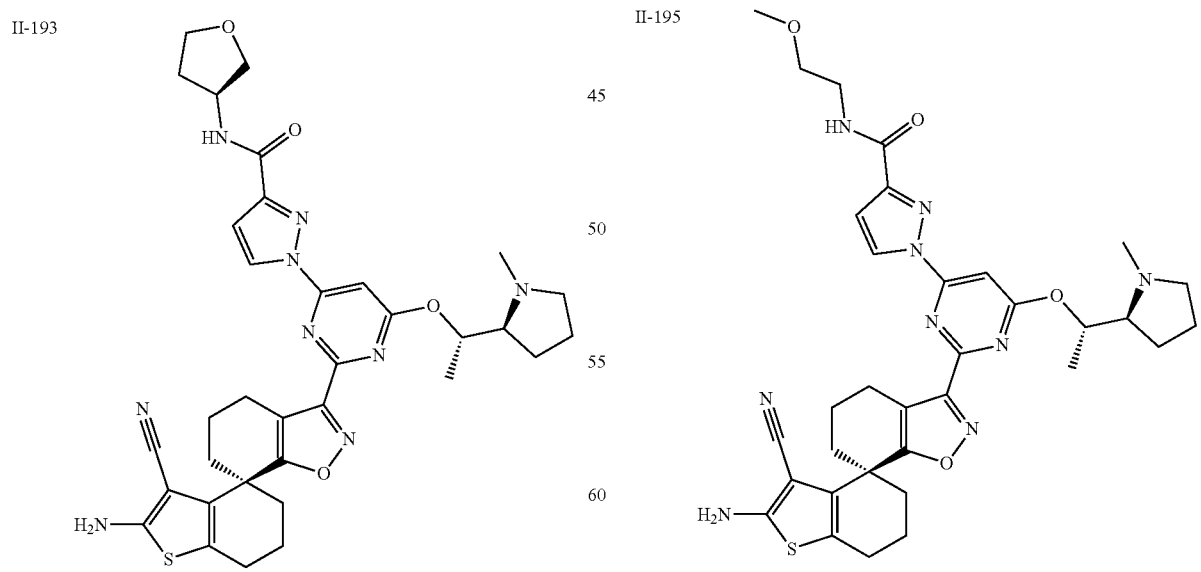 |
| II-195 | 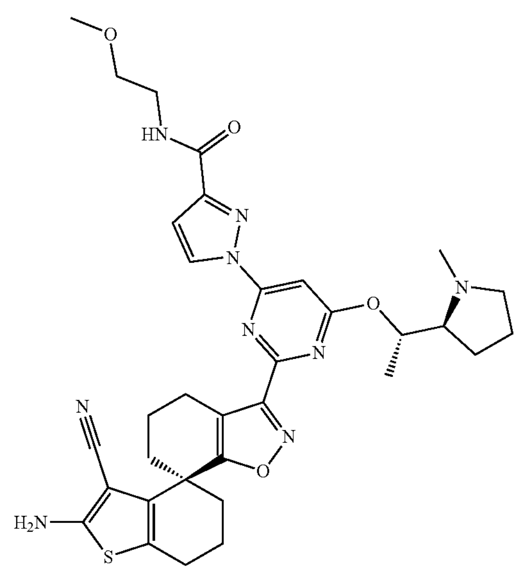 [SMILES: COCCNC(=O)c1ccn(-c2cc(O[C@@H](C)[C@@H]3CCCN3C)nc(-c3noc4c3CCC[C@@]43CCCc4sc(N)c(C#N)c43)n2)n1] |

| # | structure |
|---|---|
| II-196 | 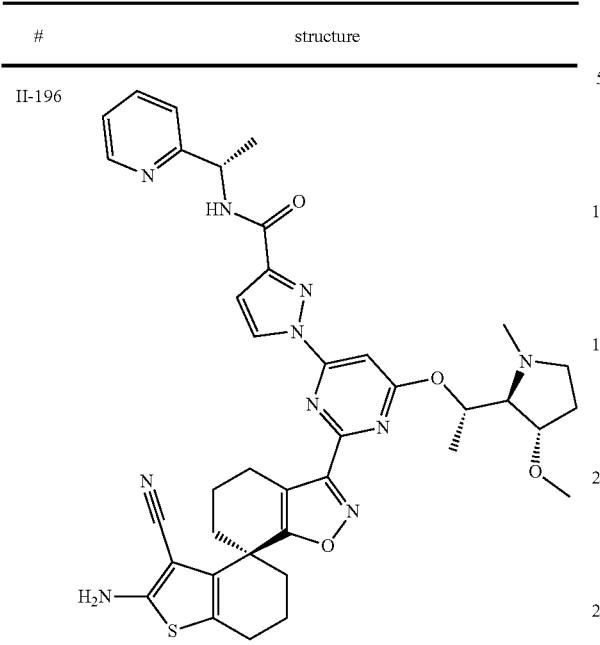 |
| II-197 | 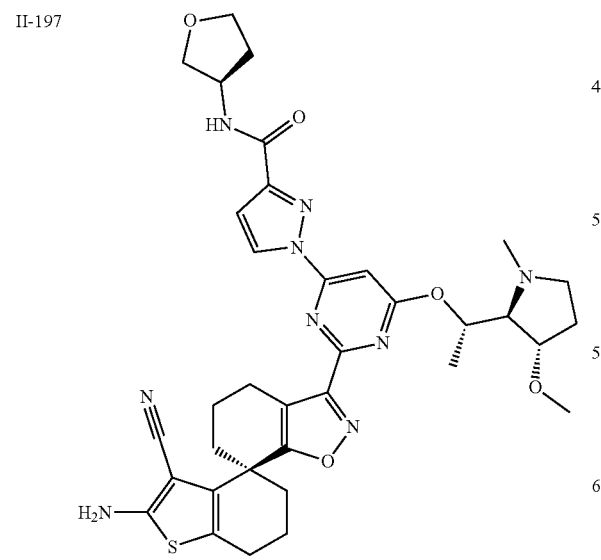 |
| # | structure |
|---|---|
| II-198 | 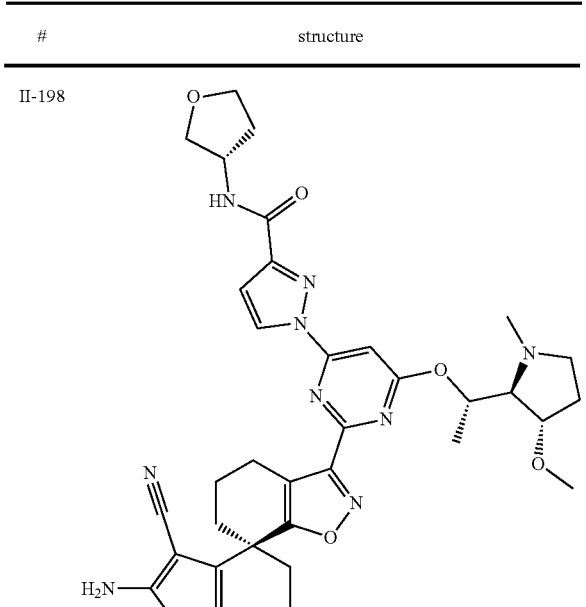 |
| II-199 | 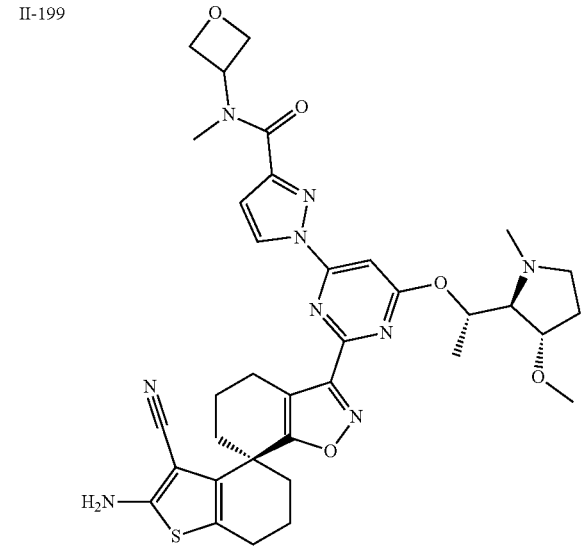 |

| # | structure |
|---|---|
| II-200 | 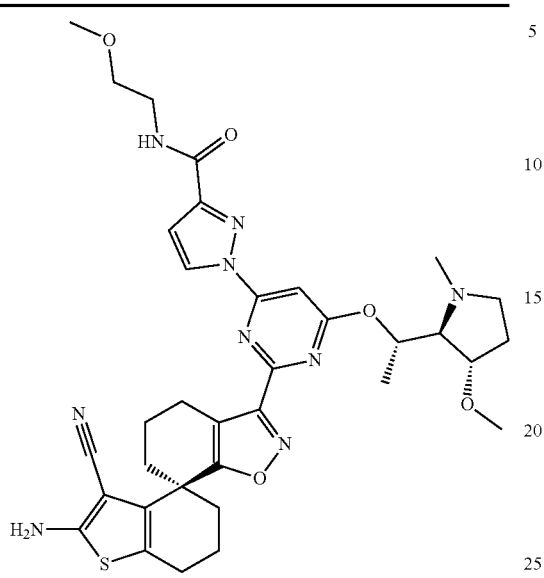 |
| II-201 | 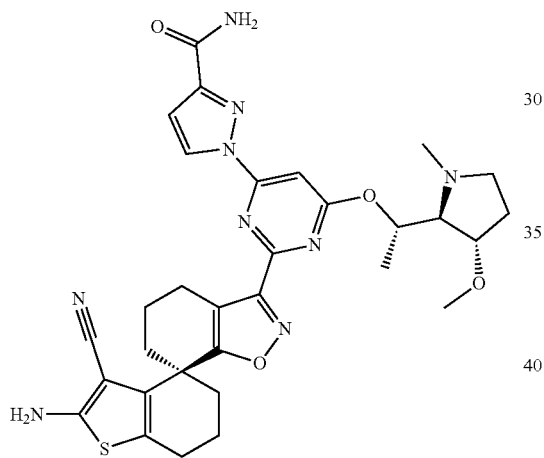 |
| II-202 | 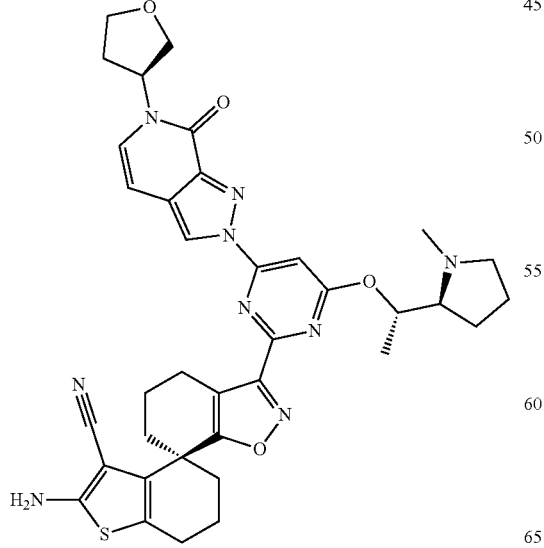 |
| # | structure |
|---|---|
| II-203 | 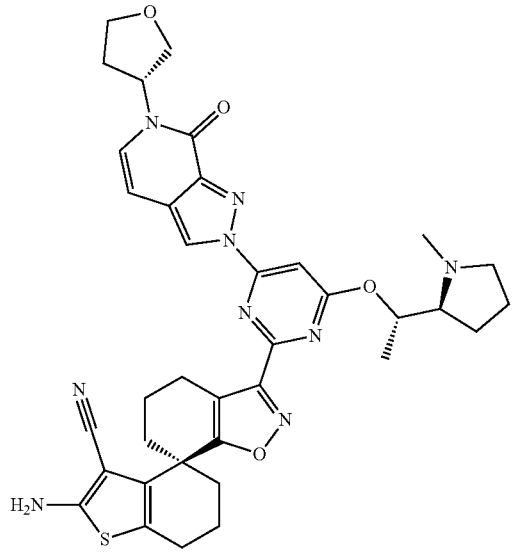 [SMILES: C[C@H](Oc1cc(-n2cc3ccn([C@@H]4CCOC4)c(=O)c3n2)nc(-c2noc3c2CCC[C@@]32CCCc3sc(N)c(C#N)c32)n1)[C@@H]1CCCN1C] |
| II-204 | 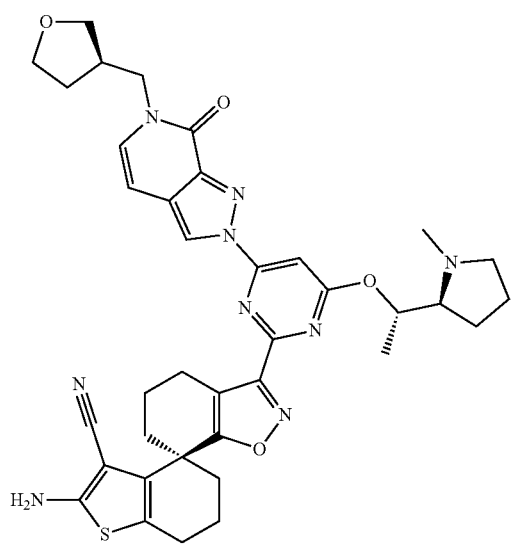 [SMILES: C[C@H](Oc1cc(-n2cc3ccn(C[C@H]4CCOC4)c(=O)c3n2)nc(-c2noc3c2CCC[C@@]32CCCc3sc(N)c(C#N)c32)n1)[C@@H]1CCCN1C] |

-continued
| # | structure |
|---|---|
| II-205 | 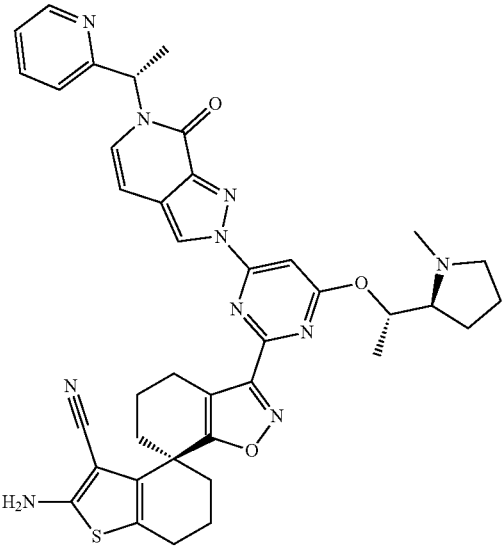 [SMILES: C[C@H](Oc1cc(-n2cc3ccn([C@@H](C)c4ccccn4)c(=O)c3n2)nc(-c2noc3c2CCC[C@@]32CCCc3sc(N)c(C#N)c32)n1)[C@@H]1CCCN1C] |
| II-206 | 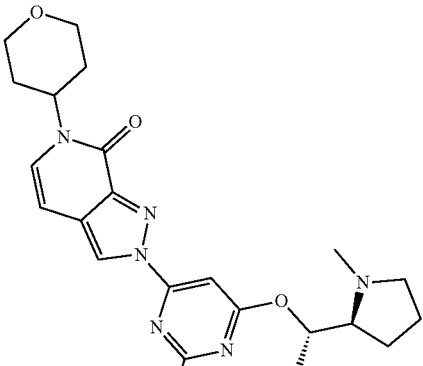 |
| II-207 | 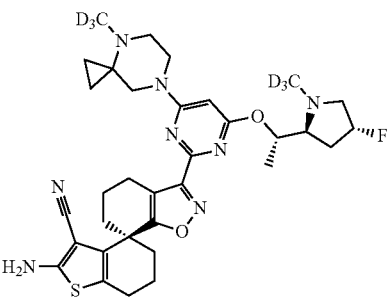 [SMILES: [2H]C([2H])([2H])N1C[C@H](F)C[C@H]1[C@H](C)Oc1cc(N2CCN(C([2H])([2H])[2H])C3(CC3)C2)nc(-c2noc3c2CCC[C@@]32CCCc3sc(N)c(C#N)c32)n1] |
-continued
| # | structure |
|---|---|
| II-208 | 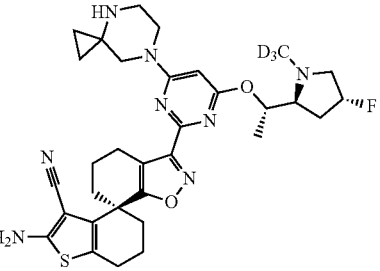 |
| II-209 | 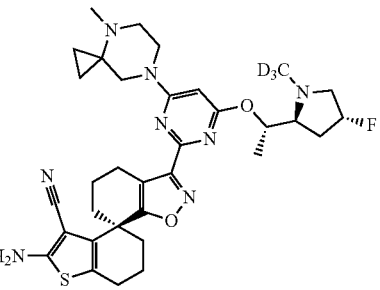 |
| II-210 | 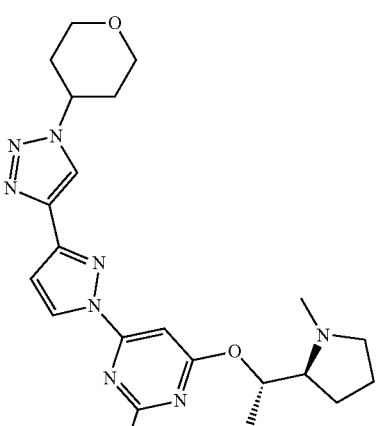 |

| # | structure |
|---|---|
| II-211 | 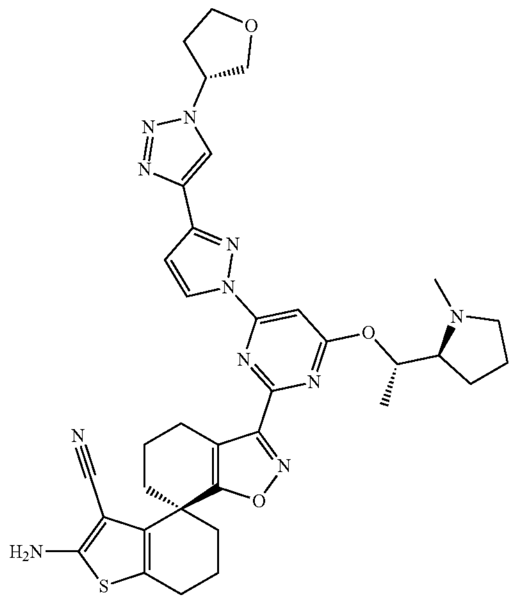 [SMILES: C[C@H](Oc1cc(-n2ccc(-c3cn([C@@H]4CCOC4)nn3)n2)nc(-c2noc3c2CCC[C@@]32CCCc3sc(N)c(C#N)c32)n1)[C@@H]1CCCN1C] |
| II-212 | 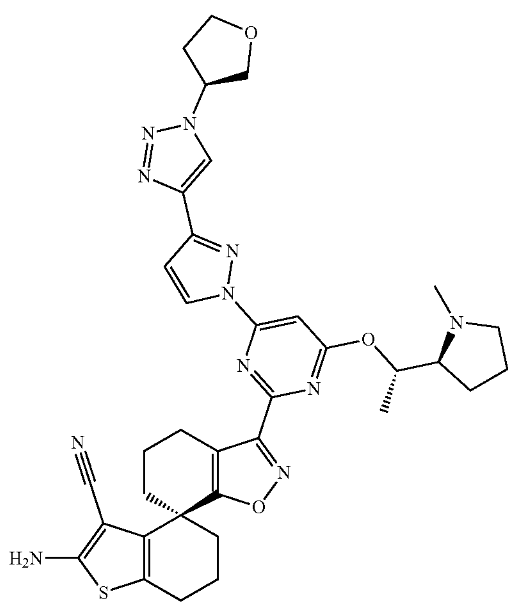 [SMILES: C[C@H](Oc1cc(-n2ccc(-c3cn([C@H]4CCOC4)nn3)n2)nc(-c2noc3c2CCC[C@@]32CCCc3sc(N)c(C#N)c32)n1)[C@@H]1CCCN1C] |
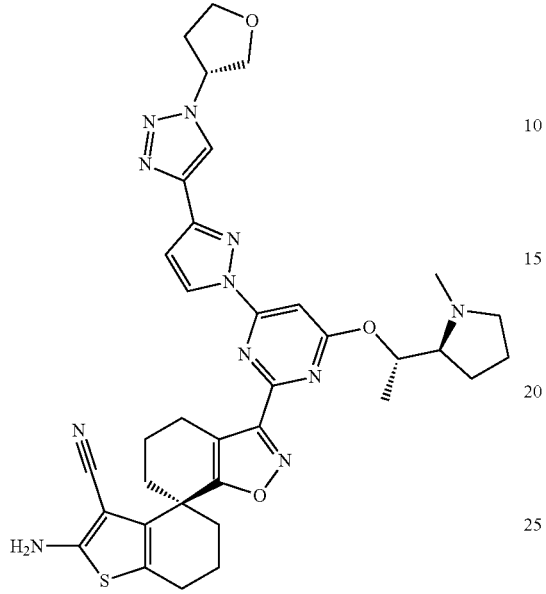
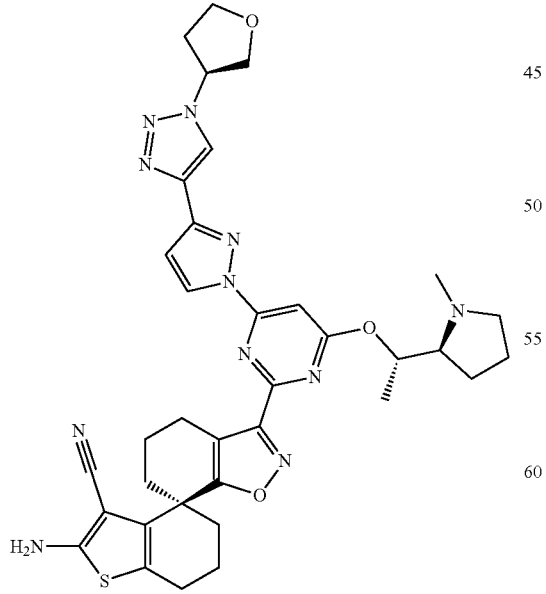
| # | structure |
|---|---|
| II-213 | 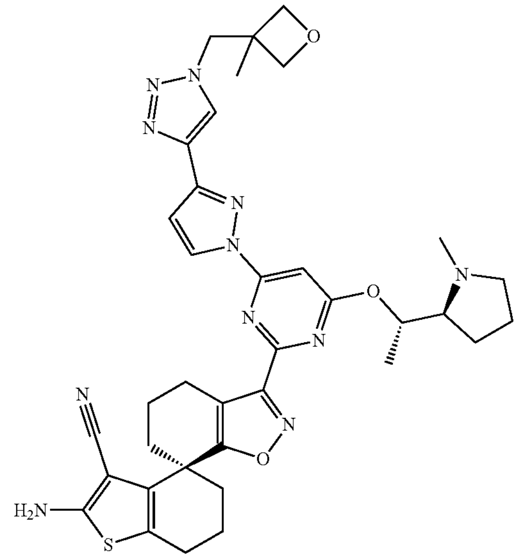 [SMILES: C[C@H](Oc1cc(-n2ccc(-c3cn(CC4(C)COC4)nn3)n2)nc(-c2noc3c2CCC[C@@]32CCCc3sc(N)c(C#N)c32)n1)[C@@H]1CCCN1C] |
| II-214 | 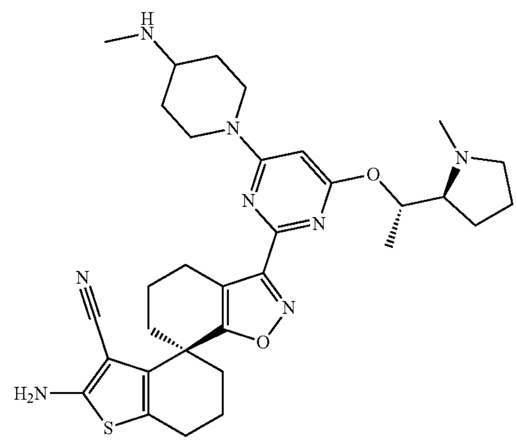 [SMILES: CNC1CCN(c2cc(O[C@@H](C)[C@@H]3CCCN3C)nc(-c3noc4c3CCC[C@@]43CCCc4sc(N)c(C#N)c43)n2)CC1] |
21. A compound according to claim 20 in the form of its pharmaceutically acceptable salt.
22. A compound having the following structure, or a pharmaceutically acceptable salt thereof:
| # | structure |
|---|---|
| I-34 | |

23. A compound having the following structure:
| # | structure |
|---|---|
| I-34 | 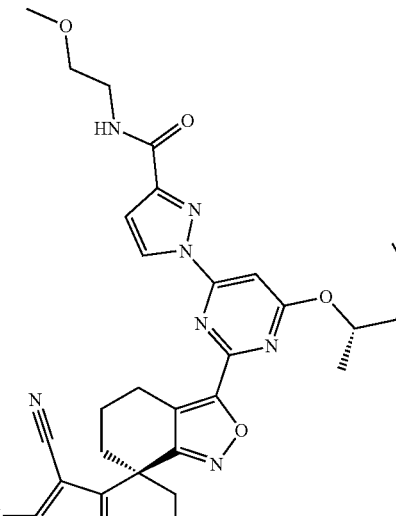 |
24. A compound having the following structure, or a pharmaceutically acceptable salt thereof:
| # | structure |
|---|---|
| I-58 | 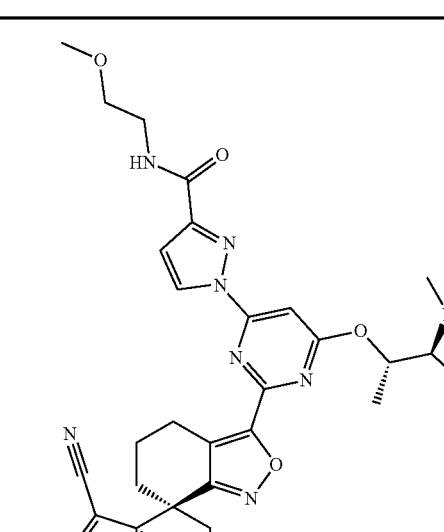 |
25. A compound having the following structure:
| # | structure |
|---|---|
| I-58 | 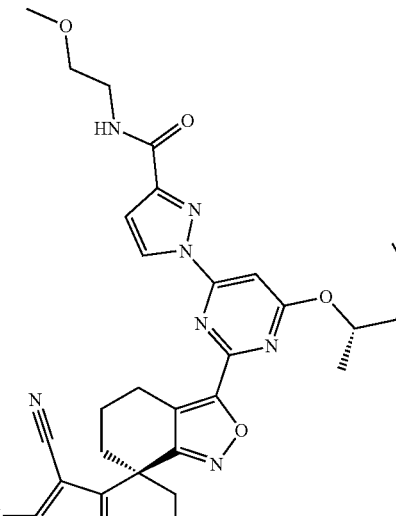 |
26. A compound having the following structure, or a pharmaceutically acceptable salt thereof:
| # | structure |
|---|---|
| II-20 | 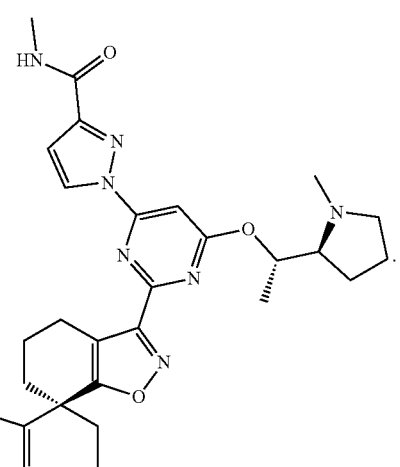 |

27. A compound having the following structure:

| # | structure |
|---|---|
| II-20 | 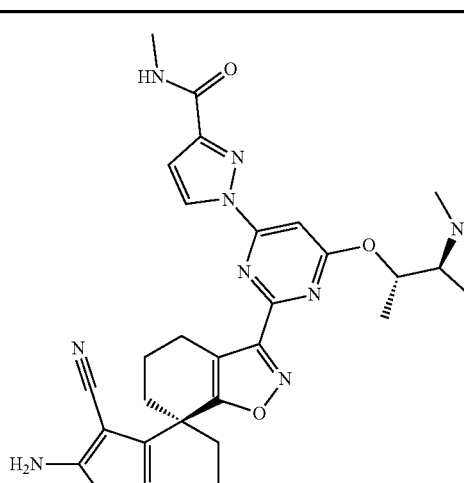 |

28. A compound having the following structure, or a pharmaceutically acceptable salt thereof:

| # | structure |
|---|---|
| II-21 | 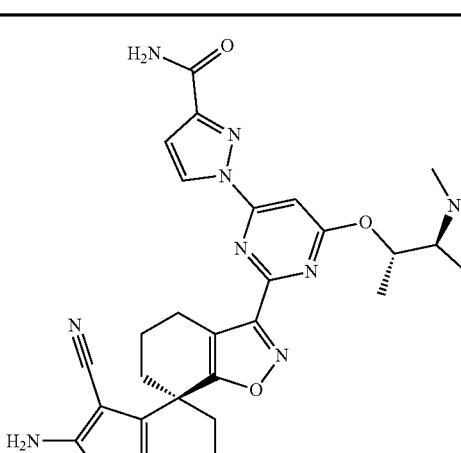 |

29. A compound having the following structure:

| # | structure |
|---|---|
| II-21 | |

30. A compound having the following structure, or a pharmaceutically acceptable salt thereof:

| # | structure |
|---|---|
| II-86 | |

31. A compound having the following structure:

| # | structure |
|---|---|
| II-86 | |

32. A compound having the following structure, or a pharmaceutically acceptable salt thereof:

| # | structure |
|---|---|
| II-110 | 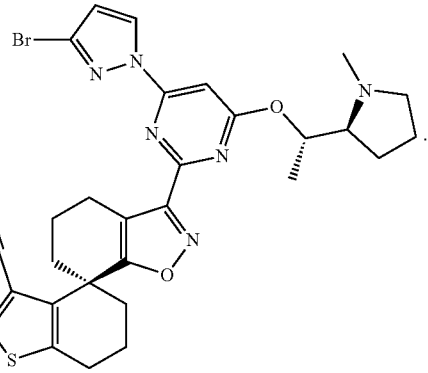 |

33. A compound having the following structure:

| # | structure |
|---|---|
| II-110 | 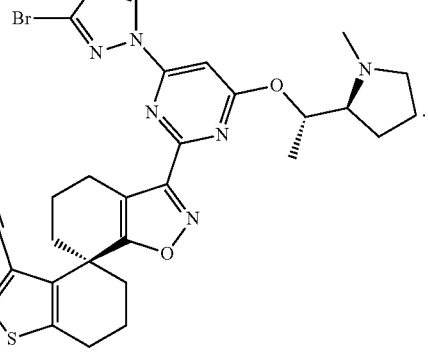 |

34. A compound having the following structure, or a pharmaceutically acceptable salt thereof:

| # | structure |
|---|---|
| II-111 | 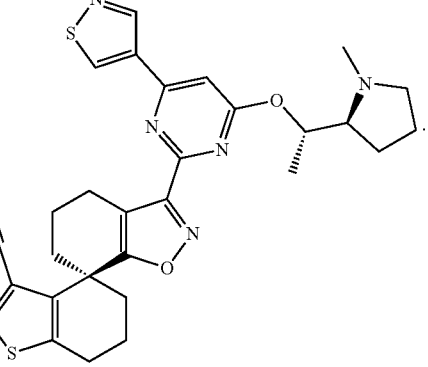 |

35. A compound having the following structure:

| # | structure |
|---|---|
| II-111 | 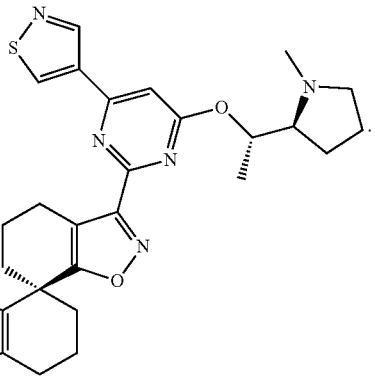 |

36. A compound having the following structure, or a pharmaceutically acceptable salt thereof:

| # | structure |
|---|---|
| II-130 | 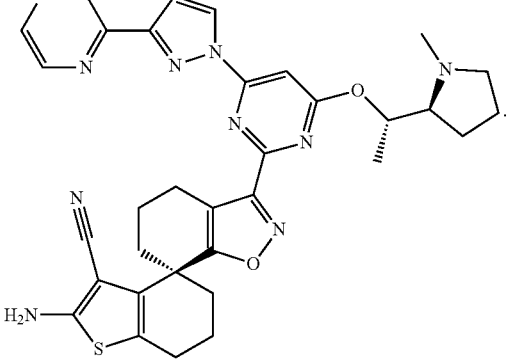 |

37. A compound having the following structure:

| # | structure |
|---|---|
| II-130 | 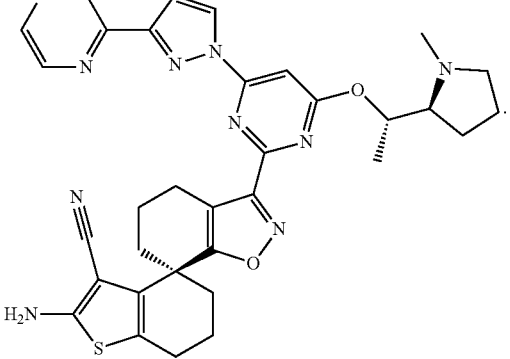 |

38. A compound having the following structure, or a pharmaceutically acceptable salt thereof:
| # | structure |
|---|---|
| II-182 | 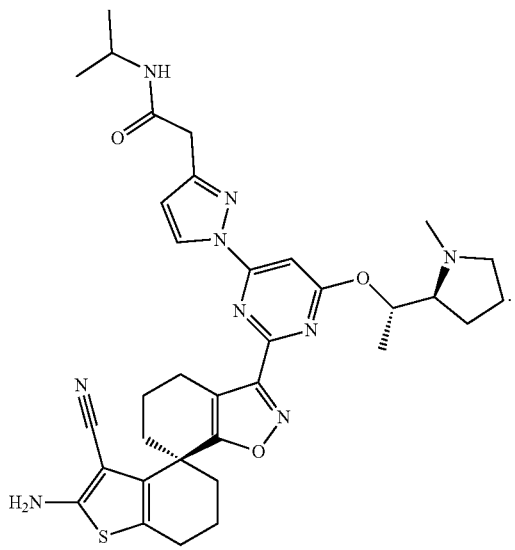 [SMILES: CC(C)NC(=O)Cc1ccn(-c2cc(O[C@@H](C)[C@@H]3CCCN3C)nc(-c3noc4c3CCC[C@@]43CCCc4sc(N)c(C#N)c43)n2)n1] |
39. A compound having the following structure:
| # | structure |
|---|---|
| II-182 | 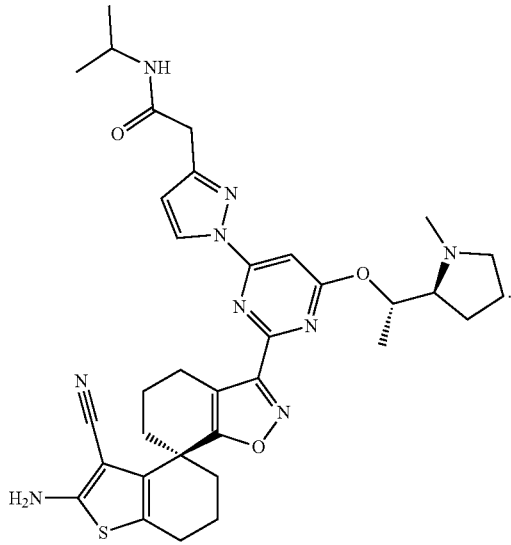 [SMILES: CC(C)NC(=O)Cc1ccn(-c2cc(O[C@@H](C)[C@@H]3CCCN3C)nc(-c3noc4c3CCC[C@@]43CCCc4sc(N)c(C#N)c43)n2)n1] |
40. A compound having the following structure, or a pharmaceutically acceptable salt thereof:
| # | structure |
|---|---|
| II-189 | 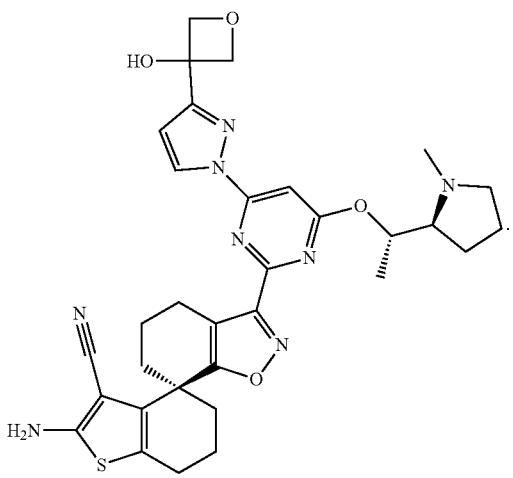 [SMILES: C[C@H](Oc1cc(-n2ccc(C3(O)COC3)n2)nc(-c2noc3c2CCC[C@@]32CCCc3sc(N)c(C#N)c32)n1)[C@@H]1CCCN1C] |
41. A compound having the following structure:
| # | structure |
|---|---|
| II-189 | 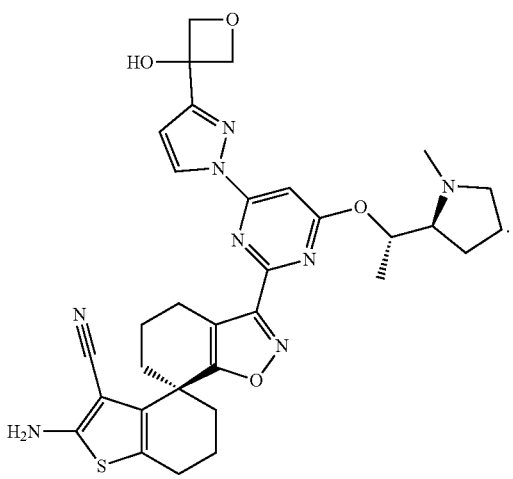 [SMILES: C[C@H](Oc1cc(-n2ccc(C3(O)COC3)n2)nc(-c2noc3c2CCC[C@@]32CCCc3sc(N)c(C#N)c32)n1)[C@@H]1CCCN1C] |

42. A compound having the following structure, or a pharmaceutically acceptable salt thereof:
| # | structure |
|---|---|
| II-191 | 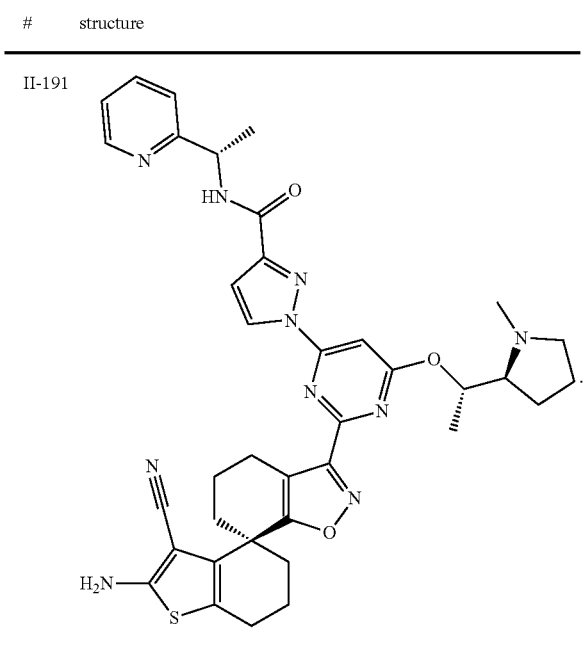 |
43. A compound having the following structure:
| # | structure |
|---|---|
| II-191 | 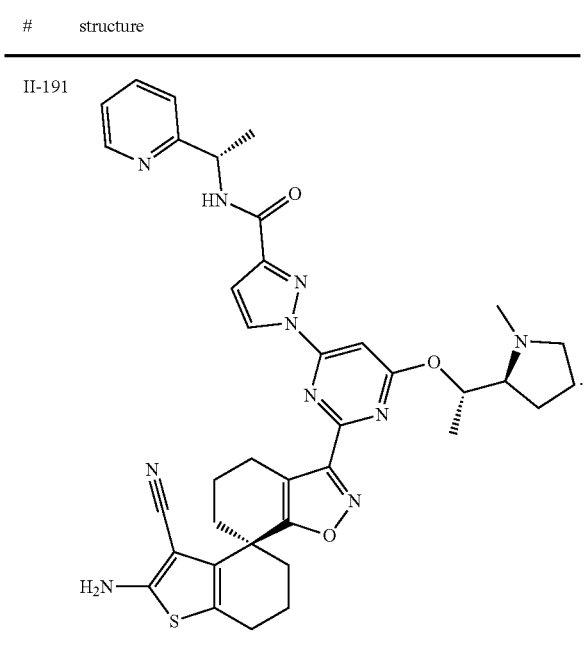 |
44. A compound having the following structure, or a pharmaceutically acceptable salt thereof:
| # | structure |
|---|---|
| II-192 | 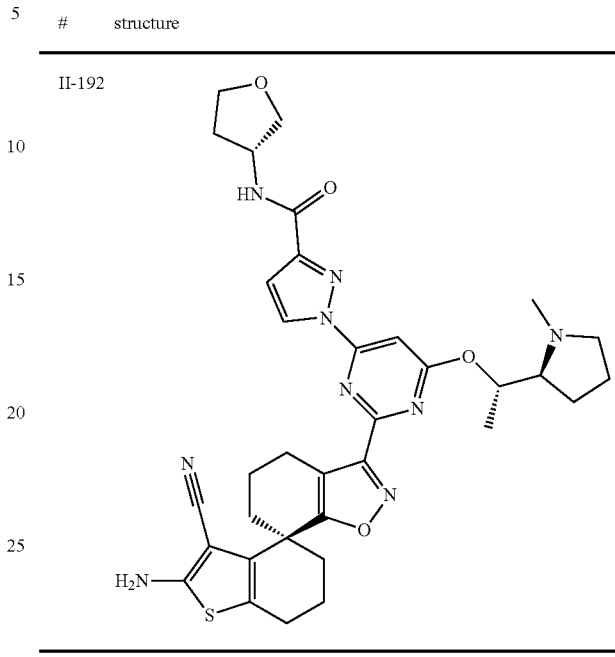 |
45. A compound having the following structure:
| # | structure |
|---|---|
| II-192 | 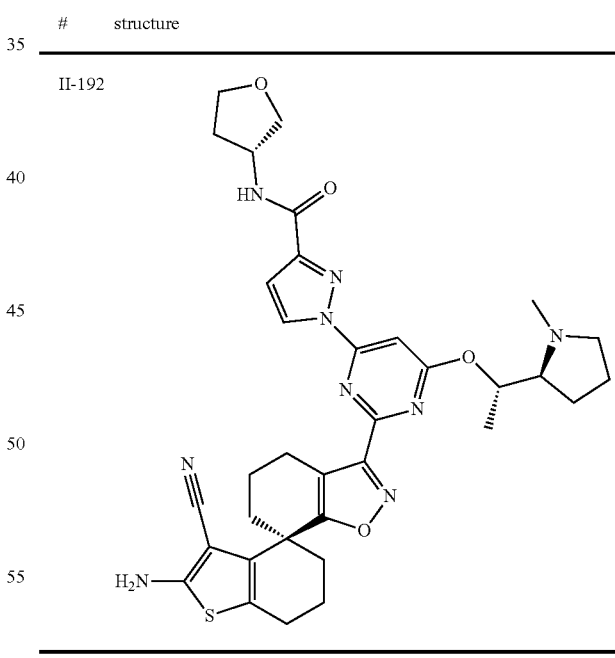 |

46. A compound having the following structure, or a pharmaceutically acceptable salt thereof:
| # | structure |
|---|---|
| II-194 | 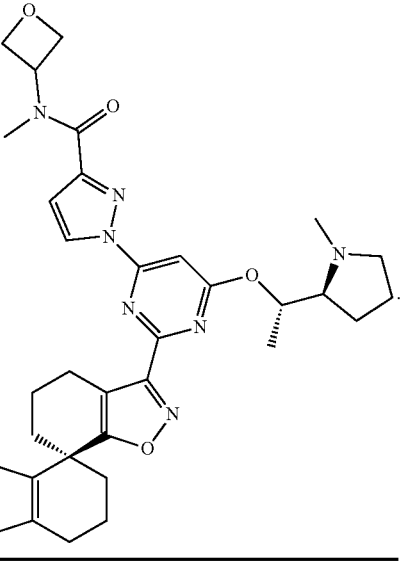 |
47. A compound having the following structure:
| # | structure |
|---|---|
| II-194 | 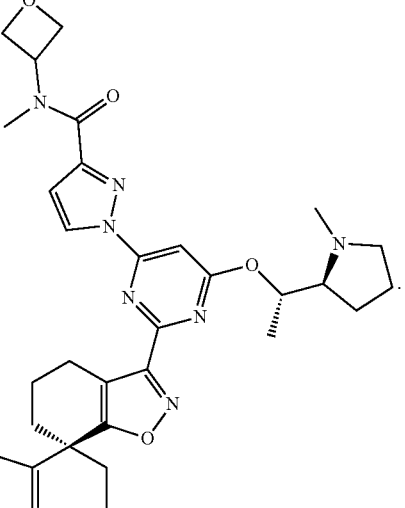 |
48. A compound having the following structure, or a pharmaceutically acceptable salt thereof:
| # | structure |
|---|---|
| II-201 | 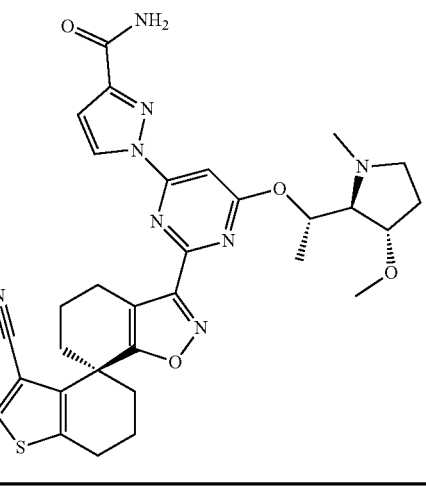 |
49. A compound having the following structure:
| # | structure |
|---|---|
| II-201 | 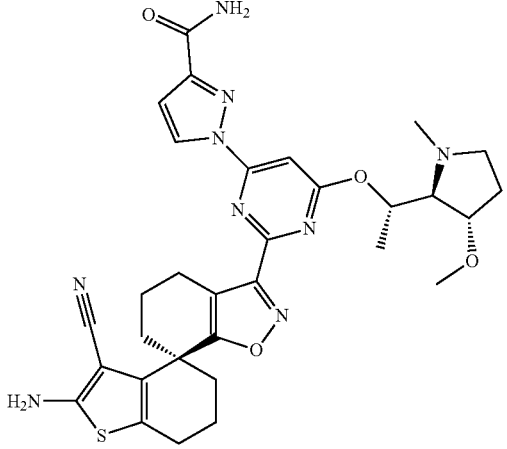 [SMILES: CO[C@H]1CCN(C)[C@@H]1[C@H](C)Oc1cc(-n2ccc(C(N)=O)n2)nc(-c2noc3c2CCC[C@@]32CCCc3sc(N)c(C#N)c32)n1] |
* * * * *